United States Patent
Xu et al.

(10) Patent No.: US 10,543,213 B2
(45) Date of Patent: *Jan. 28, 2020

(54) TREATMENT OF RELAPSED AND/OR REFRACTORY SOLID TUMORS AND NON-HODGKIN'S LYMPHOMAS

(71) Applicant: Celgene Quanticel Research, Inc., San Diego, CA (US)

(72) Inventors: Jiangchun Xu, San Diego, CA (US); Robert Cho, Sunnyvale, CA (US); Aaron Nguyen, San Jose, CA (US)

(73) Assignee: Celgene Quanticel Research, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/387,255

(22) Filed: Apr. 17, 2019

(65) Prior Publication Data

US 2019/0240222 A1 Aug. 8, 2019

Related U.S. Application Data

(63) Continuation of application No. 15/673,084, filed on Aug. 9, 2017, now Pat. No. 10,328,077.

(60) Provisional application No. 62/373,263, filed on Aug. 10, 2016, provisional application No. 62/468,424, filed on Mar. 8, 2017.

(51) Int. Cl.

| | |
|---|---|
| *A61K 31/513* | (2006.01) |
| *A61P 35/00* | (2006.01) |
| *A61K 31/7048* | (2006.01) |
| *A61K 31/357* | (2006.01) |
| *A61K 31/436* | (2006.01) |
| *A61K 31/5377* | (2006.01) |
| *A61K 31/551* | (2006.01) |
| *A61K 31/5685* | (2006.01) |
| *C07D 401/14* | (2006.01) |
| *C07D 405/14* | (2006.01) |
| *C07D 401/04* | (2006.01) |

(52) U.S. Cl.
CPC ......... *A61K 31/513* (2013.01); *A61K 31/357* (2013.01); *A61K 31/436* (2013.01); *A61K 31/5377* (2013.01); *A61K 31/551* (2013.01); *A61K 31/5685* (2013.01); *A61K 31/7048* (2013.01); *A61P 35/00* (2018.01); *C07D 401/04* (2013.01); *C07D 401/14* (2013.01); *C07D 405/14* (2013.01)

(58) Field of Classification Search
None
See application file for complete search history.

(56) References Cited

U.S. PATENT DOCUMENTS

| | | |
|---|---|---|
| 2015/0225375 A1 | 8/2015 | Wu et al. |
| 2015/0315187 A1 | 11/2015 | Chen et al. |

FOREIGN PATENT DOCUMENTS

| | | |
|---|---|---|
| WO | 2012009475 A1 | 1/2012 |

OTHER PUBLICATIONS

International Search Report and Written Opinion dated Oct. 30, 2017, in related International Application No. PCT/US2017/046098, filed Aug. 9, 2017.
Yokoyama et al., 'Identification of Myelin Transcription Factor 1 (MyT1) as a Subunit of the Neural Cell Type-specific Lysine-specific Demethylase 1 (LSD1) Complex', The Journal of Biological Chemistry, 2014, vol. 289, pp. 18152-18162, p. 18156, col. 2, para 2.
Official Action issued in co-pending U.S. Appl. No. 16/387,318, dated May 6, 2019.
Notice of Allowance issued in co-pending U.S. Appl. No. 16/387,318, dated Sep. 11, 2019.

*Primary Examiner* — Jared Barsky
(74) *Attorney, Agent, or Firm* — Foley & Lardner LLP

(57) ABSTRACT

Methods are provided for the treatment of relapsed and/or refractory solid tumors (including neuroendocrine carcinomas (NEC)) and non-Hodgkin's lymphomas (NHLs) and the like, using substituted heterocyclic derivative compounds and pharmaceutical compositions comprising compounds useful for the inhibition of lysine specific demethylase-1 (LSD-1).

5 Claims, 30 Drawing Sheets

Tumor volumes plotted as mean ± standard error (SEM)

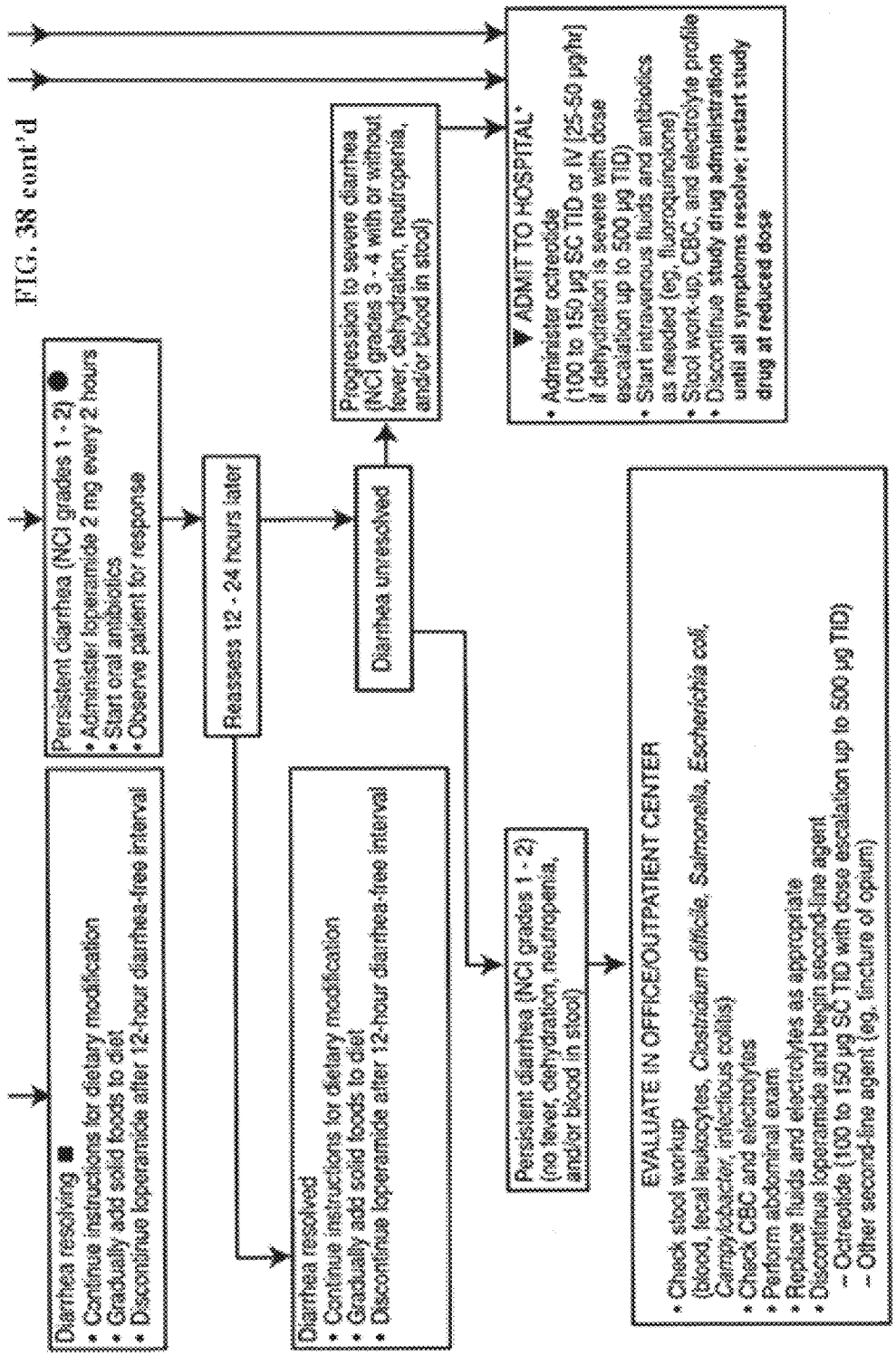

TREATMENT OF RELAPSED AND/OR REFRACTORY SOLID TUMORS AND NON-HODGKIN'S LYMPHOMAS

RELATED APPLICATION

This application is a continuation of U.S. application Ser. No. 15/673,084, filed Aug. 9, 2017, which claims priority benefit of U.S. Provisional Patent Application No. 62/373,263 filed Aug. 10, 2016, and U.S. Provisional Patent Application No. 62/468,424, filed Mar. 8, 2017, both of which are incorporated fully herein by reference for all purposes.

FIELD

The embodiments described herein provide compositions, formulations, and methods for treating cancer and neoplastic diseases; in which such treatments include therapies comprising administration of a lysine specific demethylase-1 (LSD-1) inhibitor.

BACKGROUND

There remains a need for compositions, formulations, and methods for treating subjects with cancers such as, for example, basal cell carcinoma, relapsed or refractory non-Hodgkin's lymphomas (NHL), glioblastoma multiforme, anaplastic astrocytoma, or other advanced solid tumors.

For example, basal cell carcinoma (BCC) is a common cancer throughout the world, and its incidence is increasing. In the United States alone, more than 3.5 million new patients are diagnosed annually with non-melanoma skin cancer. Most BCCs can be cured by topical therapy, surgery, radiotherapy, or a combination thereof. Advanced BCC, however, often causes significant disfigurement and morbidity with associated physical and psychological sequelae, because BCC occurs commonly in sun-exposed areas such as the face. Further, a small proportion of these cancers are metastatic and not amenable to typical therapy. Near all BCCs are associated with aberrant hedgehog (Hh) signaling, which stimulates unregulated cell growth, and several therapeutic Hh inhibitors have proved useful in treating BCC. Unfortunately, about 20% of BCCs develop resistance to current Hh inhibitors, usually via Hh pathway reactivation by mutations that either interfere with the drug binding pocket, increase Hh signaling activity, or act through concurrent copy number changes in suppressor genes. Patients will benefit from the development of well-tolerated agents that overcome these resistance pathways by, for example, targeting proteins downstream in relevant signaling pathways.

BRIEF SUMMARY OF THE INVENTION

The aspects and embodiments of the present disclosure provide for methods and pharmaceutical compositions for treating subjects with cancer and neoplastic disease; such as those with advanced solid tumors, relapsed or refractory solid tumors (including neuroendocrine carcinomas (NEC) and non-Hodgkin's lymphomas), glioblastoma multiforme, anaplastic astrocytoma, basal cell carcinoma, or other cancers. At least one embodiment provides a method for treating cancer and neoplastic disease comprising administering to a subject in need thereof a therapeutically effective amount of at least one LSD-1 inhibitor.

One embodiment provides treatment methods involving a compound having the structure of Formula (I), or a pharmaceutically acceptable salt thereof,

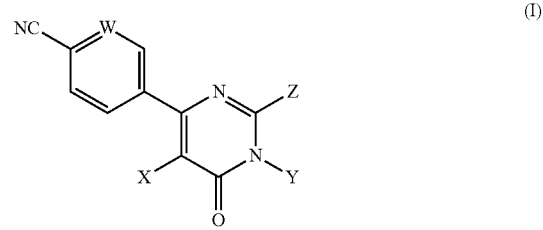

(I)

wherein,

W is N, C—H, or C—F;

X is hydrogen, halogen, —CN, optionally substituted alkyl, optionally substituted alkynyl, optionally substituted carbocyclylalkynyl, optionally substituted aryl, or optionally substituted heteroaryl;

Y is hydrogen, optionally substituted alkyl, optionally substituted cycloalkyl, or optionally substituted cycloalkylalkyl;

Z is an optionally substituted group chosen from alkyl, carbocyclyl, C-attached heterocyclyl, N-attached heterocyclyl, heterocyclylalkyl, heterocyclylalkenyl, —O-heterocyclyl, —N(R)-heterocyclyl, —O-heterocyclylalkyl, —N(R)-heterocyclylalkyl, —N(R)($C_1$-$C_4$alkylene)-$NR_2$, —O($C_1$-$C_4$alkylene)-$NR_2$, and R is hydrogen or $C_1$-$C_4$alkyl.

One embodiment provides treatment methods involving a compound having the structure of Formula (Ia), or a pharmaceutically acceptable salt thereof,

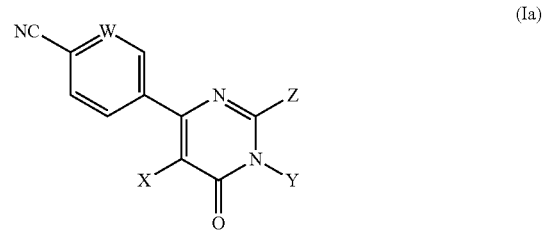

(Ia)

wherein,

W is N, C—H, or C—F;

X is hydrogen, halogen, —CN, optionally substituted alkynyl, optionally substituted carbocyclylalkynyl, optionally substituted aryl, or optionally substituted heteroaryl;

Y is hydrogen, optionally substituted alkyl, optionally substituted cycloalkyl, or optionally substituted cycloalkylalkyl; and Z is an optionally substituted group chosen from N-attached heterocyclyl, —O-heterocyclylalkyl, —N(H)-heterocyclyl, —N(Me)-heterocyclyl, —N(H)-heterocyclylalkyl, or —N(Me)-heterocyclylalkyl.

One embodiment provides treatment methods involving a compound having the structure of Formula (Ib), or a pharmaceutically acceptable salt thereof,

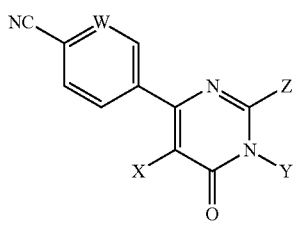

(Ib)

wherein,

W is N, C—H, or C—F;

X is hydrogen, halogen, optionally substituted alkynyl, optionally substituted carbocyclylalkynyl, optionally substituted aryl, or optionally substituted heteroaryl;

Y is hydrogen, optionally substituted alkyl, or optionally substituted cycloalkyl; and Z is an optionally substituted group chosen from N-heterocyclyl, —O-heterocyclylalkyl, —N(H)-heterocyclylalkyl, or —N(Me)-heterocyclylalkyl.

One embodiment provides treatment methods involving a pharmaceutical composition comprising a compound of Formula (I), or a pharmaceutically acceptable salt thereof, and a pharmaceutically acceptable excipient. One embodiment provides treatment methods involving a pharmaceutical composition comprising a compound of Formula (Ia), or a pharmaceutically acceptable salt thereof, and a pharmaceutically acceptable excipient. One embodiment provides treatment methods involving a pharmaceutical composition comprising a compound of Formula (Ib), or a pharmaceutically acceptable salt thereof, and a pharmaceutically acceptable excipient.

One embodiment provides treatment methods involving the regulation of gene transcription in a cell comprising inhibiting lysine-specific demethylase 1 activity by exposing the lysine-specific demethylase 1 enzyme to a compound of Formula (I). One embodiment provides treatment methods involving the regulation of gene transcription in a cell comprising inhibiting lysine-specific demethylase 1 activity by exposing the lysine-specific demethylase 1 enzyme to a compound of Formula (Ia). One embodiment provides treatment methods involving the regulation of gene transcription in a cell comprising inhibiting lysine-specific demethylase 1 activity by exposing the lysine-specific demethylase 1 enzyme to a compound of Formula (Ib).

One embodiment provides a method of treating cancer in a patient in need thereof, comprising administering to the patient a compound of Formula (I), or a pharmaceutically acceptable salt thereof. One embodiment provides a method of treating cancer in a patient in need thereof, comprising administering to the patient a compound of Formula (Ia), or a pharmaceutically acceptable salt thereof. One embodiment provides a method of treating cancer in a patient in need thereof, comprising administering to the patient a compound of Formula (Ib), or a pharmaceutically acceptable salt thereof.

INCORPORATION BY REFERENCE

Figure 1:
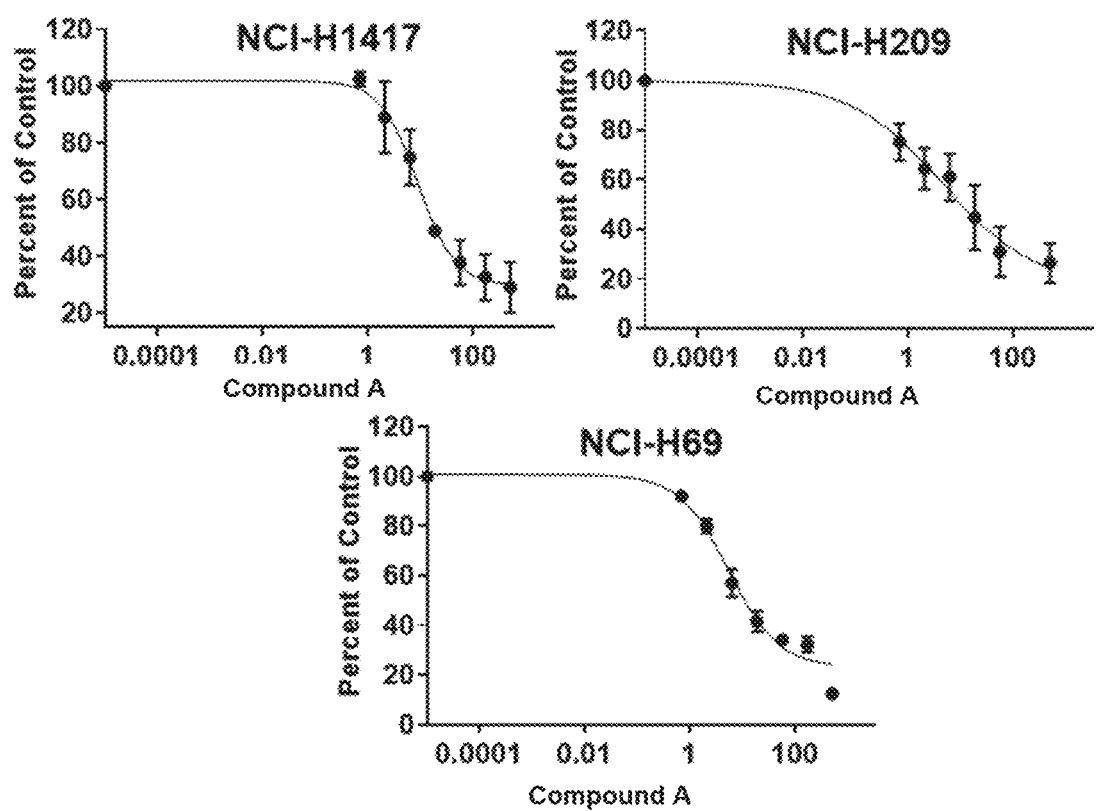
FIG. 1 shows the effect of Compound A on Gastrin Releasing Peptide Messenger RibonucleicAcid Expression in NCI-H1417, NCI-H209, and NCI-H69 Cells. DMSO=imethylsulfoxide; GRP=gastrin-releasing peptide; IC50=alf-maximal inhibitory concentration; mRNA=essenger ribonucleic acid; RNA=ribonucleic acid. Data are presented as the mean percent activity for three independent experiments for NCI-H1417 and NCI-H209 and two independent experiments for NCI-H69, and error bars represent the standard deviation.

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)N($R^a$)$_2$, —N($R^a$)C(O)$OR^a$, —OC(O)—N($R^a$)$_2$, —N($R^a$)C(O)$R^a$, —N($R^a$)S(O)$_t$$R^a$ (where t is 1 or 2), —S(O)$_t$$OR^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)N($R^a$)$_2$, —N($R^a$)C(O)$OR^a$, —OC(O)—N($R^a$)$_2$, —N($R^a$)C(O)$R^a$, —N($R^a$)S(O)$_t$$R^a$ (where t is 1 or 2), —S(O)$_t$$OR^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The point(s) of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkynylene). In other embodiments, an alkynylene comprises five to eight carbon atoms (e.g., $C_5$-$C_5$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hackel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $-R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $-R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula $-O-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

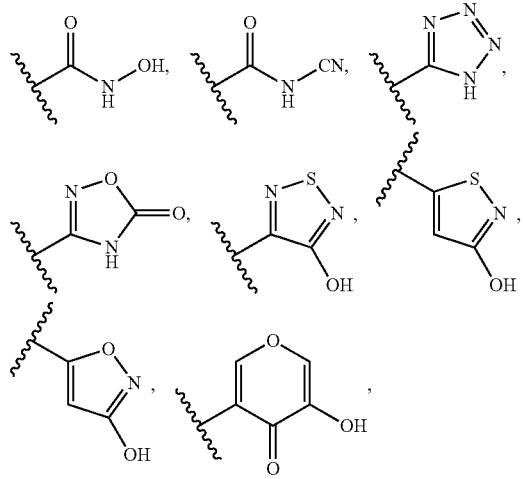

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heterocyclyl" or "N-attached heterocyclyl" refers to a heterocyclyl radical, as defined above, containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzo- ranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetra-hydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]-pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetra-hydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tR^a$ (where t is 1 or 2), —$R^b$—S(O)$_tOR^a$ (where t is 1 or 2) and —$R^b$—S(O)$_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

nic acid, salicylic acid, and the like. Exemplary salts thus include sulfates, pyrosulfates, bisulfates, sulfites, bisulfites, nitrates, phosphates, monohydrogen-phosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitro-benzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, e.g., Berge S. M. et al., *Pharmaceutical Salts*, J. Pharma. Sci. 66:1-19 (1997)). Acid addition salts of basic compounds are, in some embodiments, prepared by contacting the free base forms with a sufficient amount of the desired acid to produce the salt according to methods and techniques with which a skilled artisan is familiar.

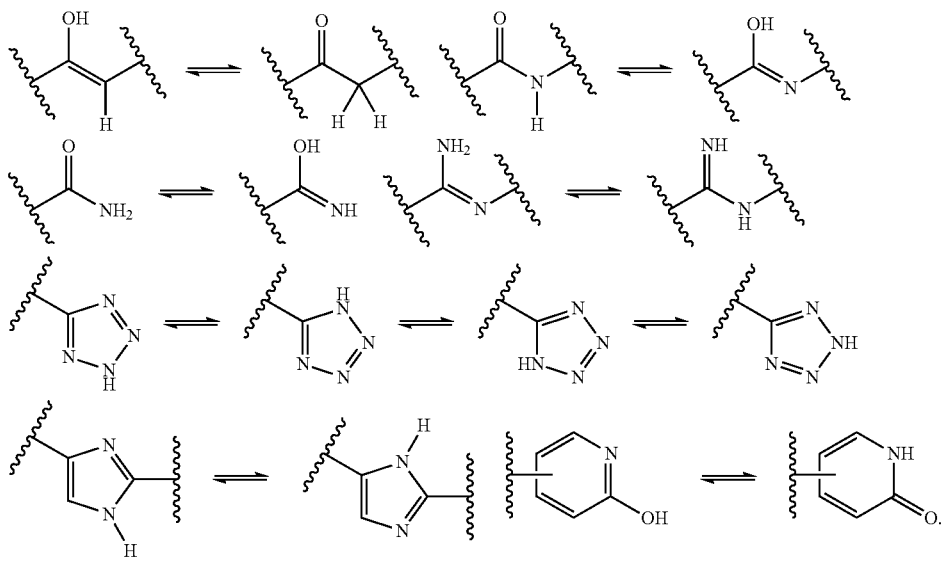

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfo- "Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., DESIGN OF PRODRUGS (1985), pp. 7-9, 21-24 (Elsevier, Amsterdam).

A discussion of prodrugs is provided in Higuchi, T., et al., *Pro-drugs as Novel Delivery Systems*, A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Heterocyclic Derivative Compounds

Methods are provided herein for the treatment of relapsed and/or refractory solid tumors (including neuroendocrine carcinomas (NEC)) and non-Hodgkin's lymphomas (NHLs) and the like, using substituted heterocyclic derivative compounds and pharmaceutical compositions comprising compounds useful for the inhibition of lysine specific demethylase-1 (LSD-1). Suitable substituted heterocyclic derivative compounds useful for the inhibition of LSD-1 include those described in U.S. patent application Ser. No. 14/701,304, filed Apr. 30, 2015 (now U.S. Pat. No. 9,255, 097), U.S. patent application Ser. No. 14/988,022, filed Jan. 5, 2016, U.S. patent application Ser. No. 15/018,814, filed Feb. 8, 2016, and International patent application No. PCT/US2015/028635, all of which claim the priority benefit of U.S. patent application Ser. No. 61/987,354, filed May 1, 2014; as well as those described in U.S. patent application Ser. No. 62/251,507, filed Nov. 5, 2015. The contents of each and every one of these applications are hereby incorporated by reference in their entireties for all purposes.

One embodiment provides a compound having the structure of Formula (I), or a pharmaceutically acceptable salt thereof,

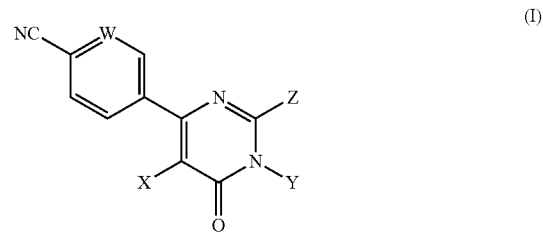

wherein,

W is N, C—H, or C—F;

X is hydrogen, halogen, —CN, optionally substituted alkyl, optionally substituted alkynyl, optionally substituted carbocyclylalkynyl, optionally substituted aryl, or optionally substituted heteroaryl;

Y is hydrogen, optionally substituted alkyl, optionally substituted cycloalkyl, or optionally substituted cycloalkylalkyl;

Z is an optionally substituted group chosen from alkyl, carbocyclyl, C-attached heterocyclyl, N-attached heterocyclyl, heterocyclylalkyl, heterocyclylalkenyl, —O-heterocyclyl, —N(R)-hetero-cyclyl, —O-heterocyclylalkyl, —N(R)-heterocyclylalkyl, —N(R)(C$_1$-C$_4$alkylene)-NR$_2$, —O(C$_1$-C$_4$alk-ylene)-NR$_2$, and R is hydrogen or C$_1$-C$_4$alkyl.

One embodiment provides a compound of Formula (I) having the structure of Formula (Ia), or a pharmaceutically acceptable salt thereof,

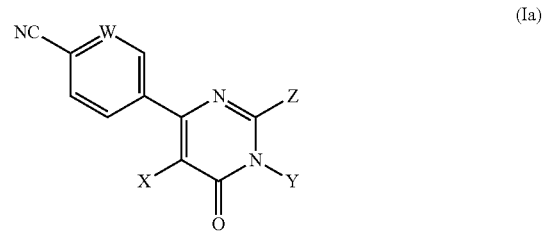

wherein,

W is N, C—H, or C—F;

X is hydrogen, halogen, —CN, optionally substituted alkynyl, optionally substituted carbocyclylalkynyl, optionally substituted aryl, or optionally substituted heteroaryl;

Y is hydrogen, optionally substituted alkyl, optionally substituted cycloalkyl, or optionally substituted cycloalkylalkyl; and Z is an optionally substituted group chosen from N-attached heterocyclyl, —O-heterocyclylalkyl, —N(H)-heterocyclyl, —N(Me)-heterocyclyl, —N(H)-heterocyclylalkyl, or —N(Me)-heterocyclylalkyl.

One embodiment provides a compound of Formula (I) or (Ia) having the structure of Formula (Ib), or a pharmaceutically acceptable salt thereof,

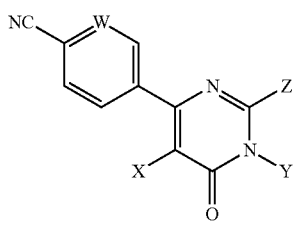

(Ib)

wherein,

W is N, C—H, or C—F;

X is hydrogen, halogen, optionally substituted alkynyl, optionally substituted carbocyclylalkynyl, optionally substituted aryl, or optionally substituted heteroaryl;

Y is hydrogen, optionally substituted alkyl, or optionally substituted cycloalkyl; and Z is an optionally substituted group chosen from N-heterocyclyl, —O-heterocyclylalkyl, —N(H)-heterocyclylalkyl, or —N(Me)-heterocyclylalkyl.

Another embodiment provides the compound of Formula (Ib), or a pharmaceutically acceptable salt thereof, wherein W is C—H. Another embodiment provides the compound of Formula (Ib), or a pharmaceutically acceptable salt thereof, wherein W is C—F. Another embodiment provides the compound of Formula (Ib), or a pharmaceutically acceptable salt thereof, wherein W is N.

Another embodiment provides the compound of Formula (Ib), or a pharmaceutically acceptable salt thereof, wherein X is hydrogen. Another embodiment provides the compound of Formula (Ib), or a pharmaceutically acceptable salt thereof, wherein X is halogen. Another embodiment provides the compound of Formula (Ib), or a pharmaceutically acceptable salt thereof, wherein X is optionally substituted alkynyl. Another embodiment provides the compound of Formula (Ib), or a pharmaceutically acceptable salt thereof, wherein X is optionally substituted carbocyclylalkynyl. Another embodiment provides the compound of Formula (Ib), or a pharmaceutically acceptable salt thereof, wherein X is optionally substituted aryl, or optionally substituted heteroaryl. Another embodiment provides the compound of Formula (Ib), or a pharmaceutically acceptable salt thereof, wherein X is optionally substituted aryl. Another embodiment provides the compound of Formula (Ib), or a pharmaceutically acceptable salt thereof, wherein X is an optionally substituted phenyl. Another embodiment provides the compound of Formula (Ib), or a pharmaceutically acceptable salt thereof, wherein X is optionally substituted heteroaryl. Another embodiment provides the compound of Formula (Ib), or a pharmaceutically acceptable salt thereof, wherein X is chosen from an optionally substituted pyridinyl, optionally substituted pyrazolyl, or optionally substituted indazolyl.

Another embodiment provides the compound of Formula (Ib), or a pharmaceutically acceptable salt thereof, wherein Y is hydrogen. Another embodiment provides the compound of Formula (Ib), or a pharmaceutically acceptable salt thereof, wherein Y is optionally substituted cycloalkyl. Another embodiment provides the compound of Formula (Ib), or a pharmaceutically acceptable salt thereof, wherein Y is optionally substituted alkyl. Another embodiment provides the compound of Formula (Ib), or a pharmaceutically acceptable salt thereof, wherein Y is an optionally substituted $C_1$-$C_3$ alkyl. Another embodiment provides the compound of Formula (Ib), or a pharmaceutically acceptable salt thereof, wherein Y is an optionally substituted $C_1$ alkyl. Another embodiment provides the compound of Formula (Ib), or a pharmaceutically acceptable salt thereof, wherein Y is a methyl group.

Another embodiment provides the compound of Formula (Ib), or a pharmaceutically acceptable salt thereof, wherein Z is an optionally substituted —O-heterocyclylalkyl. Another embodiment provides the compound of Formula (Ib), or a pharmaceutically acceptable salt thereof, wherein Z is an optionally substituted —N(H)-heterocyclylalkyl. Another embodiment provides the compound of Formula (Ib), or a pharmaceutically acceptable salt thereof, wherein Z is an optionally substituted —N(Me)-heterocyclylalkyl.

Another embodiment provides the compound of Formula (Ib), or a pharmaceutically acceptable salt thereof, wherein Z is an optionally substituted —O-heterocyclylalkyl and the heterocyclylalkyl group has the formula —$R^c$-heterocyclyl and the $R^c$ is an optionally substituted $C_1$-$C_3$ alkylene chain. Another embodiment provides the compound of Formula (Ib), or a pharmaceutically acceptable salt thereof, wherein Z is an optionally substituted —O-heterocyclyl-alkyl and the heterocyclylalkyl group has the formula —$R^c$-heterocyclyl and the $R^c$ is an optionally substituted $C_1$ alkylene chain.

Another embodiment provides the compound of Formula (Ib), or a pharmaceutically acceptable salt thereof, wherein Z is an optionally substituted —O-heterocyclylalkyl and the heterocyclylalkyl group has the formula —$R^c$-heterocyclyl and the heterocyclyl is an optionally substituted nitrogen-containing 4-, 5-, 6-, or 7-membered heterocyclyl.

Another embodiment provides the compound of Formula (Ib), or a pharmaceutically acceptable salt thereof, wherein Z is an optionally substituted —N(H)-heterocyclylalkyl and the heterocyclylalkyl group has the formula —$R^c$-heterocyclyl and the $R^c$ is an optionally substituted $C_1$-$C_3$ alkylene chain. Another embodiment provides the compound of Formula (Ib), or a pharmaceutically acceptable salt thereof, wherein Z is an optionally substituted —N(H)-heterocyclylalkyl and the heterocyclylalkyl group has the formula —$R^c$-heterocyclyl and the $R^c$ is an optionally substituted $C_1$ alkylene chain.

Another embodiment provides the compound of Formula (Ib), or a pharmaceutically acceptable salt thereof, wherein Z is an optionally substituted —N(H)-heterocyclylalkyl and the heterocyclylalkyl group has the formula —$R^c$-heterocyclyl and the heterocyclyl is an optionally substituted nitrogen-containing 4-, 5-, 6-, or 7-membered heterocyclyl.

Another embodiment provides the compound of Formula (Ib), or a pharmaceutically acceptable salt thereof, wherein Z is an optionally substituted —N(Me)-heterocyclylalkyl and the heterocyclylalkyl group has the formula —$R^c$-heterocyclyl and the $R^c$ is an optionally substituted $C_1$-$C_3$ alkylene chain. Another embodiment provides the compound of Formula (Ib), or a pharmaceutically acceptable salt thereof, wherein Z is an optionally substituted —N(Me)-hetero-cyclylalkyl and the heterocyclylalkyl group has the formula —$R^c$-heterocyclyl and the $R^c$ is an optionally substituted $C_1$ alkylene chain.

Another embodiment provides the compound of Formula (Ib), or a pharmaceutically acceptable salt thereof, wherein Z is an optionally substituted —N(Me)-heterocyclylalkyl and the heterocyclylalkyl group has the formula —$R^c$-heterocyclyl and the heterocyclyl is an optionally substituted nitrogen-containing 4-, 5-, 6-, or 7-membered heterocyclyl.

Another embodiment provides the compound of Formula (Ib), or a pharmaceutically acceptable salt thereof, wherein Z is an optionally substituted N-heterocyclyl. Another embodiment provides the compound of Formula (Ib), or a pharmaceutically acceptable salt thereof, wherein Z is a 4-, 5-, 6-, or 7-membered N-heterocyclyl. Another embodiment provides the compound of Formula (Ib), or a pharmaceutically acceptable salt thereof, wherein Z is a 6-membered N-heterocyclyl. Another embodiment provides the compound of Formula (Ib), or a pharmaceutically acceptable salt thereof, wherein Z is an optionally substituted piperidine.

Another embodiment provides the compound of Formula (Ib), or a pharmaceutically acceptable salt thereof, wherein Z is an optionally substituted 4-aminopiperidine.

In some embodiments, the substituted heterocyclic derivative compound described in Formula (I), (Ia), or (Ib) has a structure provided in Table 1.

TABLE 1

| Chemical Synthesis Example | Structure | Name |
|---|---|---|
| 1 | 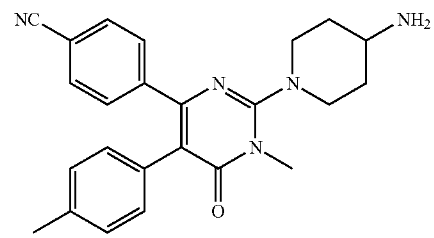 | 4-(2-(4-aminopiperidin-1-yl)-1-methyl-6-oxo-5-p-tolyl-1,6-dihydropyrimidin-4-yl)-benzonitrile |
| 2 | 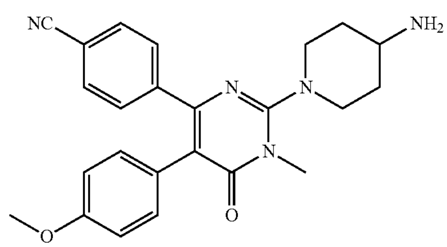 [SMILES: COc1ccc(-c2c(-c3ccc(C#N)cc3)nc(N3CCC(N)CC3)n(C)c2=O)cc1] | 4-[2-(4-amino-piperidin-1-yl)-5-(4-methoxyphenyl)-1-methyl-6-oxo-1,6-dihydro-pyrimidin-4-yl]-benzonitrile |
| 3 | 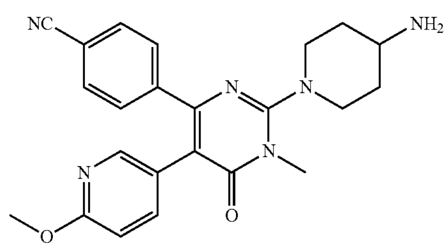 | 4-[2-(4-amino-piperidin-1-yl)-5-(6-methoxypyridin-3-yl)-1-methyl-6-oxo-1,6-dihydro-pyrimidin-4-yl]-benzonitrile |
| 4 | 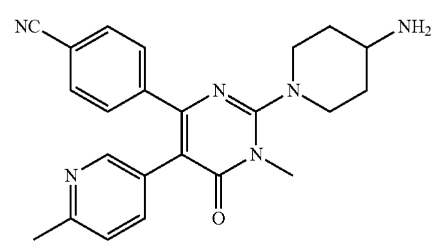 | 4-[2-(4-amino-piperidin-1-yl)-1-methyl-5-(6-methylpyridin-3-yl)-6-oxo-1,6-dihydro-pyrimidin-4-yl]-benzonitrile |
| 5 | 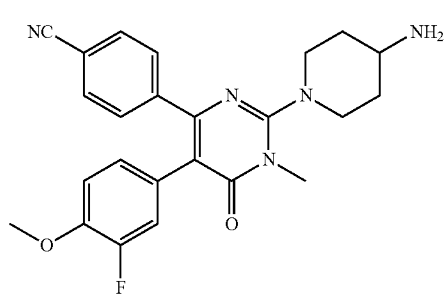 [SMILES: COc1ccc(-c2c(-c3ccc(C#N)cc3)nc(N3CCC(N)CC3)n(C)c2=O)cc1F] | 4-[2-(4-amino-piperidin-1-yl)-5-(4-methoxyphenyl)-1-methyl-6-oxo-1,6-dihydropyrimidin-4-yl]-benzonitrile |

TABLE 1-continued

| Chemical Synthesis Example | Structure | Name |
|---|---|---|
| 6 | 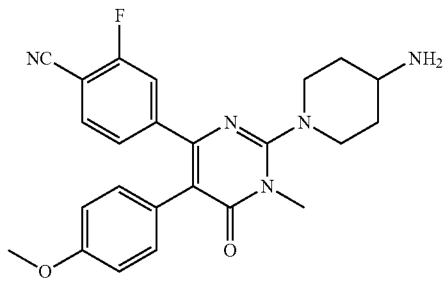 | 4-[2-(4-amino-piperidin-1-yl)-5-(4-methoxyphenyl)-1-methyl-6-oxo-1,6-dihydro-pyrimidin-4-yl]-2-fluorobenzonitrile |
| 7 | 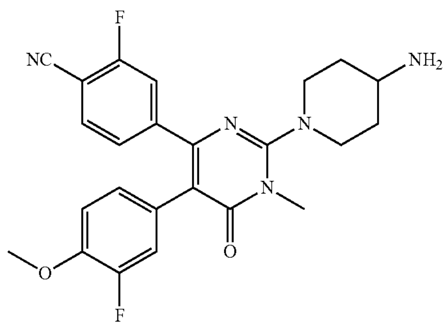 [SMILES: COc1ccc(-c2c(-c3ccc(C#N)c(F)c3)nc(N3CCC(N)CC3)n(C)c2=O)cc1F] | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile |
| 8 | 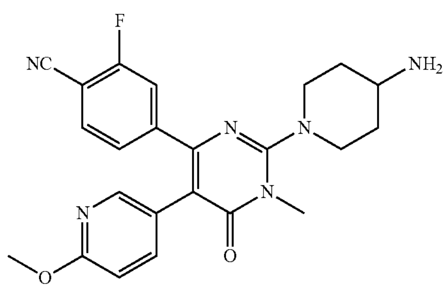 | 4[2-(4-amino-piperidin-1-yl)-5-(6-methoxypyridin-3-yl)-1-methyl-6-oxo-1,6-dihydro-pyrimidin-4-yl]-2-fluoro-benzonitrile |
| 9 | 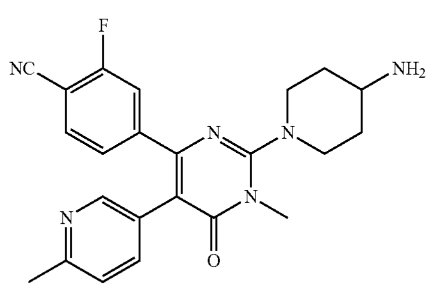 [SMILES: Cc1ccc(-c2c(-c3ccc(C#N)c(F)c3)nc(N3CCC(N)CC3)n(C)c2=O)cn1] | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile |
| 10 | 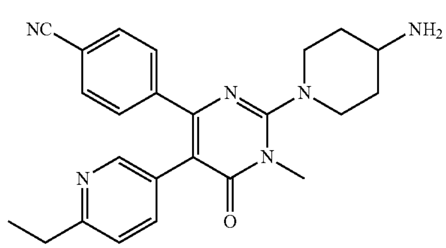 [SMILES: CCc1ccc(-c2c(-c3ccc(C#N)cc3)nc(N3CCC(N)CC3)n(C)c2=O)cn1] | 4-[2-(4-amino-piperidin-1-yl)-5-(6-ethyl-pyridin-3-yl)-1-methyl-6-oxo-1,6-dihydro-pyrimidin-4-yl]-benzonitrile |

TABLE 1-continued

| Chemical Synthesis Example | Structure | Name |
|---|---|---|
| 11 | 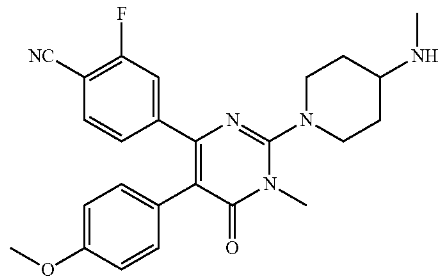 | 2-fluoro-4-[5-(4-methoxy-phenyl)-1-methyl-2-(4-methylamino-piperidin-1-yl)-6-oxo-1,6-dihydro-pyrimidin-4-yl]-benzonitrile |
| 12 | 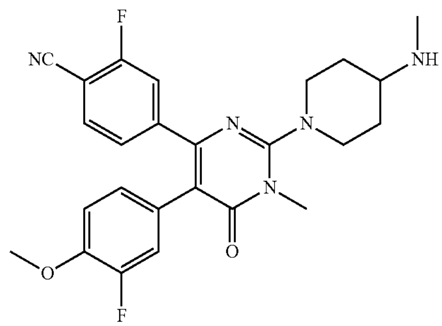 | 2-fluoro-4-[5-(3-fluoro-4-methoxy-phenyl)-1-methyl-2-(4-methylamino-piperidin-1-yl)-6-oxo-1,6-dihydro-pyrimidin-4-yl]-benzonitrile |
| 13 | 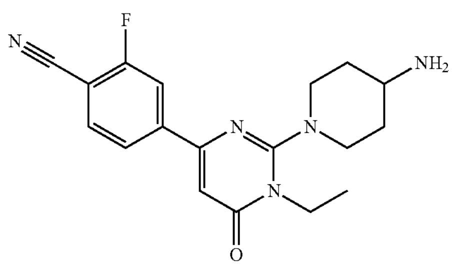 [SMILES: CCn1c(N2CCC(N)CC2)nc(-c2ccc(C#N)c(F)c2)cc1=O] | 4-[2-(4-amino-piperidin-1-yl)-1-ethyl-6-oxo-1,6-dihydro-pyrimidin-4-yl]-2-fluoro-benzonitrile |
| 14 | 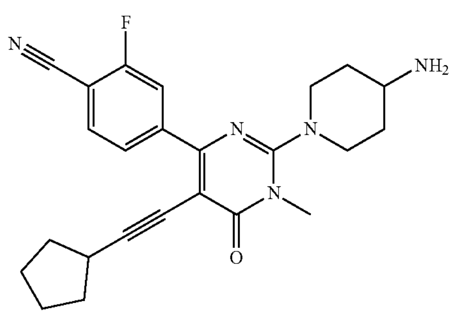 [SMILES: Cn1c(N2CCC(N)CC2)nc(-c2ccc(C#N)c(F)c2)c(C#CC2CCCC2)c1=O] | 4-[2-(4-amino-piperidin-1-yl)-5-cyclopentylethynyl-1-methyl-6-oxo-1,6-dihydro-pyrimidin-4-yl]-2-fluoro-benzonitrile |
| 15 | 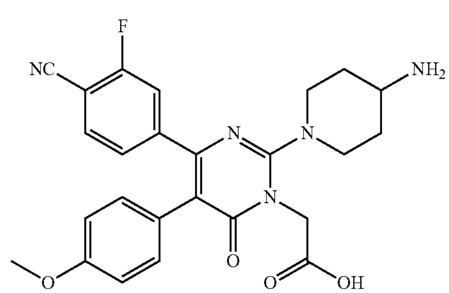 [SMILES: COc1ccc(-c2c(-c3ccc(C#N)c(F)c3)nc(N3CCC(N)CC3)n(CC(=O)O)c2=O)cc1] | [2-(4-amino-piperidin-1-yl)-4-(4-cyano-3-fluoro-phenyl)-5-(4-methoxy-phenyl)-6-oxo-6H-pyrimidin-1-yl]-acetic acid |

TABLE 1-continued

| Chemical Synthesis Example | Structure | Name |
|---|---|---|
| 16 | 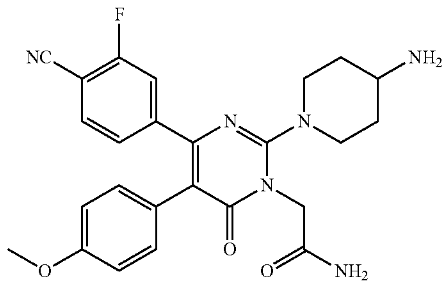 [SMILES: COc1ccc(-c2c(-c3ccc(C#N)c(F)c3)nc(N3CCC(N)CC3)n(CC(N)=O)c2=O)cc1] | 2-[2-(4-amino-piperidin-1-yl)-4-(4-cyano-3-fluoro-phenyl)-5-(4-methoxy-phenyl)-6-oxo-6H-pyrimidin-1-yl]-acetamide |
| 17 | 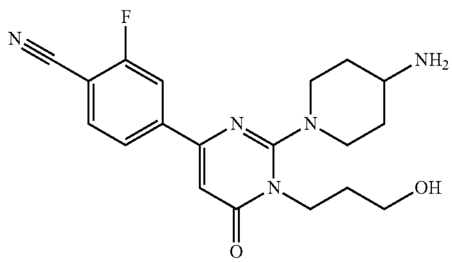 [SMILES: N#Cc1ccc(-c2cc(=O)n(CCCO)c(N3CCC(N)CC3)n2)cc1F] | 4-[2-(4-amino-piperidin-1-yl)-1-(3-hydroxy-propyl)-6-oxo-1,6-dihydro-pyrimidin-4-yl]-2-fluoro-benzonitrile |
| 18 | 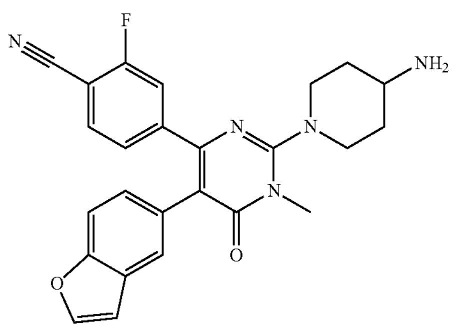 [SMILES: Cn1c(N2CCC(N)CC2)nc(-c2ccc(C#N)c(F)c2)c(-c2ccc3occc3c2)c1=O] | 4-[2-(4-amino-piperidin-1-yl)-5-benzofuran-5-yl-1-methyl-6-oxo-1,6-dihydro-pyrimidin-4-yl]-2-fluoro-benzonitrile |
| 19 | 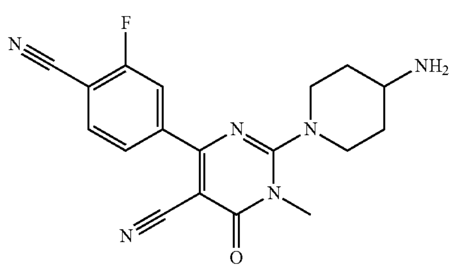 [SMILES: Cn1c(N2CCC(N)CC2)nc(-c2ccc(C#N)c(F)c2)c(C#N)c1=O] | 2-(4-amino-piperidin-1-yl)-4-(4-cyano-3-fluoro-phenyl)-1-methyl-6-oxo-1,6-dihydro-pyrimidine-5-carbonitrile |
| 20 | 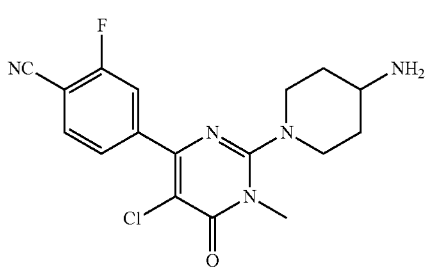 [SMILES: Cn1c(N2CCC(N)CC2)nc(-c2ccc(C#N)c(F)c2)c(Cl)c1=O] | 4-[2-(4-aminopiperidin-1-yl)-5-chloro-1-methyl-6-oxopyrimidin-4-yl]-2-fluorobenzonitrile |

TABLE 1-continued

| Chemical Synthesis Example | Structure | Name |
|---|---|---|
| 21 | 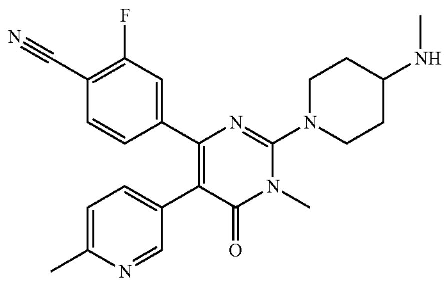 [SMILES: CNC1CCN(c2nc(-c3ccc(C#N)c(F)c3)c(-c3ccc(C)nc3)c(=O)n2C)CC1] | 2-fluoro-4-[1-methyl-2-(4-methylamino-piperidin-1-yl)-5-(6-methyl-pyridin-3-yl)-6-oxo-1,6-dihydro-pyrimidin-4-yl]-benzonitrile |
| 22 | 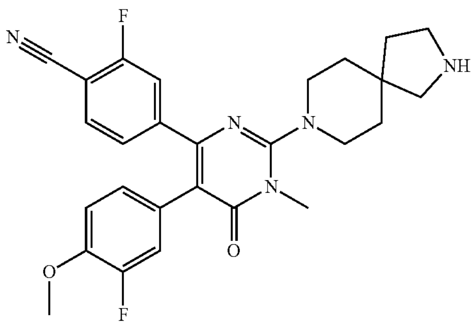 [SMILES: COc1ccc(-c2c(-c3ccc(C#N)c(F)c3)nc(N3CCC4(CCNC4)CC3)n(C)c2=O)cc1F] | 4-[2-(2,8-diaza-spiro[4.5]dec-8-yl)-5-(3-fluoro-4-methoxy-phenyl)-1-methyl-6-oxo-1,6-dihydro-pyrimidin-4-yl]-2-fluorobenzonitrile |
| 23 | 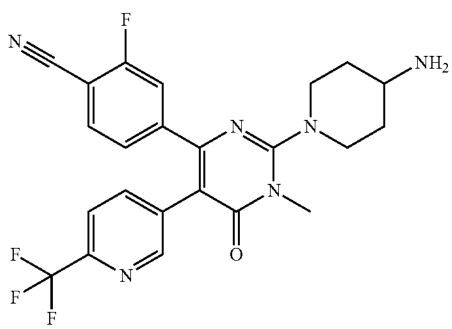 [SMILES: Cn1c(N2CCC(N)CC2)nc(-c2ccc(C#N)c(F)c2)c(-c2ccc(C(F)(F)F)nc2)c1=O] | 4-{2-(4-aminopiperidyl)-1-methyl-6-oxo-5-[6-(trifluoromethyl) (3-pyridyl)]hydropyrimidin-4-yl}-2-fluorobenzenecarbonitrile |
| 24 | 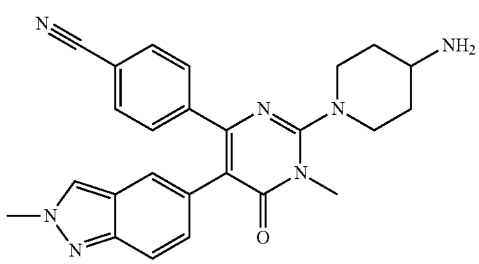 [SMILES: Cn1cc2cc(-c3c(-c4ccc(C#N)cc4)nc(N4CCC(N)CC4)n(C)c3=O)ccc2n1] | 4-[2-(4-aminopiperidyl)-1-methyl-5-(2-methyl(2H-indazol-5-yl))-6-oxohydropyrimidin-4-yl]benzenecarbonitrile |
| 25 | 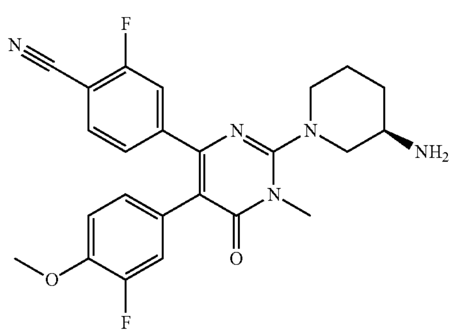 [SMILES: COc1ccc(-c2c(-c3ccc(C#N)c(F)c3)nc(N3CCC[C@@H](N)C3)n(C)c2=O)cc1F] | 4-[2-((3R)-3-aminopiperidyl)-5-(3-fluoro-4-methoxyphenyl)-1-methyl-6-oxohydropyrimidin-4-yl]-2-fluorobenzenecarbonitrile |

TABLE 1-continued

| Chemical Synthesis Example | Structure | Name |
|---|---|---|
| 26 | 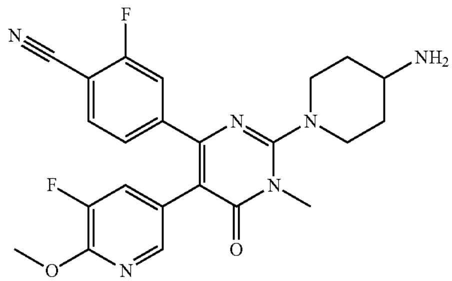 [SMILES: COc1ncc(-c2c(-c3ccc(C#N)c(F)c3)nc(N3CCC(N)CC3)n(C)c2=O)cc1F] | 4-[2-(4-aminopiperidyl)-5-(5-fluoro-6-methoxy(3-5,6-dihydropyridyl))-1-methyl-6-oxohydropyrimidin-4-yl]-2-fluorobenzenecarbonitrile |
| 27 | 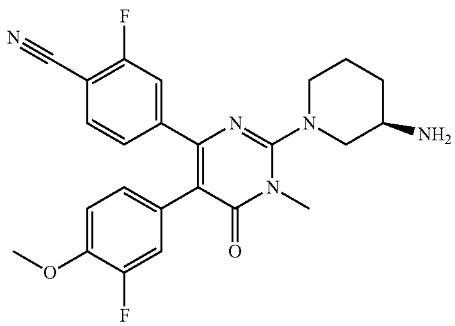 [SMILES: COc1ccc(-c2c(-c3ccc(C#N)c(F)c3)nc(N3CCC[C@@H](N)C3)n(C)c2=O)cc1F] | 4-[2-((3R)-3-aminopyrrolidinyl)-5-(3-fluoro-4-methoxyphenyl)-1-methyl-6-oxohydropyrimidin-4-yl]-2-fluorobenzenecarbonitrile |
| 28 | 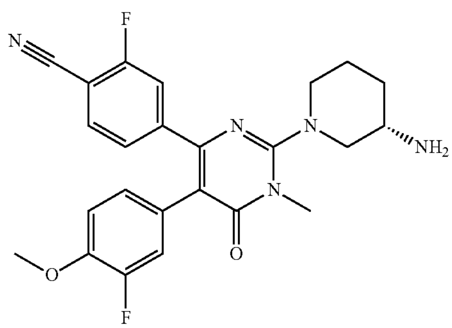 [SMILES: COc1ccc(-c2c(-c3ccc(C#N)c(F)c3)nc(N3CCC[C@H](N)C3)n(C)c2=O)cc1F] | 4-[2-((3S)-3-amino-piperidin-1-yl)-5-(3-fluoro-4-methoxy-phenyl)-1-methyl-6-oxo-1,6-dihydro-pyrimidin-4-yl]-2-fluoro-benzonitrile |
| 29 | 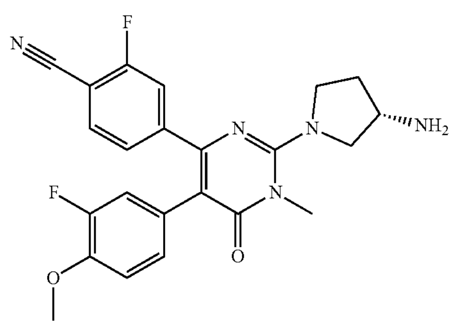 [SMILES: COc1ccc(-c2c(-c3ccc(C#N)c(F)c3)nc(N3CC[C@H](N)C3)n(C)c2=O)cc1F] | 4-[2-((3S)-3-amino-pyrrolidin-1-yl)-5-(3-fluoro-4-methoxy-phenyl)-1-methyl-6-oxo-1,6-dihydro-pyrimidin-4-yl]-2-fluoro-benzonitrile |
| 30 | 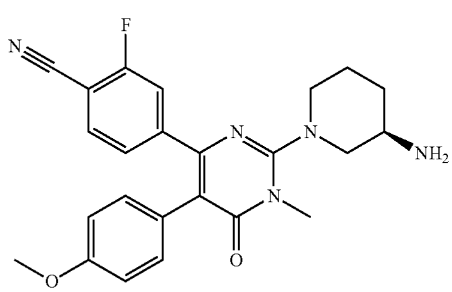 [SMILES: COc1ccc(-c2c(-c3ccc(C#N)c(F)c3)nc(N3CCC[C@@H](N)C3)n(C)c2=O)cc1] | 4-[2-((3R)-3-aminopiperidyl)-5-(4-methoxyphenyl)-1-methyl-6-oxohydro-pyrimidin-4-yl]-2-fluorobenzenecarbonitrile |

TABLE 1-continued

| Chemical Synthesis Example | Structure | Name |
|---|---|---|
| 31 | 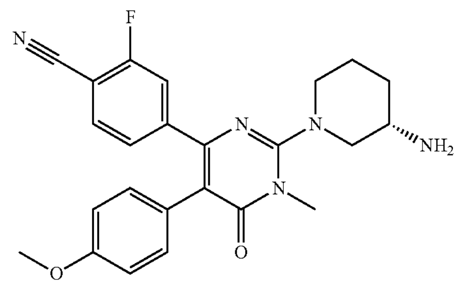 [SMILES: COc1ccc(-c2c(-c3ccc(C#N)c(F)c3)nc(N3CCC[C@H](N)C3)n(C)c2=O)cc1] | 4-[2-((3S)-3-amino-piperidin-1-yl)-5-(4-methoxy-phenyl)-1-methyl-6-oxo-1,6-dihydro-pyrimidin-4-yl]-2-fluoro-benzonitrile |
| 32 | 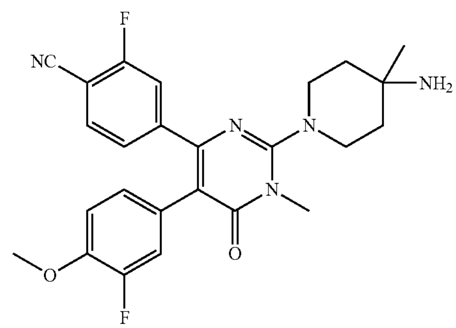 [SMILES: COc1ccc(-c2c(-c3ccc(C#N)c(F)c3)nc(N3CCC(C)(N)CC3)n(C)c2=O)cc1F] | 4-[2-(4-amino-4-methyl-piperidin-1-yl)-5-(3-fluoro-4-methoxy-phenyl)-1-methyl-6-oxo-1,6-dihydro-pyrimidin-4-yl]-2-fluoro-benzonitrie |
| 33 | 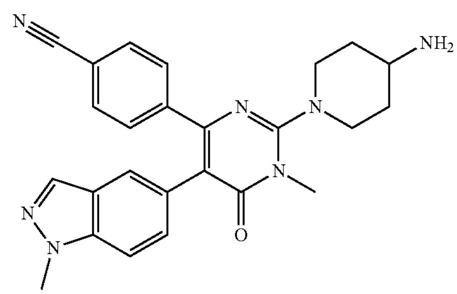 [SMILES: Cn1c(N2CCC(N)CC2)nc(-c2ccc(C#N)cc2)c(-c2ccc3c(cnn3C)c2)c1=O] | 4-[2-(4-aminopiperidyl)-1-methyl-5-(1-methyl(1H-indazol-5-yl))-6-oxohydropyrimidin-4-yl]benzenecarbonitrile |
| 34 | 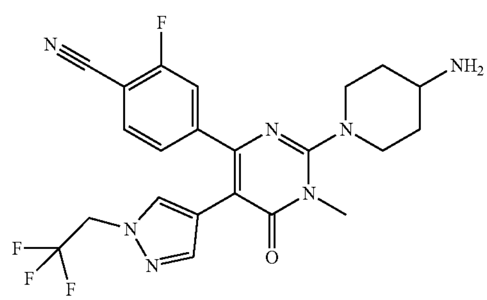 [SMILES: Cn1c(N2CCC(N)CC2)nc(-c2ccc(C#N)c(F)c2)c(-c2cnn(CC(F)(F)F)c2)c1=O] | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile |
| 35 | 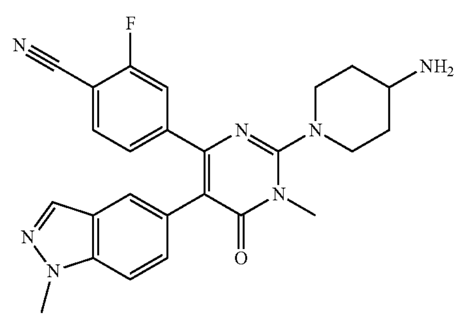 [SMILES: Cn1c(N2CCC(N)CC2)nc(-c2ccc(C#N)c(F)c2)c(-c2ccc3c(cnn3C)c2)c1=O] | 4-[2-(4-amino-piperidin-1-yl)-1-methyl-5-(1-methyl-1H-indazol-5-yl)-6-oxo-1,6-dihydro-pyrimidin-4-yl]-2-fluoro-benzonitrile |

TABLE 1-continued

| Chemical Synthesis Example | Structure | Name |
|---|---|---|
| 36 | 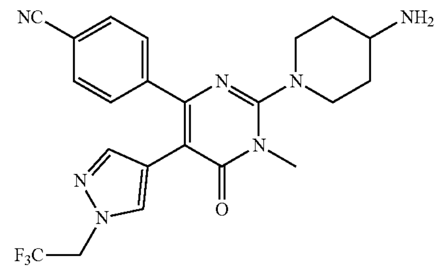 [SMILES: Cn1c(N2CCC(N)CC2)nc(-c2ccc(C#N)cc2)c(-c2cnn(CC(F)(F)F)c2)c1=O] | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-benzonitrile |
| 37 | 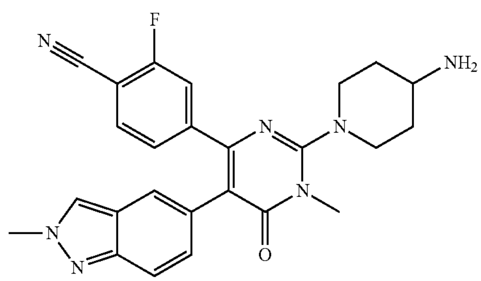 [SMILES: Cn1cc2cc(-c3c(-c4ccc(C#N)c(F)c4)nc(N4CCC(N)CC4)n(C)c3=O)ccc2n1] | 4-[2-(4-aminopiperidyl)-1-methyl-5-(2-methyl(2H-indazol-5-yl)) 6-oxohydropyrimidin-4-yl]-2-fluorobenzenecarbonitrile |
| 38 | 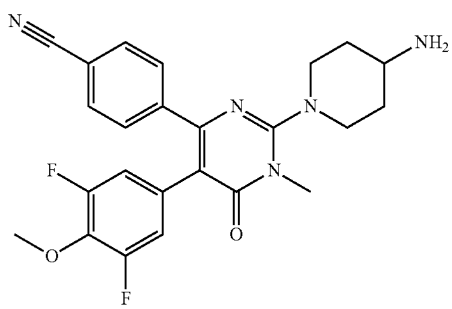 [SMILES: COc1c(F)cc(-c2c(-c3ccc(C#N)cc3)nc(N3CCC(N)CC3)n(C)c2=O)cc1F] | 4-[2-(4-aminopiperidyl)-5-(3,5-difluoro-4-methoxyphenyl)-1-methyl-6-oxohydropyrimidin-4-yl]benzenecarbonitrile |
| 39 | 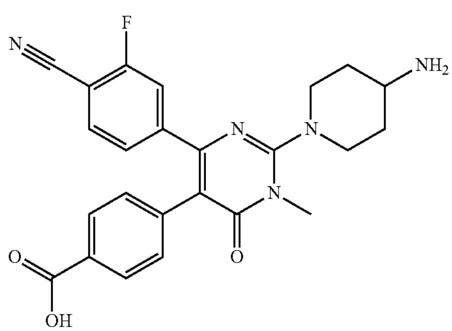 [SMILES: Cn1c(N2CCC(N)CC2)nc(-c2ccc(C#N)c(F)c2)c(-c2ccc(C(=O)O)cc2)c1=O] | 4-[2-(4-aminopiperidyl)-6-(4-cyano-3-fluorophenyl)-3-methyl-4-oxo-3-hydropyrimidin-5-yl] benzoic acid |
| 40 | 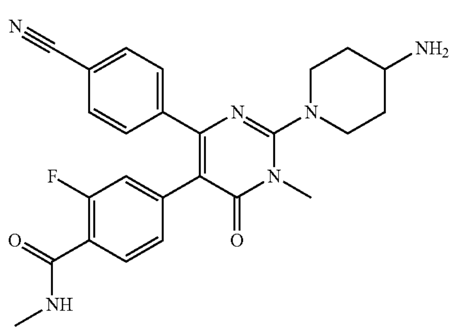 [SMILES: CNC(=O)c1ccc(-c2c(-c3ccc(C#N)cc3)nc(N3CCC(N)CC3)n(C)c2=O)cc1F] | {4-[2-(4-aminopiperidyl)-6-(4-cyanophenyl)-3-methyl-4-oxo (3-hydro pyrimidin-5-yl)]-2-fluorophenyl}-N-methylcarboxamide |

TABLE 1-continued

| Chemical Synthesis Example | Structure | Name |
|---|---|---|
| 41 | 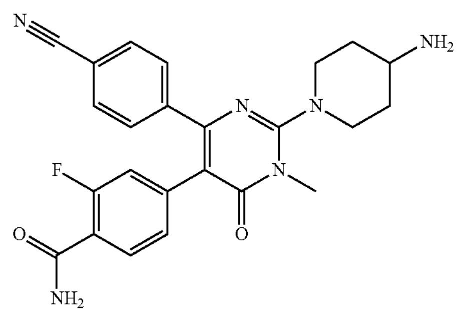 [SMILES: Cn1c(N2CCC(N)CC2)nc(-c2ccc(C#N)cc2)c(-c2ccc(C(N)=O)c(F)c2)c1=O] | 4-[2-(4-aminopiperidyl)-6-(4-cyanophenyl)-3-methyl-4-oxo(3-hydro pyrimidin-5-yl)]-2-fluorobenzamide |
| 42 | 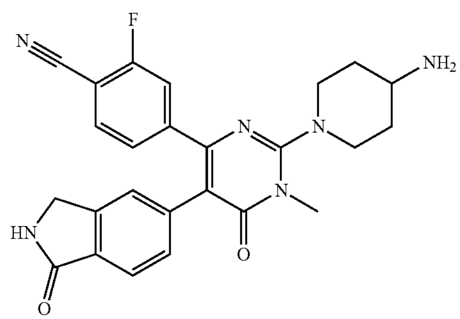 [SMILES: Cn1c(N2CCC(N)CC2)nc(-c2ccc(C#N)c(F)c2)c(-c2ccc3c(c2)CNC3=O)c1=O] | 4-[2-(4-amino-piperidin-1-yl)-1-methyl-6-oxo-5-(1-oxo-2,3-dihydro-1H-isoindol-5-yl)-1,6-dihydro-pyrimidin-4-yl]-2-fluoro-benzonitrile |
| 43 | 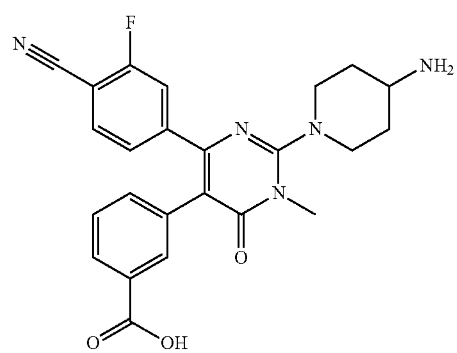 [SMILES: Cn1c(N2CCC(N)CC2)nc(-c2ccc(C#N)c(F)c2)c(-c2cccc(C(=O)O)c2)c1=O] | 3-[2-(4-amino-piperidin-1-yl)-4-(4-cyano-3-fluoro-phenyl)-1-methyl-6-oxo-1,6-dihydro-pyrimidin-5-yl]-benzoic acid |
| 44 | 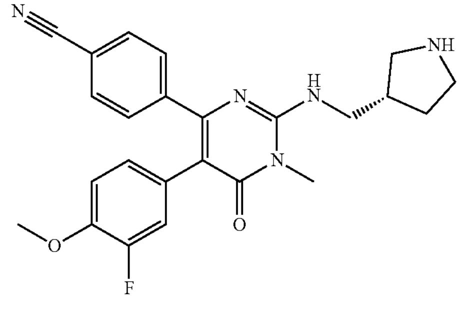 [SMILES: COc1ccc(-c2c(-c3ccc(C#N)cc3)nc(NC[C@H]3CCNC3)n(C)c2=O)cc1F] | 4-{5-(3-fluoro-4-methoxy-phenyl)-1-methyl-6-oxo-2-[(3S)-(pyrrolidin-3-ylmethyl)-amino]-1,6-dihydro-pyrimidin-4-yl}-benzonitrile |

TABLE 1-continued

| Chemical Synthesis Example | Structure | Name |
|---|---|---|
| 45 | 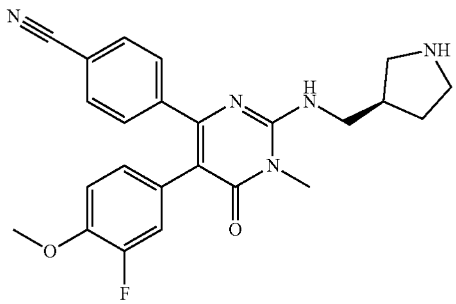 [SMILES: COc1ccc(-c2c(-c3ccc(C#N)cc3)nc(NC[C@@H]3CCNC3)n(C)c2=O)cc1F] | 4-{5-(3-fluoro-4-methoxy-phenyl)-1-methyl-6-oxo-2-[(3R)-(pyrrolidin-3-ylmethyl)-amino]-1,6-dihydro-pyrimidin-4-yl}-benzonitrile |
| 46 | 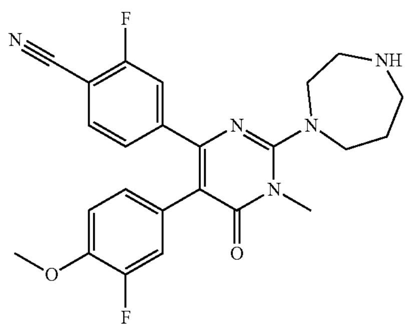 [SMILES: COc1ccc(-c2c(-c3ccc(C#N)c(F)c3)nc(N3CCCNCC3)n(C)c2=O)cc1F] | 4-[2-[1,4]diazepan-1-yl-5-(3-fluoro-4-methoxy-phenyl)-1-methyl-6-oxo-1,6-dihydro-pyrimidin-4-yl]-2-fluoro-benzonitrile |
| 47 | 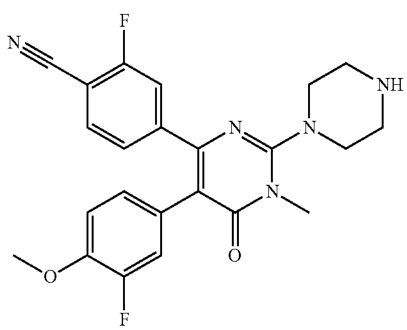 [SMILES: COc1ccc(-c2c(-c3ccc(C#N)c(F)c3)nc(N3CCNCC3)n(C)c2=O)cc1F] | 2-fluoro-4-[5-(3-fluoro-4-methoxy-phenyl)-1-methyl-6-oxo-2-piperazin-1-yl-1,6-dihydro-pyrimidin-4-yl]-benzonitrile |
| 48 | 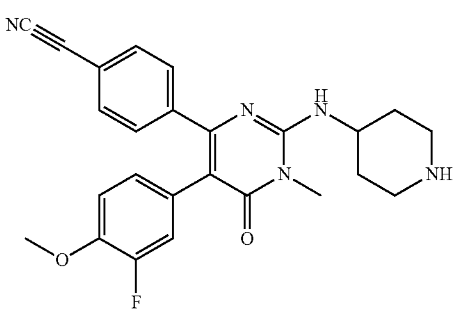 | 4-[5-(3-fluoro-4-methoxy-phenyl)-1-methyl-6-oxo-2-(piperidin-4-ylamino)-1,6-dihydro-pyrimidin-4-yl]-benzonitrile |

TABLE 1-continued

| Chemical Synthesis Example | Structure | Name |
|---|---|---|
| 49 | 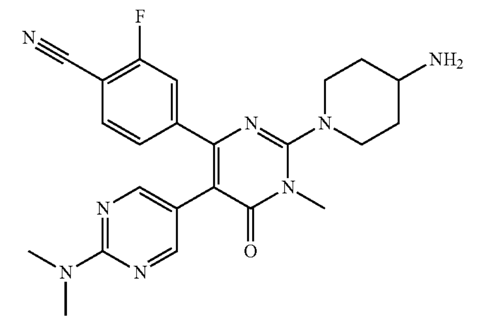 [SMILES: CN(C)c1ncc(-c2c(-c3ccc(C#N)c(F)c3)nc(N3CCC(N)CC3)n(C)c2=O)cn1] | 4-[2-(4-amino-piperidin-1-yl)-2'-dimethylamino-1-methyl-6-oxo-1,6-dihydro-[5,5']pyrimidinyl-4-yl]-2-fluoro-benzonitrile |
| 50 | 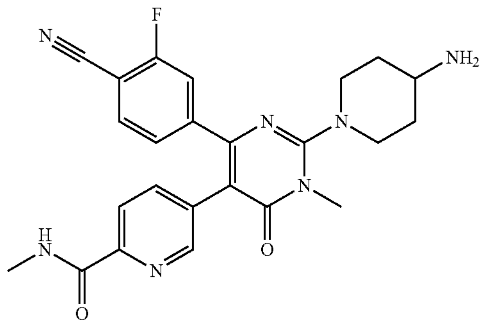 [SMILES: CNC(=O)c1ccc(-c2c(-c3ccc(C#N)c(F)c3)nc(N3CCC(N)CC3)n(C)c2=O)cn1] | 5-[2-(4-amino-piperidin-1-yl)-4-(4-cyano-3-fluoro-phenyl)-1-methyl-6-oxo-1,6-dihydro-pyrimidin-5-yl]-pyridine-2-carboxylic acid methylamide |
| 51 | 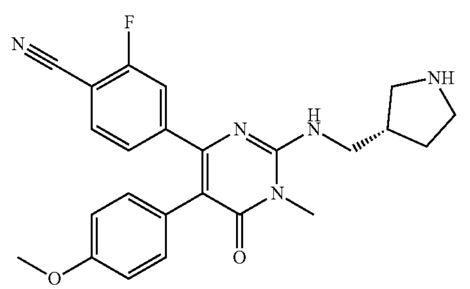 [SMILES: COc1ccc(-c2c(-c3ccc(C#N)c(F)c3)nc(NC[C@H]3CCNC3)n(C)c2=O)cc1] | 2-fluoro-4-{5-(4-methoxy-phenyl)-1-methyl-6-oxo-2-[(3S)-(pyrrolidin-3-ylmethyl)-amino]-1,6-dihydro-pyrimidin-4-yl}-benzonitrile |
| 52 | 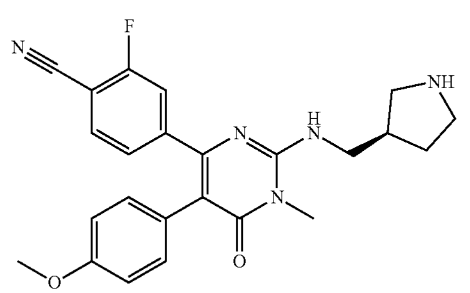 | 2-fluoro-4-{5-(4-methoxy-phenyl)-1-methyl-6-oxo-2-[(3R)-(pyrrolidin-3-ylmethyl)-amino]-1,6-dihydro-pyrimidin-4-yl}-benzonitrile |
| 53 | 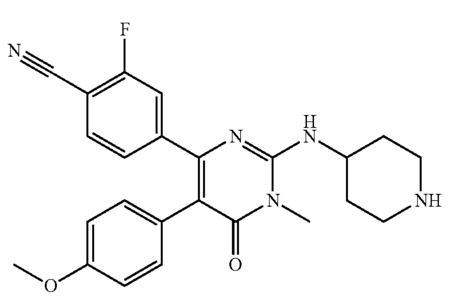 [SMILES: COc1ccc(-c2c(-c3ccc(C#N)c(F)c3)nc(NC3CCNCC3)n(C)c2=O)cc1] | 2-fluoro-4-[5-(4-methoxy-phenyl)-1-methyl-6-oxo-2-(piperidin-4-ylamino)-1,6-dihydro-pyrimidin-4-yl]-benzonitrile |

TABLE 1-continued

| Chemical Synthesis Example | Structure | Name |
|---|---|---|
| 54 | 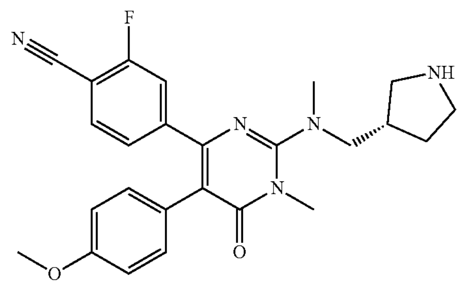 [SMILES: COc1ccc(-c2c(-c3ccc(C#N)c(F)c3)nc(N(C)C[C@H]3CCNC3)n(C)c2=O)cc1] | 2-fluoro-4-[5-(4-methoxy-phenyl)-1-methyl-2-(methyl-(3S)-pyrrolidin-3-ylmethyl-amino)-6-oxo-1,6-dihydro-pyrimidin-4-yl]-benzonitrile |
| 55 | 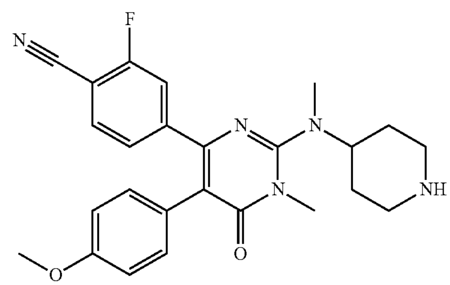 [SMILES: COc1ccc(-c2c(-c3ccc(C#N)c(F)c3)nc(N(C)C3CCNCC3)n(C)c2=O)cc1] | 2-fluoro-4-[5-(4-methoxy-phenyl)-1-methyl-2-(methyl-piperidin-4-yl-amino)-6-oxo-1,6-dihydro-pyrimidin-4-yl]-benzonitrile |
| 56 | 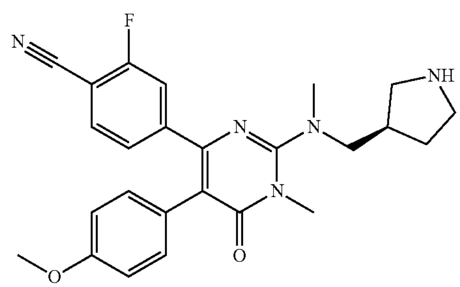 [SMILES: COc1ccc(-c2c(-c3ccc(C#N)c(F)c3)nc(N(C)C[C@@H]3CCNC3)n(C)c2=O)cc1] | 2-fluoro-4-[5-(4-methoxy-phenyl)-1-methyl-2-(methyl-pyrrolidin-3-ylmethyl-amino)-6-oxo-1,6-dihydro-pyrimidin-4-yl]-benzonitrile |
| 57 | 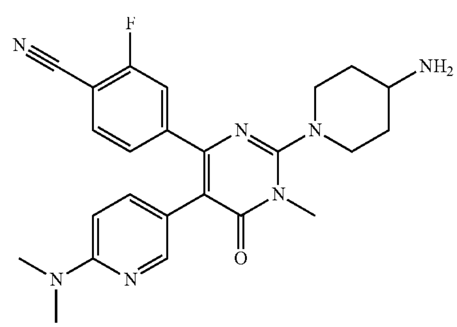 [SMILES: CN(C)c1ccc(-c2c(-c3ccc(C#N)c(F)c3)nc(N3CCC(N)CC3)n(C)c2=O)cn1] | 4-[2-(4-amino-piperidin-1-yl)-5-(6-dimethylamino-pyridin-3-yl)-1-methyl-6-oxo-1,6-dihydro-pyrimidin-4-yl]-2-fluoro-benzonitrile |
| 58 | 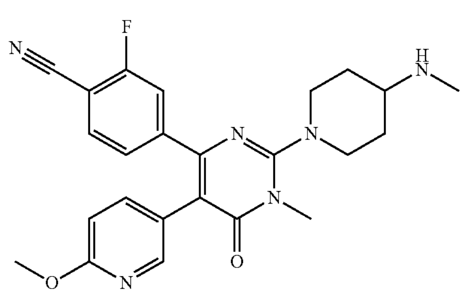 [SMILES: CNC1CCN(c2nc(-c3ccc(C#N)c(F)c3)c(-c3ccc(OC)nc3)c(=O)n2C)CC1] | 2-fluoro-4-[5-(6-methoxy-pyridin-3-yl)-1-methyl-2-(4-methylamino-piperidin-1-yl)-6-oxo-1,6-dihydro-pyrimidin-4-yl]-benzonitrile |

TABLE 1-continued

| Chemical Synthesis Example | Structure | Name |
|---|---|---|
| 59 | 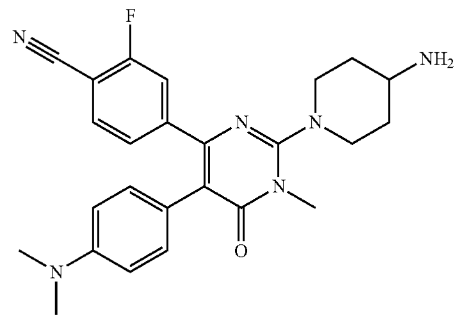 [SMILES: CN(C)c1ccc(-c2c(-c3ccc(C#N)c(F)c3)nc(N3CCC(N)CC3)n(C)c2=O)cc1] | 4-[2-(4-amino-piperidin-1-yl)-5-(4-dimethylamino-phenyl)-1-methyl-6-oxo-1,6-dihydro-pyrimidin-4-yl]-2-fluoro-benzonitrile |
| 60 | 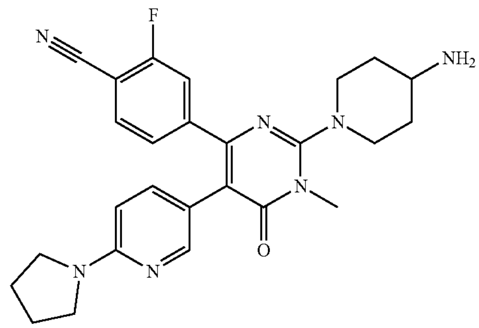 [SMILES: Cn1c(N2CCC(N)CC2)nc(-c2ccc(C#N)c(F)c2)c(-c2ccc(N3CCCC3)nc2)c1=O] | 4-[2-(4-amino-piperidin-1-yl)-1-methyl-6-oxo-5-(6-pyrrolidin-1-yl-pyridin-3-yl)-1,6-dihydro-pyrimidin-4-yl]-2-fluoro-benzonitrile |
| 61 | 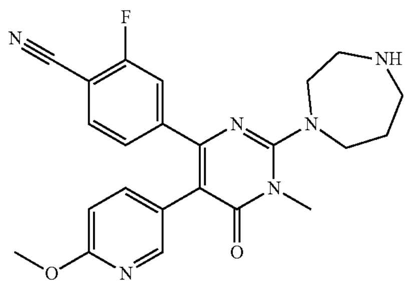 [SMILES: COc1ccc(-c2c(-c3ccc(C#N)c(F)c3)nc(N3CCCNCC3)n(C)c2=O)cn1] | 4-[2-[1,4]diazepan-1-yl-5-(6-methoxy-pyridin-3-yl)-1-methyl-6-oxo-1,6-dihydro-pyrimidin-4-yl]-2-fluoro benzonitrile |
| 62 | 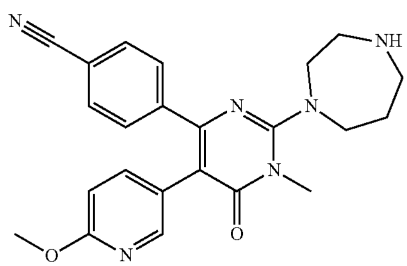 [SMILES: COc1ccc(-c2c(-c3ccc(C#N)cc3)nc(N3CCCNCC3)n(C)c2=O)cn1] | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile |
| 63 | 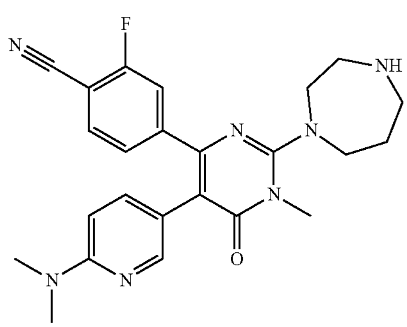 [SMILES: CN(C)c1ccc(-c2c(-c3ccc(C#N)c(F)c3)nc(N3CCCNCC3)n(C)c2=O)cn1] | 4-[2-[1,4]diazepan-1-yl-5-(6-dimethylamino-pyridin-3-yl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 64 | 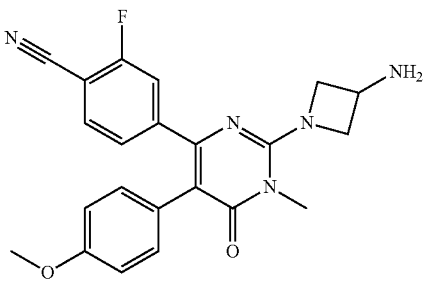 [SMILES: COc1ccc(-c2c(-c3ccc(C#N)c(F)c3)nc(N3CC(N)C3)n(C)c2=O)cc1] | 4-[2-(3-amino-azetidin-1-yl)-5-(4-methoxy-phenyl)-1-methyl-6-oxo-1,6-dihydro-pyrimidin-4-yl]-2-fluoro-benzonitrile |
| 65 | 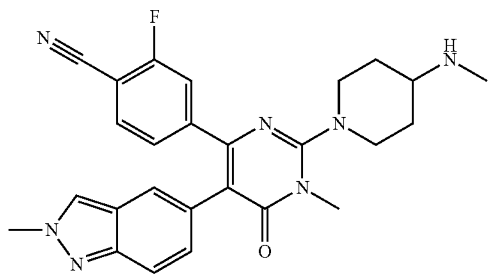 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile |
| 66 | 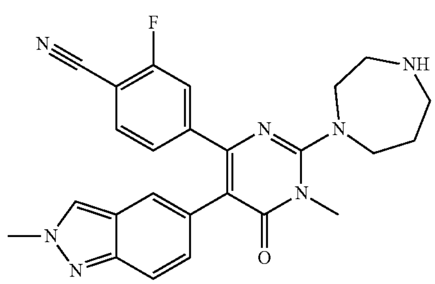 [SMILES: Cn1cc2cc(-c3c(-c4ccc(C#N)c(F)c4)nc(N4CCCNCC4)n(C)c3=O)ccc2n1] | 4-[2-[1,4]diazepan-1-yl-1-methyl-5-(2-methyl-2H-indazol-5-yl)-6-oxo-1,6-dihydro-pyrimidin-4-yl]-2-fluoro-benzonitrile |
| 67 | 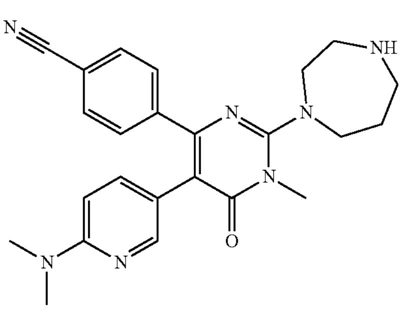 [SMILES: CN(C)c1ccc(-c2c(-c3ccc(C#N)cc3)nc(N3CCCNCC3)n(C)c2=O)cn1] | 4-[2-[1,4]diazepan-1-yl-5-(6-dimethylamino-pyridin-3-yl)-1-methyl-6-oxo-1,6-dihydro-pyrimidin-4-yl]-benzonitrile |
| 68 | 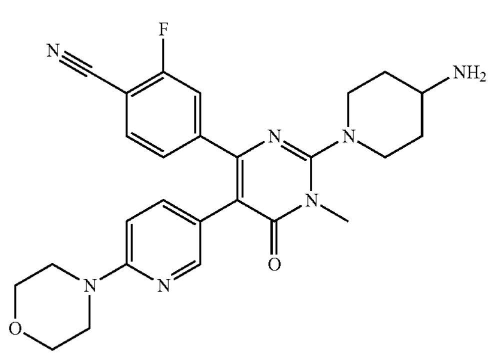 [SMILES: Cn1c(N2CCC(N)CC2)nc(-c2ccc(C#N)c(F)c2)c(-c2ccc(N3CCOCC3)nc2)c1=O] | 4-[2-(4-amino-piperidin-1-yl)-1-methyl-5-(6-morpholin-4-yl-pyridin-3-yl)-6-oxo-1,6-dihydro-pyrimidin-4-yl]-2-fluoro-benzonitrile |

TABLE 1-continued

| Chemical Synthesis Example | Structure | Name |
|---|---|---|
| 69 | 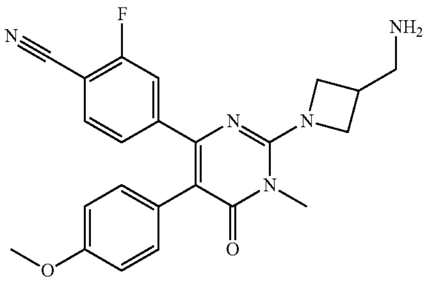 [SMILES: COc1ccc(-c2c(-c3ccc(C#N)c(F)c3)nc(N3CC(CN)C3)n(C)c2=O)cc1] | 4-[2-(3-aminomethyl-azetidin-1-yl)-5-(4-methoxy-phenyl)-1-methyl-6-oxo-1,6-dihydro-pyrimidin-4-yl]-2-fluoro-benzonitrile |
| 70 | 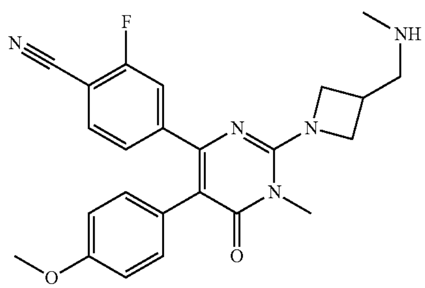 [SMILES: CNCC1CN(c2nc(-c3ccc(C#N)c(F)c3)c(-c3ccc(OC)cc3)c(=O)n2C)C1] | 2-fluoro-4-[5-(4-methoxy-phenyl)-1-methyl-2-(3-methylaminomethyl-azetidin-1-yl)-6-oxo-1,6-dihydro-pyrimidin-4-yl]-benzonitrile |
| 71 | 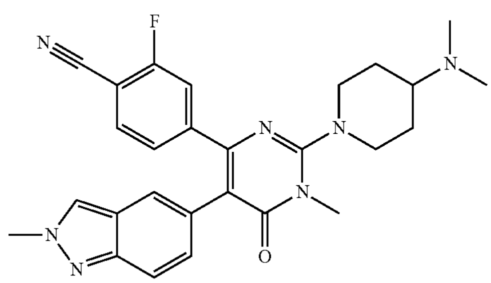 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile |
| 72 | 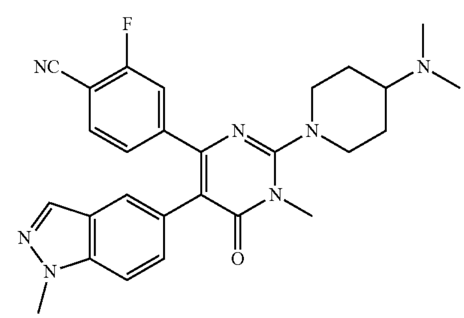 [SMILES: CN(C)C1CCN(c2nc(-c3ccc(C#N)c(F)c3)c(-c3ccc4c(cnn4C)c3)c(=O)n2C)CC1] | 4-[2-(4-dimethylamino-piperidin-1-yl)-1-methyl-5-(1-methyl-1H-indazol-5-yl)-6-oxo-1,6-dihydro-pyrimidin-4-yl]-2-fluoro-benzonitrile |
| 73 | 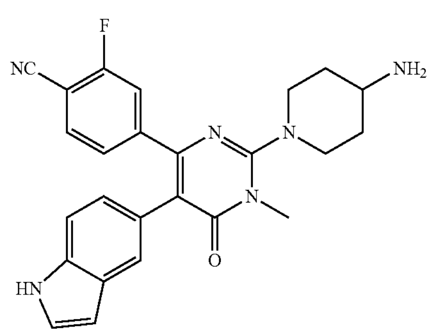 [SMILES: Cn1c(N2CCC(N)CC2)nc(-c2ccc(C#N)c(F)c2)c(-c2ccc3[nH]ccc3c2)c1=O] | 4-[2-(4-amino-piperidin-1-yl)-5-(1H-indol-5-yl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 74 | 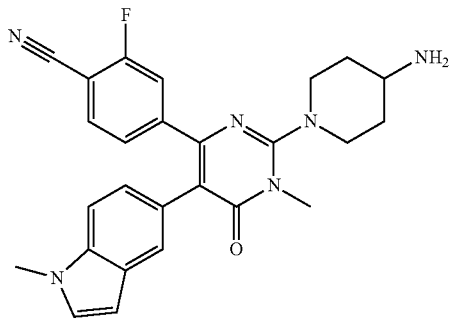 [SMILES: Cn1c(N2CCC(N)CC2)nc(-c2ccc(C#N)c(F)c2)c(-c2ccc3c(ccn3C)c2)c1=O] | 4-[2-(4-amino-piperidin-1-yl)-1-methyl-5-(1-methyl-1H-indol-5-yl)-6-oxo-1,6-dihydro-pyrimidin-4-yl]-2-fluoro-benzonitrile |
| 75 | 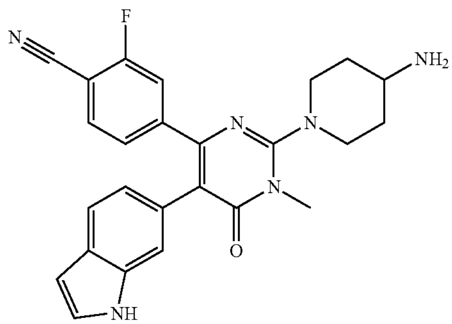 [SMILES: Cn1c(N2CCC(N)CC2)nc(-c2ccc(C#N)c(F)c2)c(-c2ccc3cc[nH]c3c2)c1=O] | 4-[2-(4-amino-piperidin-1-yl)-5-(1H-indol-6-yl)-1-methyl-6-oxo-1,6-dihydro-pyrimidin-4-yl]-2-fluoro-benzonitrile |
| 76 | 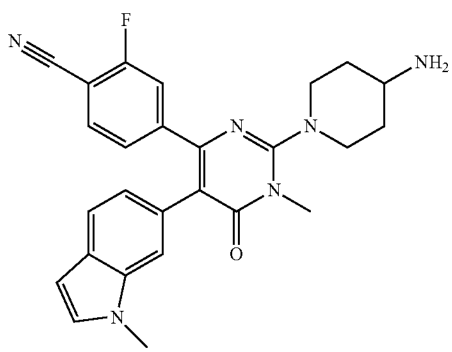 [SMILES: Cn1c(N2CCC(N)CC2)nc(-c2ccc(C#N)c(F)c2)c(-c2ccc3ccn(C)c3c2)c1=O] | 4-[2-(4-amino-piperidin-1-yl)-1-methyl-5-(1-methyl-1H-indol-6-yl)-6-oxo-1,6-dihydro-pyrimidin-4-yl]-2-fluoro-benzonitrile |
| 77 | 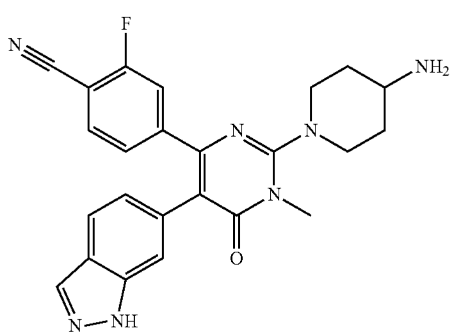 [SMILES: Cn1c(N2CCC(N)CC2)nc(-c2ccc(C#N)c(F)c2)c(-c2ccc3cn[nH]c3c2)c1=O] | 4-[2-(4-amino-piperidin-1-yl)-5-(1H-indazol-6-yl)-1-methyl-6-oxo-1,6-dihydro-pyrimidin-4-yl]-2-fluoro-benzonitrile |

TABLE 1-continued

| Chemical Synthesis Example | Structure | Name |
|---|---|---|
| 78 | 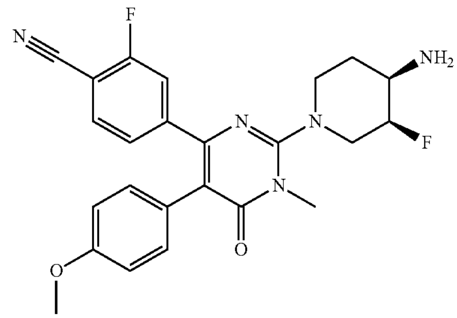 [SMILES: COc1ccc(-c2c(-c3ccc(C#N)c(F)c3)nc(N3CC[C@@H](N)[C@@H](F)C3)n(C)c2=O)cc1] | 4-[2-((4R,3S)-4-amino-3-fluoro-piperidin-1-yl)-5-(4-methoxy-phenyl)-1-methyl-6-oxo-1,6-dihydro-pyrimidin-4-yl]-2-fluoro-benzonitrile |
| 79 | 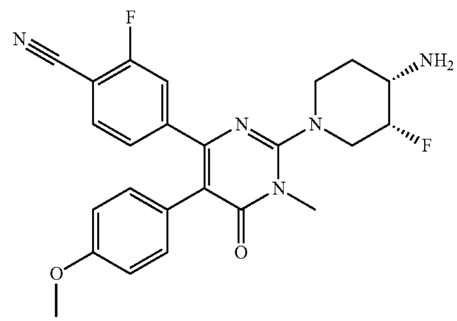 [SMILES: COc1ccc(-c2c(-c3ccc(C#N)c(F)c3)nc(N3CC[C@H](N)[C@H](F)C3)n(C)c2=O)cc1] | 4-[2-((4S,3R)-4-amino-3-fluoro-piperidin-1-yl)-5-(4-methoxy-phenyl)-1-methyl-6-oxo-1,6-dihydro-pyrimidin-4-yl]-2-fluoro-benzonitrile |
| 80 | 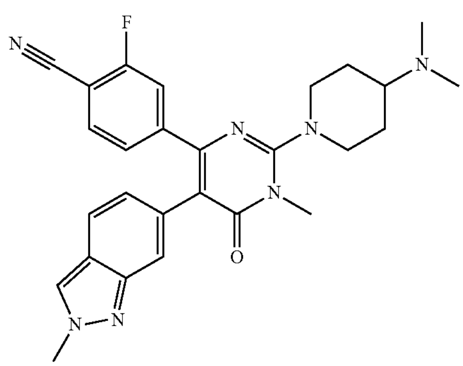 [SMILES: CN(C)C1CCN(c2nc(-c3ccc(C#N)c(F)c3)c(-c3ccc4cn(C)nc4c3)c(=O)n2C)CC1] | 4-[2-(4-dimethylamino-piperidin-1-yl)-1-methyl-5-(2-methyl-2H-indazol-6-yl)-6-oxo-1,6-dihydro-pyrimidin-4-yl]-2-fluoro-benzonitrile |
| 81 | 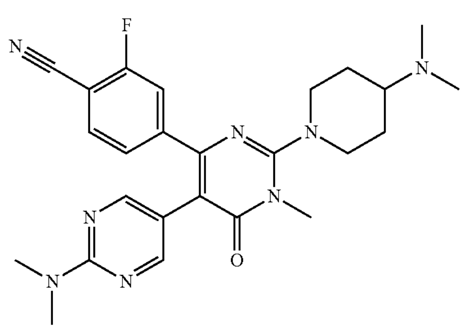 [SMILES: CN(C)c1ncc(-c2c(-c3ccc(C#N)c(F)c3)nc(N3CCC(N(C)C)CC3)n(C)c2=O)cn1] | 4-[2'-dimethylamino-2-(4-dimethylamino-piperidin-1-yl)-1-methyl-6-oxo-1,6-dihydro-[5,5']bipyrimidinyl-4-yl]-2-fluoro-benzonitrile |

TABLE 1-continued

| Chemical Synthesis Example | Structure | Name |
|---|---|---|
| 82 | 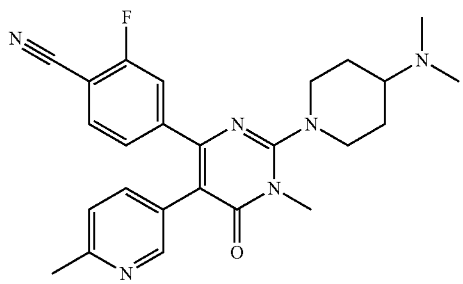 [SMILES: Cc1ccc(-c2c(-c3ccc(C#N)c(F)c3)nc(N3CCC(N(C)C)CC3)n(C)c2=O)cn1] | 4-[2-(4-dimethylamino-piperidin-1-yl)-1-methyl-5-(6-methyl-pyridin-3-yl)-6-oxo-1,6-dihydro-pyrimidin-4-yl]-2-fluoro-benzonitrile |
| 83 | 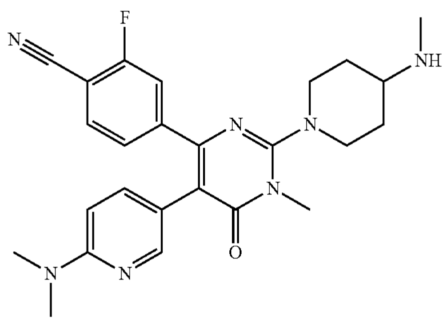 [SMILES: CNC1CCN(c2nc(-c3ccc(C#N)c(F)c3)c(-c3ccc(N(C)C)nc3)c(=O)n2C)CC1] | 4-[5-(6-dimethylamino-pyridin-3-yl)-1-methyl-2-(4-methylamino-piperidin-1-yl)-6-oxo-1,6-dihydro-pyrimidin-4-yl]-2-fluoro-benzonitrile |
| 84 | 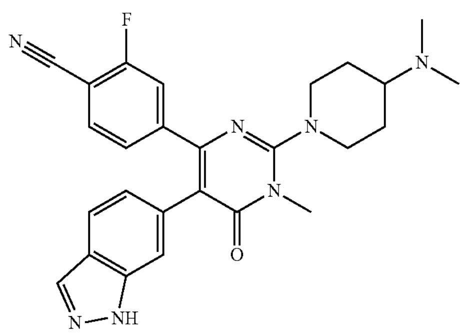 [SMILES: CN(C)C1CCN(c2nc(-c3ccc(C#N)c(F)c3)c(-c3ccc4cn[nH]c4c3)c(=O)n2C)CC1] | 4-[2-(4-dimethylamino-piperidin-1-yl)-5-(2H-indazol-6-yl)-1-methyl-6-oxo-1,6-dihydro-pyrimidin-4-yl]-2-fluoro-benzonitrile |
| 85 | 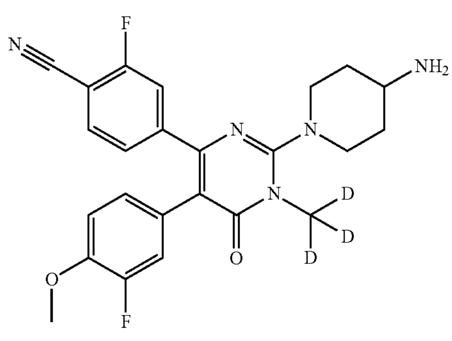 [SMILES: [2H]C([2H])([2H])n1c(N2CCC(N)CC2)nc(-c2ccc(C#N)c(F)c2)c(-c2ccc(OC)c(F)c2)c1=O] | 4-[2-(4-amino-piperidin-1-yl)-5-(3-fluoro-4-methoxy-phenyl)-1-deuteratedmethyl-6-oxo-1,6-dihydro-pyrimidin-4-yl]-2-fluoro-benzonitrile |

TABLE 1-continued

| Chemical Synthesis Example | Structure | Name |
|---|---|---|
| 86 | 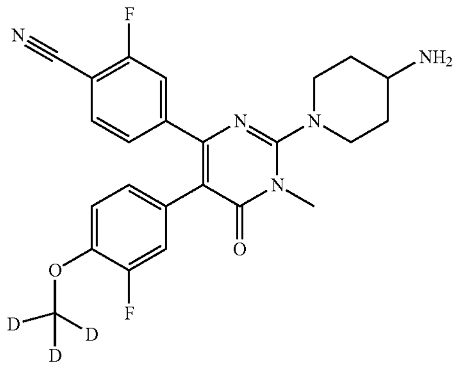 [SMILES: [2H]C([2H])([2H])Oc1ccc(-c2c(-c3ccc(C#N)c(F)c3)nc(N3CCC(N)CC3)n(C)c2=O)cc1F] | 4-[2-(4-amino-piperidin-1-yl)-5-(3-fluoro-4-deuteratedmethoxy-phenyl)-1-methyl-6-oxo-1,6-dihydro-pyrimidin-4-yl]-2-fluoro-benzonitrile |
| 87 | 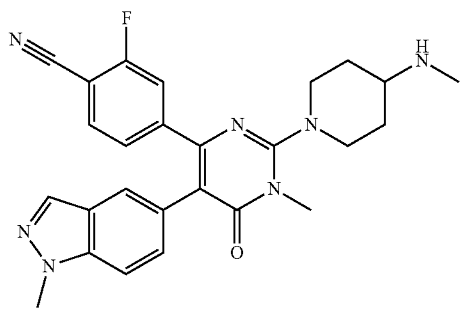 [SMILES: CNC1CCN(c2nc(-c3ccc(C#N)c(F)c3)c(-c3ccc4c(cnn4C)c3)c(=O)n2C)CC1] | 2-fluoro-4-[1-methyl-2-[4-(methylamino)piperidin-1-yl]-5-(1-methylindazol-5-yl)-6-oxopyrimidin-4-yl] benzonitrile |
| 88 | 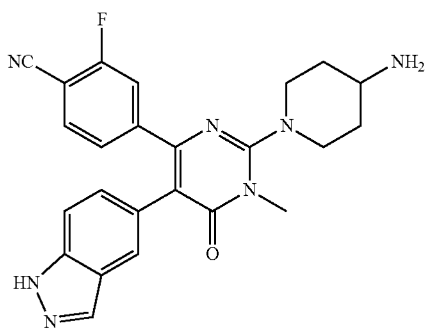 [SMILES: Cn1c(N2CCC(N)CC2)nc(-c2ccc(C#N)c(F)c2)c(-c2ccc3[nH]ncc3c2)c1=O] | 4-[2-(4-aminopiperidin-1-yl)-5-(1H-indazol-5-yl)-1-methyl-6-oxopyrimidin-4-yl]-2-fluorobenzonitrile |
| 89 | 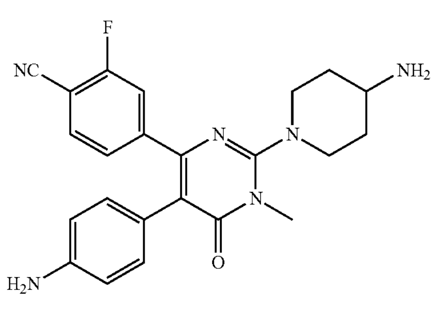 [SMILES: Cn1c(N2CCC(N)CC2)nc(-c2ccc(C#N)c(F)c2)c(-c2ccc(N)cc2)c1=O] | 4-[5-(4-aminophenyl)-2-(4-aminopiperidin-1-yl)-1-methyl-6-oxopyrimidin-4-yl]-2-fluorobenzonitrile |

TABLE 1-continued

| Chemical Synthesis Example | Structure | Name |
|---|---|---|
| 90 | 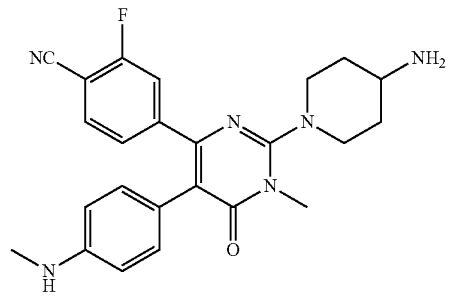 [SMILES: CNc1ccc(-c2c(-c3ccc(C#N)c(F)c3)nc(N3CCC(N)CC3)n(C)c2=O)cc1] | 4-[2-(4-aminopiperidin-1-yl)-1-methyl-5-[4-(methylamino)phenyl]-6-oxopyrimidin-4-yl]-2-fluorobenzonitrile |
| 91 | 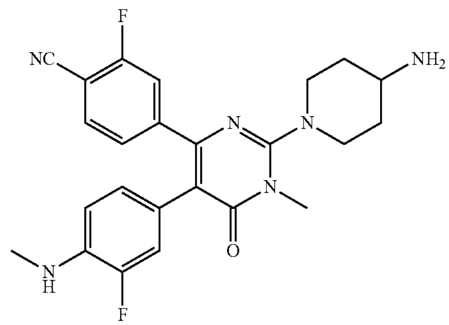 | 4-[2-(4-aminopiperidin-1-yl)-5-[3-fluoro-4-(methylamino)phenyl]-1-methyl-6-oxopyrimidin-4-yl]-2-fluorobenzonitrile |
| 92 | 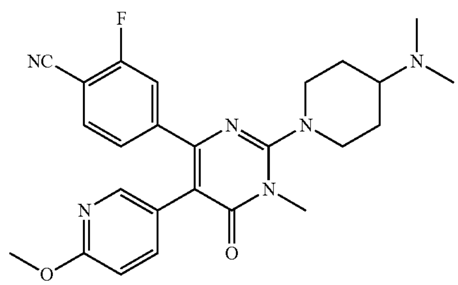 | 4-[2-[4-(dimethylamino)piperidin-1-yl]-5-(6-methoxypyridin-3-yl)-1-methyl-6-oxopyrimidin-4-yl]-2-fluorobenzonitrile |
| 93 | 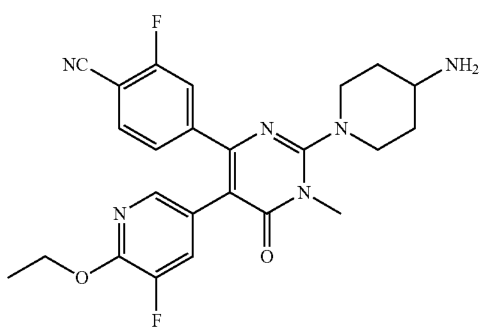 [SMILES: CCOc1ncc(-c2c(-c3ccc(C#N)c(F)c3)nc(N3CCC(N)CC3)n(C)c2=O)cc1F] | 4-[2-(4-aminopiperidin-1-yl)-5-(6-ethoxy-5-fluoropyridin-3-yl)-1-methyl-6-oxopyrimidin-4-yl]-2-fluorobenzonitrile |
| 94 | 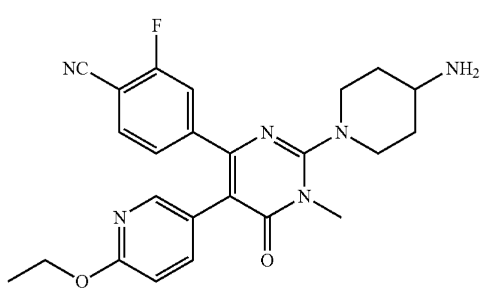 [SMILES: CCOc1ccc(-c2c(-c3ccc(C#N)c(F)c3)nc(N3CCC(N)CC3)n(C)c2=O)cn1] | 4-[2-(4-aminopiperidin-1-yl)-5-(6-ethoxypyridin-3-yl)-1-methyl-6-oxopyrimidin-4-yl]-2-fluorobenzonitrile |

TABLE 1-continued

| Chemical Synthesis Example | Structure | Name |
|---|---|---|
| 95 | 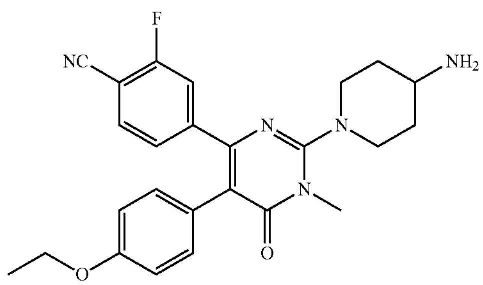 [SMILES: CCOc1ccc(-c2c(-c3ccc(C#N)c(F)c3)nc(N3CCC(N)CC3)n(C)c2=O)cc1] | 4-[2-(4-aminopiperidin-1-yl)-5-(4-ethoxyphenyl)-1-methyl-6-oxopyrimidin-4-yl]-2-fluorobenzonitrile |
| 96 | 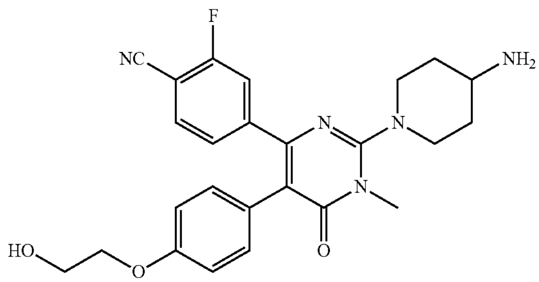 [SMILES: Cn1c(N2CCC(N)CC2)nc(-c2ccc(C#N)c(F)c2)c(-c2ccc(OCCO)cc2)c1=O] | 4-[2-(4-aminopiperidin-1-yl)-5-[4-(2-hydroxyethoxy)phenyl]-1-methyl-6-oxopyrimidin-4-yl]-2-fluorobenzonitrile |
| 97 | 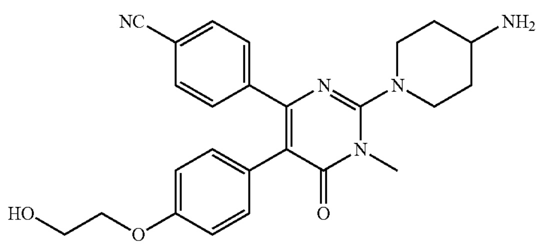 [SMILES: Cn1c(N2CCC(N)CC2)nc(-c2ccc(C#N)cc2)c(-c2ccc(OCCO)cc2)c1=O] | 4-[2-(4-aminopiperidin-1-yl)-5-[4-(2-hydroxyethoxy)phenyl]-1-methyl-6-oxopyrimidin-4-yl]benzonitrile |
| 98 | 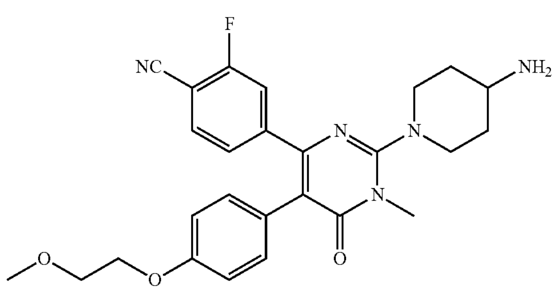 [SMILES: COCCOc1ccc(-c2c(-c3ccc(C#N)c(F)c3)nc(N3CCC(N)CC3)n(C)c2=O)cc1] | 4-[2-(4-aminopiperidin-1-yl)-5-[4-(2-methoxyethoxy)phenyl]-1-methyl-6-oxopyrimidin-4-yl]-2-fluorobenzonitrile |
| 99 | 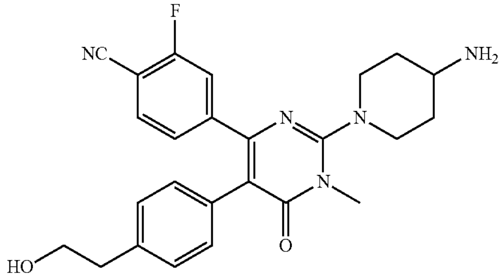 [SMILES: Cn1c(N2CCC(N)CC2)nc(-c2ccc(C#N)c(F)c2)c(-c2ccc(CCO)cc2)c1=O] | 4-[2-(4-aminopiperidin-1-yl)-5-[4-(2-hydroxyethyl)phenyl]-1-methyl-6-oxopyrimidin-4-yl]-2-fluorobenzonitrile |

TABLE 1-continued

| Chemical Synthesis Example | Structure | Name |
|---|---|---|
| 100 | 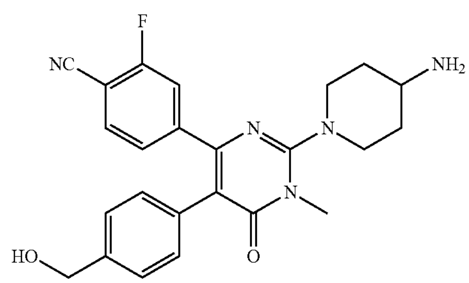 [SMILES: Cn1c(N2CCC(N)CC2)nc(-c2ccc(C#N)c(F)c2)c(-c2ccc(CO)cc2)c1=O] | 4-[2-(4-aminopiperidin-1-yl)-5-[4-(hydroxymethyl)phenyl]-1-methyl-6-oxopyrimidin-4-yl]-2-fluorobenzonitrile |
| 101 | 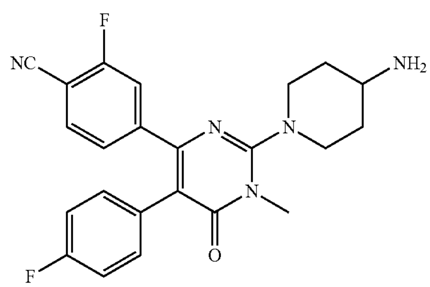 | 4-[2-(4-aminopiperidin-1-yl)-5-(4-fluorophenyl)-1-methyl-6-oxopyrimidin-4-yl]-2-fluorobenzonitrile |
| 102 | 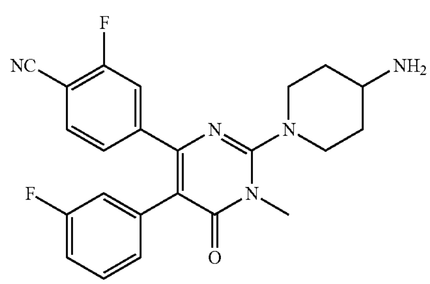 [SMILES: Cn1c(N2CCC(N)CC2)nc(-c2ccc(C#N)c(F)c2)c(-c2cccc(F)c2)c1=O] | 4-[2-(4-aminopiperidin-1-yl)-5-(3-fluorophenyl)-1-methyl-6-oxopyrimidin-4-yl]-2-fluorobenzonitrile |
| 103 | 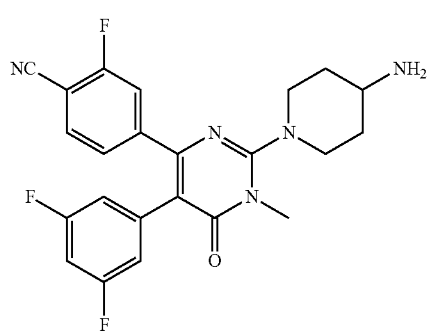 [SMILES: Cn1c(N2CCC(N)CC2)nc(-c2ccc(C#N)c(F)c2)c(-c2cc(F)cc(F)c2)c1=O] | 4-[2-(4-aminopiperidin-1-yl)-5-(3,5-difluorophenyl)-1-methyl-6-oxopyrimidin-4-yl]-2-fluorobenzonitrile |
| 104 | 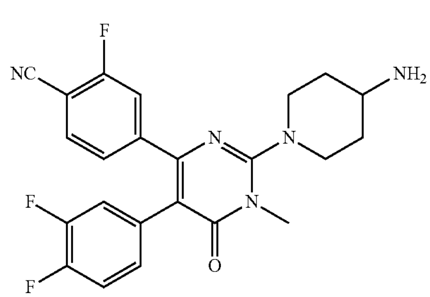 [SMILES: Cn1c(N2CCC(N)CC2)nc(-c2ccc(C#N)c(F)c2)c(-c2ccc(F)c(F)c2)c1=O] | 4-[2-(4-aminopiperidin-1-yl)-5-(3,4-difluorophenyl)-1-methyl-6-oxopyrimidin-4-yl]-2-fluorobenzonitrile |

TABLE 1-continued

| Chemical Synthesis Example | Structure | Name |
|---|---|---|
| 105 | 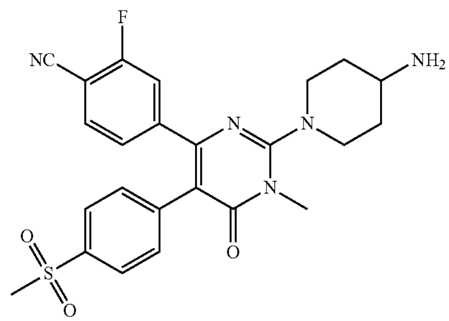 [SMILES: Cn1c(N2CCC(N)CC2)nc(-c2ccc(C#N)c(F)c2)c(-c2ccc(S(C)(=O)=O)cc2)c1=O] | 4-[2-(4-aminopiperidin-1-yl)-1-methyl-5-(4-methylsulfonylphenyl)-6-oxopyrimidin-4-yl]-2-fluorobenzonitrile |
| 106 | 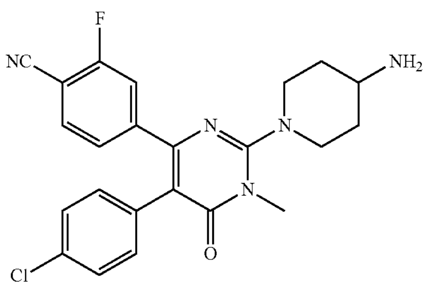 [SMILES: Cn1c(N2CCC(N)CC2)nc(-c2ccc(C#N)c(F)c2)c(-c2ccc(Cl)cc2)c1=O] | 4-[2-(4-aminopiperidin-1-yl)-5-(4-chlorophenyl)-1-methyl-6-oxopyrimidin-4-yl]-2-fluorobenzonitrile |
| 107 | 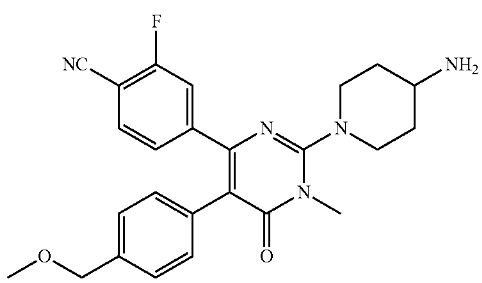 | 4-[2-(4-aminopiperidin-1-yl)-5-[4-(methoxymethyl)phenyl]-1-methyl-6-oxopyrimidin-4-yl]-2-fluorobenzonitrile |
| 108 | 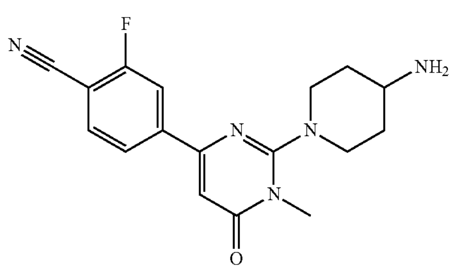 [SMILES: Cn1c(N2CCC(N)CC2)nc(-c2ccc(C#N)c(F)c2)cc1=O] | 4-[2-(4-aminopiperidin-1-yl)-1-methyl-6-oxopyrimidin-4-yl]-2-fluorobenzonitrile |
| 109 | 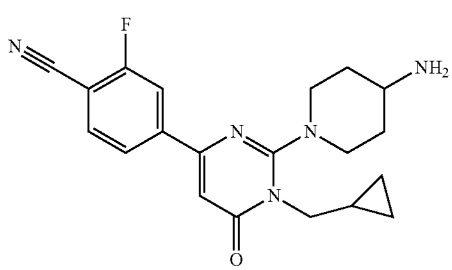 [SMILES: N#Cc1ccc(-c2cc(=O)n(CC3CC3)c(N3CCC(N)CC3)n2)cc1F] | 4-[2-(4-amino-piperidin-1-yl)-1-cyclopropylmethyl-6-oxo-1,6-dihydro-pyrimidin-4-yl]-2-fluoro-benzonitrile |

TABLE 1-continued

| Chemical Synthesis Example | Structure | Name |
|---|---|---|
| 110 | 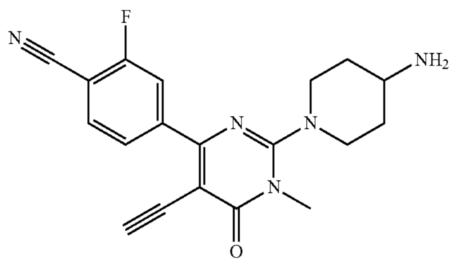 | 4-[2-(4-amino-piperidin-1-yl)-1-cyclopropylmethyl-6-oxo-1,6-dihydro-pyrimidin-4-yl]-2-fluoro-benzonitrile |
| 111 | 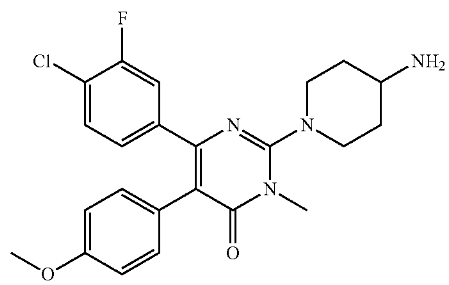 [SMILES: COc1ccc(-c2c(-c3ccc(Cl)c(F)c3)nc(N3CCC(N)CC3)n(C)c2=O)cc1] | 2-(4-amino-piperidin-1-yl)-6-(4-chloro-3-fluoro-phenyl)-5-(4-methoxy-phenyl)-3-methyl-3H-pyrimidin-4-one |
| 112 | 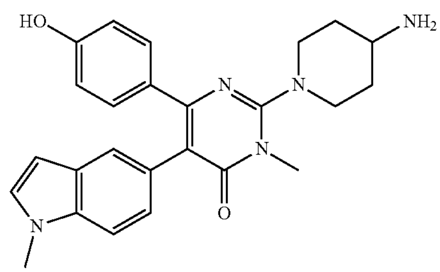 [SMILES: Cn1c(N2CCC(N)CC2)nc(-c2ccc(O)cc2)c(-c2ccc3c(ccn3C)c2)c1=O] | 2-(4-amino-piperidin-1-yl)-6-(4-hydroxy-phenyl)-3-methyl-5-(1-methyl-1H-indol-5-yl)-3H-pyrimidin-4-one |
| 113 | 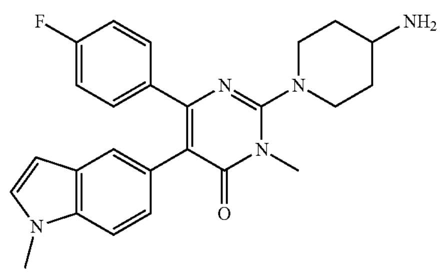 [SMILES: Cn1c(N2CCC(N)CC2)nc(-c2ccc(F)cc2)c(-c2ccc3c(ccn3C)c2)c1=O] | 2-(4-amino-piperidin-1-yl)-6-(4-fluoro-phenyl)-3-methyl-5-(1-methyl-1H-indol-5-yl)-3H-pyrimidin-4-one |
| 114 | 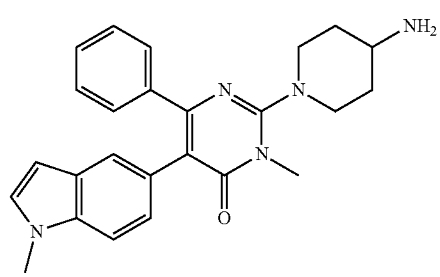 [SMILES: Cn1c(N2CCC(N)CC2)nc(-c2ccccc2)c(-c2ccc3c(ccn3C)c2)c1=O] | 2-(4-amino-piperidin-1-yl)-3-methyl-5-(1-methyl-1H-indol-5-yl)-6-phenyl-3H-pyrimidin-4-one |

TABLE 1-continued

| Chemical Synthesis Example | Structure | Name |
|---|---|---|
| 115 | 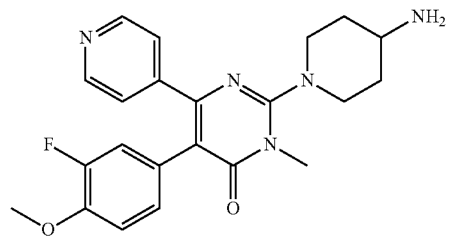 [SMILES: COc1ccc(-c2c(-c3ccncc3)nc(N3CCC(N)CC3)n(C)c2=O)cc1F] | 2-(4-amino-piperidin-1-yl)-5-(3-fluoro-4-methoxy-phenyl)-3-methyl-6-pyridin-4-yl-3H-pyrimidin-4-one |
| 116 | 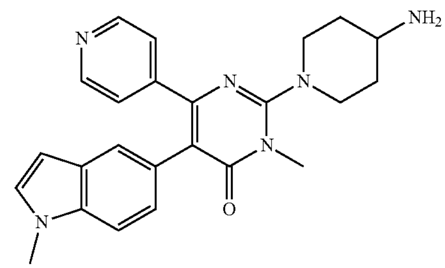 [SMILES: Cn1c(N2CCC(N)CC2)nc(-c2ccncc2)c(-c2ccc3c(ccn3C)c2)c1=O] | 2-(4-amino-piperidin-1-yl)-3-methyl-5-(1-methyl-1H-indol-5-yl)-6-pyridin-4-yl-3H-pyrimidin-4-one |
| 117 | 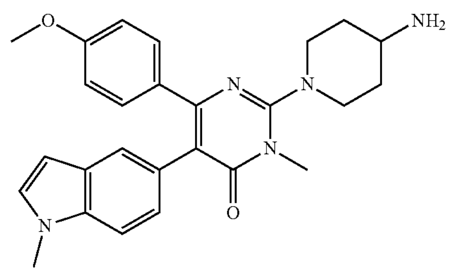 [SMILES: COc1ccc(-c2nc(N3CCC(N)CC3)n(C)c(=O)c2-c2ccc3c(ccn3C)c2)cc1] | 2-(4-amino-piperidin-1-yl)-6-(4-methoxy-phenyl)-3-methyl-5-(1-methyl-1H-indol-5-yl)-3H-pyrimidin-4-one |
| 118 | 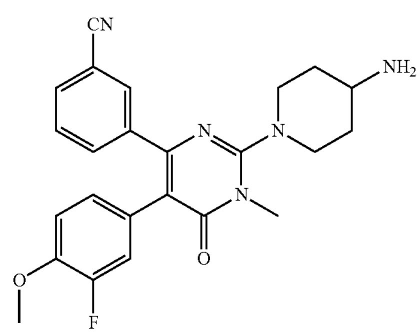 [SMILES: COc1ccc(-c2c(-c3cccc(C#N)c3)nc(N3CCC(N)CC3)n(C)c2=O)cc1F] | 3-[2-(4-aminopiperidin-1-yl)-5-(3-fluoro-4-methoxyphenyl)-1-methyl-6-oxopyrimidin-4-yl]benzonitrile |
| 119 | 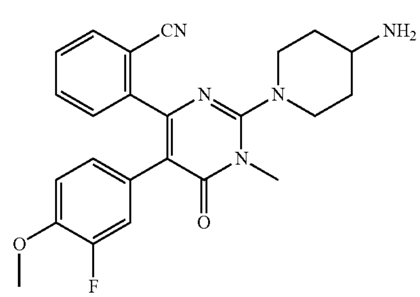 [SMILES: COc1ccc(-c2c(-c3ccccc3C#N)nc(N3CCC(N)CC3)n(C)c2=O)cc1F] | 2-[2-(4-aminopiperidin-1-yl)-5-(3-fluoro-4-methoxyphenyl)-1-methyl-6-oxopyrimidin-4-yl]benzonitrile |

TABLE 1-continued

| Chemical Synthesis Example | Structure | Name |
|---|---|---|
| 120 | 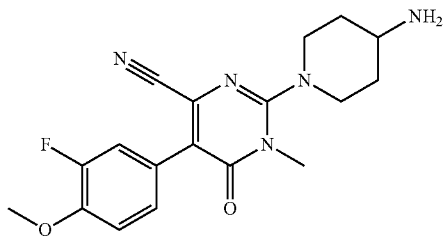 [SMILES: COc1ccc(-c2c(C#N)nc(N3CCC(N)CC3)n(C)c2=O)cc1F] | 2-(4-amino-piperidin-1-yl)-5-(3-fluoro-4-methoxy-phenyl)-1-methyl-6-oxo-1,6-dihydro-pyrimidine-4-carbonitrile |
| 121 | 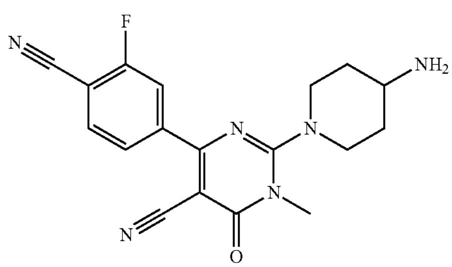 [SMILES: Cn1c(N2CCC(N)CC2)nc(-c2ccc(C#N)c(F)c2)c(C#N)c1=O] | 2-(4-amino-piperidin-1-yl)-4-(4-cyano-3-fluoro-phenyl)-1-methyl-6-oxo-1,6-dihydro-pyrimidine-5-carbonitrile |
| 122 | 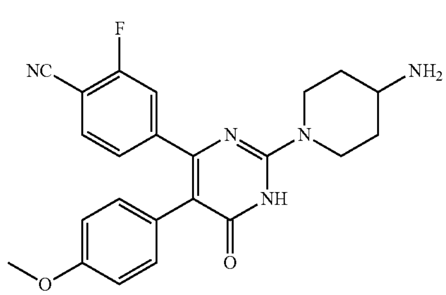 [SMILES: COc1ccc(-c2c(-c3ccc(C#N)c(F)c3)nc(N3CCC(N)CC3)[nH]c2=O)cc1] | 4-[2-(4-aminopiperidin-1-yl)-5-(4-methoxyphenyl)-6-oxo-1H-pyrimidin-4-yl]-2-fluorobenzonitrile |

In some embodiments, the substituted heterocyclic derivative compound described herein has the structure provided in Table 2.
TABLE 2
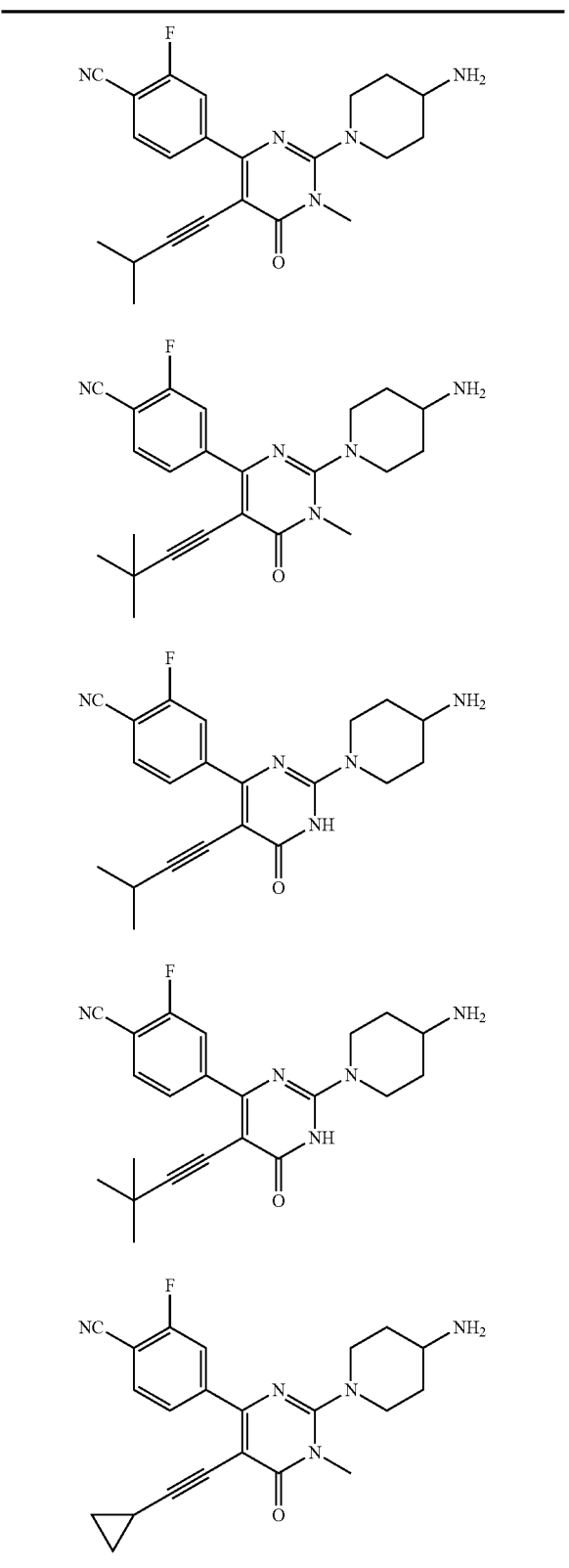
TABLE 2-continued
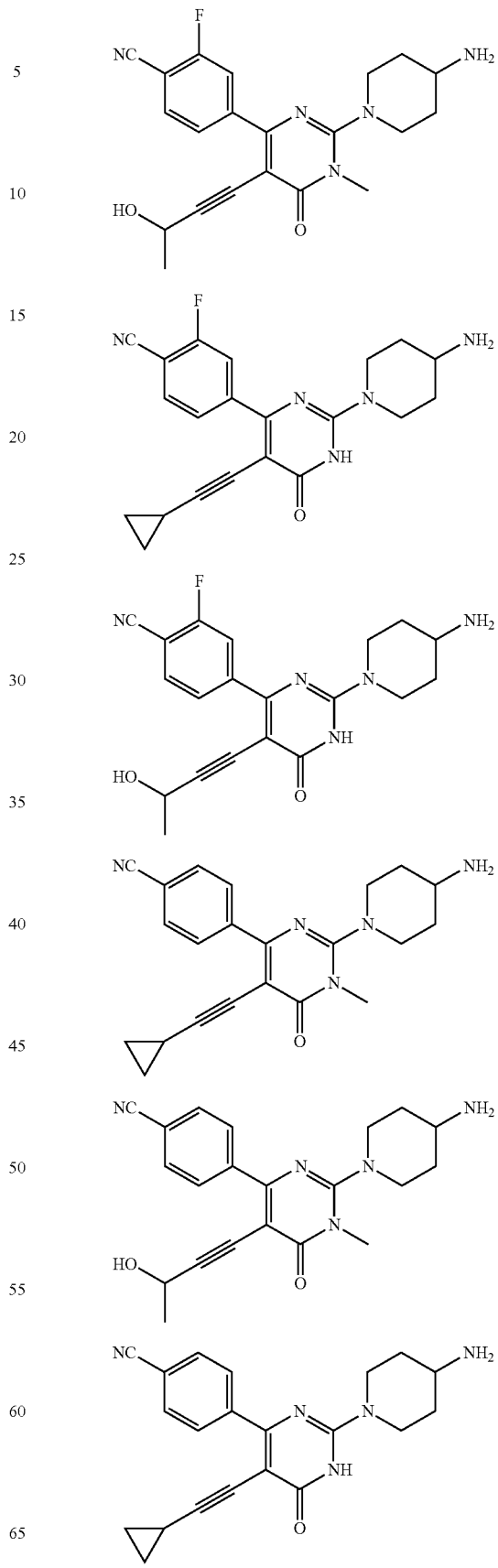

TABLE 2-continued
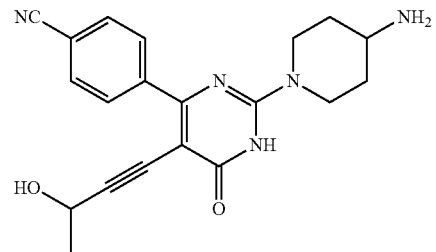 [SMILES: CC(O)C#Cc1c(-c2ccc(C#N)cc2)nc(N2CCC(N)CC2)[nH]c1=O]
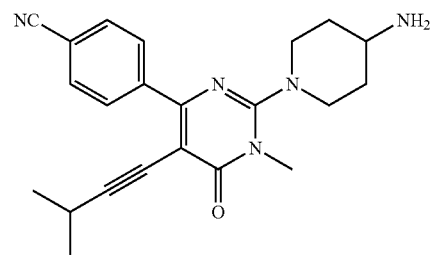 [SMILES: CC(C)C#Cc1c(-c2ccc(C#N)cc2)nc(N2CCC(N)CC2)n(C)c1=O]
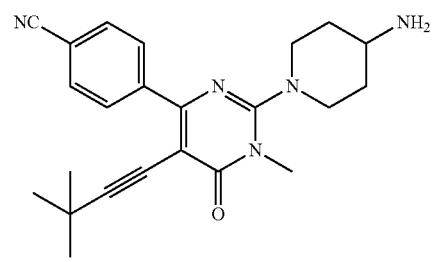 [SMILES: Cn1c(N2CCC(N)CC2)nc(-c2ccc(C#N)cc2)c(C#CC(C)(C)C)c1=O]
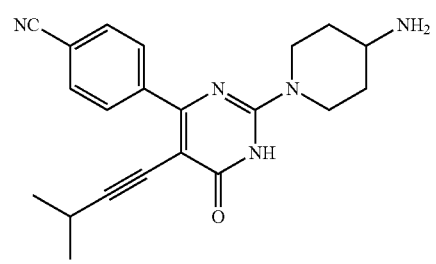 [SMILES: CC(C)C#Cc1c(-c2ccc(C#N)cc2)nc(N2CCC(N)CC2)[nH]c1=O]
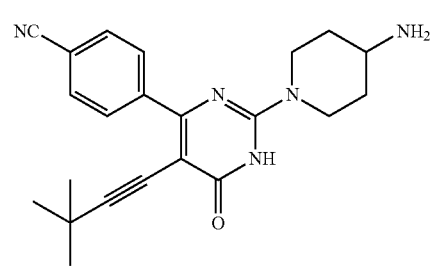
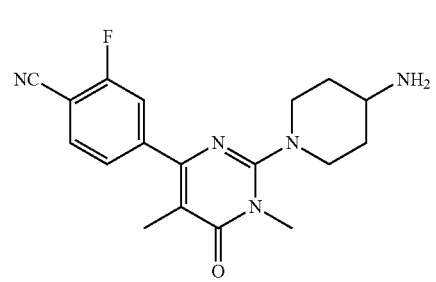 [SMILES: Cc1c(-c2ccc(C#N)c(F)c2)nc(N2CCC(N)CC2)n(C)c1=O]
TABLE 2-continued
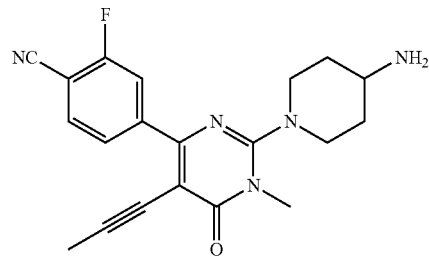 [SMILES: CC#Cc1c(-c2ccc(C#N)c(F)c2)nc(N2CCC(N)CC2)n(C)c1=O]
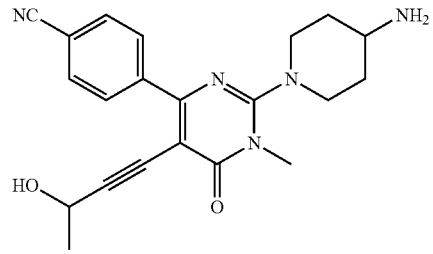 [SMILES: CC(O)C#Cc1c(-c2ccc(C#N)cc2)nc(N2CCC(N)CC2)n(C)c1=O]
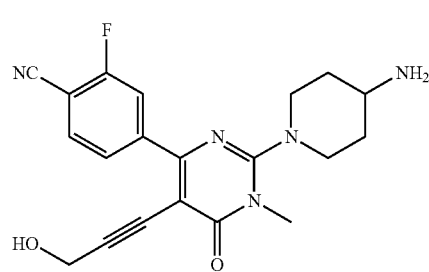 [SMILES: Cn1c(N2CCC(N)CC2)nc(-c2ccc(C#N)c(F)c2)c(C#CCO)c1=O]
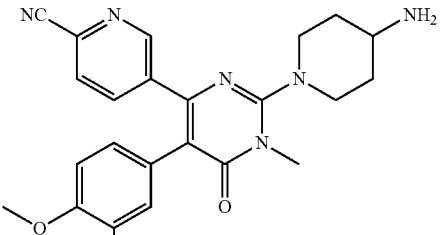 [SMILES: COc1ccc(-c2c(-c3ccc(C#N)nc3)nc(N3CCC(N)CC3)n(C)c2=O)cc1]
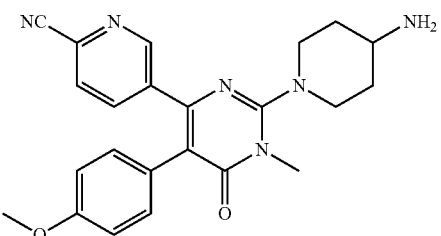
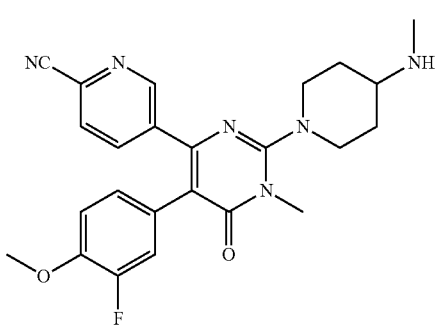

TABLE 2-continued
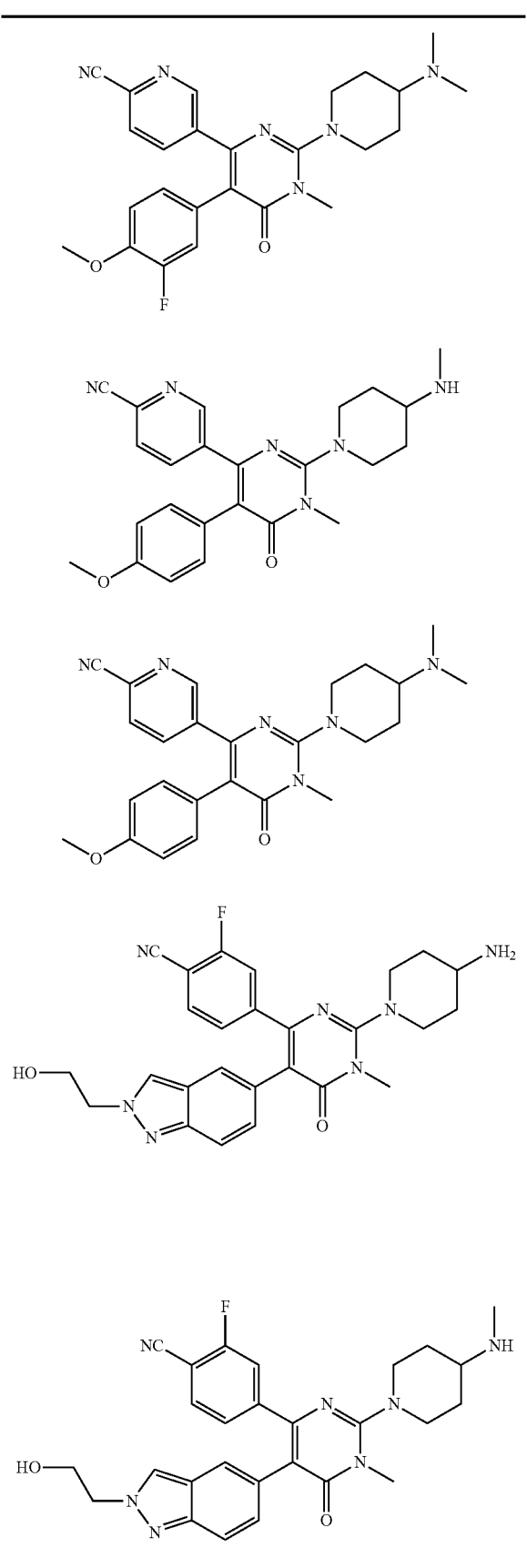
TABLE 2-continued
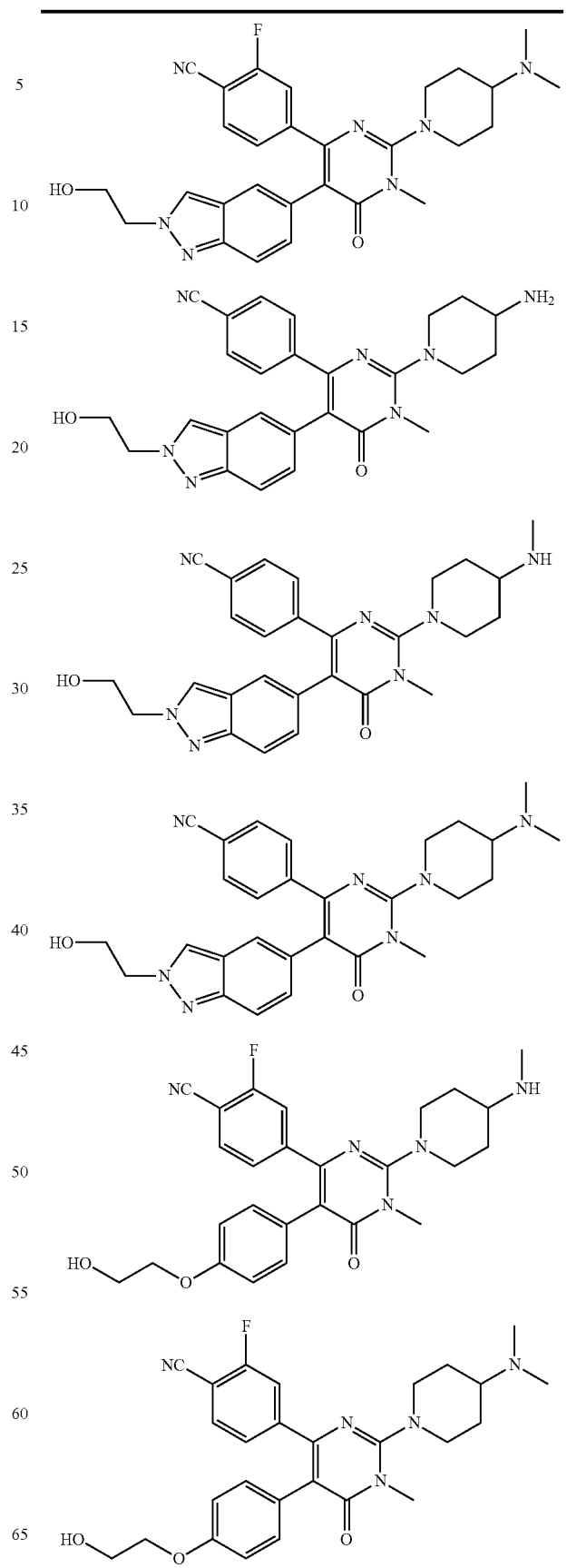

TABLE 2-continued
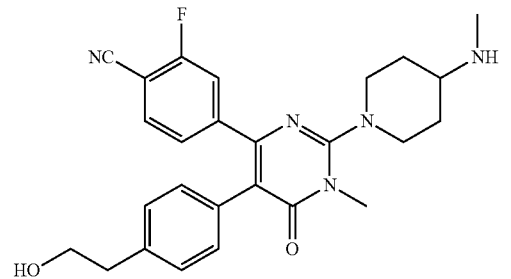 [SMILES: CNC1CCN(c2nc(-c3ccc(C#N)c(F)c3)c(-c3ccc(CCO)cc3)c(=O)n2C)CC1]
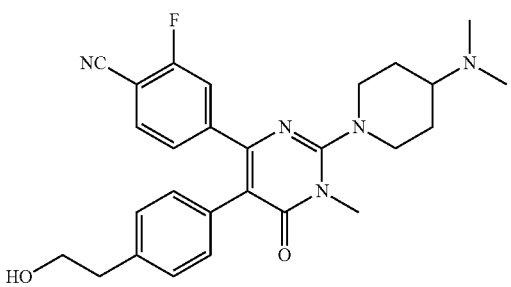 [SMILES: CN(C)C1CCN(c2nc(-c3ccc(C#N)c(F)c3)c(-c3ccc(CCO)cc3)c(=O)n2C)CC1]
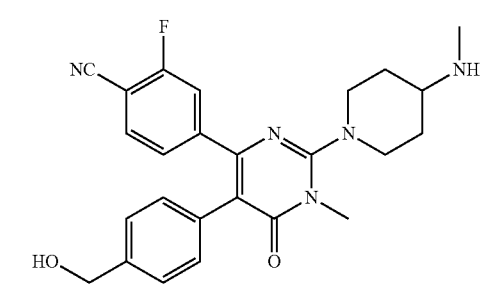 [SMILES: CNC1CCN(c2nc(-c3ccc(C#N)c(F)c3)c(-c3ccc(CO)cc3)c(=O)n2C)CC1]
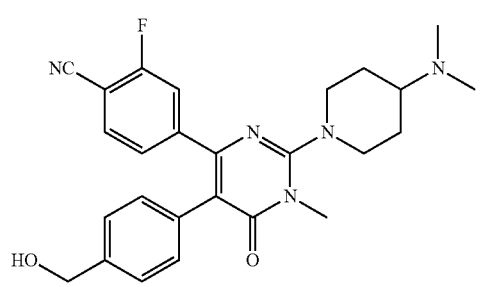 [SMILES: CN(C)C1CCN(c2nc(-c3ccc(C#N)c(F)c3)c(-c3ccc(CO)cc3)c(=O)n2C)CC1]
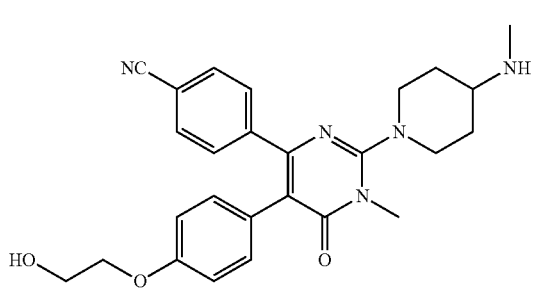 [SMILES: CNC1CCN(c2nc(-c3ccc(C#N)cc3)c(-c3ccc(OCCO)cc3)c(=O)n2C)CC1]
TABLE 2-continued
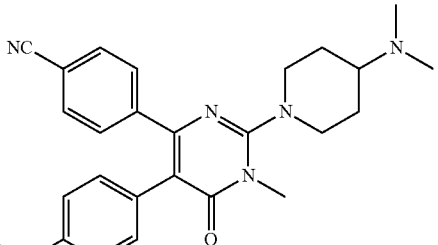
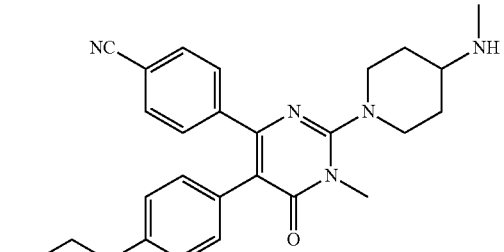
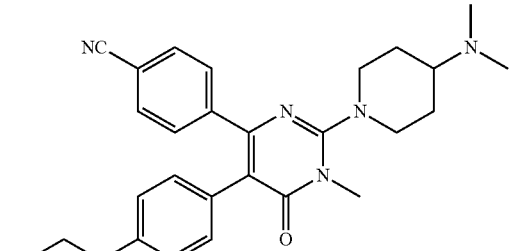
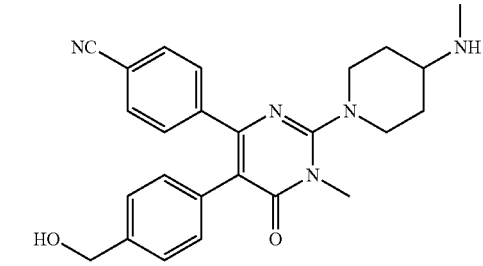 [SMILES: CNC1CCN(c2nc(-c3ccc(C#N)cc3)c(-c3ccc(CO)cc3)c(=O)n2C)CC1]
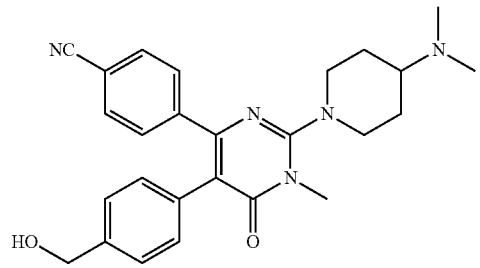 [SMILES: CN(C)C1CCN(c2nc(-c3ccc(C#N)cc3)c(-c3ccc(CO)cc3)c(=O)n2C)CC1]

TABLE 2-continued
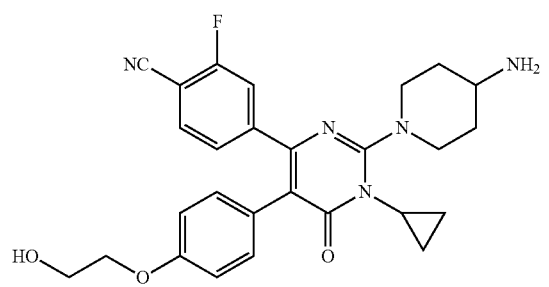 [SMILES: N#Cc1ccc(-c2nc(N3CCC(N)CC3)n(C3CC3)c(=O)c2-c2ccc(OCCO)cc2)cc1F]
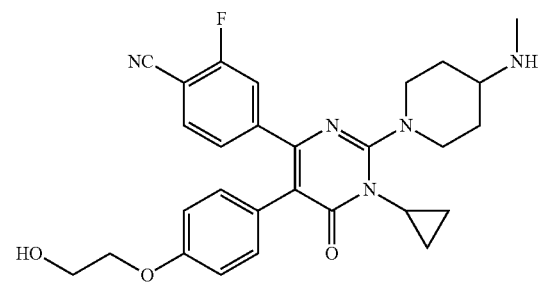 [SMILES: CNC1CCN(c2nc(-c3ccc(C#N)c(F)c3)c(-c3ccc(OCCO)cc3)c(=O)n2C2CC2)CC1]
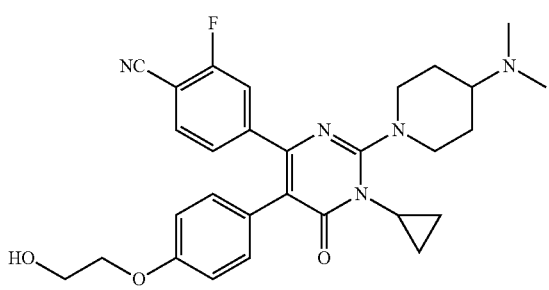 [SMILES: CN(C)C1CCN(c2nc(-c3ccc(C#N)c(F)c3)c(-c3ccc(OCCO)cc3)c(=O)n2C2CC2)CC1]
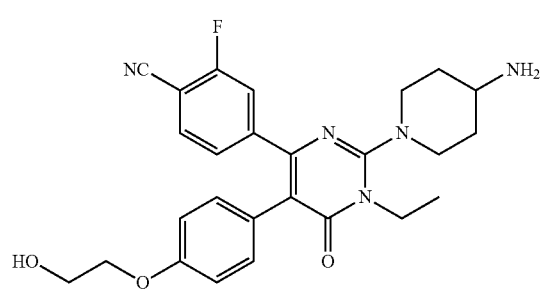 [SMILES: CCn1c(N2CCC(N)CC2)nc(-c2ccc(C#N)c(F)c2)c(-c2ccc(OCCO)cc2)c1=O]
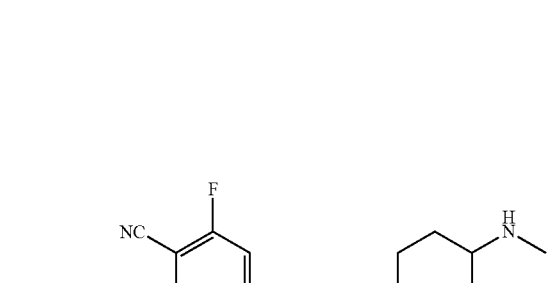
TABLE 2-continued
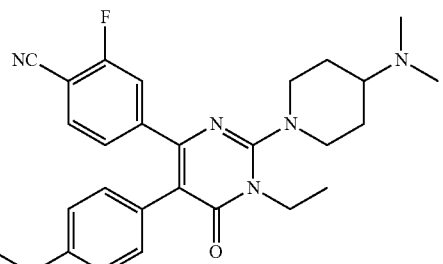
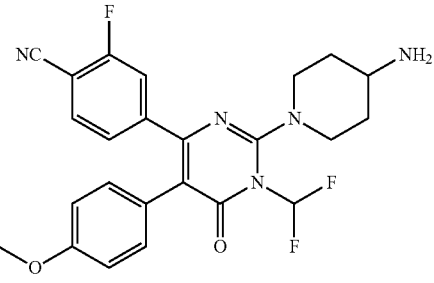
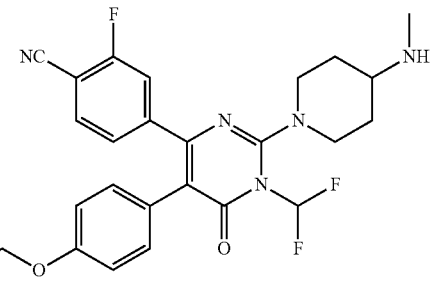
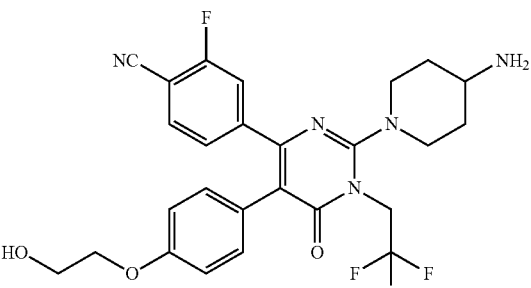

TABLE 2-continued
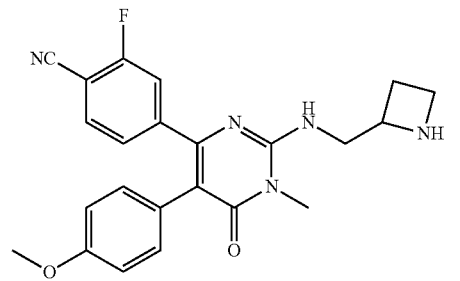 [SMILES: COc1ccc(-c2c(-c3ccc(C#N)c(F)c3)nc(NCC3CCN3)n(C)c2=O)cc1]
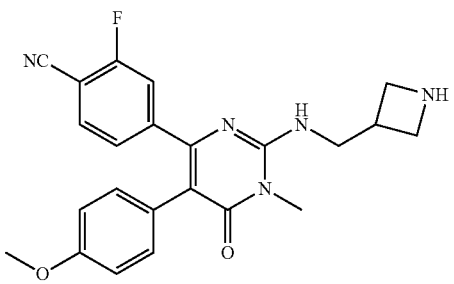 [SMILES: COc1ccc(-c2c(-c3ccc(C#N)c(F)c3)nc(NCC3CNC3)n(C)c2=O)cc1]
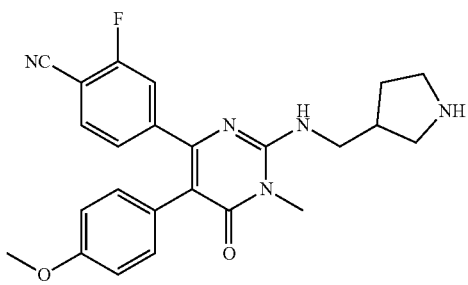 [SMILES: COc1ccc(-c2c(-c3ccc(C#N)c(F)c3)nc(NCC3CCNC3)n(C)c2=O)cc1]
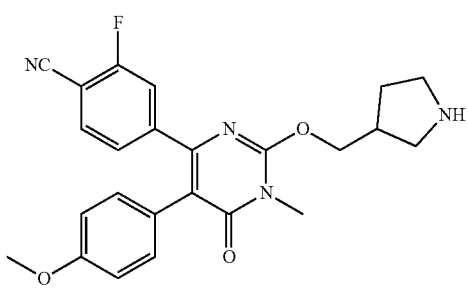
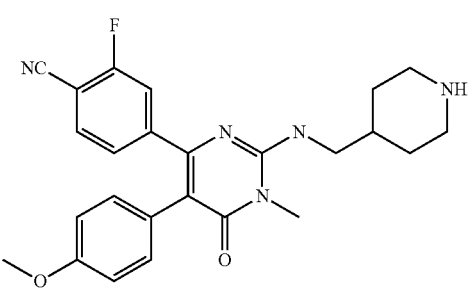 [SMILES: COc1ccc(-c2c(-c3ccc(C#N)c(F)c3)nc(NCC3CCNCC3)n(C)c2=O)cc1]
TABLE 2-continued
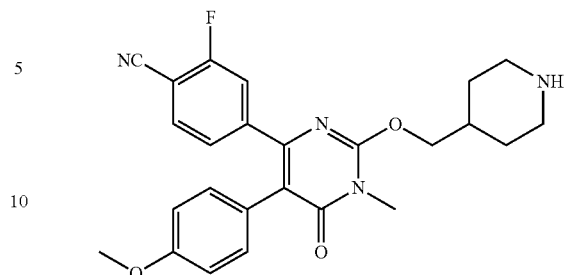
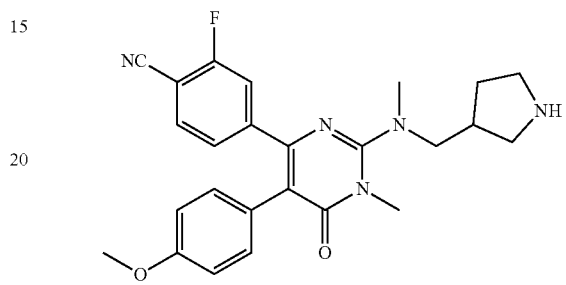
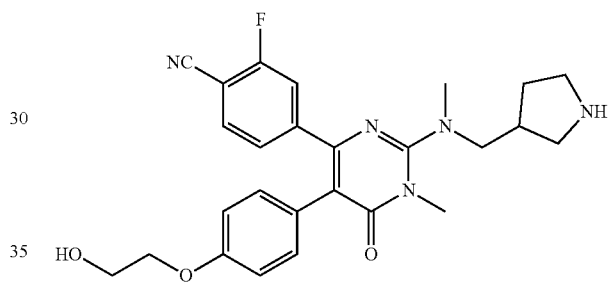
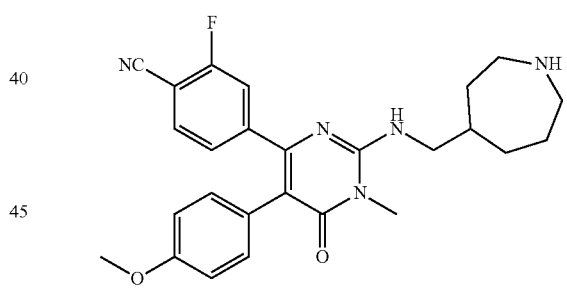
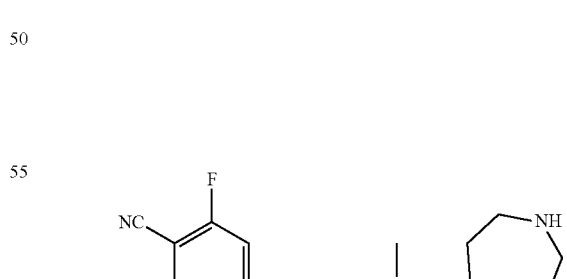

TABLE 2-continued
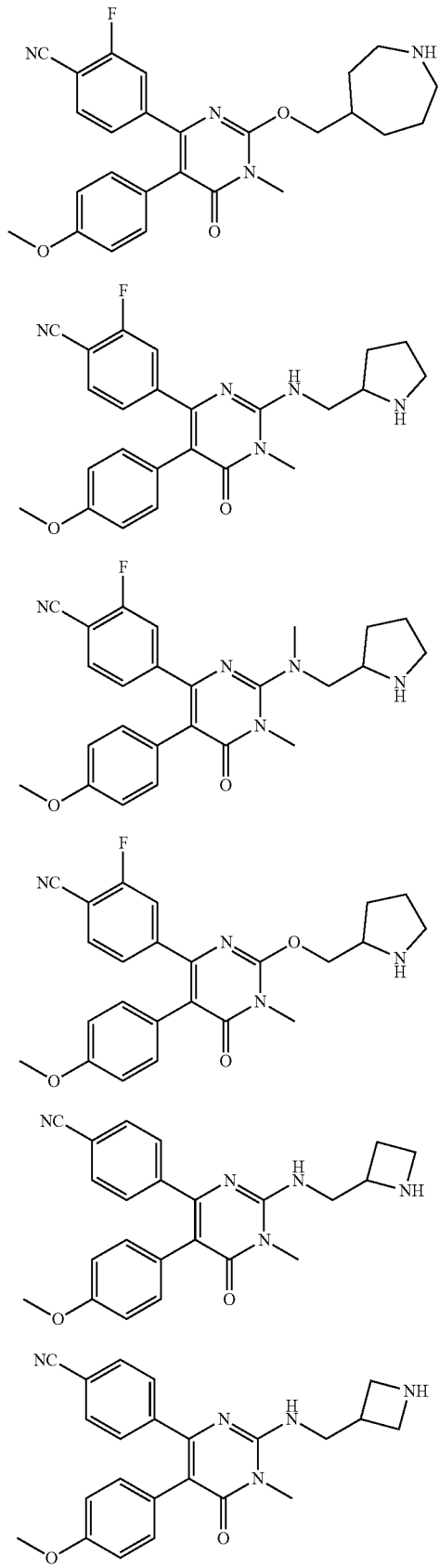
TABLE 2-continued
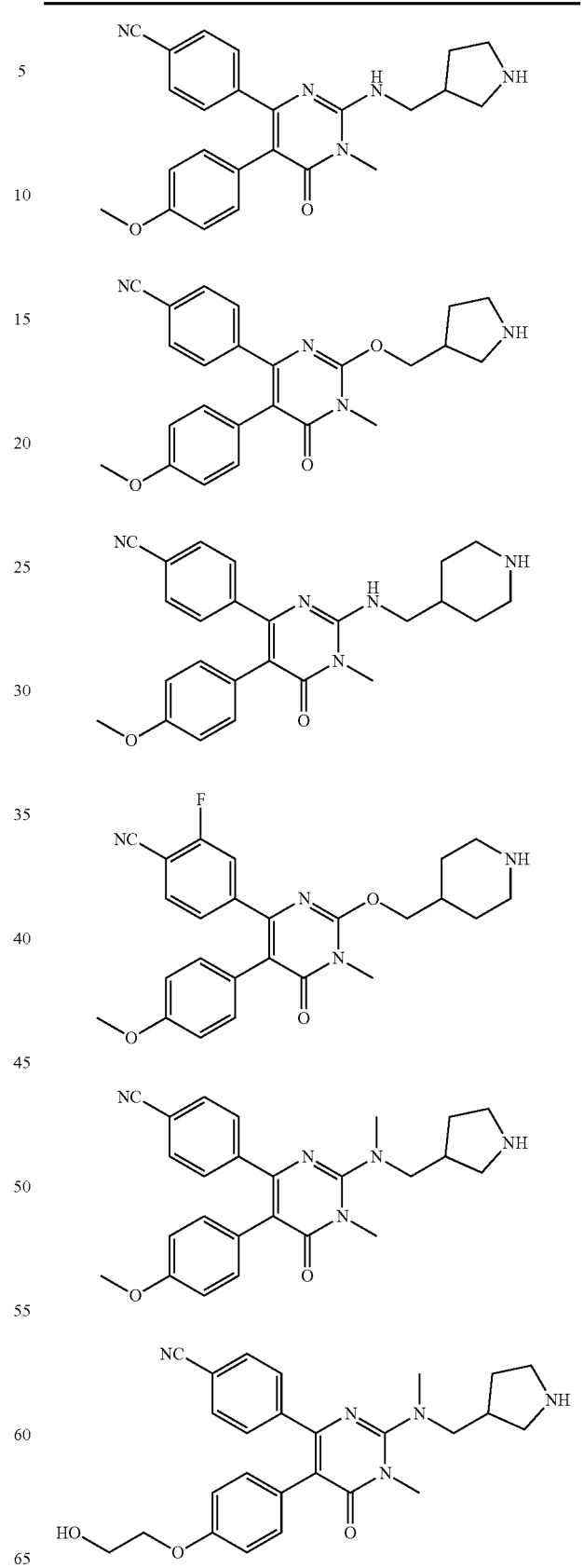

TABLE 2-continued
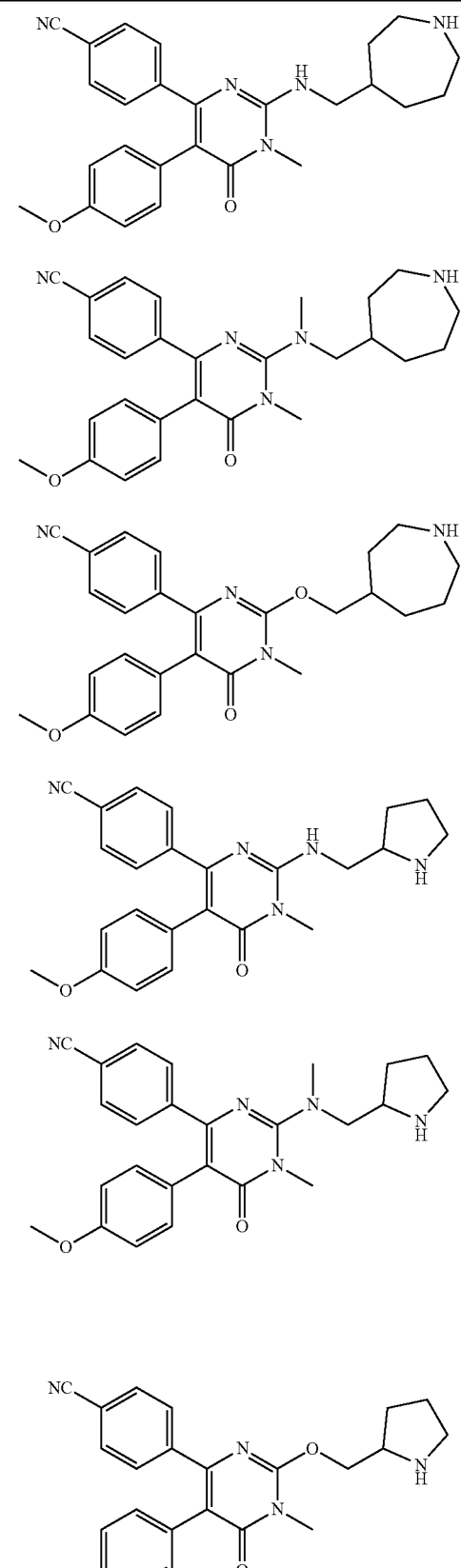
TABLE 2-continued
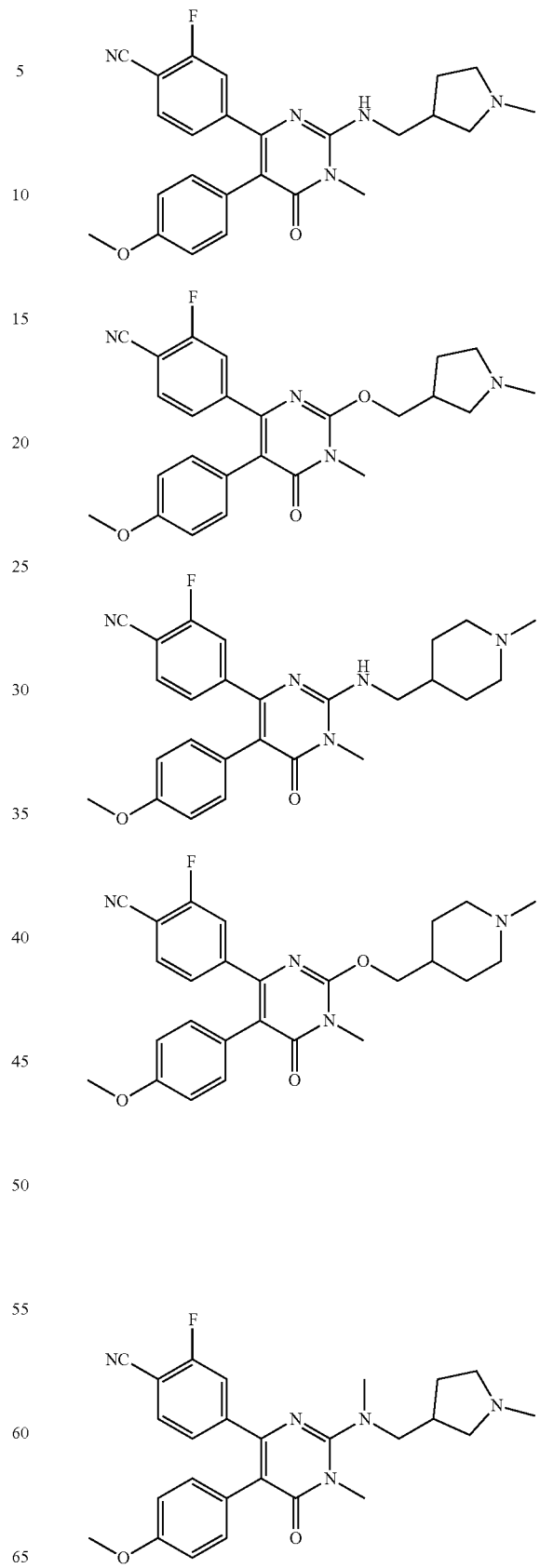

TABLE 2-continued
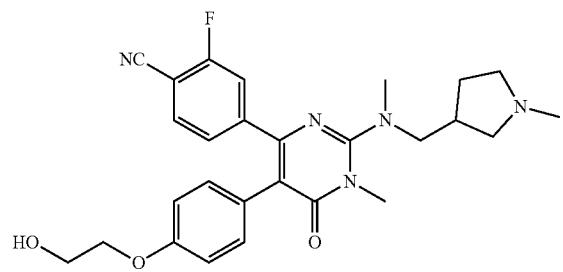 [SMILES: CN1CCC(CN(C)c2nc(-c3ccc(C#N)c(F)c3)c(-c3ccc(OCCO)cc3)c(=O)n2C)C1]
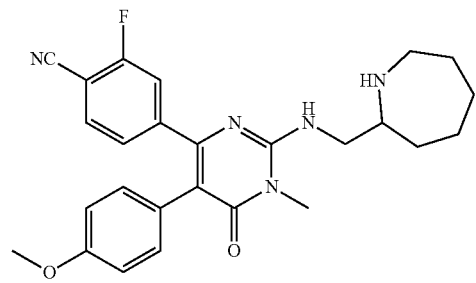 [SMILES: COc1ccc(-c2c(-c3ccc(C#N)c(F)c3)nc(NCC3CCCCCN3)n(C)c2=O)cc1]
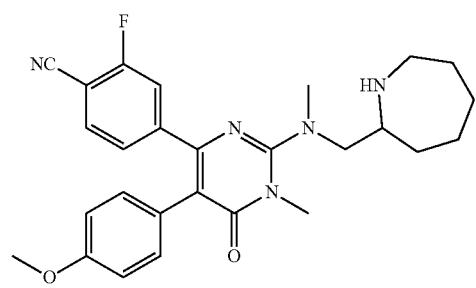 [SMILES: COc1ccc(-c2c(-c3ccc(C#N)c(F)c3)nc(N(C)CC3CCCCCN3)n(C)c2=O)cc1]
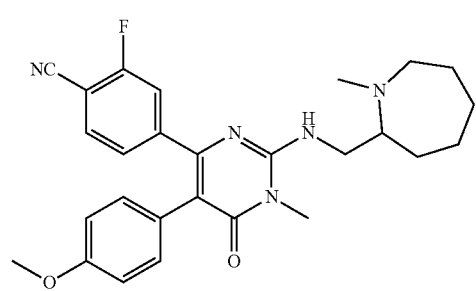 [SMILES: COc1ccc(-c2c(-c3ccc(C#N)c(F)c3)nc(NCC3CCCCCN3C)n(C)c2=O)cc1]
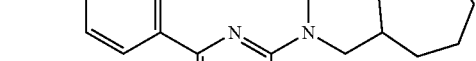
TABLE 2-continued
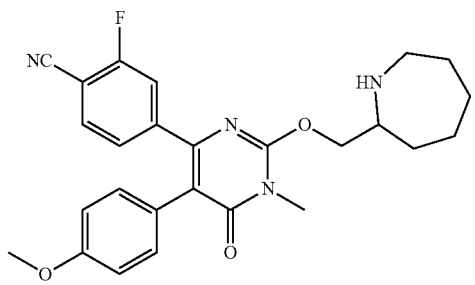 [SMILES: COc1ccc(-c2c(-c3ccc(C#N)c(F)c3)nc(OCC3CCCCCN3)n(C)c2=O)cc1]
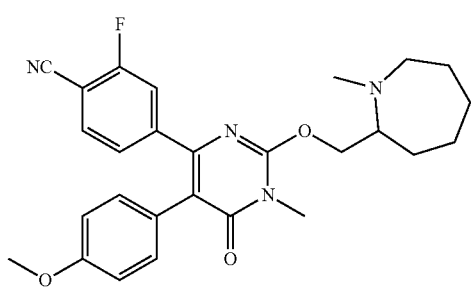 [SMILES: COc1ccc(-c2c(-c3ccc(C#N)c(F)c3)nc(OCC3CCCCCN3C)n(C)c2=O)cc1]
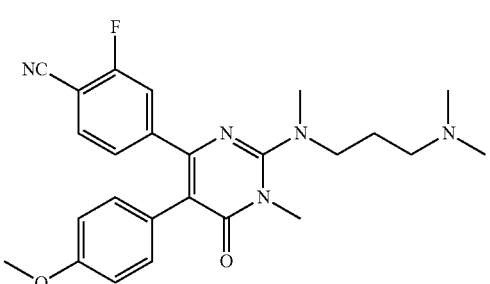
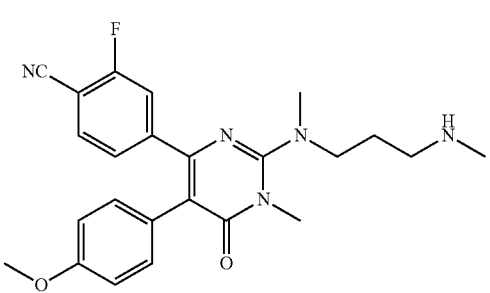
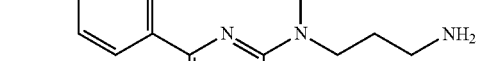

TABLE 2-continued
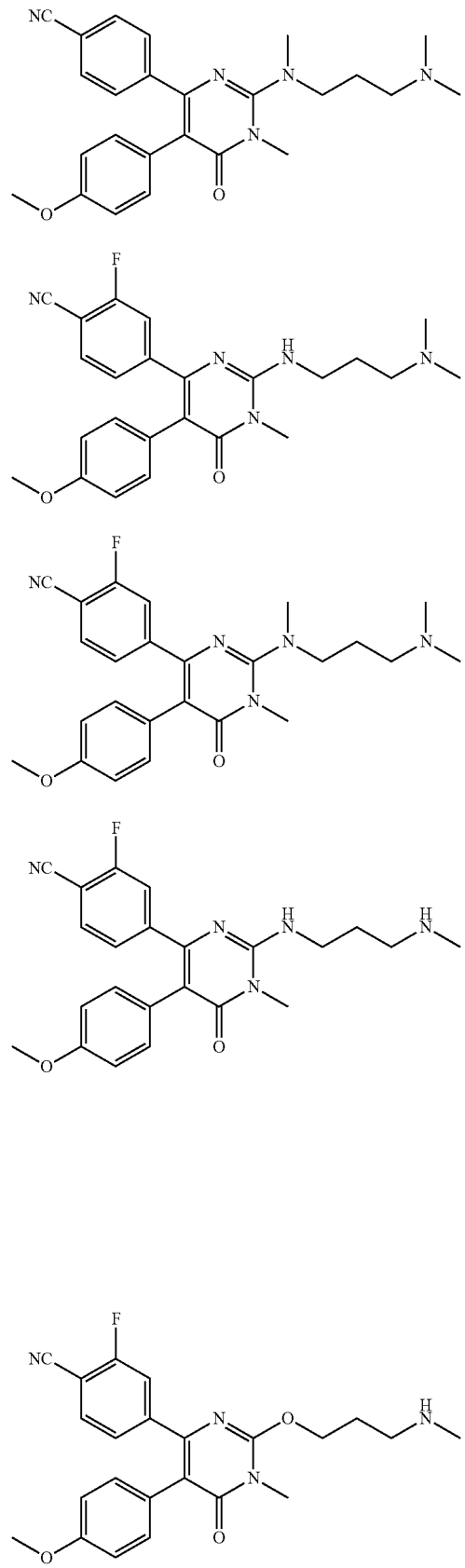
TABLE 2-continued
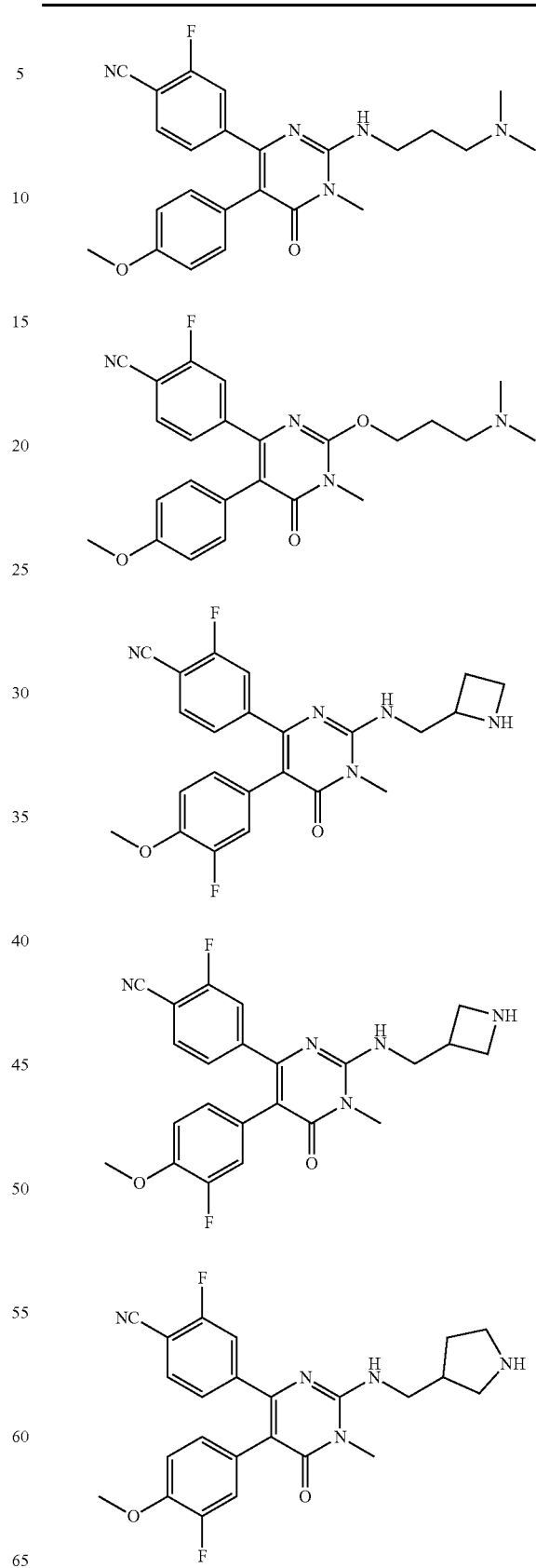

TABLE 2-continued
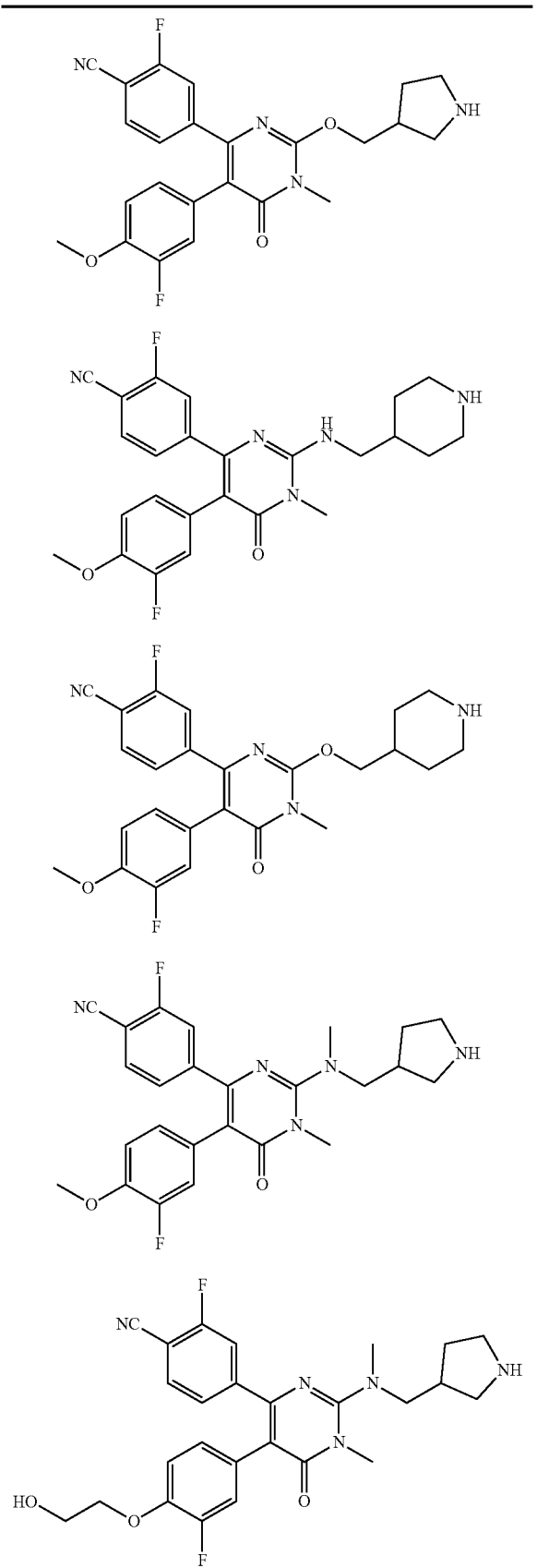
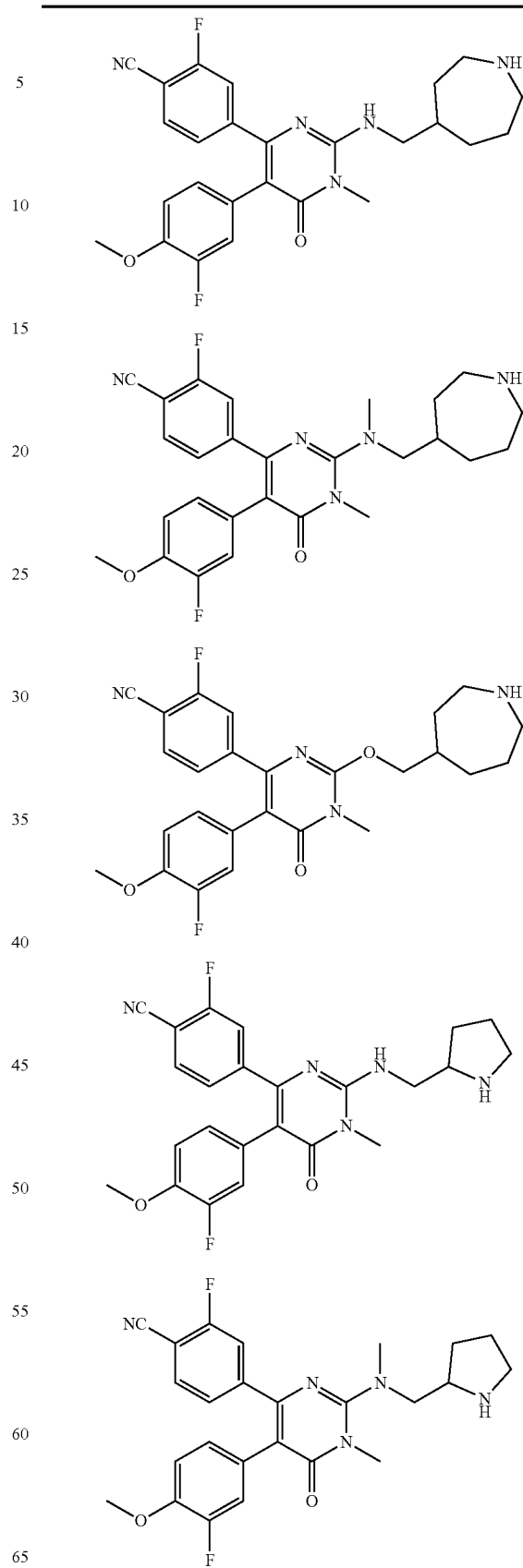

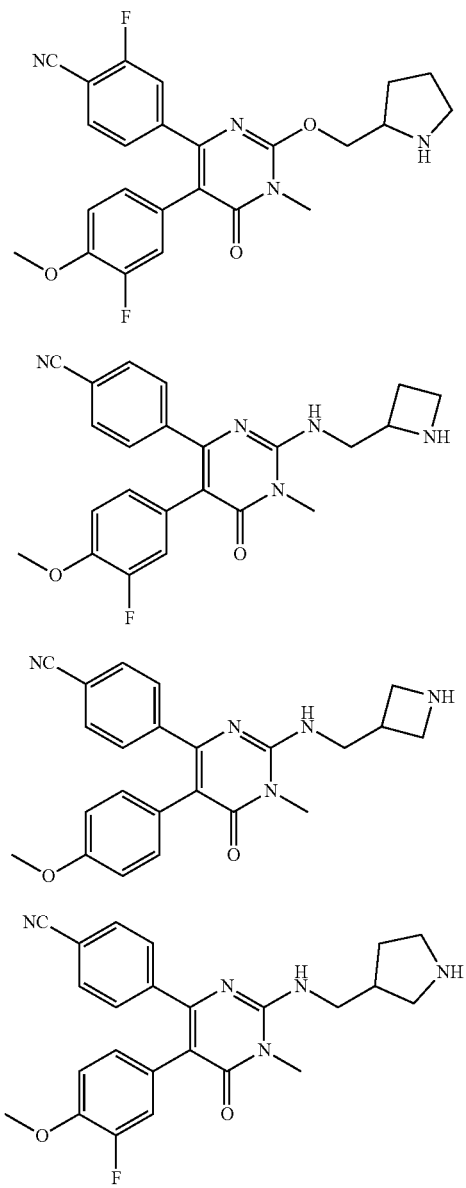
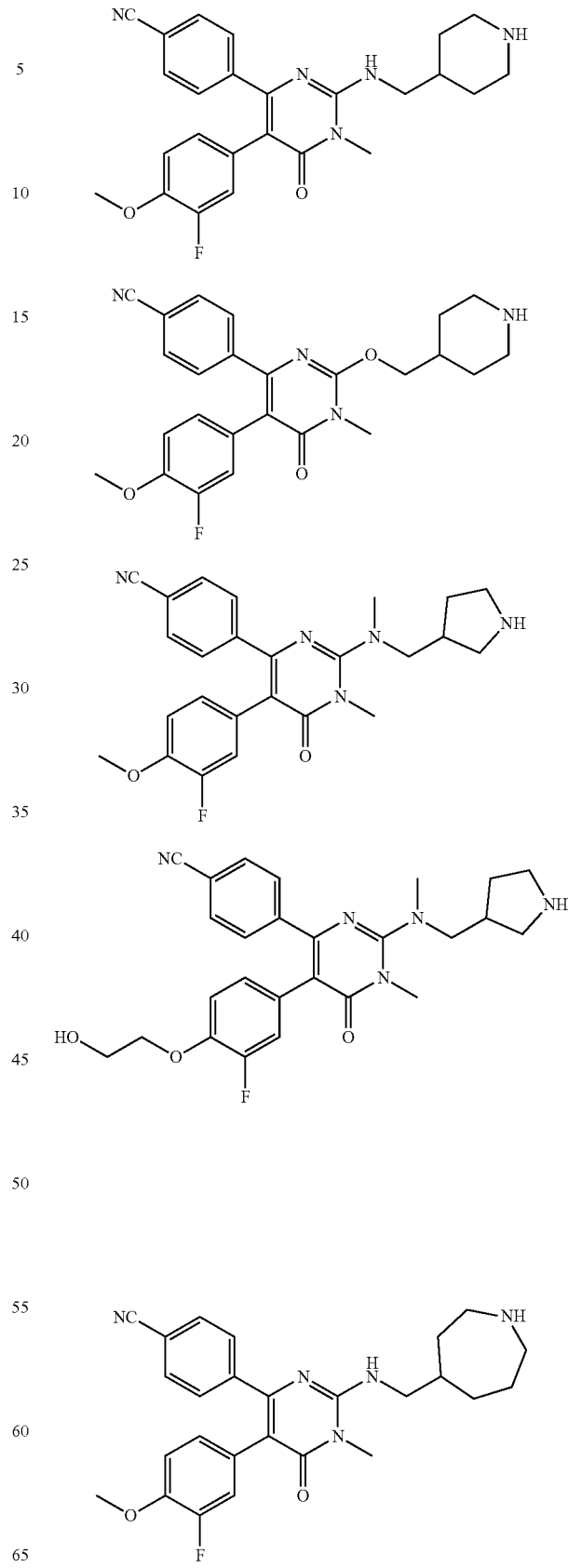

TABLE 2-continued
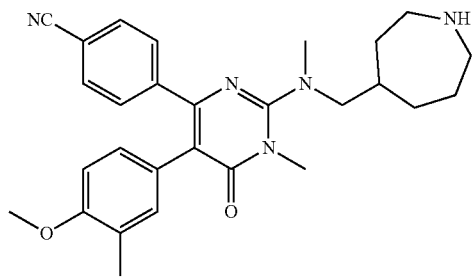 [SMILES: COc1ccc(-c2c(-c3ccc(C#N)cc3)nc(N(C)CC3CCCNCC3)n(C)c2=O)cc1C]
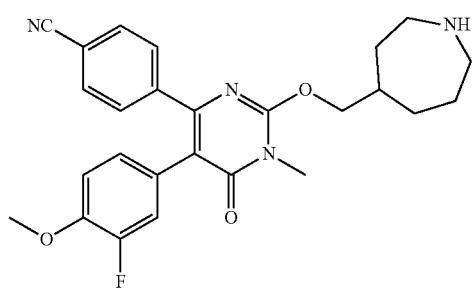 [SMILES: COc1ccc(-c2c(-c3ccc(C#N)cc3)nc(OCC3CCCNCC3)n(C)c2=O)cc1F]
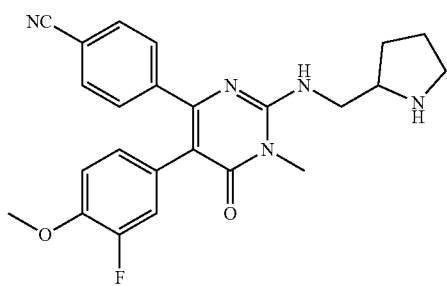
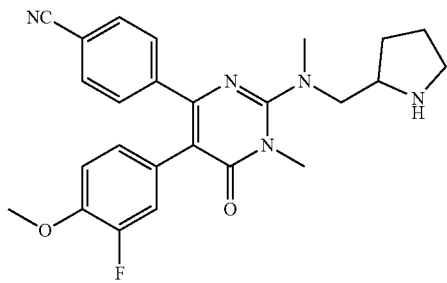 [SMILES: COc1ccc(-c2c(-c3ccc(C#N)cc3)nc(N(C)CC3CCCN3)n(C)c2=O)cc1F]
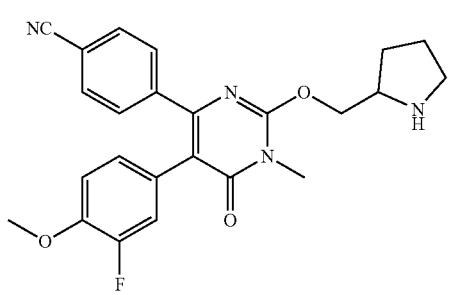 [SMILES: COc1ccc(-c2c(-c3ccc(C#N)cc3)nc(OCC3CCCN3)n(C)c2=O)cc1F]
TABLE 2-continued
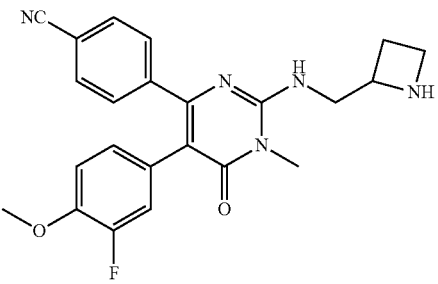 [SMILES: COc1ccc(-c2c(-c3ccc(C#N)cc3)nc(NCC3CCN3)n(C)c2=O)cc1F]
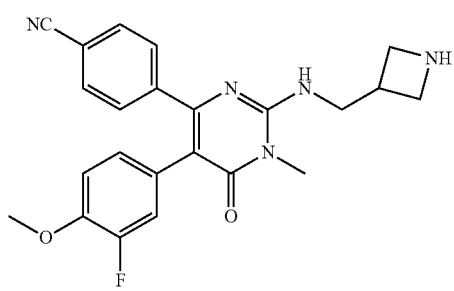 [SMILES: COc1ccc(-c2c(-c3ccc(C#N)cc3)nc(NCC3CNC3)n(C)c2=O)cc1F]
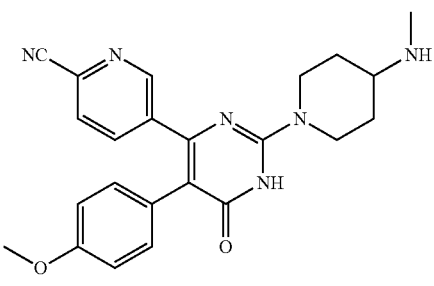
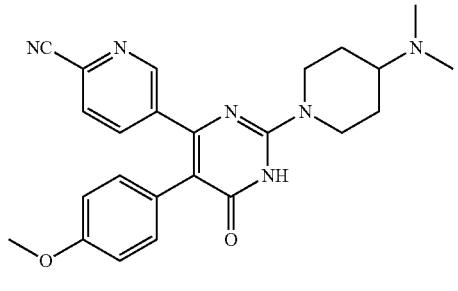
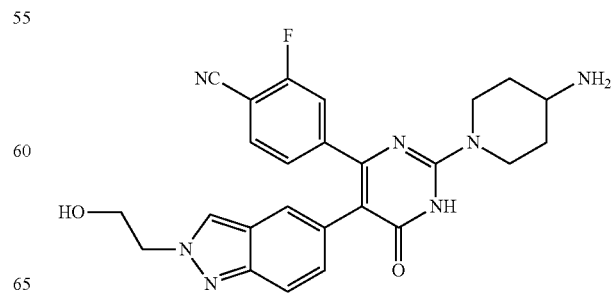

101
TABLE 2-continued
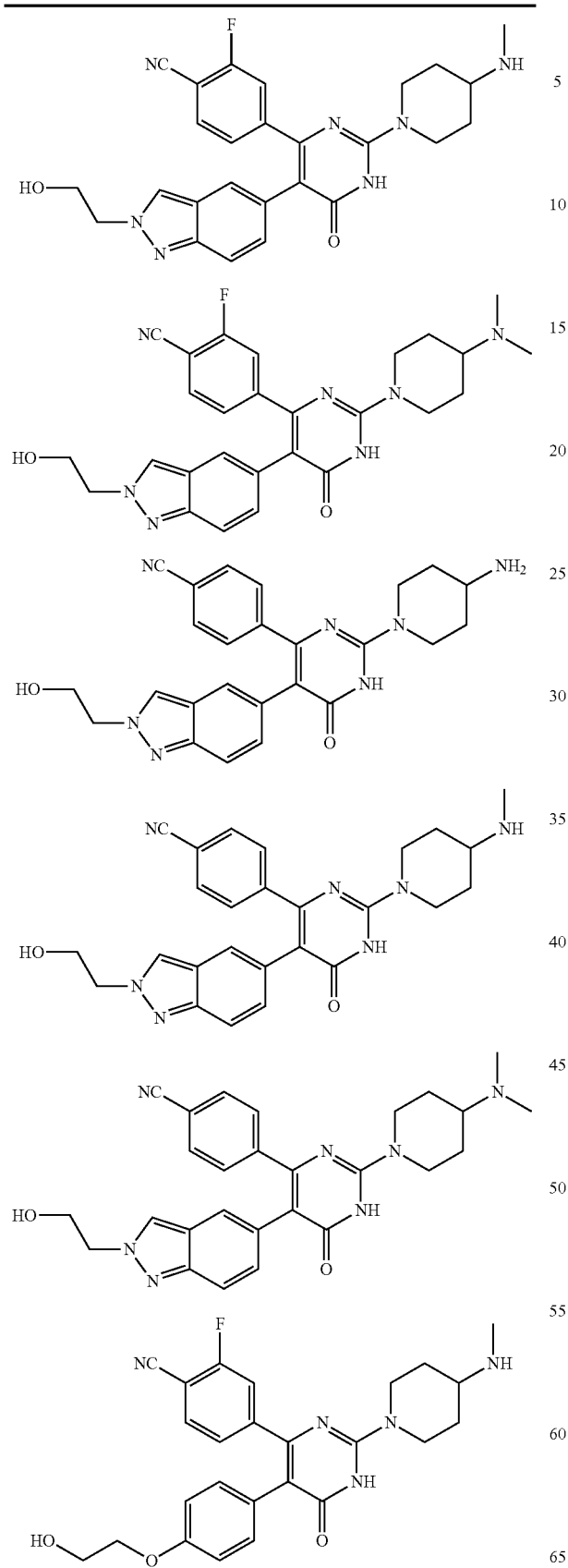
102
TABLE 2-continued
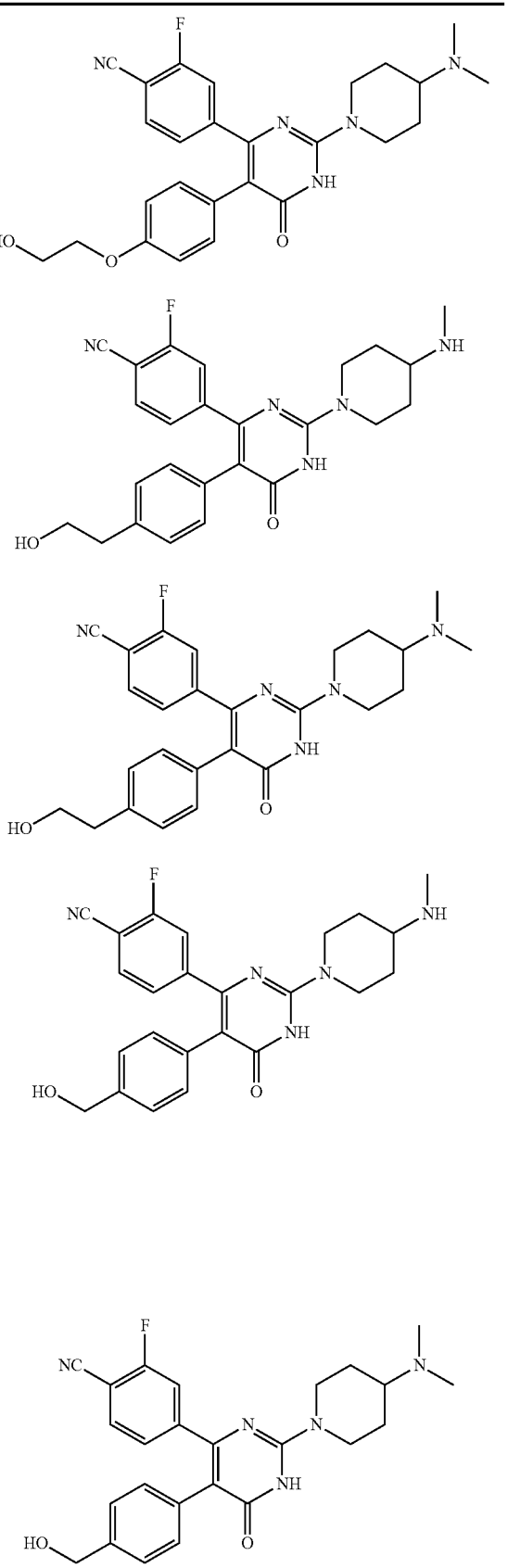

TABLE 2-continued
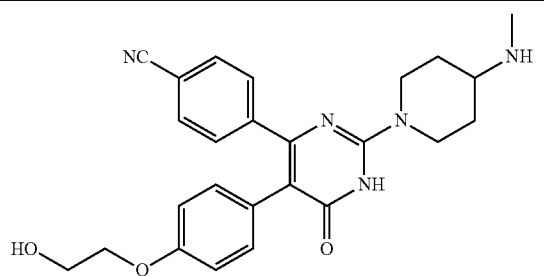
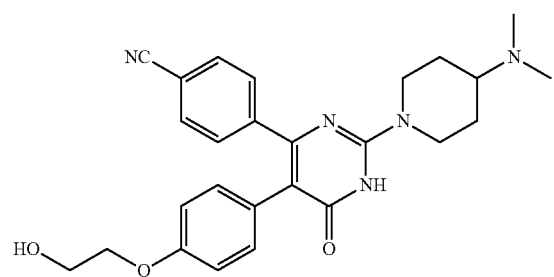 [SMILES: CN(C)C1CCN(c2nc(-c3ccc(C#N)cc3)c(-c3ccc(OCCO)cc3)c(=O)[nH]2)CC1]
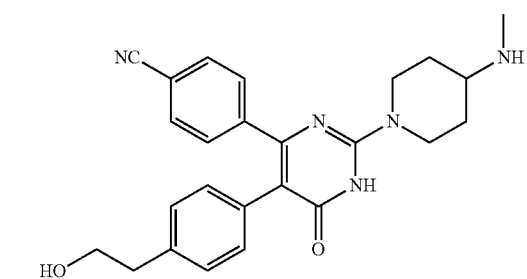 [SMILES: CNC1CCN(c2nc(-c3ccc(C#N)cc3)c(-c3ccc(CCO)cc3)c(=O)[nH]2)CC1]
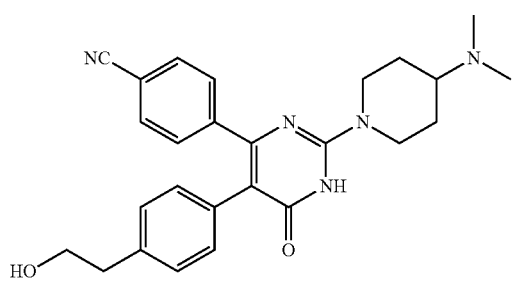 [SMILES: CN(C)C1CCN(c2nc(-c3ccc(C#N)cc3)c(-c3ccc(CCO)cc3)c(=O)[nH]2)CC1]
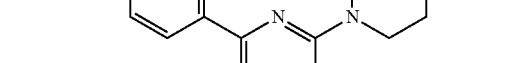
TABLE 2-continued
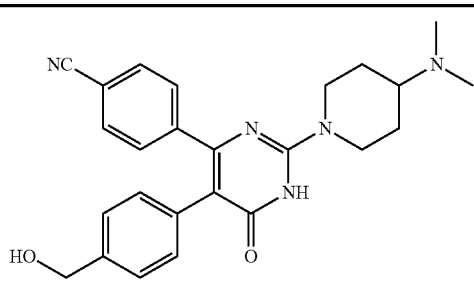
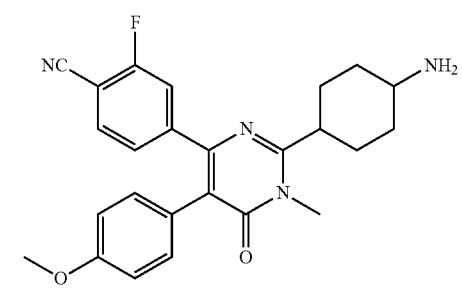 [SMILES: COc1ccc(-c2c(-c3ccc(C#N)c(F)c3)nc(C3CCC(N)CC3)n(C)c2=O)cc1]
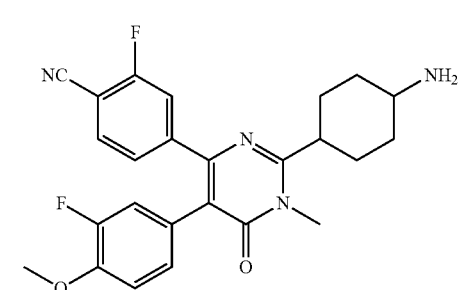
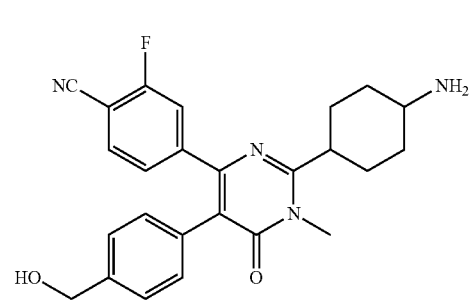

TABLE 2-continued
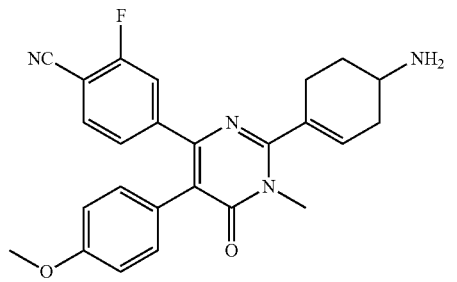 [SMILES: COc1ccc(-c2c(-c3ccc(C#N)c(F)c3)nc(C3=CCC(N)CC3)n(C)c2=O)cc1]
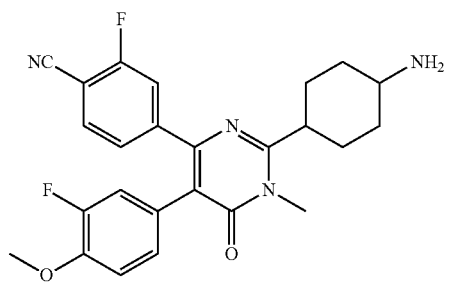 [SMILES: COc1ccc(-c2c(-c3ccc(C#N)c(F)c3)nc(C3CCC(N)CC3)n(C)c2=O)cc1F]
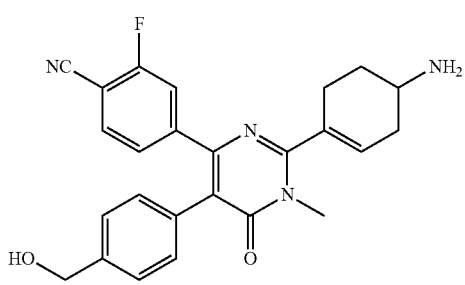 [SMILES: Cn1c(C2=CCC(N)CC2)nc(-c2ccc(C#N)c(F)c2)c(-c2ccc(CO)cc2)c1=O]
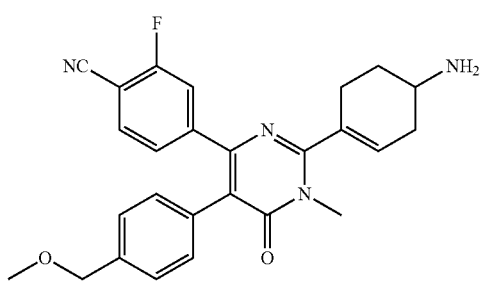 [SMILES: COCc1ccc(-c2c(-c3ccc(C#N)c(F)c3)nc(C3=CCC(N)CC3)n(C)c2=O)cc1]
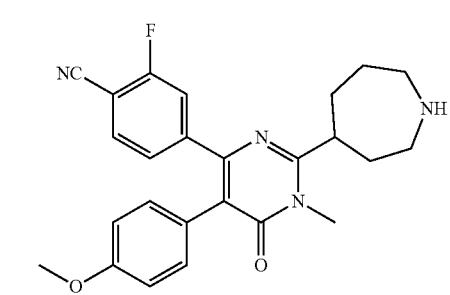 [SMILES: COc1ccc(-c2c(-c3ccc(C#N)c(F)c3)nc(C3CCCNCC3)n(C)c2=O)cc1]
TABLE 2-continued
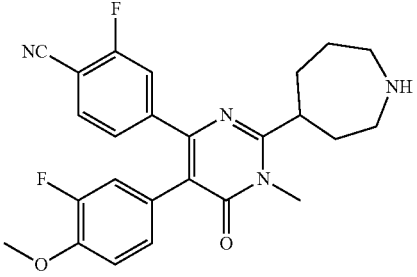 [SMILES: COc1ccc(-c2c(-c3ccc(C#N)c(F)c3)nc(C3CCCNCC3)n(C)c2=O)cc1F]
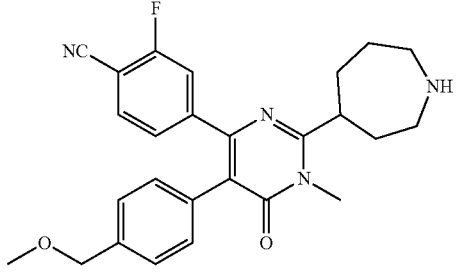 [SMILES: COCc1ccc(-c2c(-c3ccc(C#N)c(F)c3)nc(C3CCCNCC3)n(C)c2=O)cc1]
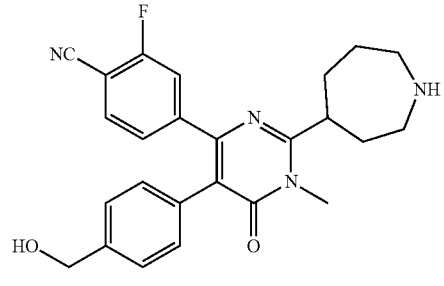 [SMILES: Cn1c(C2CCCNCC2)nc(-c2ccc(C#N)c(F)c2)c(-c2ccc(CO)cc2)c1=O]
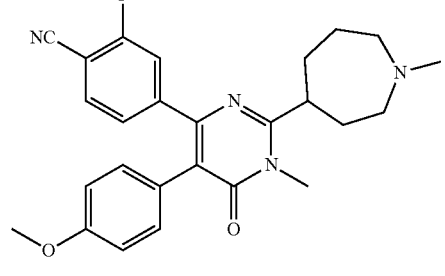
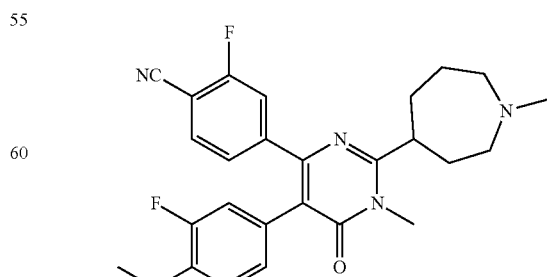

TABLE 2-continued

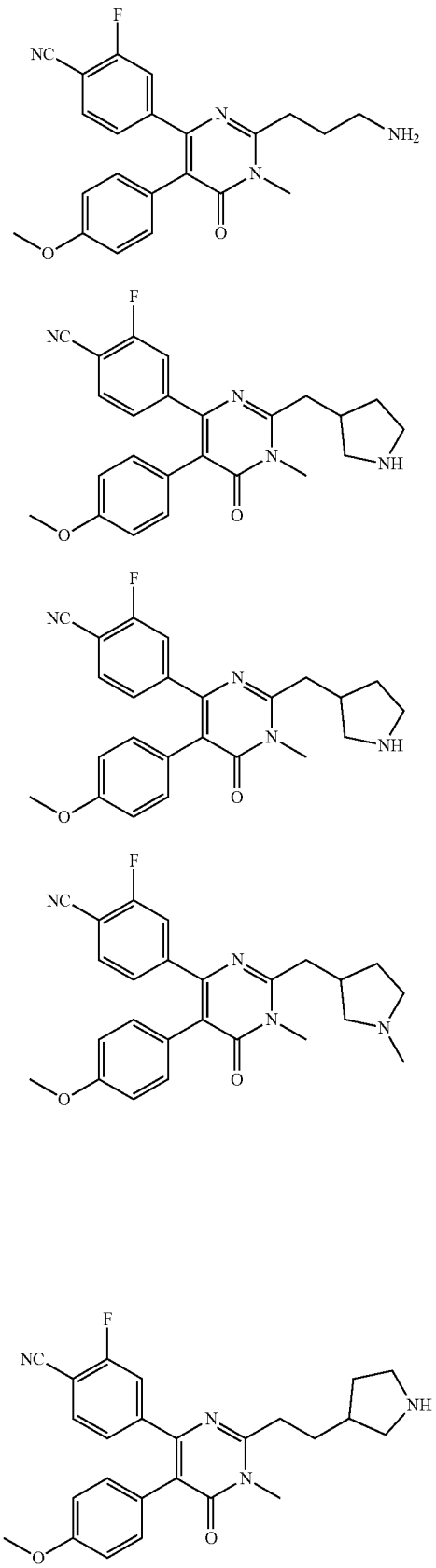

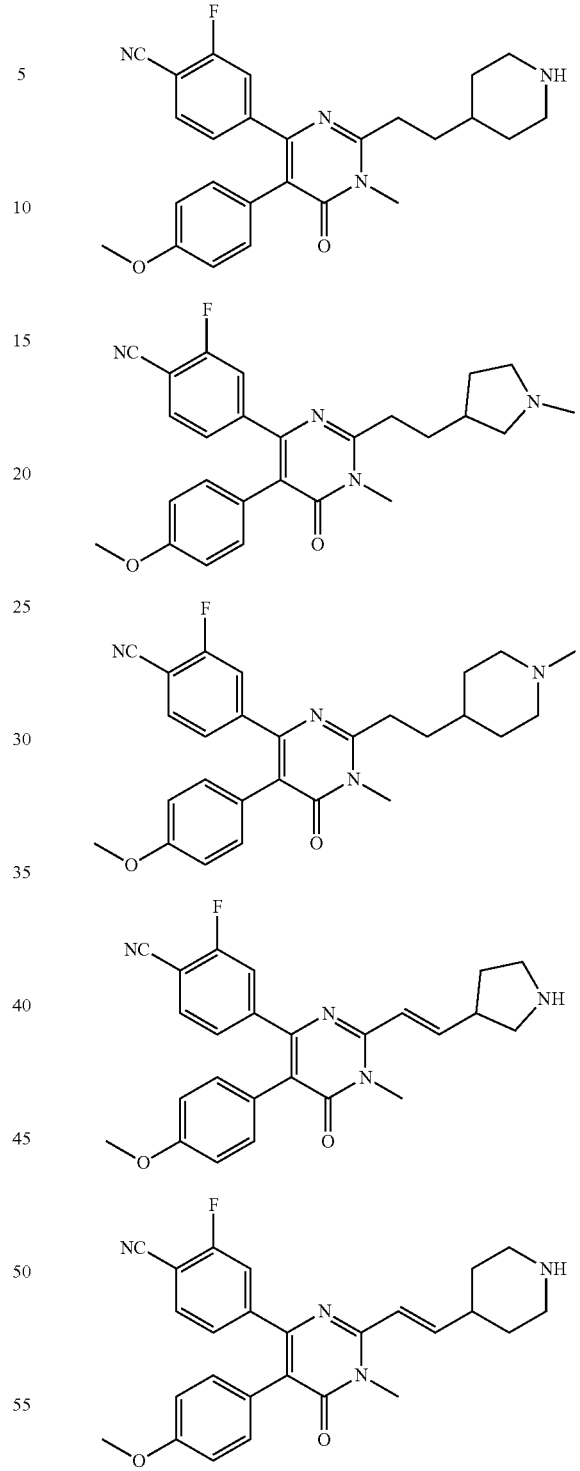

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, UT), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, SYNTHETIC ORGANIC CHEMISTRY, John Wiley & Sons, Inc., New York; S. R. Sandler et al., ORGANIC FUNCTIONAL GROUP PREPARATIONS, 2nd Ed., Academic Press, New York, 1983; H. O. House, MODERN SYNTHETIC REACTIONS, 2nd Ed., W. A. Benjamin, Inc. Menlo Park, Calif. 1972; T. L. Gilchrist, HETEROCYCLIC CHEMISTRY, 2nd Ed., John Wiley & Sons, New York, 1992; J. March, ADVANCED ORGANIC CHEMISTRY: REACTIONS, MECHANISMS & STRUCTURE, 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G., ORGANIC SYNTHESIS: CONCEPTS, METHODS, STARTING MATERIALS, SECOND, REVISED & ENLARGED EDITION (1994) John Wiley & Sons ISBN: 3-527-29074-5; Hoffman, R. V., ORGANIC CHEMISTRY, AN INTERMEDIATE TEXT (1996) Oxford University Press, ISBN 0-19-509618-5; Larock, R. C. COMPREHENSIVE ORGANIC TRANSFORMATIONS: A GUIDE TO FUNCTIONAL GROUP PREPARATION, 2nd Ed. (1999) Wiley-VCH, ISBN: 0-471-19031-4; March, J. ADVANCED ORGANIC CHEMISTRY: REACTIONS, MECHANISMS, & STRUCTURE, 4th Ed. (1992) John Wiley & Sons, ISBN: 0-471-60180-2; Otera, J. (ed.), MODERN CARBONYL CHEMISTRY, (2000) Wiley-VCH, ISBN: 3-527-29871-1; Patai, S., PATAI'S 1992 GUIDE TO THE CHEMISTRY OF FUNCTIONAL GROUPS, (1992) Interscience ISBN: 0-471-93022-9; Solomons, T. W. G., ORGANIC CHEMISTRY, 7th Ed. (2000) John Wiley & Sons, ISBN: 0-471-19095-0; Stowell, J. C., INTERMEDIATE Organic Chemistry, 2nd Ed. (1993) Wiley-Interscience, ISBN: 0-471-57456-2; INDUSTRIAL ORGANIC CHEMICALS: STARTING MATERIALS & INTERMEDIATES: AN ULLMANN'S ENCYCLOPEDIA, (1999) John Wiley & Sons, ISBN: 3-527-29645-X, in 8 volumes; ORGANIC REACTIONS (1942-2000) John Wiley & Sons, in over 55 volumes; and CHEMISTRY OF FUNCTIONAL GROUPS, John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is P. H. Stahl & C. G. Wermuth, HANDBOOK OF PHARMACEUTICAL SALTS, Verlag Helvetica Chimica Acta, Zurich, 2002.

The substituted heterocyclic derivative compounds are prepared by the general synthetic route described below in Scheme 1.

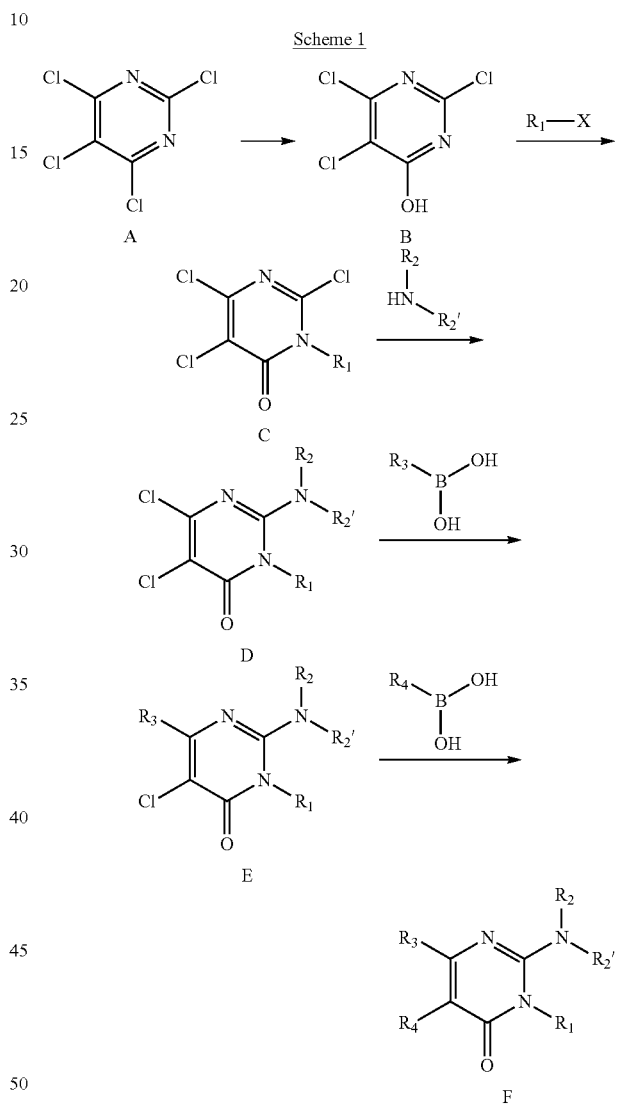

Referring to Scheme 1, molecule A is selectively hydrolyzed to give molecule B. molecule C is obtained from N-alkylation of molecule B with a variety of alkyl halides $R_1$—X. Selective displacement of trichloride molecule C is carried out with a variety of amines $HN(R_2)(R_2')$ under basic conditions to form molecule D. Molecule E is prepared from molecule D under palladium-mediated cross coupling conditions with boronic acids, e.g. $R_3$—$B(OH)_2$, or boronic esters. Molecule F is prepared from compound E under palladium-mediated cross coupling conditions with boronic acids, e.g., $R_3$—$B(OH)_2$, or boronic esters.

Pharmaceutical Compositions of the Substituted Heterocyclic Derivative Compounds In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in REMINGTON: THE SCIENCE & PRACTICE OF PHARMACY (Gennaro, 21st Ed. Mack Pub. Co., Easton, Pa. (2005)).

Provided herein is a pharmaceutical composition comprising at least one substituted heterocyclic derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (Ia), or a pharmaceutically acceptable salt thereof, and a pharmaceutically acceptable excipient. One embodiment provides a pharmaceutical composition comprising a compound of Formula (Ib), or a pharmaceutically acceptable salt thereof, and a pharmaceutically acceptable excipient.

In certain embodiments, the substituted heterocyclic derivative compound as described by Formula (I) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., REMINGTON: THE SCIENCE & PRACTICE OF PHARMACY (Gennaro, 21$^{st}$ Ed. Mack Pub. Co., Easton, Pa. (2005)).

The dose of the composition comprising at least one substituted heterocyclic derivative compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Use of the Substituted Heterocyclic Derivative Compounds

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell. Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which modify histones at various sites.

There are a total of six classes of histones (HI, H2A, H2B, H3, H4, and H5) organized into two groups: core histones (H2A, H2B, H3, and H4) and linker histones (HI and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications are acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

Histone methylation is one of the most important chromatin marks; these play important roles in transcriptional regulation, DNA-damage response, heterochromatin formation and maintenance, and X-chromosome inactivation. A recent discovery also revealed that histone methylation affects the splicing outcome of pre-mRNA by influencing the recruitment of splicing regulators. Histone methylation includes mono-, di-, and tri-methylation of lysines, and mono-, symmetric di-, and asymmetric di-methylation of arginines. These modifications can be either an activating or repressing mark, depending on the site and degree of methylation.

Histone Demethylases

A "demethylase" or "protein demethylase," as referred to herein, refers to an enzyme that removes at least one methyl group from polypeptide. Demethylases comprise a JmjC domain, and can be a methyl-lysine or methyl-arginine demethylase. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD-1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found used a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.
LSD-1

Lysine-specific demethylase 1 (LSD-1) is a histone lysine demethylase that specifically demethylates monomethylated and dimethylated histone H3 at K4 and also demethylates dimethylated histone H3 at K9. Although the main target of LSD-1 appears to be mono- and di-methylated histone lysines, specifically H3K4 and H3K9, there is evidence in the literature that LSD-1 can demethylate methylated lysines on non-histone proteins like p53, E2F1, Dnmt1 and STAT3.

LSD-1 has a fair degree of structural similarity and amino acid identity/homology to polyamine oxidases and monoamine oxidases, all of which (i.e., MAO-A, MAO-B and LSD-1) are flavin dependent amine oxidases which catalyze the oxidation of nitrogen-hydrogen bonds and/or nitrogen-carbon bonds. LSD-1 also includes an N-terminal SWRIM domain. There are two transcript variants of LSD-1 produced by alternative splicing.

In some embodiments, the compounds disclosed herein are capable of inhibiting LSD-1 activity in a biological sample by contacting the biological sample with a substituted heterocyclic compound as disclosed herein. In some embodiments, a substituted heterocyclic compound as disclosed herein is capable of modulating the level of histone-4 lysine-3 methylation in the biological sample. In some embodiments, a substituted heterocyclic compound as disclosed herein is capable of modulating histone-3 lysine-9 methylation levels in the biological sample.

The substituted heterocyclic compounds disclosed herein lack significant MAO-A or MAO-B inhibitory activity. In some embodiments, a substituted heterocyclic compound as disclosed herein inhibits LSD-1 inhibitory activity to a greater extent than MAO-A and/or MAO-B inhibitory activity.

One embodiment provides a method of regulating gene transcription in a cell comprising inhibiting lysine-specific demethylase 1 activity by exposing the lysine-specific demethylase 1 enzyme to a compound of Formula (I). One embodiment provides a method of regulating gene transcription in a cell comprising inhibiting lysine-specific demethylase 1 activity by exposing the lysine-specific demethylase 1 enzyme to a compound of Formula (Ia). One embodiment provides a method of regulating gene transcription in a cell comprising inhibiting lysine-specific demethylase 1 activity by exposing the lysine-specific demethylase 1 enzyme to a compound of Formula (Ib).
Methods of Treatment Disclosed herein are methods of modulating demethylation in a cell or in a subject, either generally or with respect to one or more specific target genes. Demethylation is modulated to control a variety of cellular functions, including without limitation: differentiation; proliferation; apoptosis; tumorigenesis, leukemogenesis or other oncogenic transformation events; hair loss; or sexual differentiation.

One embodiment provides a method of treating cancer in a patient in need thereof, comprising administering to the patient a compound of Formula (I), or a pharmaceutically acceptable salt thereof. One embodiment provides a method of treating cancer in a patient in need thereof, comprising administering to the patient a compound of Formula (Ia), or a pharmaceutically acceptable salt thereof. One embodiment provides a method of treating cancer in a patient in need thereof, comprising administering to the patient a compound of Formula (Ib), or a pharmaceutically acceptable salt thereof.

In a further embodiment methods are provided for the treatment of relapsed and/or refractory solid tumors (including neuroendocrine carcinomas (NEC)) and non-Hodgkin's lymphomas (NHLs) and the like, using substituted heterocyclic derivative compounds and pharmaceutical compositions comprising compounds useful for the inhibition of lysine specific demethylase-1 (LSD-1). Relapse refers to the return of a disease or the signs and symptoms of a disease after a period of improvement. Refractory refers to a disease or condition that does not respond to treatment. Refrcatory cancer refers cancer that does not respond to treatment and includes circumstances where the cancer may be resistant at the beginning of treatment or the cancer becomes resistant during treatment.

A neuroendocrine tumor begins in the hormone-producing cells of the body's neuroendocrine system, which is made up of cells that are a cross between traditional hormone-producing endocrine cells and nerve cells. Neuroendocrine cells are found throughout the body in organs such as the lungs and gastrointestinal tract, including the stomach and intestines. They perform specific functions, such as regulating the air and blood flow through the lungs and controlling the speed at which food is moved through the gastrointestinal tract. There are many types of neuroendocrine tumors, including three specific types: pheochromocytoma, Merkel cell cancer, and neuroendocrine carcinoma.

Pheochromocytoma is a rare tumor that begins in the chromaffin cells of the adrenal gland. These specialized cells release the hormone adrenaline during times of stress. Pheochromocytoma most often occurs in the adrenal medulla, the area inside the adrenal glands. This type of tumor increases the production of the hormones adrenaline and noradrenaline, which increase blood pressure and heart rate. Even though a pheochromocytoma is usually benign, it may still be life-threatening because the tumor may release large amounts of adrenaline into the bloodstream after injury. Eighty percent (80%) of people with pheochromocytoma have a tumor on only one adrenal gland, 10% have tumors on both glands, and 10% have a tumor outside the adrenal glands.

Merkel cell cancer, also called neuroendocrine carcinoma of the skin or trabular cancer, is a highly aggressive (fast-growing), rare cancer. It starts in hormone-producing cells just beneath the skin and in the hair follicles, and it is found in the head and neck region.

Approximately 60% of neuroendocrine tumors cannot be described as a specific type of cancer other than neuroendocrine carcinoma. Neuroendocrine carcinoma can start in a number of places in the body, including the lungs, brain, and gastrointestinal tract.

Symptoms of neuroendocrine carcinoma can include: Hyperglycemia (too much sugar in the blood); Hypoglycemia (too little sugar in the blood); Diarrhea; Persistent pain in a specific area; Loss of appetite/weight loss; Persistent cough or hoarseness; Thickening or lump in any part of the body; Changes in bowel or bladder habits; Unexplained weight gain or loss; Jaundice (yellowing of the skin); Unusual bleeding or discharge; Persistent fever or night sweats; Headache; Anxiety; and Gastric ulcer disease.

Non-Hodgkin lymphoma (NHL) is a disease in which malignant (cancer) cells form in the lymph system. There are many different types of NHL that form from different types of white blood cells (B-cells, T-cells, NK cells). Most types of NHL form from B-cells. NHL may be indolent (slow-growing) or aggressive (fast-growing). The most common types of NHL in adults are diffuse large B-cell lymphoma, which is usually aggressive, and follicular lymphoma, which is usually indolent. Mycosis fungoides and the Sézary syndrome are types of NHL that start in white blood cells in the skin. Primary central nervous system lymphoma is a rare type of NHL that starts in white blood cells in the brain, spinal cord, or eye.

Non-Hodgkin lymphoma grows and spreads at different rates and can be indolent or aggressive. Indolent lymphoma tends to grow and spread slowly, and has few signs and symptoms. Aggressive lymphoma grows and spreads quickly, and has signs and symptoms that can be severe.

Indolent NHL may include follicular lymphoma, lymphoplasmacytic lymphoma, marginal zone lymphoma, monocytoid B cell lymphoma, gastric mucosa-associated lymphoid tissue (MALT) lymphoma, extragastric MALT lymphoma, Mediterranean abdominal lymphoma, splenic marginal zone lymphoma, and primary cutaneous anaplastic large cell lymphoma. Aggressive NHL may include diffuse large B-cell lymphoma, primary mediastinal large B-cell lymphoma, follicular large cell lymphoma, stage III, anaplastic large cell lymphoma (including cutaneous anaplastic large cell lymphoma and systemic anaplastic large cell lymphoma), extranodal NK-/T-cell lymphoma, lymphomatoid granulomatosis, angioimmunoblastic T-cell lymphoma, peripheral T-cell lymphoma, hepatosplenic T-cell lymphoma, subcutaneous panniculitis-like T-cell lymphoma, enteropathy-type intestinal T-cell lymphoma, intravascular large B-cell lymphoma, Burkitt lymphoma, lymphoblastic lymphoma, adult T-cell leukemia/lymphoma, mantle cell lymphoma, posttransplantation lymphoproliferative disorder, true histiocytic lymphoma, primary effusion lymphoma, and plasmablastic lymphoma.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1A: 2,5,6-trichloropyrimidin-4-ol

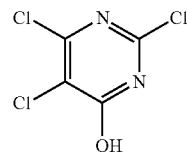

To a solution of 2,4,5,6-tetrachloropyrimidine (5 g, 22.9 mmol) in THF (50 mL) was added 1N NaOH (31 mL, 31.2 mmol) dropwise, and the mixture was stirred overnight at RT. The solution was acidified with 1N HCl and extracted with DCM (3×). The organics were combined, dried, and concentrated in vacuo. The solids were slurried in Et$_2$O for 30 min at RT, filtered, washed with Et$_2$O, and dried to give 3.0 g (66%) of the title compound. [M+H] Calc'd for C$_4$HCl$_3$N$_2$O, 201; Found, 201.

Preparation 1B:
2,5,6-trichloro-3-methyl-3-hydropyrimidin-4-one

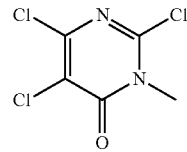

To a mixture of 2,5,6-trichloropyrimidin-4-ol (1 g, 5.0 mmol) and K$_2$CO$_3$ (759 mg, 5.5 mmol) in THF (50 mL) at 0° C. was added iodomethane (714 mg, 5.0 mmol) dropwise, and the reaction was stirred at RT overnight. The reaction mixture was diluted with ethyl acetate (EA). The organic phase was washed with brine, dried and concentrated in vacuo. The residue was purified by silica gel chromatography (10:1, PE:EA) to give 760 mg (71%) of the title compound. $^1$H NMR (400 MHz, CDCl$_3$): δ 3.74 (s, 3H). [M+H] Calc'd for C$_5$H$_3$C$_{13}$N$_2$O, 213; Found, 213.

Preparation 1C: N-[1-(5,6-dichloro-3-methyl-4-oxo (3-hydropyrimidin-2-yl)) (4-piperidyl)](tert-butoxy) carboxamide

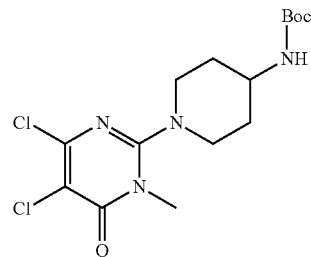 [SMILES: Cn1c(N2CCC(NC(=O)OC(C)(C)C)CC2)nc(Cl)c(Cl)c1=O]

A solution of 2,5,6-trichloro-3-methyl-3-hydropyrimidin-4-one (426 mg, 2.0 mmol), DIEA (536 mg, 4.0 mmol) and tert-butyl piperidin-4-ylcarbamate (400 mg, 2 mmol) in DMF (10 mL) was heated at 120° C. for 1 h. The solvent was removed in vacuo and the residue was purified by silica gel chromatography (1:1, PE:EA) to give 550 mg (73%) of the title compound. ¹H NMR (400 MHz, CDCl₃): δ 1.45 (s, 9H), 1.50-1.58 (m, 2H), 2.06-2.10 (m, 2H), 2.98-3.05 (m, 2H), 3.48 (s, 3H), 3.53-3.56 (m, 2H), 3.70 (s, 1H), 4.52 (s, 1H). [M+H] Calc'd for C₁₅H₂₂Cl₂N₄O₃, 213; Found, 213.

Preparation 1D: tert-butyl 1-(5-chloro-4-(4-cyanophenyl)-1-methyl-6-oxo-1,6-dihydropyrimidin-2-yl)piperidin-4-ylcarbamate

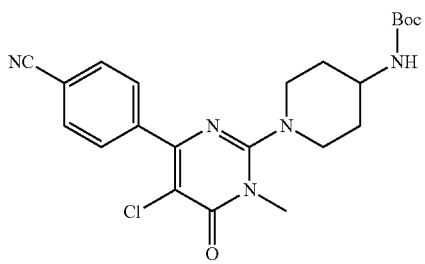 [SMILES: Cn1c(N2CCC(NC(=O)OC(C)(C)C)CC2)nc(-c2ccc(C#N)cc2)c(Cl)c1=O]

A mixture of N-[1-(5,6-dichloro-3-methyl-4-oxo(3-hydropyrimidin-2-yl))(4-piperidyl)](tert-butoxy)carboxamide (500 mg, 1.3 mmol), 4-cyanophenylboronic acid (195 mg, 1.3 mmol), [1,1'-bis(di-tert-butylphosphino)ferrocene]dichloropalladium(II) (81 mg, 0.13 mmol) and K₂CO₃ (359 mg, 2.6 mmol) in DMF (10 mL) was flushed with nitrogen and stirred at 85° C. for 2 h. Water was added, and the mixture was extracted with EA (3×). The organics were combined, washed with water, washed with brine, dried and concentrated in vacuo. The residue was purified purified by silica chromatography (1:1, EA:PE) to give 250 mg (40%) of the title compound. ¹H NMR (400 MHz, CDCl₃): δ 1.45 (s, 9H), 1.54-1.61 (m, 2H), 2.05-2.10 (m, 2H), 2.99-3.05 (m, 2H), 3.48-3.56 (s, 5H), 3.70 (s, 1H), 4.56 (s, 1H), 7.73 (d, J=8.0 Hz, 2H), 7.93 (d, J=8.0 Hz, 2H). [M+H] Calc'd for C₂₂H₂₆ClN₅O₃, 444; Found, 444.

Preparation 1E: tert-butyl 1-(4-(4-cyanophenyl)-1-methyl-6-oxo-5-p-tolyl-1,6-dihydropyrimidin-2-yl)piperidin-4-ylcarbamate

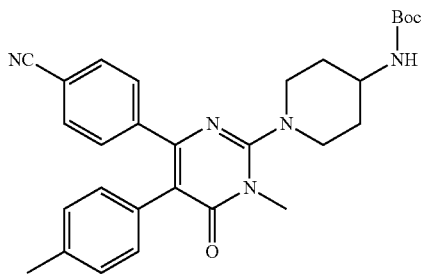 [SMILES: Cc1ccc(-c2c(-c3ccc(C#N)cc3)nc(N3CCC(NC(=O)OC(C)(C)C)CC3)n(C)c2=O)cc1]

A mixture of tert-butyl 1-(5-chloro-4-(4-cyanophenyl)-1-methyl-6-oxo-1,6-dihydropyrimidin-2-yl)piperidin-4-ylcarbamate (200 mg, 0.45 mmol), p-tolylboronic acid (123 mg, 0.90 mmol), [1,1'-bis(di-tert-butylphosphino)ferrocene]dichloropalladium(II) (28 mg, 0.045 mol) and K₂CO₃ (124 mg, 0.90 mmol) in DMF (10 mL) was flushed with nitrogen and stirred at 85° C. for 2 h. Water was added, and the mixture was extracted with EA (3×). The organics were combined, washed with water, washed with brine, dried and concentrated in vacuo. The residue was purified by silica chromatography (1:1, EA:PE) to give 50 mg (22%) of the title compound. [M+H] Calc'd for C₂₉H₃₃N₅O₃, 500; Found, 500.

Example 1: 4-(2-(4-aminopiperidin-1-yl)-1-methyl-6-oxo-5-p-tolyl-1,6-dihydropyrimidin-4-yl)benzonitrile, HCl salt

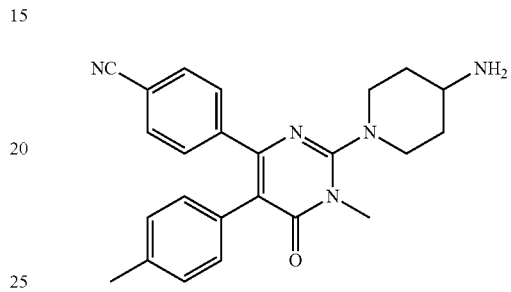

To a solution of tert-butyl 1-(4-(4-cyanophenyl)-1-methyl-6-oxo-5-p-tolyl-1,6-dihydro pyrimidin-2-yl)piperidin-4-ylcarbamate (50 mg, 0.1 mmol) in EA (10 mL) was added a 4N HCl solution in EA (5 mL) and the mixture was stirred at RT for 2 h. The solvent was concentrated in vacuo, and the residue was purified by preparative HPLC to give 20 mg (46%) of the title compound as the hydrochloride salt. ¹H NMR (400 MHz, CDCl₃): δ 1.74-1.79 (m, 2H), 2.00-2.04 (m, 2H), 2.21 (s, 3H), 2.96-3.03 (m, 2H), 3.29-3.03 (m, 1H), 3.48 (s, 3H), 3.71-3.74 (m, 2H), 6.89 (d, J=8.0 Hz, 2H), 6.99 (d, J=8.0 Hz, 2H), 7.38 (d, J=8.0 Hz, 2H), 7.44 (d, J=8.4 Hz, 2H). [M+H] Calc'd for C₂₄H₂₅N₅O, 400; Found, 400.

Example 2: 4-[2-(4-amino-piperidin-1-yl)-5-(4-methoxy-phenyl)-1-methyl-6-oxo-1,6-dihydro-pyrimidin-4-yl]-benzonitrile

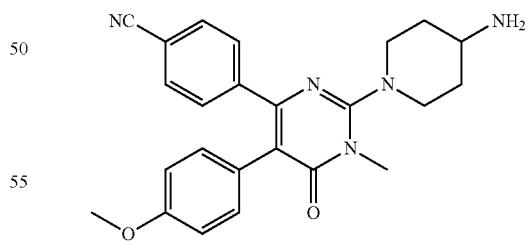

The title compound was prepared as the hydrochloride salt in 5% overall yield according to the general procedure for the preparation of Example 1. ¹H NMR (400 MHz, CD₃OD): δ 1.74-1.78 (m, 2H), 2.00-2.03 (m, 2H), 2.98-3.02 (m, 2H), 3.26-3.00 (m, 1H), 3.48 (s, 3H), 3.69 (s, 3H), 3.70-3.73 (m, 2H), 6.72 (d, J=8.8 Hz, 2H), 6.93 (d, J=8.4 Hz, 2H), 7.39 (d, J=8.0 Hz, 2H), 7.46 (d, J=8.0 Hz, 2H). [M+H] Calc'd for C₂₄H₂₅N₅O₂, 416; Found, 416.

Example 3: 4-[2-(4-amino-piperidin-1-yl)-5-(6-methoxy-pyridin-3-yl)-1-methyl-6-oxo-1,6-dihydro-pyrimidin-4-yl]-benzonitrile

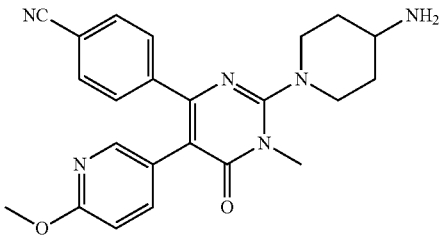 [SMILES: COc1ccc(-c2c(-c3ccc(C#N)cc3)nc(N3CCC(N)CC3)n(C)c2=O)cn1]

The title compound was prepared as the hydrochloride salt in 11% overall yield according to the general procedure for the preparation of Example 1. $^1$H NMR (400 MHz, CD$_3$OD): δ 1.87-1.95 (m, 2H), 2.14-2.17 (m, 2H), 3.15-3.24 (m, 2H), 3.43-3.48 (m, 1H), 3.62 (s, 3H), 3.93-3.98 (m, 2H), 4.23 (s, 3H), 7.46 (d, J=9.2 Hz, 1H), 7.63 (d, J=8.0 Hz, 2H), 7.71 (d, J=8.4 Hz, 2H), 8.12 (dd, J=8.8, 1.6 Hz, 1H), 8.28 (d, J=2.0 Hz, 1H). [M+H] Calc'd for C$_{23}$H$_{24}$N$_6$O$_2$, 417; Found, 417.

Example 4: 4-[2-(4-amino-piperidin-1-yl)-1-methyl-5-(6-methyl-pyridin-3-yl)-6-oxo-1,6-dihydro-pyrimidin-4-yl]-benzonitrile

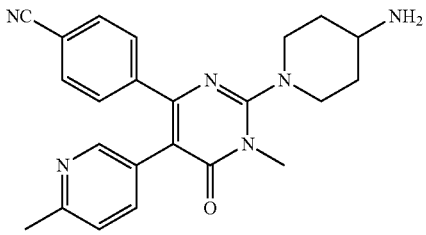

The title compound was prepared as the hydrochloride salt in 4% overall yield according to the general procedure for the preparation of Example 1. $^1$H NMR (400 MHz, CD$_3$OD): δ 1.79-1.80 (m, 2H), 2.03-2.05 (m, 2H), 2.66 (s, 3H), 3.04-3.09 (m, 2H), 3.30-3.34 (m, 1H), 3.50 (s, 3H), 3.83-3.88 (m, 2H), 7.48 (d, J=8.4 Hz, 2H), 7.58 (d, J=8.4 Hz, 2H), 7.64 (d, J=8.4 Hz, 1H), 8.00 (dd, J=8.4, 2.0 Hz, 1H), 8.54 (d, J=8.0 Hz, 1H). [M+H] Calc'd for C$_{23}$H$_{24}$N$_6$O, 401; Found, 401.

Example 5: 4-[2-(4-amino-piperidin-1-yl)-5-(4-methoxy-phenyl)-1-methyl-6-oxo-1,6-dihydro-pyrimidin-4-yl]-benzonitrile

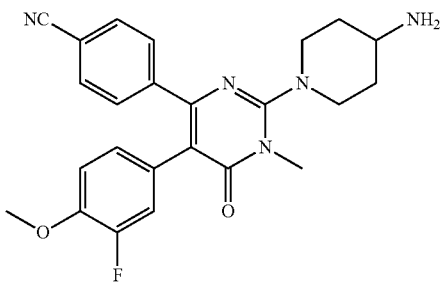 [SMILES: COc1ccc(-c2c(-c3ccc(C#N)cc3)nc(N3CCC(N)CC3)n(C)c2=O)cc1F]

The title compound was prepared as the hydrochloride salt in 7% overall yield according to the general procedure for the preparation of Example 1. $^1$H NMR (400 MHz, CD$_3$OD): δ 1.89-1.95 (m, 2H), 2.15-2.18 (m, 2H), 3.14-3.18 (m, 2H), 3.44-3.46 (m, 1H), 3.60 (s, 3H), 3.88-3.90 (m, 5H), 6.79 (d, J=8.4 Hz, 1H), 6.96-7.02 (m, 2H), 7.54 (d, J=8.0 Hz, 2H), 7.64 (d, J=8.0 Hz, 2H). [M+H] Calc'd for C$_{24}$H$_{24}$FN$_5$O$_2$, 434; Found, 434.

Example 6: 4-[2-(4-amino-piperidin-1-yl)-5-(4-methoxy-phenyl)-1-methyl-6-oxo-1,6-dihydro-pyrimidin-4-yl]-2-fluoro-benzonitrile

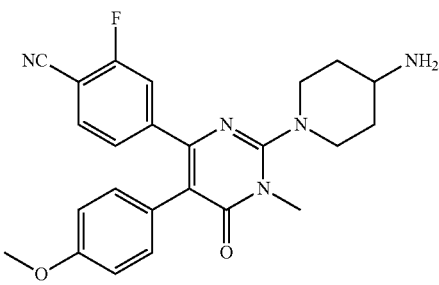 [SMILES: COc1ccc(-c2c(-c3ccc(C#N)c(F)c3)nc(N3CCC(N)CC3)n(C)c2=O)cc1]

The title compound was prepared as the hydrochloride salt in 5% overall yield according to the general procedure for the preparation of Example 1. $^1$H NMR (400 MHz, CD$_3$OD): δ 1.83-1.89 (m, 2H), 2.10-2.13 (m, 2H), 3.05-3.11 (m, 2H), 3.35-3.38 (m, 1H), 3.55 (s, 3H), 3.76 (s, 3H), 3.77-3.82 (m, 2H), 6.84 (d, J=8.8 Hz, 2H), 7.04 (d, J=8.8 Hz, 2H), 7.21 (d, J=8.0 Hz, 1H), 7.35 (d, J=8.0 Hz, 1H), 7.53-7.56 (m, 1H). [M+H] Calc'd for C$_{24}$H$_{24}$FN$_5$O$_2$, 434; Found, 434.

Preparation 7A: tert-butyl 1-(5-chloro-4-(3-fluoro-4-cyanophenyl)-1-methyl-6-oxo-1,6-dihydropyrimidin-2-yl)piperidin-4-ylcarbamate

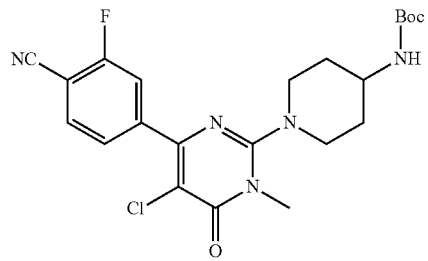 [SMILES: Cn1c(N2CCC(NC(=O)OC(C)(C)C)CC2)nc(-c2ccc(C#N)c(F)c2)c(Cl)c1=O]

A mixture of N-[1-(5,6-dichloro-3-methyl-4-oxo(3-hydropyrimidin-2-yl))(4-piperidyl)](tert-butoxy)carboxamide (150 g, 0.40 mol), 3-fluoro-4-cyanophenylboronic acid (65.8 g, 0.40 mol), Pd(Ph$_3$P)$_4$ (9.3 g, 8 mmol) and 0.4 N Na$_2$CO$_3$ (2 L, 0.80 mol) in ACN (4 L) was flushed with nitrogen and stirred at 85° C. for 2 h. Water was added and the mixture was extracted with EA (3×). The organics were combined, washed with water, washed with brine, dried and concentrated in vacuo. The residue was purified purified by silica chromatography (1:1, EA:PE) to give 95 g (57%) of the title compound. $^1$H NMR (400 MHz, CDCl$_3$): δ 1.45 (s, 9H), 1.54-1.61 (m, 2H), 2.05-2.13 (m, 2H), 2.99-3.08 (m, 2H), 3.53-3.58 (s, 5H), 3.70 (s, 1H), 4.54 (d, J=6.0 Hz, 1H), 7.68-7.80 (m, 3H).

Preparation 7B: tert-butyl N-[1-[4-(4-cyano-3-fluorophenyl)-5-(3-fluoro-4-methoxyphenyl)-1-methyl-6-oxopyrimidin-2-yl]piperidin-4-yl]carbamate

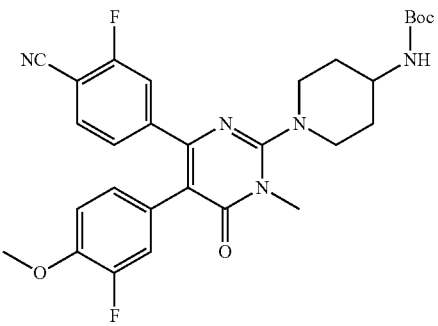 [SMILES: COc1ccc(-c2c(-c3ccc(C#N)c(F)c3)nc(N3CCC(NC(=O)OC(C)(C)C)CC3)n(C)c2=O)cc1F]

A mixture of (tert-butoxy)-N-{1-[5-chloro-6-(4-cyano-3-fluorophenyl)-3-methyl-4-oxo(3-hydropyrimidin-2-yl)](4-piperidyl)}carboxamide (1 g, 2.169 mmol), 3-fluoro-4-methoxy benzeneboronic acid (740 mg, 4.338 mmol), Pd(dppf)Cl$_2$ (480 mg, 0.651 mmol) and Na$_2$CO$_3$ (690 mg, 6.51 mmol) in dioxane:H$_2$O (3:1, 15 mL) was flushed with nitrogen, capped and stirred at 145° C. for 2 h in the microwave. The reaction mixture was concentrated and the residue was purified by FC (1:1, EA:PE) to give 800 mg (71%) of the title compound. [M+H] Calc'd for C$_{29}$H$_{31}$F$_2$N$_5$O$_4$, 552; Found, 552. $^1$H NMR (400 MHz, CDCl$_3$): δ ppm 1.46 (s, 9H), 1.60 (d, J=10.11 Hz, 2H), 2.11 (d, J=11.62 Hz, 2H), 3.06 (t, J=12.00 Hz, 2H), 3.54 (s, 3H), 3.60 (d, J=13.64 Hz, 2H), 3.72 (br. s., 1H), 3.88 (s, 3H), 4.52 (br. s., 1H), 6.79-6.89 (m, 2H), 6.97 (d, J=12.38 Hz, 1H), 7.13 (d, J=8.34 Hz, 1H), 7.31 (d, J=9.85 Hz, 1H), 7.42 (br. s., 1 H).

Example 7: 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile (Compound A)

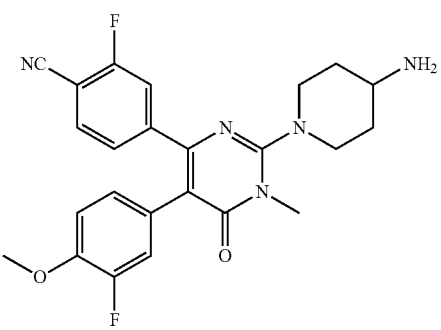 [SMILES: COc1ccc(-c2c(-c3ccc(C#N)c(F)c3)nc(N3CCC(N)CC3)n(C)c2=O)cc1F]

To a solution of tert-butyl N-[1-[4-(4-cyano-3-fluorophenyl)-5-(3-fluoro-4-methoxyphenyl)-1-methyl-6-oxopyrimidin-2-yl]piperidin-4-yl]carbamate (5.2 g, 9.44 mmol) in EA (20 mL) was added a 1N HCl in EA (30 mL). The mixture was stirred at RT for 2 h. The solvent was concentrated in vacuo to give the title product as the HCl salt (4.05 g, 88%). $^1$H NMR (400 MHz, CD$_3$OD): δ 1.77-1.79 (m, 2H), 2.02-2.04 (m, 2H), 2.99-3.04 (m, 2H), 3.26-3.00 (m, 1H), 3.38 (s, 3H), 3.73 (s, 3H), 3.73-3.75 (m, 2H), 6.67-6.68 (m, 1H), 6.84-6.95 (m, 2H), 7.12-7.14 (m, 1H), 7.24-7.36 (m, 1H), 7.46-7.50 (m, 1H). [M+H] Calc'd for C$_{24}$H$_{23}$F$_2$N$_5$O$_2$, 452; Found, 452.

Example 8: 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile

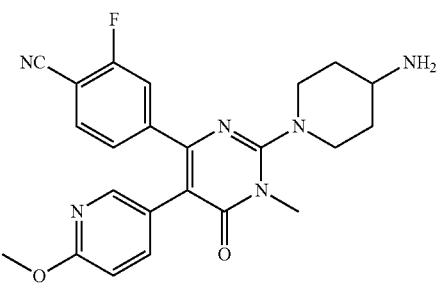 [SMILES: COc1ccc(-c2c(-c3ccc(C#N)c(F)c3)nc(N3CCC(N)CC3)n(C)c2=O)cn1]

The title compound was prepared as the hydrochloride salt in 6% overall yield according to the general procedure for the preparation of Example 1. $^1$H NMR (400 MHz, CD$_3$OD): δ 1.79-1.83 (m, 2H), 2.02-2.06 (m, 2H), 3.04-3.11 (m, 2H), 3.21-3.22 (m, 1H), 3.49 (s, 3H), 3.81-3.85 (m, 2H), 4.12 (s, 3H), 7.22-7.24 (m, 1H), 7.38 (d, J=9.2 Hz, 1H), 7.49 (d, J=9.2 Hz, 1H), 7.57-7.61 (m, 1H), 8.04-8.07 (m, 1H), 8.21 (s, 1H). [M+H] Calc'd for C$_{23}$H$_{23}$FN$_6$O$_2$, 435; Found, 435.

Example 9: 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile

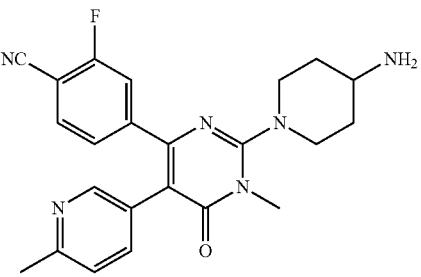 [SMILES: Cc1ccc(-c2c(-c3ccc(C#N)c(F)c3)nc(N3CCC(N)CC3)n(C)c2=O)cn1]

The title compound was prepared as the hydrochloride salt in 8% overall yield according to the general procedure for the preparation of Example 1. $^1$H NMR (400 MHz, CD$_3$OD): δ 1.92-1.96 (m, 2H), 2.16-2.19 (m, 2H), 2.80 (s, 3H), 3.19-3.25 (m, 2H), 3.45-3.49 (m, 1H), 3.62 (s, 3H), 3.96-3.99 (m, 2H), 7.34 (d, J=8.0 Hz, 1H), 7.60 (d, J=7.2 Hz, 1H), 7.71 (t, J=7.6 Hz, 1H), 7.80 (d, J=8.4 Hz, 1H), 8.18 (d, J=8.4 Hz, 1H), 8.71 (s, 1H). [M+H] Calc'd for C$_{23}$H$_{23}$FN$_6$O, 419; Found, 419.

Example 10: 4-[2-(4-amino-piperidin-1-yl)-5-(6-ethyl-pyridin-3-yl)-1-methyl-6-oxo-1,6-dihydro-pyrimidin-4-yl]-benzonitrile

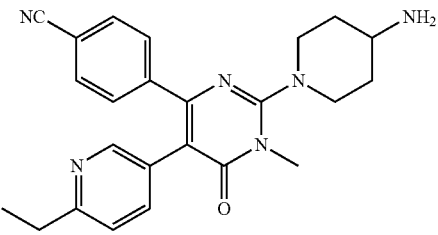 [SMILES: CCc1ccc(-c2c(-c3ccc(C#N)cc3)nc(N3CCC(N)CC3)n(C)c2=O)cn1]

The title compound was prepared as the hydrochloride salt in 7% overall yield according to the general procedure for the preparation of Example 1. $^1$H NMR (400 MHz, CD$_3$OD): δ 1.30 (t, J=4.0 Hz, 3H), 1.83-1.88 (m, 2H), 2.06-2.09 (m, 2H), 2.96-2.99 (m, 2H), 3.09-3.16 (m, 2H), 3.26-3.31 (m, 1H), 3.51 (s, 3H), 3.86-3.89 (m, 2H), 7.35 (d, J=8.0 Hz, 2H), 7.61 (d, J=8.0 Hz, 2H), 7.71 (d, J=8.4 Hz, 1H), 8.08 (d, J=8.4 Hz, 1H), 8.57 (s, 1H). [M+H] Calc'd for C$_{24}$H$_{26}$N$_6$O, 415; Found, 415.

Example 11: 2-fluoro-4-[5-(4-methoxy-phenyl)-1-methyl-2-(4-methylamino-piperidin-1-yl)-6-oxo-1,6-dihydro-pyrimidin-4-yl]-benzonitrile

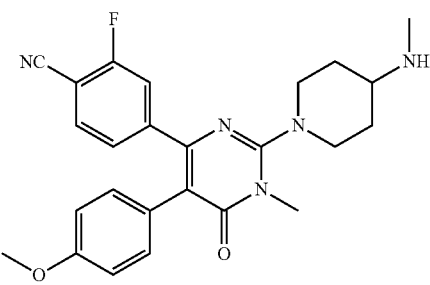

The title compound was prepared as the hydrochloride salt in 7% overall yield according to the general procedure for the preparation of Example 1. $^1$H NMR (400 MHz, CD$_3$OD): δ 1.80-1.90 (m, 2H), 2.19-2.23 (m, 2H), 2.75 (s, 3H), 3.06-3.12 (m, 2H), 3.32-3.36 (m, 1H), 3.56 (s, 3H), 3.76 (s, 3H), 3.84-3.87 (m, 2H), 6.84 (d, J=8.4 Hz, 2H), 7.04 (d, J=8.4 Hz, 2H), 7.22 (d, J=8.0 Hz, 1H), 7.36 (d, J=10.8 Hz, 1H), 8.54-7.58 (m, 1H). [M+H] Calc'd for C$_{25}$H$_{26}$FN$_5$O$_2$, 448; Found, 448.

Example 12: 2-fluoro-4-[5-(3-fluoro-4-methoxy-phenyl)-1-methyl-2-(4-methylamino-piperidin-1-yl)-6-oxo-1,6-dihydro-pyrimidin-4-yl]-benzonitrile

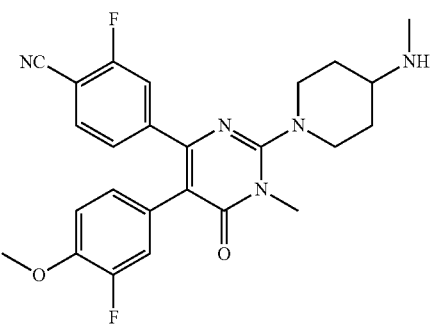

The title compound was prepared as the hydrochloride salt in 7% overall yield according to the general procedure for the preparation of Example 1. $^1$H NMR (400 MHz, CD$_3$OD): δ 1.78-1.88 (m, 2H), 2.17-2.20 (m, 2H), 2.73 (s, 3H), 3.05-3.11 (m, 2H), 3.30-3.35 (m, 1H), 3.54 (s, 3H), 3.82 (s, 3H), 3.83-3.86 (m, 2H), 6.76 (d, J=8.4 Hz, 1H), 6.93-6.99 (m, 2H), 7.20 (d, J=8.4 Hz, 1H), 7.38 (d, J=10.4 Hz, 1H), 8.55-7.589 (m, 1H). [M+H] Calc'd for C$_{25}$H$_{25}$F$_2$N$_5$O$_2$, 466; Found, 466.

Preparation 13A: 2,6-dichloro-3-ethyl-3H-pyrimidin-4-one

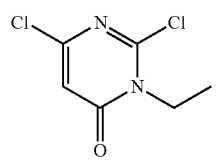

A solution of 2,6-dichloro-pyrimidin-4-ol (1.0 g, 6.1 mmol) and K$_2$CO$_3$ (1.1 g, 7.9 mmol) in DMF (10 mL) was stirred at RT for 15 min. The reaction mixture was cooled to 0° C., and iodoethane (1.1 mL, 6.7 mmol) was added dropwise. After stirring overnight at RT, the reaction mixture was diluted with EA, washed with brine, dried (Na$_2$SO$_4$) and concentrated in vacuo. The residue was purified by silica chromatography (20:1, EA:PE) to give 330 mg (28%) of the title compound. $^1$H NMR (400 MHz, CDCl$_3$): δ 1.37 (t, J=7.6 Hz, 3H), 4.76 (q, J=6.8 Hz, 2H), 6.67 (s, 1H). [M+H] Calc'd for C$_6$H$_6$C$_{12}$N$_2$O, 193, 195, 197; Found, 193, 195, 197.

Preparation 13B: [1-(4-chloro-1-ethyl-6-oxo-1,6-dihydro-pyrimidin-2-yl)-piperidin-4-yl]-carbamic acid tert-butyl ester

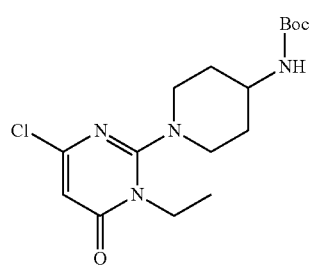 [SMILES: CCn1c(N2CCC(NC(=O)OC(C)(C)C)CC2)nc(Cl)cc1=O]

A solution of 2,6-dichloro-3-ethyl-3H-pyrimidin-4-one (320 mg, 1.64 mmol), DIEA (423 mg, 3.28 mmol) and (tert-butoxy)-N-(4-piperidyl)carboxamide (328 mg, 1.64 mmol) in DMF (10 mL) was heated to 120° C. for 1 h. The solvent was concentrated in vacuo and the residue was purified by silica chromatography (1:5, EA:PE) to give 210 mg (36%) of the title compound as a yellow solid. $^1$H NMR (400 MHz, CDCl$_3$): δ 1.25-1.32 (m 2H), 1.35 (t, J=7.2 Hz, 3H), 1.96-2.02 (m, 2H), 2.98-3.06 (m, 2H), 3.70 (br, 1H), 4.30 (q, J=5.2 Hz, 2H), 4.44 (br, 1H), 4.57-4.61 (m, 2H), 5.95 (s, 1H). [M+H] Calc'd for C$_{16}$H$_{25}$ClN$_4$O$_3$, 357, 359; Found, 357, 359.

Preparation 13C: {1-[4-(4-cyano-3-fluoro-phenyl)-1-ethyl-6-oxo-1,6-dihydro-pyrimidin-2-yl]-piperidin-4-yl}-carbamic acid tert-butyl ester

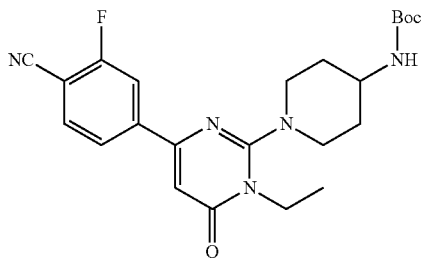 [SMILES: CCn1c(N2CCC(NC(=O)OC(C)(C)C)CC2)nc(-c2ccc(C#N)c(F)c2)cc1=O]

A mixture of [1-(4-chloro-1-ethyl-6-oxo-1,6-dihydro-pyrimidin-2-yl)-piperidin-4-yl]-carbamic acid tert-butyl ester (210 mg, 0.59 mmol) in CH$_3$CN (10 mL), 3-fluoro-4-cyanophenylboronic acid (126 mg, 0.77 mmol), Pd(PPh)$_4$ (14 mg, 0.012 mmol) and 0.4 M Na$_2$CO$_3$ (4.5 mL, 1.77 mmol) was stirred at 90° C. overnight under N$_2$ atmosphere. The organic was concentrated in vacuo, and the aqueous extracted with DCM (2×). The combined organics were washed with brine, dried (Na$_2$SO$_4$) and concentrated. The residue was purified by silica chromatography (1:2, EA:PE) to give 185 mg (64%) of the title compound as a yellow solid. [M+H] Calc'd for C$_{23}$H$_{28}$FN$_5$O$_3$, 442; Found, 442.

Example 13: 4-[2-(4-amino-piperidin-1-yl)-1-ethyl-6-oxo-1,6-dihydro-pyrimidin-4-yl]-2-fluoro-benzonitrile

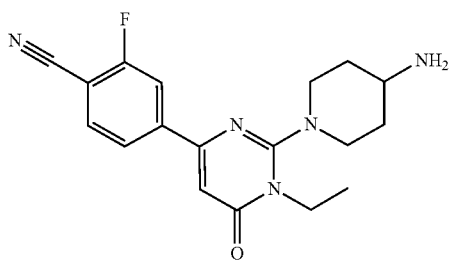 [SMILES: CCn1c(N2CCC(N)CC2)nc(-c2ccc(C#N)c(F)c2)cc1=O]

To a mixture of {1-[4-(4-cyano-3-fluoro-phenyl)-1-ethyl-6-oxo-1,6-dihydro-pyrimidin-2-yl]-piperidin-4-yl}-carbamic acid tert-butyl ester (180 mg, 0.41 mmol) in EA (5 mL) was added a 4 M solution of HCl in EA (3 mL). The reaction mixture was stirred for 30 min. The solvent was evaporated in vacuo to give 150 mg of the titled compound (97%) as a yellow solid (HCl salt). $^1$H NMR (400 MHz, CD$_3$OD): δ 1.28 (t, J=7.2 Hz, 1H), 1.48-1.52 (m, 2H), 1.99-2.02 (m, 2H), 2.94-3.01 (m, 2H), 3.33-3.38 (m, 1H), 6.81 (q, J=6.8 Hz, 2H), 4.85-4.88 (m, 2H), 6.95 (s, 1H), 7.73 (t, J=8.0 Hz, 1H), 7.90-7.95 (m, 2H). [M+H] Calc'd for C$_{18}$H$_{20}$FN$_5$O, 342; Found, 342.

Preparation 14A: {1-[4-(4-cyano-3-fluoro-phenyl)-5-cyclopentylethynyl-1-methyl-6-oxo-1,6-dihydro-pyrimidin-2-yl]-piperidin-4-yl}-carbamic acid tert-butyl ester

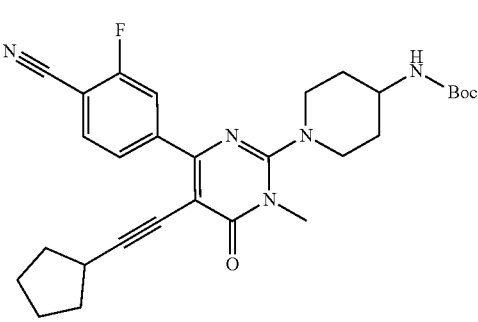 [SMILES: Cn1c(N2CCC(NC(=O)OC(C)(C)C)CC2)nc(-c2ccc(C#N)c(F)c2)c(C#CC2CCCC2)c1=O]

A mixture of tert-butyl 1-(5-chloro-4-(3-fluoro-4-cyano-phenyl)-1-methyl-6-oxo-1,6-dihydropyrimidin-2-yl)piperidin-4-ylcarbamate (200 mg, 0.43 mmol), ethynyl-cyclopentane (82 mg, 0.87 mmol), Pd(MeCN)$_2$Cl$_2$ (4.5 mg, 0.017 mmol), X-Phos (10 mg, 0.022 mmol) and K$_2$CO$_3$ (120 mg, 0.87 mmol) in ACN (15 mL) was stirred overnight at 95° C. in a sealed tube. The reaction mixture was cooled to RT and the solvent was concentrated in vacuo. The residue was purified by silica chromatography (1:2, EA:PE) to give 100 mg (45%) of the title compound. [M+H] Calc'd for C$_{29}$H$_{34}$FN$_5$O$_3$, 519; Found, 519.

Example 14: 4-[2-(4-amino-piperidin-1-yl)-5-cyclopentylethynyl-1-methyl-6-oxo-1,6-dihydro-pyrimidin-4-yl]-2-fluoro-benzonitrile

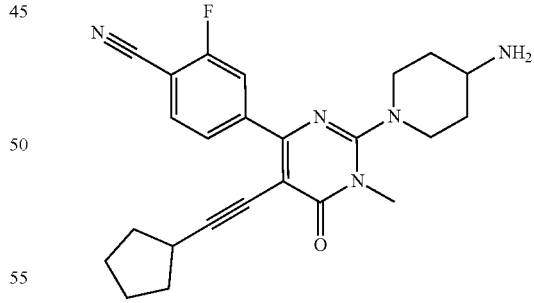

The title compound was prepared as the hydrochloride salt in 70% overall yield according to the general procedure for the preparation of Example 1. $^1$H NMR (400 MHz, CDCl$_3$): δ 1.50-1.74 (m, 8H), 1.94-1.99 (m, 4H), 2.88-3.01 (m, 4H), 3.51 (s, 3H), 3.60 (d, J=13.2 Hz, 2H), 7.63-7.67 (m, 1H), 8.07-8.11 (m, 2H). [M+H] Calc'd for C$_{24}$H$_{26}$FN$_5$O, 419; Found, 419.

127

Preparation 15A:
(2,4,5-trichloro-6-oxo-6H-pyrimidin-1-yl)-acetic acid methyl ester

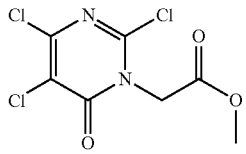

To a solution of 2,5,6-trichloro-3H-pyrimidin-4-one (20.0 g, 0.1 mol) in DMF (150 mL) was added NaH (60% in mineral oil, 6.0 g, 0.12 mol) in portions at 0° C. and the mixture was stirred for 30 min. Bromoacetic acid methyl ester (18.3 g, 0.12 mol) was then added, and the reaction mixture was stirred at RT overnight. The solution was diluted with water (800 mL) and extracted with EA (200 mL, 3×). The combined organics were washed with water (800 mL, 3×), washed with brine (500 mL), dried ($Na_2SO_4$) and concentrated. The residue was purified by silica chromatography (1:50, EA:PE) to give 6.0 g of the title product (22%). $^1$H NMR (400 MHz, $CDCl_3$): δ 3.80 (s, 3H), 5.04 (s, 2H). [M+H] Calc'd for $C_7H_5Cl_3N_2O_3$, 271; Found, 271.

Preparation 15B: [2-(4-tert-butoxycarbonylamino-piperidin-1-yl)-4,5-dichloro-6-oxo-6H-pyrimidin-1-yl]-acetic acid methyl ester

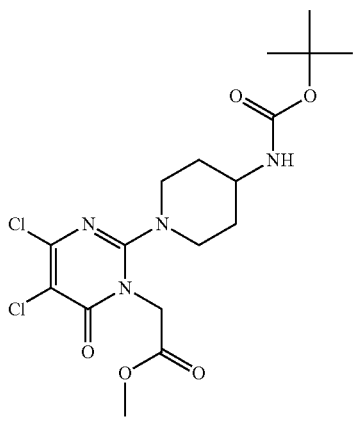 [SMILES: COC(=O)Cn1c(N2CCC(NC(=O)OC(C)(C)C)CC2)nc(Cl)c(Cl)c1=O]

To a solution of (2,4,5-trichloro-6-oxo-6H-pyrimidin-1-yl)-acetic acid methyl ester (6.0 g, 22.4 mmol) and piperidin-4-yl-carbamic acid tert-butyl ester (4.9 g, 24.4 mmol) in DMF (50 mL) was added DIPEA (5.7 g, 44.3 mmol) dropwise at RT, and the mixture was stirred overnight. The reaction mixture was diluted with water (500 mL), and the solids were collected by filtration. The solids were then dissolved in DCM (100 mL), washed with water (100 mL, 3×), washed with brine (100 mL), dried ($Na_2SO_4$) and concentrated. The residue was purified by silica chromatography (1:2 to 1:1, DCM:PE) to give 6.3 g of the title product (64%). $^1$H NMR (400 MHz, $CDCl_3$): δ 1.22-1.34 (m, 2H), 1.45 (s, 9H), 1.97-2.03 (m, 2H), 2.96-3.09 (m, 2H), 3.68-3.69 (m, 1H), 3.75 (s, 3H), 4.42-4.44 (m, 3H), 4.84 (s, 2H). [M+H] Calc'd for $C_{17}H_{24}Cl_2N_4O_5$, 435; Found, 435.

128

Preparation 15C: [2-(4-tert-butoxycarbonylamino-piperidin-1-yl)-5-chloro-4-(4-cyano-3-fluoro-phenyl)-6-oxo-6H-pyrimidin-1-yl]acetic acid methyl ester

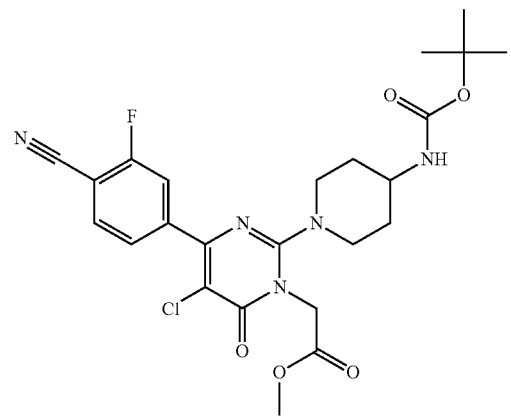 [SMILES: COC(=O)Cn1c(N2CCC(NC(=O)OC(C)(C)C)CC2)nc(-c2ccc(C#N)c(F)c2)c(Cl)c1=O]

A mixture of [2-(4-tert-butoxycarbonylamino-piperidin-1-yl)-4,5-dichloro-6-oxo-6H-pyrimidin-1-yl]-acetic acid methyl ester (5.76 g, 13.2 mmol), 4-cyano-3-fluoro benzeneboronic acid (2.24 g, 16.1 mmol), $Pd(PPh_3)_4$ (306 mmol, 0.26 mmol) and $Na_2CO_3$ (2.8 g, 26.5 mmol) in DMF:$H_2O$ (50 mL:10 mL) was stirred at 65° C. overnight under nitrogen atmosphere. The reaction mixture was concentrated, and the residue was purified by silica chromatography (1:20 to 1:0, EA:PE) to give 2.4 g of the title product (43%). $^1$H NMR (400 MHz, $CDCl_3$): δ 1.27-1.37 (m, 2H), 1.45 (s, 9H), 1.99-2.02 (m, 2H), 2.99-3.06 (m, 2H), 3.68-3.76 (m, 1H), 3.78 (s, 3H), 4.42-4.52 (m, 3H), 4.90 (s, 2H), 7.63-7.66 (m, 1H), 7.67-7.71 (m, 2H). [M+H] Calc'd for $C_{24}H_{27}ClFN_5O_5$, 520; Found, 520.

Preparation 15D: [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic acid methyl ester

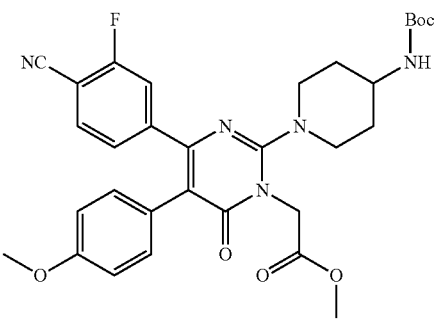 [SMILES: COC(=O)Cn1c(N2CCC(NC(=O)OC(C)(C)C)CC2)nc(-c2ccc(C#N)c(F)c2)c(-c2ccc(OC)cc2)c1=O]

A solution of [2-(4-tert-butoxycarbonylamino-piperidin-1-yl)-5-chloro-4-(4-cyano-3-fluoro-phenyl)-6-oxo-6H-pyrimidin-1-yl]acetic acid methyl ester (2.2 g, 4.2 mmol), p-methoxyboronic acid (1.9 g, 12.7 mmol), Pd-118 (274 mg, 0.42 mmol) and $K_2CO_3$ (1.2 g, 8.4 mmol) in DMF (50 mL) was stirred at 145° C. for 6 h under nitrogen atmosphere. The reaction mixture was diluted with water and extracted with EA (3×). The combined organics were washed with water, washed brine, dried (Na$_2$SO$_4$) and concentrated. The residue was purified by preparative HPLC to give 600 mg of the title product (24%). [M+H] Calc'd for C$_{31}$H$_{34}$FN$_5$O$_6$, 592; Found, 592.

Preparation 15E: 4-[2-(4-amino-piperidin-1-yl)-1-cyclopropylmethyl-6-oxo-1,6-dihydro-pyrimidin-4-yl]-2-fluoro-benzonitrile

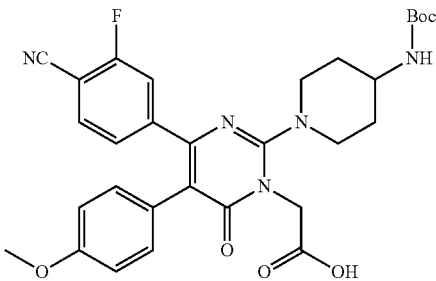 [SMILES: COc1ccc(-c2c(-c3ccc(C#N)c(F)c3)nc(N3CCC(NC(=O)OC(C)(C)C)CC3)n(CC(=O)O)c2=O)cc1]

To a solution of [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic acid methyl ester (600 mg, 1.02 mmol) in MeOH (10 mL) was added a 2N NaOH solution (5 mL). After completion of the reaction, the solution was acidified with 1N HCl and extracted with EA (3×). The combined organics were washed with brine, dried (Na$_2$SO$_4$) and concentrated. The residue was purified by preparative HPLC to give 240 mg of the title product as a yellow solid (41%). [M+H] Calc'd for C$_{30}$H$_{32}$FN$_5$O$_6$, 578; Found, 578.

Example 15: [2-(4-amino-piperidin-1-yl)-4-(4-cyano-3-fluoro-phenyl)-5-(4-methoxy-phenyl)-6-oxo-6H-pyrimidin-1-yl]-acetic acid

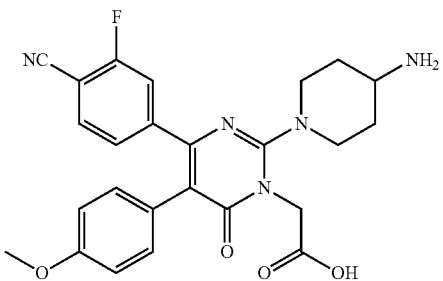 [SMILES: COc1ccc(-c2c(-c3ccc(C#N)c(F)c3)nc(N3CCC(N)CC3)n(CC(=O)O)c2=O)cc1]

To a solution of [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic acid (100 mg, 0.15 mmol) in EA (10 mL) was added a 5N HCl solution in EA (5 mL). The reaction mixture was stirred at RT for 2 h, and the solvent was concentrated in vacuo. The residue was purified by preparative HPLC to give 25 mg of the title product as HCl salt (32%). $^1$H NMR (400 MHz, CD$_3$OD): δ 1.53-1.56 (m, 2H), 2.00-2.03 (m, 2H), 3.00-3.07 (m, 2H), 3.35-3.39 (m, 1H), 3.67 (s, 3H), 4.70 (s, 2H), 4.76-4.77 (m, 2H), 6.74 (d, J=8.4 Hz, 2H), 6.96 (d, J=8.8 Hz, 2H), 7.17 (d, J=8.4 Hz, 1H), 7.26 (d, J=10.0 Hz, 1H), 7.50 (dd, J=7.2, 8.0 Hz, 1H). [M+H] Calc'd for C$_{25}$H$_{24}$FN$_5$O$_4$, 478; Found, 478.

Preparation 16A: {1-[1-carbamoylmethyl-4-(4-cyano-3-fluoro-phenyl)-5-(4-methoxy-phenyl)-6-oxo-1,6-dihydro-pyrimidin-2-yl]-piperidin-4-yl}-carbamic acid tert-butyl ester

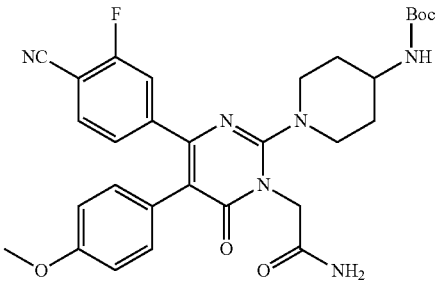 [SMILES: COc1ccc(-c2c(-c3ccc(C#N)c(F)c3)nc(N3CCC(NC(=O)OC(C)(C)C)CC3)n(CC(N)=O)c2=O)cc1]

To a solution of [2-(4-tert-butoxycarbonylamino-piperidin-1-yl)-4-(4-cyano-3-fluoro-phenyl)-5-(4-methoxy-phenyl)-6-oxo-6H-pyrimidin-1-yl]-acetic acid (120 mg, 0.2 mmol) in DMF (5 mL) was added NH$_4$Cl (17 mg, 0.3 mmol), HATU (95 mg, 0.25 mmol) and DIEA (25 mg, 0.4 mmol). After completion of the reaction, the solution was diluted with H$_2$O and extracted with DCM for (3×). The combined organics were dried (Na$_2$SO$_4$) and concentrated. The residue was purified by preparative HPLC to give 50 mg of the title product as a yellow solid (43%). [M+H] Calc'd for C$_{30}$H$_{33}$FN$_6$O$_5$, 577; Found, 577.

Example 16: 2-[2-(4-amino-piperidin-1-yl)-4-(4-cyano-3-fluoro-phenyl)-5-(4-methoxy-phenyl)-6-oxo-6H-pyrimidin-1-yl]-acetamide

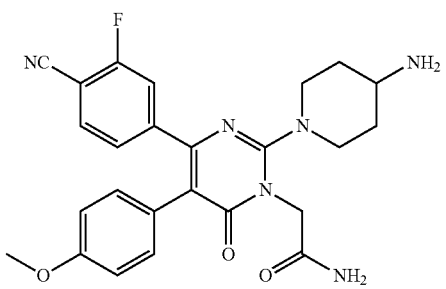 [SMILES: COc1ccc(-c2c(-c3ccc(C#N)c(F)c3)nc(N3CCC(N)CC3)n(CC(N)=O)c2=O)cc1]

The title compound was prepared as the hydrochloride salt in 96% yield according to the procedure for the preparation of Example 15. $^1$H NMR (400 MHz, CD$_3$OD): δ 1.49-1.53 (m, 2H), 1.98-2.01 (m, 2H), 2.97-3.04 (m, 2H), 3.33-3.36 (m, 1H), 3.68 (s, 3H), 4.69 (s, 2H), 4.75-4.78 (m, 2H), 6.75 (d, J=8.4 Hz, 2H), 6.99 (d, J=8.8 Hz, 2H), 7.16 (dd, J=1.2, 8.0 Hz, 1H), 7.25 (dd, J=0.8, 10.4 Hz, 1H), 7.49 (dd, J=7.2, 8.0 Hz, 1H). [M+H] Calc'd for C$_{25}$H$_{25}$FN$_6$O$_3$, 477; Found, 477.

Preparation 17A: 2,6-dichloro-3-(3-methoxy-propyl)-3H-pyrimidin-4-one

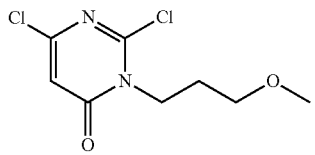

To a solution of 2,6-dichloro-3H-pyrimidin-4-one (600 mg, 3.65 mmol) in DMF (10 mL) was added $K_2CO_3$ (1.0 g, 7.3 mmol) and the mixture was stirred at RT for 10 min. 1-Bromo-3-methoxy-propane (101 mg, 7.3 mmol) was then added dropwise at 0° C., and the mixture was stirred at RT overnight. DMF was concentrated in vacuo, and the residue was purified by silica chromatography to give 400 mg of the title compound (47%). [M+H] Calc'd for; Calc'd for $C_8H_{10}Cl_2N_2O_2$, 237; Found, 237.

Preparation 17B: {1-[4-chloro-1-(3-methoxy-propyl)-6-oxo-1,6-dihydro-pyrimidin-2-yl]-piperidin-4-yl}-carbamic acid tert-butyl ester

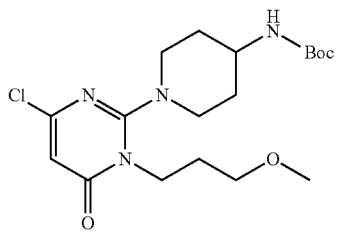 [SMILES: COCCCn1c(N2CCC(NC(=O)OC(C)(C)C)CC2)nc(Cl)cc1=O]

A solution of 2,6-dichloro-3-(3-methoxy-propyl)-3H-pyrimidin-4-one (400 mg, 1.68 mmol), piperidin-4-yl-carbamic acid tert-butyl ester (405 mg, 2 mmol) and DIEA (260 mg, 2.0 mmol) in DMF (20 mL) was stirred at 85° C. for 2 h. The solvent was concentrated, and the residue was purified by silica chromatography to give 500 mg of the title compound (75%). [M+H] Calc'd for $C_{18}H_{29}ClN_4O_4$, 400; Found, 400.

Preparation 17C: {1-[4-(4-cyano-3-fluoro-phenyl)-1-(3-methoxy-propyl)-6-oxo-1,6-dihydro-pyrimidin-2-yl]-piperidin-4-yl}-carbamic acid tert-butyl ester

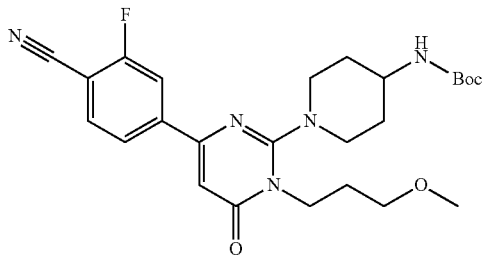 [SMILES: COCCCn1c(N2CCC(NC(=O)OC(C)(C)C)CC2)nc(-c2ccc(C#N)c(F)c2)cc1=O]

A mixture of {1-[4-chloro-1-(3-hydroxy-propyl)-6-oxo-1,6-dihydro-pyrimidin-2-yl]-piperidin-4-yl}-carbamic acid tert-butyl ester (200 mg, 0.5 mmol), 4-cyano-3-fluorophenyl boric acid (107 mg, 0.65 mmol), $Pd(PPh_3)_4$ (12 mg, 0.01 mmol) and 0.4M $Na_2CO_3$ solution (4 mL) in ACN was stirred at 85° C. overnight. The reaction mixture was diluted with water and extracted with EA (3×). The reaction mixture was stirred at RT for 2 h and the solvent was concentrated in vacuo. The residue was purified by silica chromatography to give 240 mg of the title product (99%). [M+H] Calc'd for $C_{25}H_{32}FN_5O_4$, 485; Found, 485.

Example 17: 4-[2-(4-amino-piperidin-1-yl)-1-(3-hydroxy-propyl)-6-oxo-1,6-dihydro-pyrimidin-4-yl]-2-fluoro-benzonitrile

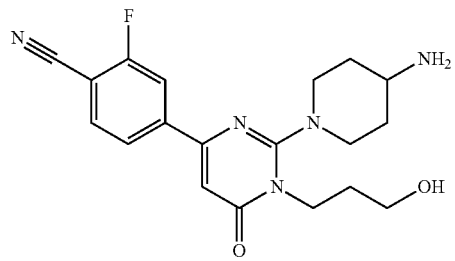 [SMILES: N#Cc1ccc(-c2cc(=O)n(CCCO)c(N3CCC(N)CC3)n2)cc1F]

To a solution of {1-[4-(4-cyano-3-fluoro-phenyl)-1-(3-methoxy-propyl)-6-oxo-1,6-dihydro-pyrimidin-2-yl]-piperidin-4-yl}-carbamic acid tert-butyl ester (200 mg, 0.41 mmol) in DCM was added 1M $BBr_3$ (4 mL) at −78° C. The mixture was stirred at RT for 2 h and quenched at 0° C. with MeOH. The solution was washed with aqueous saturated $NaHCO_3$. The organic layer was dried and concentrated. The residue was purified by preparative HPLC to give 35 mg of the title product as the hydrochloride salt (23%). $^1$H NMR (400 MHz, $CD_3OD$): 1.65-1.69 (m, 2H), 1.97-2.19 (m, 4H), 3.13-3.22 (m, 2H), 3.48-3.55 (m, 1H), 3.73 (t, J=8.0 Hz, 2H), 4.55 (t, J=8.0 Hz, 2H), 4.94-4.95 (m, 2H), 6.71 (s, 1H), 7.88-8.05 (m, 3H). [M+H] Calc'd for $C_{19}H_{22}FN_5O_2$, 371; Found, 371.

Preparation 18A: {1-[5-benzofuran-5-yl-4-(4-cyano-3-fluoro-phenyl)-1-methyl-6-oxo-1,6dihydro-pyrimidin-2-yl]-piperidin-4-yl}-carbamic acid tert-butyl ester

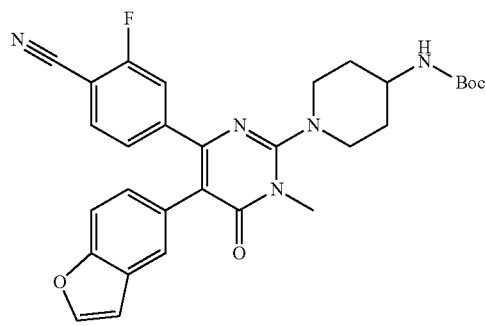 [SMILES: Cn1c(N2CCC(NC(=O)OC(C)(C)C)CC2)nc(-c2ccc(C#N)c(F)c2)c(-c2ccc3occc3c2)c1=O]

A mixture of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (200 mg, 0.45 mmol), benzofuran-5-boronic acid (120 mg, 0.68 mmol), $Pd(PPh_3)_4$ (26 mg, 0.05 mmol) and 2M $Na_2CO_3$ (0.9 mL) in 1,4- dioxane (200 mL) was refluxed overnight under N₂ atmosphere. The reaction mixture was diluted with water and extracted with EA (3×). The combined organics were washed with brine, dried (Na₂SO₄) and concentrated. The residue was purified by silica chromatography to give 100 mg of the title product (42%). [M+H] Calc'd for C₃₀H₃₀FN₅O₄, 543; Found, 543.

Example 18: 4-[2-(4-amino-piperidin-1-yl)-5-benzofuran-5-yl-1-methyl-6-oxo-1,6-dihydro-pyrimidin-4-yl]-2-fluoro-benzonitrile

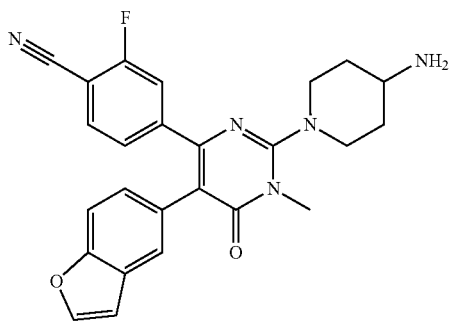 [SMILES: Cn1c(N2CCC(N)CC2)nc(-c2ccc(C#N)c(F)c2)c(-c2ccc3occc3c2)c1=O]

To a solution of Preparation 18A (60 mg, 0.11 mmol) in EA (20 mL) was added a 4M HCl solution in EA (10 mL). The mixture was stirred at RT for 2 h. The solvent was concentrated in vacuo to give 43 mg of the title product as the hydrochloride salt (53%). ¹H NMR (400 MHz, CD₃OD): 1.85-1.92 (m, 2H), 2.13-2.18 (m, 2H), 3.10 (t, J=4.0 Hz, 2H), 3.31-3.33 (m, 1H), 3.61 (s, 3H), 3.87 (d, J=13.2 Hz, 2H), 6.65-7.21 (m, 3H), 7.38-7.76 (m, 4H), 7.76 (s, 1H). [M+H] Calc'd for C₂₅H₂₂FN₅O₂, 443; Found, 443.

Preparation 19A: {1-[5-cyano-4-(4-cyano-3-fluoro-phenyl)-1-methyl-6-oxo-1,6-dihydro-pyrimidin-2-yl]-piperidin-4-yl}-carbamic acid tert-butyl ester

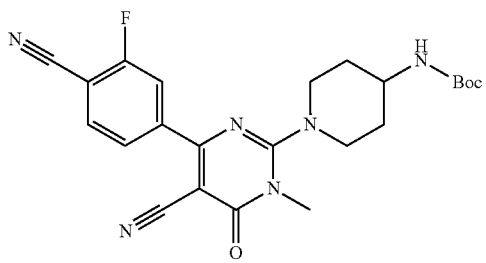 [SMILES: Cn1c(N2CCC(NC(=O)OC(C)(C)C)CC2)nc(-c2ccc(C#N)c(F)c2)c(C#N)c1=O]

A mixture of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (460 mg, 1 mmol), Zn(CN)₂ (175 mg, 1.5 mmol) and Pd(PPh₃)₄ (116 mg, 0.0.1 mmol) in DMF (5 mL) was stirred for 4 h at 150° C. under N₂ atmosphere. The reaction mixture was cooled to RT and filtered. The filtrate was concentrated in vacuo, and the residue was purified by preparative HPLC to give 150 mg of the title product as a yellow solid (33%). [M+H] Calc'd for C₂₃H₂₅FN₆O₃, 453; Found, 453.

Example 19: 2-(4-amino-piperidin-1-yl)-4-(4-cyano-3-fluoro-phenyl)-1-methyl-6-oxo-1,6-dihydro-pyrimidine-5-carbonitrile

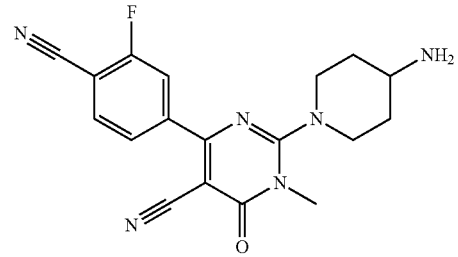 [SMILES: Cn1c(N2CCC(N)CC2)nc(-c2ccc(C#N)c(F)c2)c(C#N)c1=O]

To a solution of {1-[5-cyano-4-(4-cyano-3-fluoro-phenyl)-1-methyl-6-oxo-1,6-dihydro-pyrimidin-2-yl]-piperidin-4-yl}-carbamic acid tert-butyl ester (150 mg, 0.33 mmol) in EA (5 mL) was added a 5N HCl solution in EA (5 mL). The reaction mixture was stirred at RT for 2 h, and the solvent was concentrated in vacuo to give 120 mg of the title product as HCl salt (94%). ¹H NMR (400 MHz, CD₃OD): δ 1.67-1.72 (m, 2H), 2.02-2.06 (m, 2H), 3.13-3.16 (m, 2H), 3.34-3.38 (m, 1H), 3.42 (s, 3H), 3.98-4.02 (m, 2H), 7.82-7.90 (m, 3H). [M+H] Calc'd for C₁₈H₁₇FN₆O, 353; Found, 353.

Example 20: 4-[2-(4-aminopiperidin-1-yl)-5-chloro-1-methyl-6-oxopyrimidin-4-yl]-2-fluorobenzonitrile

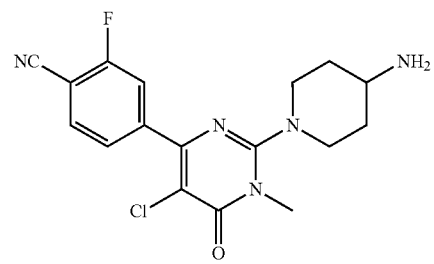 [SMILES: Cn1c(N2CCC(N)CC2)nc(-c2ccc(C#N)c(F)c2)c(Cl)c1=O]

To a solution of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (150 mg, 0.33 mmol) in EA (5 mL) was added a 5N HCl solution in EA (5 mL). The reaction mixture was stirred at RT for 2 h, and the solvent was concentrated in vacuo to give 120 mg of the title product as HCl salt (94%). ¹H NMR (400 MHz, CD₃OD): δ 1.67-1.72 (m, 2H), 2.02-2.06 (m, 2H), 3.13-3.16 (m, 2H), 3.34-3.38 (m, 1H), 3.42 (s, 3H), 3.98-4.02 (m, 2H), 7.82-7.90 (m, 3H). [M+H] Calc'd for C₁₈H₁₇FN₆O, 353; Found, 353. ¹H NMR (400 MHz, METHANOL-d₄): δ ppm 1.73-1.91 (m, 2H), 2.18 (d, J=12.13 Hz, 2H), 3.06 (t, J=12.76 Hz, 2H), 3.33-3.40 (m, 1H), 3.57 (s, 3H), 3.83 (d, J=13.14 Hz, 2H), 7.75-7.93 (m, 3H).

TABLE 3

| Chemical Synthesis Example | Structure (prepared by procedure of cited Example) | MS (ESI) m/z | NMR spectrum data |
|---|---|---|---|
| 21 | Prepared by the procedure of Example 1 | 433 | ¹H NMR (400 MHz, CD$_3$OD): δ 1.89-1.93 (m, 2H), 2.18-2.21 (m, 2H), 2.73 (s, 3H), 2.74 (s, 3H), 3.11-3.17 (m, 2H), 3.33-3.39 (m, 1H), 3.57 (s, 3H), 3.4-3.97 (m, 2H), 7.28 (d, J = 8.0 Hz, 1H), 7.55 (d, J = 10.0 Hz, 1H), 7.63-7.67 (m, 1H), 7.74 (d, J = 8.4 Hz, 1H), 8.12 (d, J = 8.4 Hz, 1H), 8.65 (s, 1H). |
| 22 | Prepared by the procedure of Example 1 | 492 | ¹H NMR (400 MHz, CDCl$_3$): δ 1.74-1.80 (m, 4H), 1.93-1.97 (m, 2H), 3.11 (s, 2H), 3.26-3.35 (m, 6H), 3.47 (s, 3H), 3.75 (s, 3H), 6.68 (dd, J = 1.2, 8.4 Hz, 1H), 6.86-6.72 (m, 2H), 7.11 (dd, J = 1.2, 8.0 Hz, 1H), 7.30 (dd J = 1.2, 10.8 Hz, 1H), 7.46 (dd J = 6.8, 7.6 Hz, 1H). |
| 23 | Prepared by the procedure of Example 1 | 472 | ¹H NMR (400 MHz, CD$_3$OD): 1.75-1.82 (m, 2H), 2.03-2.06 (m, 2H), 3.06-3.12 (m, 2H), 3.22-3.34 (m, 1H), 3.49 (s, 3H), 3.1(d, J = 13.6 Hz, 2H), 7.07-7.09 (m, 1H), 7.36-7.38 (m, 1H), 7.51-7.55 (m, 1H), 7.66 (d, J = 8.0 Hz, 1H), 7.79-7.82 (m, 1H), 8.33 (s, 1H). |
| 24 | Prepared by the procedure of Example 1 | 439 | ¹H NMR (400 MHz, CD$_3$OD): 1.96-2.01 (m, 2H), 2.20-2.22 (m, 2H), 3.23-3.32 (m, 2H), 3.46-3.49 (m, 1H), 3.65 (s, 3H), 3.94-3.97 (m, 2H), 4.39 (s, 3H), 7.55-7.77 (m, 7H), 8.76 (s, 1H). |

TABLE 3-continued

| Chemical Synthesis Example | Structure (prepared by procedure of cited Example) | MS (ESI) m/z | NMR spectrum data |
|---|---|---|---|
| 25 | Prepared by the procedure of Example 1 | 452 | ¹H NMR (300 MHz, CD₃OD): δ 1.72-1.93 (m, 3H), 1.97-2.23 (m, 1H), 3.16-3.30 (m, 2H), 3.50-3.55 (m, 2H), 3.60 (s, 3H), 3.83-3.84 (m, 1H), 3.86 (s, 3H), 6.82 (d, J = 8.1 Hz, 1H), 6.97-7.05 (m, 2H), 7.25 (d, 7 = 8.1 Hz, 1H), 7.44 (d, J = 10.8 Hz, 1H), 7.62 (t, J = 7.5 Hz, 1H). |
| 26 | Prepared by the procedure of Example 1 | 453 | ¹H NMR (400 MHz, CD₃OD): 1.64-1.69 (m, 2H), 1.89-1.92 (m, 2H), 2.85-2.91 (m, 2H), 3.15-3.20 (m, 1H), 3.34 (s, 3H), 3.62 (d, J = 8.4 Hz, 2H), 3.71 (s, 3H), 6.99 (d, J = 8.4 Hz, 1H), 7.20-7.40 (m, 4H). |
| 27 | Prepared by the procedure of Example 1 | 438 | ¹H NMR (400 MHz, CD₃OD): δ 2.19-2.22 (m, 1H), 2.49-2.51 (m, 1H), 3.63 (s, 3H), 3.75-3.81 (m, 2H), 3.87 (s, 3H), 3.87-3.93 (m, 1H), 4.02-4.06 (m, 2H), 6.80 (d, J = 8.4 Hz, 1H), 7.00 (t, J = 10.8 Hz, 2H), 7.25 (d, J = 9.6 Hz, 1H), 7.44 (d, J =10.8 Hz, 1H), 7.61 (t, J = 7.4 Hz, |
| 28 | Prepared by the procedure of Example 1 | 452 | ¹H NMR (400 MHz, CD₃OD): δ 1.69-1.99 (m, 3H), 2.14-2.19 (m, 1H), 3.09-3.24 (m, 2H), 3.43-3.46 (m, 1H), 3.56-3.60 (m, 4H), 3.77-3.80 (m, 1H), 3.82 (s, 3H), 6.77 (d, J = 8.0 Hz, 1H), 6.94-7.00 (m, 2H), 7.21 (d, J = 8.0 Hz, 1H), 7.39 (d, J = 10.4 Hz, 1H), 8.56-7.60 (m, 1H). |

TABLE 3-continued

| Chemical Synthesis Example | Structure (prepared by procedure of cited Example) | MS (ESI) m/z | NMR spectrum data |
|---|---|---|---|
| 29 | Prepared by the procedure of Example 1 | 438 | $^1$H NMR (400 MHz, CD$_3$OD): δ 2.25-2.29 (m, 1H), 2.50-2.55 (m, 1H), 3.69 (s, 3H), 3.89-3.84 (m, 5H), 3.99-4.03 (m, 1H), 5.05-4.16 (m, 2H), 6.80 (d, J = 8.4 Hz, 1H), 6.97-7.03 (m, 2H), 7.29 (dd, J = 2.4, 8.0 Hz, 1H), 7.47 (d, J = 10.4 Hz, 1H), 7.64 (dd, J = 6.8, 8.0 Hz, 1H). |
| 30 | Prepared by the procedure of Example 1 | 434 | $^1$H NMR (400 MHz, CD$_3$OD): δ 1.73-2.02 (m, 3H), 2.19-2.23 (m, 1H), 3.13-3.26 (m, 2H), 3.49-3.52 (m, 2H), 3.60 (s, 3H), 3.77-3.85 (m, 1H), 3.85 (s, 3H), 6.89 (d, J = 11.6 Hz, 2H), 7.08-7.10 (d, J = 11.6 Hz, 2H), 7.24 (d, J = 8.0 Hz, 1H), 7.41 (d, J = 10.8 Hz, 1H), 7.57-7.61 (m, 1H). |
| 31 | Prepared by the procedure of Example 1 | 434 | $^1$H NMR (400 MHz, CD$_3$OD): δ 1.69-1.99 (m, 3H), 2.07-2.10 (m, 1H), 3.09-3.24 (m, 2H), 3.43-3.46 (m, 1H), 3.56-3.60 (m, 4H), 3.68 (s, 3H), 3.76-3.79 (m, 1H), 6.75 (d, J = 8.8 Hz, 2H), 6.96 (d, J = 9.2 Hz, 2H), 7.13 (dd, J = 2.0, 8.0 Hz, 1H), 7.27 (dd, J = 0.8, 10.4 Hz, 1H), 7.47 (dd, J = 6.8, 8.0 Hz, 1H). |
| 32 | Prepared by the procedure of Example 1 | 466 | $^1$H NMR (400 MHz, (CD$_3$OD): δ 1.41 (s, 3H), 1.82-1.85 (m, 2H), 1.91-1.99 (m, 2H), 3.22-3.25 (m, 2H), 3.47 (s, 3H), 3.50-3.57 (m, 2H), 3.75 (s, 3H), 6.69 (d, J = 8.4 Hz, 1H), 6.86-6.92 (m, 2H), 7.14 (d, J = 8.4 Hz, 1H), 7.32 (d, J = 10.8 Hz, 1H), 7.47-7.51 (m, 1H). |

TABLE 3-continued

| Chemical Synthesis Example | Structure (prepared by procedure of cited Example) | MS (ESI) m/z | NMR spectrum data |
|---|---|---|---|
| 33 | *[structure]* Prepared by the procedure of Example 1 | 439 | $^1$H NMR (400 MHz, CD3OD): δ 1.95-1.99 (m, 2H), 2.19-2.22 (m, 2H), 3.20-3.26 (m, 2H), 3.45-3.50 (m, 1H), 3.63 (s, 3H), 3.90 (d, J = 12.8 Hz, 2H), 4.06 (s, 3H), 7.21 (d, J = 8.4 Hz, 1H), 7.48-7.57 (m, 6H), 7.96 (s, 1H). |
| 34 | *[structure]* Prepared by the procedure of Example 1 | 476 | $^1$H NMR (400 MHz, CD$_3$OD): δ 1.75-1.79 (m, 2H), 2.02-2.05 (m, 2H), 3.00-3.06 (m, 2H), 3.21-3.31 (m, 1H), 3.48 (s, 3H), 3.72-3.75 (m, 2H), 4.77-4.81 (m, 2H), 7.22 (s, 1H), 7.31 (d, J = 8.0 Hz, 1H), 7.39 (d, J = 2.0 Hz, 1H), 7.60-7.64 (m, 2H). |
| 35 | *[structure]* Prepared by the procedure of Example 1 | 457 | $^1$H NMR (400 MHz, CD$_3$OD): 1.85-1.99 (m, 2H), 2.18-2.20 (m, 2H), 3.19-3.24 (m, 2H), 3.46-3.50 (m, 1H), 3.86 (s, 3H), 3.86-3.92 (m, 2H), 4.10 (s, 3H), 7.21-7.25 (m, 2H), 7.40-7.53 (m, 4H), 8.01 (s, 1H). |
| 36 | *[structure]* Prepared by the procedure of Example 1 | 458 | $^1$H NMR (400 MHz, CD$_3$OD): δ 1.79-1.82 (m, 2H), 2.04-2.07 (m, 2H), 3.09-3.15 (m, 2H), 3.32-3.38 (m, 1H), 3.50 (s, 3H), 3.76-3.79 (m, 2H), 4.74-4.78 (m, 2H), 7.12 (s, 1H), 7.55 (d, J = 8.4 Hz, 2H), 7.62 (s, 1H), 7.67 (d, J = 8.0 Hz, 2H). |

TABLE 3-continued

| Chemical Synthesis Example | Structure (prepared by procedure of cited Example) | MS (ESI) m/z | NMR spectrum data |
|---|---|---|---|
| 37 | Prepared by the procedure of Example 1 | 458 | ¹H NMR (400 MHz, CD₃OD): δ 1.98-2.04 (m, 2H), 2.21-2.24 (m, 2H), 3.27-3.30 (m, 2H), 3.50-3.52 (m, 1H), 3.65 (s, 3H), 3.98 (d, J = 12.8 Hz, 2H), 4.42 (s, 3H), 7.33 (d, J = 8.0 Hz, 1H), 7.49 (d, J = 10.0 Hz, 1H), 7.60-7.73 (m, 3H), 7.84 (s, 1H), 8.85 (s, 1H). |
| 38 | Prepared by the procedure of Example 1 | 452 | ¹H NMR (400 MHz, CD₃OD): 1.87-1.94 (m, 2H), 2.15 (d, J = 12.0 Hz, 2H), 3.13 (t, J = 8.4 Hz, 2H), 3.39-3.43 (m, 1H), 3.59 (s, 3H), 3.87 (d, J = 12.8 Hz, 2H), 3.97 (s, 3H), 6.79 (d, J = 8.8 Hz, 2H), 7.55 (d, J = 8.4 Hz, 2H), 7.70 (d, J = 8.4 Hz, 2H). |
| 39 | Prepared by the procedure of Example 1 | 448 | ¹H NMR (400 MHz, CD₃OD): δ 1.91-1.94 (m, 2H), 2.16-2.19 (m, 2H), 3.15-3.21 (m, 2H), 3.50-3.52 (m, 1H), 3.61 (s, 3H), 3.90 (d, J = 12.4 Hz, 2H), 7.22 (d, J = 8.0 Hz, 1H), 7.30 (d, J = 8.0 Hz, 2H), 7.43 (d, J = 10.8 Hz, 1H), 7.59 (t, J = 7.2 Hz, 1H), 7.86 (d, J = 8.0 Hz, 2H). |
| 40 | Prepared by the procedure of Example 1 | 461 | ¹H NMR (400 MHz, CD₃OD): δ 1.88-1.91 (m, 2H), 2.12-2.13 (m, 2H), 2.94 (s, 3H), 3.13-3.15 (m, 2H), 3.30-3.34 (m, 1H), 3.61 (s, 3H), 3.89 (d, J = 14.4 Hz, 2H), 7.00 (d, J = 8.0 Hz, 1H), 7.11 (d, J = 12.0 Hz, 1H), 7.53 (d, J = 12.0 Hz, 2H), 7.61-7.64 (m, 3H). |

TABLE 3-continued

| Chemical Synthesis Example | Structure (prepared by procedure of cited Example) | MS (ESI) m/z | NMR spectrum data |
|---|---|---|---|
| 41 | Prepared by the procedure of Example 1 | 447 | ¹H NMR (400 MHz, CD₃OD): δ 1.87-1.91 (m, 2H), 2.14-2.16 (m, 2H), 3.15 (t, J = 12.0 Hz, 2H), 3.30-3.40 (m, 1H), 3.61 (s, 3H), 3.89 (d, J = 14.0 Hz, 2H), 7.01(d, J = 8.0 Hz, 1H), 7.13 (d, J = 12.0 Hz, 1H), 7.52-7.77 (m, 5H). |
| 42 | Prepared by the procedure of Example 1 | 459 | ¹H NMR (400 MHz, CD₃OD): δ 178-1.79 (m, 2H), 2.03-2.05 (m, 2H), 3.00-3.06 (m, 2H), 3.21-3.31 (m, 1H), 3.49 (s, 3H), 3.75-3.78 (m, 2H), 4.32 (s, 2H), 7.06 (dd, J = 1.2, 8.0 Hz, 1H), 7.12 (dd, J = 1.2, 8.0 Hz, 1H), 7.31-7.36 (m, 2H), 7.42 (dd, J = 6.4, 7.6 Hz, 1H), 7.58 (d, J = 7.6 Hz, 1H). |
| 43 | Prepared by the procedure of Example 1 | 448 | ¹H NMR (400 MHz, CD₃OD): δ 1.77-1.80 (m, 2H), 2.02-2.05 (m, 2H), 3.01-3.05 (m, 2H), 3.35-3.36 (m, 1H), 3.49 (s, 3H), 3.74-3.98 (m, 2H), 7.07 (dd, J = 1.6, 8.4 Hz, 1H), 7.27-7.32 (m, 3H), 7.44 (dd, J = 6.8, 8.0 Hz, 1H), 7.73 (d, J = 1.2 Hz, 1H), 7.84 (d, J = 7.2 Hz, 1H). |
| 44 | Prepared by the procedure of Example 1 | 434 | ¹H NMR (400 MHz, CD₃OD): δ 1.87-1.91 (m, 1H), 2.25-2.28 (m, 1H), 2.87-2.92 (m, 1H), 3.11-3.17 (m, 1H), 3.30-3.32 (m, 1H), 3.41-3.56 (m, 5H), 3.69-3.71 (m, 2H), 3.84 (s, 3H), 6.75 (d, J = 8.4 Hz, 1H), 6.92-6.96 (m, 2H), 7.53 (d, J = 8.0 Hz, 2H), 7.66 (d, J = 8.4 Hz, 2H). |

TABLE 3-continued

| Chemical Synthesis Example | Structure (prepared by procedure of cited Example) | MS (ESI) m/z | NMR spectrum data |
|---|---|---|---|
| 45 | Prepared by the procedure of Example 1 | 434 | ¹H NMR (400 MHz, CD₃OD): δ 1.74-1.80 (m, 1H), 2.14-2.19 (m, 1H), 2.77-2.81 (m, 1H), 3.01-3.06 (m, 1H), 3.31-3.34 (m, 1H), 3.36-3.45 (m, 5H), 3.59-3.60 (m, 2H) 3.71 (s, 3H), 6.63 (d, J = 8.4 Hz, 1H), 6.80-6.84 (m, 2H), 7.44 (d, J = 8.0 Hz, 2H), 7.60 (d, J = 8.4 Hz, 2H). |
| 46 | Prepared by the procedure of Example 1 | 452 | ¹H NMR (400 MHz, CD₃OD): δ 2.15-2.18 (m, 2H), 3.31-3.34 (m, 2H), 3.46-3.51 (m, 5H), 3.56-3.59 (m, 2H), 3.74 (s, 3H), 3.78-3.81 (m, 2H), 6.68 (dd, J = 1.2, 8.4 Hz, 1H), 6.85-6.89 (m, 2H), 7.12 (dd, J = 1.2, 7.6 Hz, 1H), 7.28 (dd, J = 1.6, 10.8 Hz, 1H), 7.47 (dd, J = 6.8, 8.0 Hz, 1H). |
| 47 | Prepared by the procedure of Example 1 | 438 | ¹H NMR (400 MHz, DMSO-d₆): δ 3.27-3.34 (m, 4H), 3.45 (s, 3H), 3.51-3.53 (m, 4H), 3.81 (s, 3H), 6.78 (d, J = 8.4 Hz, 1H), 7.02-7.08 (m, 2H), 7.18 (dd, J = 1.6, 8.4 Hz, 1H), 7.45 (dd, J = 1.6, 10.8 Hz, 1H), 7.80 (dd, J = 7.2, 8.0 Hz, 1H), 9.41 (br, 1H). |
| 48 | Prepared by the procedure of Example 1 | 434 | ¹H NMR (400 MHz, CD₃OD): δ 184-1.94 (m, 2H), 2.20-2.23 (m, 2H), 3.00-3.07 (m, 2H), 3.38-3.42 (m, 5H), 3.72 (s, 3H), 4.22-4.27 (m, 1H), 6.61 (d, J = 8.8 Hz, 1H), 6.79-6.83 (m, 2H), 7.39 (d, J = 8.0 Hz, 2H), 7.51 (d, J = 8.0 Hz, 2H). |

TABLE 3-continued

| Chemical Synthesis Example | Structure (prepared by procedure of cited Example) | MS (ESI) m/z | NMR spectrum data |
|---|---|---|---|
| 49 | Prepared by the procedure of Example 1 | 449 | $^1$H NMR (400 MHz, CD$_3$OD): δ 1.82-1.87 (m, 2H), 2.04-2.07 (m, 2H), 3.06-3.12 (m, 2H), 3.25 (s, 6H), 3.28-3.39 (m, 1H), 3.49 (s, 3H), 3.81-3.84 (m, 2H), 7.37 (d, J = 8.0 Hz, 1H), 7.56 (d, J = 9.6 Hz, 1H), 7.42 (t, J = 6.8 Hz, 1H), 8.31 (s, 2H). |
| 50 | Prepared by the procedure of Example 1 | 462 | $^1$H NMR (400 MHz, CD$_3$OD): δ 1.93-1.97 (m, 2H), 2.17-2.20 (m, 2H), 3.03 (s, 3H), 3.20-3.26 (m, 2H), 3.47-3.53 (m, 1H), 3.62 (s, 3H), 3.98-4.02 (m, 2H), 7.32 (d, J = 8.0 Hz, 1H), 7.60 (d, J = 10.0 Hz, 1H), 7.67 (t, J = 6.4 Hz, 1H), 8.32 (s, 2H), 8.83 (s, 1H). |
| 51 | Prepared by the procedure of Example 1 | 434 | $^1$H NMR (400 MHz, CD$_3$OD): δ 1.89-1.91 (m, 1H), 2.26-2.28 (m, 1H), 2.91-2.93 (m, 1H), 3.12-3.15 (m, 1H), 3.30-3.32 (m, 1H), 3.42-3.55 (m, 5H), 3.70-3.72 (m, 2H) 3.84 (s, 3H), 6.84 (d, J = 8.4 Hz, 2H), 7.03 (d, J = 8.4 Hz, 2H), 7.29 (d, J = 8.0 Hz, 1H), 7.39 (d, J = 10.0 Hz, 1H), 7.64 (t, J = 7.2 Hz 1H). |
| 52 | Prepared by the procedure of Example 1 | 434 | $^1$H NMR (400 MHz, CD$_3$OD): δ 1.86-1.91 (m, 1H), 2.22-2.28 (m, 1H), 2.97-2.91 (m, 1H), 3.10-3.13 (m, 1H), 3.29-3.32 (m, 1H), 3.40-3.51 (m, 5H), 3.67-3.69 (m, 2H) 3.82 (s, 3H), 6.84 (d, J = 8.0 Hz, 2H), 7.02 (d, J = 8.4 Hz, 2H), 7.27 (d, J = 8.0 Hz, 1H), 7.35 (d, J = 10.4 Hz, 1H), 7.64 (t, J = 7.2 Hz, 1H). |

TABLE 3-continued

| Chemical Synthesis Example | Structure (prepared by procedure of cited Example) | MS (ESI) m/z | NMR spectrum data |
|---|---|---|---|
| 53 | Prepared by the procedure of Example 1 | 434 | ¹H NMR (400 MHz, CD₃OD): δ 2.03-2.06 (m, 2H), 2.32-2.35 (m, 2H), 3.14-3.21 (m, 2H), 3.51-3.56 (m, 5H), 3.78 (s, 3H), 4.37-4.39 (m, 1H), 6.84 (d, J = 7.2 Hz, 2H), 7.02 (d, J = 8.0 Hz, 2H), 7.27 (d, J = 8.0 Hz, 1H), 7.38 (d, J = 10.4 Hz, 1H), 7.62 (t, J = 7.2 Hz, 1H). |
| 54 | Prepared by the procedure of Example 1 | 448 | ¹H NMR (400 MHz, CD₃OD): δ 1.66-1.71 (m, 1H), 2.11-2.16 (m, 1H), 2.77-2.81 (m, 1H), 2.93-2.97 (m, 4H), 3.16-3.20 (m, 1H), 3.30-3.38 (m, 2H), 3.43-3.50 (m, 5H), 3.69 (s, 3H), 6.75 (d, J = 8.4 Hz, 2H), 6.95 (d, J = 8.4 Hz, 2H), 7.16 (d, J = 8.4 Hz, 1H), 7.28 (d, J = 10.8 Hz, 1H), 7.50 (dd, J = 6.8, 8.0 Hz, 1H). |
| 55 | Prepared by the procedure of Example 1 | 448 | ¹H NMR (400 MHz, CD₃OD): δ 2.03-2.13 (m, 4H), 2.84 (s, 3H), 3.01-3.05 (m, 2H), 3.39-3.43 (m, 2H), 3.48 (s, 3H), 3.67 (s, 3H), 3.87-3.92 (m, 1H), 6.74 (d, J = 8.8 Hz, 2H), 6.95 (d, J = 8.8 Hz, 2H), 7.13 (dd, J = 1.2, 8.0 Hz, 1H), 7.21 (dd, J = 1.6, 10.4 Hz, 1H), 7.45 (dd, J = 6.8, 7.6 Hz, 1H). |
| 56 | Prepared by the procedure of Example 1 | 448 | ¹H NMR (400 MHz, CD₃OD): δ 1.77-1.80 (m, 1H), 2.22-2.26 (m, 1H), 2.90-2.92 (m, 1H), 3.03-3.07 (m, 4H), 3.27-3.30 (m, 1H), 3.39-3.41 (m, 2H), 3.44-3.46 (m, 5H), 3.77 (s, 3H), 6.86 (d, J = 8.4 Hz, 2H), 7.06 (d, J = 8.0 Hz, 2H), 7.29 (d, J = 8.4 Hz, 1H), 7.36 (d, J = 8.4 Hz, 1H), 7.58 (dd, J = 6.8, 7.6 Hz, 1HV |

TABLE 3-continued

| Chemical Synthesis Example | Structure (prepared by procedure of cited Example) | MS (ESI) m/z | NMR spectrum data |
|---|---|---|---|
| 57 | Prepared by the procedure of Example 1 | 448 | ¹H NMR (400 MHz, CD$_3$OD): δ 1.77-1.85 (m, 2H), 2.03-2.06 (m, 2H), 3.03-3.09 (m, 2H), 3.18 (s, 6H), 3.31-3.38 (m, 1H), 3.48 (s, 3H), 3.78-3.81 (m, 2H), 7.03 (d, J = 9.2 Hz, 1H), 7.28 (d, J = 7.6 Hz, 1H), 7.46 (d, J = 10.0 Hz, 1H), 7.59-7.63 (m, 2H), 7.71 (s, 1H). |
| 58 | Prepared by the procedure of Example 1 | 449 | ¹H NMR (400 MHz, CD$_3$OD): δ 1.83-1.88 (m, 2H), 2.21-2.24 (m, 2H), 2.77 (s, 3H), 3.06-3.14 (m, 2H), 3.31-3.32 (m, 1H), 3.58 (s, 3H), 3.87-3.91 (m, 5H), 6.83 (d, J =11.2 Hz, 1H), 7.22 (dd, J = 2.0, 10.8 Hz, 1H), 7.42 (dd, J = 2.0, 14.4 Hz, 1H), 7.59-7.65 (m, 2H), 7.84 (d, J = 3.2 Hz, 1H). |
| 59 | Prepared by the procedure of Example 1 | 447 | ¹H NMR (400 MHz, CD$_3$OD): δ 1.88-1.89 (m, 2H), 2.14-2.19 (m, 2H), 3.13-3.19 (m, 2H), 3.28 (s, 6H), 3.41-3.46 (m, 1H), 3.60 (s, 3H), 3.87-3.91 (m, 2H), 7.24 (d, J = 10.8 Hz, 1H), 7.39-7.44 (m, 3H), 7.59-7.67 (m, 3H). |
| 60 | Prepared by the procedure of Example 1 | 474 | ¹H NMR (400 MHz, CD$_3$OD): δ 1.91-1.97 (m, 2H), 2.16-2.20 (m, 6H), 3.14-3.20 (m, 2H), 3.47-3.49 (m, 1H), 3.60-3.63 (m, 7H), 3.89-3.92 (m, 2H), 7.31 (d, J = 9.6 Hz, 1H), 7.01 (d, J = 9.6 Hz, 1H), 7.41 (d, J = 8.0 Hz, 1H), 7.58 (d, J = 10.0 Hz, 1H), 7.68-7.75 (m, 2H), 7.79 (s, 1H). |

TABLE 3-continued

| Chemical Synthesis Example | Structure (prepared by procedure of cited Example) | MS (ESI) m/z | NMR spectrum data |
|---|---|---|---|
| 61 | Prepared by the procedure of Example 1 | 435 | ¹H NMR (400 MHz, CD₃OD): δ 2.27-2.30 (m, 2H), 3.44-.347 (m, 2H), 3.60-3.64 (m, 5H), 3.70-3.73 (m, 2H), 3.91-3.94 (m, 5H), 6.83 (d, J = 8.4 Hz, 1H), 7.24 (dd, J = 1.6, 8.0 Hz, 1H), 7.43 (dd, J = 1.2, 10.4 Hz, 1H), 7.59-7.66 (m, 2H), 7.84 (d, J = 2.4 Hz, 1H). |
| 62 | Prepared by the procedure of Example 1 | 417 | ¹H N MR (400 MHz, CD₃OD): δ 2.27-2.31 (m, 2H), 3.44-.347 (m, 2H), 3.60-3.64 (m, 5H), 3.70-3.73 (m, 2H), 3.91-3.94 (m, 5H), 6.81 (d, J = 8.4 Hz, 1H), 7.53 (d, J = 8.4 Hz, 2H), 7.58 (dd, J = 2.4, 8.8 Hz, 1H), 7.64 (d, J = 8.8 Hz, 2H), 7.84 (d, J = 1.2 Hz, 1H). |
| 63 | Prepared by the procedure of Example 1 | 448 | ¹H NMR (400 MHz, CD₃OD): δ 2.31-2.33 (m, 2H), 3.27 (s, 6H) 3.44-.347 (m, 2H), 3.60-3.67 (m, 5H), 3.73-3.76 (m, 2H), 3.96-3.99 (m, 2H), 6.81 (d, J = 8.4 Hz, 1H), 7.53 (d, J = 8.4 Hz, 1H), 7.58 (dd, J = 2.4, 8.8 Hz, 1H), 7.64 (d, J = 8.8 Hz, 2H), 7.84 (d, J = 1.2 Hz, 1H). |
| 64 | Prepared by the procedure of Example 1 | 406 | ¹H NMR (400 MHz, CD₃OD): δ 3.39 (s, 3H), 3.67 (s, 3H), 4.09-4.10 (m, 1H), 4.17-4.21 (m, 2H), 4.55-4.59 (m, 2H), 6.74 (d, J = 8.8 Hz, 2H), 6.96 (d, J = 8.8 Hz, 2H), 7.10 (dd, J = 1.6, 8.4 Hz, 1H), 7.23 (dd, J = 1.6, 10.8 Hz, 1H), 7.45 (dd, J = 6.8, 8.0 Hz, 1H). |

TABLE 3-continued

| Chemical Synthesis Example | Structure (prepared by procedure of cited Example) | MS (ESI) m/z | NMR spectrum data |
|---|---|---|---|
| 65 | Prepared by the procedure of Example 1 | 472 | $^1$H NMR (400 MHz, CD$_3$OD): δ 1.85-1.98 (m, 2H), 2.23-2.27 (m, 2H), 2.78 (s, 3H), 3.38-3.40 (m, 1H), 3.62 (s, 3H), 3.90-3.95 (m, 2H), 4.41 (s, 3H), 7.26 (d, J = 10.8 Hz, 1H), 7.40 (d, J = 13.6 Hz, 1H), 7.49-7.57 (m, 2H), 7.65 (dd, J = 6.8, 11.6 Hz, 1H), 7.73 (s, 1H), 8.66 (s, 1H). |
| 66 | Prepared by the procedure of Example 1 | 458 | $^1$H NMR (400 MHz, CD$_3$OD): δ 2.19-2.20 (m, 2H), 3.33-3.36 (m, 2H), 3.50-3.53 (m, 5H), 3.60-3.63 (m, 2H), 3.83-3.85 (m, 2H), 4.42 (s, 3H), 7.13 (d, J = 7.6 Hz, 1H), 7.28 (d, J = 10.4 Hz, 1H), 7.34 (d, J = 9.2 Hz, 1H), 7.40 (t, J = 7.2 Hz, 1H), 7.52 (d, J = 8.8 Hz, 1H), 7.58 (s, 1H), 8.48 (s, 1H). |
| 67 | Prepared by the procedure of Example 1 | 430 | $^1$H NMR (400 MHz, CD$_3$OD): δ 2.33-2.35 (m, 2H), 3.27 (s, 6H), 3.46-3.49 (m, 2H), 3.62-3.66 (m, 5H), 3.75-3.78 (m, 2H), 3.98-4.02 (m, 2H), 6.73 (d, J = 9.2 Hz, 1H), 7.67-7.72 (m, 5H), 7.80 (s, 1H). |
| 68 | Prepared by the procedure of Example 1 | 490 | $^1$H NMR (400 MHz, CD$_3$OD): δ 1.89-1.97 (m, 2H), 2.15-2.18 (m, 2H), 3.15-3.21 (m, 2H), 3.43-3.49 (m, 1H), 3.61 (s, 3H), 3.69-3.71 (m, 4H), 3.86-3.94 (m, 6H), 7.31 (d, J = 9.6 Hz, 1H), 7.41 (d, J = 8.0 Hz, 1H), 7.59 (d, J = 10.0 Hz, 1H), 7.72-7.80 (m, 2H), 7.91 (s, 1H). |

TABLE 3-continued

| Chemical Synthesis Example | Structure (prepared by procedure of cited Example) | MS (ESI) m/z | NMR spectrum data |
|---|---|---|---|
| 69 | Prepared by the procedure of Example 1 | 420 | ¹H NMR (400 MHz, CD₃OD): δ 2.99-3.06 (m, 1H), 3.30-3.32 (m, 2H), 3.49 (s, 3H), 3.78 (s, 3H), 4.10-4.15 (m, 2H), 4.46-4.52 (m, 2H), 6.83 (d, J = 8.4 Hz, 2H), 7.01 (d, J = 8.8 Hz, 2H), 7.19 (dd, J = 2.0, 10.8 Hz, 1H), 7.33 (dd, J = 2.0, 14.4 Hz, 1H), 7.45 (dd, J = 8.8, 10.8 Hz, 1H). |
| 70 | Prepared by the procedure of Example 1 | 434 | ¹H NMR (400 MHz, CD₃OD): δ 2.78 (s, 3H), 3.07-3.10 (m, 1H), 3.37-3.39 (m, 2H), 3.48 (s, 3H), 3.78 (s, 3H), 4.12-4.15 (m, 2H), 4.47-4.52 (m, 2H), 6.84 (d, J = 8.8 Hz, 2H), 7.01 (d, J = 8.8 Hz, 2H), 7.20 (d, J = 8.0 Hz, 1H), 7.33 (d, J = 10.4 Hz, 1H), 7.45 (t, J = 7.2 Hz, 1H). |
| 71 | Prepared by the procedure of Example 1 | 486 | ¹H NMR (400 MHz, CD₃OD): δ 1.67-1.73 (m, 2H), 2.02-2.06 (m, 2H), 2.33 (s, 6H), 2.41-2.45 (m, 1H), 2.95-3.03 (m, 2H), 3.59 (s, 3H), 3.79-3.84 (m, 2H), 4.18 (s, 3H), 7.10 (dd, J = 2.0,12.0 Hz, 1H), 7.23 (dd, J = 1.6, 10.8 Hz, 1H), 7.37 (dd, J = 2.0, 14.4 Hz, 1H), 7.46-7.56 (m, 3H), 8.11 (s, 1H). |
| 72 | Prepared by the procedure of Example 1 | 486 | ¹H NMR (400 MHz, DMSO-d₆): δ 1.50-1.63 (m, 2H), 1.85-1.89 (m, 2H), 2.18 (s, 6H), 2.21-2.27 (m, 1H), 2.85-2.92 (m, 2H), 3.45 (s, 3H), 3.67-3.71 (m, 2H), 4.00 (s, 3H), 7.09-7.17 (m, 2H), 7.39 (dd, J = 1.6, 14.4 Hz, 1H), 7.51-7.54 (m, 2H), 7.69 (t, J = 9.2 Hz, 1H), 7.97 (s, 1H). |

TABLE 3-continued

| Chemical Synthesis Example | Structure (prepared by procedure of cited Example) | MS (ESI) m/z | NMR spectrum data |
|---|---|---|---|
| 73 | Prepared by the procedure of Example 18 | 443 | $^1$H NMR (300 MHz, CD$_3$OD): δ 1.85-1.91 (m, 2H), 2.11-2.16 (m, 2H), 3.06-3.14 (m, 2H), 3.36-3.40 (m, 1H), 3.57 (s, 3H), 3.81-3.85 (m, 2H), 6.85 (d, J = 8.4 Hz, 2H), 7.22 (d, J = 3.0 Hz, 1H), 7.24 (s, 1H), 7.33-7.48 (m, 4H). |
| 74 | Prepared by the procedure of Example 18 | 456 | $^1$H NMR (400 MHz, CD$_3$OD): δ 1.53-1.56 (m, 2H), 1.88-1.91 (m, 2H), 2.87-2.95 (m, 3H), 3.49 (s, 3H), 3.62 (d, J = 13.6 Hz, 2H), 3.69 (s, 3H), 6.26 (s, 1H), 6.81 (d, J = 4.0 Hz, 1H), 7.04-7.35 (m, 6H). |
| 75 | Prepared by the procedure of Example 18 | 442 | $^1$H NMR (400 MHz, CD$_3$OD): δ 1.88-1.94 (m, 2H), 2.13-2.16 (m, 2H), 3.05-3.16 (m, 2H), 3.33-3.42 (m, 1H), 3.60 (s, 3H), 3.84-3.86 (m, 2H), 6.74-6.77 (m, 1H), 7.20-7.50 (m, 7H). |
| 76 | Prepared by the procedure of Example 1 | 457 | $^1$H NMR (400 MHz, CD$_3$OD): δ 1.51-1.54 (m, 2H), 1.88-1.91 (m, 2H), 2.84-2.97 (m, 3H), 3.49 (s, 3H), 3.62-3.65 (m, 5H), 6.31 (d, J = 2.8 Hz, 1H), 6.61 (d, J = 8.0 Hz, 1H), 7.06 (d, J = 3.2 Hz, 1H), 7.13-7.18 (m, 3H), 7.27 (d, J = 10.8 Hz, 1H), 7.33-7.37 (m, 2H). |

TABLE 3-continued

| Chemical Synthesis Example | Structure (prepared by procedure of cited Example) | MS (ESI) m/z | NMR spectrum data |
|---|---|---|---|
| 77 | Prepared by the procedure of Example 1 | 444 | ¹H NMR (400 MHz, CD₃OD): δ 1.65-1.68 (m, 2H), 2.01-2.04 (m, 2H), 2.98-3.12 (m, 3H), 3.63 (s, 3H), 3.78-3.82 (m, 2H), 6.94 (d, J = 8.4 Hz, 1H), 7.24 (d, J = 8.0 Hz, 1H), 7.43-7.45 (m, 2H), 7.50 (t, J = 7.2 Hz, 1H), 7.72 (d, J = 8.4 Hz, 1H), 8.06 (s, 1H). |
| 78 | Prepared by the procedure of Example 1 | 452 | ¹H NMR (300 MHz, CD₃OD): δ 1.84-1.91 (m, 1H), 2.01-2.06 (m, 1H), 3.00-3.08 (m, 2H), 3.16-3.21 (m, 1H), 3.58 (s, 3H), 3.75-3.82 (m, 4H), 3.93-4.01 (m, 1H), 4.70-4.82 (m, 1H), 6.86 (d, J = 9.0 Hz, 2H), 7.06 (d, J = 8.7 Hz, 2H), 7.24 (dd, J = 0.9, 8.1 Hz, 1H), 7.34 (dd, J = 1.5, 10.8 Hz, 1H), 7.54-7.58 (m, 1H). |
| 79 | Prepared by the procedure of Example 1 | 452 | ¹H NMR (400 MHz, CD₃OD): δ 1.87-1.91 (m, 1H), 2.03-2.07 (m, 1H), 3.02-3.08 (m, 2H), 3.19-3.29 (m, 1H), 3.59 (s, 3H), 3.77-3.83 (m, 4H), 3.95-4.01 (m, 1H), 4.73-4.85 (m, 1H), 6.87 (d, J = 8.8 Hz, 2H), 7.07 (d, J = 8.8 Hz, 2H), 7.26 (dd, J = 1.2, 8.4 Hz, 1H), 7.36 (dd, J = 1.2, 10.8 Hz, 1H), 7.56 (t, J = 6.8 Hz, 1H). |
| 80 | Prepared by the procedure of Example 1 | 486 | ¹H NMR (400 MHz, CD₃OD): δ 1.71-1.77 (m, 2H), 2.05-2.08 (m, 2H), 2.38 (s, 6H), 2.45-2.48 (m, 1H), 2.98-3.05 (m, 2H), 3.61 (s, 3H), 3.83-3.86 (m, 2H), 4.20 (s, 3H), 6.93 (dd, J = 1.2, 8.8 Hz, 1H), 7.27 (dd, J = 1.2, 7.6 Hz, 1H), 7.36-7.41 (m, 2H), 7.49-7.53 (m, 1H), 7.66 (d, J = 8.8 Hz, 1H), 8.18 (s, 1H). |

TABLE 3-continued

| Chemical Synthesis Example | Structure (prepared by procedure of cited Example) | MS (ESI) m/z | NMR spectrum data |
|---|---|---|---|
| 81 | Prepared by the procedure of Example 1 | 477 | ¹H NMR (400 MHz, CD₃OD): δ 2.03-2.06 (m, 2H), 2.25-2.27 (m, 2H), 2.98 (s, 6H), 3.14-3.20 (m, 2H), 3.36 (s, 6H), 3.56-3.60 (m, 1H), 3.62 (s, 3H), 4.01-4.04 (m, 2H), 7.49 (d, J = 4.4 Hz, 1H), 7.67 (d, J = 10.0 Hz, 1H), 7.75-7.78 (m, 1H), 8.43 (s, 2H). |
| 82 | Prepared by the procedure of Example 1 | 447 | ¹H NMR (400 MHz, CD₃OD): δ 1.56-1.62 (m, 2H), 1.91-1.94 (m, 2H), 2.25 (s, 6H), 2.31-2.37 (m, 1H), 2.41 (s, 3H), 2.87-2.93 (m, 2H), 3.47 (s, 3H), 3.72-3.76 (m, 2H), 7.10 (dd, J = 1.2, 8.0 Hz, 1H), 7.15 (d, J = 8.0 Hz, 1H), 7.28-7.31 (m, 1H), 7.49-7.52 (m, 2H), 7.80 (d, J = 2.0 Hz, 1H). |
| 83 | Prepared by the procedure of Example 1 | 462 | ¹H NMR (400 MHz, CD₃OD): δ 1.92-2.04 (m, 2H), 2.24-2.26 (m, 2H), 2.79 (s, 3H), 3.14-3.20 (m, 2H), 3.30 (s, 6H), 3.37-3.40 (m, 1H), 3.61(s, 3H), 3.94-3.98 (m, 2H), 7.16 (d, J = 9.6 Hz, 1H), 7.42 (d, J = 8.0 Hz, 1H), 7.61 (d, J = 10.0 Hz, 1H), 7.71-7.76 (m, 2H), 7.84 (d, J = 1.2 Hz, 1H). |
| 84 | Prepared by the procedure of Example 1 | 472 | ¹H NMR (400 MHz, CDCl₃): δ 1.61-1.69 (m, 2H), 1.98-2.01 (m, 2H), 2.32 (s, 6H), 2.32-2.33 (m, 1H), 2.88-2.94 (m, 2H), 3.53 (s, 3H), 3.65-3.69 (m, 2H), 6.73 (dd, J = 1.2, 8.8 Hz, 1H), 7.00 (dd, J = 1.2, 8.0 Hz, 1H), 7.19-7.30 (m, 2H), 7.37 (s, 1H), 7.52 (d, J = 8.4 Hz, 1H), 7.90 (s, 1H), 10.65 (br, 1H). |

TABLE 3-continued

| Chemical Synthesis Example | Structure (prepared by procedure of cited Example) | MS (ESI) m/z | NMR spectrum data |
|---|---|---|---|
| 85 | Prepared by the procedure of Example 1 | 455 | ¹H NMR (400 MHz, CD₃OD): δ 1.88-1.92 (m, 2H), 2.15-2.18 (m, 2H), 3.12-3.18 (m, 2H), 3.40-3.46 (m, 1H), 3.85-3.88 (m, 5H), 6.81 (d, J = 8.4 Hz, 1H), 6.98-7.05 (m, 2 H), 7.25 (dd, J = 1.2, 8.4 Hz, 1H), 7.42 (d, J = 11.2 Hz, 1H), 7.61 (t, J = 7.2 Hz, 1H). |
| 86 | Prepared by the procedure of Example 1 | 455 | ¹H NMR (400 MHz, CD₃OD): δ 1.88-1.92 (m, 2H), 2.14-2.17 (m, 2H), 3.11-3.17 (m, 2H), 3.42-3.47 (m, 1H), 3.59 (s, 3H), 3.85-3.88 (m, 2H), 6.81 (d, J = 8.4 Hz, 1H), 6.98-7.05 (m, 2 H), 7.25 (dd, J = 1.2, 8.0 Hz, 1H), 7.42 (d, J = 10.4 Hz, 1H), 7.60 (dd, J = 0.8, 7.6 Hz, 1H). |
| 87 | Prepared by the procedure of Example 1 | 472 | ¹H NMR (400 MHz, DMSO-d₆): δ ppm 1.79 (br. s., 2 H) 2.11 (br. s., 2 H) 2.97 (br. s., 2 H) 3.10-3.31 (m, 1 H) 3.46 (br. s., 3H) 3.74 (d, J = 18.19 Hz, 2 H) 4.03 (br. s., 3 H) 7.12 (d, J = 13.39 Hz, 1 H) 7.40-7.61 (m, 4 H) 7.71 (br. s., 1 H) 7.87-8.07 (m, 1 H) 9.15 (br. s., 2 H). |
| 88 | Prepared by the procedure of Example 1 | 444 | ¹H NMR (400 MHz, Methanol-d₄): δ ppm 1.84 (d, J = 13.39 Hz, 2 H) 2.11 (d, J = 13.14 Hz, 2 H) 3.05-3.17 (m, 2 H) 3.35-3.40 (m, 1 H) 3.59 (s, 3 H) 3.83 (d, J = 14.40 Hz, 2 H) 7.17 (d, J = 8.08 Hz, 2 H) 7.41 (d, J = 10.61 Hz, 1 H) 7.44-7.52 (m, 2 H) 7.57 (s, 1 H) 7.98 (s, 1 H) 8.54 (br. s., 1 H). |

TABLE 3-continued

| Chemical Synthesis Example | Structure (prepared by procedure of cited Example) | MS (ESI) m/z | NMR spectrum data |
|---|---|---|---|
| 89 | (structure shown) Prepared by the procedure of Example 1 | 419 | $^1$H NMR (400 MHz, Methanol-$d_4$): δ ppm 1.74-1.96 (m, 2 H) 2.11 (d, J = 12.13 Hz, 2 H) 3.08 (q, J = 11.54 Hz, 2 H) 3.38 (br. s., 1 H) 3.57 (br. s., 3 H) 3.71-3.93 (m, 2 H) 6.64 (d, J = 8.08 Hz, 2 H) 6.86 (d, J = 8.08 Hz, 2 H) 7.07-7.17 (m, 1H) 7.18-7.30 (m, 1 H) 7.31-7.43 (m, 1 H). |
| 90 | (structure shown) Prepared by the procedure of Example 1 | 433 | $^1$H NMR (400 MHz, Methanol-$d_4$): δ ppm 1.72-1.93 (m, 2 H) 2.09 (d, J = 11.62 Hz, 2 H) 2.75 (s, 3 H) 2.99-3.14 (m, 2 H) 3.36-3.43 (m, 1 H) 3.56 (s, 3 H) 3.78 (d, J = 12.38 Hz, 2 H) 6.54 (d, J = 7.83 Hz, 2 H) 6.89 (d, J = 7.83 Hz, 2 H) 7.27 (d, J = 8.34 Hz, 1 H) 7.32-7.43 (m, 1 H) 7.48-7.62 (m, 1 H). |
| 91 | (structure shown) Prepared by the procedure of Example 1 | 451 | $^1$H NMR (400 MHz, Methanol-$d_4$): δ ppm 1.86 (d, J = 11.87 Hz, 2 H) 2.12 (d, J = 11.12 Hz, 2 H) 2.96 (s, 3 H) 3.11 (t, J = 12.25 Hz, 2 H) 3.40 (br. s., 1 H) 3.57 (s, 3 H) 3.84 (d, J = 12.38 Hz, 2 H) 6.90 (d, J = 8.59 Hz, 1 H) 7.05 (t, J = 8.46 Hz, 1 H) 7.12 (d, J = 12.38 Hz, 1 H) 7.26 (d, J = 8.34 Hz, 1 H) 7.40 (d, J = 10.61 Hz, 1 H) 7.60 (t, J = 7.20 Hz, 1 H). |
| 92 | (structure shown) Prepared by the procedure of Example 1 | 463 | $^1$H NMR (400 MHz, Chloroform-d): δ ppm 1.71 (m, J = 11.37 Hz, 2 H) 1.74 (br. s., 1 H) 2.04 (d, J = 11.87 Hz, 2 H) 2.38 (br. s., 6 H) 2.96 (t, J = 12.76 Hz, 2 H) 3.55 (s, 3 H) 3.71 (d, J = 12.88 Hz, 2 H) 3.91 (s, 3 H) 6.73 (d, J = 8.59 Hz, 1 H) 7.12 (d, J = 7.83 Hz, 1 H) 7.34 (d, J = 10.11 Hz, 1 H) 7.43 (t, J = 7.07 Hz, 1 H) 7.53 (d, J = 8.34 Hz, 1 H) 7.81 (br. s., 1 H). |

TABLE 3-continued

| Chemical Synthesis Example | Structure (prepared by procedure of cited Example) | MS (ESI) m/z | NMR spectrum data |
|---|---|---|---|
| 93 | Prepared by the procedure of Example 1 | 467 | $^1$H NMR (400 MHz, DMSO-$d_6$): δ ppm 1.32 (td, J = 7.01, 1.39 Hz, 3 H) 1.58 (d, J = 11.62 Hz, 2 H) 1.92 (d, J = 11.62 Hz, 2 H) 2.80 (s, 3 H) 2.91-3.03 (m, 2 H) 3.08 (br. s., 1 H) 3.69 (d, J = 10.36 Hz, 2 H) 4.29-4.40 (m, 2 H) 6.86 (s, 1 H) 6.89 (d, J = 8.08 Hz, 1H) 7.21 (d, J = 8.08 Hz, 1 H) 7.56 (d, J = 1.77 Hz, 1 H) 7.81-7.86 (m, 1 H) 8.33 (s, 3 H). |
| 94 | Prepared by the procedure of Example 1 | 449 | $^1$H NMR (400 MHz, DMSO-$d_6$) δ ppm 1.28 (td, J = 7.01, 2.40 Hz, 3 H) 1.58 (br. s., 2 H) 1.89 (br. s., 2 H) 2.92-3.02 (m, 2 H) 3.07 (br. s., 1 H) 3.43 (s, 3 H) 3.68 (d, J = 13.39 Hz, 2 H) 4.21-4.29 (m, 2 H) 6.73 (d, J = 3.79 Hz, 1 H) 6.80 (s, 1 H) 6.93 (d, J = 7.83 Hz, 1 H) 7.20 (d, J = 8.59 Hz, 1 H) 7.54 (d, J = 8.08 Hz, 1 H) 7.80-7.85 (m, 1 H) 8.31 (s, 3 H). |
| 95 | Prepared by the procedure of Example 1 | 448 | $^1$H NMR (400 MHz, DMSO-$d_6$): δ ppm 1.31 (t, J = 6.69 Hz, 3 H) 1.73 (d, J = 9.09 Hz, 2 H) 2.00 (d, J = 12.13 Hz, 2 H) 2.99 (t, J = 12.51 Hz, 2 H) 3.28 (br. s., 1 H) 3.43 (s, 3 H) 3.71 (d, J = 12.38 Hz, 2 H) 3.95-4.06 (m, 2 H) 6.83 (d, J = 8.08 Hz, 2 H) 7.01 (d, J = 8.59 Hz, 2 H) 7.18 (d, J = 8.59 Hz, 1 H) 7.41 (d, J = 10.86 Hz, 1 H) 7.61 (m, 1 H) 7.79 (t, J = 7.83 Hz, 1 H) 8.07 (br. s., 3 H). |
| 96 | Prepared by the procedure of Example 1 | 464 | $^1$H NMR (400 MHz, DMSO-$d_6$) δ ppm 1.74 (d, J = 10.36 Hz, 2 H) 2.00 (d, J = 11.62 Hz, 2 H) 2.99 (t, J = 12.25 Hz, 2 H) 3.43 (s, 3 H) 3.64 (br. s., 2 H) 3.71 (d, J = 11.87 Hz, 2 H) 4.07 (br. s., 2 H) 6.85 (d, J = 8.34 Hz, 2 H) 7.01 (d, J = 8.34 Hz, 2 H) 7.18 (d, J = 8.08 Hz, 1 H) 7.41 (d, J = 10.36 Hz, 1 H) 7.58-7.67 (m, 1 H) 7.79 (t, J = 7.45 Hz, 1 H) 8.14 (br. s., 3 H). |

TABLE 3-continued

| Chemical Synthesis Example | Structure (prepared by procedure of cited Example) | MS (ESI) m/z | NMR spectrum data |
|---|---|---|---|
| 97 | (structure shown) Prepared by the procedure of Example 1 | 446 | $^1$H NMR (400 MHz, Methanol-d$_4$): δ ppm 1.87 (d, J = 11.12 Hz, 2 H) 2.13 (d, J = 12.13 Hz, 2 H) 3.04-3.21 (m, 2 H) 3.38 (d, J = 10.61 Hz, 1 H) 3.57 (s, 3 H) 3.77-3.88 (m, 4 H) 4.02 (br. s., 2 H) 6.86 (d, J = 7.83 Hz, 2 H) 7.04 (d, J = 8.34 Hz, 2 H) 7.47-7.53 (m, 2 H) 7.57 (d, J = 7.58 Hz, 2 H). |
| 98 | (structure shown) Prepared by the procedure of Example 1 | 478 | $^1$H NMR (400 MHz, DMSO-d$_6$) δ ppm: 1.74 (d, J = 11.87 Hz, 2 H) 2.00 (d, J = 12.38 Hz, 2 H) 2.99 (t, J = 12.25 Hz, 2 H) 3.28 (br. s., 1 H) 3.43 (s, 3 H) 3.44-3.54 (m, 2 H) 3.70 (m, 5 H) 3.90-4.05 (m, 2 H) 6.85 (d, J = 8.34 Hz, 2 H) 7.01 (d, J = 7.83 Hz, 2 H) 7.18 (d, J = 8.08 Hz, 1 H) 7.42 (d, J = 10.61 Hz, 1 H) 7.79 (t, J = 7.20 Hz, 1 H) 8.11 (br. s., 3H). |
| 99 | (structure shown) Prepared by the procedure of Example 1 | 448 | $^1$H NMR (400 MHz, DMSO-d$_6$): δ ppm 1.73 (d, J = 11.37 Hz, 2 H) 2.00 (d, J = 12.63 Hz, 2 H) 2.64-2.76 (m, 2 H) 3.00 (t, J = 12.13 Hz, 2 H) 3.29 (br. s., 1 H) 3.43 (br. s., 3 H) 3.48 (d, J = 9.85 Hz, 2 H) 3.69-3.77 (m, 2 H) 7.00 (d, J = 7.33 Hz, 2 H) 7.13 (d, J = 7.83 Hz, 2 H) 7.18 (d, J = 8.34 Hz, 1 H) 7.34-7.42 (m, 1 H) 7.75-7.80 (m, 1 H) 8.06 (br. s., 3 H). |
| 100 | (structure shown) Prepared by the procedure of Example 1 | 434 | $^1$H NMR (400 MHz, DMSO-d$_6$): δ ppm 1.73 (d, J = 12.13 Hz, 2 H) 1.94-2.03 (m, 2 H) 3.00 (br. s., 2 H) 3.29 (br. s., 1 H) 3.44 (s, 3 H) 3.48 (d, J = 9.60 Hz, 2 H) 3.70 (br. s., 2 H) 7.06 (d, J = 7.33 Hz, 2 H) 7.16 - 7.25 (m, 3 H) 7.41 (d, J = 10.86 Hz, 1 H) 7.75-7.82 (m, 1 H) 8.05 (br. s., 3 H). |
| 101 | (structure shown) Prepared by the procedure of Example 1 | 422 | $^1$H NMR (400 MHz, Methanol-d$_4$): δ ppm 1.78-1.94 (m, 2 H) 2.13 (d, J = 11.87 Hz, 2 H) 3.10 (t, J = 12.51 Hz, 2 H) 3.39 (d, J = 12.13 Hz, 1 H) 3.57 (s, 3 H) 3.73-3.93 (m, 2 H) 6.99-7.09 (m, 2 H) 7.12-7.25 (m, 3 H) 7.37 (d, J = 10.36 Hz, 1H) 7.57 (t, J = 6.95 Hz, 1 H). |

TABLE 3-continued

| Chemical Synthesis Example | Structure (prepared by procedure of cited Example) | MS (ESI) m/z | NMR spectrum data |
|---|---|---|---|
| 102 | Prepared by the procedure of Example 1 | 422 | ¹H NMR (400 MHz, Methanol-d$_6$): δ ppm 1.79-1.93 (m, 2 H) 2.13 (d, J = 12.38 Hz, 2 H) 3.11 (t, J = 12.63 Hz, 2 H) 3.39 (d, J = 11.62 Hz, 1H) 3.57 (s, 3 H) 3.85 (d, J = 13.64 Hz, 2 H) 6.89 (d, J = 7.83 Hz, 1 H) 6.96-7.07 (m, 2 H) 7.23 (d, J = 8.34 Hz, 1 H) 7.25 7.33 (m, 1 H) 7.38 (d, J = 10.36 Hz, 1 H) 7.58 (t, J = 7.20 Hz, 1 H). |
| 103 | Prepared by the procedure of Example 1 | 440 | ¹H NMR (400 MHz, Methanol-d$_4$): δ ppm 1.77-1.95 (m, 2 H) 2.13 (d, J = 11.62 Hz, 2 H) 3.12 (t, J = 12.76 Hz, 2 H) 3.36-3.45 (m, 1 H) 3.55 (s, 3 H) 3.86 (d, J = 13.64 Hz, 2 H) 6.78 (d, J = 6.57 Hz, 2 H) 6.89 (t, J = 9.22 Hz, 1H) 7.24 (d, J = 8.08 Hz, 1 H) 7.43 (d, J = 10.11 Hz, 1 H) 7.62 (t, J = 7.07 Hz, 1 H). |
| 104 | Prepared by the procedure of Example 1 | 440 | ¹H NMR (400 MHz, Methanol-d$_4$): δ ppm 1.79-1.93 (m, 2 H) 2.12 (d, J = 11.62 Hz, 2 H) 3.11 (t, J = 12.63 Hz, 2 H) 3.33-3.49 (m, 1 H) 3.57 (s, 3 H) 3.85 (d, J = 13.64 Hz, 2 H) 6.87 (br. s., 1 H) 7.11-7.25 (m, 3 H) 7.42 (d, J = 10.36 Hz, 1 H) 7.60 (t, J = 7.20 Hz, 1 H). |
| 105 | Prepared by the procedure of Example 1 | 482 | ¹H NMR (400 MHz, Methanol-d$_4$): δ ppm 1.79-1.92 (m, 2 H) 2.12 (d, J = 11.62 Hz, 2 H) 3.05-3.29 (m, 5 H) 3.40 (br. s., 1 H) 3.58 (s, 3 H) 3.80-3.94 (m, 2 H) 7.16 (d, J = 7.58 Hz, 1 H) 7.36 - 7.48 (m, 3 H) 7.58 (t, J = 7.20 Hz, 1 H) 7.87 (d, J = 8.08 Hz, 2 H). |

TABLE 3-continued

| Chemical Synthesis Example | Structure (prepared by procedure of cited Example) | MS (ESI) m/z | NMR spectrum data |
|---|---|---|---|
| 106 | Prepared by the procedure of Example 1 | 438 | ¹H NMR (400 MHz, Chloroform-d): δ ppm 1.89 (d, J = 11.12 Hz, 2 H) 2.16 (d, J = 10.86 Hz, 2 H) 3.05 (t, J = 11.87 Hz, 2 H) 3.28 (br. s., 1 H) 3.55 (s, 3 H) 3.71 (d, J = 12.13 Hz, 2 H) 7.04 (d, J = 8.34 Hz, 1 H) 7.10 (d, J = 8.08 Hz, 2 H) 7.27-7.30 (m, 1 H) 7.33-7.44 (m, 2 H) 8.31 (br. s., 1 H). |
| 107 | Prepared by the procedure of Example 1 | 448 | ¹H NMR (400 MHz, Methanol-d₄): δ ppm 1.81-1.94 (m, 2 H) 2.13 (d, J = 12.13 Hz, 2 H) 3.12 (t, J = 12.38 Hz, 2 H) 3.36 (s, 3 H) 3.41 (br. s., 1 H) 3.58 (s, 3 H) 3.84 (d, J = 12.63 Hz, 2 H) 4.45 (s, 2 H) 7.14 (d, J = 7.58 Hz, 2 H) 7.23 (d, J = 7.83 Hz, 1 H) 7.28 (d, J = 7.83 Hz, 2 H) 7.34 (d, J = 10.61 Hz, 1 H) 7.55 (t, J = 7.20 Hz, 1 H). |
| 108 | Prepared by the procedure of Example 13 | 328 | ¹H NMR (400 MHz, DMSO-d₆): δ ppm 1.62-1.78 (m, 2 H) 2.00 (d, J = 11.87 Hz, 2 H) 3.02 (t, J = 12.00 Hz, 2 H) 3.32 (s, 3 H) 3.76 (d, J = 12.88 Hz, 2 H) 6.87 (s, 1 H) 7.95 (br. s., 3 H) 8.01-8.08 (m, 1 H) 8.08- 8.12 (m, 1 H) 8.16 (d. J = 11.12 Hz, 1 H). |
| 109 | Prepared by the procedure of Example 13 | 368 | ¹HNMR (400 MHz, CD₃OD): δ 0.37-0.39 (m, 2H), 0.60-0.65 (m, 2H), 1.29-1.32 (m, 1H), 1.59-1.64 (m, 2H), 2.10-2.14 (m, 2H), 3.07-3.14 (m, 2H), 3.43-3.47 (m, 1H), 6.81 (d, J = 7.2 Hz, 2H), 4.92-4.95 (m, 2 H), 6.66 (s, 1H), 7.84-7.88 (m, 1H), 7.99-8.05 (m, 2H). |
| 110 | Prepared by the procedure of Example 14 | 352 | ¹H NMR (400 MHz, CD₃OD): δ 1.40-1.41 (m, 2H), 1.81-1.84 (m, 2H), 2.75-2.78 (m, 1H), 2.89-2.95 (m, 2H), 3.37 (s, 3H), 3.65-3.68 (m, 2H), 3.77 (s, 1H), 7.66 (t, J = 8.0 Hz, 1H), 7.89 (d, J = 8.0 Hz, 1H), 7.96 (d, J = 8.4 Hz, 1H). |

TABLE 3-continued

| Chemical Synthesis Example | Structure (prepared by procedure of cited Example) | MS (ESI) m/z | NMR spectrum data |
|---|---|---|---|
| 111 | Prepared by the procedure of Example 1 | 442 | $^1$H NMR (400 MHz, DMSO-d$_6$): 1.75-1.83 (m, 2H), 2.06 ( d, J = 10.8 Hz, 2H), 2.99 (t, J = 11.6 Hz, 2H), 3.28-3.30 (m, 1H), 3.42 (s, 3H), 3.68-3.74 (m, 5H), 6.85 (d, J = 8.0 Hz, 2H), 7.02-7.08 (m, 3H), 7.28-7.45 (m, 2H), 8.38-8.44 (m, 2H). |
| 112 | Prepared by the procedure of Example 1 | 429 | $^1$H NMR (400 MHz, CD$_3$OD): 1.09-1.17 (m, 2H), 1.57-1.62 (m, 2H), 2.46-2.56 (m, 3H), 2.96-3.03 (m, 2H), 3.35 (s, 3H), 3.78 (s, 3H), 6.02 (s, 1H), 6.37 (s, 1H), 6.79-6.97 (m, 3H), 7.13-7.27 (m, 2H), 7.42-7.52 (m, 2H). |
| 113 | Prepared by the procedure of Example 1 | 431 | $^1$H NMR (400 MHz, CD$_3$OD): 1.06-1.17 (m, 2H), 1.57-1.62 (m, 2H), 2.49-2.56 (m, 3H), 2.96-3.09 (m, 2H), 3.36 (s, 3H), 3.78 (s, 3H), 6.07 (s, 1H), 6.40 (s, 1H), 6.97-7.20 (m, 4H), 7.27 (d, J = 11.8 Hz, 1H), 7.45 (s, 1H), 7.61-7.66 (m, 1H). |
| 114 | Prepared by the procedure of Example 1 | 414 | $^1$H NMR (400 MHz, CD$_3$OD): δ 152-1.55 (m, 2H), 1.87-1.90 (m, 2H), 2.83-3.95 (m, 3H), 3.49 (s, 3H), 3.59-3.67 (m, 5H), 6.23 (s, 1H), 6.81 (d, J = 8.4 Hz, 1H), 6.98-7.08 (m, 4H), 8.14 (t, J = 8.0 Hz, 1H), 7.24 (m, 3H). |
| 115 | Prepared by the procedure of Example 1 | 410 | $^1$H NMR (400 MHz, CD$_3$OD): δ 1.90-2.05 (m, 2H), 2.16-2.19 (m, 2H), 3.12-3.20 (m, 2H), 3.44-3.49 (m, 1H), 3.62 (s, 3H), 3.88 (s, 3H), 3.90-3.92 (m, 2H), 6.88-6.90 (m, 1H), 7.02-7.06 (m, 1H), 7.08-7.13 (m, 1H), 8.07 (d, J = 6.0 Hz, 2H), 8.79 (d, J = 6.0 Hz, 2H). |

TABLE 3-continued

| Chemical Synthesis Example | Structure (prepared by procedure of cited Example) | MS (ESI) m/z | NMR spectrum data |
|---|---|---|---|
| 116 | Prepared by the procedure of Example 1 | 415 | $^1$H NMR (400 MHz, CD$_3$OD): δ 1.50-1.53 (m, 2H), 1.86-1.89 (m, 2H), 2.82-3.95 (m, 3H), 3.48 (s, 3H), 3.60-3.69 (m, 5H), 6.24 (s, 1H), 6.81 (d, J = 8.4 Hz, 1H), 7.03 (s, 1H), 7.18-7.24 (m 4H), 8.17 (t, J = 4.4 Hz, 1H). |
| 117 | Prepared by the procedure of Example 1 | 444 | $^1$H NMR (400 MHz, CD$_3$OD): δ 1.62-1.68 (m, 2H), 2.01-2.03 (m, 2H), 2.96-3.06 (m, 3H), 3.55 (s, 3H), 3.71-3.74 (m, 5H), 3.81 (s, 3H), 6.36 (d, J = 3.2 Hz, 1H), 6.65 (d, J = 8.8 Hz, 1H), 6.93 (t, J = 8.8 Hz, 1H), 7.13 (d, J = 3.2 Hz, 1H), 7.29-7.38 (m, 4H). |
| 118 | Prepared by the procedure of Example 1 | 434 | $^1$H NMR (300 MHz, CD$_3$OD): δ 1.84-1.89 (m, 2H), 2.12-2.16 (m, 2H), 3.13 (t, J = 12.0 Hz, 2H), 3.31-3.41 (m, 1H), 3.57 (s, 3H), 3.84 (s, 3H), 3.84-3.86 (m, 2H), 6.79-6.82 (m, 1H), 6.93-7.00 (m, 2 H), 7.38 (t, J = 7.5 Hz, 1H), 7.54 (d, J = 8.4 Hz, 1H), 7.64 (d, J = 7.8 Hz, 1H), 7.78 (s, 1H). |
| 119 | Prepared by the procedure of Example 1 | 434 | $^1$H NMR (300 MHz, DMSO-d6): δ 1.70-1.74 (m, 2H), 1.99-2.03 (m, 2H), 2.95 (t, J = 12.0 Hz, 2H), 3.23-3.24 (m. 1H), 3.44 (s, 3H), 3.74 (s, 3H), 3.84-3.86 (m, 2H), 6.68-6.70 (m, 1H), 6.91-6.96 (m, 2 H), 7.31-7.34 (m, 1H), 7.40-7.59 (m, 2H), 7.77-7.80 (m, 1H), 8.34 (m, 3H). |

Preparation 120A: [1-(5-chloro-4-cyano-1-methyl-6-oxo-1,6-dihydro-pyrimidin-2-yl)-piperidin-4-yl]-carbamic acid tert-butyl ester

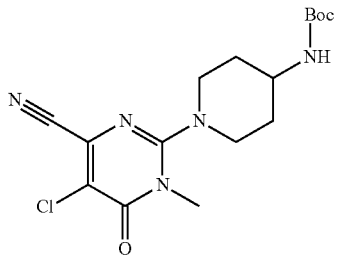 [SMILES: Cn1c(N2CCC(NC(=O)OC(C)(C)C)CC2)nc(C#N)c(Cl)c1=O]

A mixture of N-[1-(5,6-dichloro-3-methyl-4-oxo(3-hydropyrimidin-2-yl))(4-piperidyl)](tert-butoxy)carboxamide (2.4 g, 6.38 mmol), Zn(CN)$_2$ (388 mg, 3.32 mmol) and Pd(PPh$_3$)$_4$ (740 mg, 0.64 mmol) in DMF (20 mL) was stirred at 130° C. for 5 h under N$_2$ atmosphere. The reaction mixture was cooled to RT and filtered. The filtrate was concentrated in vacuo, and the residue was purified by preperative HPLC to give 200 mg of the title product (9%). [M+H] Calc'd for C$_{16}$H$_{22}$ClN$_5$O$_3$, 368; Found, 368.

Preparation 120B: {1-[4-cyano-5-(3-fluoro-4-methoxy-phenyl)-1-methyl-6-oxo-1,6-dihydro-pyrimidin-2-yl]-piperidin-4-yl}-carbamic acid tert-butyl ester

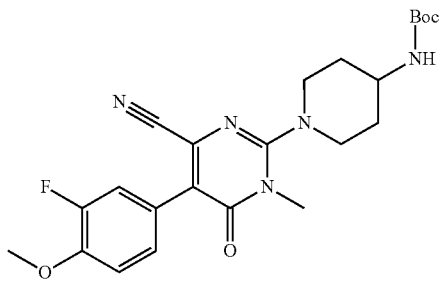 [SMILES: COc1ccc(-c2c(C#N)nc(N3CCC(NC(=O)OC(C)(C)C)CC3)n(C)c2=O)cc1F]

A mixture of [1-(5-chloro-4-cyano-1-methyl-6-oxo-1,6-dihydro-pyrimidin-2-yl)-piperidin-4-yl]-carbamic acid tert-butyl ester (200 mg, 0.54 mmol), 3-fluoro-4-methoxybenzeneboronic acid (278 mg, 1.63 mmol), Pd(dppf)$_2$Cl$_2$ (119 mg, 0.16 mmol), and Na$_2$CO$_3$ (173 mg, 1.63 mmol) in dioxane (5 mL) and H$_2$O (1 mL) was degassed with N$_2$ and stirred at 145° C. in the microwave for 2 h. The reaction mixture was cooled to RT and filtered. The filtrate was concentrated in vacuo and the residue purified by preperative HPLC to to give 110 mg of the desired product (45%). [M+H] Calc'd for C$_{23}$H$_{28}$FN$_5$O$_4$, 458; Found, 458.

Example 120: 2-(4-amino-piperidin-1-yl)-5-(3-fluoro-4-methoxy-phenyl)-1-methyl-6-oxo-1,6-dihydro-pyrimidine-4-carbonitrile

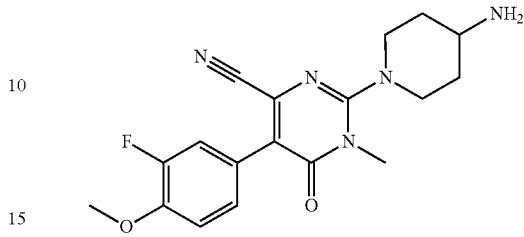

A mixture of {1-[4-cyano-5-(3-fluoro-4-methoxy-phenyl)-1-methyl-6-oxo-1,6-dihydro-pyrimidin-2-yl]-piperidin-4-yl}-carbamic acid tert-butyl ester (100 mg, 0.23 mmol) in EA (5 mL) was added a 5N HCl solution in EA (5 mL) was stirred at RT for 2 h. The solvent was concentrated in vacuo to give 85 mg of the title product as the HCl salt (93%). $^1$H NMR (400 MHz, CD$_3$OD): δ 1.71-1.75 (m, 2H), 1.89-2.03 (m, 2H), 2.96-3.02 (m, 2H), 3.27-3.31 (m, 1H), 3.42 (s, 3H), 3.69-3.73 (m, 2H), 3.83 (s, 3H), 7.06 (t, J=8.0 Hz, 1H), 7.17-2.01 (m, 2H). [M+H] Calc'd for C$_{18}$H$_{20}$FN$_5$O$_2$, 358; Found, 358.

Preparation 121A: {1-[5-cyano-4-(4-cyano-3-fluoro-phenyl)-1-methyl-6-oxo-1,6-dihydro-pyrimidin-2-yl]-piperidin-4-yl}-carbamic acid tert-butyl ester

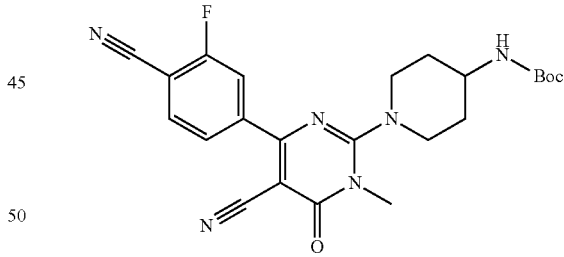

A mixture of {1-[5-chloro-4-(4-cyano-3-fluoro-phenyl)-1-methyl-6-oxo-1,6-dihydro-pyrimidin-2-yl]-piperidin-4-yl}-carbamic acid tert-butyl ester (460 mg, 1 mmol), Zn(CN)$_2$ (175 mg, 1.5 mmol) and Pd(PPh$_3$)$_4$ (116 mg, 0.0.1 mmol) in DMF (5 mL) was stirred 4 h at 150° C. under N$_2$ atmosphere. The mixture was cooled to RT and filtered. The filtrate was concentrated in vacuo, and the residue purified by preperative HPLC to give 150 mg of the title product as a yellow solid (33%). [M+H] Calc'd for C$_{23}$H$_{25}$FN$_6$O$_3$, 453; Found, 453.

Example 121: 2-(4-amino-piperidin-1-yl)-4-(4-cyano-3-fluoro-phenyl)-1-methyl-6-oxo-1,6-dihydro-pyrimidine-5-carbonitrile

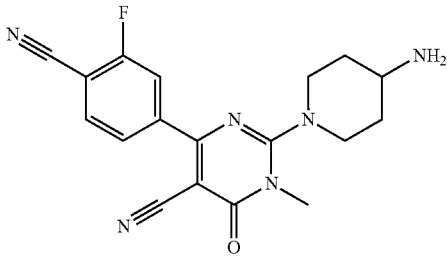 [SMILES: Cn1c(N2CCC(N)CC2)nc(-c2ccc(C#N)c(F)c2)c(C#N)c1=O]

To a mixture of {1-[5-cyano-4-(4-cyano-3-fluoro-phenyl)-1-methyl-6-oxo-1,6-dihydro-pyrimidin-2-yl]-piperidin-4-yl}-carbamic acid tert-butyl ester (150 mg, 0.33 mmol) in EA (5 mL) was added a 5 N HCl solution in EA (5 mL), and the mixture was stirred at RT for 2 h. The solvent was concentrated in vacuo to give 120 mg the title product as HCl salt (94%). $^1$H NMR (400 MHz, CD$_3$OD): δ 1.67-1.72 (m, 2H), 2.02-2.06 (m, 2H), 3.13-3.16 (m, 2H), 3.34-3.38 (m, 1H), 3.42 (s, 3H), 3.98-4.02 (m, 2H), 7.82-7.90 (m, 3H). [M+H] Calc'd for C$_{18}$H$_{17}$FN$_6$O, 353; Found, 353.

Preparation 122A: 4-cyano-3-fluoro-benzoyl chloride

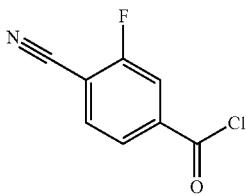 [SMILES: N#Cc1ccc(C(=O)Cl)cc1F]

A mixture of 4-cyano-3-fluoro-benzoic acid (2.0 g, 12.12 mmol) in SOCl$_2$ (20 mL) was refluxed for 2 h, and SOCl$_2$ was removed in vacuo to give 4-cyano-3-fluoro-benzoyl chloride (2.2 g, 99%). The crude was carried to the next step without further purification.

Preparation 122B: 3-(4-cyano-3-fluoro-phenyl)-2-(4-methoxy-phenyl)-3-oxo-propionic acid methyl ester

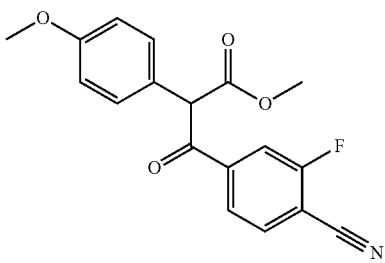 [SMILES: COC(=O)C(C(=O)c1ccc(C#N)c(F)c1)c1ccc(OC)cc1]

To a solution of (4-methoxy-phenyl)-acetic acid (2.18 g, 12.12 mmol) in THF (20 mL) was added LiHMDS (18.2 mL, 18.18 mmol) at −78° C. and the mixture was stirred for 30 min. A solution of 4-cyano-3-fluoro-benzoyl chloride (2.2 g, 12 mmol) in THF was added dropwise at −78° C.; and the reaction mixture was allowed to warm up to RT and stirred at overnight. Aqueous NH$_4$Cl was added and the aqueous was extracted with EA (3×). The combined organics were concentrated in vacuo and the residue was purified by silica column chrmatography (1:5, EA: PE) to give 1.8 g (45%) of the title compound. [M+H] Calc'd for C$_{18}$H$_{14}$FNO$_4$, 328; Found, 328.

Preparation 122C: {1-[4-(4-cyano-3-fluoro-phenyl)-5-(4-methoxy-phenyl)-6-oxo-1,6-dihydro-pyrimidin-2-yl]-piperidin-4-yl}-carbamic acid tert-butyl ester

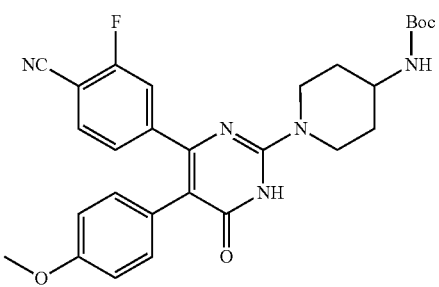 [SMILES: COc1ccc(-c2c(-c3ccc(C#N)c(F)c3)nc(N3CCC(NC(=O)OC(C)(C)C)CC3)[nH]c2=O)cc1]

A mixture of 3-(4-cyano-3-fluoro-phenyl)-2-(4-methoxy-phenyl)-3-oxo-propionic acid methyl ester (1.8 g, 5.5 mmol), (1-carbamimidoyl-piperidin-4-yl)-carbamic acid tert-butyl ester (2.6 g, 9.2 mmol), DIEA (2.4 g, 18.3 mmol) in toluene (50 mL) was refluxed overnight. The solvent was concentrated in vacuo. The residue was suspended in MeOH and the solids were filtered to give 100 mg (4%) of the title compound. [M+H] Calc'd for C$_{28}$H$_{30}$FN$_5$O$_4$, 520; Found, 520.

Example 122: 4-[2-(4-amino-piperidin-1-yl)-5-(4-methoxy-phenyl)-6-oxo-1,6-dihydro-pyrimidin-4-yl]-2-fluoro-benzonitrile

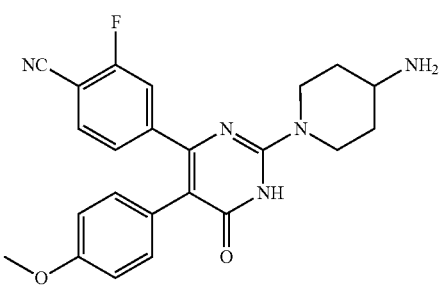 [SMILES: COc1ccc(-c2c(-c3ccc(C#N)c(F)c3)nc(N3CCC(N)CC3)[nH]c2=O)cc1]

To a solution of {1-[4-(4-cyano-3-fluoro-phenyl)-5-(4-methoxy-phenyl)-6-oxo-1,6-dihydro-pyrimidin-2-yl]-piperidin-4-yl}-carbamic acid tert-butyl ester (50 mg, 0.096 mmol) in EA (10 mL) was added a 5M HCl solution in EA and the mixture was stirred at RT for 2 h. The solvent was removed in vacuo and the residue was purified by preparative HPLC to give 18 mg (40%) of the title compound as the hydrochloride salt. $^1$H NMR (400 MHz, CD$_3$OD): δ 1.81-

1.87 (m, 2H), 2.22-2.25 (m, 2H), 3.34-3.38 (m, 2H), 3.56-3.60 (m, 1H), 3.78 (s, 3H), 4.61-4.64 (m, 2H), 6.86 (d, J=7.2 Hz, 2H), 7.08 (d, J=8.4 Hz, 2H), 7.37-7.38 (m, 1H), 7.51-7.53 (m, 1H), 7.74 (s, 1H). [M+H] Calc'd for $C_{23}H_{22}FN_5O_2$, 420; Found, 420.

II. Biological Evaluation

Example 1a: In Vitro Enzyme Inhibition Assay—LSD-1

This assay determines the ability of a test compound to inhibit LSD-1 demethylase activity. *E. coli* expressed full-length human LSD-1 (Accession number 060341) was purchased from Active Motif (Cat#31334).

The enzymatic assay of LSD-1 activity is based on Time Resolved-Fluorescence Resonance Energy Transfer (TR-FRET) detection. The inhibitory properties of compounds to LSD-1 were determined in 384-well plate format under the following reaction conditions: 0.1-0.5 nM LSD-1, 50 nM H3K4me1-biotin labeled peptide (Anaspec cat #64355), 2 µM FAD in assay buffer of 50 mM HEPES, pH7.3, 10 mM NaCl, 0.005% Brij35, 0.5 mM TCEP, 0.2 mg/ml BSA. Reaction product was determined quantitatively by TR-FRET after the addition of detection reagent Phycolink Streptavidin-allophycocyanin (Prozyme) and Europium-anti-unmodified histone H3 lysine 4 (H3K4) antibody (PerkinElmer) in the presence of LSD-1 inhibitor such as 1.8 mM of Tranylcypromine hydrochloride (2-PCPA) in LANCE detection buffer (PerkinElmer) to final concentration of 12.5 nM and 0.25 nM respectively.

The assay reaction was performed according to the following procedure: 2 µL of the mixture of 150 nM H3K4me1-biotin labeled peptide with 2 µL of 11-point serial diluted test compound in 3% DMSO were added to each well of plate, followed by the addition of 2 µL of 0.3 nM LSD-1 and 6 µM of FAD to initiate the reaction. The reaction mixture was then incubated at room temperature for one hour, and terminated by the addition of 6 µL of 1.8 mM 2-PCPA in LANCE detection buffer containing 25 nM Phycolink Streptavidin-allophycocyanin and 0.5 nM Europium-anti-unmodified H3K4 antibody. Enzymatic reaction is terminated within 15 minutes if 0.5 LSD-1 enzyme is used in the plate. Plates were read by EnVision Multilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

The ability of the compounds disclosed herein to inhibit LSD-1 activity was quantified and the respective IC50 value was determined. Table 4 provides the IC50 values of various substituted heterocyclic compounds disclosed herein.

TABLE 4

| Chemical Synthesis Example | Name | LSD-1 $IC_{50}$ (µM) |
|---|---|---|
| 1 | 4-(2-(4-aminopiperidin-1-yl)-1-methyl-6-oxo-5-p-tolyl-1,6-dihydropyrimidin-4-yl)benzonitrile | A |
| 2 | 4-[2-(4-amino-piperidin-1-yl)-5-(4-methoxy-phenyl)-1-methyl-6-oxo-1,6-dihydro-pyrimidin-4-yl]-benzonitrile | A |
| 3 | 4-[2-(4-amino-piperidin-1-yl)-5-(6-methoxy-pyridin-3-yl)-1-methyl-6-oxo-1,6-dihydro-pyrimidin-4-yl]-benzonitrile | A |
| 4 | 4-[2-(4-amino-piperidin-1-yl)-1-methyl-5-(6-methyl-pyridin-3-yl)-6-oxo-1,6-dihydro-pyrimidin-4-yl]-benzonitrile | A |
| 5 | 4-[2-(4-amino-piperidin-1-yl)-5-(4-methoxy-phenyl)-1-methyl-6-oxo-1,6-dihydro-pyrimidin-4-yl]-benzonitrile | A |
| 6 | 4-[2-(4-amino-piperidin-1-yl)-5-(4-methoxy-phenyl)-1-methyl-6-oxo-1,6-dihydro-pyrimidin-4-yl]-2-fluoro-benzonitrile | A |
| 7 | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 8 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 9 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 10 | 4-[2-(4-amino-piperidin-1-yl)-5-(6-ethyl-pyridin-3-yl)-1-methyl-6-oxo-1,6-dihydro-pyrimidin-4-yl]-benzonitrile | A |
| 11 | 2-fluoro-4-[5-(4-methoxy-phenyl)-1-methyl-2-(4-methylamino-piperidin-1-yl)-6-oxo-1,6-dihydro-pyrimidin-4-yl]-benzonitrile | A |
| 12 | 2-fluoro-4-[5-(3-fluoro-4-methoxy-phenyl)-1-methyl-2-(4-methylamino-piperidin-1-yl)-6-oxo-1,6-dihydro-pyrimidin-4-yl]-benzonitrile | A |
| 13 | 4-[2-(4-amino-piperidin-1-yl)-1-ethyl-6-oxo-1,6-dihydro-pyrimidin-4-yl]-2-fluoro-benzonitrile | B |
| 14 | 4-[2-(4-amino-piperidin-1-yl)-5-cyclopentylethynyl-1-methyl-6-oxo-1,6-dihydro-pyrimidin-4-yl]-2-fluoro-benzonitrile | A |
| 15 | [2-(4-amino-piperidin-1-yl)-4-(4-cyano-3-fluoro-phenyl)-5-(4-methoxy-phenyl)-6-oxo-6H-pyrimidin-1-yl]-acetic acid | A |
| 16 | 2-[2-(4-amino-piperidin-1-yl)-4-(4-cyano-3-fluoro-phenyl)-5-(4-methoxy-phenyl)-6-oxo-6H-pyrimidin-1-yl]-acetamide | A |
| 17 | 4-[2-(4-amino-piperidin-1-yl)-1-(3-hydroxy-propyl)-6-oxo-1,6-dihydro-pyrimidin-4-yl]-2-fluoro-benzonitrile | B |
| 18 | 4-[2-(4-amino-piperidin-1-yl)-5-benzofuran-5-yl-1-methyl-6-oxo-1,6-dihydro-pyrimidin-4-yl]-2-fluoro-benzonitrile | A |
| 19 | 2-(4-amino-piperidin-1-yl)-4-(4-cyano-3-fluoro-phenyl)-1-methyl-6-oxo-1,6-dihydro-pyrimidine-5-carbonitrile | A |
| 20 | 4-[2-(4-aminopiperidin-1-yl)-5-chloro-1-methyl-6-oxopyrimidin-4-yl]-2-fluorobenzonitrile | A |
| 21 | 2-fluoro-4-[1-methyl-2-(4-methylamino-piperidin-1-yl)-5-(6-methyl-pyridin-3-yl)-6-oxo-1,6-dihydro-pyrimidin-4-yl]-benzonitrile | A |

TABLE 4-continued

| Chemical Synthesis Example | Name | LSD-1 IC$_{50}$ (μM) |
|---|---|---|
| 22 | 4-[2-(2,8-diaza-spiro[4.5]dec-8-yl)-5-(3-fluoro-4-methoxy-phenyl)-1-methyl-6-oxo-1,6-dihydro-pyrimidin-4-yl]-2-fluoro-benzonitrile | A |
| 23 | 4-{2-(4-aminopiperidyl)-1-methyl-6-oxo-5-[6-(trifluoromethyl) (3-pyridyl)] hydropyrimidin-4-yl}-2-fluorobenzenecarbonitrile | A |
| 24 | 4-[2-(4-aminopiperidyl)-1-methyl-5-(2-methyl(2H-indazol-5-yl))-6-oxohydropyrimidin-4-yl]benzenecarbonitrile | A |
| 25 | 4-[2-((3R)-3-aminopiperidyl)-5-(3-fluoro-4-methoxyphenyl)-1-methyl-6-oxohydropyrimidin-4-yl]-2-fluorobenzenecarbonitrile | A |
| 26 | 4-[2-(4-aminopiperidyl)-5-(5-fluoro-6-methoxy(3-5,6-dihydropyridyl))-1-methyl-6-oxohydropyrimidin-4-yl]-2-fluorobenzenecarbonitrile | A |
| 27 | 4-[2-((3R)-3-aminopyrronyl)-5-(3-fluoro-4-methoxyphenyl)-1-methyl-6-oxohydropyrimidin-4-yl]-2-fluorobenzenecarbonitrile | A |
| 28 | 4-[2-((3S)-3-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 29 | 4-[2-((3S)-3-amino-pyrrolidin-1-yl)-5-(3-fluoro-4-methoxy-phenyl)-1-methyl-6-oxo-1,6-dihydro-pyrimidin-4-yl]-2-fluoro-benzonitrile | A |
| 30 | 4-[2-((3R)-3-aminopiperidyl)-5-(4-methoxyphenyl)-1-methyl-6-oxohydro pyrimidin-4-yl]-2-fluorobenzenecarbonitrile | A |
| 31 | 4-[2-((3S)-3-amino-piperidin-1-yl)-5-(4-methoxy-phenyl)-1-methyl-6-oxo-1,6-dihydro-pyrimidin-4-yl]-2-fluoro-benzonitrile | A |
| 32 | 4-[2-(4-amino-4-methyl-piperidin-1-yl)-5-(3-fluoro-4-methoxy-phenyl)-1-methyl-6-oxo-1,6-dihydro-pyrimidin-4-yl]-2-fluoro-benzonitrile | A |
| 33 | 4-[2-(4-aminopiperidyl)-1-methyl-5-(1-methyl(1H-indazol-5-yl))-6-oxohydropyrimidin-4-yl]benzenecarbonitrile | A |
| 34 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile | A |
| 35 | 4-[2-(4-amino-piperidin-1-yl)-1-methyl-5-(1-methyl-1H-indazol-5-yl)-6-oxo-1,6-dihydro-pyrimidin-4-yl]-2-fluoro-benzonitrile | A |
| 36 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl]}-benzonitrile | A |
| 37 | 4-[2-(4-aminopiperidyl)-1-methyl-5-(2-methyl(2H-indazol-5-yl))-6-oxohydropyrimidin-4-yl]-2-fluorobenzenecarbonitrile | A |
| 38 | 4-[2-(4-aminopiperidyl)-5-(3,5-difluoro-4-methoxyphenyl)-1-methyl-6-oxohydropyrimidin-4-yl]benzenecarbonitrile | A |
| 39 | 4-[2-(4-aminopiperidyl)-6-(4-cyano-3-fluorophenyl)-3-methyl-4-oxo-3-hydropyrimidin-5-yl]benzoic acid | B |
| 40 | {4-[2-(4-aminopiperidyl)-6-(4-cyanophenyl)-3-methyl-4-oxo(3-hydro pyrimidin-5-yl)]-2-fluorophenyl]}-N-methylcarboxamide | A |
| 41 | 4-[2-(4-aminopiperidyl)-6-(4-cyanophenyl)-3-methyl-4-oxo(3-hydro pyrimidin-5-yl)]-2-fluorobenzamide | A |
| 42 | 4-[2-(4-amino-piperidin-1-yl)-1-methyl-6-oxo-5-(1-oxo-2,3-dihydro-1H-isoindol-5-yl)-1,6-dihydro-pyrimidin-4-yl]-2-fluoro-benzonitrile | A |
| 43 | 3-[2-(4-amino-piperidin-1-yl)-4-(4-cyano-3-fluoro-phenyl)-1-methyl-6-oxo-1,6-dihydro-pyrimidin-5-yl]-benzoic acid | C |
| 44 | 4-{5-(3-fluoro-4-methoxy-phenyl)-1-methyl-6-oxo-2-[(3S)-(pyrrolidin-3-ylmethyl)-amino]-1,6-dihydro-pyrimidin-4-yl]}-benzonitrile | A |
| 45 | 4-{5-(3-fluoro-4-methoxy-phenyl)-1-methyl-6-oxo-2-[(3R)-(pyrrolidin-3-ylmethyl)-amino]-1,6-dihydro-pyrimidin-4-yl]}-benzonitrile | A |
| 46 | 4-[2-[1,4]diazepan-1-yl-5-(3-fluoro-4-methoxy-phenyl)-1-methyl-6-oxo-1,6-dihydro-pyrimidin-4-yl]-2-fluoro-benzonitrile | A |
| 47 | 2-fluoro-4-[5-(3-fluoro-4-methoxy-phenyl)-1-methyl-6-oxo-2-piperazin-1-yl-1,6-dihydro-pyrimidin-4-yl]-benzonitrile | A |
| 48 | 4-[5-(3-fluoro-4-methoxy-phenyl)-1-methyl-6-oxo-2-(piperidin-4-ylamino)-1,6-dihydro-pyrimidin-4-yl]-benzonitrile | A |
| 49 | 4-[2-(4-amino-piperidin-1-yl)-2'-dimethylamino-1-methyl-6-oxo-1,6-dihydro-[5,5']bipyrimidinyl-4-yl]-2-fluoro-benzonitrile | A |
| 50 | 5-[2-(4-amino-piperidin-1-yl)-4-(4-cyano-3-fluoro-phenyl)-1-methyl-6-oxo-1,6-dihydro-pyrimidin-5-yl]-pyridine-2-carboxylic acid methylamide | A |
| 51 | 2-fluoro-4-{5-(4-methoxy-phenyl)-1-methyl-6-oxo-2-[(3S)-(pyrrolidin-3-ylmethyl)-amino]-1,6-dihydro-pyrimidin-4-yl]}-benzonitrile | A |
| 52 | 2-luoro-4-{5-(4-methoxy-phenyl)-1-methyl-6-oxo-2-[(3R)-(pyrrolidin-3-ylmethyl)-amino]-1,6-dihydro-pyrimidin-4-yl]}-benzonitrile | A |
| 53 | 2-fluoro-4-[5-(4-methoxy-phenyl)-1-methyl-6-oxo-2-(piperidin-4-yl amino)-1,6-dihydro-pyrimidin-4-yl]-benzonitrile | A |
| 54 | 2-fluoro-4-[5-(4-methoxy-phenyl)-1-methyl-2-(methyl-(3S)-pyrrolidin-3-ylmethyl-amino)-6-oxo-1,6-dihydro-pyrimidin-4-yl]-benzonitrile | A |
| 55 | 2-fluoro-4-[5-(4-methoxy-phenyl)-1-methyl-2-(methyl-piperidin-4-yl-amino)-6-oxo-1,6-dihydro-pyrimidin-4-yl]-benzonitrile | A |
| 56 | 2-fluoro-4-[5-(4-methoxy-phenyl)-1-methyl-2-(methyl-pyrrolidin-3-ylmethyl-amino)-6-oxo-1,6-dihydro-pyrimidin-4-yl]-benzonitrile | A |
| 57 | 4-[2-(4-amino-piperidin-1-yl)-5-(6-dimethylamino-pyridin-3-yl)-1-methyl-6-oxo-1,6-dihydro-pyrimidin-4-yl]-2-fluoro-benzonitrile | A |
| 58 | 2-fluoro-4-[5-(6-methoxy-pyridin-3-yl)-1-methyl-2-(4-methylamino-piperidin-1-yl)-6-oxo-1,6-dihydro-pyrimidin-4-yl]-benzonitrile | A |

TABLE 4-continued

| Chemical Synthesis Example | Name | LSD-1 IC$_{50}$ (μM) |
|---|---|---|
| 59 | 4-[2-(4-amino-piperidin-1-yl)-5-(4-dimethylamino-phenyl)-1-methyl-6-oxo-1,6-dihydro-pyrimidin-4-yl]-2-fluoro-benzonitrile | A |
| 60 | 4-[2-(4-amino-piperidin-1-yl)-1-methyl-6-oxo-5-(6-pyrrolidin-1-yl-pyridin-3-yl)-1,6-dihydro-pyrimidin-4-yl]-2-fluoro-benzonitrile | A |
| 61 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | A |
| 62 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | A |
| 63 | 4-[2-[1,4]diazepan-1-yl-5-(6-dimethylamino-pyridin-3-yl)-1-methyl-6-oxo-1,6-dihydro-pyrimidin-4-yl]-2-fluoro-benzonitrile | A |
| 64 | 4-[2-(3-amino-azetidin-1-yl)-5-(4-methoxy-phenyl)-1-methyl-6-oxo-1,6-dihydro-pyrimidin-4-yl]-2-fluoro-benzonitrile | A |
| 65 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile | A |
| 66 | 4-[2-[1,4]diazepan-1-yl-1-methyl-5-(2-methyl-2H-indazol-5-yl)-6-oxo-1,6-dihydro-pyrimidin-4-yl]-2-fluoro-benzonitrile | A |
| 67 | 4-[2-[1,4]diazepan-1-yl-5-(6-dimethylamino-pyridin-3-yl)-1-methyl-6-oxo-1,6-dihydro-pyrimidin-4-yl]-benzonitrile | A |
| 68 | 4-[2-(4-amino-piperidin-1-yl)-1-methyl-5-(6-morpholin-4-yl-pyridin-3-yl)-6-oxo-1,6-dihydro-pyrimidin-4-yl]-2-fluoro-benzonitrile | A |
| 69 | 4-[2-(3-aminomethyl-azetidin-1-yl)-5-(4-methoxy-phenyl)-1-methyl-6-oxo-1,6-dihydro-pyrimidin-4-yl]-2-fluoro-benzonitrile | A |
| 70 | 2-fluoro-4-[5-(4-methoxy-phenyl)-1-methyl-2-(3-methylaminomethyl-azetidin-1-yl)-6-oxo-1,6-dihydro-pyrimidin-4-yl]-benzonitrile | A |
| 71 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile | A |
| 72 | 4-[2-(4-dimethylamino-piperidin-1-yl)-1-methyl-5-(1-methyl-1H-indazol-5-yl)-6-oxo-1,6-dihydro-pyrimidin-4-yl]-2-fluoro-benzonitrile | A |
| 73 | 4-[2-(4-amino-piperidin-1-yl)-5-(1H-indol-5-yl)-1-methyl-6-oxo-1,6-dihydro-pyrimidin-4-yl]-2-fluoro-benzonitrile | A |
| 74 | 4-[2-(4-amino-piperidin-1-yl)-1-methyl-5-(1-methyl-1H-indol-5-yl)-6-oxo-1,6-dihydro-pyrimidin-4-yl]-2-fluoro-benzonitrile | A |
| 75 | 4-[2-(4-amino-piperidin-1-yl)-5-(1H-indol-6-yl)-1-methyl-6-oxo-1,6-dihydro-pyrimidin-4-yl]-2-fluoro-benzonitrile | A |
| 76 | 4-[2-(4-amino-piperidin-1-yl)-1-methyl-5-(1-methyl-1H-indol-6-yl)-6-oxo-1,6-dihydro-pyrimidin-4-yl]-2-fluoro-benzonitrile | A |
| 77 | 4-[2-(4-amino-piperidin-1-yl)-5-(1H-indazol-6-yl)-1-methyl-6-oxo-1,6-dihydro-pyrimidin-4-yl]-2-fluoro-benzonitrile | A |
| 78 | 4-[2-((4R, 3S)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 79 | 4-[2-((4S, 3R)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 80 | 4-[2-(4-dimethylamino-piperidin-1-yl)-1-methyl-5-(2-methyl-2H-indazol-6-yl)-6-oxo-1,6-dihydro-pyrimidin-4-yl]-2-fluoro-benzonitrile | A |
| 81 | 4-[2'-dimethylamino-2-(4-dimethylamino-piperidin-1-yl)-1-methyl-6-oxo-1,6-dihydro-[5,5']bipyrimidinyl-4-yl]-2-fluoro-benzonitrile | A |
| 82 | 4-[2-(4-dimethylamino-piperidin-1-yl)-1-methyl-5-(6-methyl-pyridin-3-yl)-6-oxo-1,6-dihydro-pyrimidin-4-yl]-2-fluoro-benzonitrile | A |
| 83 | 4-[5-(6-dimethylamino-pyridin-3-yl)-1-methyl-2-(4-methylamino-piperidin-1-yl)-6-oxo-1,6-dihydro-pyrimidin-4-yl]-2-fluoro-benzonitrile | A |
| 84 | 4-[2-(4-dimethylamino-piperidin-1-yl)-5-(2H-indazol-6-yl)-1-methyl-6-oxo-1,6-dihydro-pyrimidin-4-yl]-2-fluoro-benzonitrile | A |
| 85 | 4-[2-(4-amino-piperidin-1-yl)-5-(3-fluoro-4-methoxy-phenyl)-1-deuteratedmethyl-6-oxo-1,6-dihydro-pyrimidin-4-yl]-2-fluoro-benzonitrile | A |
| 86 | 4-[2-(4-amino-piperidin-1-yl)-5-(3-fluoro-4-deuteratedmethoxy-phenyl)-1-methyl-6-oxo-1,6-dihydro-pyrimidin-4-yl]-2-fluoro-benzonitrile | A |
| 87 | 2-fluoro-4-[1-methyl-2-[4-(methylamino)piperidin-1-yl]-5-(1-methylindazol-5-yl)-6-oxopyrimidin-4-34+benzonitrile | A |
| 88 | 4-[2-(4-aminopiperidin-1-yl)-5-(1H-indazol-5-yl)-1-methyl-6-oxopyrimidin-4-yl]-2-fluorobenzonitrile | A |
| 89 | 4-[5-(4-aminophenyl)-2-(4-aminopiperidin-1-yl)-1-methyl-6-oxopyrimidin-4-yl]-2-fluorobenzonitrile | A |
| 90 | 4-[2-(4-aminopiperidin-1-yl)-1-methyl-5-[4-(methylamino)phenyl]-6-oxopyrimidin-4-yl]-2-fluorobenzonitrile | A |
| 91 | 4-[2-(4-aminopiperidin-1-yl)-5-[3-fluoro-4-(methylamino)phenyl]-1-methyl-6-oxopyrimidin-4-yl]-2-fluorobenzonitrile | A |
| 92 | 4-[2-[4-(dimethylamino)piperidin-1-yl]-5-(6-methoxypyridin-3-yl)-1-methyl-6-oxopyrimidin-4-yl]-2-fluorobenzonitrile | A |
| 93 | 4-[2-(4-aminopiperidin-1-yl)-5-(6-ethoxy-5-fluoropyridin-3-yl)-1-methyl-6-oxopyrimidin-4-yl]-2-fluorobenzonitrile | A |
| 94 | 4-[2-(4-aminopiperidin-1-yl)-5-(6-ethoxypyridin-3-yl)-1-methyl-6-oxopyrimidin-4-yl]-2-fluorobenzonitrile | A |
| 95 | 4-[2-(4-aminopiperidin-1-yl)-5-(4-ethoxyphenyl)-1-methyl-6-oxopyrimidin-4-yl]-2-fluorobenzonitrile | A |
| 96 | 4-[2-(4-aminopiperidin-1-yl)-5-[4-(2-hydroxyethoxy)phenyl]-1-methyl-6-oxopyrimidin-4-yl]-2-fluorobenzonitrile | A |

TABLE 4-continued

| Chemical Synthesis Example | Name | LSD-1 IC$_{50}$ (μM) |
|---|---|---|
| 97 | 4-[2-(4-aminopiperidin-1-yl)-5-[4-(2-hydroxyethoxy)phenyl]-1-methyl-6-oxopyrimidin-4-yl]benzonitrile | A |
| 98 | 4-[2-(4-aminopiperidin-1-yl)-5-[4-(2-methoxyethoxy)phenyl]-1-methyl-6-oxopyrimidin-4-yl]-2-fluorobenzonitrile | A |
| 99 | 4-[2-(4-aminopiperidin-1-yl)-5-[4-(2-hydroxyethyl)phenyl]-1-methyl-6-oxopyrimidin-4-yl]-2-fluorobenzonitrile | A |
| 100 | 4-[2-(4-aminopiperidin-1-yl)-5-[4-(hydroxymethyl)phenyl]-1-methyl-6-oxopyrimidin-4-yl]-2-fluorobenzonitrile | A |
| 101 | 4-[2-(4-aminopiperidin-1-yl)-5-(4-fluorophenyl)-1-methyl-6-oxopyrimidin-4-yl]-2-fluorobenzonitrile | A |
| 102 | 4-[2-(4-aminopiperidin-1-yl)-5-(3-fluorophenyl)-1-methyl-6-oxopyrimidin-4-yl]-2-fluorobenzonitrile | A |
| 103 | 4-[2-(4-aminopiperidin-1-yl)-5-(3,5-difluorophenyl)-1-methyl-6-oxopyrimidin-4-yl]-2-fluorobenzonitrile | A |
| 104 | 4-[2-(4-aminopiperidin-1-yl)-5-(3,4-difluorophenyl)-1-methyl-6-oxopyrimidin-4-yl]-2-fluorobenzonitrile | A |
| 105 | 4-[2-(4-aminopiperidin-1-yl)-1-methyl-5-(4-methylsulfonylphenyl)-6-oxopyrimidin-4-yl]-2-fluorobenzonitrile | A |
| 106 | 4-[2-(4-aminopiperidin-1-yl)-5-(4-chlorophenyl)-1-methyl-6-oxopyrimidin-4-yl]-2-fluorobenzonitrile | A |
| 107 | 4-[2-(4-aminopiperidin-1-yl)-5-[4-(methoxymethyl)phenyl]-1-methyl-6-oxopyrimidin-4-yl]-2-fluorobenzonitrile | A |
| 108 | 4-[2-(4-aminopiperidin-1-yl)-1-methyl-6-oxopyrimidin-4-yl]-2-fluorobenzonitrile | A |
| 109 | 4-[2-(4-amino-piperidin-1-yl)-1-cyclopropylmethyl-6-oxo-1,6-dihydro-pyrimidin-4-yl]-2-fluoro-benzonitrile | B |
| 110 | 4-[2-(4-amino-piperidin-1-yl)-1-cyclopropylmethyl-6-oxo-1,6-dihydro-pyrimidin-4-yl]-2-fluoro-benzonitrile | A |
| 111 | 2-(4-amino-piperidin-1-yl)-6-(4-chloro-3-fluoro-phenyl)-5-(4-methoxy-phenyl)-3-methyl-3H-pyrimidin-4-one | B |
| 112 | 2-(4-amino-piperidin-1-yl)-6-(4-hydroxy-phenyl)-3-methyl-5-(1-methyl-1H-indol-5-yl)-3H-pyrimidin-4-one | D |
| 113 | 2-(4-amino-piperidin-1-yl)-6-(4-fluoro-phenyl)-3-methyl-5-(1-methyl-1H-indol-5-yl)-3H-pyrimidin-4-one | B |
| 114 | 2-(4-amino-piperidin-1-yl)-3-methyl-5-(1-methyl-1H-indol-5-yl)-6-phenyl-3H-pyrimidin-4-one | D |
| 115 | 2-(4-amino-piperidin-1-yl)-5-(3-fluoro-4-methoxy-phenyl)-3-methyl-6-pyridin-4-yl-3H-pyrimidin-4-one | C |
| 116 | 2-(4-amino-piperidin-1-yl)-3-methyl-5-(1-methyl-1H-indol-5-yl)-6-pyridin-4-yl-3H-pyrimidin-4-one | B |
| 117 | 2-(4-amino-piperidin-1-yl)-6-(4-methoxy-phenyl)-3-methyl-5-(1-methyl-1H-indol-5-yl)-3H-pyrimidin-4-one | C |
| 118 | 3-[2-(4-aminopiperidin-1-yl)-5-(3-fluoro-4-methoxyphenyl)-1-methyl-6-oxopyrimidin-4-yl]benzonitrile | D |
| 119 | 2-[2-(4-aminopiperidin-1-yl)-5-(3-fluoro-4-methoxyphenyl)-1-methyl-6-oxopyrimidin-4-yl]benzonitrile | D |
| 120 | 2-(4-amino-piperidin-1-yl)-5-(3-fluoro-4-methoxy-phenyl)-1-methyl-6-oxo-1,6-dihydro-pyrimidine-4-carbonitrile | C |
| 121 | 2-(4-amino-piperidin-1-yl)-4-(4-cyano-3-fluoro-phenyl)-1-methyl-6-oxo-1,6-dihydro-pyrimidine-5-carbonitrile | B |
| 122 | 4-[2-(4-aminopiperidin-1-yl)-5-(4-methoxyphenyl)-6-oxo-1H-pyrimidin-4-yl]-2-fluorobenzonitrile | A |

Note:
Biochemical assay IC$_{50}$ data are designated within the following ranges:
A: ≤ 0.10 μM;
B: > 0.10 μM to ≤ 1.0 μM;
C: > 1.0 μM to ≤ 10 μM;
D: > 10 μM Lysine-specific demethylase 1A enzymatic inhibition by Compound A was assessed using either LSD1 or LSD1-CoREST complex (Report QC6688 Pharm 1001). The IC50 of Compound A for the inhibition of LSD1 and LSD1-CoREST induced demethylation of H3K4me1/2 was determined by serial dilution methods with the appropriate substrates. Compound A was a potent and selective inhibitor of LSD1 alone or in a complex with CoREST, yielding respective mean IC50±SD values of 0.25±0.04 nM and 3.5±0.55 nM. Preincubation with LSD1 protein did not affect the observed IC50, indicating Compound A binding to LSD1 is reversible. Since the mean IC50 value for the LSD1-CoREST complex was at the lower detection limit of the assay method, it was not possible to determine if the apparent differences in IC50 represent real differences in inhibition between free and complex form of LSD1 (Table 5).

TABLE 5

Inhibition of Lysine-specific Demethylase 1A and Lysine (K)-specific Demethylase 1A-Corepressor for RE1-silencing Transcription Factor by Compound A.

| Enzymes | Mean $IC_{50}$ (nM) [replicates] | SD |
|---|---|---|
| LSD1 | 0.25 [4] | 0.04 |
| LSD1-CoREST | 3.5 [6][a] | 0.55 |

CoREST = corepressor for RE1-silencing transcription factor;
LSD1 = lysine-specific demethylase 1A;
mean $IC_{50}$ = the mean half-maximal inhibitory concentration of (n) independent experiments;
SD = standard deviation.
[a] Lower limit $IC_{50}$ (~50% LSD1-CoREST concentration).

The inhibitory mechanism of Compound A against LSD1 was studied using H3K4me1 substrate at various concentrations. The linear correlation between the IC50 value and substrate concentration indicates that Compound A is a competitive inhibitor of LSD1 with a Ki of 0.12 nM.

Example 2: In Vitro Enzyme Inhibition Assay—MAO Selectivity

Human recombinant monoamine oxidase proteins MAO-A and MAO-B are obtained. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay is performed. 3-(2-Aminophenyl)-3-oxopropanamine (kynuramine dihydrobromide, Sigma Aldrich), a non-fluorescent compound is chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µl. The assay buffer was 100 mM HEPES, pH 7.5. Each experiment was performed in triplicate within the same experiment.

Briefly, a fixed amount of MAO (0.25 µg for MAO-A and 0.5 µg for AO-B) was incubated on ice for 15 minutes in the reaction buffer, in the absence and/or in the presence of various concentrations of compounds as disclosed herein (e.g., from 0 to 50 µM, depending on the inhibitor strength). Tranylcypromine (Biomol International) was used as a control for inhibition.

After leaving the enzyme(s) interacting with the test compound, 60 to 90 µM of kynuramine was added to each reaction for MAO-B and MAO-A assay respectively, and the reaction was left for 1 hour at 37° C. in the dark. The oxidative deamination of the substrate was stopped by adding 50 µl of 2N NaOH. The conversion of kynuramine to 4-hydroxyquinoline was monitored by fluorescence (excitation at 320 nm, emission at 360 nm) using a microplate reader (Infinite 200, Tecan). Arbitrary units were used to measure levels of fluorescence produced in the absence and/or in the presence of test compound.

The maximum of oxidative deamination activity was obtained by measuring the amount of 4-hydroxyquinoline formed from kynuramine deamination in the absence of test compound and corrected for background fluorescence. The Ki ($IC_{50}$) of each inhibitor was determined at Vmax/2. Chemical synthesis examples 1-94, 101-106, 108-117, and 120-122 were tested in the above described assay and found to have an IC50 greater than 2 micromolar.

The selectivity of Compound A for LSD1 inhibition was further established in screening assays using closely related FAD-containing enzymes: LSD2, MAO-A, and MAO-B. The experimentally-determined mean IC50 value for the inhibition of LSD2 by Compound A was 16,550±6,378 nM. The mean IC50 values for inhibition of MAO-A and MAO-B by Compound A were >20,000 nM. These results demonstrate that Compound A is more than 60,000-fold selective for LSD1 compared with LSD2, MAO-A, or MAO-B (Table 6).

TABLE 6

Selectivity of Compound A for Lysine-specific Demethylase 1A versus Lysine-specific Demethylase 1B, Monoamine Oxidase A, and Monoamine Oxidase B

| Enzymes | Mean IC50 (nM) [replicates] | SD | LSD1 Relative Selectivity |
|---|---|---|---|
| LSD2 | 16550 [4] | 6378 | 66200 |
| MAO-A | >20000 [2] | NC | >80000 |
| MAO-B | >20000 [3] | NC | >80000 |
| LSD1 | 0.25 [4] | 0.04 | 1 |
| LSD1-CoREST | 3.5 [6]a | 0.55 | 14 |

CoREST = corepressor for RE1-silencing transcription factor;
LSD1(2) = lysine-specific demethylase 1A (1B);
mean $IC_{50}$ = the mean half-maximal inhibitory concentration of (n) independent experiments performed across multiple Compound A batches;
MAO-A(B) = monoamine oxidase A (B);
NC = not calculated;
SD = standard deviation.
aLower limit $IC_{50}$ (~50% LSD1-CoREST concentration).

Example 3: LSD-1 CD11b Cellular Assay

To analyze LSD-1 inhibitor efficacy in cells, a CD11b flow cytometry assay was performed. LSD-1 inhibition induces CD11b expression in THP-1 (AML) cells which is measured by flow cytometry. THP-1 cells were seeded at 100,000 cells/well in 10% Fetal Bovine Serum containing RPMI 1640 media in a 24 well plate with a final volume of 500 µL per well. LSD-1 test compounds were serially diluted in DMSO. The dilutions were added to each well accordingly to a final concentration of 0.2% DMSO. The cells were incubated at 37 degrees Celsius in 5% $CO_2$ for 4 days. 250 µL of each well was transferred to a well in a 96 well round bottom plate. The plate was centrifuged at 1200 rpm at 4 degrees Celsius in a Beckman Coulter Alegra 6KR centrifuge for 5 minutes. The media was removed leaving the cells at the bottom of the wells. The cells were washed in 100 µL cold HBSS (Hank's Balanced Salt Solution) plus 2% BSA (Bovine Serum Albumin) solution and centrifuged at 1200 rpm at 4 degrees Celsius for 5 minutes. The wash was removed. The cells were resuspended in 100 µL HBSS plus 2% BSA containing 1:15 dilution of APC conjugated mouse anti-CD11b antibody (BD Pharmingen Cat#555751) and incubated on ice for 25 minutes. The cells were centrifuged and washed two times in 100 µl HBSS plus 2% BSA. After the final spin the cells were resuspended in 100 µL HBSS plus 2% BSA containing 1 ug/mL DAPI (4',6-diamidino-2-phenylindole). The cells were then analyzed by flow cytometry in a BD FACSAria machine. Cells were analyzed for CD11b expression. The percent of CD11b expressing cells for each inhibitor concentration was used to determine an $IC_{50}$ curve for each compound analyzed.

Table 7 provides the cellular IC50 values of various substituted heterocyclic compounds disclosed herein.

TABLE 7

| Chemical Synthesis Example | Name | THP-1 IC$_{50}$ (μM) |
|---|---|---|
| 1 | 4-(2-(4-aminopiperidin-1-yl)-1-methyl-6-oxo-5-p-tolyl-1,6-dihydropyrimidin-4-yl)benzonitrile | A |
| 2 | 4-[2-(4-amino-piperidin-1-yl)-5-(4-methoxy-phenyl)-1-methyl-6-oxo-1,6-dihydro-pyrimidin-4-yl]-benzonitrile | A |
| 3 | 4-[2-(4-amino-piperidin-1-yl)-5-(6-methoxy-pyridin-3-yl)-1-methyl-6-oxo-1,6-dihydro-pyrimidin-4-yl]-benzonitrile | A |
| 4 | 4-[2-(4-amino-piperidin-1-yl)-1-methyl-5-(6-methyl-pyridin-3-yl)-6-oxo-1,6-dihydro-pyrimidin-4-yl]-benzonitrile | A |
| 5 | 4-[2-(4-amino-piperidin-1-yl)-5-(4-methoxy-phenyl)-1-methyl-6-oxo-1,6-dihydro-pyrimidin-4-yl]-benzonitrile | A |
| 6 | 4-[2-(4-amino-piperidin-1-yl)-5-(4-methoxy-phenyl)-1-methyl-6-oxo-1,6-dihydro-pyrimidin-4-yl]-2-fluoro-benzonitrile | A |
| 7 | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 8 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 9 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 10 | 4-[2-(4-amino-piperidin-1-yl)-5-(6-ethyl-pyridin-3-yl)-1-methyl-6-oxo-1,6-dihydro-pyrimidin-4-yl]-benzonitrile | B |
| 11 | 2-fluoro-4-[5-(4-methoxy-phenyl)-1-methyl-2-(4-methylamino-piperidin-1-yl)-6-oxo-1,6-dihydro-pyrimidin-4-yl]-benzonitrile | A |
| 12 | 2-fluoro-4-[5-(3-fluoro-4-methoxy-phenyl)-1-methyl-2-(4-methylamino-piperidin-1-yl)-6-oxo-1,6-dihydro-pyrimidin-4-yl]-benzonitrile | A |
| 14 | 4-[2-(4-amino-piperidin-1-yl)-5-cyclopentylethynyl-1-methyl-6-oxo-1,6-dihydro-pyrimidin-4-yl]-2-fluoro-benzonitrile | A |
| 15 | [2-(4-amino-piperidin-1-yl)-4-(4-cyano-3-fluoro-phenyl)-5-(4-methoxy-phenyl)-6-oxo-6H-pyrimidin-1-yl]acetic acid | C |
| 16 | 2-[2-(4-amino-piperidin-1-yl)-4-(4-cyano-3-fluoro-phenyl)-5-(4-methoxy-phenyl)-6-oxo-6H-pyrimidin-1-yl]-acetamide | A |
| 18 | 4-[2-(4-amino-piperidin-1-yl)-5-benzofuran-5-yl-1-methyl-6-oxo-1,6-dihydro-pyrimidin-4-yl]-2-fluoro-benzonitrile | A |
| 20 | 4-[2-(4-aminopiperidin-1-yl)-5-chloro-1-methyl-6-oxopyrimidin-4-yl]-2-fluorobenzonitrile | B |
| 22 | 4-[2-(2,8-diaza-spiro[4.5]dec-8-yl)-5-(3-fluoro-4-methoxy-phenyl)-1-methyl-6-oxo-1,6-dihydro-pyrimidin-4-yl]-2-fluoro-benzonitrile | A |
| 23 | 4-{2-(4-aminopiperidyl)-1-methyl-6-oxo-5-[6-(trifluoromethyl)-(3-pyridyl)] hydropyrimidin-4-yl}-2-fluorobenzenecarbonitrile | A |
| 24 | 4-[2-(4-aminopiperidyl)-1-methyl-5-(2-methyl(2H-indazol-5-yl))-6-oxohydropyrimidin-4-yl]benzenecarbonitrile | A |
| 25 | 4-[2-((3R)-3-aminopiperidyl)-5-(3-fluoro-4-methoxyphenyl)-1-methyl-6-oxohydropyrimidin-4-yl]-2-fluorobenzenecarbonitrile | A |
| 26 | 4-[2-(4-aminopiperidyl)-5-(5-fluoro-6-methoxy(3-5,6-dihydropyridyl))-1-methyl-6-oxohydropyrimidin-4-yl]-2-fluorobenzenecarbonitrile | A |
| 27 | 4-[2-((3R)-3-aminopyrrolidinyl)-5-(3-fluoro-4-methoxyphenyl)-1-methyl-6-oxohydropyrimidin-4-yl]-2-fluorobenzenecarbonitrile | A |
| 29 | 4-[2-((3S)-3-amino-pyrrolidin-1-yl)-5-(3-fluoro-4-methoxy-phenyl)-1-methyl-6-oxo-1,6-dihydro-pyrimidin-4-yl]-2-fluoro-benzonitrile | B |
| 30 | 4-[2-((3R)-3-aminopiperidyl)-5-(4-methoxy-phenyl)-1-methyl-6-oxohydro pyrimidin-4-yl]-2-fluorobenzenecarbonitrile | A |
| 31 | 4-[2-((3S)-3-amino-piperidin-1-yl)-5-(4-methoxy-phenyl)-1-methyl-6-oxo-1,6-dihydro-pyrimidin-4-yl]-2-fluoro-benzonitrile | A |
| 32 | 4-[2-(4-amino-4-methyl-piperidin-1-yl)-5-(3-fluoro-4-methoxy-phenyl)-1-methyl-6-oxo-1,6-dihydro-pyrimidin-4-yl]-2-fluoro-benzonitrile | A |
| 33 | 4-[2-(4-aminopiperidyl)-1-methyl-5-(1-methyl(1H-indazol-5-yl))-6-oxohydropyrimidin-4-yl]benzenecarbonitrile | A |
| 34 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile | A |
| 35 | 4-[2-(4-amino-piperidin-1-yl)-1-methyl-5-(1-methyl-1H-indazol-5-yl)-6-oxo-1,6-dihydro-pyrimidin-4-yl]-2-fluoro-benzonitrile | A |
| 36 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-benzonitrile | A |
| 37 | 4-[2-(4-aminopiperidyl)-1-methyl-5-(2-methyl (2H-indazol-5-yl)) 6-oxohydropyrimidin-4-yl]-2-fluorobenzenecarbonitrile | A |
| 38 | 4-[2-(4-aminopiperidyl)-5-(3,5-difluoro-4-methoxyphenyl)-1-methyl-6-oxohydropyrimidin-4-yl]benzenecarbonitrile | A |
| 40 | {4-[2-(4-aminopiperidyl)-6-(4-cyanophenyl)-3-methyl-4-oxo(3-hydro pyrimidin-5-yl)]-2-fluorophenyl}-N-methylcarboxamide | B |
| 41 | 4-[2-(4-aminopiperidyl)-6-(4-cyanophenyl)-3-methyl-4-oxo(3-hydro pyrimidin-5-yl)]-2-fluorobenzamide | B |
| 42 | 4-[2-(4-amino-piperidin-1-yl)-1-methyl-6-oxo-5-(1-oxo-2,3-dihydro-1H-isoindol-5-yl)-1,6-dihydro-pyrimidin-4-yl]-2-fluoro-benzonitrile | B |
| 44 | 4-{5-(3-fluoro-4-methoxy-phenyl)-1-methyl-6-oxo-2-[(3S)-(pyrrolidin-3-ylmethyl)-amino]-1,6-dihydro-pyrimidin-4-yl}-benzonitrile | B |
| 45 | 4-{5-(3-fluoro-4-methoxy-phenyl)-1-methyl-6-oxo-2-[(3R)-(pyrrolidin-3-ylmethyl)-amino]-1,6-dihydro-pyrimidin-4-yl}-benzonitrile | B |

TABLE 7-continued

| Chemical Synthesis Example | Name | THP-1 IC$_{50}$ (μM) |
|---|---|---|
| 46 | 4-[2-[1,4]diazepan-1-yl-5-(3-fluoro-4-methoxy-phenyl)-1-methyl-6-oxo-1,6-dihydro-pyrimidin-4-yl]-2-fluoro-benzonitrile | A |
| 47 | 2-fluoro-4-[5-(3-fluoro-4-methoxy-phenyl)-1-methyl-6-oxo-2-piperazin-1-yl-1,6-dihydro-pyrimidin-4-yl]-benzonitrile | B |
| 48 | 4-[5-(3-fluoro-4-methoxy-phenyl)-1-methyl-6-oxo-2-(piperidin-4-ylamino)-1,6-dihydro-pyrimidin-4-yl]-benzonitrile | B |
| 49 | 4-[2-(4-amino-piperidin-1-yl)-2'-dimethylamino-1-methyl-6-oxo-1,6-dihydro-[5,5']bipyrimidinyl-4-yl]-2-fluoro-benzonitrile | A |
| 50 | 5-[2-(4-amino-piperidin-1-yl)-4-(4-cyano-3-fluoro-phenyl)-1-methyl-6-oxo-1,6-dihydro-pyrimidin-5-yl]-pyridine-2-carboxylic acid methylamide | A |
| 51 | 2-fluoro-4-{5-(4-methoxy-phenyl)-1-methyl-6-oxo-2-[(3S)-(pyrrolidin-3-ylmethyl)-amino]-1,6-dihydro-pyrimidin-4-yl}-benzonitrile | B |
| 52 | 2-luoro-4-(5-(4-methoxy-phenyl)-1-methyl-6-oxo-2-[(3R)-(pyrrolidin-3-ylmethyl)-amino]-1,6-dihydro-pyrimidin-4-yl}-benzonitrile | B |
| 53 | 2-fluoro-4-[5-(4-methoxy-phenyl)-1-methyl-6-oxo-2-(piperidin-4-ylamino)-1,6-dihydro-pyrimidin-4-yl]-benzonitrile | B |
| 54 | 2-fluoro-4-[5-(4-methoxy-phenyl)-1-methyl-2-(methyl-(3S)-pyrrolidin-3-ylmethyl-amino)-6-oxo-1,6-dihydro-pyrimidin-4-yl]-benzonitrile | A |
| 55 | 2-fluoro-4-[5-(4-methoxy-phenyl)-1-methyl-2-(methyl-piperidin-4-yl-amino)-6-oxo-1,6-dihydro-pyrimidin-4-yl]-benzonitrile | B |
| 56 | 2-fluoro-4-[5-(4-methoxy-phenyl)-1-methyl-2-(methyl-pyrrolidin-3-ylmethyl-amino)-6-oxo-1,6-dihydro-pyrimidin-4-yl]-benzonitrile | A |
| 57 | 4-[2-(4-amino-piperidin-1-yl)-5-(6-dimethylamino-pyridin-3-yl)-1-methyl-6-oxo-1,6-dihydro-pyrimidin-4-yl]-2-fluoro-benzonitrile | A |
| 58 | 2-fluoro-4-[5-(6-methoxy-pyridin-3-yl)-1-methyl-2-(4-methylamino-piperidin-1-yl)-6-oxo-1,6-dihydro-pyrimidin-4-yl]-benzonitrile | A |
| 59 | 4-[2-(4-amino-piperidin-1-yl)-5-(4-dimethylamino-phenyl)-1-methyl-6-oxo-1,6-dihydro-pyrimidin-4-yl]-2-fluoro-benzonitrile | A |
| 60 | 4-[2-(4-amino-piperidin-1-yl)-1-methyl-6-oxo-5-(6-pyrrolidin-1-yl-pyridin-3-yl)-1,6-dihydro-pyrimidin-4-yl]-2-fluoro-benzonitrile | A |
| 61 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | A |
| 62 | 4-[2-[1,4]diazepan-1-yl-5-(6-methoxy-pyridin-3-yl)-1-methyl-6-oxo-1,6-dihydro-pyrimidin-4-yl]-2-fluoro-benzonitrile | B |
| 63 | 4-[2-[1,4]diazepan-1-yl-5-(6-dimethylamino-pyridin-3-yl)-1-methyl-6-oxo-1,6-dihydro-pyrimidin-4-yl]-2-fluoro-benzonitrile | A |
| 64 | 4-[2-(3-amino-azetidin-1-yl)-5-(4-methoxy-phenyl)-1-methyl-6-oxo-1,6-dihydro-pyrimidin-4-yl]-2-fluoro-benzonitrile | B |
| 65 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile | A |
| 66 | 4-[2-[1,4]diazepan-1-yl--1-methyl-5-(2-methyl-2H-indazol-5-yl)-6-oxo-1,6-dihydro-pyrimidin-4-yl]-2-fluoro-benzonitrile | A |
| 67 | 4-[2-[1,4]diazepan-1-yl-5-(6-dimethylamino-pyridin-3-yl)-1-methyl-6-oxo-1,6-dihydro-pyrimidin-4-yl]-benzonitrile | A |
| 68 | 4-[2-(4-amino-piperidin-1-yl)-1-methyl-5-(6-morpholin-4-yl-pyridin-3-yl)-6-oxo-1,6-dihydro-pyrimidin-4-yl]-2-fluoro-benzonitrile | A |
| 69 | 4-[2-(3-aminomethyl-azetidin-1-yl)-5-(4-methoxy-phenyl)-1-methyl-6-oxo-1,6-dihydro-pyrimidin-4-yl]-2-fluoro-benzonitrile | B |
| 70 | 2-fluoro-4-[5-(4-methoxy-phenyl)-1-methyl-2-(3-methylaminomethyl-azetidin-1-yl)-6-oxo-1,6-dihydro-pyrimidin-4-yl]-benzonitrile | A |
| 71 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile | A |
| 72 | 4-[2-(4-dimethylamino-piperidin-1-yl)-1-methyl-5-(1-methyl-1H-indazol-5-yl)-6-oxo-1,6-dihydro-pyrimidin-4-yl]-2-fluoro-benzonitrile | A |
| 73 | 4-[2-(4-amino-piperidin-1-yl)-5-(1H-indol-5-yl)-1-methyl-6-oxo-1,6-dihydro-pyrimidin-4-yl]-2-fluoro-benzonitrile | A |
| 74 | 4-[2-(4-amino-piperidin-1-yl)-1-methyl-5-(1-methyl-1H-indol-5-yl)-6-oxo-1,6-dihydro-pyrimidin-4-yl]-2-fluoro-benzonitrile | A |
| 75 | 4-[2-(4-amino-piperidin-1-yl)-5-(1H-indol-6-yl)-1-methyl-6-oxo-1,6-dihydro-pyrimidin-4-yl]-2-fluoro-benzonitrile | A |
| 76 | 4-[2-(4-amino-piperidin-1-yl)-1-methyl-5-(1-methyl-1H-indol-6-yl)-6-oxo-1,6-dihydro-pyrimidin-4-yl]-2-fluoro-benzonitrile | A |
| 77 | 4-[2-(4-amino-piperidin-1-yl)-5-(1H-indazol-6-yl)-1-methyl-6-oxo-1,6-dihydro-pyrimidin-4-yl]-2-fluoro-benzonitrile | A |
| 78 | 4-[2-((4R, 3S)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 79 | 4-[2-((4S, 3R)-4-amino-3-fluoro-piperidin-1-yl)-5-(4-methoxy-phenyl)-1-methyl-6-oxo-1,6-dihydro-pyrimidin-4-yl]-2-fluoro-benzonitrile | A |
| 80 | 4-[2-(4-dimethylamino-piperidin-1-yl)-1-methyl-5-(2-methyl-2H-indazol-6-yl)-6-oxo-1,6-dihydro-pyrimidin-4-yl]-2-fluoro-benzonitrile | A |
| 81 | 4-[2'-dimethylamino-2-(4-dimethylamino-piperidin-1-yl)-1-methyl-6-oxo-1,6-dihydro-[5,5']bipyrimidinyl-4-yl]-2-fluoro-benzonitrile | B |
| 82 | 4-[2-(4-dimethylamino-piperidin-1-yl)-1-methyl-5-(6-methyl-pyridin-3-yl)-6-oxo-1,6-dihydro-pyrimidin-4-yl]-2-fluoro-benzonitrile | B |
| 83 | 4-[5-(6-dimethylamino-pyridin-3-yl)-1-methyl-2-(4-methylamino-piperidin-1-yl)-6-oxo-1,6-dihydro-pyrimidin-4-yl]-2-fluoro-benzonitrile | A |

TABLE 7-continued

| Chemical Synthesis Example | Name | THP-1 IC$_{50}$ (μM) |
|---|---|---|
| 84 | 4-[2-(4-dimethylamino-piperidin-1-yl)-5-(2H-indazol-6-yl)-1-methyl-6-oxo-1,6-dihydro-pyrimidin-4-yl]-2-fluoro-benzonitrile | A |
| 85 | 4-[2-(4-amino-piperidin-1-yl)-5-(3-fluoro-4-methoxy-phenyl)-1-deuteratedmethyl-6-oxo-1,6-dihydro-pyrimidin-4-yl]-2-fluoro-benzonitrile | A |
| 86 | 4-[2-(4-amino-piperidin-1-yl)-5-(3-fluoro-4-deuteratedmethoxy-phenyl)-1-methyl-6-oxo-1,6-dihydro-pyrimidin-4-yl]-2-fluoro-benzonitrile | A |
| 87 | 2-fluoro-4-[1-methyl-2-(4-(methylamino)piperidin-1-yl]-5-(1-methylindazol-5-yl)-6-oxopyrimidin-4-yl]benzonitrile | A |
| 88 | 4-[2-(4-aminopiperidin-1-yl)-5-(1H-indazol-5-yl)-1-methyl-6-oxopyrimidin-4-yl]-2-fluorobenzonitrile | A |
| 89 | 4-[5-(4-aminophenyl)-2-(4-aminopiperidin-1-yl)-1-methyl-6-oxopyrimidin-4-yl]-2-fluorobenzonitrile | A |
| 90 | 4-[2-(4-aminopiperidin-1-yl)-1-methyl-5-[4-(methylamino)phenyl]-6-oxopyrimidin-4-yl]-2-fluorobenzonitrile | A |
| 91 | 4-[2-(4-aminopiperidin-1-yl)-5-[3-fluoro-4-(methylamino)phenyl]-1-methyl-6-oxopyrimidin-4-yl]-2-fluorobenzonitrile | A |
| 92 | 4-[2-[4-(dimethylamino)piperidin-1-yl]-5-(6-methoxypyridin-3-yl)-1-methyl-6-oxo-pyrimidin-4-yl]-2-fluorobenzonitrile | A |
| 93 | 4-[2-(4-aminopiperidin-1-yl)-5-(6-ethoxy-5-fluoropyridin-3-yl)-1-methyl-6-oxopyrimidin-4-yl]-2-fluorobenzonitrile | A |
| 94 | 4-[2-(4-aminopiperidin-1-yl)-5-(6-ethoxypyridin-3-yl)-1-methyl-6-oxopyrimidin-4-yl]-2-fluorobenzonitrile | A |
| 95 | 4-[2-(4-aminopiperidin-1-yl)-5-(4-ethoxyphenyl)-1-methyl-6-oxopyrimidin-4-yl]-2-fluorobenzonitrile | A |
| 96 | 4-[2-(4-aminopiperidin-1-yl)-5-[4-(2-hydroxyethoxy)phenyl]-1-methyl-6-oxopyrimidin-4-yl]-2-fluorobenzonitrile | A |
| 97 | 4-[2-(4-aminopiperidin-1-yl)-5-[4-(2-hydroxyethoxy)phenyl]-1-methyl-6-oxopyrimidin-4-yl]benzonitrile | A |
| 98 | 4-[2-(4-aminopiperidin-1-yl)-5-[4-(2-methoxyethoxy)phenyl]-1-methyl-6-oxopyrimidin-4-yl]-2-fluorobenzonitrile | A |
| 99 | 4-[2-(4-aminopiperidin-1-yl)-5-[4-(2-hydroxyethyl)phenyl]-1-methyl-6-oxopyrimidin-4-yl]-2-fluorobenzonitrile | A |
| 100 | 4-[2-(4-aminopiperidin-1-yl)-5-[4-(hydroxymethyl)phenyl]-1-methyl-6-oxopyrimidin-4-yl]-2-fluorobenzonitrile | A |
| 101 | 4-[2-(4-aminopiperidin-1-yl)-5-(4-fluorophenyl)-1-methyl-6-oxopyrimidin-4-yl]-2-fluorobenzonitrile | A |
| 102 | 4-[2-(4-aminopiperidin-1-yl)-5-(3-fluorophenyl)-1-methyl-6-oxopyrimidin-4-yl]-2-fluorobenzonitrile | A |
| 103 | 4-[2-(4-aminopiperidin-1-yl)-5-(3,5-difluorophenyl)-1-methyl-6-oxopyrimidin-4-yl]-2-fluorobenzonitrile | A |
| 104 | 4-[2-(4-aminopiperidin-1-yl)-5-(3,4-difluorophenyl)-1-methyl-6-oxopyrimidin-4-yl]-2-fluorobenzonitrile | A |
| 105 | 4-[2-(4-aminopiperidin-1-yl)-1-methyl-5-(4-methylsulfonylphenyl)-6-oxo-pyrimidin-4-yl]-2-fluorobenzonitrile | A |
| 106 | 4-[2-(4-aminopiperidin-1-yl)-5-(4-chlorophenyl)-1-methyl-6-oxopyrimidin-4-yl]-2-fluorobenzonitrile | A |
| 107 | 4-[2-(4-aminopiperidin-1-yl)-5-[4-(methoxymethyl)phenyl]-1-methyl-6-oxopyrimidin-4-yl]-2-fluorobenzonitrile | A |
| 108 | 4-[2-(4-aminopiperidin-1-yl)-1-methyl-6-oxo-pyrimidin-4-yl]-2-fluorobenzonitrile | B |
| 110 | 4-[2-(4-amino-piperidin-1-yl)-1-cyclopropylmethyl-6-oxo-1,6-dihydro-pyrimidin-4-yl]-2-fluoro-benzonitrile | B |
| 111 | 2-(4-amino-piperidin-1-yl)-6-(4-chloro-3-fluoro-phenyl)-5-(4-methoxy-phenyl)-3-methyl-3H-pyrimidin-4-one | B |
| 122 | 4-[2-(4-aminopiperidin-1-yl)-5-(4-methoxyphenyl)-6-oxo-1H-pyrimidin-4-yl]-2-fluorobenzonitrile | A |

Note:
Cellular assay IC$_{50}$ data are designated within the following ranges:
A: ≤ 0.10 μM;
B: > 0.10 μM to ≤ 1.0 μM;
C: > 1.0 μM to ≤ 10 μM;
D: > 10 μM Example 4: Kasumi-1 AML Cell Line Proliferation Assay (Cell-MTS Assay)

Colorimetric cellular assay to assess the ability of LSD-1 small molecule inhibitors to effect the proliferation of the established AML cancer cell line Kasumi-1.

Assay Background

The LSD-1 protein has been shown to play a key role in the biology of a variety of cancer types including SCLC and AML. To demonstrate small molecule inhibition of LSD-1 as a potential anti-cancer therapy, an assay to measure the degree of proliferative inhibition in an established cancer cell line of AML was implemented.

Assay Principle

This Cell-MTS assay is a 7-day plate based colorimetric assay which quantifies the amount of newly generated NADH in the presence and absence of test compound. These NADH levels are used as a proxy for the quantification of cancer cell proliferation.

Assay Method

The established cancer cell line Kasumi-1 with a verified p53 mutation were purchased from American Type Culture Collection (ATCC) and routinely passaged according to ATCC published protocols. For routine assay these cells were seeded at a density of 20,000 cells per 96-well. 24 hours after plating, cells received an 11 point dilution of test compound with final concentration ranges from 100 μM to 2.0 nM. Cells are incubated in the presence of compound for 168 hours at 37° C., 5% $CO_2$. At the end of this compound incubation period, 80 μl of media is removed and 20 μL of CellTiter 96® AQueous Non-Radioactive Cell Proliferation Assay solution (Promega) is added. The cells are incubated until the OD490 is >0.6. $IC_{50}$ values are calculated using the IDBS XLfit software package and include background subtracted OD490 values and normalization to DMSO controls.

Table 8 provides the Kasumi-1 cellular $IC_{50}$ values of various substituted heterocyclic compounds disclosed herein.

TABLE 8

| Chemical Synthesis Example | Name | Kasumi-1 $IC_{50}$ (μM) |
|---|---|---|
| 1 | 4-(2-(4-aminopiperidin-1-yl)-1-methyl-6-oxo-5-p-tolyl-1,6-dihydropyrimidin-4-yl)benzonitrile | A |
| 3 | 4-[2-(4-amino-piperidin-1-yl)-5-(6-methoxy-pyridin-3-yl)-1-methyl-6-oxo-1,6-dihydro-pyrimidin-4-yl]-benzonitrile | A |
| 4 | 4-[2-(4-amino-p iperidin-1-yl)-1-methyl-5-(6-methyl-pyridin-3-yl)-6-oxo-1,6-dihydro-pyrimidin-4-yl]-benzonitrile | B |
| 5 | 4-[2-(4-amino-piperidin-1-yl)-5-(4-methoxy-phenyl)-1-methyl-6-oxo-1,6-dihydro-pyrimidin-4-yl]-benzonitrile | A |
| 6 | 4-[2-(4-amino-piperidin-1-yl)-5-(4-methoxy-phenyl)-1-methyl-6-oxo-1,6-dihydro-pyrimidin-4-yl]-2-fluoro-benzonitrile | A |
| 7 | 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile | A |
| 8 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 9 | 4-[2-(4-amino-piperidin-1-yl)-5-(6-methoxy-pyridin-3-yl)-1-methyl-6-oxo-1,6-dihydro-pyrimidin-4-yl]-2-fluoro-benzonitrile | A |
| 24 | 4-[2-(4-aminopiperidyl)-1-methyl-5-(2-methyl(2H-indazol-5-yl))-6-oxohydropyrimidin-4-yl]benzenecarbonitrile | A |
| 34 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-2-fluoro-benzonitrile | A |
| 35 | 4-[2-(4-amino-piperidin-1-yl)-1-methyl-5-(1-methyl-1H-indazol-5-yl)-6-oxo-1,6-dihydro-pyrimidin-4-yl]-2-fluoro-benzonitrile | A |
| 36 | 4-{2-(4-amino-piperidin-1-yl)-1-methyl-6-oxo-5-[1-(2,2,2-trifluoro-ethyl)-1H-pyrazol-4-yl]-1,6-dihydro-pyrimidin-4-yl}-benzonitrile | A |
| 65 | 2-fluoro-4-[1-methyl-2-(4-methylamino-piperidin-1-yl)-5-(2-methyl-2H-indazol-5-yl)-6-oxo-1,6-dihydro-pyrimidin-4-yl]-benzonitrile | A |
| 66 | 4-[2-[1,4]diazepan-1-yl-1-methyl-5-(2-methyl-2H-indazol-5-yl)-6-oxo-1,6-dihydro-pyrimidin-4-yl]-2-fluoro-benzonitrile | A |
| 71 | 4-[2-(4-dimethylamino-piperidin-1-yl)-1-methyl-5-(2-methyl-2H-indazol-5-yl)-6-oxo-1,6-dihydro-pyrimidin-4-yl]-2-fluoro-benzonitrile | A |
| 88 | 4-[2-(4-aminopiperidin-1-yl)-5-(1H-indazol-5-yl)-1-methyl-6-oxopyrimidin-4-yl]-2-fluorobenzonitrile | A |

Example 5: In Vivo Xenograph Study—MCF-7 Xenograph

Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1\times10^7$ cells/mL. MCF-7 cells are subcutaneously injected (100 μL/animal) on the right flank 2-3 days post pellet implantation and tumor volume (length× width²/2) is monitored bi-weekly. When tumors reach an average volume of ~200 mm³ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 6: In Vivo Xenograph Study—LNCaP Xenograph

LNCaP cells with a stable knockdown of LSD-1 (shLSD-1 cells) or control cells (such as shNTC cells) are inoculated in the dorsal flank of nude mice by subcutaneous injection (such as $3\times10^6$ cells in 100 μl of 50% RPMI 1640BD Matrigel). Mouse weight and tumor size are measured once per week and tumor volume is estimated using the formula (7i/6)(L×W), where L=length of tumor and W=width of tumor. A two sample t-test is performed to determine statistical differences in mean tumor volume between the two groups.

Unmodified LNCaP cells are inoculated by subcutaneous injection into the dorsal flank of nude mice (such as $3\times10^6$ cells in 100 μl of 50% RPMI 1640BD Matrigel). After three weeks, mice are injected intraperitoneally once per day with water (control), pargyline (0.53 mg or 1.59 mg; 1 or 3 mM final concentration, assuming 70% bioavailability), or XB154 (4 or 20 μg; 1 or 5 μM final concentration, assuming 70% bioavailability) or treated with a test compound (5 mg/kg each week or 10 mg/kg each week). Treatment continues for three weeks, during which time mouse weight and tumor volume are measured as above.

shLSD-1 LNCaP cells or control cells are injected in nude mice as above. After three weeks, mice are treated with 2.6 μg mitomycin C (predicted final concentration of 1 μM assuming 40% bioavailability), olaparib (for example, about 0.5 mg/kg to 25 mg/kg), or vehicle intraperitoneally once per day for three weeks. In other examples, unmodified LNCaP cells are injected in nude mice as above.

After three weeks, mice are treated with test compounds, or vehicle as above, plus MMC or olaparib. Treatment continues for three weeks, during which time mouse weight and tumor volume are measured as above.

A decrease in tumor volume compared to control in mice injected with shLSD-1 cells indicates that LSD-1 inhibition decreases tumor growth in vivo.

Similarly, a decrease in tumor volume compared to control in mice injected with LNCaP cells and treated with a compound disclosed herein indicates that LSD-1 inhibition decreases tumor growth in vivo. Finally, a decrease in tumor volume in mice injected with LNCaP cells and treated with a compound disclosed herein plus olaparib as compared to mice treated with a compound disclosed herein alone indicates that inhibition of LSD-1 plus inhibition of PARP decreases tumor growth in vivo.

The harvested xenograft tissue is examined for evidence of LSD-1 inhibition. This is assessed with Western blots to examine global levels of the 2MK4 and 2MK9 histone marks, expression of FA/BRCA genes, FANCD2 ubiquitination, and LSD-1 protein levels in the cases of the shRNA cells. A decrease in one or more of these parameters indicates the effective inhibition of LSD-1. Additionally, effects on DNA damage repair are assessed with staining for $H_2AX$ foci.

Example 7: Antiproliferative Activity in Normal Human Fibroblast and Small Cell Lung Cancer Cells The effect of Compound A on cell viability was investigated in various established NCI SCLC cell lines (Report QC6688-Pharm-1002). Half maximal inhibitory concentration values for IMR-90, the normal human fibroblast cell line, and a panel of 6 SCLC cell lines were measured over the respective concentration ranges of 0.17 to 10,000 nM and 0.7 to 500 nM for Compound A. Compound A demonstrated potent antiproliferative activity in 5 of the 6 SCLC cell lines tested. In the NCI-H69, NCI-H146, NCI-H209, NCI-H526, and NCI-H1417 cell lines, Compound A exhibited respective mean IC50±SD values of 7.0±2.5 nM, 9.9±9.6 nM, 3.9±0.2 nM, 36.4±28.8 nM, and 14.6±12.6 nM. Compound A had limited effect on cell proliferation in the NCI-H841 SCLC cell line, yielding an IC50 value of >500 nM. Compound A showed no effect on cell proliferation in the IMR-90 normal human fibroblast cell line at the concentrations tested (IC50 value>10,000 nM) (Table 9).

TABLE 9

Compound A Half-maximal Inhibition Values for the Normal Human Fibroblast and Small Cell Lung Cancer Cell lines

| Cell Line | Mean IC50 (nM) | SD | n | pIC50 | Format | Readout |
|---|---|---|---|---|---|---|
| IMR-90 | >10000 | NC | 1 | <5.0 | 2D assaya | CellTiter 96 ® AQueous |
| NCI-H69 | 7.0 | 2.5 | 3 | 8.2 | 3D assayb | Calcein AM |
| NCI-H146 | 9.9 | 9.6 | 3 | 8.0 | 3D assayb | Calcein AM |
| NCI-H209 | 3.9 | 0.2 | 2 | 8.4 | 3D assayb | Calcein AM |
| NCI-H526 | 36.4 | 28.8 | 3 | 7.4 | 3D assayb | Calcein AM |
| NCI-H1417 | 14.6 | 12.6 | 2 | 7.8 | 2D assaya | CellTiter-Glo ® |
| NCI-H841 | >500 | NC | 3 | <6.3 | 3D assayb | Calcein AM |

2 (or 3) D = 2 (or 3) dimensional;
mean IC50 = the mean half-maximal inhibitory concentration of (n) independent experiments;
NC = not calculated;
pIC50 = -log10(mean IC50) in mol/L;
SD = standard deviation.
a2D Assay = assay with cells adhered to a two dimensional solid surface.
b3D Assay = assay with cells suspended in a three dimensional extracellular matrix.

Example 8: Effect on Pharmacodynamic Biomarker Gastrin Releasing Peptide in Small Cell Lung Cancer Cells Lysine-specific demethylase 1A inhibition was shown to modulate the expression of neuroendocrine tumor-related genes such as human GRP in SCLC cell lines. The effect of Compound A-mediated inhibition of LSD1 on the expression of GRP in the human SCLC cell lines, NCI-H1417, NCI-H209, and NCI-H69, was evaluated using quantitative reverse transcription polymerase chain reaction (qRT-PCR). After the incubation period, total RNA was extracted and fold-changes in GRP mRNA levels were measured by using qRT-PCR. The IC50 for Compound A inhibition of GRP expression was determined by calculating the percent change in GRP mRNA expression versus respective Compound A concentration (relative to DMSO control). Percent of Control=100×2−ΔΔCt, GRP mRNA levels post treatment normalized to a housekeeping gene transcript. Treatment with Compound A resulted in concentration dependent down-regulation of GRP messenger ribonucleic acid (mRNA) levels in NCI-H1417, NCI-H209, and NCI-H69 cells, yielding respective IC50±SD values of 8.9±4.6 nM, 7.2±4.7 nM, and 6.0±3.8 nM (FIG. 1).

Figure 2:
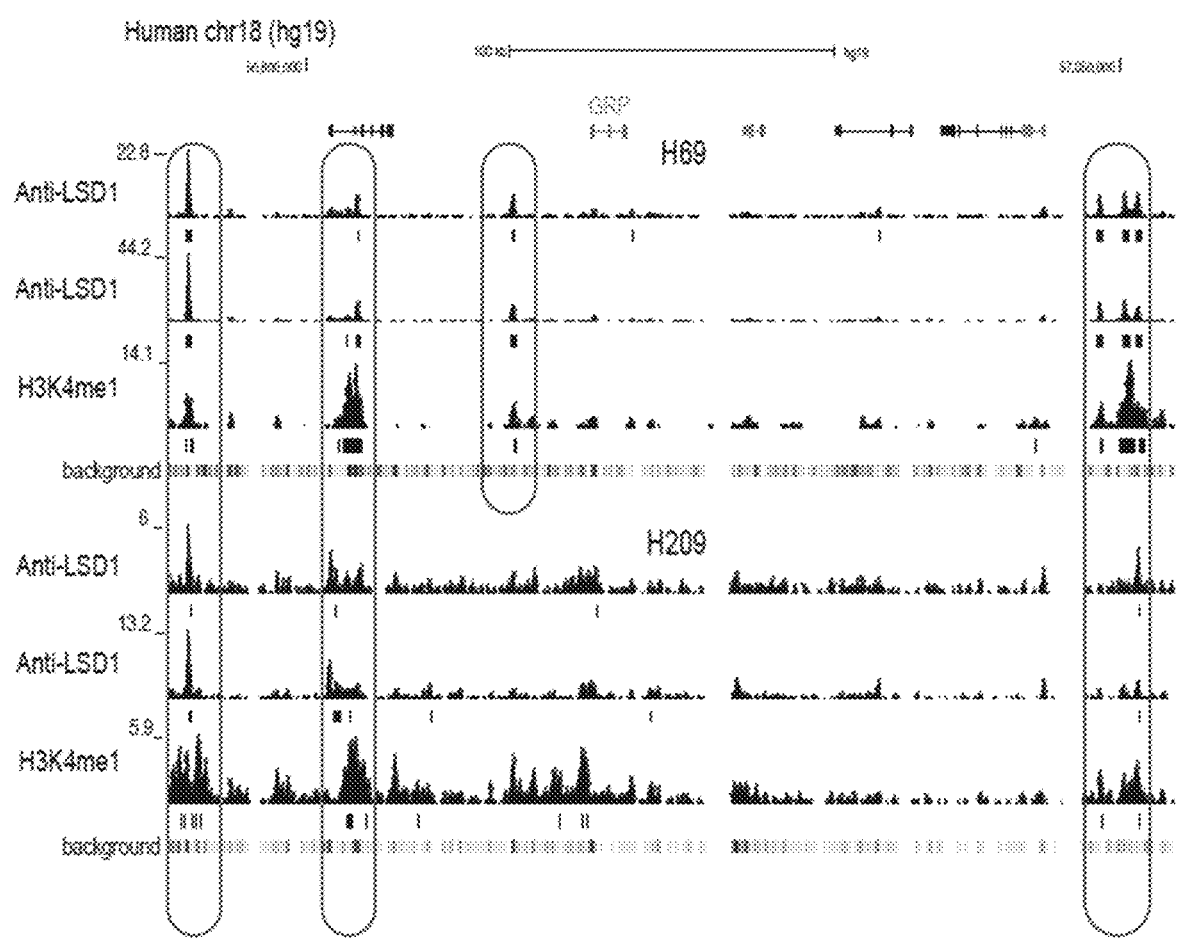
FIG. 2 shows Chromatin Immunoprecipitation and Sequencing Analysis of Lysine-specific Demethylase 1 Binding to Deoxyribonucleic Acid of NCI-H69 and NCI-H209 Cells. Chr=chromosome; GRP=gastrin releasing peptide; H3K4me1=monomethyl histone H3 lysine 4; LSD1=lysine-specific demethylase 1; SCLC=small cell lung cancer; Results from two LSD1 antibodies (anti-KDM1/LSD1 antibody [Abcam®, Cambridge, Mass. Cat No. ab17721] and anti-BHC110/LSD1 antibody [Bethyl Laboratories, Montgomery, Tex. Cat No. A300-215A]) and H3K4me1 antibody (Abcam®, Cambridge, Mass. Cat No. ab8895), are shown in the browser track as normalized reads per million. Black bars beneath each track indicate regions enriched over background (ie, bound). Red ovals indicate regulatory regions co-occupied by LSD1 and H3K4me1. The position of the GRP gene on human chromosome 18 is shown. Boxes indicate the exons connected by lines with arrows indicating direction of transcription with the first exon on the left. Adjacent genes to GRP are shown in gray. The reads from input control are shown for each cell line (Background).

Additionally, the binding of LSD1 to the GRP gene locus was investigated in the SCLC cell lines NCI-H69 and NCI-H209 using ChIP-seq. Chromatin immunoprecipitation and sequencing results showed that LSD1 co-occupies enhancer elements, identified as H3K4me1-positive regions, which are within 100 kilobases of the GRP gene locus. These results suggest that LSD1 binds at possible regulatory sites for GRP locus and LSD1 may directly regulate GRP gene expression, thereby supporting GRP as a pharmacodynamic (PD) biomarker for LSD1 inhibition in SCLC (FIG. 2).

Figure 3:
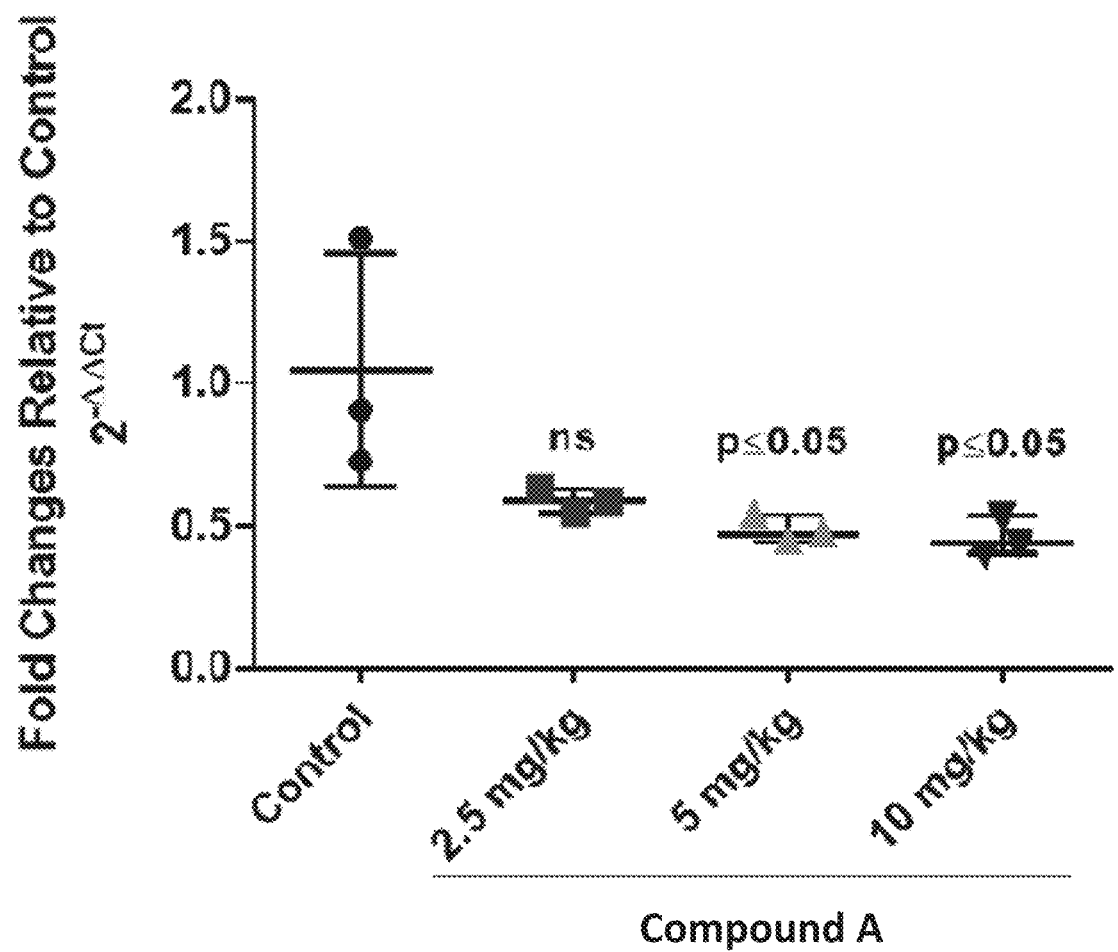
FIG. 3 shows Effect of Compound A on Human Gastrin-releasing Peptide Messenger Ribonucleic Acid Expression in the NCI-H1417 Small Cell Lung Cancer Xenograft Model. ANOVA=analysis of variance; ns=not statistically significant. Plot shows individual 2−ΔΔCt values calculated as described, with horizontal lines at mean±standard deviation; p-value calculated using one-way ANOVA followed by Dunnett's multiple comparisons test (Compound A versus control).

Example 9: Effect of Lysine-Specific Demethylase 1A Inhibition by Compound A on Human Gastrin Releasing Peptide Messenger Ribonucleic Acid Expression in NCI-H1417 Small Cell Lung Cancer Xenograft Model To translate the effects of Compound A mediated LSD1 inhibition observed in vitro to an in vivo setting, TGI and target gene expression changes after Compound A treatment were measured in several SCLC in vivo models. The modulation of human GRP expression, following LSD1 inhibition by Compound A, was evaluated in a human NCI-H1417 SCLC xenograft model in athymic nude mice. Female mice bearing SC-implanted NCI-H1417 SCLC tumors were treated orally with Compound A at 2.5, 5, or 10 mg base/kg QD for 4 days and the GRP expression levels were determined. Treatment with Compound A resulted in dose-related down regulation of GRP mRNA levels in treated tumor bearing mice compared with vehicle-treated control animals, as determined by qRT-PCR. Comparing mean expression values, Compound A at 2.5, 5, and 10 mg base/kg reduced GRP gene expression by 44%, 53%, and 56%, respectively, relative to control animals. The decrease in GRP gene expression was statistically significant for doses of Compound A≥5 mg base/kg (p≤0.05) (FIG. 3).

Figure 4:
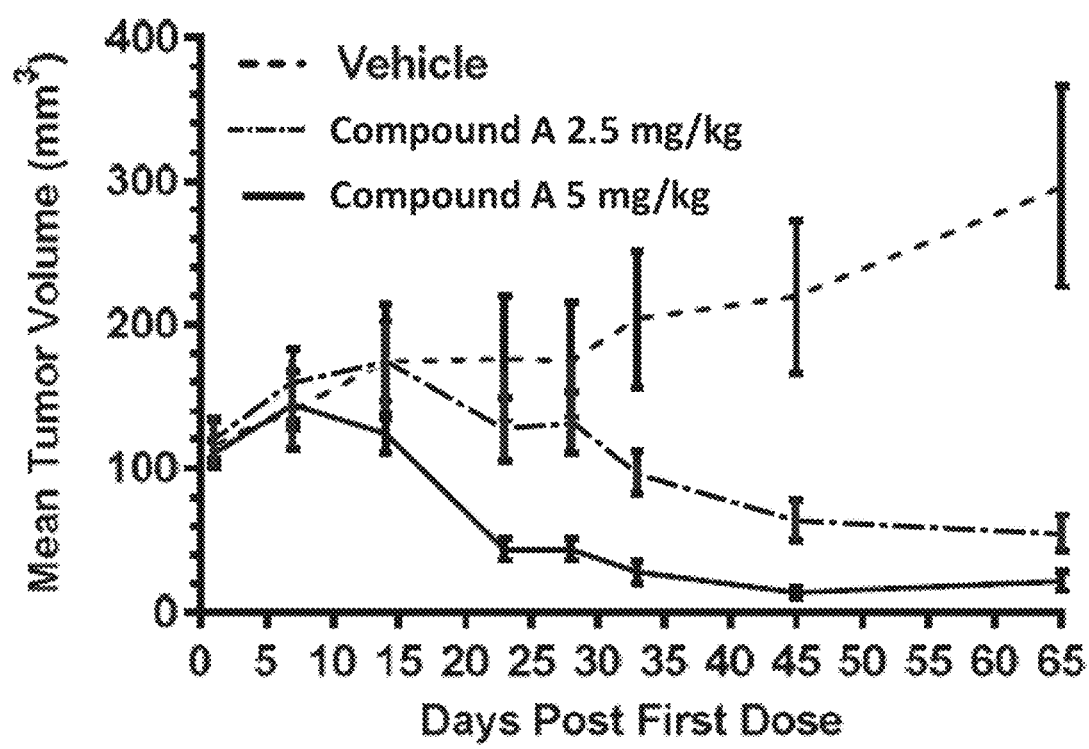
FIG. 4. is a graph showing tumor growth inhibition of SCLC xenografts by administration of Compound A, or vehicle control. Tumor volumes were plotted as mean±standard error of the mean (SEM).

Example 10. Efficacy of Compound A in NCI-H1417 Small Cell Lung Cancer Xenograft Model The efficacy and tolerability of Compound A was evaluated in a human NCI-H1417 SCLC xenograft SC model in female athymic nude mice. Female mice bearing NCI-H1417 SCLC tumors were dosed orally, QD for 65 consecutive days (QD×65), with either 2.5 or 5 mg base/kg Compound A or 10 mL/kg 0.5% methyl cellulose vehicle as a control. Tumor growth inhibition analysis on Day 65 demonstrated that Compound A treatment was efficacious in the NCI-H1417 model, resulting in TGI of 159% at 2.5 mg base/kg dose (p≤0.001) and 178% at 5 mg base/kg dose (p≤0.0001) (Table 10). Six out of seven control animals exhibited an increase in net tumor volume at the end of study. Conversely, all but 1 tumor (14 out of 15) from Compound A-treated animals regressed in net volume. Mean tumor growth in the control animals progressed over the course of the study whereas tumors in the 2 Compound A-treated groups declined after Day 14 (FIG. 4). Compound A appeared well tolerated, and animals receiving the 2.5 or 5 mg base/kg doses exhibited respective mean body weight gains of 1% and 7.5% by the end of study. All animals survived the duration of the study.

TABLE 10

Response Summary for NCI-H1417 Study

| Group | n | Agent | Dose (mg base/kg) | Route | Schedule | Median Tumor Volumes (mm$^3$) Day 0 | Day 65 | Diff. | % TGI | Statistical Significance |
|---|---|---|---|---|---|---|---|---|---|---|
| 1 | 7 | Vehicle | 0 | PO | QDx65 | 105.3 | 223.6 | 118.3 | NC | NC |
| 2 | 7 | Compound A | 2.5 | PO | QDx65 | 109.2 | 39.3 | −69.9 | 159% | p ≤ 0.001 |
| 3 | 8 | Compound A | 5 | PO | QDx65 | 108.2 | 15.9 | −92.3 | 178% | p ≤ 0.0001 |

ANOVA = analysis of variance;
Diff. = difference;
NC = not calculated;
PO = oral dosing;
QD = once daily dosing;
TGI = tumor growth inhibition.
Note:
P-value calculated using one-way ANOVA followed by Dunnett's multiple comparisons test (Compound A versus vehicle).

Example 11: Efficacy of Compound A in LU2514 and LU1480 HuPrime® Small Cell Lung Cancer Patient Derived Xenograft Models Compound A was evaluated in the patient-derived HuPrime SCLC models LU2514 and LU1480, that were SC implanted in female BALB/c nude mice.

Figure 5:
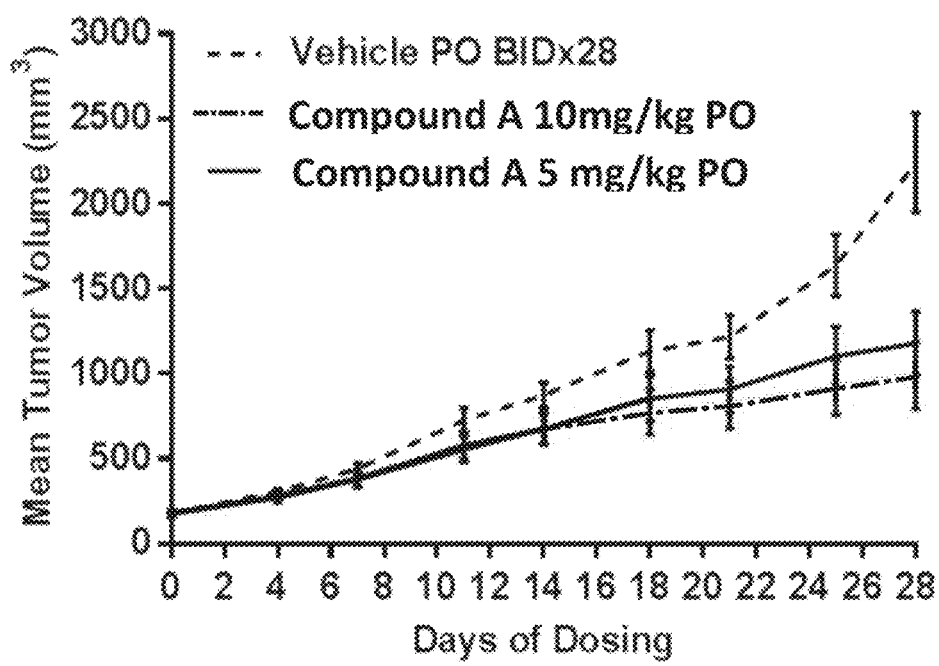
FIG. 5 is a graph showing tumor growth inhibition of SCLC xenografts by administration of Compound A, or vehicle control. BID is twice daily; PO is oral dosing; QDX28 is once everyday for 28 days; Tumor volumes were plotted as mean±standard error of the mean (SEM).

In the LU2514 study, treated female mice received Compound A at either 10 mg base/kg (n=10) or at 5 mg base/kg (n=8), orally, QD for 28 days (QDx28). Tumor growth inhibition analysis was performed on Day 28 post treatment, the last day of dosing. Compound A was efficacious, causing a TGI of 61% and 43% at 10 mg base/kg and at 5 mg base/kg, respectively (p≤0.01) (Table 11). Tumor growth was reduced in both Compound A-treated groups relative to control animals (FIG. 5).

TABLE 11

Response Summary for QC-TR-L021 (LU2514) Study

| Group | n | Agent | Dose (mg base/kg) | Route | Schedule | Median Tumor Volumes (mm$^3$) Day 1 | Day 28 | Diff. | % TGI | Statistical Significance |
|---|---|---|---|---|---|---|---|---|---|---|
| 1 | 10 | Vehicle$^a$ | 0 | PO | BIDx28 | 166.6 | 2046.5 | 1879.9 | NC | NC |
| 2 | 10 | Compound A | 10 | PO | QDx28 | 173.7 | 906.0 | 732.3 | 61% | p ≤ 0.01 |
| 3 | 8 | Compound A | 5 | PO | QDx28 | 173.2 | 1244.8 | 1071.6 | 43% | p ≤ 0.01 |

BID = twice daily;
Diff. = difference;
NC = not calculated;
PO = oral dosing;
QD = once daily dosing;
TGI = tumor growth inhibition.
$^a$vehicle was dosed BID to match additional dosing regimens not included in this table.
Length of study = 70 days,
TGI determined on Day 28, the last day of dosing.

Figure 6:
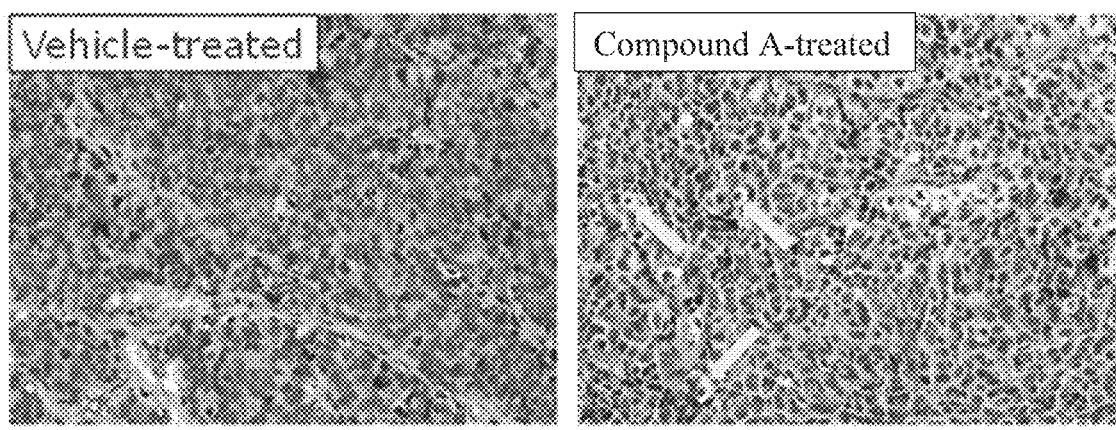
FIG. 6 is hematoxylin and eosin staining images of tumor tissues from LU2514 Study.

In LU2514 study, Compound A dosed orally at 10 mg base/kg for 22 days yielded a TGI of 62%. Mean tumor growth in the Compound A-treated group was reduced relative to control animals. The histological analysis revealed that tumors from the control animal showed classic poorly differentiated round cell morphology and granular chromatin. Tumors from Compound A-treated animals displayed cells with "looser" structure, a decreased nucleus to cytoplasm ratio, and a higher number of apoptotic bodies (FIG. 6). In both studies with LU2514 animal model, Compound A appeared well tolerated with mean body weight losses <10%.

Figure 7:
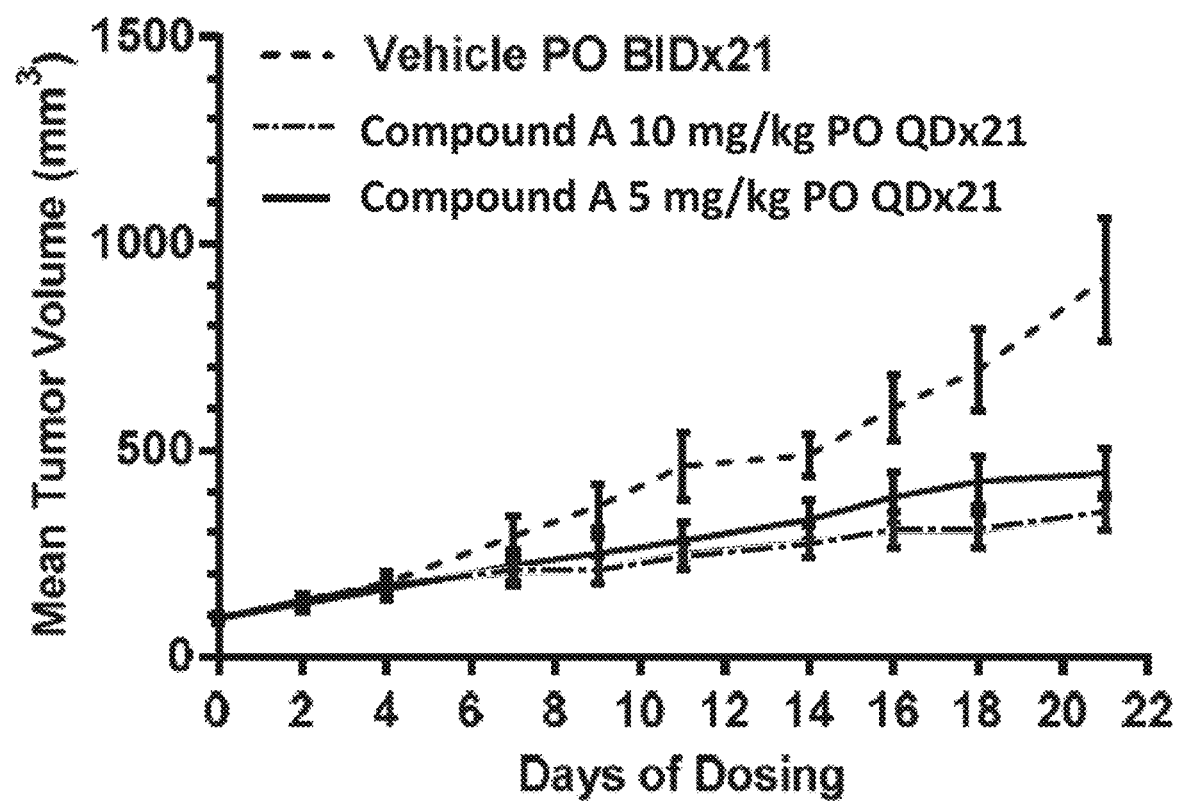
FIG. 7 is a graph showing tumor growth inhibition of SCLC xenografts by administration of Compound A, or vehicle control. BID is twice daily; PO is oral dosing; QDX21 is once everyday for 21 days; Tumor volumes were plotted as mean±standard error of the mean (SEM).

In the LU1480 study, oral administration of Compound A for 21 days was efficacious, attaining a TGI of 72% at 10 mg base/kg dose (p≤0.001) and 53% at 5 mg base/kg dose (p≤0.01) (Table 12). Mean tumor growth in the Compound A treated groups was reduced relative to control animals (FIG. 7). In the LU1480 experiment, Compound A dosed orally at 10 mg base/kg for 15 days yielded a TGI of 46%. In these LU1480 studies, a generalized and sustained body weight loss, likely due to the inherent cachectic nature of the LU1480 model, was reported.

In summary, Compound A, when dosed orally at 5 or 10 mg base/kg, was shown to be efficacious in the LU2514 and LU1480 PDX models of SCLC. The dose-related TGI (43% to 72%) for Compound A treated versus control animals were statistically significant in all studies except LU2514, where the sample size was small.

Figure 8:
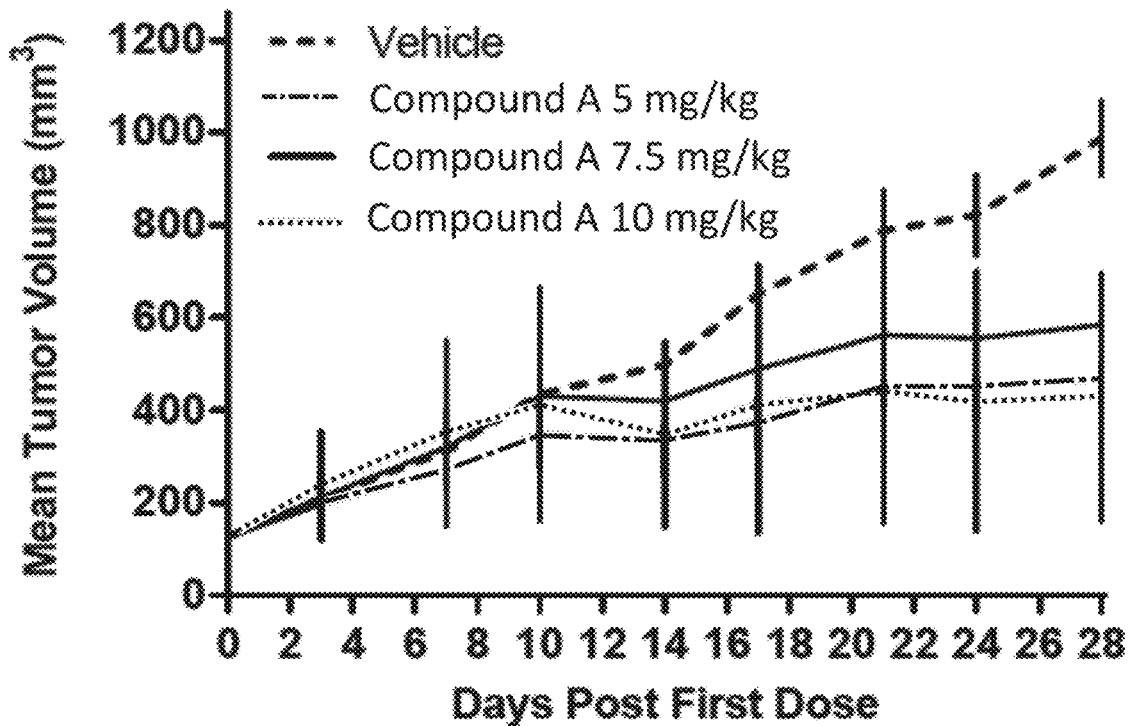
FIG. 8 is a graph showing tumor growth inhibition of SCLC xenografts by administration of Compound A, or vehicle control. Tumor volumes were plotted as mean±standard error of the mean (SEM).

Example 12: Efficacy of Compound A in LXFS 573, LXFS 615, LXFS 1129, and LXFS 2156 Small Cell Lung Cancer Patient Derived Xenograft Models The antitumor effects of orally administered Compound A were also evaluated in 4 different SCLC PDX models, LXFS 573, LXFS 615, LXFS 1129, and LXFS 2156, that were implanted SC in female immunodeficient NMRI-Foxn1nu mice. Treatment with Compound A was efficacious in the LXFS 573 PDX model of SCLC, attaining an end of study (Day 28) TGI of 78% at 5 mg base/kg dose (p≤0.001), 58% at 7.5 mg base/kg dose (p≤0.01), and 71% at 10 mg/kg dose (p≤0.001) (Table 13). Mean tumor growth in the Compound A treated groups was reduced relative to control animals after Day 10 (FIG. 8). Compound A appeared well tolerated with mean body weight losses ≤3%.

TABLE 12

Response Summary for LU1480 Study

| | | Treatment Regimen | | | Median Tumor Volumes (mm³) | | | | |
|---|---|---|---|---|---|---|---|---|---|
| Group | n | Agent | Dose (mg base/kg) | Route | Schedule | Day 1 | Day 21 | Diff. | % TGI | Statistical Significance |
| 1 | 10 | Vehicle[a] | 0 | PO | BIDx21 | 89.1 | 934.5 | 845.4 | NC | NC |
| 2 | 10 | Compound A | 10 | PO | QDx21 | 87.1 | 321.4 | 234.3 | 72% | p ≤ 0.001 |
| 3 | 8 | Compound A | 5 | PO | QDx21 | 89.5 | 490.1 | 400.6 | 53% | p ≤ 0.01 |

BID = twice daily;
Diff. = difference;
NC = not calculated;
PO = oral dosing;
QD = once daily dosing;
TGI = tumor growth inhibition
[a]vehicle was dosed BID to match additional dosing regimens not included in this table.
Length of study = 66 days;
TGI determined after 21 doses, on the last day when at least 8 animals remained in each study group.

TABLE 13

Response Summary for LXFS 573 Experiment

| | | Treatment Regimen | | | Median Tumor Volumes (mm³) | | | | |
|---|---|---|---|---|---|---|---|---|---|
| Group | n | Agent | Dose (mg base/kg) | Route | Schedule | Day 0 | Day 28 | Diff. | % TGI | Statistical Significance |
| 1 | 8 | Vehicle | 0 | PO | QDx28 | 117.2 | 1037.3 | 920.1 | NC | NC |
| 2 | 8 | Compound A | 5 | PO | QDx28 | 108.4 | 308.3 | 199.9 | 78% | p ≤ 0.001 |
| 3 | 8 | Compound A | 7.5 | PO | QDx28 | 113.2 | 496.6 | 383.4 | 58% | p ≤ 0.01 |
| 4 | 8 | Compound A | 10 | PO | QDx28 | 113.8 | 376.8 | 263.0 | 71% | p ≤ 0.001 |

ANOVA = analysis of variance;
Diff = difference;
NC = not calculated;
PO = oral dosing;
QD = once daily dosing;
TGI = tumor growth inhibition.
Note:
One-way ANOVA followed by Dunnett's multiple comparisons test for experiments with more than two groups and unpaired t test for experiments comparing two groups, evaluated differences in distribution of tumor volumes in Compound A treated versus control animals.

Figure 9:
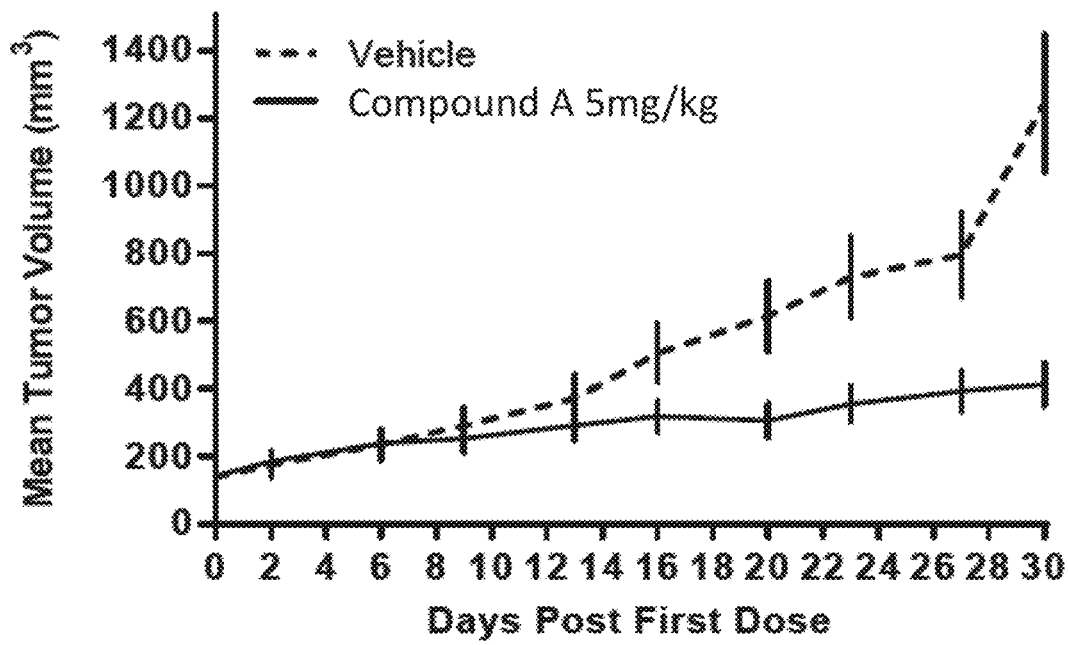
FIG. 9 is a graph showing tumor growth inhibition of SCLC xenografts by administration of Compound A, or vehicle control. Tumor volumes were plotted as mean±standard error of the mean (SEM).

In the LXFS 615 PDX model, oral administration of Compound A at 5 mg base/kg for 30 days caused 78% of TGI (p≤0.001). Mean tumor growth in the Compound A-treated group was reduced relative to control animals (FIG. 9). Compound A appeared well-tolerated with mean body weight losses <1%. Pharmacokinetic analysis performed on plasma samples collected following the final dose demonstrated that $AUC_{0-24}$ of Compound A at 5 mg base/kg was 1,617 ng·hr/mL.

Figure 10:
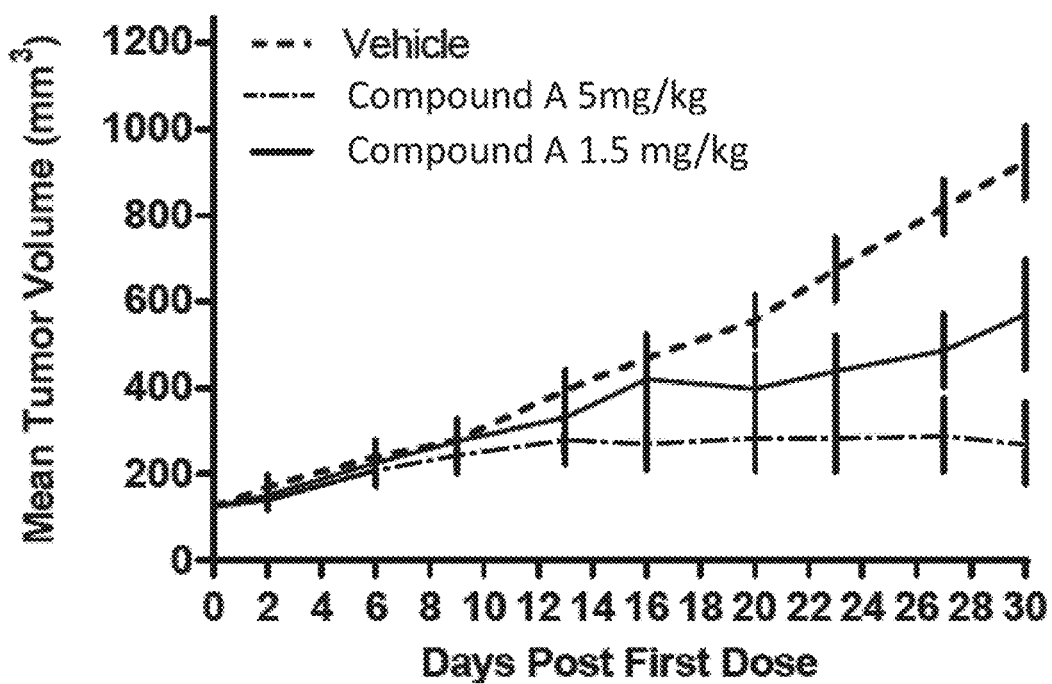
FIG. 10 is a graph showing tumor growth inhibition of SCLC xenografts by administration of Compound A, or vehicle control. Tumor volumes were plotted as mean±standard error of the mean (SEM).

The administration of Compound A, QD for 30 days, was efficacious in the LXFS 1129 PDX model of SCLC, attaining an end of study TGI of 89% at 5 mg base/kg dose (p≤0.001) and 55% at 1.5 mg base/kg dose (p≤0.05). After Day 12, mean tumor growth in both Compound A treated groups was reduced relative to control animals (FIG. 10). Compound A appeared well-tolerated with mean body weight losses <6%. The AUC0-24 values of Compound A at 1.5 and 5 mg base/kg were 243 and 1,262 ng·hr/mL, respectively, and thus, a greater than proportional increase in exposure at the 5 mg base/kg dose was observed relative to the 1.5 mg base/kg dose.

Compound A, when dosed orally QD×23 at 5 mg base/kg, was not efficacious in the LXFS 2156 PDX model yielding a TGI of −7%.

In summary, oral administration of Compound A was efficacious in the LXFS 573, LXFS 615, and LXFS 1129 PDX models of SCLC. The level of TGI (55% to 89%) for Compound A treated versus control animals was significant. Compound A appeared well tolerated in all 4 models tested, with body weight losses <6%.

Example 13. In Vivo Efficacy of Compound A in the Respective HuPrime® Subcutaneous Lung and Gastric Neuroendocrine Carcinoma Patient-Derived Xenograft Models LU2527 and GA0087 in Female BALB/c Nude Mice The in vivo efficacy and tolerability of compound A were evaluated preclinically on a once daily (QD) dosing schedule using the respective HuPrime® subcutaneous lung and gastric neuroendocrine carcinoma (NEC) patient-derived xenograft (PDX) models LU2527 and GA0087 established in female immunodeficient BALB/c nude mice. LU2527 and GA0087 were characterized as an atypical carcinoid of the lung and a carcinoid of the gastric cardia, respectively. Efficacy was determined based on percent tumor growth inhibition (% TGI) and differences between treated and control animals in mean net tumor volumes on the day of TGI analysis and mean tumor growth over the course of the study. Tolerability was assessed based on differences in mean body weights between treated and control animals.

LU2527 tumor fragments were obtained from xenografts in serial passage (R3P6) in stock mice. After removal from donor mice, tumors were cut into fragments (2 to 3 mm in diameter) and inoculated subcutaneously in the right flank of recipient female immunodeficient BALB/c mice. Tumors were allowed to grow for 50 days until they attained ~159 mm3. Tumor bearing mice (11-12 weeks of age) were then randomized into three groups of eight mice with mean tumor volumes of 159.7±13.6 mm3, 159.7±13.9 mm3, and 159.7±13.5 mm3. This day was denoted as Day 0 and dosing was initiated according to the pre-determined regimen shown in Table 14.

TABLE 14

Treatment Plan for LU2527

| | | Treatment Regimen | | | |
|---|---|---|---|---|---|
| Group | n | Agent | Dose (mg/kg) | Route | Schedule |
| 1[a] | 8 | Vehicle | — | PO[b] | QD[c] × 57 |
| 2 | 8 | compound A | 1.5 | PO | QD × 57 |
| 3 | 8 | compound A | 5 | PO | QD × 57 |

[a]control group dosed 10 mL/kg of vehicle alone and Compound A dosed at 10 mL/kg as mg/kg free base equivalents;
[b]oral dosing (PO);
[c]once daily dosing (QD)

GA0087 tumor fragments were obtained from xenografts in serial passage (R15P7) in stock mice. After removal from donor mice, tumors were cut into fragments (2 to 3 mm in diameter) and inoculated subcutaneously in the right flank of recipient female immunodeficient BALB/c mice. Tumors were allowed to grow for 24 days until they attained ~133 mm³. Tumor bearing mice (13-14 weeks of age) were then randomized into three groups of eight mice with mean tumor volumes of 133.2±7.6 mm³, 133.0±7.8 mm³, and 133.1±8.5 mm³. This day was denoted as Day 0 and dosing was initiated according to the pre-determined regimen shown in 15.

TABLE 15

Treatment Plan for GA0087

| | | Treatment Regimen | | | |
|---|---|---|---|---|---|
| Group | n | Agent | Dose (mg/kg) | Route | Schedule |
| 1[a] | 8 | Vehicle | — | PO[b] | QD[c] × 62 |
| 2 | 8 | compound A | 1.5 | PO | QD × 62 |
| 3 | 8 | compound A | 5 | PO | QD × 62 |

[a]control group dosed 10 mL/kg of vehicle alone and Compound A dosed at 10 mL/kg as mg/kg free base equivalents;
[b]oral dosing (PO);
[c]once daily dosing (QD)

Individual tumors were measured twice weekly in two dimensions using a caliper, and the tumor volumes (TV) in mm3 were calculated using the formula: TV=0.5 a×b2, where a and b are the long and short diameters in millimeters, respectively. Animals were weighed twice each week. Mean tumor growth curves and mean body weight plots as percent change from Day 0 were constructed.

Percent TGI was calculated using median tumor volumes according to the following formula:

$$TGI_x\ [\%] = \left(1 - \frac{T_x - T_0}{C_x - C_0}\right) \times 100$$

where $T_0$ and $C_0$ were the respective median tumor volumes in Compound A-treated and control groups prior to the start of dosing and Tx and Cx were the corresponding median tumor volumes on Day "x", the day of TGI analysis.

TGIs in the LU2527 and GA0087 studies were calculated on Day 46 and Day 53, respectively, the last day tumor volume measurements were available for all compound A-treated animals. In both studies, one animal in each control group was censored due to poor tumor engraftment and, in the LU2527 study, a second control animal that exited the study on Day 21 was censored as an accidental death possibly due to oral gavage error. In the GA0087 study, one animal that received 1.5 mg/kg compound A attained the tumor volume endpoint (≥3000 mm3) on Day 53 but was not sacrificed until Day 57. As a result, the Day 56 measurement was censored, establishing Day 53 as the day of TGI analysis.

Table and Table summarize the respective treatment plans for the LU2527 and GA0087 studies. For each tumor type, test animals were sorted into three groups of eight mice per group, and treatments were initiated on Day 0 when the average tumor size met the randomization criteria. Control mice received a 0.5% methyl cellulose vehicle at 10 mL/kg of body weight administered by oral gavage (PO) on a once daily (QD) schedule as shown. Treated mice received Compound A at 10 mL/kg dosed as mg/kg free base equivalents, PO, on the QD schedules as shown. Two animals in each study received dosing holidays which had no effect on the outcomes. The test article Compound A was prepared daily as a salt (74% active compound) suspended in vehicle.

Figure 11:
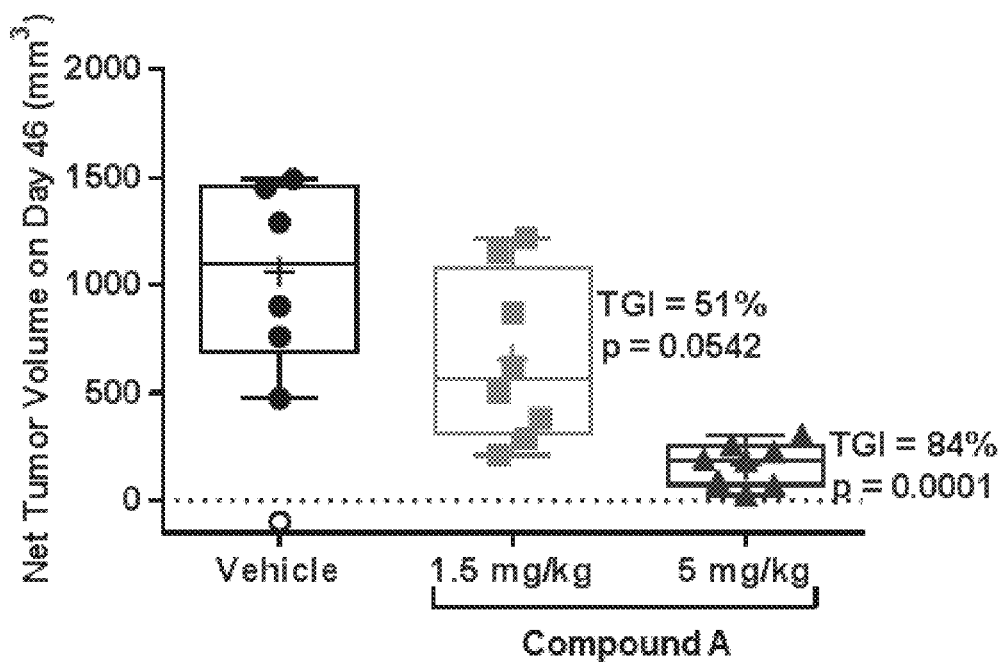
FIG. 11 is a graph showing mean net tumor volume differences on Day 46 for LU2527 study. Open symbol represents data censored due to poor tumor engraftment; Data (not shown) for another control animal that exited the study on Day 21 was censored as an accidental death possibly due to oral gavage error.
Figure 12:
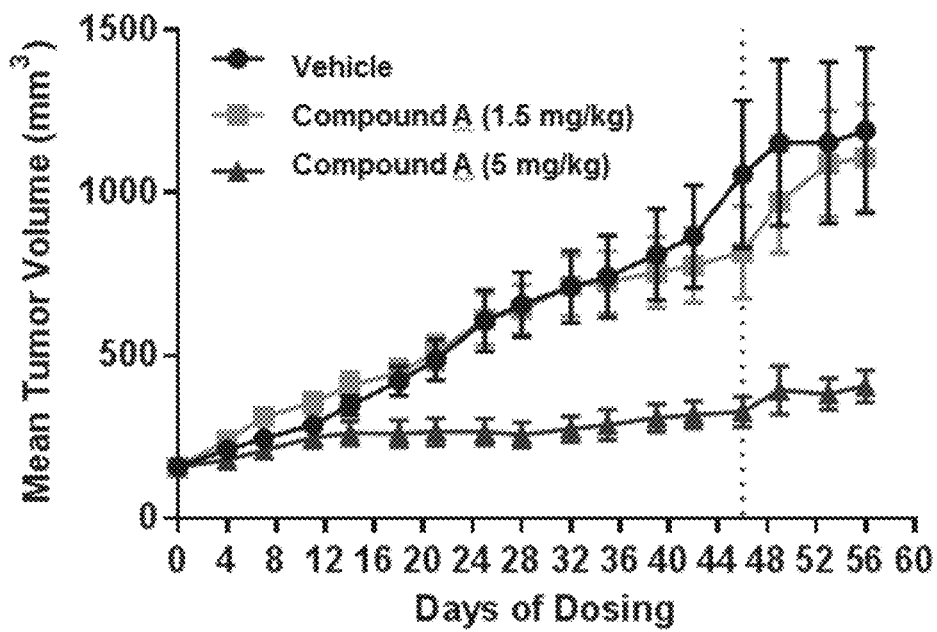
FIG. 12 is a graph showing mean tumor growth for LU2527. Tumor volumes plotted as mean±standard error (SEM). Vertical line at Day 46 denotes day of TGI analysis.
Figure 13:
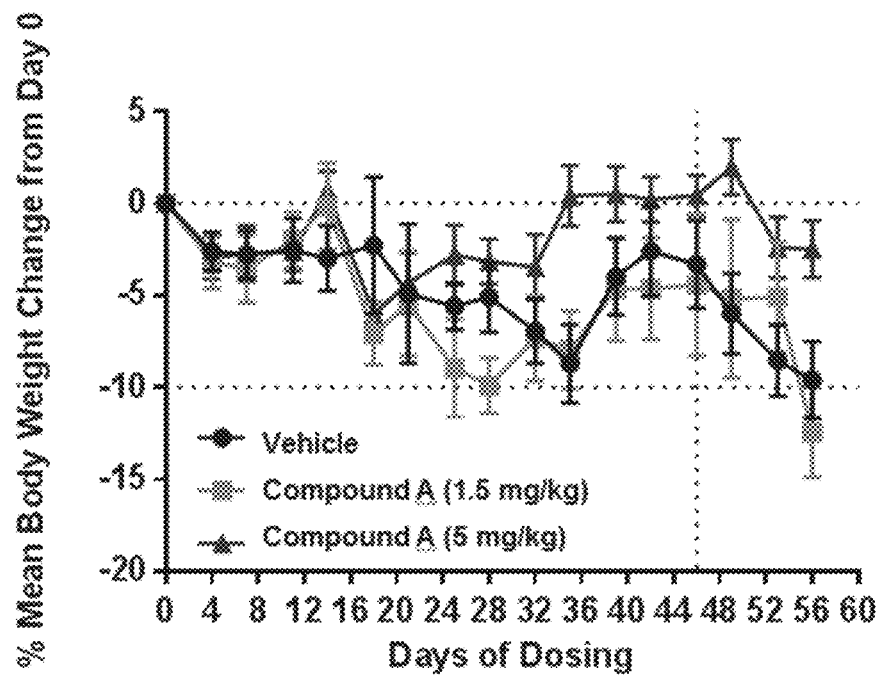
FIG. 13 is a graph showing percent mean body weight change for LU2527. Body weights plotted as % mean±standard error (SEM). Vertical line at Day 46 denotes day of TGI analysis and horizontal lines at 0% and −10% mean body weight change.

Results for the LU2527 study are shown in Table 16. Compound A when dosed orally QD for 46 days yielded dose-dependent TGIs of 51% at 1.5 mg/kg and 84% at 5 mg/kg in the LU2527 PDX model of lung cancer. As shown in FIG. 11, the difference in mean net tumor volumes on the day of TGI analysis for 5 mg/kg Compound A-treated vs. control animals was significant (p=0.0001). Mean tumor growth in the 5 mg/kg Compound A-treated group was considerably reduced relative to control animals, as shown in FIG. 12. Compound A appeared acceptably tolerated exhibiting mean body weight changes that did not substantially differ from those for the vehicle control, as shown in FIG. 13. Progressive mean body weight losses occurred in all groups, including the vehicle control group, after the day of TGI analysis suggesting the body weight loss may be tumor load related.

TABLE 16

Response Summary for LU2527 on Day 46

| | | Treatment Regimen | | | Median Tumor Volumes (mm$^3$) | | | | |
|---|---|---|---|---|---|---|---|---|---|
| Group | n | Agent | Dose (mg/kg) | Route | Schedule | Day 0 | Day 46 | Diff | % TGI | Statistical Significance |
| 1[a] | 6 | Vehicle | — | PO[b] | QD[c] x 46 | 148.7 | 1269.8 | 1121.2 | — | — |
| 2 | 8 | Compound A | 1.5 | PO | QD x 46 | 148.2 | 698.5 | 550.3 | 51 | p = 0.0542 |
| 3 | 8 | Compound A | 5 | PO | QD x 46 | 151.8 | 329.7 | 177.9 | 84 | p = 0.0001 |

[a] control group dosed 10 mL/kg of vehicle alone and Compound A dosed at 10 mL/kg as mg/kg free base equivalents;
[b] oral dosing (PO);
[c] once daily dosing (QD)

Figure 14:
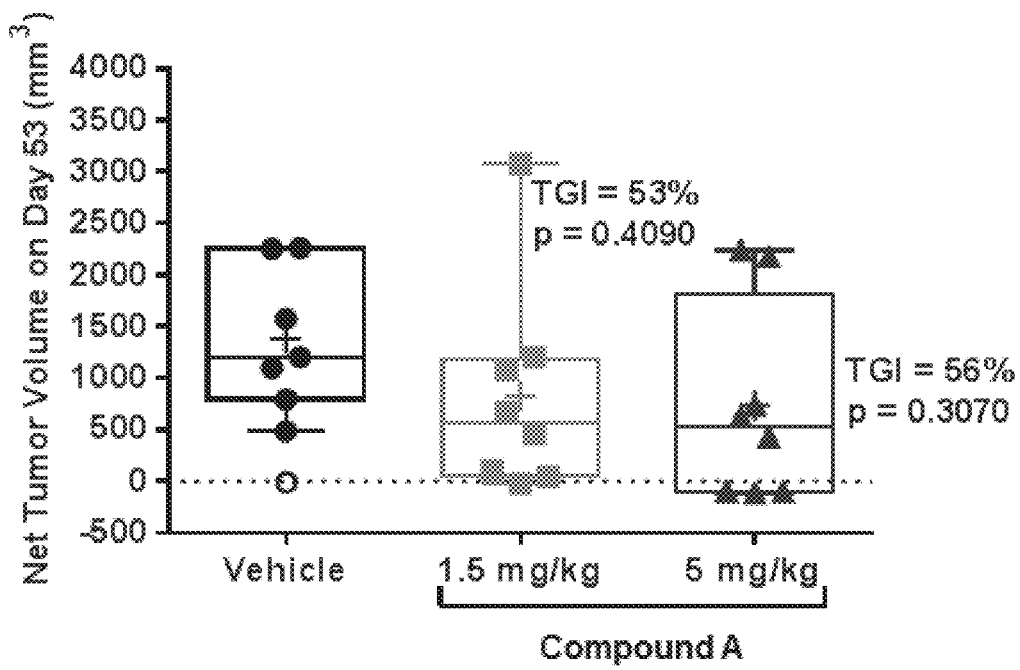
FIG. 14 is a graph showing mean net tumor volume differences on day 53 for GA0087 study. Open symbol represents data censored due to poor tumor engraftment.
Figure 15:
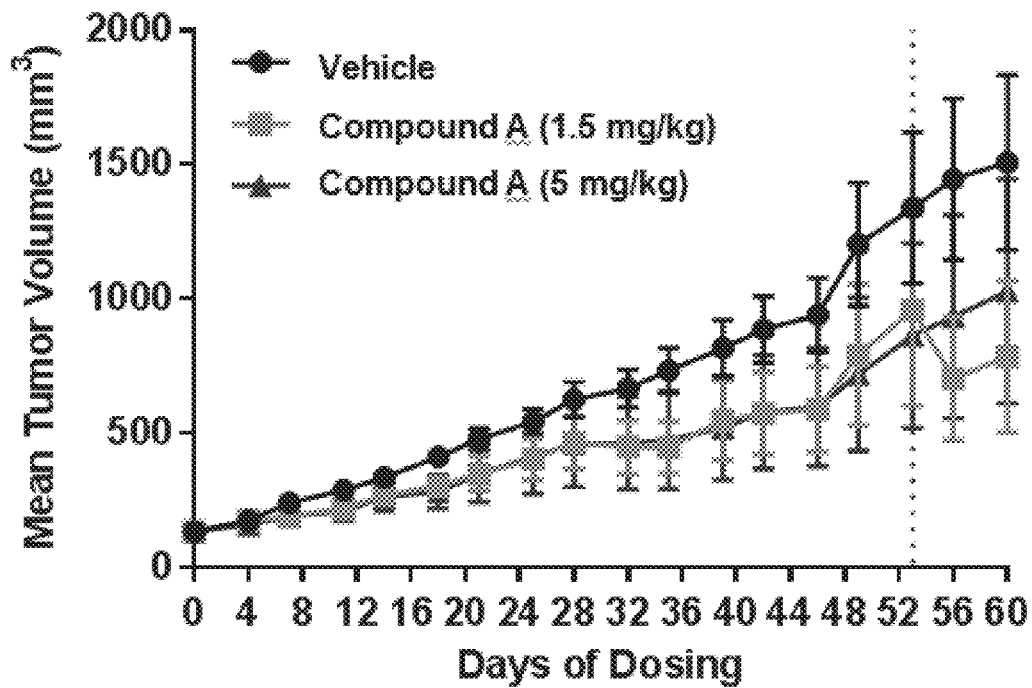
FIG. 15 is a graph showing mean tumor growth for GA0087. Tumor volumes plotted as mean±standard error (SEM). Vertical line at Day 53 denotes day of TGI analysis.
Figure 16:
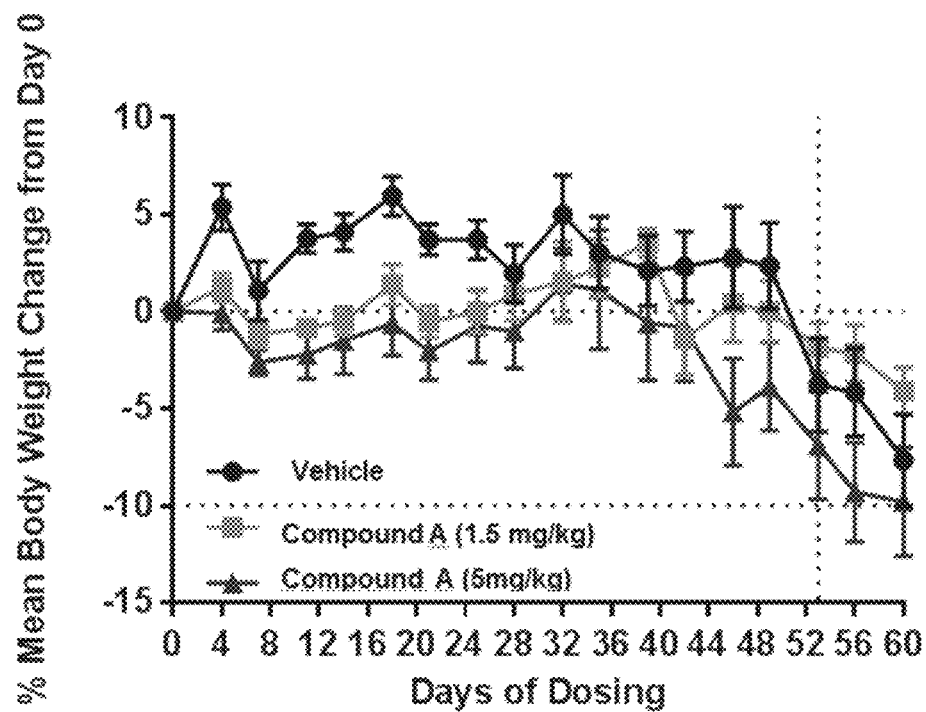
FIG. 16 is a graph showing percent mean body weight change for GA0087. Body weights plotted as % mean±standard error (SEM). Vertical line at Day 53 denotes day of TGI analysis and horizontal lines at 0% and −10% mean body weight change.

Results for the GA0087 study are shown in Table 17. Compound A when dosed orally QD for 53 days yielded TGIs of 53% at 1.5 mg/kg and 56% at 5 mg/kg in the GA0087 PDX model of gastric cancer. As shown in FIG. 14, the differences in mean net tumor volumes on the day of TGI analysis for Compound A-treated vs. control animals were not significant (p>0.05). Mean tumor growth in the Compound A-treated groups was reduced relative to control animals, as shown in FIG. 15. Compound A appeared acceptably tolerated exhibiting mean body weight changes that did not substantially differ from those for the vehicle control, as shown in FIG. 16. Progressive mean body weight losses occurred in all groups, including the vehicle control group, beginning around Day 49 suggesting the body weight loss may be tumor load related. One animal that received 1.5 mg/kg Compound A attained the tumor volume endpoint (≥3000 mm3) on Day 53 but was not sacrificed until Day 57. As a result, the Day 56 measurements were censored for mean tumor growth and mean body weight analyses.

TABLE 17

Response Summary for E0288-U1604-GA0087 on Day 53

| | | Treatment Regimen | | | Median Tumor Volumes (mm$^3$) | | | | |
|---|---|---|---|---|---|---|---|---|---|
| Group | n | Agent | Dose (mg/kg) | Route | Schedule | Day 0 | Day 53 | Diff | % TGI | Statistical Significance |
| 1[a] | 7 | Vehicle | — | PO[b] | QD[c] x 53 | 125.6 | 1364.9 | 1239.3 | — | — |
| 2 | 8 | Compound A | 1.5 | PO | QD x 53 | 128.9 | 706.4 | 956.7 | 53 | p = 0.4090 |

TABLE 17-continued

Response Summary for E0288-U1604-GA0087 on Day 53

| | | Treatment Regimen | | | Median Tumor Volumes (mm³) | | | | |
|---|---|---|---|---|---|---|---|---|---|
| Group | n | Agent | Dose (mg/kg) | Route | Schedule | Day 0 | Day 53 | Diff | % TGI | Statistical Significance |
| 3 | 8 | Compound A | 5 | PO | QD x 53 | 127.6 | 673.2 | 863.3 | 56 | p = 0.3070 |

[a]control group dosed 10 mL/kg of vehicle alone and Compound A dosed at 10 mL/kg as mg/kg free base equivalents;
[b]oral dosing (PO);
[c]once daily dosing (QD)

Oral Compound A dosed daily was efficacious in the LU2527 PDX model of lung cancer. Response was dose-dependent yielding TGIs of 51% at 1.5 mg/kg and 84% at 5 mg/kg. The difference in mean net tumor volumes on the day of TGI analysis for 5 mg/kg Compound A-treated vs. control animals was significant and mean tumor growth was considerably reduced relative to control animals.

Oral Compound A dosed daily was modestly efficacious in the GA0087 PDX model of gastric cancer. Response yielded TGIs of 53% at 1.5 mg/kg and 56% at 5 mg/kg and the differences in mean net tumor volumes on the day of TGI analysis for treated vs. control animals were not significant. Mean tumor growth for treated animals was moderately reduced relative to control animals.

Compound A appeared acceptably tolerated in both studies. All groups exhibited late progressive mean body weight losses implying that body weight loss was not treatment related.

Example 14: In Vitro and In Vivo Efficacy of Compound A in Two Human Merkel Cell Carcinoma Models MKL-1 and MS-1

Human Merkel Cell Carcinoma is classified as an aggressive cutaneous neuroendocrine tumor that expresses LSD1. These tumors are more accessible than SCLC tumors and may prove useful for pharmacodynamic efforts in human studies. Effective hMCC treatment is a highly unmet need that could offer an additional indication for Compound A. In the present non-Good Laboratory Practice (GLP) preclinical study, in vitro cell proliferation inhibition assays were performed to determine IC50 values for cultured MKL-1 and MS-1 cell lines treated with Compound A. In addition, Compound A was evaluated for in vivo efficacy and tolerability as monotherapy in two hMCC xenograft models MKL-1 and MS-1 established in female NSG mice.

The purpose of this study was to determine IC50 values for cultured MKL-1 and MS-1 cells treated with Compound A using in vitro cell proliferation inhibition assays and to determine the in vivo efficacy and tolerability of Compound A, dosed orally as monotherapy at 5 mg/kg on an intermittent schedule, in MKL-1 and MS-1 xenograft models established in female NSG mice.

Female NSG mice (NOD. Cg-Prkdcscid Il2rgtm1Wj1/SzJ, The Jackson Laboratory, Bar Harbor, Me.) were used for this study. Test mice were 7 to 9 weeks old on the day of tumor implantation. Animals were acclimated for one week prior to tumor implantation.

Animals were fed ad libitum water (reverse osmosis, acidified) and PicoLab® Rodent Diet consisting of 20% crude protein, 5.6% fat (acid hydrolysis), and 4.7% crude fiber. The mice were housed in a barrier facility on ALPHA-dri® on a 12-hour light cycle at 72±2° F. and at 30-70% humidity.

Celgene Quanticel Research specifically complied with the recommendations of the Guide for Care and Use of Laboratory Animals (National Academy of Sciences) with respect to restraint, husbandry, surgical procedures, feed and fluid regulation, and veterinary care. The animal care and use program at CQR conforms to the relevant regulatory standards as approved by the Celgene Quanticel Research Institutional Animal Care and Use Committee, which assures compliance with accepted standards for the care and use of laboratory animals.

MKL-1 hMCC cells were cultured in vitro in RPMI-1640 culture medium (Life Technologies, Carlsbad, Calif.) containing 100 units/mL penicillin G sodium and 100 μg/mL streptomycin sulfate (cRPMI) supplemented with 10% fetal bovine serum (FBS). MS-1 hMCC cells were cultured in vitro in cRPMI supplemented with 20% FBS. Both cell lines were cultured in a humidified incubator at 37° C., in an atmosphere of 5% carbon dioxide and 95% air.

For in vitro cell proliferation inhibition studies, Compound A stock solutions were prepared in dimethylsulfoxide (DMSO) and serially diluted in culture medium. For in vivo xenograft studies, Compound A was suspended in 0.5% methylcellulose in water at a dosing volume of 10 mL/kg, and administered.

MKL-1 and MS-1 hMCC cells were seeded into multiwell plates containing growth medium in a two dimensional (2D) assay format. Cells were then treated with Compound A for a pre-determined number of days. Cell viability for each cell line was quantified and IC50 values were calculated.

Female NSG mice bearing palpable hMCC MKL-1 and MS-1 tumors (respective mean tumor volumes ~63 and ~45 mm3) were randomized into two groups each. One group was orally administered 5 mg/kg Compound A as monotherapy on an intermittent schedule (five days on followed by two days with no dosing [5 on/2 off]) and the other was orally administered vehicle as a control on the same schedule.

Efficacy was determined based on statistical assessment of differences in TGI and mean tumor growth for treated vs. control animals. Tolerability was assessed by monitoring each individual animal's health status.

The viability of the MKL-1 and MS-1 cell lines was assessed using a 2D assay format performed in a black walled 96-well multiwell plate. Each test well received 5,000 MKL-1 cells suspended in 100 μL RPMI 1640 supplemented with 10% FBS or 7,500 MS-1 cells suspended in 100 μL RPMI 1640 supplemented with 20% FBS. Compound A was serially diluted in DMSO and then diluted in RPMI 1640 (1:1000) to make a series of 50× stocks. Each test well received 2 μL of one of the stocks or 2 μL of DMSO in RPMI 1640, as a negative control, to give final concentrations of Compound A at 0.0, 0.7, 2.1, 6.2, 18.5, 55.5, 166.7, and 500 nM. Four to six replicates were performed at each concentration. Multiwell plates were incubated for 7 days, and the number of viable cells in each test well was assessed using the CellTiter-Glo® Luminescent Cell Viability Assay in accordance with the manufacturer's instructions and readout with a luminometer (FilterMax F3, Molecular Devices). The CellTiter-Glo® Luminescent Cell Viability Assay measured the number of viable cells based on quantitation of ATP.

On the day of tumor cell inoculation, MKL-1 and MS-1 cells were harvested during log phase growth and resuspended in 100% Matrigel® (BD Biosciences, San Jose, Calif.) at a concentration of 2×108 cells/mL. Each test mouse received 0.1 mL cell suspension (2×107 cells) subcutaneously implanted in the right flank. MKL-1 and MS-1 tumors were allowed to grow for 14 days until they attained respective mean tumor volumes of ~63 mm3 and ~45 mm3. MKL-1 tumor bearing mice were then randomized into two groups of eight mice each with mean tumor volumes of 63.0±12.4 mm3 and 62.9±12.4 mm3. MS-1 tumor bearing mice were randomized into two groups of eight mice with mean tumor volumes of 43.4±9.7 mm3 and 48.1±15.9 mm3. The day of randomization was denoted as Day −3 and dosing was initiated on Day 1 according to the pre-determined regimen shown in Table 18.

TABLE 18

Treatment Plan for MKL-1 or MS-1

Treatment Regimen

| Group | n | Agent | Dose (mg/kg) | Route | Schedule |
|---|---|---|---|---|---|
| 1 | 8 | Vehicle | — | PO | 5 on/2 off |
| 2 | 8 | Compound A | 5 | PO | 5 on/2 off | n = number of animals;
PO = oral dosing;
5 on/2 off = dosing for five days followed by two days with no dosing;
— = no test-article administration.
A dosing volume of 10 mL/kg was scaled to the weight of individual animals and Compound A dosed as mg/kg free base equivalents.

As shown in Table 18, control mice received aqueous 0.5% methylcellulose vehicle administered orally (PO) for 5 on/2 off, repeated to study end. A Compound A monotherapy group received 5 mg/kg Compound A, PO, 5 on/2 off. The test article Compound A was prepared daily as the benzenesulfonate salt (74% active compound) suspended in vehicle and dosed as mg/kg free base equivalents. In all groups, a dosing volume of 10 mL/kg was scaled to the weight of individual animals.

Individual tumors were measured twice weekly in three dimensions using a caliper, and the tumor volumes (TV) in mm3 were calculated using the formula: TV=0.5×l×w×h, where l, w, and h are the length, width, and height in millimeters, respectively. The tumor volume endpoint for these studies was 2000 mm3. At the same time, animals were weighed and each individual animal's health status was monitored for body weight loss and for signs of lethargy by means of a physical examination.

When an animal exited the study having attained the tumor volume endpoint, the final tumor volume recorded for the animal was included with the data used to calculate the mean volume at subsequent time points. Tumor growth curves were plotted showing group mean tumor volumes (±standard error of the mean [SEM]) as a function of time and mean body weights were plotted as the percentage change from Day 1.

Using the respective readouts in each test well, the number of viable cells was normalized to the mean number of viable cells in the wells treated with DMSO and expressed as a percent. The percent viable cells were plotted against the corresponding Compound A concentration and the IC50 value was determined from a four parameter logistics (4PL) non-linear regression curve generated by the IDBS XLfit program add-in for Microsoft Excel using equation 251 (ID Business Solutions Ltd., UK). The IC50 value was computed as the concentration where inhibition was half-maximal. The inhibition assays for each cell line were performed as four to six biological replicates and the IC50±standard deviation (SD) was reported.

In the MKL-1 and MS-1 studies, respective TGI analyses were performed on Day 15 and Day 36, the first day one or more control animals attained endpoint. Percent TGI was calculated using median tumor volumes according to the following formula:

$$TGI_x \, [\%] = \left(1 - \frac{T_x - T_0}{C_x - C_0}\right) \times 100$$

where $T_0$ and $C_0$ are the respective median tumor volumes in treated and control groups prior to the start of dosing (Day −3) and $T_x$ and $C_x$ are the corresponding median tumor volumes on Day "x", the day of TGI analysis.

Individual tumor volumes on the day of TGI analysis were corrected for their volumes prior to the start of dosing, and the resulting net tumor volumes for each group were graphed on a Box and Whiskers plot. The differences in the net tumor volume distributions for treated versus control animals were evaluated statistically using a t-test. Calculated probability (p)≤0.05 was considered statistically significant. The t-test is a test of statistical significance and does not provide an estimate of the size of the difference between groups or a measure of clinical or biological significance.

Figure 17:
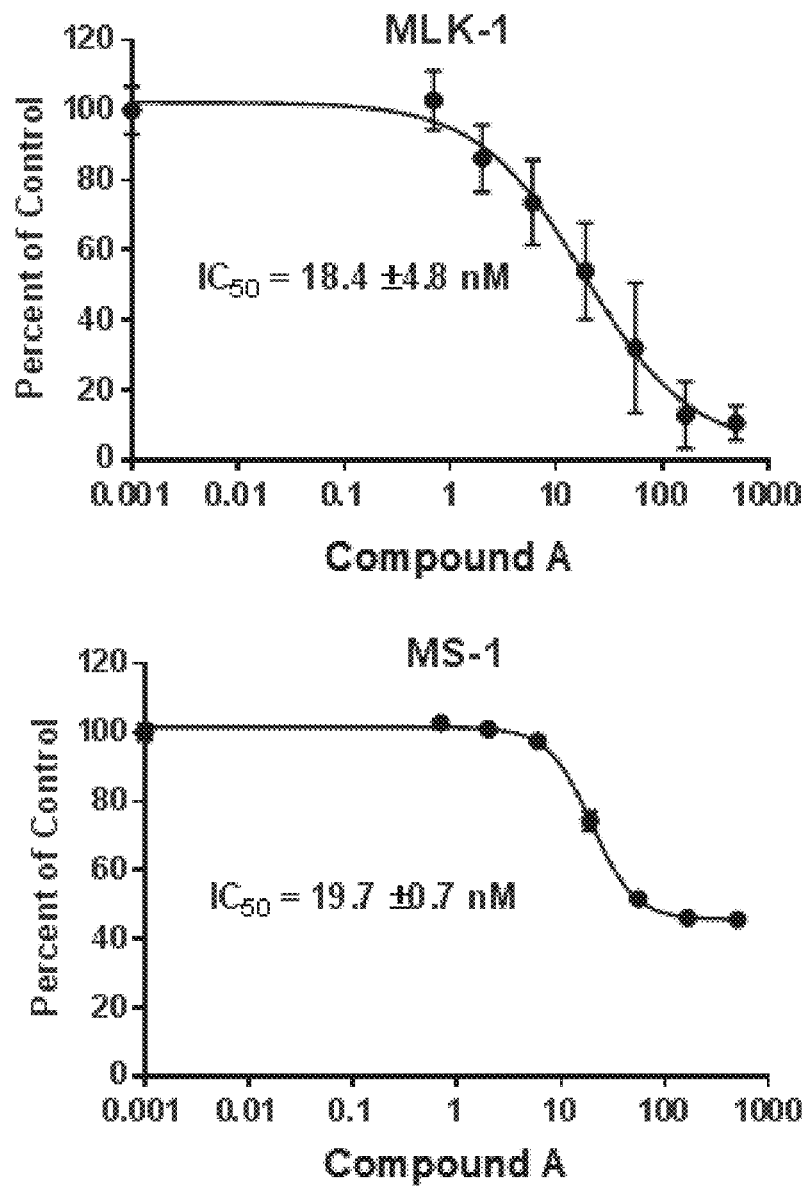
FIG. 17 is a graph showing proliferation inhibition for hMCC cell lines with Compound A. Percent of Control=number of viable Compound A-treated cells normalized to the mean number of viable negative control cells, expressed as a percent, as described in the data analysis section; For each graph, data are presented as the mean percent of control±standard deviation for the biological replicates.

Experimentally determined IC50 values for the 2D cell proliferation inhibition assays are summarized in Table 19. The IC50 values for the MKL-1 and MS-1 hMCC cell lines were measured over the concentration range of 0.0 to 500 nM Compound A and were determined from the resulting titration curves using 4PL non-linear regression. Assays included a DMSO negative control that established the baseline for 100% cell proliferation. As shown in Table 18 and FIG. 17, Compound A yielded respective IC50±SD values of 18.4±4.8 nM and 19.7±0.7 nM for cultured MKL 1 and MS-1 cell lines assayed in the 2D format.

TABLE 19

Half-maximal Inhibition for hMCC Cell Proliferation.

| Cell Line | IC$_{50}$ (nM) | SD | [n] |
|---|---|---|---|
| MKL-1 | 18.4 | 4.8 | 6 |
| MS-1 | 19.7 | 0.7 | 4 |

IC$_{50}$ = half-maximal inhibitory concentration;
[n] = number of biological replicates;
SD = standard deviation Test animals in this study were treated in accordance with the protocol in Table 18 and TGI analyses for the MKL-1 and MS-1 studies were performed on Day 15 and Day 36, respectively, the first day one or more control animals attained endpoint.

Figure 18:
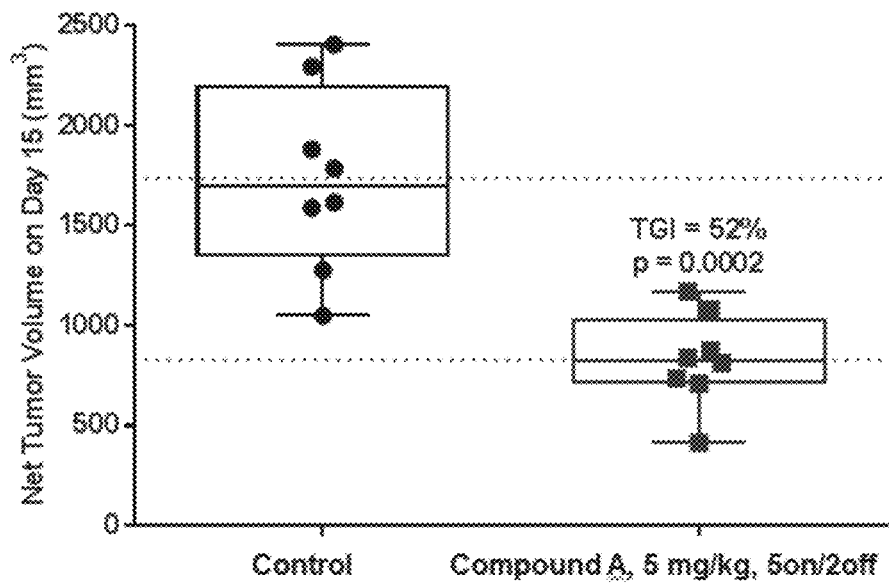
FIG. 18 is a graph showing MKL-1 net tumor volumes on Day 15. Symbols represent net tumor volumes. Percent (%) TGI and statistical outcome are shown for the difference in mean net tumor volumes between the Compound A treated and vehicle control groups as shown by the dotted lines.
Figure 19:
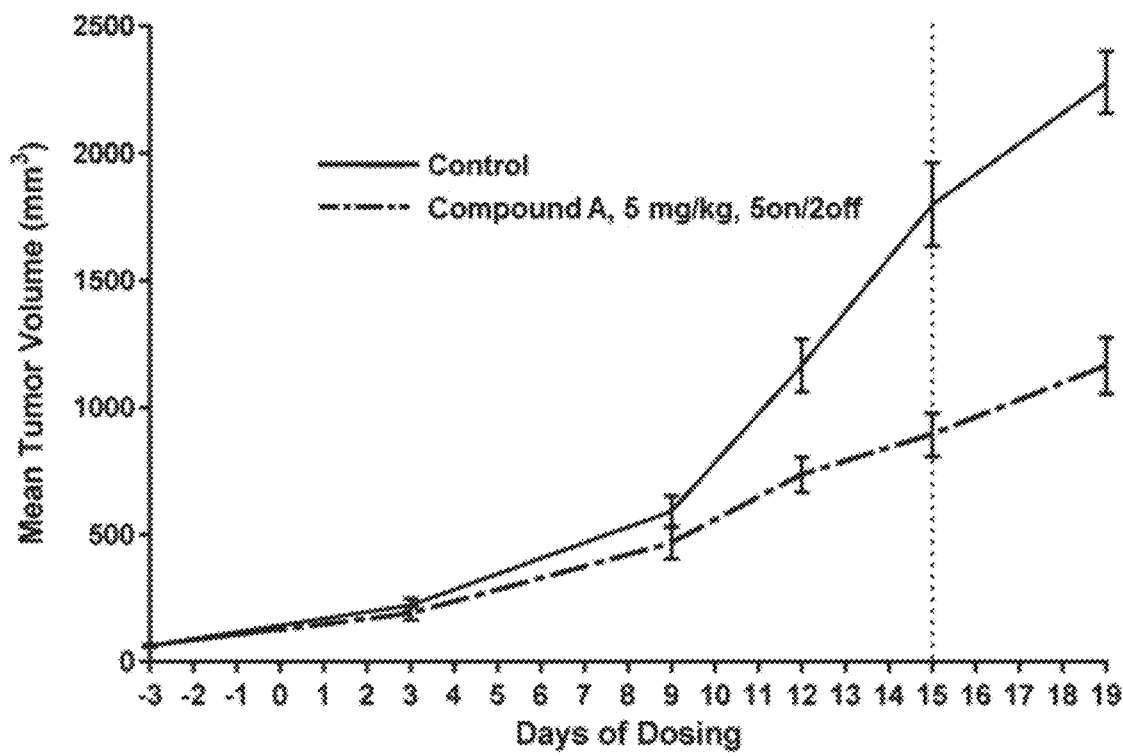
FIG. 19 is a graph showing MKL-1 mean tumor growth. Tumor volumes plotted as mean±standard error (SEM). A vertical dotted line is shown at Day 15, the day of TGI analysis.
Figure 20:
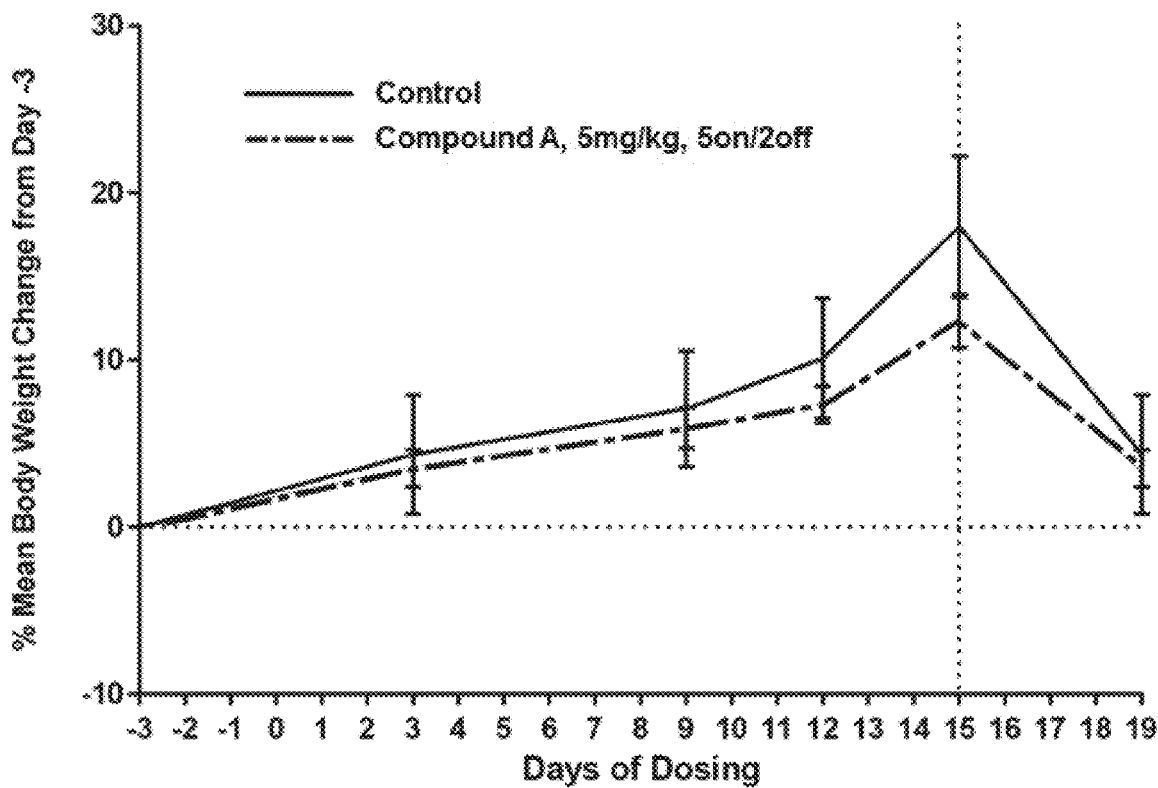
FIG. 20 is a graph showing percent mean body weight change for MKL-1. Body weights plotted as % mean±standard error (SEM). A vertical dotted line is shown at Day 15, the day of TGI analysis, and a horizontal dotted line at 0% mean body weight change.

As shown in Table 20, Compound A monotherapy was efficacious in vivo in the MKL-1 hMCC model resulting in tumor growth inhibition of 52% on Day 15. As shown in FIG. 18, the difference in mean net tumor volumes on Day 15 for treated vs. vehicle control animals was significant (p=0.0002). Mean tumor growth progressed steadily in the control group, as seen in FIG. 19. In the Compound A monotherapy group, mean tumor progression was somewhat slower compared to that observed in the control. As shown in FIG. 20, the groups that received vehicle or Compound A monotherapy exhibited progressive mean body weight gains until Day 15 of the study after which both groups showed a similar decrease in net body weight gain.

TABLE 20

TGI Response Summary for MKL-1

| Group | n | Treatment Regimen | Median Tumor Volumes (mm³) | | | Statistical |
|---|---|---|---|---|---|---|
| | | | Day-3 | Day 15 | Diff | % TGI | Significance (p) |
| 1 | 7 | Vehicle | 65 | 1767 | 1702 | — | — |
| 2 | 8 | 5 mg/kg Compound A 5 on/2 off | 65 | 880 | 815 | 52% | 0.0002 |

TGI = tumor growth inhibition;
Diff = difference;
n = number of animals;
5 on/2 off = dosing for five days followed by two days with no dosing;
— = not applicable.
A dosing volume of 10 mL/kg was scaled to the weight of individual animals and Compound A dosed as mg/kg free base equivalents;
p-value calculated using a t-test.

Figure 21:
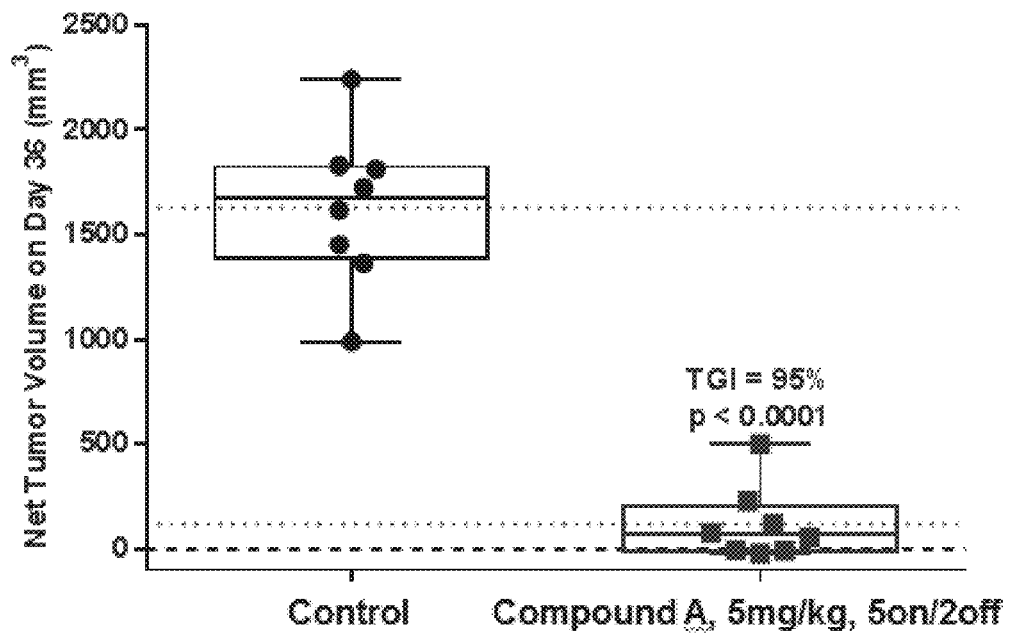
FIG. 21 is a graph showing MS-1 net tumor volumes on Day 36. Symbols represent net tumor volumes with a horizontal dashed line at 0 mm$^3$ net tumor volume. Percent (%) TGI and statistical outcome are shown for the difference in mean net tumor volumes between the Compound A treated and vehicle control groups as shown by the dotted lines.
Figure 22:
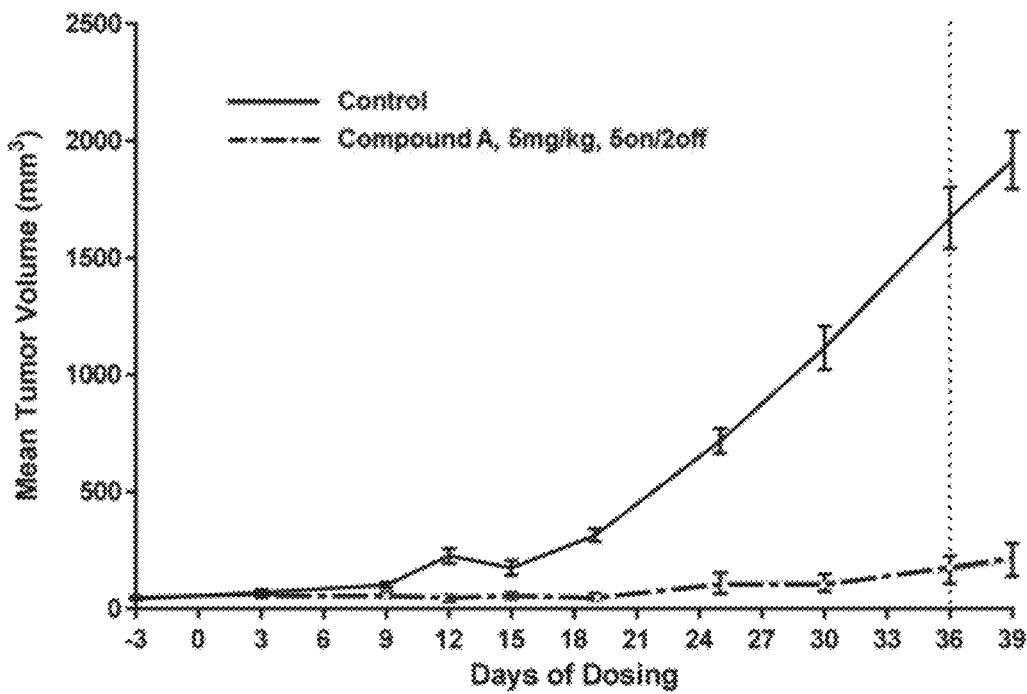
FIG. 22 is a graph showing MS-1 mean tumor growth. Tumor volumes plotted as mean±standard error (SEM). A vertical line is shown at Day 36, the day of TGI analysis.
Figure 23:
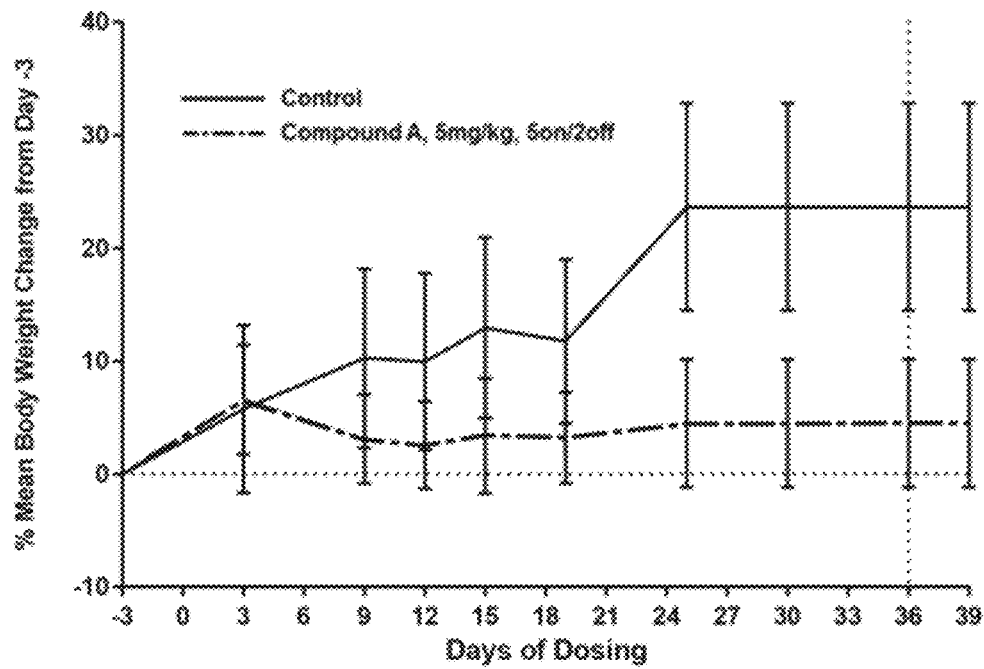
FIG. 23 is a graph showing percent mean body weight change for MS-1. Body weights plotted as % mean±standard error (SEM). A vertical dotted line is shown at Day 36, the day of TGI analysis, and a horizontal dotted line at 0% mean body weight change.

As shown in Table 21, Compound A monotherapy was efficacious in vivo in the MS-1 hMCC model resulting in tumor growth inhibition of 95% on Day 36. As shown in FIG. 21, the difference in mean net tumor volumes on Day 36 for treated vs. vehicle control animals was significant (p<0.0001). Mean tumor growth progressed rapidly in the control group, as seen in FIG. 6. In the Compound A monotherapy group, mean tumor progression was nearly static through Day 18 then gradually increased. Three Compound A treated tumors initially regressed and two rebounded on Day 25 as illustrated in the inset to FIG. 22. As shown in FIG. 23, the groups that received vehicle or Compound A monotherapy exhibited mean body weight gains over the course of the study.

TABLE 21

TGI Response Summary for MS-1

| Group | n | Treatment Regimen | Median Tumor Volumes (mm³) | | | Statistical |
|---|---|---|---|---|---|---|
| | | | Day-3 | Day 36 | Diff | % TGI | Significance (p) |
| 1 | 7 | Vehicle | 44 | 1723 | 1679 | — | — |
| 2 | 8 | 5 mg/kg Compound A 5 on/2 off | 49 | 129 | 80 | 95% | <0.0001 |

TGI = tumor growth inhibition;
Diff = difference;
n = number of admals;
5 on/2 off = dosing for five days followed by two days with no dosing;
— = not applicable.
A dosing volume of 10 mL/kg was scaled to the weight of individual animals and Compound A dosed as mg/kg free base equivalents;
p-value calculated using a t-test.

In cell proliferation inhibition assays performed in vitro, Compound A demonstrated potent activity in cultured MKL-1 and MS-1 cell lines yielding respective IC50±SD values of 18.4±4.8 nM and 19.7±0.7 nM.

Compound A monotherapy was efficacious in vivo in the MKL-1 hMCC model resulting in tumor growth inhibition of 52% and a significant difference in mean net tumor volumes on Day 15 for treated vs. vehicle control animals (p=0.0002). In the Compound A monotherapy group, mean tumor progression was somewhat slower compared to that observed in the control.

Compound A monotherapy was efficacious in vivo in the MS-1 hMCC model resulting in tumor growth inhibition of 95% and a significant difference in mean net tumor volumes on Day 36 for treated vs. vehicle control animals (p<0.0001). In the Compound A monotherapy group, mean tumor progression was nearly static through Day 18 then gradually increased.

Groups that received vehicle or Compound A monotherapy exhibited mean body weight gains over the course of these studies. Compound A was considered acceptably tolerated in the MKL-1 and MS-1 xenograft studies.

Example 15. In Vitro and In Vivo Effect of Compound A on Pharmacodynamic Biomarkers in Merkel Cell Carcinoma Human Merkel Cell Carcinoma is classified as an aggressive cutaneous neuroendocrine tumor that expresses LSD1. These tumors are more accessible than SCLC tumors and may prove useful for PD efforts in human studies. Effective hMCC treatment is a highly unmet need that could offer an additional indication for Compound A.

In the present non-Good Laboratory Practice (GLP) preclinical study, modulation of human mRNA expression, following LSD1 inhibition by Compound A, was evaluated in two hMCC models MKL-1 and MS-1 in vitro as cell cultures and in vivo as xenografts using RNA-seq and qRT-PCR. In addition, direct binding of LSD1 to the ST18 and FREM2 gene loci and changes in H3K4me2 status upon Compund A treatment was investigated in the MKL-1 and MS-1 cell lines using ChIP-seq.

The purpose of this study was to determine the effect of Compound A mediated inhibition of LSD1 on gene expression in vitro and in vivo in the human hMCC cell lines MKL-1 and MS-1. Additionally, the direct binding of LSD1 to the ST18 and FREM2 gene loci and changes in H3K4me2 status upon Compund A treatment was investigated in the MKL-1 and MS-1 cell lines using ChIP-seq.

For in vitro cell culture studies, Compund A stock solutions were prepared in dimethylsulfoxide (DMSO) and serially diluted in culture medium. For in vivo xenograft studies, Compound A was suspended in 0.5% methylcellulose in water and administered at a dosing volume of 10 mL/kg.

MKL-1 hMCC cells were cultured in vitro in RPMI-1640 culture medium (Life Technologies, Carlsbad, Calif.) containing 100 units/mL penicillin G sodium and 100 μg/mL streptomycin sulfate (cRPMI) supplemented with 10% fetal bovine serum (FBS). MS-1 hMCC cells were cultured in vitro in cRPMI supplemented with 20% FBS. Both cell lines were cultured in a humidified incubator at 37° C., in an atmosphere of 5% carbon dioxide and 95% air.

The modulation of gene expression by Compund A for a panel of human genes was determined by culturing MKL-1 or MS-1 cells (Sigma-Aldrich, St. Louis, Mo.) for three days in the presence of 0, 10, or 100 nM Compund A and extracting total RNA for assessment by RNA-seq. Genes that were downregulated or upregulated in both hMCC lines at both concentrations were further evaluated. Then, genes that exhibited dose-dependent gene expression changes of at least two fold in both hMCC lines at both concentrations were identified as candidate PD biomarker genes.

Next, the candidate PD biomarker genes were further evaluated in follow-on studies. In an in vitro study, the EC50 values for Compund A modulation of gene expression were determined for the candidate PD biomarker genes in cultured MKL-1 or MS-1 cell lines using qRT-PCR. In an in vivo xenograft dose-response study, female non-obese diabetic severe combined immune deficiency (NOD-SCID) gamma (NSG) mice bearing palpable MKL-1 or MS-1 tumors were orally administered vehicle or Compund A monotherapy at 1, 2.5, or 5 mg/kg twice daily (BID) for five days. Four hours after receiving the last dose, tumors were collected and total RNA was extracted for qRT-PCR assessment of changes in gene expression for the candidate PD biomarkers. In a final study, candidate PD biomarkers were analyzed by ChIP-seq for LSD1 occupancy and changes in H3K4me2 status in the presence of Compound A.

From these analyses, genes that exhibited EC50 values that correlated with the IC50 values for Compund A inhibition of cell proliferation, a strong correlation between in vitro and in vivo dose response, and LSD1 occupancy and H3K4me2 modulation in the presence of Compound A were identified as potential PD biomarkers for Compund A inhibition of LSD1 in the hMCC model.

The RNA-seq and qRT-PCR assays were performed in triplicate in multi-well culture plates seeded with MKL-1 or MS-1 cells suspended in cRPMI supplemented with 10% or 20% FBS, respectively. Compund A was diluted in DMSO and then subsequently diluted again into supplemented cRPMI to make stock solutions. Each test well received an aliquot of DMSO, as a vehicle control, or Compund A to give final concentrations of Compund A at 0, 10, or 100 nM for RNA-seq analysis or at 0, 2.5, 7.4, 22, 66, or 200 nM for qRT-PCR analysis. The culture plates were incubated for 3 days in a humidified incubator at 37° C., in an atmosphere of 5% CO2 and 95% air. After the incubation period, the cultured MKL-1 or MS-1 cells were harvested and total RNA was purified using the RNeasy Mini Kit (QIAGEN, Valencia, Calif.) in accordance with the manufacturer's instructions.

Female NSG mice bearing palpable hMCC MKL-1 and MS-1 tumors were randomized into four groups of three mice each. Three groups were orally administered Compund A as monotherapy at 1, 2.5, or 5 mg/kg on a twice daily dosing schedule for nine doses (BID×4.5). The fourth group was orally administered vehicle as a control on the BID schedule. Four hours after the last dosing, tumors were collected into RNAlater and stored frozen.

Tumor samples were thawed and total RNA was purified using the RNeasy Mini Kit in accordance with the manufacturer's instructions. Residual deoxyribonucleic acid (DNA) was removed using an on-column DNase treatment with the RNase Free DNase Set (QIAGEN, Valencia, Calif.) in accordance with the manufacturer's instructions. Total RNA was eluted in RNase-free water and analyzed by qRT-PCR.

Purified total RNA (1 μg) extracted from treated and control MKL-1 or MS-1 cultured cells was converted into sequencing libraries using the KAPA Stranded mRNA-Seq Kit for the Illumina® platform (Kapa Biosystems, Wilmington, Mass.) in accordance with the manufacturer's instructions. Libraries were sequenced on an Illumina Next-Seq® 500 System (Illumina, San Diego, Calif.) using 75 base paired-end RNA sequencing. Sequenced reads were mapped to the hg19 human genome build and differential expression was determined by analysis of variance across all replicates relative to the vehicle control.

Complementary (c) DNA was generated from purified total RNA extracted from treated and control MKL-1 or MS-1 cultured cells or tumor samples in a reverse transcription reaction using the High-Capacity cDNA Reverse Transcription Kit (Life Technologies, Grand Island, N.Y.) in accordance with the manufacturer's instructions. A 1.5× reverse transcription master mix containing deoxyribonucleotides, random primers, reverse transcriptase, RNase inhibitor, and reverse transcription buffer was prepared and 20 μL was added to each test well of a 96-well multiwell plate. Each test well then received 10 μL of total RNA, and the multiwell plate was sealed to prevent evaporation. Reverse transcription was performed in a T100™ Thermal Cycler (Bio-Rad, Hercules, Calif.) programmed using optimized parameters provided by the kit manufacturer.

Expression levels of mRNA in response to Compound A treatment were measured in duplicate by qPCR. TaqMan® qPCR was performed on cDNA made from total RNA extracted from treated and control MKL-1 or MS-1 cultured cells or tumor samples using primer sets for the human genes ST18, FREM2, and actin beta (ACTB), as a reference sequence for normalizing the absolute readout for the target genes. Total levels of mRNA transcript were normalized to the ACTB reference transcript. Changes in mRNA expression were quantified by calculating the fold changes in gene expression following Compound A treatment relative to the vehicle-treated control.

ChIP-seq assays were performed with MKL-1 or MS-1 cells grown in suspension in cRPMI supplemented with 10% or 20% FBS, respectively. Compund A was diluted in DMSO and then subsequently diluted again into supplemented cRPMI to make a stock solution. Each test well received an aliquot of DMSO, as a vehicle control, or Compund A to give final concentrations of Compund A at 0 or 100 nM. The culture plates were incubated for 3 days in a humidified incubator at 37° C., in an atmosphere of 5% CO2 and 95% air. After the incubation period, the cultured MKL-1 or MS-1 cells were harvested and cross-linked at ambient temperature by the addition of one-tenth volume of a fresh 11% formaldehyde solution to each well followed by incubation for 20 minutes. The cross-linking reaction was quenched by the addition of 1/20 volume of 2.5 M glycine. Then, cross-linked cells were harvested and rinsed twice with ice-cold phosphate buffered saline (PBS). Cells were pelleted by centrifugation and aliquots containing 6×106 MS 1 cells or 4.5×106 MKL-1 cells were flash frozen in liquid nitrogen, and stored at −80° C.

Frozen cell pellets containing formaldehyde-fixed cells were lysed and sonicated to solubilize and shear cross-linked chromatin (Bioruptor®, Diagenode, Denville, N.J.). Chromatin was prepared using the iDeal ChIP-seq Kit for Transcription Factors (Diagenode, Denville, N.J.) according to manufacturer's instructions. LSD1 associated chromatin was immunoprecipitated with anti-LSD1 antibody (Abcam, Cambridge, Mass.) using the iDeal ChIP-seq Kit for Transcription Factors. H3K4me2 associated chromatin was immunoprecipitated with H3K4me2 polyclonal antibody (Millipore, Billerica, Mass.) using iDeal ChIP-seq Kit for Histones (Diagenode, Denville, N.J.). Chromatin prepared from each sample but not subjected to any immunoprecipitation was used as input controls and processed in parallel to ChIPed samples. Each sample was treated for cross-link reversal and DNA was purified by treatment with RNAse A, proteinase K and phenol: chloroform:isoamyl alcohol extraction followed by ethanol precipitation. ChIP libraries were prepared using the MicroPlex Library Preparation Kit v2 (Diagenode, Denville, N.J.) according to manufacturer's instructions. ChIP libraries were size selected using AMpure XP beads (Beckman Coulter, Indianapolis, Ind.) according to manufacturer's instructions prior to being sequenced on an Illumina NextSeq® 500 System using single-end read lengths of 75 bases.

Sequenced reads were mapped to the hg19 human genome build using the Spliced Transcripts Alignment to a Reference (STAR) software tool (©Alexander Dobin, 2009-2016) and transcript counts were normalized using the Empirical Analysis of Digital Gene Expression Data in R (edgeR) and Differential gene expression analysis based on the negative binomial distribution (DESeq2) software tools (©Bioconductor, 2003-2017). Differential expression was determined by analysis of variance across all replicates relative to the vehicle control.

In qPCR expression analysis, the cycle threshold (Ct) is defined as the number of cycles required for the PCR signal to exceed background. Delta Ct (ΔCt) corresponds to the Ct value of the ST18 or FREM2 target gene normalized to the Ct value of the ACTB reference sequence, where $$\Delta Ct_{target} = CT_{target} - Ct_{ACTB}.$$

Quantitation of relative target expression was computed by the comparative Ct method. The comparative Ct method involved calculating the difference between the ΔCttarget for each treated and control sample and the mean ΔCttarget for the control sample as shown below:

$$\Delta\Delta Ct_{target} = \Delta Ct_{target,treated\ or\ control} - \text{mean } \Delta Ct_{target, control}.$$

The fold change, calculated as 2-ΔΔCt, in target mRNA expression versus Compund A concentration (relative to the control) was calculated for each Compund A concentration tested. Then, the EC50 was determined from a 4PL non-linear regression curve fitted to that data using the IDBS XLfit program add-in for Microsoft Excel and equation 251 (ID Business Solutions Ltd., UK).

ChIP library sequences were aligned to the hg19 human genome build using Bowtie 2 short read alignment software (Langmead, 2012). Enriched or "bound" regions for LSD1 or H3K4me2 in MKL-1 or MS-1 cells were determined relative to background reads from the whole cell extract sample. Only reads passing the Illumina mapping quality (MAPQ) filter with scores of at least 20 were used for subsequent analysis. Reads originating from PCR duplicates were removed using the Picard MarkDuplicates tool (http://broadinstitute.github.io/picard, Broad Institute, Cambridge, Mass.). The number of reads per ChIP-seq was normalized between the control and treated samples by random down-sampling to the total number of reads from the sample with the minimal number of reads. ChIP peaks were called using Model-based Analysis of ChIP-seq (MACS) (http://liulab.dfci.harvard.edu/MACS/; Zhang, 2008). Genome coverage tracks were generated using the deepTools bamCoverage tool (http://deeptools.readthedocs.io/en/latest/content/tools/bamCoverage.html; Ramirez, 2016). Integrative genomics viewer IGV (http://software.broadinstitute.org/software/igv/; Robinson, 2011; Thorvaldsdóttir, 2013) was used to visualize ChIP-seq tracks.

Figure 24:
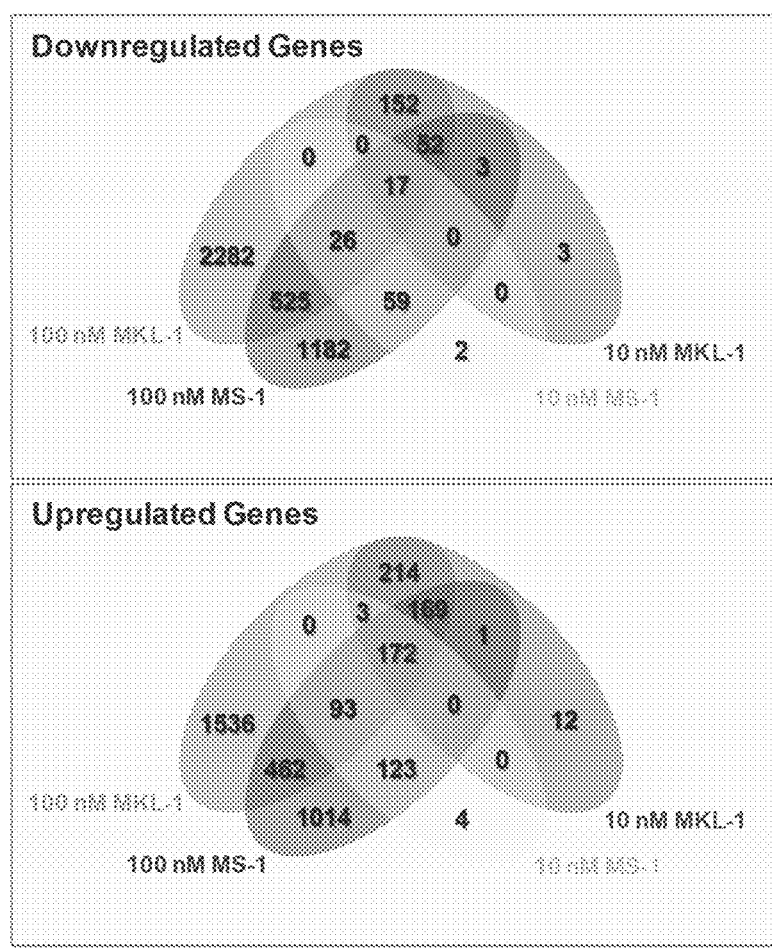
FIG. 24 is a graph showing Compound A modulation of gene expression as identified by RNA-seq. Venn Diagrams showing the genes downregulated (top) or upregulated (bottom) in response to 10 nM and/or 100 nM Compound A in two hMCC cell lines MKL-1 and MS-1.

The modulation of gene expression by Compund A for a panel of human genes was determined by culturing MKL-1 or MS-1 cells for three days in the presence of 0, 10, or 100 nM Compund A and extracting total RNA for assessment by RNA-seq. As shown in FIG. 24, 17 of 4303 downregulated genes (Table 22) and 172 of 3803 upregulated genes (Table 23) exhibited gene expression changes in both hMCC lines at both concentrations.

TABLE 22

| | Symbol | Description |
|---|---|---|
| | \multicolumn{2}{c}{Downregulated genes identified by RNA-Seq.} | |
| 1 | CRYBG3 | Crystallin Beta-Gamma Domain Containing 3 |
| 2 | ADRA2B | Adrenoceptor Alpha 2B |
| 3 | AHNAK | AHNAK Nucleoprotein |
| 4 | CD44 | CD44 Molecule (Indian Blood Group) |
| 5 | CDKN1C | Cyclin Dependent Kinase Inhibitor 1C |
| 6 | CNPY1 | Canopy FGF Signaling Regulator 1 |
| 7 | FBLN7 | Fibulin 7 |
| 8 | KCNH5 | Potassium Voltage-Gated Channel Subfamily H Member 5 |
| 9 | MARVELD3 | MARVEL Domain Containing 3 |
| 10 | MEGF10 | Multiple EGF Like Domains 10 |
| 11 | NID1 | Nidogen 1 |
| 12 | PKHD1L1 | Polycystic Kidney And Hepatic Disease 1 (Autosomal Recessive)-Like 1 |
| 13 | PLD5 | Phospholipase D Family Member 5 |
| 14 | RASSF6 | Ras Association Domain Family Member 6 |
| 15 | SEMA3E | Semaphorin 3E |
| 16 | T | T Brachyury Transcription Factor |
| 17 | ZNF215 | Zinc Finger Protein 215 |

TABLE 23

Upregulated genes identified by RNA-Seq.

| | Symbol | Description |
|---|---|---|
| 1 | ABLIM1 | Actin Binding LIM Protein 1 |
| 2 | AC079354.1 | Uncharacterized protein KIAA2012 |
| 3 | ACVR1 | Activin A Receptor Type 1 |
| 4 | ACVR2A | Activin A Receptor Type 2A |
| 5 | AIM1 | Absent In Melanoma 1 |
| 6 | AMER2 | APC Membrane Recruitment Protein 2 |
| 7 | AMOTL2 | Angiomotin Like 2 |
| 8 | ANK3 | Ankyrin 3 |
| 9 | ANTXR1 | Anthrax Toxin Receptor 1 |
| 10 | ARHGEF26 | Rho Guanine Nucleotide Exchange Factor 26 |
| 11 | ARPP21 | CAMP Regulated Phosphoprotein 21 |
| 12 | ATOH8 | Atonal BHLH Transcription Factor 8 |
| 13 | AUTS2 | Autism Susceptibility Candidate 2 |
| 14 | B3GALT5 | Beta-1,3-Galactosyltransferase 5 |
| 15 | BACH2 | BTB Domain And CNC Homolog 2 |
| 16 | BASP1 | Brain Abundant Membrane Attached Signal Protein 1 |
| 17 | BCL11A | B-Cell CLL/Lymphoma 11A |
| 18 | BICD1 | BICD Cargo Adaptor 1 |
| 19 | BRINP2 | BMP/Retinoic Acid Inducible Neural Specific 2 |
| 20 | C11orf87 | Chromosome 11 Open Reading Frame 87 |
| 21 | CA10 | Carbonic Anhydrase 10 |
| 22 | CACNA2D1 | Calcium Voltage-Gated Channel Auxiliary Subunit Alpha2delta 1 |
| 23 | CADM1 | Cell Adhesion Molecule 1 |
| 24 | CADPS | Calcium Dependent Secretion Activator |
| 25 | CAMK4 | Calcium/Calmodulin Dependent Protein Kinase IV |
| 26 | CAMSAP2 | Calmodulin Regulated Spectrin Associated Protein Family Member 2 |
| 27 | CBLB | Cbl Proto-Oncogene B |
| 28 | CDC14B | Cell Division Cycle 14B |
| 29 | CDC42EP3 | CDC42 Effector Protein 3 |
| 30 | CDH10 | Cadherin 10 |
| 31 | CDH11 | Cadherin 11 |
| 32 | CDHR1 | Cadherin Related Family Member 1 |
| 33 | CLIP3 | CAP-Gly Domain Containing Linker Protein 3 |
| 34 | CLVS1 | Clavesin 1 |
| 35 | CMIP | C-Maf Inducing Protein |
| 36 | CNN3 | Calponin 3 |
| 37 | COL1A2 | Collagen Type 1 Alpha 2 Chain |
| 38 | CRB1 | Crumbs 1, Cell Polarity ComplexComponent |
| 39 | CREB5 | CAMP Responsive Element Binding Protein 5 |
| 40 | CRISPLD2 | Cysteine Rich Secretory Protein LCCL Domain Containing 2 |
| 41 | CTTNBP2NL | CTTNBP2 N-Terminal Like |
| 42 | CYP27C1 | Cytochrome P450 Family 27 Subfamily C Member 1 |
| 43 | DCN | Decorin |
| 44 | DCX | Doublecortin |
| 45 | DFNA5 | DFNA5, Deafness Associated Tumor Suppressor |
| 46 | DISP1 | Dispatched RND Transporter Family Member 1 |
| 47 | DLL1 | Delta Like Canonical Notch Ligand 1 |
| 48 | DNAJB5 | DnaJ Heat Shock Protein Family (Hsp40) Member B5 |
| 49 | DYNC1I1 | Dynein Cytoplasmic 1 Intermediate Chain 1 |
| 50 | EBF2 | Early B-Cell Factor 2 |

Upon further evaluation, two upregulated genes, ST18 and FREM2, that exhibited dose-dependent gene expression changes of at least 2-fold in both hMCC lines at both concentrations were identified as candidate PD biomarker genes, as shown in Table 24. ST18 has been shown to act as a tumor suppressor in breast cancer (Jandrig, 2004) and to regulate pro-apoptotic and pro-inflammatory gene expression in fibroblasts (Yang, 2008). Distal metastases occur frequently in patients diagnosed with lung adenocarcinoma. A recent study demonstrated that FREM2 regulated the migration and invasion rather than proliferation of the non-small cell lung cancer A549 cell line through down-regulation of focal adhesion kinase signaling (Zhan, 2014).

TABLE 24

Candidate Pharmacodynamic Biomarker Genes

| | Gene | Description |
|---|---|---|
| Up_Reg | ST18 | ST18, C2H2C-Type Zinc Finger |
| | FREM2 | FRAS1 Related Extracellular Matrix Protein 2 |

Up_Reg = upregulated

Figure 25:
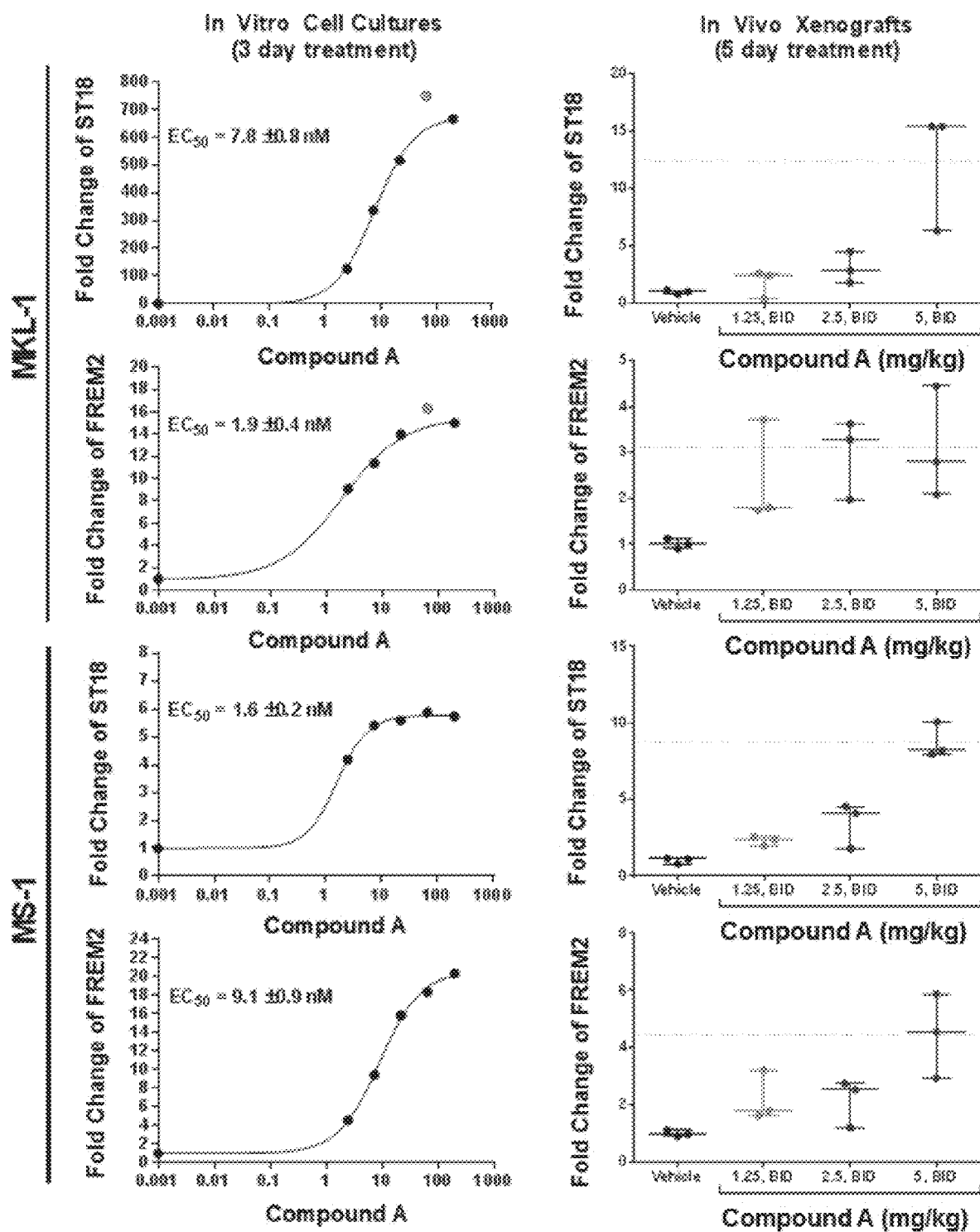
FIG. 25 is a graph showing Compound A dose response of pharmacodynamic biomarker gene expression in vitro and in vivo. Titration curves showing dose response and EC50 values for in vitro cell cultures (left) where open circle symbols with an "x" are censored data points. The corresponding Box and Whisker plots showing in vivo dose response in xenograft studies (right). The dotted lines indicate the maximum mean responses.

As shown in FIG. 25, the EC50 values for Compund A modulation of gene expression were determined by qRT-PCR for the candidate PD biomarker genes in MKL-1 or MS-1 cell lines cultured for three days in the presence of 0, 2.5, 7.4, 22, 66, or 200 nM Compund A. ST18 and FREM2 exhibited EC50 values that correlated with the IC50 values for Compund A inhibition of cell proliferation in these cell lines (<20 nM, data not shown).

In the in vivo xenograft dose-response study, groups of three tumor bearing female NSG mice were PO administered vehicle or Compund A at 1, 2.5, or 5 mg/kg BID×4.5. Four hours after receiving the last dose, tumors were collected and total RNA was extracted for qRT-PCR assessment of changes in gene expression for the candidate PD biomarkers. As shown in FIG. 25, ST18 and FREM2 showed a ≥2-fold change in gene expression and exhibited dose-dependent response in vivo in both models.

Figure 26:
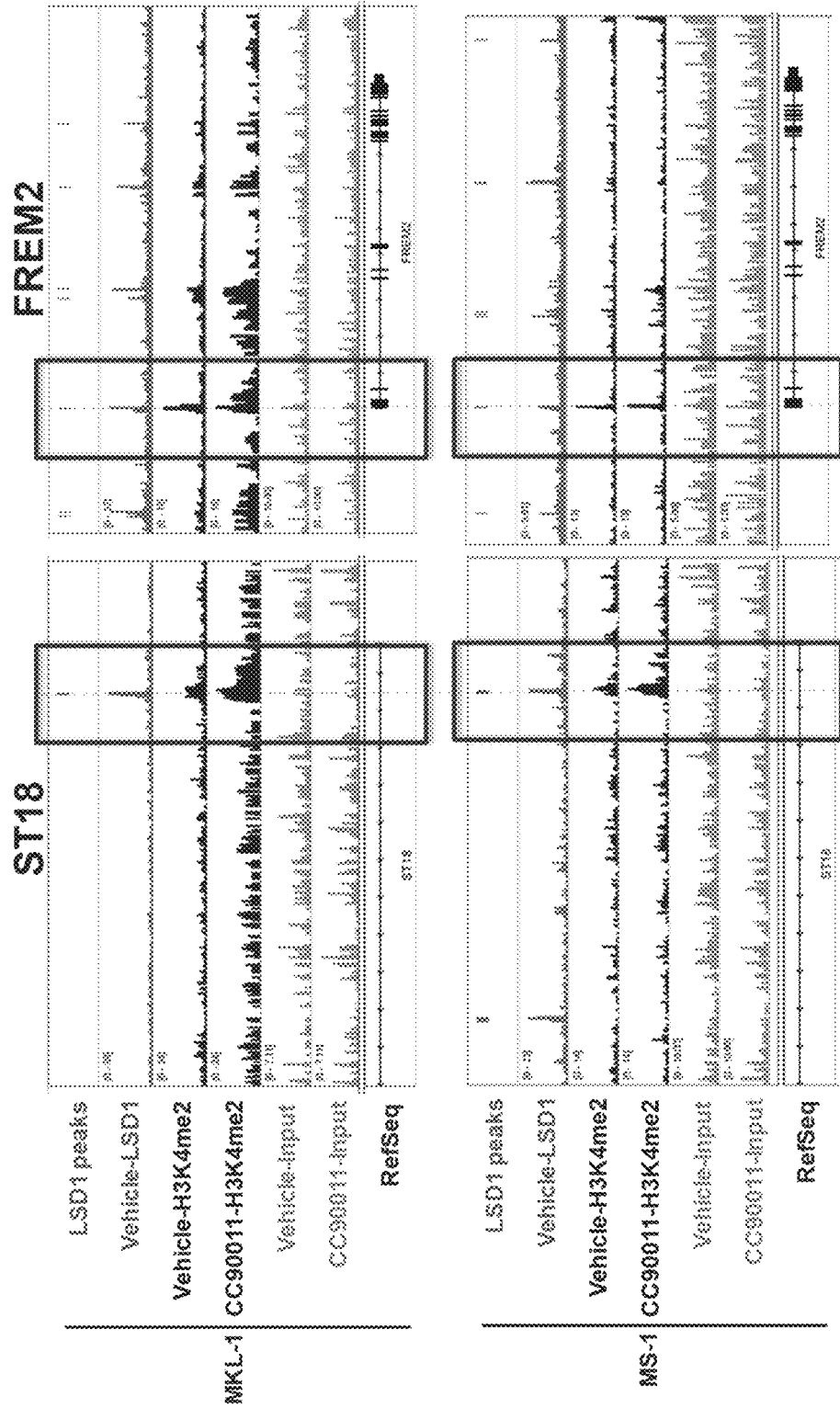
FIG. 26 is a graph showing ChIP-seq analysis of LSD1 occupancy and H3K4me2 status. Genome browser view of LSD1 and H3K4me2 enrichment at the ST18 and FREM2 genes in hMCC cell lines MKL-1 and MS-1. LSD1 peak track (green) demonstrates the location of the LSD1 enriched regions compared to background. H3K4me2 ChIP-seq tracks (blue) show H3K4me2 binding in vehicle or Compound A-treated samples. Input tracks are shown as control. RefSeq track denotes the location and direction of the genes.

As shown in FIG. 26, ChIP-seq analysis demonstrated LSD1 binding at the ST18 and FREM2 genes in cultured MKL-1 and MS-1 cells. Consistent with a LSD1-dependent modulation of H3K4 methylation in ST18 gene, Compund A treatment led to increased H3K4me2 at the LSD1 binding site in both MKL 1 and MS-1 models. In addition, Compund A treatment led to increased H3K4me2 at the LSD1 binding site at the FREM2 gene in the MKL-1 but in not the MS-1 model. These results are consistent with ST18, and potentially FREM2, as direct target genes of LSD1, supporting them as potential PD biomarkers for inhibition of LSD1 by Compund A in hMCC.

Modulation of mRNA expression following inhibition of LSD1 by Compund A was evaluated for a panel of genes in two hMCC models, MKL-1 and MS-1. Two genes ST18 and FREM2 were selected for further evaluation for the effect of Compund A mediated inhibition of LSD1 on in vitro and in vivo gene expression and for direct binding of LSD1 and LSD1-dependent modulation of H3K4 methylation at their gene loci in the MKL 1 and MS-1 models.

The modulation of gene expression by Compund A for a panel of human genes assessed by RNA-seq in cultured MKL-1 or MS-1 cells found that 17 of 4303 downregulated genes and 172 of 3803 upregulated genes exhibited expression changes in both hMCC lines at both concentrations. Upon further evaluation, two upregulated genes, ST18 and FREM2, that exhibited dose-dependent gene expression changes of at least 2-fold and were identified as candidate PD biomarker genes.

The EC50 values for Compund A modulation of ST18 and FREM2 gene expression were determined in cultured MKL-1 or MS-1 cell lines using qRT-PCR. Both genes exhibited EC50 values that correlated with the IC50 values for inhibition of cell proliferation in these cell lines by Compund A (<20 nM, data not shown).

In an in vivo xenograft dose-response study, the ST18 and FREM2 genes showed a ≥2-fold change in expression and exhibited dose-dependent response in both hMCC models.

ChIP-seq analysis demonstrated LSD1 binding at the ST18 and FREM2 gene loci in cultured MKL 1 and MS-1 cells. Consistent with a LSD1-dependent modulation of H3K4 methylation at the ST18 gene locus, Compund A treatment led to increased H3K4me2 at the LSD1 binding site in both models. In addition, Compund A treatment leads to increased H3K4me2 at the FREM2 gene's LSD1 binding site in the MKL-1 but not the MS-1 model. These results are consistent with ST18, and potentially FREM2, as direct target genes of LSD1, supporting them as potential PD biomarkers for inhibition of LSD1 by Compund A in hMCC.

Example 16. In Vivo Efficacy of Compound a Alone and in Combination with Etoposide in the Subcutaneous Small Cell Lung Cancer Patient-Derived Xenograft Model LXFS 573 in Female Nude Mice The in vivo efficacy and tolerability of Compund A alone and in combination with etoposide were evaluated preclinically using the subcutaneous small cell lung cancer (SCLC) patient-derived xenograft (PDX) model LXFS 573 established in female immunodeficient Foxn1nu mice. Efficacy was determined based on differences in tumor growth delay (TGD), study survival, and mean tumor growth for treated versus (vs.) control animals over the course of the study. Tolerability was assessed based on differences in mean body weights between treated and control animals.

LXFS 573 tumor fragments were obtained from xenografts in serial passage in nude mice. After removal from donor mice, tumors were cut into fragments (3 to 4 mm edge length) and placed in phosphate-buffered saline (PBS) containing 10% of a penicillin and streptomycin solution. Recipient female immunodeficient Foxn1nu mice were anesthetized by inhalation of isoflurane and received unilateral tumor implants subcutaneously in the flank. Tumors were allowed to grow for 35 days until they attained ~132 mm3. Tumor bearing mice were then randomized into six groups of eight mice with mean tumor volumes of 134.3±68.2 mm3, 130.7±68.9 mm3, 132.4±66.3 mm3, 133.1±64.9 mm3, 132.1±62.6 mm3, and 132.4±63.2 mm3. This day was denoted as Day 0 and dosing was initiated according to the pre-determined regimen shown in Table 25.

TABLE 25

Treatment Plan

| | | Treatment Regimen | | | |
|---|---|---|---|---|---|
| Group | N | Agent | Dose (mg/kg/day) | Route | Schedule (days) |
| 1 | 8 | Vehicle | — | PO | 1-133 |
| 2 | 8 | Compound A | 5 | PO | 1-133 |
|   |   | Etoposide | 24 | SC | 1-3 |
| 3 | 8 | Vehicle | — | PO | 4-133 |
| 4 | 8 | Etoposide | 24 | SC | 1-3 |
|   |   | Compound A | 1 | PO | 4-133 |
| 5 | 8 | Etoposide | 24 | SC | 1-3 |
|   |   | Compound A | 2.5 | PO | 4-133 |
| 6 | 8 | Etoposide | 24 | SC | 1-3 |
|   |   | Compound A | 5 | PO | 4-133 |

Vehicle dosed at 10 mL/kg and Compound A dosed as mg/kg free base equivalents;
PO = oral dosing;
SC = subcutaneous dosing.

Individual tumors were measured twice weekly in two dimensions using a caliper, and the tumor volumes (TV) in $mm^3$ were calculated using the formula: $TV=0.5\ a \times b^2$, where a and b are the long and short diameters in millimeters, respectively. Tumor growth curves plotted group mean tumor volumes (±standard error of the mean [SEM]) as a function of time. Multiple t tests, corrected for the number of comparisons, assessed the significance of the difference in mean tumor volumes at each time point for 5 mg/kg Compound A administered as monotherapy or in combination with etoposide. When an animal exited the study having attained the tumor volume endpoint (2000 $mm^3$) or was euthanized due to moribundity, the final tumor volume recorded for the animal was included with the data used to calculate the mean volume at subsequent time points. Animals were weighed twice each week and mean body weight plots as the percentage change from Day 0 were constructed. Both plots were truncated when more than 50% of the assessable animals in a group exited the study. A regimen was considered acceptably tolerated if the mean body weight loss was less than 20% during the test and no more than one animal exited the study due to treatment-related causes.

Each test animal was euthanized when its tumor reached the endpoint volume of 2000 mm³ or on the final day of the study (Day 133), whichever came first. The time-to-endpoint (TTE) for each mouse was calculated from the following equation:

$$TTE \text{ (days)} = \frac{\log_{10}(2000 \text{ mm}^3) - b}{m}$$

where b is the intercept and m is the slope of the line obtained by linear regression of a $\log_{10}$-transformed tumor volume composed of the first observation that exceeded 2000 mm³ and the three preceding measurements. Animals that did not reach endpoint were assigned a TTE value equal to the last day of the study. Animals euthanized as moribund were assigned a TTE value equal to their day of sacrifice.

Treatment outcome was determined from tumor growth delay (TGD), defined as the change in the median TTE in a treatment group compared to the vehicle control group:

TGD=T-C, expressed in days, or as a percentage of the median TTE of the vehicle control group:

$$\% TGD = \frac{T-C}{C} \times 100$$

where:
T=median TTE for a treatment group, and
C=median TTE for the vehicle control group.

Treatment efficacy was also determined from the SS(MTV) defined as the number of study survivors (SS) on Day 133 bearing tumors with the median tumor volume (MTV) indicated.

Kaplan-Meier plots showing the percentage of animals remaining in the study over time were constructed. The Log-rank (Mantel-Cox) test was employed to assess the significance of the differences in the Kaplan-Meier plots between groups. A calculated p-value ≤(0.05/number of comparisons) adjusted for multiple comparisons was considered statistically significant. The Log-rank test is a test of statistical significance and does not provide an estimate of the size of the difference between groups or a measure of clinical or biological significance.

Table 24 summarizes the treatment plan for the P380E4_R400_LXFS 573 study. Test animals were sorted into six groups of eight mice per group, and treatments were initiated on Day 0 when the average tumor size met the randomization criteria. Control mice received a 0.5% methyl cellulose vehicle administered by oral gavage (PO) on the once daily schedule as shown. Treated mice received oral Compound A or subcutaneous (SC) etoposide, alone or in combination, on the once daily schedules shown. The test article Compound A was prepared daily as the benzenesulfonate salt (74% active compound) suspended in vehicle and dosed as mg/kg free base equivalents. In all groups, a dosing volume of 10 mL/kg was scaled to the weight of individual animals and scheduled dosing was continued until the animal exited the study. Two animals received dosing holidays which had no effect on the outcomes.

Figure 27:
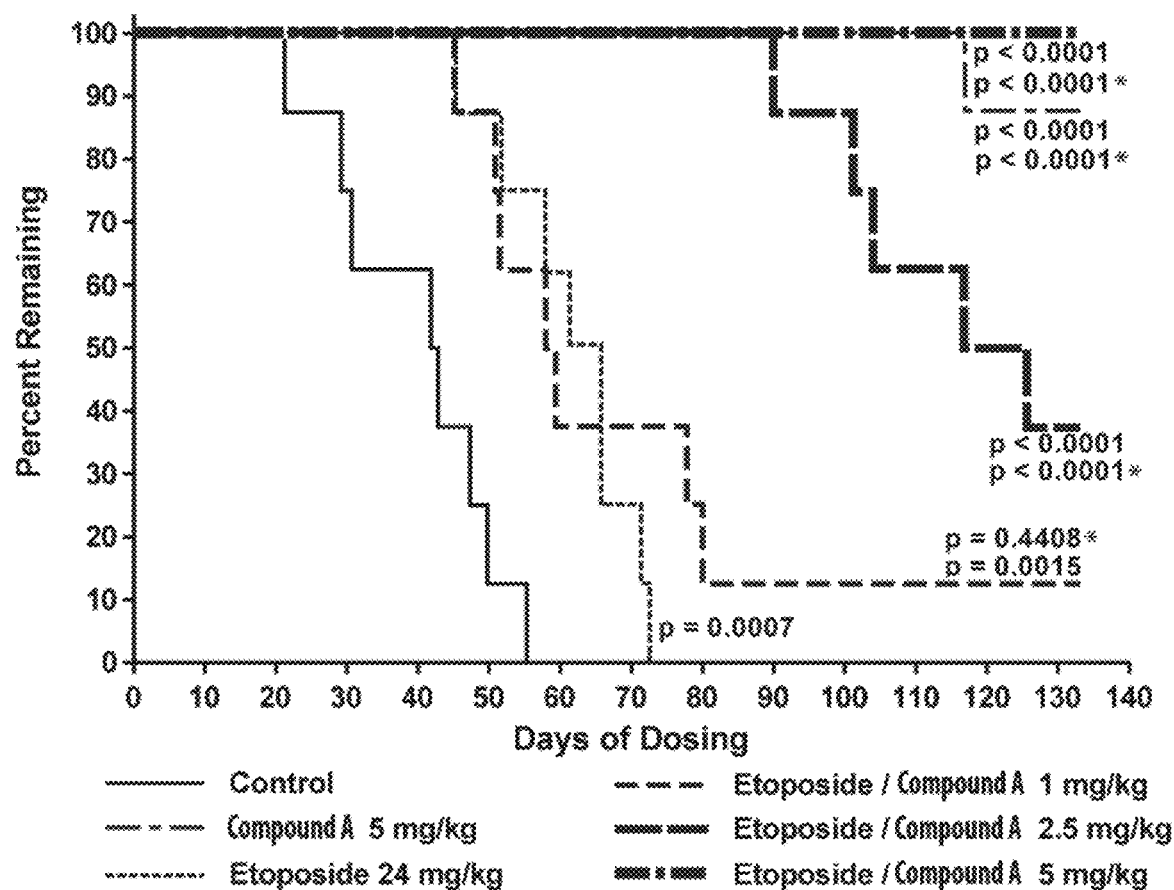
FIG. 27 is a graph showing Kaplan-Meier Plots. p-values without * are for Log-rank comparisons with the control and −values with * are for Log-rank comparisons with etoposide monotherapy. Fifteen comparisons were performed yielding a level of significance of p≤0.003 (Alpha=[0.05/15]).
Figure 28:
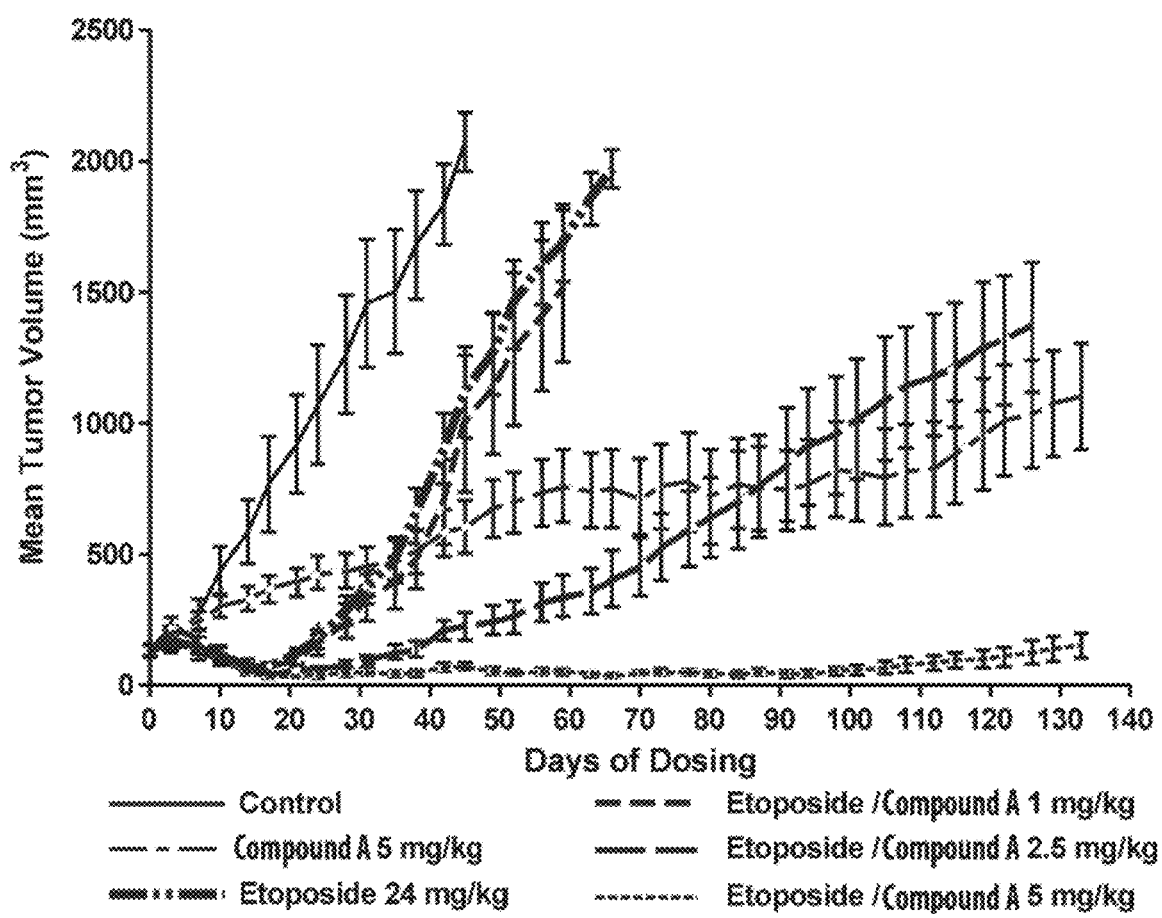
FIG. 28 is a graph showing mean tumor growth. Tumor volumes plotted as mean±standard error (SEM). Plots were truncated when more than 50% of the assessable animals in a group exited the study.
Figure 29:
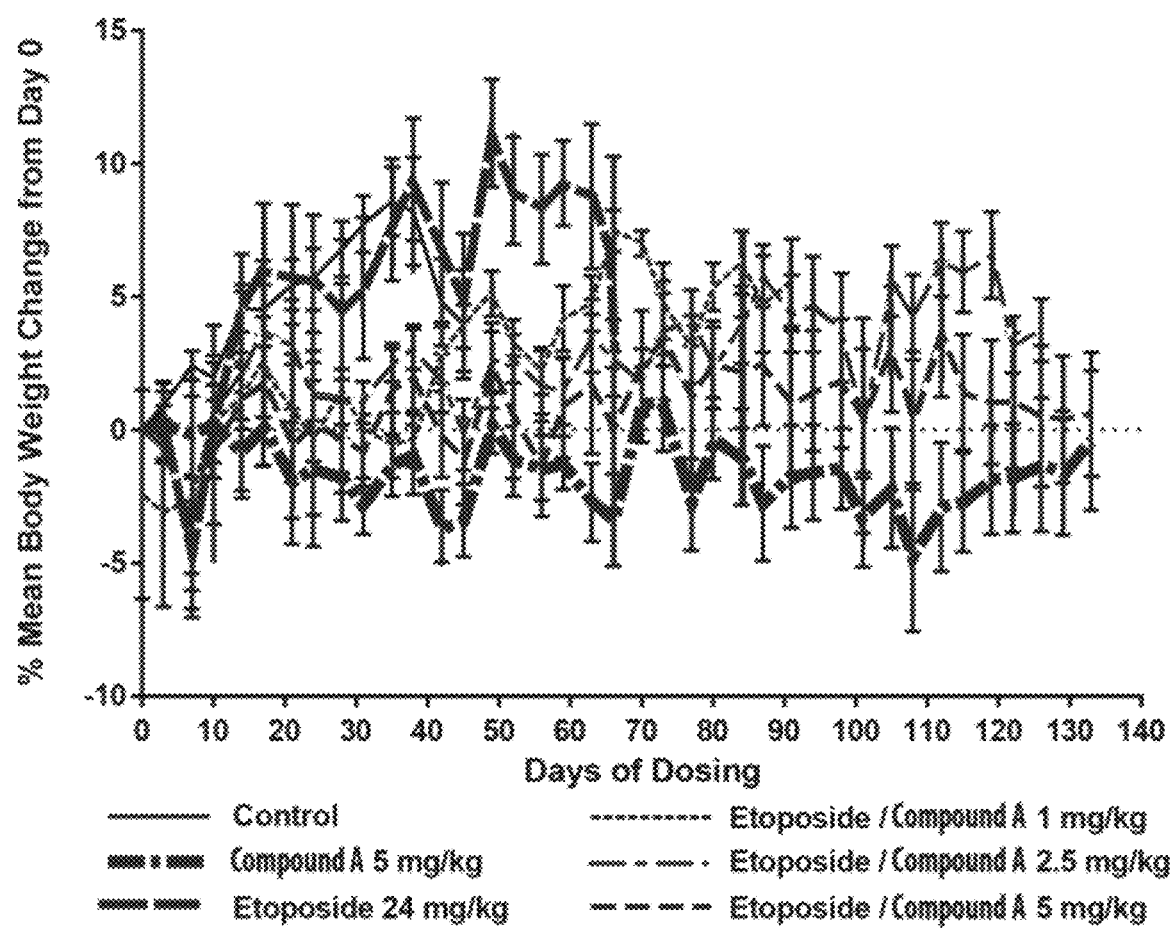
FIG. 29 is a graph showing percent mean body weight change. Body weights plotted as % mean±standard error (SEM). Horizontal line at 0% mean body weight change. Plots were truncated when more than 50% of the assessable animals in a group exited the study.

Test animals were treated in accordance with the protocol in Table 19 and the study was terminated on Day 133. Table 26 summarizes the TGD responses and FIG. 27 shows the Kaplan-Meier plots for all groups. The Log-rank test was employed to assess the significance of the differences in the Kaplan-Meier plots between groups. A calculated p-value ≤0.003 (0.05/15) adjusted for multiple comparisons was considered statistically significant. FIG. 28 presents mean tumor growth curves for the six groups of test animals. FIG. 29 presents the percent group mean body weight changes from Day 0. Since no regimen caused a mean body weight loss >20% during the test and no treatment-related deaths were reported, all regimens were considered acceptably tolerated.

TABLE 26

TGD Response Summary

| Group | N | Treatment Regimen | Median TTE (Days) | T-C (Days) | % TGD | SS(MTV) |
|---|---|---|---|---|---|---|
| 1 | 8 | Vehicle at 10 mL/kg/day | 42 | — | — | 0 (na) |
| 2 | 8 | Compound A at 5 mg/kg/day | 133 | 91 | 217 | 7 (1064) |
| 3 | 8 | Etoposide at 24 mg/kg/day + Vehicle | 63 | 21 | 50 | 0 (na) |
| 4 | 8 | Etoposide then Compound A at 1 mg/kg/day | 59 | 16 | 38 | 1 (1430) |
| 5 | 8 | Etoposide then Compound A at 2.5 mg/kg/day | 121 | 79 | 188 | 3 (1121) |
| 6 | 8 | Etoposide then Compound A at 5 mg/kg/day | 133 | 91 | 217 | 8 (121) |

Vehicle dosed at 10 mL/kg of 0.5% methyl cellulose and Compound A dosed at 10 mL/kg as mg/kg free base equivalents;
N = number of animals evaluated for each group;
TTE = time-to-endpoint;
T-C difference between median TTE (days) for treated versus control groups;
% TGD = (T-C)/C x 100; maximum possible TGD = 91 days (217 % TGD);
SS(MTV) = number of study survivors (SS) bearing tumors with a median tumor volume (mm³) (MTV),
na = not applicable.

As shown in Table 26 and FIG. 27, eight tumors in control mice grew to the 2000 mm³ endpoint between 21.2 and 55.3 days. As reported in Table 26, the median TTE for control mice was 42 days, establishing a maximum possible TGD of 91 days (217% TGD) for this study. Mean tumor growth progressed rapidly, as seen in FIG. 28. As shown in FIG. 29, the vehicle control group exhibited a mean body weight gain of 4% on Day 45, the last day at least half of the animals remained on study.

As reported in Table 26, Compound A monotherapy at 5 mg/kg yielded a median TTE of 133 days, corresponding to the maximum possible TGD (91 days, 217%). As shown in Table 26 and FIG. 27, one animal attained endpoint on Day 117 and seven animals survived the study bearing tumors with an MTV of 1064 mm3. As annotated in FIG. 27, the Log-rank test found a significant difference in overall survival when compared to the control group (p<0.0001). Mean tumor progression was markedly delayed compared to that observed in the control, as seen in FIG. 28. The Compound A monotherapy group exhibited a mean body weight loss of 0.4% at the end of the study, as shown in FIG. 29.

Etoposide monotherapy at 24 mg/kg yielded a median TTE of 63 days, corresponding to a 21 day or 50% TGD. Tumors in eight test animals grew to endpoint between 45.1 and 72.5 days. The Log-rank test found a significant difference in overall survival when compared to the control group (p=0.0007) and significantly less efficacy when compared to the 5 mg/kg Compound A monotherapy group (p<0.0001). Mean tumor volume decreased for ~17 days before rebounding to a growth rate similar to that for tumors in control animals. The etoposide monotherapy group exhibited a mean body weight gain of 6.3% on Day 66, the last day half of the animals remained on study.

Compound A at 1, 2.5, or 5 mg/kg administered in combination with etoposide yielded respective dose-dependent median TTEs of 59, 121, and 133 days corresponding to TGDs of 16 days (38%), 79 days (188%), and 91 days (217%, the maximum possible).

In the group that received 1 mg/kg Compound A combination therapy, tumors in seven test animals grew to endpoint between 45.3 and 79.8 days and one animal survived the study bearing a tumor with a volume of 1430 mm3. The Log-rank test found a significant difference in overall survival when compared to the control group (p=0.0015), no difference when compared to the etoposide monotherapy group (p=0.4408), and significantly less efficacy when compared to the 5 mg/kg Compound A monotherapy group (p=0.0008). Mean tumor volume decreased for ~17 days before rebounding to a growth rate similar to that for tumors in control animals. Mean tumor progression was similar to that observed with etoposide monotherapy. The 1 mg/kg Compound A combination therapy group exhibited a mean body weight gain of 5.5% on Day 59, the last day at least half of the animals remained on study.

In the group that received 2.5 mg/kg Compound A combination therapy, tumors in five test animals grew to endpoint between 89.6 and 125.6 days and three animal survived the study bearing tumors with an MTV of 1121 mm3. The Log-rank test found a significant difference in overall survival when compared to the control and etoposide monotherapy groups (p<0.0001) and no difference in efficacy when compared to the 5 mg/kg Compound A monotherapy (p=0.0351) or the 1 mg/kg Compound A combination therapy (p=0.0132) groups. Mean tumor volume decreased for ~17 days before gradually rebounding to a growth rate slower than that observed for tumors in control animals. The 2.5 mg/kg Compound A combination therapy group exhibited a mean body weight gain of 3.8% on Day 126, the last day half of the animals remained on study.

In the group that received 5 mg/kg Compound A combination therapy, eight animals survived the study bearing tumors with an MTV of 121 mm3. On Day 91, one tumor regressed to below the limit of palpability where it remained to study end. The Log-rank test found a significant difference in overall survival when compared to the control and etoposide monotherapy (p<0.0001) and the 1 mg/kg Compound A combination therapy (p=0.0004) groups and no difference in efficacy when compared to the 5 mg/kg Compound A monotherapy (p=0.3173) or the 2.5 mg/kg Compound A combination therapy (p=0.0085) groups. Mean tumor volume decreased for ~17 days then remained nearly static over the course of the study. Multiple t tests found that the difference in mean tumor volumes at each time point for 5 mg/kg Compound A administered as the combination therapy compared to monotherapy were significant beginning with the Day 7 measurements and remained significant to study end (p 0.01). The 5 mg/kg Compound A combination therapy group exhibited a mean body weight gain of 0.6% at the end of the study.

The in vivo efficacy and tolerability of Compound A (1, 2.5, or 5 mg/kg) alone and in combination with etoposide (24 mg/kg) were evaluated preclinically using the SCLC PDX model LXFS 573 established in female immunodeficient Foxn1nu mice Etoposide monotherapy at 24 mg/kg yielded a median TTE of 63 days, corresponding to a 21 day or 50% TGD. Tumors in eight test animals grew to endpoint between 45.1 and 72.5 days. The Log-rank test found a significant difference in overall survival when compared to the control group (p=0.0007) and significantly less efficacy when compared to the 5 mg/kg Compound A monotherapy group (p<0.0001).

Oral Compound A at 1, 2.5, or 5 mg/kg dosed daily on Days 4-133 (study end) in combination with 24 mg/kg etoposide dosed daily on Days 1-3 was efficacious in the LXFS 573 PDX model of SCLC. Tumor growth delay was dose-dependent yielding respective median TTEs of 59, 121, and 133 days corresponding to TGDs of 16 days (38%), 79 days (188%), and 91 days (217%, the maximum possible TGD for this study). Study survival also exhibited dose-dependency yielding 1, 3, and 8 survivors on Day 133, respectively, and significant differences in overall survival when compared to the control group (p≤0.0015). Mean tumor volume for the etoposide plus 5 mg/kg Compound A group decreased for ~17 days then remained nearly static over the course of the study with an MTV of 121 mm3 on Day 133.

Oral Compound A monotherapy at 5 mg/kg dosed daily on Days 1-133 also elicited the maximum response with a median TTE of 133 days corresponding to a TGD of 91 days or 217% and yielded a significant difference in overall survival when compared to the control group (p=0.0001). Mean tumor progression was markedly delayed with an MTV of 1064 mm3 on Day 133. Assessments of the differences in median TTEs, in the number of study survivors, in mean tumor growth, and in the percentage of animals remaining in the study over time found that the responses to 5 mg/kg Compound A administered alone or in combination with etoposide were superior to all other treatment regimens. Although the overall survival for animals that received 5 mg/kg Compound A monotherapy vs. combination therapy was not significantly different (p=0.9998), mean tumor volumes on Days 7-133 were significantly less for test animals that received etoposide then 5 mg/kg Compound A compared to those that received 5 mg/kg Compound A alone (p≤0.01).

All treatment regimens appeared acceptably tolerated yielding minimal changes in group mean body weights between the first and last days of measurement and no deaths classified as treatment-related.

Example 17. Efficacy of Compound a Alone or in Combination with Etoposide in the NCI-H1417 Small Cell Lung Cancer Xenograft Model The purpose of this study was to determine the efficacy and tolerability of Compound A, dosed orally at 5 mg/kg on a 5 on/2 off intermittent schedule, as monotherapy or in combination with 24 mg/kg etoposide in the NCI-H1417 SCLC xenograft model established in female NSG mice.

Female NSG mice (NOD. Cg-Prkdcscid Il2rgtm1Wjl/SzJ, The Jackson Laboratory, Bar Harbor, Me.) were used for this study. Test mice were 9 weeks old on the day of tumor implantation. Animals were acclimated for one week prior to tumor implantation.

Animals were fed ad libitum water (reverse osmosis, acidified) and PicoLab® Rodent Diet consisting of 20% crude protein, 5.6% fat (acid hydrolysis), and 4.7% crude fiber. The mice were housed in a barrier facility on ALPHA-dri® on a 12-hour light cycle at 72±2° F. and at 30-70% humidity.

NCI-H1417 cells were cultured in RPMI-1640 medium supplemented with 10% fetal bovine serum (cRPMI), 100 units/mL penicillin G sodium and 100 µg/mL streptomycin sulfate. Cells were cultured in a humidified incubator at 37° C., in an atmosphere of 5% carbon dioxide and 95% air.

Compound A was formulated in 0.5% methylcellulose in water with a dosing volume of 10 mL/kg.

Female NSG mice bearing palpable NCI-H1417 SCLC tumors (mean tumor volumes ~230 mm3) were randomized into four groups. Two groups were administered 5 mg/kg Compound A orally on a 5 on/2 off intermittent schedule as monotherapy or following an initial three-day treatment with 24 mg/kg etoposide. The study included an etoposide monotherapy and a vehicle control group.

Efficacy was determined based on statistical assessment of differences in TGD and differences in TTE values and mean tumor growth for treated vs. control animals over the course of the study. Tolerability was assessed by monitoring each individual animal's body weight and health status.

On the day of tumor cell inoculation, human NCI-H1417 cells were harvested during log phase growth and resuspended in 100% Matrigel® at a concentration of 7.5×10$^7$ cells/mL. Each test mouse then received 0.1 mL cell suspension (7.5×10$^6$ cells) subcutaneously implanted in the right flank. Tumors were allowed to grow for 43 days until they attained ~230 mm3. Tumor bearing mice were then randomized into four groups of seven mice with mean tumor volumes of 241.7±29.4 mm3, 220.4±33.2 mm3, 222.7±35.9 mm3, and 232.4±41.1 mm3. This day was denoted as Day 1 and dosing was initiated according to the pre-determined regimen shown in Table 27.

TABLE 27

Treatment Plan

| Group | n | Agent | Dose (mg/kg) | Route | Schedule |
|---|---|---|---|---|---|
| 1 | 7 | Vehicle | — | PO | 5 on/2 off |
| 2 | 7 | Compound A | 5 | PO | 5 on/2 off |
| 3 | 7 | Etoposide | 24 | SC | QD × 3 |
| 4 | 7 | Etoposide then | 24 | SC | QD × 3 |
|   |   | Compound A | 5 | PO | 5 on/2 off | n = number of animals;
PO = oral dosing;
SC = subcutaneous dosing;
5 on/2 off = dosing for five days followed by two days with no dosing to study end;
QD × 3 = once daily dosing for three days;
— = no test-article administration. A dosing volume of 10 mL/kg was scaled to the weight of individual animals and Compound A dosed as mg/kg free base equivalents.

As shown in Table 27, control mice received aqueous 0.5% methylcellulose vehicle administered orally (PO) for five days followed by two days with no dosing, repeated to study end (5 on/2 off). A Compound A monotherapy group received 5 mg/kg Compound A, PO, 5 on/2 off. An etoposide monotherapy group received 24 mg/kg etoposide administered subcutaneously (SC), once daily for three consecutive days (QD×3). An etoposide followed by Compound A combination therapy group received 24 mg/kg etoposide, SC, QD×3, then 5 mg/kg Compound A, PO, 5 on/2 off. The test article Compound A was prepared daily as the benzenesulfonate salt (74% active compound) suspended in vehicle and dosed as mg/kg free base equivalents. In all groups, a dosing volume of 10 mL/kg was scaled to the weight of individual animals.

Individual tumors were measured twice weekly in three dimensions using a caliper, and the tumor volumes (TV) in mm$^3$ were calculated using the formula: TV=0.5×l×w×h, where l, w, and h are the length, width, and height in millimeters, respectively. At the same time, animals were weighed and each individual animal's health status was monitored for body weight loss exceeding 20% and for signs of lethargy by means of a physical examination. The study was terminated on Day 195.

Each test animal was euthanized when its tumor reached the endpoint volume of 2000 mm3 or when its body weight loss exceeded 20%. For animals that experienced >10% weight loss, body weight was monitored daily. The animal was sacrificed when body weight loss >20% or it exhibited lethargy. When an animal was euthanized or was found dead in the cage (FDIC), the final tumor volume recorded for the animal was included with the data used to calculate the mean volume at subsequent time points. Tumor growth curves were then plotted showing group mean tumor volumes (±standard error of the mean [SEM]) as a function of time and mean body weights were plotted as the percentage change from Day 1. Both plots were truncated when more than 50% of the assessable animals in a group exited the study. Multiple t tests, corrected for the number of comparisons, assessed the significance of the difference in Compound A monotherapy vs. combination therapy mean tumor volumes for each time point plotted on the tumor growth curves.

The TTE for each mouse was calculated from the following equation:

$$TTE(\text{days}) = \frac{\log_{10}(2000\ \text{mm}^3) - b}{m}$$

where b is the intercept and m is the slope of the line obtained by linear regression of a log 10-transformed tumor volume composed of the first observation that exceeded 2000 mm3 and the three preceding measurements. Animals found dead or euthanized due to body weight loss were assigned a TTE value equal to their day of sacrifice. Animals that survived the study were assigned a TTE value equal to the last day of the study.

Treatment outcome was determined from TGD, defined as the change in the median TTE in a treatment group compared to the vehicle control group:

TGD=T−C, expressed in days, or as a percentage of the median TTE of the vehicle control group:

$$\% TGD = \frac{T - C}{C} \times 100$$

where:
T=median TTE for a treatment group, and
C=median TTE for the vehicle control group.

Kaplan-Meier plots showing the percentage of animals remaining in the study over time were constructed. The Log-rank (Mantel-Cox) test was employed to assess the significance of the differences in the Kaplan-Meier plots between groups. A calculated p-value ≤(0.05/number of comparisons) was considered statistically significant. The Log-rank test is a test of statistical significance and does not provide an estimate of the size of the difference between groups or a measure of clinical or biological significance.

Figure 30:
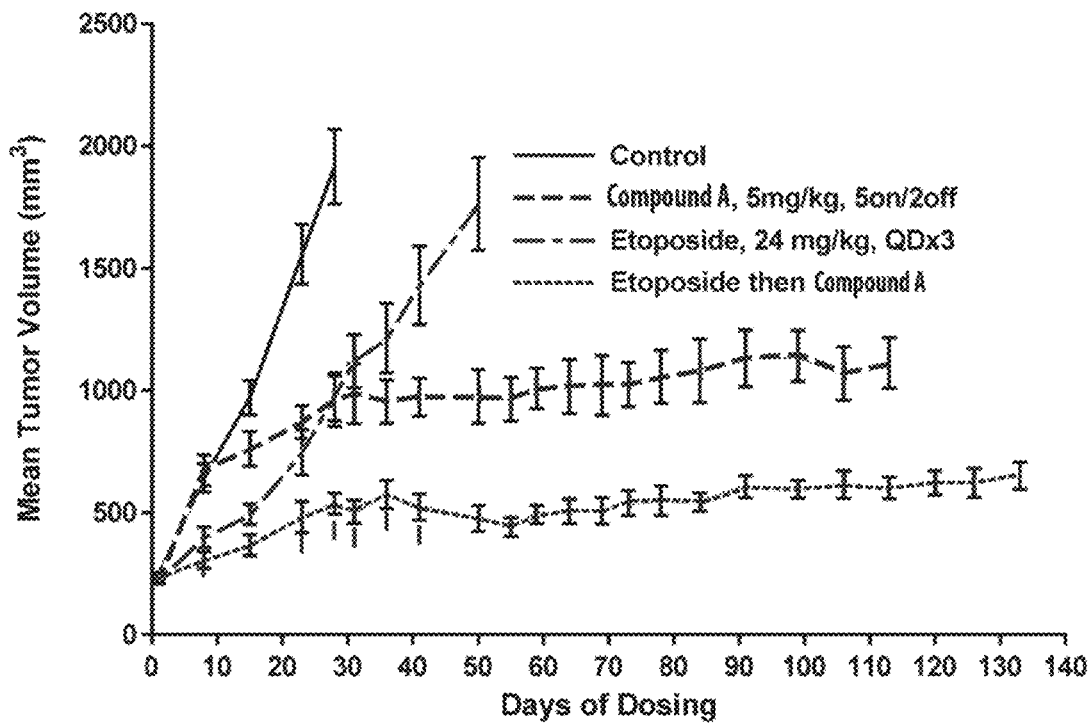
FIG. 30 is a graph showing mean tumor growth. QD×3=once daily dosing for three days; 5 on/2 off=dosing for five days followed by two days with no dosing. Tumor volumes plotted as mean±standard error (SEM). Plots were truncated when more than 50% of the assessable animals in a group exited the study.
Figure 31:
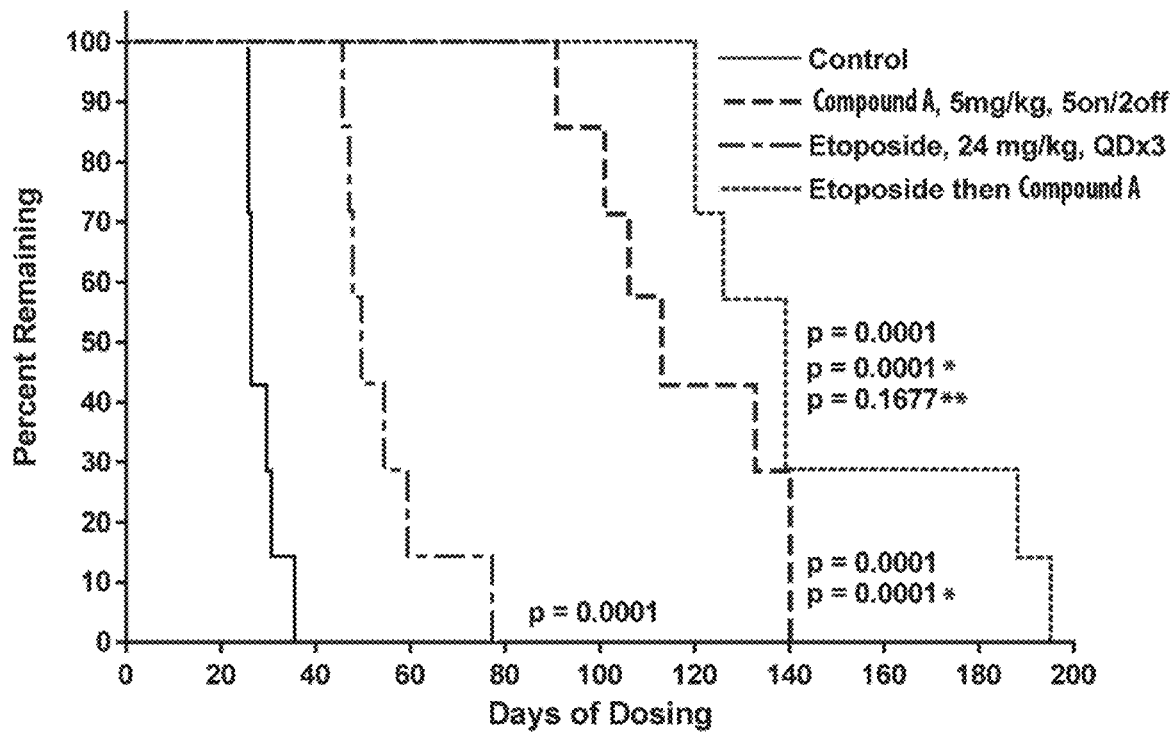
FIG. 31 is a graph showing Kaplan-Meier plots. QD×3=once daily dosing for three days; 5 on/2 off=dosing for five days followed by two days with no dosing. P-values without * are for Log-rank comparisons with the control, p-values with * for comparisons with etoposide monotherapy, and p-values with ** for comparison with Compound A monotherapy. Six comparisons were performed yielding a level of significance of p≤0.008 (Alpha=[0.05/6]).
Figure 32:
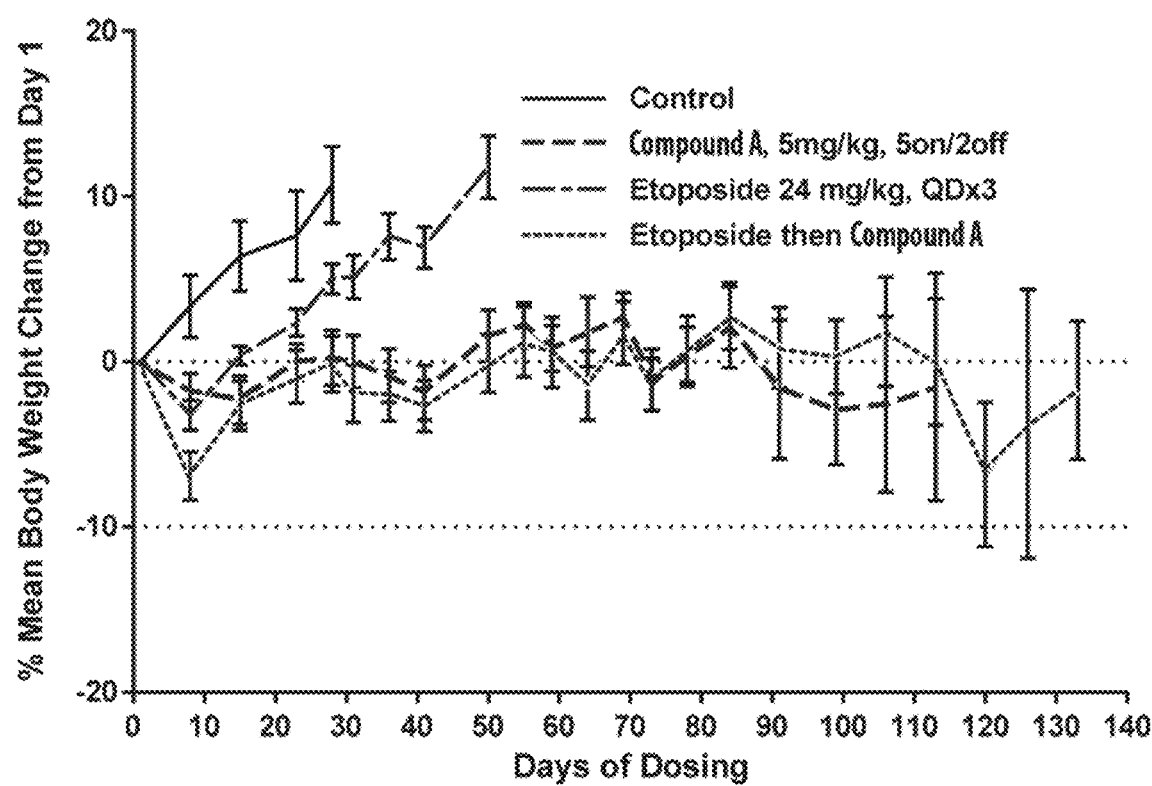
FIG. 32 is a graph showing percent mean body weight change. QD×3=once daily dosing for three days; 5 on/2 off=dosing for five days followed by two days with no dosing. Body weights plotted as % mean±standard error (SEM). Horizontal lines at 0% and −10% mean body weight change. Plots were truncated when more than 50% of the assessable animals in a group exited the study.

Test animals in the study were treated in accordance with the protocol in Table 21 and the study was terminated on Day 195. Table 28 summarizes the TGD responses for all groups. FIG. 30 shows the mean tumor growth curves and FIG. 31 shows the Kaplan-Meier plots for the groups indicated. FIG. 32 presents the percent group mean body weight changes from Day 1.

TABLE 28

TGD Response Summary

| Group | n | Treatment Regimen | Median TTE (Days) | T − C (Days) | % TGD |
|---|---|---|---|---|---|
| 1 | 7 | Vehicle | 26 | — | — |
| 2 | 7 | 5 mg/kg Compound A 5 on/2 off | 113 | 87 | 335 |
| 3 | 7 | 24 mg/kg Etoposide QD × 3 | 50 | 24 | 92 |
| 4 | 6 | Etoposide then Compound A | 139 | 113 | 435 |

TGD = tumor growth delay;
5 on/2 off = dosing for five days followed by two days with no dosing to study end;
QD × 3 = once daily dosing for three days. A dosing volume of 10 mL/kg was scaled to the weight of individual animals and Compound A dosed as 5 mg/kg free base equivalents;
n = number of animals evaluated for each group;
TTE = time-to-endpoint;
T − C = difference between median TTE (days) for treated versus control groups;
% TGD = (T − C)/C × 100;
maximum possible TGD = 169 days (650% TGD).

As shown in FIG. 31, seven tumors in control mice grew to the 2000 mm3 endpoint between 25.8 and 35.7 days. As reported in Table 23, the median TTE for control mice was 26 days, establishing a maximum possible TGD of 169 days (650% TGD) for this study. Mean tumor growth progressed rapidly, as seen in FIG. 30.

As reported in Table 28, Compound A monotherapy at 5 mg/kg yielded a median TTE of 113 days, corresponding to an 87-day or 335% TGD. As shown in FIG. 31, seven animals exited the study between 91 and 140 days. As annotated in FIG. 31, the Log-rank test found a significant difference in overall survival when compared to the control group (p=0.0001). Mean tumor progression was initially unrestricted to Day 8 then slowed before becoming nearly static after Day 28, as seen in FIG. 30.

Etoposide monotherapy at 24 mg/kg yielded a median TTE of 50 days, corresponding to a 24 day or 92% TGD. Tumors in seven test animals grew to endpoint between 45.5 and 77.3 days. The Log-rank test found a significant difference in overall survival when compared to the control group (p=0.0001) and significantly less efficacy when compared to the 5 mg/kg Compound A monotherapy group (p=0.0001). Mean tumor progression was delayed compared to that observed in the control.

Etoposide at 24 mg/kg followed by Compound A at 5 mg/kg yielded a median TTE of 139 days, corresponding to a 113 day or 435% TGD. Seven animals exited the study between 120 and 195 days. The Log-rank test found a significant difference in overall survival when compared to the control and etoposide monotherapy groups (p=0.0001) but no difference when compared to the Compound A monotherapy group (p=0.1677). Mean tumor progression was initially slow before becoming nearly static after Day 28. Multiple t tests found that the differences in mean tumor volumes at each time point for the etoposide+Compound A combination therapy compared to Compound A monotherapy were significant for Days 8-113 (p≤0.004).

As shown in FIG. 32, the groups that received vehicle or etoposide monotherapy exhibited mean body weight gains, where as the groups that received Compound A alone or following etoposide experienced little to no change in mean body weight for about the first 100 days of the study. In the Compound A monotherapy group, seven animals were found dead or were euthanized due to body weight loss >20% between 91 and 140 days and, in the etoposide followed by Compound A group, six animals were found dead or were euthanized due to body weight loss between 126 and 195 days.

An examination of individual animals failed to establish a relationship between tumor burden and body weight loss potentially ruling out cachexia. In addition, no clinical observations consistent with Compound A treatment-related toxicity (lethargy, lack of appetite, and petechia) were recorded. Based on these observations, Compound A was considered acceptably tolerated in this study.

Compound A, dosed orally at 5 mg/kg on a 5 on/2 off intermittent schedule, as monotherapy or following an initial three-day treatment with 24 mg/kg etoposide was efficacious and acceptably tolerated in the NCI-H1417 SCLC xenograft model established in female NOD scid gamma (NSG) mice.

Oral Compound A monotherapy at 5 mg/kg yielded a median TTE of 113 days, corresponding to an 87-day or 335% TGD and a significant difference in overall survival when compared to the control group by the Log-rank test (p=0.0001). Etoposide monotherapy at 24 mg/kg yielded a median TTE of 50 days, corresponding to a 24 day or 92% TGD and a significant difference in overall survival when compared to the control group by the Log-rank test (p=0.0001). The Log-rank test found significantly less efficacy for the etoposide monotherapy group when compared to the 5 mg/kg Compound A monotherapy group (p=0.0001). Etoposide followed by Compound A at 5 mg/kg yielded a median TTE of 139 days, corresponding to a 113 day or 435% TGD. The Log-rank test found a significant difference in overall survival for the etoposide Compound A combination group when compared when compared to the control and etoposide monotherapy groups (p=0.0001) but no difference when compared to the Compound A monotherapy group (p=0.1677). Mean tumor growth over the course of the study was consistent with the TGD results. Assessments of the differences in median TTEs, in mean tumor growth, and in the percentage of animals remaining in the study over time found that the responses to 5 mg/kg Compound A administered alone or following etoposide were superior to all other treatment regimens. Although the overall survival for animals that received 5 mg/kg Compound A monotherapy vs. combination therapy was not significantly different (p=0.1677), mean tumor volumes on Days 8-113 were significantly less for test animals that received etoposide then 5 mg/kg Compound A compared to those that received 5 mg/kg Compound A alone (p≤0.004).

Animals that received vehicle or etoposide monotherapy exhibited mean body weight gains and exited the study as their tumors attained the tumor volume endpoint. The animals that received Compound A alone or following etoposide experienced little to no change in mean body weight for about the first 100 days of the study. Animals in both groups were found dead or were euthanized due to body weight loss >20% between 91 and 195 days. An examination of individual animals failed to establish a relationship between tumor burden and body weight loss potentially ruling out cachexia. In addition, no clinical observations consistent with Compound A treatment-related toxicity (lethargy, lack of appetite, and petechia) were recorded. Based on these observations, Compound A was considered acceptably tolerated in this study.

Figure 33:
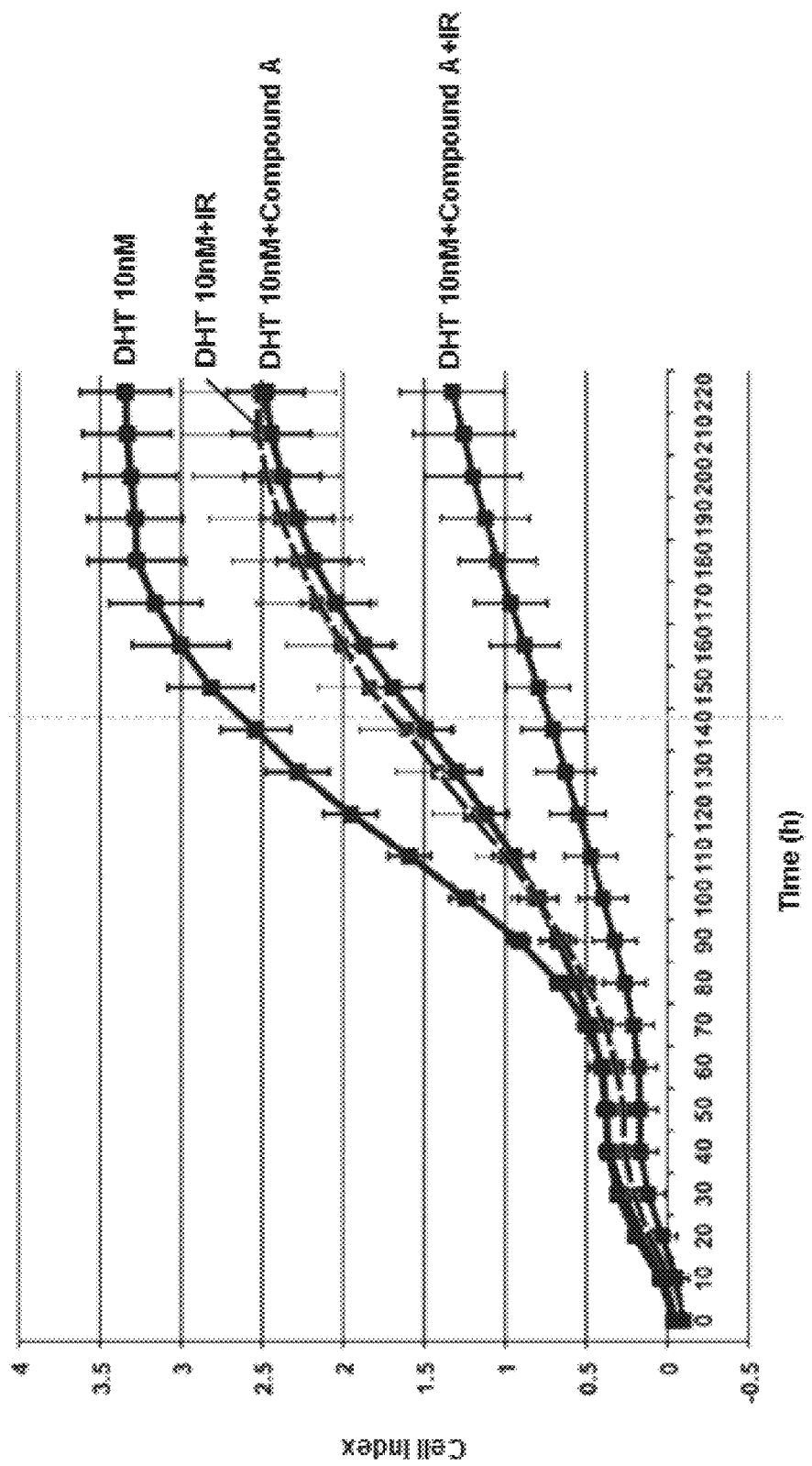
FIG. 33 is a graph showing the results of LNCaP cell proliferation assay overtime with the treatment of 10 nM DHT, 10 nM DHT plus 2Gy irradiations, 10 nM DHT plus 100 nM Compound A, and 10 nM DHT plus 100 nM Compound A and 2Gy irradiations.
Figure 34:
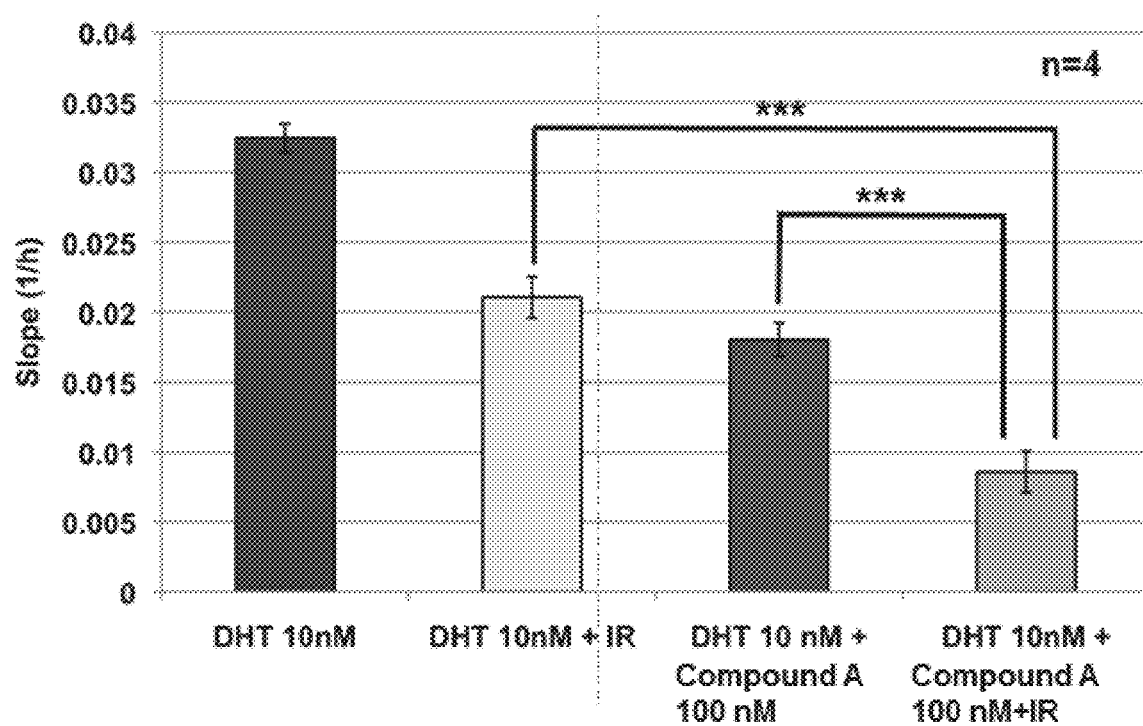
FIG. 34 is a graph showing the results of LNCaP cell proliferation assay with the treatment of 10 nM DHT, 10 nM DHT plus 2Gy irradiations, 10 nM DHT plus 100 nM Compound A, and 10 nM DHT plus 100 nM Compound A and 2Gy irradiations

Example 18. Compound A Increases the Sensitivity of Prostate Cancel Cells LNCaP to Irradiation LNCaP cells are androgen-sensitive human prostate adenocarcinoma cells. LNCap cells were trated with androgen receptor ligand DiHydroxyTestosterone (DHT; 10 nM) with or without irridation (2Gy) or LSD1 inhibitor Compound A (100 nM). The proliferation of the LNCap cells was monitored for 220 hours. FIG. 33 shows that the combination of DHT, compound A and irradiation displays better inhibition of LNCap cell proliferation compared to DHT with irradiation. FIG. 34 shows that the combination of DHT, compound A and irradiation significantly inhibits LNCaP cell proliferation compared to DHT combined with irradiation or DHT combined with Compound A. These findings suggest that Compound A is effective in presence of androgen receptor ligand DHT slow down the proliferation of LNCaP cells after 2Gy irradiation.

Figure 35:
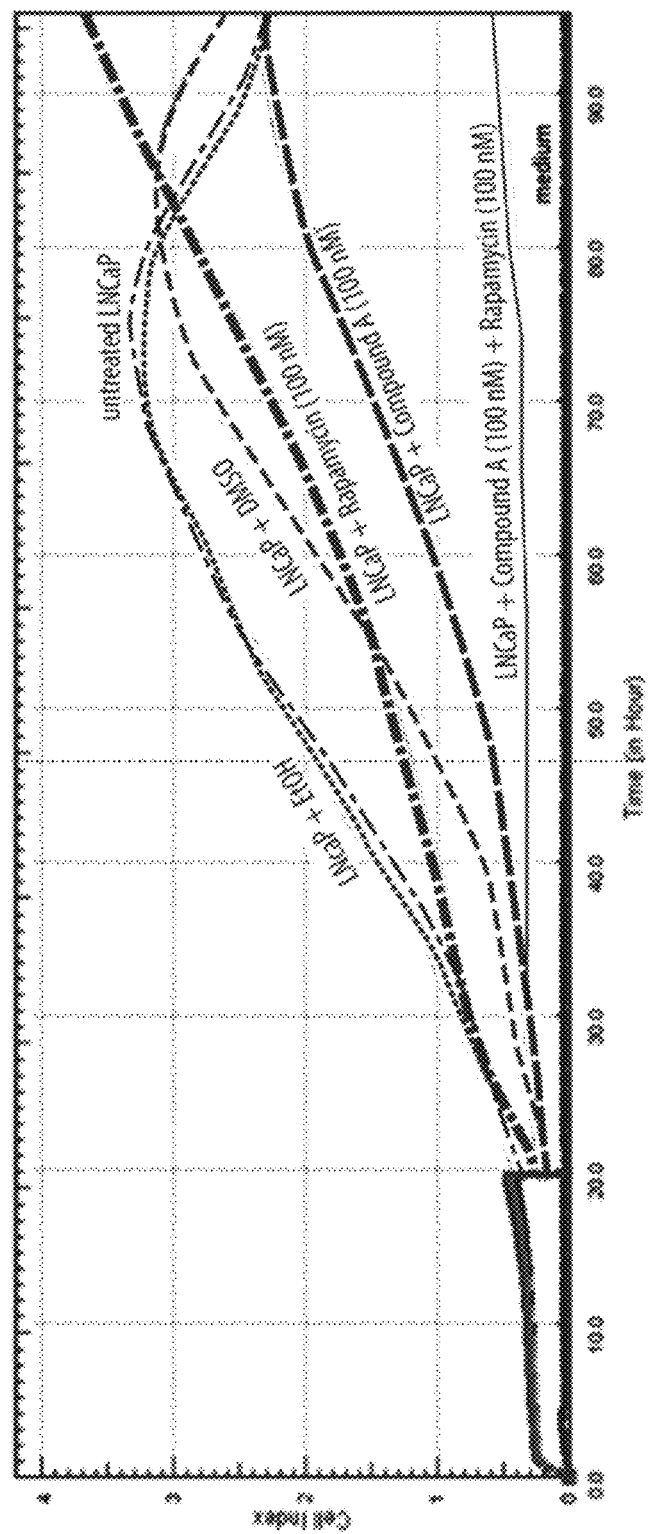
FIG. 35 is a graph showing the results of LNCaP cell proliferation assay overtime without any treatment, or with the treatment of EtOH, DMSO, 100 nM Rapamycin, 100 nM Compound A or the combination of 100 nM Rapamycin and 100 nM Compound A.
Figure 36:
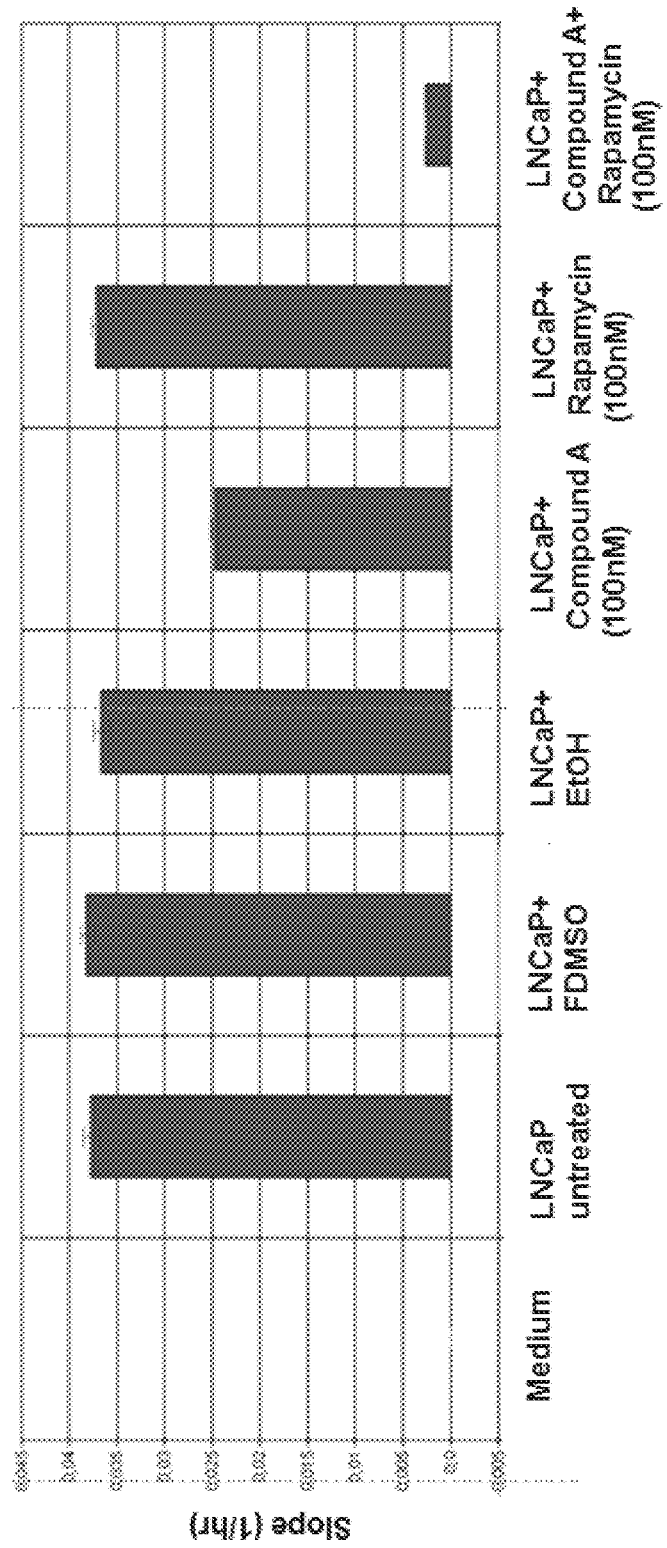
FIG. 36 is a graph showing the results of LNCaP cell proliferation assay overtime without any treatment, or with the treatment of EtOH, DMSO, 100 nM Rapamycin, 100 nM Compound A or the combination of 100 nM Rapamycin and 100 nM Compound A.

Example 19. Compound a Enhances the Sensitivity of Prostate Cancel Cells LNCaP to Rapamycine Treatment LNCap cells were treated with 100 nM rapamaycine only, 100 nM Compound A alone or the combination of 100 nM rapamaycine with 100 nM Compound A. The proliferation of the LNCap cells was monitored for 90 hours. FIG. 35 and FIG. 36 show that the combination of rapamaycine with Compound A displays greater inhibition of LNCap cell proliferaton compared to Rapmycine alone. These data suggest that Compound A enhances the sensitivity of prostate cancel cells LNCaP to Rapamycine treatment.

III. Secondary Pharmacodynamics

Example 1: Effect of Compound A in In Vitro Pharmacology Panel of Receptors, Ion Channels, Neurotransmitter Transporters, Kinase, and Non-Kinase Enzymes The Compound A-mediated inhibition of ligand or substrate binding for a panel of receptors, ion channels, neurotransmitter transporters, kinases, and non-kinase enzymes was assessed at 10 µM in a series of CEREP study reports. Inhibition greater than 50% was observed only for the muscarinic M1 receptor (76% inhibition) and the Na+ channel (site 2) (62% inhibition). The Ki values determined for Compound A against muscarinic M1 receptor and Na+ channel (site 2) were 1.6 µM and 11 µM, respectively. These measured Ki values were more than 10,000-fold higher than the Ki observed for LSD1. These data demonstrate that Compound A binds with high specificity to LSD1 compared with the 140 targets tested and Compound A is a selective inhibitor of LSD1.

IV. Safety Pharmacology

Example 1: In Vitro Effect of Compound A on Cardiovascular and Respiratory Systems In vitro effects of Compound A on the hERG potassium channel (a surrogate for IKr, the rapidly activating delayed rectifier cardiac potassium current) were evaluated. Compound A was tested at concentrations of 0.3, 1, 3, and 10 µM in human embryonic kidney cells (HEK293) that stably expressed hERG channels. Compound A inhibited hERG current (mean±standard error of mean) by 5.9±1.3% at 0.3 µM (n=3), 17.8±0.3% at 1 µM (n=4), 47.0±1.9% at 3 µM (n=4), and 77.3±0.2% at 10 µM (n=3). The IC50 value for the inhibitory effect of Compound A on hERG current was determined to be 3.4 µM (Hill coefficient=1.2).

Example 2: Effect of Compound A on Hemodynamic and Electrocardiographic Parameters in Male Dunkin Hartley Guinea Pigs The effects of Compound Aon hemodynamic and ECG parameters were examined in anesthetized, male Dunkin Hartley guinea pigs. Male guinea pigs were administered IV either vehicle alone (10% dimethylsulfoxide, 30% polyethylene glycol 400 in water; n=4 animals) or Compound A (n=4 animals, with each animal being administered 5, 10, 15, and 20 mg base/kg) via a 10-minute infusion into the jugular vein. An escalating dose design was utilized in which doses were administered sequentially at 20-minute intervals. Animals were monitored throughout the experiment.

Mean arterial pressure (MAP) and its components tended to decrease over the period of vehicle infusion. At the end of the monitoring period, MAP was decreased by 24% as compared with baseline. With the infusion of vehicle alone, a decrease of 23% in HR and an increase of 26% in PR interval were also observed at the end of the monitoring period.

No notable effect in MAP or its components was observed with administration of Compound A, as compared with time-matched vehicle. At 20 mg base/kg, Compound A caused a slight decrease in HR with a maximum suppression of 19% observed at 9 minutes into the 10-minute infusion period, as compared with vehicle. Heart rate remained decreased by 18% at the end of the monitoring period. A notable dose-dependent increase in QT and QTcB intervals was observed with 10, 15, and 20 mg base/kg doses of Compound A. A maximum increase of QTcB interval by approximately 9%, 13%, and 16% at 10 to 18 minutes after infusion initiation was observed with Compound A at 10, 15, and 20 mg base/kg doses respectively, as compared with time-matched vehicle. QTcB interval remained increased by 10% at the end of the monitoring period. At the end of each infusion (10 minutes) the mean plasma concentrations were 1166, 2362, 4269, and 6707 ng/mL, respectively, for 5, 10, 15, and 20 mg base/kg. There were no remarkable Compound A-related effects on arterial pressure, PR interval, QRS duration, or qualitative ECG parameters. Based on these results the NOAEL for hemodynamic and ECG endpoints was 10 mg base/kg following IV administration.

Example 3: 4-Week Oral Gavage Pivotal Toxicity Study with a 4-Week Recovery Period in the Dog Compound A was administered via oral gavage to 5 groups of male and female purebred Beagle dogs (4 or 6/sex/group) at dose levels of 0.375, 0.75, and 1.5 mg base/kg/dose QW for up to 4 weeks; or 0.375 mg base/kg/dose BIW for up to 4 weeks. Vehicle control animals (0.5% w/v methylcellulose in reverse osmosis water) were also dosed BIW and served as concurrent controls. Following the last dose, two animals/sex/group in all but the 0.375 mg base/kg/dose group were scheduled for a 4-week treatment-free recovery period.

Weekly oral administration of Compound A resulted in moribund euthanasia of 11 animals (1 male at 0.375 mg base/kg/dose administered QW, 2 males and 1 female at 0.75 mg base/kg/dose, and 3 males and 4 females at 1.5 mg base/kg/dose) between study Days 13 and 23. The moribund condition of these animals was attributed to Compound A-related gastric mucosal ulceration and/or acute inflammation. All other animals survived to their scheduled necropsy. As a result of severe toxicity in the 1.5 mg base/kg/dose, dosing of this group was suspended on Day 15 for the remaining 3 males and 2 females; these animals remained on study and underwent at least 4 weeks of recovery following the last dose.

Electrocardiograms were recorded once during the predose phase, and predose and approximately 3 hours postdose for all animals dosed on Day 22 of the dosing phase. Electrocardiograms were recorded using eight leads and routine quantitative measurements of ECGs were made on a single lead. The QTc interval was calculated using the Fridericia method. A qualitative review for rhythm abnormalities and disturbances of collected ECGs was performed.

No Compound A-related abnormalities in rhythm or waveform morphology or on HR, RR interval, PR interval, QRS duration, QT interval, or QTc interval were found at any dose level evaluated (ie, <1.5 mg base/kg/dose). Therefore, the NOEL for CV and respiratory changes were 0.75 mg base/kg/dose QW and 0.375 mg base/kg/dose BIW, the highest dose levels with CV and respiratory endpoints evaluated. Steady state Cmax values at 0.75 mg base/kg/dose QW were 36.2 ng/mL (males) and 40.8 ng/mL (females); and at 0.375 mg base/kg/dose BIW were 17.7 ng/mL (males) and 19.0 ng/mL (females).

V. Nonclinical Pharmacokinetics and Metabolism

In vitro and in vivo studies were conducted to characterize the absorption, PK, distribution, excretion, and metabolism of Compound A. Compound A is a besylate salt of the free base and all concentrations and PK parameters refer to the free base. Robust and reproducible bioanalytical methods for the determination of Compound A free base concentrations were developed and used in PK and TK studies. Pharmacokinetics and oral bioavailability of Compound A were evaluated in mice, rats, dogs, and monkeys. Human PK parameters and exposures were predicted using allometric scaling. Mice and dogs were the species used for nonclinical toxicology assessment. In vitro studies were conducted to assess Compound A absorption, metabolism, plasma protein binding, CYP reaction phenotyping, and the inhibition and induction potential for CYP enzymes. Excretion of non-radiolabeled Compound A was studied in rats.

Example 1: Absorption and Pharmacokinetics

The PK of Compound A was evaluated in CD-1 mice, Sprague Dawley rats, Beagle dogs, and Cynomolgus monkeys (Report QC6688-ADME-2004) following IV and oral administration. The plasma concentration of Compound A was determined by liquid chromatography with mass spectrometric detection (LC-MS/MS). Mean PK parameters following IV or oral administration of Compound A are presented in Table 29 and Table 30.

TABLE 29

Mean Plasma Pharmacokinetic Parameters of Compound A Following a Single Intravenous Dose to Animals

| Species[a] | Sex | Dose (mg base/kg) | $AUC_{last}$ (ng · hr/mL) | $AUC_\infty$ (ng · hr/mL) | CL (mL/min/kg) | $V_{ss}$ (mL/kg) | $t_{1/2, z}$ (hr) |
|---|---|---|---|---|---|---|---|
| Mouse | Female | 5 | 2215 | 2664 | 32 | 7510 | 3.8 |
| Rat | Female | 5 | 680 | 733 | 115 | 26250 | 3.6 |
|  |  |  | (56) | (74) | (12) | (2442) | (0.5) |
| Dog | Male | 1 | 1302 | 1944 | 9 | 11058 | 15.5 |
|  |  |  | (250) | (519) | (3) | (1183) | (1.3) |
| Monkey | Male | 1 | 912 | 983 | 18 | 17119 | 12.0 |
|  |  |  | (191) | (228) | (5) | (1696) | (1.6) |

$AUC_{last}$ = area under the plasma concentration-time curve from time zero to last measurable concentration;
$AUC_\infty$ = area under the plasma concentration-time curve extrapolated from time 0 to infinity;
CL = clearance;
hr = hour;
PK = pharmacokinetic;
SD = standard deviation;
$t_{1/2, z}$ = apparent half-life of the terminal phase of the concentration-time curve;
$V_{ss}$ = volume of distribution at steady state.
[a]In mouse, composite PK sampling was obtained from n = 3 animals/time point. In other species, PK parameters are from n = 3 animals and values shown are mean and SD (in parentheses).

TABLE 30

Mean Plasma Pharmacokinetic Parameters of Compound A Following a Single Oral Dose to Animals

| Species[a] | Sex | Dose[a] (mg base/kg) | $t_{max}$ (hr) | $C_{max}$ (ng/mL) | $AUC_{last}$ (ng · hr/mL) | $tt_{1/2, z}$ (hr) | % F |
|---|---|---|---|---|---|---|---|
| Mouse | Female | 10 | 0.5 | 510 | 2007 | 1.7 | 38 |
| Rat | Female | 5 | 2.0 | 47 | 222 | 3.0 | 33 |
|  |  |  | (2.0-4.0) | (14) | (52) | (0.7) | (10) |
|  | Female | 15 | 2.0 | 123 | 570 | 2.9 | 28 |
|  |  |  | (0.25-2.0) | (70) | (246) | (0.3) | (14) |
|  | Female | 50 | 6.0 | 621 | 4652 | 3.0 | 74 |
|  |  |  | (2.0-8.0) | (215) | (1672) |  | (34) |
| Dog | Male | 1 | 2.0 | 69 | 1089 | 15.0 | 84 |
|  |  |  | (1.0-6.0) | (18) | (245) | (3.0) | (41) |
|  | Male | 3 | 1.0 | 298 | 3792 | 19.4 | 100 |
|  |  |  | (0.5-1.0) | (63) | (674) | (4.5) | (80) |
|  | Male | 6 | 1.0 | 627 | 8792 | 17.8 | 100 |
|  |  |  | (1.0-2.0) | (84) | (512) | (2.4) | (46) |
| Monkey | Male | 5 | 6.0 | 187 | 3618 | 12.9 | 82 |
|  |  |  | (6.0-6.0) | (49) | (1537) | (2.7) | (70) |

$AUC_{last}$ = area under the plasma concentration-time curve from time zero to time of last measurable concentration;
$C_{max}$ = maximum plasma concentration;
F = oral bioavailability;
hr = hour;
PK = pharmacokinetic;
SD = standard deviation;
$t_{1/2, z}$ = apparent half-life of the terminal phase of the concentration-time curve;
$t_{max}$ = time of Cmax.
[a]In mouse, PK parameters were determined using composite plasma samples obtained from n = 3 animals/time point. In other species, PK parameters are from n = 3 animals and values shown are mean and SD (in par Following IV dosing, the systemic clearance of Compound A was moderate in mice, dogs, and monkeys (approximately 30% to 40% of liver blood flow) and high in rats (greater than liver blood flow). The volume of distribution across species ranged from approximately 12- to 43-fold the total body water volume, suggesting extensive distribution into tissues. Disparate half-lives were noted between rodents and non-rodents with values ranging from either 2 to 4 hours in rodents or from 12 to 20 hours in non-rodents.

The permeability of Compound A in MDR1(human P-gp)-MDCK cells was $0.5 \times 10^{-6}$ cm/s in A→B direction and $16.5 \times 10^{-6}$ cm/s in B→A direction with an efflux ratio of 33, indicating that Compound A is a P-gp substrate.

Following oral dosing, Compound A was rapidly and well absorbed in mice, rats, dogs, and monkeys with a median time to peak plasma concentration ($t_{max}$) ranging from 0.5 to 6 hours postdose and oral bioavailability ranging from 28% to 74% in rodents and from 82% to 100% in dogs and monkeys.

Due to disparate half-lives between mice and dogs, toxicology studies in mice were conducted following daily dosing (5 consecutive dosing days per week for 4 weeks) while studies in dogs followed either a QW, BIW, or Q2W dosing regimen for 4 weeks. Following multiple oral doses of Compound A to mice, the systemic exposure increased in a greater than dose-proportional manner from 5 to 15 mg base/kg and in a dose-proportional manner from 15 to 45 mg base/kg (Report QC6688-TOX-3001), while in dogs, Compound A exposure increased in a dose-proportional manner (Report QC6688-TOX-3002, Report-QC6688-TOX-3006). No accumulation was observed in either species following repeat administration in the dosing schedule used in toxicology studies and no sex differences in TK were noted in either species.

Example 2: Distribution

The volume of distribution was very high in mice, rats, dogs and monkeys (approximately 12- to 43-fold total body water volume), suggesting extensive distribution of Compound A into tissues. Compound A was highly bound (83% in human plasma, and 83% to 92% in animal plasma) to plasma proteins with no notable interspecies differences. Distribution of Compound A into tissues and the transport of Compound A across the placental barrier have not been evaluated.

Example 3: Metabolism

The metabolism of Compound A was evaluated using cryopreserved primary hepatocytes of male mouse, rat, dog, and monkey and mixed gender human (Report QC6688-ADME-2006). The metabolic stability of Compound A was greater in rat and dog followed by human and monkeys while being least stable in mouse hepatocytes. A single metabolite (M1; an oxidative deamination metabolite) was identified in all the species studied except mice and qualitatively levels of M1 formed in human hepatocytes were comparable to those formed in dog hepatocytes, one of the species used for preclinical safety testing and indicating that human hepatocytes did not form any unique metabolite.

Studies using recombinant human CYP enzymes have shown that CYP3A4 appears to be predominantly responsible for the oxidative metabolism of Compound A with minor contributions from other CYP enzymes (Report QC6688-ADME-2006). The role of non-CYP enzymes in the metabolism of Compound A is yet to be ascertained.

Example 4: Excretion

In bile duct cannulated rats, following IV dosing of non-radiolabeled Compound A, an average of 26.3% of the dose (8.5% of dose in urine and 17.8% of dose in bile) was excreted intact in the 24-hour period post dosing, indicating that metabolism may play a significant role in the elimination of Compound A and excretion of intact Compound A is not the primary mode of elimination. Excretion of Compound A or its related components into breastmilk has not been evaluated.

Example 5: In Vitro Drug-Drug Interactions

Cytochrome P450 inhibition potential of the major CYP isozymes (CYPs 1A2, 2C9, 2C19, 2D6, and 3A4) by Compound A was evaluated using pooled human liver microsomes. Compound A (up to 50 µM) had little to no direct inhibitory effect on CYPs 1A2, 2C9, and 2D6 and showed minimal inhibition of CYP2C19 and CYP3A4 with IC50 values >50 µM. Hence, at clinically relevant concentrations, Compound A is not expected to cause any drug-drug interactions due to CYP inhibition.

Cytochrome P450 induction potential of Compound A (0.03 to 10 µM) was evaluated using cultures of cryopreserved human hepatocytes and following incubation up to 3 days. Ability to induce mRNA expression of CYPs1A2, 2B6, and 3A4 was determined (Report QC6688-ADME-2007). Compound A caused no increase in mRNA (<2-fold over vehicle control) indicating that Compound A is not an inducer of CYP1A2, 2B6, and 3A4.

In summary, Compound A has minimal potential to cause drug-drug interactions with co-administered drugs that are CYP substrates.

Example 6. Compound A Predicted Human Pharmacokinetics

In oncology subjects, based on the PK parameters of Compound A in animal models and using allometric scaling, Compound A is predicted to have moderate clearance (9.4 mL/min/kg) and high volume of distribution (17.6 L/kg, approximately 31-fold total body water volume). Using the allometry derived PK parameters and an assumption of 80% oral bioavailability, the predicted steady state systemic exposure (AUCt) of Compound A following QW administration of a 1.25 mg oral dose in a 60-kg human is 29 ng·hr/mL.

VI. Toxicology

A series of exploratory and pivotal toxicity studies in mice and dogs of up to 4 weeks, and an in vitro genetic toxicity study were conducted to characterize the toxicity profile of Compound A. In vivo studies were conducted using the oral route as it is the intended route of administration in clinical trials. Pivotal toxicity studies (4-week oral repeat dose with a 4-week recovery period; mice and dogs) were conducted using Compound A administered QDx5/week or QODx3/week dosing schedule in mice, and QW, BIW, or Q2W dosing in dogs. Pivotal toxicity studies were conducted in accordance with the requirements of the United States FDA GLP Regulations for Nonclinical Laboratory Studies (21 CFR Part 58), the OECD Principles of GLP, ENV/MC/CHEM(98)17 (revised in 1997, issued January 1998), and the ICH S9 guideline, 2009.

Example 1: 4-Week Toxicity Study with a 4-Week Recovery Period in Mice

Compound A was administered by oral gavage to male and female Crl:CD1(ICR) mice (10 or 15/sex/group) at dosage levels of 0, 5, 15, and 45 mg base/kg/dose, or 25 mg base/kg/dose. One dosing schedule was QDx5/week for a total of 4 weeks (dosage levels of 5, 15, and 45 mg base/kg/dose). Animals were terminated the day after the final dose of the fourth cycle was administered. Another group of animals was administered 25 mg base/kg/dose QOD×3/week for a total of 4 weeks and were terminated the day after the final dose. Dosing was followed by a 4-week recovery period (5/sex/group at dosage levels of 0, 15, 45, or 25 mg base/kg/dose).

Additional animals (6/sex in the control group, and 36/sex/group in the test article groups) for TK evaluation were dosed on the same schedule as the toxicity animals for up to 26 days.

Assessment of toxicity was based on mortality, clinical observations, body weight, food consumption, ophthalmic evaluations, and clinical and anatomic pathology. Blood samples were collected from TK animals for TK evaluations.

Five animals (4 males and 1 female) administered 45 mg base/kg/dose were sacrificed in moribund condition as early as Day 7 of the dosing phase due to Compound A-related toxicity. All of these were TK subgroup animals. Clinical observations for these animals included: thin, ataxic, hunched, hypoactive, squinting eyes, rough haircoat, pale ears/body, and/or piloerection. Since these were the TK subgroup animals, they were not examined histologically. One 25 mg base/kg/dose female was sacrificed on Day 20 of the dosing phase because of limited use of its right hind leg, a finding consistent with an injury, and therefore, this unscheduled sacrifice was not considered Compound A-related. There were no Compound A-related unscheduled mortalities in toxicity subgroup animals.

There were no test article-related ophthalmology effects.

All other test article-related findings are presented below.
Compound A-related adverse findings:
  Rough haircoat at ≥15 mg base/kg/dose, piloerection and hunched appearance at ≥25 mg base/kg/dose, pale ears/body and thin appearance at 45 mg base/kg/dose.
  Marked decreases in platelet and reticulocyte counts at 45 mg base/kg/dose.
  Minimal to marked fibrosis in the medullary space of the sternum, associated with minimally to moderately decreased hematopoietic tissue (hypocellular) within affected sternebrae at 15 and 45 mg base/kg/dose.
  Minimal to moderate increase in periosteal, endosteal, and trabecular lamellar bone (hyperostosis) with activated osteoblasts at 15 and 45 mg base/kg/dose.
  Minimal to moderate myeloid hyperplasia in the bone marrow of the sternum at ≥15 mg base/kg/dose.
  Moderate fibrosis in the femoral bone marrow at 45 mg base/kg/dose (one male).
  Minimal to marked depletion of marginal zone lymphocytes in the spleen of males at 15 mg base/kg/dose, females at 25 mg base/kg/dose, and males and females at 45 mg base/kg/dose.

Compound A-related findings which were considered non-adverse because they occurred on a single day, were self-limiting, were without toxicological consequence, were of small magnitude, and/or did not have a microscopic correlate consisted of the following:
  Mean body weight loss at 45 mg base/kg/dose (8.6% and 12.6% lower compared to controls for males and females, respectively, on Day 27).
  Mildly to moderately lower red cell mass (RBC count, hemoglobin, and hematocrit) at ≥5 mg base/kg/dose.
  Mildly to moderately lower platelet and absolute reticulocytes at 5 and 15 mg base/kg/dose.
  Minimally to mildly lower mean corpuscular hemoglobin, mean corpuscular hemoglobin concentration, and absolute neutrophil count (also in males administered 5 mg base/kg/dose) in animals administered ≥15 mg base/kg/dose and minimally higher absolute monocyte count in males administered 15 or 25 mg base/kg/dose and females administered ≥5 mg base/kg/dose.
  Minimally lower total protein at 25 mg base/kg/dose and minimally lower albumin at 25 or 45 mg base/kg/dose.
  Minimal or slight increases (number and/or size) in megakaryocytes in the bone marrow of the sterum at ≥5 mg base/kg/dose.
  Decreased seminal vesicle weights at ≥15 mg base/kg/dose (no microscopic correlate).
  Decreased uterus weights at 15 and 45 mg base/kg/dose (no microscopic correlate).
  Decreased testes weights at 15 or 45 mg base/kg/dose at the recovery sacrifice only (no microscopic correlate).
  In the spleen, increased extramedullary hematopoiesis (minimal to marked) at ≥15 mg base/kg/dose and in one female at 5 mg base/kg/dose; correlated with increased absolute and relative spleen weights at 15 or 45 mg base/kg/dose.

All test article-related findings demonstrated partial to complete reversibility following a 4-week treatment-free period.

Compound A TK data are summarized in Table 31.

Exposure to Compound A increased with the increase in dose level from 5 to 45 mg base/kg/dose. The increases in Cmax and AUC0-24 values were generally greater than dose proportional from 5 to 15 mg base/kg/dose, and approximately dose proportional from 15 to 45 mg base/kg/dose. No consistent sex differences in mean Compound A Cmax and AUC0-24 values were observed. No accumulation of Compound A was observed after multiple dosing of Compound A in mice.

Based upon mortality, clinical signs of toxicity, hematology, and histopathology findings the STD10 was >45 mg base/kg/dose (corresponded to mean steady state Cmax and AUC0-24 values of 2,620 ng/mL and 29,000 ng·hr/mL, and 2,130 ng/mL and 26,500 ng·hr/mL, in males and females respectively) following a QD×5/week schedule, and was >25 mg base/kg/dose (corresponded to mean steady state Cmax and AUC0-24 values of 1,450 ng/mL and 17,800 ng·hr/mL, and 1,740 ng/mL and 17,500 ng·hr/mL, in males and females respectively) following a QOD×3 weekly schedule. The NOAEL was 5 mg base/kg/dose (corresponded to mean steady state Cmax and AUC0-24 values of 276 ng/mL and 2,010 ng·hr/mL, and 276 ng/mL and 2,410 ng·hr/mL, in males and females respectively) following a QD×5/week schedule. No NOAEL was identified for the QOD×3/week schedule.

TABLE 31

Summary of Compound A Toxicokinetic Parameters Following Oral Dosing in Mice

| Interval (Day) | Dose Level (mg base/kg/dose) | Sex | $C_{max}$ (ng/mL) | $AUC_{0-24}$ (ng · hr/mL) |
| --- | --- | --- | --- | --- |
| 1 | 5 | M | 230 | 2270 |
|   |   | F | 201 | 1500 |
|   | 15 | M | 1020 | 13000 |
|   |   | F | 850 | 9680 |
|   | 45 | M | 3130 | 35200 |
|   |   | F | 3570 | 36300 |
|   | 25[a] | M | 1530 | 21900 |
|   |   | F | 1830 | 20300 |
| 26 | 5 | M | 276 | 2010 |
|   |   | F | 276 | 2410 |

TABLE 31-continued

Summary of Compound A Toxicokinetic Parameters Following Oral Dosing in Mice

| Interval (Day) | Dose Level (mg base/kg/dose) | Sex | $C_{max}$ (ng/mL) | $AUC_{0-24}$ (ng · hr/mL) |
|---|---|---|---|---|
| | 15 | M | 628 | 7960 |
| | | F | 769 | 8640 |
| | 45 | M | 2620 | 29000 |
| | | F | 2130 | 26500 |
| | 25[a] | M | 1450 | 17800 |
| | | F | 1740 | 17500 |

$AUC_{0-24}$ = area under the plasma concentration curve from time zero to 24 hours;
Cmax = maximum plasma concentration;
F = female;
hr = hour;
M = male;
QOD = every other day.
[a] Animals administered 25 mg base/kg/dose were dosed QOD × 3/week. All other dose groups were dosed 5 days on/2 days off per week. Animals were terminated the day after the final dose was administered.

Example 2: 4-Week Toxicity Study with a 4-Week Recovery Period in Dogs

In an initial study, Compound A was administered via oral gavage to 5 groups of male and female purebred Beagle dogs (4 or 6/sex/group) at dose levels of 0, 0.375, 0.75, or 1.5 mg base/kg/dose QW for up to 4 weeks; or 0.375 mg base/kg/dose BIW for up to 4 weeks. Following the last dose, 2 animals/sex/group in all but the 0.375 mg base/kg/dose QW group were scheduled for a 4-week treatment-free recovery period.

Weekly oral administration of Compound A resulted in moribund euthanasia of 11 animals (1 male at 0.375 mg base/kg QW, 2 males and 1 female at 0.75 mg base/kg, and 3 males and 4 females at 1.5 mg base/kg) between study Days 13 and 23. The moribund condition of these animals was attributed to Compound A-related gastric mucosal ulceration and/or acute inflammation. As a result of severe toxicity in the 1.5 mg base/kg/dose group, dosing of this group was suspended on Day 15 (prior to the scheduled third dose) for the surviving 3 males and 2 females; these animals remained on study and underwent at least 4 weeks of recovery following the last dose. All other animals survived to their scheduled necropsy.

Adverse findings were observed at all dose levels and schedules (ie, ≥0.375 mg base/kg/dose, QW or BIW). Primary toxicities consisted of mucosal ulceration, acute and/or subacute inflammation, and mucosal epithelial atrophy of GI tract tissues.

The following changes in animals administered ≥0.375 mg base/kg/dose (QW or BIW) were considered Compound A-related, were noted in animals sacrificed in moribund condition and/or animals that survived to scheduled necropsy, and were considered adverse:
  Hypoactivity, thin appearance, vomitus, red/black/liquid/nonformed/mucoid feces, dehydration, body weight loss, decreased food consumption, pyrexia, and/or evidence of GI tract discomfort.
  Hematology findings of mildly to moderately decreased red cell mass, mildly to markedly decreased platelet count, markedly decreased reticulocyte count, mildly to moderately decreased eosinophil counts, mildly to moderately increased absolute monocyte and large unstained cell counts, moderately to markedly decreased neutrophil counts (2 females administered 1.5 mg base/kg/dose) or mildly to moderately increased neutrophil counts (other animals administered ≥0.375 mg base/kg/dose).
  Clinical chemistry findings of mildly to moderately decreased albumin and albumin:globulin ratio, mildly decreased calcium, mildly to moderately decreased inorganic phosphorus, mildly to moderately increased cholesterol, minimally to mildly increased alkaline phosphatase activity.
  Slight to marked mucosal ulceration and/or moderate acute inflammation in the stomach.
  Minimal to marked acute or subacute inflammation and ulceration in the jejunum, ileum, cecum, colon, and/or rectum.
  Slight to moderate mucosal epithelial atrophy in the jejunum and/or ileum.
  Slight ulceration in the esophagus (1 female administered 1.5 mg base/kg/dose).

The following changes were noted in animals administered ≥0.375 mg base/kg/dose (QW or BIW) that survived to their respective necropsy and were considered Compound A-related, but were not considered adverse because they were of low magnitude and/or incidence, were without consequence, and/or did not have a microscopic correlate:
  Hematology findings of minimally to mildly decreased red cell mass (animals administered 0.375 mg base/kg/dose QW [only males] or BIW, females administered 0.75 mg base/kg/dose, and males administered 1.5 mg base/kg/dose), mildly decreased absolute reticulocyte count (females administered 1.5 mg base/kg/dose), mildly to moderately increased platelet count (males administered 0.375 mg base/kg/dose QW or BIW and in animals administered 1.5 mg base/kg/dose), mildly increased white blood cell (WBC), absolute neutrophil, and large unstained cell counts (males administered 1.5 mg base/kg/dose).
  Clinical chemistry findings of minimally increased globulin (animals administered 0.375 mg base/kg/dose BIW, females administered 0.75 mg base/kg/dose, and animals administered 1.5 mg base/kg/dose), mildly increased cholesterol (females administered 0.75 mg base/kg/dose), minimally increased alkaline phosphatase activity (females administered 0.375 mg base/kg/dose BIW or 0.75 mg base/kg/dose and animals administered 1.5 mg base/kg/dose), minimally decreased calcium (males administered 1.5 mg base/kg/dose), mildly decreased inorganic phosphorus (females administered 0.75 mg base/kg/dose).

Other findings in the animals that were euthanized moribund were attributed to an inflammatory response (extramedullary hematopoiesis in the spleen and increased myeloid:erythroid ratio in the sternal marrow), septicemia secondary to mucosal ulceration in the GI tract (inflammation in multiple lymph nodes, SC edema, or acute inflammation in the heart or liver), and/or stress associated with the moribund condition (depletion of lymphocytes in the thymus).

There were no Compound A-related effects on mean body weight, food consumption, coagulation, urinalysis, electrocardiography, ophthalmology, macroscopic observations, or organ weights in any of the animals that survived to their scheduled necropsy at ≥0.375 mg base/kg/dose.

All of the above findings showed complete recovery following a 4-week treatment-free period.

Exposure to Compound A, when dosed weekly, increased in a dose-dependent manner from 0.375 to 1.5 mg base/kg/dose on Day 1 and from 0.375 to 0.75 mg base/kg/dose on Day 22. Exposures were comparable between males and females, and no consistent differences in TK parameters were observed. No accumulation of Compound A was observed after multiple dosing of Compound A in dogs. A summary of TK parameters is presented in Table 32. The concentration-time profiles in animals administered 0.375 mg base/kg/dose QW were similar to those in animals administered 0.375 mg base/kg/dose BIW on Days 1 and 22.

TABLE 32

Summary of Mean Toxicokinetic Parameters for Compound A Following Oral Dosing in Dogs in the 4-week Toxicity Study with a 4-week Recovery Period

| Interval (Day) | Dose Level (mg base/kg/dose) | Sex | $C_{max}$ (ng/mL) | $AUC_{0-168}$ (ng · hr/mL) | $AUC_{0-72}$ (ng · hr/mL) |
|---|---|---|---|---|---|
| 1 | 0.375 | M | 17.2 | 503 | NC |
|  |  | F | 17.2 | 435 | NC |
|  | 0.75 | M | 34 | 955 | NC |
|  |  | F | 41.6 | 1180 | NC |
|  | 1.5[a] | M | 90.6 | 2530 | NC |
|  |  | F | 80.0 | 2680 | NC |
|  | 0.375[b] | M | 16.9 | NC | 420 |
|  |  | F | 15.2 | NC | 383 |
| 22 | 0.375 | M | 21.9 | 384 | NC |
|  |  | F | 15.5 | 269 | NC |
|  | 0.75 | M | 36.2 | 645 | NC |
|  |  | F | 40.8 | 719 | NC |
|  | 0.375[b] | M | 17.7 | NC | 307 |
|  |  | F | 19.0 | NC | 296 |

$AUC_{0-168}$ = area under the plasma concentration curve from time zero to 168 hours;
$AUC_{0-72}$ = area under the plasma concentration curve from time zero to 72 hours;
$C_{max}$ = maximum plasma concentration;
F = female;
hr = hour;
M = male;
NC = Not calculated.
[a]Animals administered 1.5 mg base/kg/dose received two doses and then began recovery on Day 15. Therefore, no Day 22 toxicokinetic data are available.
[b]Animals were dosed twice weekly in this group, compared with once weekly for all other dose groups.

Based upon clinical signs of toxicity, mortality, adverse effects on body weights, clinical pathology, and histopathology at QW doses ≥0.375 mg base/kg/dose, the HNSTD and the NOAEL for the QW or BIW dose schedule were not determined (ie, were <0.375 mg base/kg/dose). The QW 0.375 mg base/kg/dose corresponds to respective mean Cmax and AUC0-168 values of 21.9 ng/mL and 384 ng·hr/mL (males), and 15.5 ng/mL and 269 ng·hr/mL (females) on Day 22 of the dosing phase; the BIW 0.375 mg base/kg/dose corresponds to respective mean Cmax and AUC0-72 values of 17.7 ng/mL and 307 ng·hr/mL (males), and 19.0 ng/mL and 296 ng·hr/mL (females) on Day 22 of the dosing phase.

Example 3. 4-Week Toxicity Study (No Recovery Period) in Dogs

In a second dog study, Compound A was administered via oral gavage to 4 groups of male and female purebred Beagle dogs (4/sex/group) at dose levels of 0, 0.125, or 0.25 mg base/kg/dose QW (for a total of 5 doses), or 0.5 mg base/kg/dose Q2W (for a total of 3 doses) for at least 4 weeks (Report QC6688-TOX-3006). All animals survived to the terminal sacrifice.

There were no Compound A-related changes in clinical observations, body weight parameters, food consumption, organ weights, coagulation, clinical chemistry, urinalysis parameters, or macroscopic findings.

The following changes were considered the result of Compound A administration:
Treatment-related adverse findings:
  Moderate acute inflammation in the ileum and marked acute inflammation in the cecum (single female administered 0.25 mg base/kg/dose QW)
  Minimal acute inflammation in the cecum (single male administered 0.5 mg base/kg/dose Q2W)
Treatment-related but not considered adverse due to low magnitude/severity and/or were without microscopic correlate:
  Minimal increase in absolute platelet counts (0.5 mg base/kg/dose administered Q2W)
  Minimal increase in absolute monocyte counts (females administered 0.25 mg base/kg/dose QW)
  Minimal increase in extramedullary hematopoiesis (four animals administered 0.5 mg base/kg/dose Q2W and a single female administered 0.25 mg base/kg/dose QW)
  Slight increase in myeloid:erythroid ratio in the bone marrow of the sternum and femur (single female administered 0.25 mg base/kg/dose QW).

A summary of TK parameters is presented in Table 33.

TABLE 33

Summary of Mean Toxicokinetic Parameters for Compound A Following Oral Dosing in Dogs in the 4-week Toxicity Study (No Recovery Period)

| Interval (Day) | Dose Level (mg base/kg/dose) | Sex | $C_{max}$ (ng/mL) | $AUC_{0-96}$ (ng · hr/mL) |
|---|---|---|---|---|
| 1 | 0.125 | M | 5.81 | 114 |
|  |  | F | 5.77 | 127 |
|  |  | Sexes combined | 5.79 | 120 |
|  | 0.25 | M | 11.9 | 335 |
|  |  | F | 12.1 | 343 |
|  |  | Sexes Combined | 12.0 | 339 |
|  | 0.5[a] | M | 24.0 | 762 |
|  |  | F | 26.6 | 729 |
|  |  | Sexed Combined | 25.3 | 746 |
| 15 | 0.125 | M | 4.89 | 107 |
|  |  | F | 5.54 | 141 |
|  |  | Sexes Combined | 5.26 | 127 |
|  | 0.25 | M | 10.5 | 302 |
|  |  | F | 11.5 | 272 |
|  |  | Sexes Combined | 11.0 | 287 |
|  | 0.5[a] | M | 22.7 | 653 |
|  |  | F | 21.4 | 618 |
|  |  | Sexes Combined | 22.0 | 636 |

$AUC_{0-96}$ = area under the plasma concentration curve from time zero to 96 hours; $C_{max}$ = maximum plasma concentration; F = female; hr = hour; M = male; Q2W = once every two weeks; QW = once weekly.
[a]Animals administered 0.5 mg base/kg/dose were dosed Q2W for 4 weeks (2 doses in total).
Other groups were dosed QW.

Exposure to Compound A increased with the increase in dose level from 0.125 to 0.5 mg base/kg/dose on Day 1, and increases in mean Cmax and AUC0-96 values were approximately dose-proportional. On Day 15, exposure to Compound A increased with the increase in dose level from 0.125 mg base/kg/dose QW to 0.5 mg base/kg/dose Q2W, and increases were approximately dose-proportional. No consistent sex differences in mean Cmax and AUC0-96 values were observed. No accumulation of Compound A was observed after multiple doses.

Based upon the adverse microscopic findings (inflammation in the ileum and/or cecum) of a single female at 0.25 mg base/kg/dose (QW administration) and a single male at 0.5 mg base/kg/dose (Q2W administration), the QW administration NOAEL was considered to be 0.125 mg base/kg/dose, corresponding to combined Day 15 mean Cmax and AUC values of 5.26 ng/mL and 127 ng·hr/mL, respectively. The Q2W administration NOAEL was not determined (ie, <0.5 mg base/kg/dose). For QW dosing, the HNSTD was 0.25 mg base/kg/dose QW, corresponding to combined Day 15 mean Cmax and AUC values of 11.0 ng/mL and 287 ng·hr/mL, respectively. For Q2W administration, the HNSTD was 0.5 mg base/kg/dose, corresponding to combined Day 15 mean Cmax and AUC values of 22.0 ng/mL and 636 ng·hr/mL, respectively.

Example 4: In Vitro Genotoxicity

Compound A was found to be negative for mutagenicity in a bacterial reverse mutation assay (using *Salmonella typhimurium* TA98 and TA100 strains) up to the maximum tested concentration of 500 μg/mL, both in the presence and absence of S9 exogenous mammalian metabolic activation System.

Example 5. Exploratory Toxicity Study in Mice

The purpose of this study was to determine the tolerability and TK of Compound A when administered by oral gavage to male and female CD-1 mice on two different dose schedules. One schedule consisted of 5 consecutive days of dosing, followed by a 2 day dosing holiday, followed by a further 5 days of consecutive dosing (5 days on/2 days off); another schedule consisted of dosing on Days 1, 3, 5, 8, 10 and 12 (QOD×3/week). Animals were sacrificed on the day after the final dose was administered.

Compound A was administered to groups of 6 mice/sex/group at dose levels of 0, 10, 30, or 60 mg/kg/dose on the 5 days on/2 days off schedule; or 60 mg/kg/dose on the QOD schedule. Additional animals were included for TK evaluation.

All mice survived until the scheduled sacrifice with the exception of a single TK animal. Gavage trauma was confirmed as the cause of morbidity for the TK animal; therefore, this early death was considered not Compound A-related.

A slight, dose-dependent reduction in body weight gain or body weight loss was noted at all dose levels on the 5 days on/2 days off schedule. At the 60 mg/kg/dose, there was a less severe reduction in body weight gain by the QOD schedule as compared with the 5 days on/2 days off schedule. There were no test article related clinical observations noted over the course of this study.

Changes in several hematology parameters were noted in male and female mice administered Compound A.

Circulating platelets were reduced in mice at all dose levels at the end of the study. The effect was slightly reduced in mice administered 60 mg/kg/dose QOD compared with 60 mg/kg/dose 5 days on/2 days off. At 10 mg/kg/day 5 days on/2 days off, there was a >2-fold increase in platelets on Day 8 (following the 2-day dosing holiday and compared with the end of the first dosing period); by the end of the second dosing period platelet levels were similar to those in other Compound A treated groups. An increase in mean platelet volume, suggestive of regenerative thrombopoiesis, generally accompanied the reduction in platelets at all dose levels at the end of the study, with the greatest response at 60 mg/kg/dose.

Red blood cell parameters (RBC counts, hematocrit, and hemoglobin) were generally reduced at 30 and 60 mg/kg/dose 5 days on/2 days off. A dose-dependent reduction in reticulocyte counts and percentages was generally noted at all dose levels on the 5 days on/2 days off schedule. Effects on RBC and/or reticulocyte parameters were less evident at 60 mg/kg/dose QOD.

A dose-dependent reduction in neutrophil counts was noted in all Compound A treated groups following the 5 days on/2 days off schedule, with the greatest reduction being approximately 90% compared with concurrent controls and pre-study values. At 60 mg/kg/dose following the QOD schedule, reduction ranged from 66% (females) to 83% (males) compared with concurrent controls.

Monocytes were increased at all dose levels, with the greatest effect at 30 and 60 mg/kg/dose, 5 days on/2 days off. Although the data were highly variable, basophil counts appeared to be increased in most mice at 60 mg/kg/dose 5 days on/2 days off.

Compound A-related microscopic changes were present in the sternum (bone and marrow), femur (marrow), and spleen.

In the sternal bone marrow of mice administered Compound A following the 5 days on/2 days off schedule, infarction was observed in mice at 60 mg/kg/dose, and the majority of mice at 30 mg/kg/dose. There was a dose response in incidence of affected animals and the number of affected sternebrae. Affected sternebrae also exhibited minimal to mild periosteal woven bone formation. In the femur of 1 male and 2 female mice dosed 60 mg/kg/dose 5 days on/2 days off and 1 male mouse dosed 30 mg/kg/dose, mild medullary fibrosis was present in the subphyseal diaphysis. In the spleen, at 30 or 60 mg/kg/dose 5 days on/2 days off, a minimal to moderate increase in myelopoiesis was present within the red pulp, correlating with increased spleen weights (up to 2-fold) in these groups. Minimal splenic myelopoiesis was noted in 1 male at 10 mg/kg/dose. (Mild or moderate lymphoid depletion was noted in the thymic cortex of individuals dosed 60 mg/kg/dose 5 days on/2 days off, and in a single female dosed 30 mg/kg/dose.) A minimal increase in lymphocyte apoptosis was present in the germinal follicles of mandibular and mesenteric lymph nodes of occasional males dosed 60 mg/kg/dose 5 days on/2 days off. Changes in the thymus and lymph nodes were considered nonspecific and consistent with response to general stress in affected animals.

In summary, no consistent sex differences in TK were observed. Systemic exposure ($AUC_{0-24}$ and $C_{max}$) increased with dose from 10 to 60 mg/kg/dose on Day 1 and Day 12 in both males and females. Upon repeat dosing of Compound A, no accumulation was observed. Minimal Compound A-related effects were noted in mice at 10 mg/kg/dose (5 days on/2 days off) and generally included reduced weight gain, reduced circulating platelets, neutropenia, reticulocytopenia, and a minimal increase in splenic myelopoiesis in a single male. Compound A-related effects in mice at 30 and 60 mg/kg/dose on the 5 days on/2 days off dosing schedule generally included body weight loss, reduced circulating platelets, reduced RBC parameters (RBC, hematocrit, hemoglobin, reticulocytes), neutropenia, monocytosis, and microscopic effects in the sternal bone (periosteal woven bone formation), sternal bone marrow (infarction), femur (medullary fibrosis) and spleen (increased myelopoiesis). The 60 mg/kg/dose QOD resulted in reduced weight gain, reduced platelets and neutrophils and increased monocytes. The magnitude of these effects was reduced compared with that of mice on the 5 days on/2 days off schedule.

Example 6: Exploratory Toxicity Study in Dogs

The purpose of this study was to determine the tolerability and TK of Compound A when administered by oral gavage to naïve male and female Beagle dogs following 2 different dosing schedules. The schedules compared consisted of dosing on Days 1, 3, 5, 8, 10, and 12 (QOD×3/week) or 5 consecutive days of dosing, followed by a 2 day dosing holiday, followed by a further 5 days of consecutive dosing (5 days on/2 days off) (Report SW14-1929). Animals were sacrificed on the day after the final dose was administered.

Compound A was administered to groups of 2 dogs/sex/group at dose levels of 0, 0.25, 0.5, or 1.0 mg/kg/dose QOD, or 0.5 mg/kg/dose 5 days on/2 days off.

One female dog dosed 0.5 mg/kg/day 5 days on/2 days off was sacrificed moribund in the evening on Day 12 due to adverse clinical signs (severely hypoactive, reduced respiration rate, cool to touch), body weight loss (10.8%), and reduced food consumption. Microscopic findings were generally consistent with a response to marked thrombocytopenia (noted on Days 9 to 12 for this dog) and included hemorrhage within a variety of tissues including axillary, mandibular and mesenteric lymph nodes, the lamina propria of the stomach, and the submucosa of the urinary bladder. In addition, hepatocellular atrophy was present in this animal, likely secondary to anorexia/weight loss. Moderate thymic lymphoid depletion was also present, correlated with hematologic observations of lymphopenia, and was likely secondary to general stress in this animal. The moribundity was considered Compound A-related.

All other dogs survived until the scheduled sacrifice on Day 13. Compound A-related weight loss was noted in individual dogs, primarily at 0.5 mg/kg/dose 5 days on/2 days off. Reduced food consumption was primarily noted in females at all dose levels and schedules; food consumption was only reduced in one male administered 0.5 mg/kg/dose 5 days on/2 days off during the last two days of the study.

Abnormal clinical observations were generally noted on Days 11 to 13 in animals dosed at 1 mg/kg/dose QOD or 0.5 mg/kg/dose 5 days on/2 days off, and primarily consisted of petechial or ecchymotic hemorrhage (or bruising) on the lips, gums, scrotum, abdomen, and around the mammary glands.

Reduced platelet counts were observed at 0.5 mg/kg/dose (both schedules) and 1 mg/kg/dose around Day 5; counts continued to reduce for the study duration to below 25,000/μL (marked thrombocytopenia) in most dogs at these dose levels. There was no reduction in platelet counts at 0.25 mg/kg/dose. A slight reduction in RBC parameters (RBC counts, hematocrit, and hemoglobin) was noted in some animals dosed 1 mg/kg/dose QOD or 0.5 mg/kg/dose 5 days on/2 days off towards the end of the study. White blood cell counts, primarily neutrophils, were generally reduced in females only at 1 mg/kg/dose QOD or 0.5 mg/kg/dose 5 days on/2 days off toward the end of the study.

While somewhat variable, some changes in monocytes, basophils, and eosinophils were also noted. Monocytes and basophils were generally reduced at 1 mg/kg/dose QOD or 0.5 mg/kg/dose 5 days on/2 days off, and in individual dogs at 0.25 and 0.5 mg/kg/dose QOD. In some dogs, this effect was sustained at the end of the study; however, there were several dogs in which a rebound effect was noted with a marked increase in monocyte counts on Days 12 and 13. Eosinophil data were highly variable in females but a dose-dependent reduction in eosinophil counts was generally noted in males during the second half of the study. Reduced serum potassium, calcium, and phosphorus levels were also observed in most dogs administered 0.5 and 1 mg/kg/dose.

Compound A-related microscopic findings were present primarily at 0.5 and 1 mg/kg/dose. Compound A-related microscopic findings generally occurred in more tissues or were more severe in males than in females. At 1 mg/kg/dose QOD or 0.5 mg/kg/dose 5 days on/2 days off, findings were present in the GI tract (hemorrhage and/or mucosal ulceration in the stomach/ileum and subacute inflammation in the cecum), bone marrow (decreased hematopoiesis), and/or represented hemorrhagic changes in a variety of tissues (colon, mandibular, mesenteric, cervical, inguinal and/or popliteal lymph node, epididymides, liver, testes, thymus, and scrotal skin, perithymic mediastinum, and/or mammary gland [skin]). One male at 0.5 mg/kg/dose QOD showed evidence of hemorrhage in the mandibular and mesenteric lymph nodes. Findings considered secondary to general stress and/or anorexia were noted at 1 mg/kg/dose QOD or 0.5 mg/kg/dose 5 days on/2 days off, including hepatocellular atrophy, pancreatic acinar cell atrophy, and thymic cortical lymphoid depletion (also noted at 0.5 mg/kg/dose QOD).

Exposure ($AUC_{0-24}$ and $C_{max}$) increased dose proportionally from 0.25 to 1 mg/kg/dose on Day 1 and Day 12. The exposures were comparable between males and females and no consistent sex differences in TK parameters were observed. After repeat dosing, no accumulation was noted when QOD schedule was used, while approximately 2- to 3-fold accumulation was noted after QD×5 schedule. There were generally no Compound A-related effects in dogs at 0.25 mg/kg/dose QOD. Marked thrombocytopenia and acute hemorrhage in mesenteric and mandibular lymph nodes were the primary findings at 0.5 mg/kg/dose QOD. At 1 mg/kg/dose QOD, findings generally consisted of marked thrombocytopenia, a slight reduction in RBC parameters, alterations in monocyte and basophil levels, and microscopic findings including hemorrhage and/or mucosal ulceration in the GI tract, decreased hematopoiesis in the bone marrow, and hemorrhagic changes in many tissues (colon, mandibular, mesenteric, cervical, inguinal and/or popliteal lymph node, epididymides and testes, liver, thymus, scrotal skin, perithymic mediastinum, and/or mammary gland [skin]). At 0.5 mg/kg/dose 5 days on/2 days off, findings included those described at 1 mg/kg/dose QOD in addition to weight loss in individuals and the moribund sacrifice of one female on Day 12.

VII. Preparation of Pharmaceutical Dosage Forms

Example 1: Oral Capsule

Compound A capsules are available in appropriate strengths and capsule sizes, containing only the active pharmaceutical ingredient in opaque, hard shell capsules. No excipients are used in the capsules.

VIII. Methods for the Treatment of Relapsed and/or Refractory Solid Tumors (Including Neuroendocrine Carcinomas (NEC)) and Non-Hodgkin's Lymphomas (NHLs)

Example 1: Patient Administration

Study Compound A-ST-001 is an open-label, Phase 1, dose escalation and expansion, First-In-Human (FIH) clinical study of Compound A in subjects with relapsed and/or refractory solid tumors (enriched for NECs) and Non-Hodgkin's lymphomas (NHLs). The dose escalation part (Part A) of the study will explore escalating oral doses of Compound A to estimate the MTD of Compound A. A Bayesian logistic regression model (BLRM) utilizing escalation with overdose control (EWOC) will help guide Compound A dose escalation decisions, with the final decisions made by a safety review committee (SRC). The expansion part (Part B) will further evaluate the safety and efficacy of Compound A administered at or below the MTD in selected expansion cohorts of approximately 20 evaluable subjects each, in order to further define the RP2D. One or more dosing regimens and/or disease subsets may be selected for cohort expansion (Part B).

Parts A and B will consist of 3 periods: Screening, Treatment and Follow-up. Screening Period The Screening Period starts 28 days (±3 days) prior to first dose of Compound A. The informed consent document (ICD) must be signed and dated by the subject and the administering staff prior to the start of any other study procedures. All screening tests and procedures must be completed within the 28 days (±3 days) prior to the first dose of Compound A.
Treatment Period During the Treatment Period, Compound A may initially be administered orally once weekly in each 4-week (28 day) Cycle. Compound A may be administered once weekly in the morning on an empty stomach (ie, ≥1 hour before breakfast) with at least 240 mL of water after an overnight fast lasting ≥6 hours in both Parts A and B.
Follow-Up Period In the Follow-up Period, subjects will be followed for 28 days (±3 days) after the last dose of the test compound or pharmaceutical composition for safety. After the Safety Follow-up visit, all subjects will be followed every subsequent 3 months (±2 weeks) for survival follow-up for up until 2 years or until death, lost to follow-up, or the End of Trial, whichever occurs first.
Subject Criteria Subjects must satisfy the following criteria to be enrolled in the study:

1. Subject is a man or woman ≥18 years of age, at the time of signing the informed consent document (ICD).
2. Subject must understand and voluntarily sign an ICD prior to any study-related assessments or procedures being undertaken.
3. Subject is willing and able to adhere to the study visit schedule and other protocol requirements.
4. Subjects with histological or cytological confirmation of advanced unresectable solid tumors (including small cell lung cancer (SCLC) and other neuroendocrine carcinomas (NEC)) or Non-Hodgkin's lymphomas (NHL) (diffuse large B-cell lymphoma (DLBCL) and indolent Non-Hodgkin's lymphomas (iNHL)).

Appropriate pathological features according to World Health organization (WHO) classification Expression of neuroendocrine markers (eg, synaptophysin or chromogranin A)

Serum Pro-gastrin releasing peptide (Pro-GRP) or chromogranin A (CgA) above the normal range or raised calcitonin for medullary thyroid carcinoma (MTC) subjects or raised pancreastatin for pancreatic or small bowel NEC subjects.

Specific additional criteria for certain NEC tumor types are as follows:
Small Cell Lung Cancer (SCLC);

Histologic or cytologic confirmation of SCLC according to 2015 WHO classification; or Immunohistochemistry suggestive of SCLC such as AE1/AE3 positive cytoplasmic staining, NCAM (CD56) positivity, chromogranin positivity, synaptophysin positivity, TTF1 positivity and high proliferation activity as demonstrated by Ki-67 in uncertain cases. Combined SCLC is permitted.

Large Cell Neuroendocrine Carcinoma (LCNEC);

Histologic confirmation of LCNEC according to 2015 WHO classification

Immunohistochemistry >10% of tumor cells positive for CD56, chromogranin or synaptophysin. Combined LCNEC is permitted.

Neuroendocrine Variant of EGFR Mutant Lung Cancer;

Known EGFR mutation

Progression on/following prior epidermal growth Factor (EGFR) inhibitor

Histologic or cytologic confirmation of SCLC according to 2015 WHO classification Immunohistochemistry suggestive of SCLC such as AE1/AE3 positive cytoplasmic staining, NCAM (CD56) positivity, chromogranin positivity, synaptophysin positivity, TTF1 positivity and high proliferation activity as demonstrated by Ki-67 in uncertain cases.

Subjects with mixed adenoneuroendocrine carcinoma (MANEC), which has at least 30% adenocarcinoma and 30% NEC, are eligible if serum Pro-GRP or CgA is above the normal range.

Medullary Thyroid Carcinoma (MTC);

Previously confirmed cytologic or histologic diagnosis of unresectable, locally advanced or metastatic hereditary or sporadic MTC Immunochemistry suggestive of MTC including positive staining for calcitonin Documented disease progression following prior therapy with vandetanib and/or cabozantinib Calcified lesions at baseline should not be used as a target lesion at baseline unless no other lesions are available.

Calcitonin levels above the normal range

Neuroendocrine Prostate Cancer (NEPC);

Metastatic prostate cancer and at least one of histologic diagnosis of small cell or neuroendocrine prostate cancer, supported by immunochemistry.

Histologic diagnosis of prostate adenocarcinoma plus >50% IHC staining for neuroendocrine markers (chromogranin, synaptophysin, CD56, or neuron-specific enolase (NSE))

Development of liver metastases in the absence of prostate-specific antigen (PSA) progression as defined by PCWG3

Patients with histologic evidence of pure neuroendocrine or small cell carcinoma do not need to have received prior androgen deprivation therapy or castrate levels of testosterone, but their testosterone state should be maintained for the duration of the study. Other subjects must have undergone surgical or ongoing medical castration and have baseline serum testosterone levels <50 ng/dL or <1.73 nmol/L.

Neuroendocrine Pancreatic Carcinoma:

Pathologic diagnosis of neuroendocrine pancreatic carcinoma (Klimstra WHO Classification 2010), with supportive immunochemistry Evidence of radiologic disease progression ≤12 months prior to Cycle 1, Day 1

No receptor-targeted radiolabeled therapy ≤3 months prior to Cycle 1, Day 1

No liver-directed therapy ≤4 weeks prior to Cycle 1, Day 1

Subjects with mixed adenocarcinoma are eligible if serum Pro-GRP or CgA or pancreastatin is above the normal range.

Neuroendocrine Hepatocellular Carcinoma (NEHCC)
  Histologically or cytologically-confirmed NEHCC, with supportive immunochemistry
  Platelet count ≥75×109/L (≥75,000/mm³) if subject has portal hypertension, otherwise ≥100×109/L (≥100,000/mm3)
  Child-Pugh score <7 (ie, class A liver function)
  BCLC C Advanced stage disease
  At least 4 weeks from last dose of α-interferon and/or ribavirin
  At least 4 weeks from prior percutaneous ethanol injection, radiofrequency ablation, transarterial embolization, or cryotherapy with documentation of progressive or recurrent disease.
  Measurable disease per RECIST 1.1 outside the liver or measurable disease per RECIST 1.1 on triple phase contrast enhanced hepatic computed tomography (CT) or Magnetic resonance imaging (MRI) that is suitable for repeat measurement and shows intratumoral arterial enhancement. Poorly demarcated or lesions showing atypical enhancement in the liver should be recorded as non-target lesions.
  No prior liver transplant.
  No gastrointestinal or variceal bleed in the previous 3 months requiring transfusion or endoscopic or operative intervention.
  No history of, or current, encephalopathy.
  No current clinically significant ascites (ie, not easily controlled with diuretics). Other NECs such as merkel cell carcinoma, neuroendocrine colorectal cancer, and neuroendocrine melanoma may be enrolled. Additionally NEN G2 (mitotic count 2-20 per 10 high power fields (HPF) and/or 3-20% Ki67 index) may be enrolled if they have documented progression on or following prior treatment with both a somatostatin analogue and a prior mammalian target of rapamycin (mTOR) inhibitor. However, pathology and immunochemistry must confirm the neuroendocrine element and pathologic diagnosis and subjects must have a serum Pro-gastrin releasing peptide (Pro-GRP) or Chromogranin A (CgA) above the normal range.

5. Subjects must have progressed on (or not been able to tolerate due to medical comorbidities or unacceptable toxicity), or following standard anticancer therapy or for whom no other approved conventional therapy exists or is acceptable.

6. Subject with solid tumor that has at least one site of measurable disease per RECIST 1.1, subject with NHL has at least one site of measurable disease per IWG criteria and subject with neuroendocrine hepatocellular carcinoma (NEHCC) has at least one site of measurable disease per mRECIST.

7. Subject consents to mandatory tumor biopsies (Screening and on treatment) in Part B. Tumor biopsies, whenever safe and feasible, will be collected in Part A.

8. Subject has Eastern Cooperative Oncology Group (ECOG) Performance Status of 0 to 1.

9. Subjects must have the following laboratory values:
  Absolute neutrophil count (ANC) ≥1.5×109/L without growth factor support for 7 days (14 days if subject received pegfilgastrim).
  Hemoglobin (Hgb)≥10 g/dL (≥100 g/L or >6.2 mmol/L).
  Platelet count (plt) ≥100×109/L (≥50×109/L for NHL subjects) or ≥75×109/L for NEHCC subjects with portal hypertension without transfusion for 7 days.
  Serum potassium concentration within normal range, or correctable with supplements.
  Serum Aspartate aminotransferase (SGOT) AST/SGOT and Alanine aminotransferase (SGPT) ALT/SGPT ≤3.0×Upper Limit of Normal (ULN) or ≤5.0×ULN if liver metastases are present.
  Serum total bilirubin ≤1.5×ULN.
  Subjects must have serum albumin ≥3.5 g/dL
  Adequate hepatic function for subjects with hepatocellular carcinoma (HCC) includes:
    Serum AST and ALT ≤5×ULN
    Serum total bilirubin ≤3 mg/dL (≤51 μmol/L)
    Serum albumin ≥3.0 g/dL
    Serum creatinine ≤1.5×ULN, or measured creatinine clearance ≥50 mL/min/1.73 m2 using an exogenous filtration marker such as iohexol, inulin, 51Cr EDTA or 125I iothalamate.
    Prothrombin time (PT) (or international normalized ratio (INR)) and activated partial thromboplastin time (APTT) within normal range.

10. Females of childbearing potential (FCBP)1 must:
  Either commit to true abstinence from heterosexual contact (which must be reviewed on a monthly basis and source documented) or agree to use, and be able to comply with, at least two effective contraceptive methods (oral, injectable, or implantable hormonal contraceptive; tubal ligation; intra-uterine device; barrier contraceptive with spermicide; or vasectomized partner), one of which must be barrier, from signing the ICD, throughout the study, and for up to 90 days following the last dose of the test compound or pharmaceutical composition; and have two negative pregnancy tests as verified by the Investigator prior to starting the test compound or pharmaceutical composition:
  a negative serum pregnancy test (sensitivity of at least 25 mIU/mL) at Screening
  a negative serum or urine pregnancy test within 72 hours prior to Cycle 1 Day 1 of study treatment.
  Avoid conceiving for 90 days after the last dose of the test compound or pharmaceutical composition.
  Agree to ongoing pregnancy testing during the course of the study, and after the end of study treatment. This applies even if the subject practices true abstinence from heterosexual contact.

11. Males must practice true abstinence (which must be reviewed on a monthly basis) or agree to use a condom (a latex condom is recommended) during sexual contact with a pregnant female or a FCBP and will avoid conceiving from signing the ICD, while participating in the study, during dose interruptions, and for at least 90 days following discontinuation of the administration of the test compound or pharmaceutical composition, even if he has undergone a successful vasectomy Exclusion Criteria:
The presence of any of the following will exclude a subject from enrollment:

1. low grade (G1) neuroendocrine tumors (≤2 per high power fields (HPF) and/or ≤2% Ki67 index) such as carcinoid are excluded.

2. Subject has received anti-cancer therapy (either approved or investigational)≤4 weeks or 5 half-lives, whichever is shorter, prior to signing the ICD.
  <42 days for prior nitrosureas or mitomycin C 3. Toxicities resulting from prior systemic cancer therapies must have resolved to ≤National Cancer Institute (NCI) Common Terminology Criteria for Adverse Events (CTCAE) Grade 1 prior to starting treatment with the test compound or pharmaceutical composition (with exception of grade 2 peripheral neuropathy and alopecia).

4. Prior ASCT ≤3 months before first dose or those who have not recovered.
5. Prior allogeneic stem cell transplant with either standard or reduced intensity conditioning.
6. Subject has undergone major surgery ≤4 weeks or minor surgery ≤2 weeks prior to signing the ICD or who have not recovered from surgery.
7. Subject has completed any radiation treatment <4 weeks prior to signing the ICD or <2 weeks for palliative bone radiotherapy (single fraction). Subjects with >25% of myelopoetic BM radiation are not allowed to be enrolled on this study.
8. Subject has persistent diarrhea due to a malabsorptive syndrome (such as celiac sprue or inflammatory bowel disease) ≥NCI CTCAE Grade 2, despite medical management), or any other significant GI disorder that could affect the absorption of the test compound or pharmaceutical composition.
9. Subject with symptomatic or uncontrolled ulcers (gastric or duodenal), particularly those with a history of and/or risk of perforation and GI tract hemorrhages.
10. Subject with any hemorrhage/bleeding event >CTCAE Grade 2 or haemoptysis >1 teaspoon within 4 weeks prior to the first dose
11. Symptomatic or untreated or unstable central nervous system (CNS) metastases.
  Subject recently treated with whole brain radiation or stereotactic radiosurgery for CNS metastases must have completed therapy at least 4 weeks prior to Cycle 1, Day 1 and have a follow-up brain CT or MRI demonstrating either stable or improving metastases 4 or more weeks after completion of radiotherapy (the latter to be obtained as part of the Screening Assessments.
  Subject must be asymptomatic and off steroids or on stable dose of steroids for at least 4 weeks (≤10 mg/day prednisone equivalent)
12. Subject with SCLC that has history of interstitial lung disease (ILD) OR a history of pneumonitis that has required oral or Intra Venous (IV) steroids
13. Subject has known symptomatic acute or chronic pancreatitis.
14. Subject has impaired cardiac function or clinically significant cardiac diseases, including any of the following:
  Left ventricular ejection fraction (LVEF)<45% as determined by multiple gated acquisition scan (MUGA) or echocardiogram (ECHO).
  Complete left bundle branch or bifascicular block.
  Congenital long QT syndrome.
  Persistent or clinically meaningful ventricular arrhythmias or atrial fibrillation.
  QTcF ≥480 msec on Screening ECG (mean of triplicate recordings).
  Unstable angina pectoris or myocardial infarction ≤6 months prior to starting Compound A.
15. Subject has other clinically significant heart disease such as congestive heart failure requiring treatment or uncontrolled hypertension (blood pressure ≥160/95 mm Hg).
16. Subject is a pregnant or nursing female.
17. Subject has known Human immunodeficiency virus (HIV) infection.
18. Subject has known chronic active hepatitis B or C virus (HBV, HCV) infection.
  Subjects who are seropositive due to HBV vaccination are eligible.
  Subjects who have no active viral infection and are under adequate prophylaxis against HBV re-activation are eligible.
  Subjects with HCC are exempt from the above criteria
19. Subject with ongoing treatment with chronic, therapeutic dosing of anti-coagulants (eg, warfarin, low molecular weight heparin, Factor Xa inhibitors, thrombin antagonist). Low dose low molecular weight heparin for catheter maintenance and for short-term prophylaxis for subjects with prior PE and DVT are permitted under careful consideration by the Investigator.
20. Subject has a history of concurrent second cancers requiring active, ongoing systemic treatment.
21. Subject has any significant medical condition (eg, active or uncontrolled infection or renal disease), laboratory abnormality, or psychiatric illness that would prevent the subject from participating (or compromise compliance) in the study or would place the subject at unacceptable risk if he/she were to participate in the study.
22. Subject has any condition that confounds the ability to interpret data from the study.

Part A-Dose Escalation

A minimum of 3 subjects will be enrolled at each dose level. The initial Compound A dose will be 1.25 mg once per week. The BLRM with EWOC will incorporate available prior safety information and update the model parameters after each new cohort of subjects completes Cycle 1. The decision for the next dose will be made by the SRC based on a calculation of risk assessment using the BLRM, and available safety (ie, DLT and non-DLT safety data), PK, PD, and preliminary efficacy information. In addition, relevant non-clinical data (eg, GLP (good laboratory practice) toxicity studies, in vivo pharmacology from xenograft models, etc) may be utilized in the assessment. Details of the statistical methodology are provided in Appendix E.

At all decision time points, the BLRM permits alterations in the dose increments based on the observed DLTs; however, the dose for the next cohort will not exceed a 100% increase from the prior dose. The MTD is the highest dose for which less than 33% of the population (not sample from the population) treated with Compound A suffer a DLT in the first cycle with at least 6 evaluable subjects having been treated at this dose. The SRC will make the final decision regarding the Compound A dose for each cohort.

During dose escalation, a Compound A dose can be declared the MTD after meeting the following conditions:
  at least 6 evaluable subjects have been treated at the dose,
  the posterior probability that the DLT rate lying in the target interval (16-33%) at the dose exceeds 60% or a sufficient number of subjects have been entered into the study to ensure the precision of the MTD estimate, as the posterior probability approaches but fails to exceed 60%, and
  the dose is recommended according to the BLRM and is approved by SRC.

Dose escalation may be terminated by SRC at any time based on emerging safety concerns without establishing the MTD. The SRC will include Investigators (and/or designated representatives), the Sponsor's study physician, safety physician, study statistician, and the study manager. Ad hoc attendees may include the study pharmacokineticist, the study biomarker scientist, and the study clinical scientist. Other internal and external experts may be consulted by the SRC, as necessary.

All decisions made at the SRC meetings will be formally documented (via SRC meeting minutes) and circulated to all sites in writing. No dose escalation, de-escalation, change to dosing schedule, or expansion of existing dose cohorts will commence prior to a written notification being sent to all participating sites of the respective SRC decision.

The decision to evaluate additional subjects within a dose cohort, a higher dose cohort, intermediate dose cohorts, smaller dose increments, alternative dosing schedules (eg, once every other week), or declare a MTD will also be determined by the SRC, based on the BLRM assessment and their review of available safety (ie, DLT and non-DLT data), PK, PD, and preliminary efficacy information. The final decision will be made by the SRC.

After the first dose is administered in any cohort during dose escalation, subjects in each cohort are observed for 28 days (Cycle 1, DLT window) before the next dose cohort can begin. No more than one subject per day will be enrolled in a given dose escalation cohort. A subject evaluable for DLT is defined as one that:

Has received ≥75% of the total planned dose amount of Compound A during Cycle 1 without experiencing a DLT, or Experienced a DLT after receiving at least one dose of Compound A.

Subjects non-evaluable for DLT will be replaced.

During the initial dose levels, subjects with relapsed and refractory solid tumors and NHL will be enrolled until the 2nd occurrence of a Grade ≥2, study drug-related toxicity in Cycle 1. Then enrollment will be restricted to subjects with small cell lung cancer (SCLC) and other neuroendocrine carcinomas (NEC) who secrete Pro-gastrin releasing peptide (Pro-GRP) or Chromogranin A (CgA) or pancreastatin (for pancreatic and small bowel NECs) or calcitonin (for medullary thyroid carcinoma (MTC)).

Intra-subject dose escalation will not be allowed during the DLT assessment period; however, in Cycles ≥3, subjects without evidence of disease progression who are tolerating their assigned dose of Compound A may (at the Investigator's discretion and in consultation and agreement with the Sponsor's study physician) escalate to the highest dose level shown to be adequately tolerated by at least one cohort of subjects in this study (ie, overdose risk is less than 25% based on the BLRM assessment).

Part B-Cohort Expansion

Following completion of dose escalation (Part A), selected tumor cohorts may be enrolled into an expansion phase (Part B) with approximately 20 evaluable subjects each. Expansion may occur at the MTD and schedule established in the dose escalation phase, and/or at an alternative tolerable dose and schedule, based on review of available safety, PK, PD, and efficacy data from Part A. The SRC will select the doses and schedules of interest for cohort expansion. One or more dosing regimens may be selected for cohort expansion. The SRC will continue to review safety data regularly throughout the study and make recommendations about study continuation and dose modification, as appropriate.

The study will be conducted in compliance with International Conference on Harmonisation (ICH)/Good Clinical Practices (GCPs).

Study Population

Men and women, 18 years or older, with relapsed and/or refractory solid tumors (enriched for NECs) and NHLs (DLBCL and iNHL) will be enrolled in the study.

Length of Study

Enrollment is expected to take approximately 30 months to complete (12 to 18 months for dose escalation and 9 to 12 months for expansion). Completion of active treatment and post-treatment follow-up is expected to take an additional 4 to 28 months. The entire study is expected to last approximately 5 years.

The End of Trial is defined as either the date of the last visit of the last subject to complete the post-treatment follow-up, or the date of receipt of the last data point from the last subject that is required for primary, secondary and/or exploratory analysis, as prespecified in the protocol, whichever is the later date.

Study Treatments

Celgene Corporation (Celgene) will supply the investigational product, Compound A (containing only the active pharmaceutical ingredient at dosage strengths of 0.50 mg, 0.75 mg, and 2.00 mg) capsules for oral administration, labeled appropriately for investigational use as per the regulations of the relevant country health authority.

Study treatment may be discontinued if there is evidence of clinically significant disease progression, unacceptable toxicity or subject/physician decision to withdraw.

Overview of Key Efficacy Assessments

Subjects will be evaluated for efficacy after every 2 cycles through Cycle 6, and then every 3 cycles thereafter. All subjects who discontinue treatment for reasons other than disease progression, start of a new anticancer therapy, or withdrawal of consent from the entire study will be followed until progression and/or initiation of new systemic anticancer therapies.

Tumor response will be determined by the Investigator. For solid tumors, assessment will be based on Response Evaluation Criteria in Solid Tumors (RECIST 1.1) (Eisenhauer, 2009). For NHLs, assessment will be based on the International Working Group Revised Response Criteria for Malignant Lymphoma. [18F] fluorodeoxyglucose (FDG) positron emission tomography (PET) or FDG PET/CT imaging is required to confirm a complete response in subjects with FDG-avid tumors. For neuroendocrine prostate carcinoma (NEPC), response assessment will be based on the PCWG3 criteria. For neuroendocrine hepatocellular carcinoma (NEHCC), response will be based on the mRECIST criteria Neuroendocrine carcinomas will additionally have levels of neuroendocrine markers assessed at baseline and on study.

Overview of Key Safety Assessments

The safety variables for this study include adverse events, safety clinical laboratory variables, 12-lead electrocardiograms, Eastern Cooperative Oncology Group Performance Status, left ventricular ejection fraction assessments, physical examinations, vital signs, exposure to study treatment, assessment of concomitant medications, and pregnancy testing for females of child bearing potential. The PK profiles of Compound A will be determined from serial blood collections.

Overview of Key Pharmacokinetic Assessments

The plasma PK parameters determined for Compound A will be maximum observed plasma concentration ($C_{max}$), area under the plasma concentration time-curve (AUC), time to maximum plasma concentration ($T_{max}$), terminal half-life ($t_{1/2}$), apparent clearance (CL/F), and apparent volume of distribution (Vz/F). Exposure-response analyses may be conducted, as appropriate, to assist in identification of the dosing regimen for Part B or Phase 2 studies.

Statistical Methods

The primary objectives of this study are to evaluate the safety and tolerability of treatment with Compound A, including the determination of the MTD. The analysis method for estimating the MTD is the BLRM guided by the EWOC principle.

Statistical analyses will be performed by dose level (Part A) and tumor cohort (Part B) as needed or applicable. All analyses will be descriptive in nature. All summaries of safety data will be conducted using subjects receiving any Compound A (the Treated Population).

Study data will be summarized for disposition, demographic and baseline characteristics, exposure, efficacy, safety, PK, and PD. Categorical data will be summarized by frequency distributions (number and percentages of subjects) and continuous data will be summarized by descriptive statistics (mean, standard deviation, median, minimum, and maximum).

Treatment-emergent adverse events (TEAEs) will be summarized by National Cancer Institute Common Terminology Criteria for Adverse Event grades. The frequency of TEAEs will be tabulated by Medical Dictionary for Regulatory Activities system organ class and preferred term. Grade 3 or 4 TEAEs, TEAEs leading to discontinuation of Compound A, study drug-related TEAEs, and SAEs will be tabulated separately. Changes from baseline in selected laboratory analytes, vital signs, 12-lead ECGs, and ECHO/MUGA scans will be summarized. All data will be presented in by-subject listings.

The primary efficacy variable for Part A is clinical benefit rate (CBR). CBR is defined as tumor responses (as assessed by the Investigators) of complete response (CR), partial response (PR) and durable stable disease (SD) (SD of ≥4 months duration). Point estimates and 95% confidence intervals of CBR will be reported. Objective response rate (defined as the percentage of subjects whose best response is complete response or partial response), duration of response/stable disease, time to progression, progression-free survival, and overall survival will be summarized using frequency tabulations for categorical variables, or descriptive statistics for time to event variables. Efficacy analysis will be repeated for the Treated Population and Efficacy Evaluable Population (subjects who received a baseline disease assessment evaluation, at least 75% of assigned doses in Cycle 1, and one on study disease assessment evaluation), with the result using the Treated Population considered primary.

During the Part A dose escalation, approximately 50 subjects will be enrolled. During the Part B dose expansion, at least 14 efficacy evaluable subjects for each tumor cohort will be initially accrued. The tumor cohort will be expanded to approximately 20 subjects if a responder or SD of 4 months or longer is observed.

Study Objectives

Primary Objective

The primary objectives of the study are:
- To determine the safety and tolerability of Compound A.
- To define the maximum tolerated dose (MTD) and/or the recommended Phase 2 dose (RP2D) of Compound A.

Secondary Objective(s)

The secondary objectives are
- To provide information on the preliminary efficacy of Compound A.
- To characterize the pharmacokinetics (PK) of Compound A.

Exploratory Objective(s)

The exploratory objectives are:
- To evaluate the PD effects of Compound A on gene expression in peripheral blood and if available, in tumor samples.
- To evaluate the PD effects of Compound A on secreted neuropeptide (such as Pro-GRP, CgA or calcitonin) levels in sera from NEC and SCLC subjects.
- To explore the relationship among Compound A dose, plasma exposure, and selected clinical endpoints (eg, measures of toxicities, preliminary activity, and/or biomarkers).
- To explore the relationship between baseline, on-treatment, and/or changes in gene expression in tumor samples (if available) and clinical response.
- To characterize the principal metabolites of Compound A in plasma provided sufficient data are available.
- Data from exploratory objectives may be included in the Clinical Study Report per SAP (Statistical analyses plan).

Study Endpoint

| Endpoint | Name | Description | Timeframe |
|---|---|---|---|
| Primary | Safety endpoints | DLTs and MTD evaluated using the NCI CTCAE criteria, Version 4.03 | Dose escalation |
| Secondary | Preliminary efficacy | Clinical benefit rate (CBR) determined by response and stable disease rates by disease-appropriate response criteria, ORR, DOR, and PFS | Dose escalation and expansion |
| | Overall survival | From the first dose to death due to any cause | Dose escalation and expansion |
| | PK endpoints | Maximum observed plasma concentration ($C_{max}$), area under the plasma concentration time-curve (AUC), time to maximum plasma concentration ($T_{max}$), terminal half-life ($t_{1/2}$), apparent clearance (CL/F), and apparent volume of distribution (Vz/F) of Compound A | Dose escalation |
| Exploratory | PD endpoints | Gene expression in peripheral blood cell components<br>Gene expression in tumor tissue, if available<br>Secreted neuropeptides (such as Pro-GRP, CgA, calcitonin) levels in sera from NEC and SCLC subjects | Dose escalation and expansion |
| | PK endpoints | Clinically relevant covariates of PK parameters<br>Identification of principal Compound A metabolite(s) in plasma<br>Exposure-response relationships | |

Study Design

Figure 37:
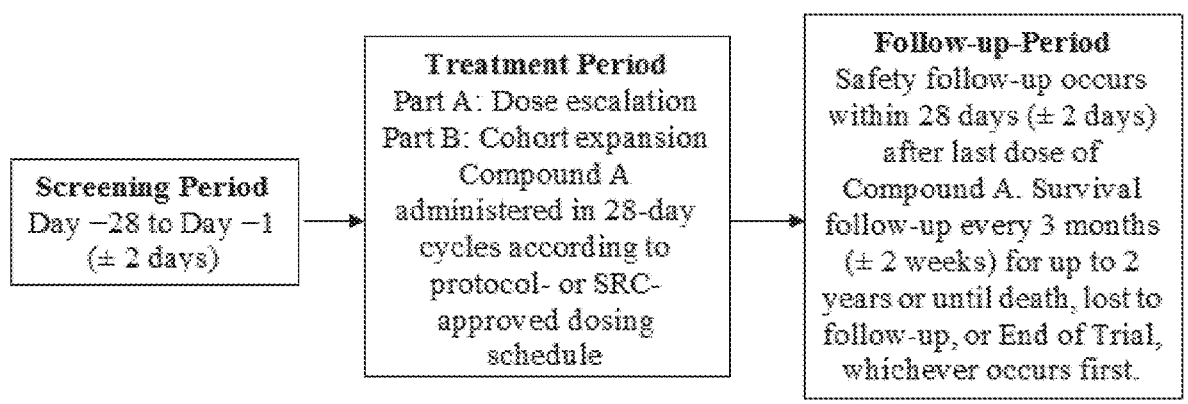
FIG. 37 is a schematic outlining an overall study design useful for demonstrating safety or efficacy of pharmaceutical compositions.

Study Compound A-ST-001 is an open-label, Phase 1a, dose escalation and expansion, FIH clinical study of Compound A in subjects with relapsed and/or refractory solid tumors (including NEC) and NHLs. The dose escalation part (Part A) of the study will explore escalating oral doses of Compound A to estimate the MTD of Compound A. A Bayesian logistic regression model (BLRM) utilizing escalation with overdose control (EWOC) (Babb, 1998; Neuenschwander, 2008) will help guide Compound A dose escalation decisions with the final decisions being made by an SRC. The expansion part (Part B) will further evaluate the safety and efficacy of Compound A administered at or below the MTD in selected expansion cohorts of approximately 20 evaluable subjects each in order to further define the RP2D. One or more dosing regimens and/or disease subsets may be selected for cohort expansion (Part B). Parts A and B will consist of 3 periods: Screening, Treatment, and Follow-up periods (refer to FIG. 37).

The study will be conducted in compliance with the International Council on Harmonisation (ICH) of Technical Requirements for Registration of Pharmaceuticals for Human Use/Good Clinical Practice (GCP) and applicable regulatory requirements.

Study Duration for Subjects

Enrollment is expected to take approximately 30 months to complete (12-18 months for dose escalation, and 9-12 months for expansion). Completion of active treatment and post-treatment follow-up is expected to take an additional 4 to 28 months. The entire study is expected to last approximately 5 years.

End of Trial

The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

Regarding procedures, questions regarding the protocol should be directed to the Medical Monitor or designee. The procedures conducted for each subject enrolled in the study are outlined in Table 34:

TABLE 34

Table of Events

| Events[a] | Screening D-28 to −1 | Cycle 1 | | | | | | Cycles 2-4 | | | | Cycles 5+ | | EOT ≤28 days | Follow-up Period | |
|---|---|---|---|---|---|---|---|---|---|---|---|---|---|---|---|---|
| | | | | | | | | | | | | | | | Safety[b] 28 days (±2 days) | Long Term[c] q3 mo (±2 wks) |
| | | WK1 D1 | D2 | D3 | WK 2 D8 | WK 3 D15 | WK 4 D22 | WK 1 D1 | WK2 D8 | WK 3 D15 | WK 4 D22 | WK 1 D1 | WK 3 D15 | | | |
| Study Entry | | | | | | | | | | | | | | | | |
| Informed consent | X | | | | | | | | | | | | | | | |
| contraceptive counseling | X | X | | | | | | X | | | | X | | X | | |
| Informed consent for optional exploratory analyses | X | | | | | | | | | | | | | | | |
| Inclusion/exclusion criteria | X | | | | | | | | | | | | | | | |
| Medical/oncologic history and therapies | X | | | | | | | | | | | | | | | |
| Demographics | X | | | | | | | | | | | | | | | |
| IRT registration | X | X | | | Day 1 of every Cycle. Please refer to IRT instruction manual. | | | | | | | | X | | | |
| Prior/concomitant medications, procedures | X | X | X | X | X | X | X | X | X | X | X | X | X | X | X | |
| Study Drug | | | | | | | | | | | | | | | | |
| Administer oral Compound A per assigned dosing schedule[d] | | Weekly Note: Alternative dosing schedules may be implemented based on SRC decsions. | | | | | | | | | | | | | | |
| Provide/review of diary card | | X | | | X | X | X | X | X | X | X | X | X | X | | |
| IP accountability | | X | | | | | | X | | | | X | | X | | |

TABLE 34-continued

Table of Events

| | | Treatment Period | | | | | | | | | | | Follow-up Period | |
|---|---|---|---|---|---|---|---|---|---|---|---|---|---|---|
| | | Cycle 1 | | | | | | Cycles 2-4 | | | | Cycles 5+ | Safety[b] | Long |
| | | | | | | | | | | | | | 28 | Term[c] |
| | Screening D-28 | WK1 | | | WK 2 | WK 3 | WK 4 | WK 1 | WK2 | WK 3 | WK 4 | WK 1 | WK 3 | EOT ≤28 | days (±2 | q3 mo (±2 |
| Events[a] | to −1 | D1 | D2 | D3 | D8 | D15 | D22 | D1 | D8 | D15 | D22 | D1 | D15 | days | days) | wks) |
| | | Safety Assessments | | | | | | | | | | | | | |
| Adverse Event Evaluation | X | X | X | X | X | X | X | X | X | X | X | X | X | X | X | |
| Height | X | | | | | | | | | | | | | | | |
| Weight | X | X | | | X | X | X | X | X (C2 only) | X | X (C2 only) | X | X | X | | |
| Vital Signs | X | X | | | X | X | X | X | X (C2 only) | X | X (C2 only) | X | X | | | |
| Physical Examination | X | X | | | | | | X | | | | X | | | | |
| ECOG PS | X | X | | | | | | X | | | | X | | | | |
| B Symptoms Assessment (only NHL; | X | | | | | | | As clinically indicated | | | | | | X | | |
| 12-lead ECG (single or triplicate)[e] | X (≥72 hours prior to D1) | X | | | X (D1 7 only) | | | X | | | | X | | X | | |
| LVEF (ECHO/ MUGA) | X | | | | | | | As clinically indicated | | | | | | X (±7 d) | | |
| Pregnancy Testing (FCBP only) | X | X | | | | | | X | | | | X | | X | | |
| Hematology laboratory | X (D-14 to −1) | X | | X | X | X | X | X | X (C2 only) | X | X (C2 only) | X | | X | | |
| Chemistry laboratory with LDH, uric acid tests | X (D-14 to −1) | X | X | X | X | X | X | X | X (C2 only) | X | X (C2 only) | X | | X | | |
| Triglycerides and cholesterol (fasting) | X | X | | | | | | X | | | | X | | X | | |
| PT (or INR), PTT | X (D-14 to −1) | X | | | | | | As clinically indicated | | | | | | X | | |
| Amylase, lipase, T-cell subsets (CD4+ and CD8+), TSH | | X | | | | | | | X (every 2 cycles) | | | X (every 2 cycles) | | X | | |
| Urinalysis | X (D-14 to −1) | X | | | | | | X | | | | X | | X | | |
| Hepatitis viral assessment for subject with HCC only | X | | | | | | | X (odd cycles only from cycle 3) | | | | X (odd cycles only from cycle 3) | | | | |
| Neuro-endocrine markers | X | X | | | | | | X | | | | X | | X[e] | | |
| Tumor markers (for any subjects with NEPC and | X | X | | | | | | X | | | | X | | X[e] | | |

TABLE 34-continued

Table of Events

| | | Treatment Period | | | | | | | | | | | Follow-up Period | |
| --- | --- | --- | --- | --- | --- | --- | --- | --- | --- | --- | --- | --- | --- | --- |
| | | Cycle 1 | | | | | | Cycles 2-4 | | | | Cycles 5+ | | Safety[b] | Long |
| | | | | | | | | | | | | | | 28 | Term[c] |
| | Screening D-28 to −1 | WK1 | | | WK 2 | WK 3 | WK 4 | WK 1 | WK2 | WK 3 | WK 4 | WK 1 | WK 3 | EOT ≤28 | days (±2 | q3 mo (±2 |
| Events[a] | | D1 | D2 | D3 | D8 | D15 | D22 | D1 | D8 | D15 | D22 | D1 | D15 | days | days) | wks) |
| NEHCC and other tumors, if relevant) | | | | | | | | | | | | | | | | |
| Bone markers | X (D-14 to −1) | | | | | | | X (every 3 cycles) | | | | | | X[k] | | |
| PK and PD Assessments | | | | | | | | | | | | | | | | |
| Blood, PK | | Refer to Table 14 for a detailed collection schedule | | | | | | | | | | | | | | |
| Blood (whole), PD | | Refer to Section for a detailed collection schedule | | | | | | | | | | | | | | |
| Serum PD (NEC and SCLC only) | X | X | | X | | | | | | | | | | | | |
| Tumor Biopsy[f] | X (D-28 to D1 predose) | | | | | X(D16 or D17)[f] | | | | | | | | X | | |
| Archival tumor tissue (FFPE) | X[g] | | | | | | | | | | | | | | | |
| Efficacy | | | | | | | | | | | | | | | | |
| Solid tumor/NHL assessments: CT/MRI imaging[h] | X | | | | | | | | X (D28 ± 7 d; C2 & C4) | | | X (D28 ±7 d in C6, then q3 cycles, i.e., end of C9, C12, etc.) | | X | | |
| NHL-specific: bone marrow evaluation if known or suspected bone marrow involvement | X[i] | | | | | | | | | | | X, only when confirming CR | | X, only when confirming CR | | |
| NHL-specific: FDG PET or PET/CT scan (not required if tumor is FDG-negative) | X | | | | | | | | | | | X, when confirming CR | | | | |

TABLE 34-continued

Table of Events

| Events[a] | Screening D-28 to −1 | Cycle 1 | | | | | | Cycles 2-4 | | | | Cycles 5+ | | EOT ≤28 days | Safety[b] 28 days (±2 days) | Long Term[c] q3 mo (±2 wks) |
|---|---|---|---|---|---|---|---|---|---|---|---|---|---|---|---|---|
| | | WK1 D1 | D2 | D3 | WK 2 D8 | WK 3 D15 | WK 4 D22 | WK 1 D1 | WK2 D8 | WK 3 D15 | WK 4 D22 | WK 1 D1 | WK 3 D15 | | | |
| Additional Follow-up | | | | | | | | | | | | | | | | |
| Follow-up anticancer therapies | | | | | | | | | | | | | | | X | X |
| SAE follow-up | | | | | | | | | | | | | | | X | |
| Survival follow-up | | | | | | | | | | | | | | | | X |

Abbreviations:
AFP = alpha fetoprotein;
anti-HBc = Hepatitis B core antibody;
anti-HCV = Hepatit's C surface antibody;
anti-HBS = Hepatitis B surface antibody;
β-hCG = beta human chorionic gonadotropin;
C = cycle;
CBC = complete blood count;
CR = complete response;
CT = computed tomography;
D = day(s);
ECHO = echocardiogram;
ECOG Eastern Cooperative Oncology Group;
FCBP = females of child bearing potential;
FDG PET = 18-Fluoro-deoxyglucose positron emission tomography;
FFPE = formalin-fixed, paraffin embedded;
HBsAg; Hepatitis B Surface Antigen;
HCC = hepatocellular carcinoma;
INR = international normalized ratio;
IRT = interactive response technology;
LVEF = left ventricular ejection fraction;
mo = months;
MUGA = multi-gated acquisition scan;
NHL = Non-Hodgkin's lymphoma;
PD = pharmacodymanamics;
PK = pharmacokinetics;
PS = performance status;
PT = prothrombin time;
PTH = parathyroid hormone;
PIT = partial thromboplastin time;
q = every;
SAE = serious adverse event;
TSH = thyroid-stimulating hormone;
WK(s) = week.

[a] This Safety follow-up assessment may be by telephone (refer to Section 6.3.1). Long Term survival follow-up for up to 2 years or until death, lost to follow-up, or End of Trial, whichever occurs first. May be conducted by record review.
[b] All study visits/procedures will have a ±3 day window and all laboratory blood samples should be drawn predose, unless otherwise specified in this table or Section 6.
[c] At Cycle 6 on and onwards only Day 1 required.
[d] Screening triplicate ECGs must be performed /hours prior to dosing on Day 1 so that the central read results are available for review.
[e] Unless PD has been previously documented.
[f] Paired tumor biopsies are mandatory for Part B and highly recommended for Part A. The Screening biopsy (D-7 to D1 predose) should be obtained after all inclusion/exclusion, criteria have been fulfilled. The Cycle 1 biopsy may be obtained on Day 16 or 17 (+7 day window) provided that 2 consecutive Compound A doses have been administered.
[g] Mandatory only if fresh biopsy is not collected during Screening.
[h] All subjects who discontinue treatment for reasons other than disease progression, start of a new anticancer therapy, or withdrawal of consent from the entire study will be followed according to the specified tumor assessment schedule until progression and/or initiation of new systemic anticancer therapies.
[i] May be omitted if results were normal on the subject's most recent historical bone marrow biopsy. Additionally, this analysis may be omitted if a prior analysis was performed within 90 days before Cycle 1 Day 1. Historical results will be recorded in the eCRF.
[j] Day 8 and 22 visits may be omitted from Cycle 3 onwards k May be omitted if it was performed in the previous 28 days.

All study visits will have a ±3 day window unless otherwise specified below or in the Table of Events (refer to Table 34). All laboratory blood samples should be drawn predose unless otherwise specified (eg, PK samples).

The study procedures should be recorded in the source document and the electronic case report forms (eCRF). In the event subjects fail Screening, minimal information will be documented on the eCRFs, per database instructions.

The Screening window starts 28 days (±3 days) prior to the first dose of Compound A. Refer to Table 34, this section, for detailed information on procedures performed and the schedule.

Waivers to the protocol will not be granted during the conduct of this trial, under any circumstances.

Safety laboratory analyses will be performed locally. Screening laboratory values must demonstrate subject eligibility, but may be repeated within the screening window, if necessary.

The ICD will be administered at the Screening visit to all subjects by qualified study staff. It must be signed and dated by the subject and the administering staff prior to the start of any other study procedures and its completion documented in source documents and in the eCRF. All screening tests and procedures must be completed within 28 days (±3 days) prior to the first dose of Compound A according to the schedule shown in Table 34.

The following will be performed at Screening, after informed consent has been obtained:

Inclusion and exclusion criteria will be assessed at Screening and recorded in the source documents and the eCRF.

Contraceptive counseling: qualified healthcare professionals will be trained by Celgene, or designee, in the requirements specific to contraceptive counseling of subjects. Once trained the healthcare staff will counsel subjects prior to the administration of Compound A to ensure that the subject has complied with all requirements including use of birth control and that the subject understands the risks associated with Compound A.

Medical, oncologic, and surgical history, and demographic data (including each subject's date of birth, sex, race, and ethnicity) will be collected during Screening as consistent with local regulations. Oncologic history will include a detailed history of the primary diagnosis and date, therapies, and responses.

Information on prior and concomitant medications and procedures will be collected Registration in the interactive response technology system (IRT).

Adverse event monitoring.

Height and weight measured.

Vital signs assessed.

Physical examination (source documented only) and ECOG performance status.

For subjects with NHL, measurements of lymph nodes and documentation of any enlargement of the spleen and/or liver will be recorded in the source document and in the eCRF.

The B symptom assessment (NHL Subjects only): B symptoms are fever (>100.5° F. or 38° C.) for 2 or more weeks without other evidence of infection, night sweats for more than 1 month without evidence of infection, and weight loss greater than 10% within the prior 6 months.

A 12-lead ECG in triplicate will be performed ≥72 hours prior to the first dose of Compound A with results received and assessed from the central read prior to dosing to fulfil eligibility criteria Left Ventricular Ejection Fraction (LVEF) assessment.

Pregnancy testing for all females of childbearing potential. Appropriate methods of contraception and potential risks of fetal exposure will be discussed with subjects during Screening. Double contraceptive methods (one of which must be a barrier method) for females of childbearing potential (eg, oral, injectable, or implantable hormonal contraceptive; intra-uterine device; barrier contraceptive with spermicide; or vasectomized partner) and a single contraceptive method for males (a condom) must be used from the time the ICD is signed, throughout the study (including dose interruptions), and for 90 days after the last dose of Compound A. This will be documented in source documents.

Clinical laboratory tests are to be completed within 14 days prior to the first dose of Compound A.

Efficacy/tumor assessments

Bone markers (N-telopeptide and bone specific alkaline phosphatase) to be collected at Screening (within 14 days of the first dose)

Neuroendocrine and tumor markers are to be completed prior to the first dose of Compound A.
SCLC—Pro-GRP and CgA
NEC—Pro-GRP and CgA
NEPC—PSA, Pro-GRP and CgA
NEHCC—Alpha fetoprotein (AFP), Pro-GRP and CgA
MTC—CEA, calcitonin, Pro-GRP and CgA
NEPancreatic Cancer—Pro-GRP, CgA and pancreastatin
Other NEC—Pro-GRP and CgA
Other tumor markers as appropriate i.e. CA125 for ovarian cancer Fresh tumor biopsy
Archival tumor tissue (FFPE) collection is mandatory only if a fresh biopsy is not collected during Screening For HCC subjects only:
AFP
HBsAg, anti-HBS, anti-HBc, and anti-HCV (screening only).
Measurement of hepatitis B viral load (HBV DNA quantitative by PCR) if HBsAg, HBcAb total, and/or HBcAb IgM is/are positive.
Confirmation of antiviral therapy with an appropriate antiviral agent for HBV is required in subjects with positive hepatitis B surface antigen, HBcAb IgM, and/or viral load—appropriate first line agents include entecavir, tenofovir, and lamivudine (note that lamivudine has higher resistance rates).
Subjects with a positive HBV viral load, HBcAb IgM, and/or HBsAg should be referred to a hepatologist if not already under the care of a hepatologist.

Visits and assessments are shown in Table 34. Subjects completing 6 cycles of treatment and continuing on study drug are only required to have clinic visits/assessments performed on Day 1 (±3 days) of each subsequent cycle (Cycles 6 and higher) unless more frequent visits are clinically indicated.

All concomitant medications and procedures taken or conducted beginning when the subject signs the ICD, throughout the study, and until 28 days after the last dose of Compound A will be recorded in the source documents and eCRF.

Adverse events and serious adverse events (SAEs) will be recorded from the time a subject signs the ICD until 28 days after the last dose of Compound A.

Subjects experiencing AEs will be monitored with relevant clinical assessments and laboratory tests, as determined by the Investigator. Every attempt will be made to document resolution dates for ongoing AEs. The AEs will be recorded on the AE page of the eCRF and in the subject's source documents. Photographs of skin rashes should be obtained whenever possible, anonymized, and stored appropriately for future retrieval.

The subject's weight will be recorded in the source document and eCRF at the visits listed in Table 34.

Vital signs include body temperature, blood pressure, pulse rate, and respiration rate (only for subjects with tumors in the lung) and will be recorded during the study at various time points for safety monitoring as described in Table 34.

Recorded measurements will be captured in the source document and eCRF.

Complete physical examination and Eastern Cooperative Oncology Group Performance Status (ECOG PS; refer to Appendix D) will be performed at the visits listed in Table 34. Results for both will be recorded in the source document. Results for the ECOG PS will also be collected on the eCRF.

Physical examination findings will be classified as either normal or abnormal. If abnormal, a description of the abnormality and clinical importance will be provided in the source documents. Clinically significant changes from baseline will be recorded in the AE section of the eCRF.

For subjects with NHL, measurements of lymph nodes and documentation of any enlargement of the spleen and/or liver will be recorded in the source document and on the eCRF.

For subjects with NHL, B symptom assessments will be performed at the visits listed in Table 34 and results recorded in the source documents and on the eCRF.

B symptoms are fever (>100.5° F. or 38° C.) for 2 or more weeks without other evidence of infection, night sweats for more than 1 month without evidence of infection, and weight loss greater than 10% within the prior 6 months.

Triplicate standard 12-lead electrocardiograms (ECGs) will be recorded at the visits listed in Table 34. The 12-lead ECG should be collected prior to any blood draws if both are scheduled for the same nominal time. The 12-lead ECGs (12-lead at 25 mm/sec reporting rhythm, ventricular rate, PR interval, QRS complex, QT interval, and QTcF interval) will be performed after the subject has been in the supine position for at least 5 minutes.

Triplicate ECGs (3 recordings within 2±1 minute intervals) will be performed at:
Screening
Cycle 1
  Day 1: predose (within 30 minutes prior to dosing) and 2, 4, 8, 24 hours (±10 minutes) postdose
  Days 8, 15 and 22: predose (within 30 minutes prior to dosing) and 4 hours (±10 minutes) postdose
Cycles 2 and higher
  Day 1: predose (within 30 minutes prior to dosing)
A single ECG will be performed at the EOT visit.

For alternative dosing schedules, the Cycle 1 Day 15 ECGs will be performed on the last day of Compound A dosing in Cycle 1.

Investigators will make immediate clinical decisions based on their interpretation of the ECG results and provide their overall assessment of the ECG in the eCRF. Clinically significant changes from baseline will be recorded in the AE section of the eCRF.

The ECG outputs will also be uploaded to the central ECG laboratory for definitive analysis and interpretation.

Left ventricular ejection fraction (LVEF), (multiple gated acquisition scan [MUGA], or echocardiogram [ECHO]) will be conducted at Screening in all subjects. Follow-up assessments should be performed as clinically indicated. Follow up assessments should use the same procedure used at the screening assessment. A clinically significant reduction is defined as either a ≥20% absolute reduction in LVEF or drop to below 45%.

A female of childbearing potential (FCBP) is defined as a sexually mature woman who has:
Not undergone a hysterectomy or bilateral oophorectomy, and
Not been naturally postmenopausal (amenorrhea following cancer therapy does not rule out childbearing potential) for at least 24 consecutive months (eg, has had menses at any time in the preceding 24 consecutive months).

The Investigator will classify a female subject as a FCBP according to this definition. Pregnancy testing is not required for non-FCBP subjects but justification must be recorded in the eCRF and the source document. Pregnancy testing will be conducted by the local laboratory.

For an FCBP, pregnancy testing will be conducted at the visits listed in Table 34
  A serum pregnancy test with sensitivity of at least 25 mIU/mL is to be obtained at Screening and serum or urine pregnancy test within 72 hours prior to Cycle 1 Day 1 of study treatment. The subject may not receive Compound A until the Investigator has verified the two screening pregnancy tests to be negative.
  A serum or urine pregnancy test (based on Investigator's discretion and minimum test sensitivity [25 mIU/mL]) should be done within 72 hours prior to Day 1 of every cycle and at the end of treatment (EOT) visit. The subject may not receive Compound A until the Investigator has verified the pregnancy test to be negative.
  An FCBP or a male subject whose partner is an FCBP must avoid activities that could lead to conception while receiving Compound A and for 90 days after the last dose of Compound A. Practice of true abstinence from sexual activity will be monitored monthly and source documented.

Results for pregnancy tests will be recorded in the source document and eCRF.

The following laboratory assessments will be performed during the study at the time points as described in Table 34. All samples should be drawn predose unless otherwise specified. Laboratory assessments will be recorded in the source document and eCRF and are the following:
Hematology: Complete blood counts (CBC) including hemoglobin, hematocrit, WBC count with absolute counts for WBC parameters and platelet count.
  On Cycle 1, Day 1, the CBC with absolute counts should be performed and results checked against entry criteria before drug administration
Serum chemistry: albumin, total protein, bicarbonate or magnesium, phosphorus, calcium, creatinine, urea/BUN, glucose (fasting ≥6 hours), potassium, sodium, chloride, total bilirubin (fractionate if outside normal range), alkaline phosphatase, AST or serum glutamic oxaloacetic transaminase (SGOT), ALT or serum glutamate pyruvic transaminase (SGPT), LDH, and uric acid.
Fasting (≥6 hours) triglycerides and cholesterol.
Special chemistry: amylase, lipase, T-cell subsets (CD4+ and CD8+), thyroid-stimulating hormone (TSH; if abnormal reflex to free T4).
Coagulation: PT (or INR), and APTT
Urinalysis: dipstick
  microscopy and urinary albumin to creatinine ratio in the event of first appearance of 2+ or greater protein or worsening proteinuria.
Measured creatinine clearance determination using an exogenous filtration marker such as iohexol, inulin, $^{51}$Cr EDTA or $^{125}$I iothalamate required at Screening to fulfill inclusion criteria if serum creatinine >1.5× ULN (refer to Section 4.2).

Bone markers (N-telopeptide and bone specific alkaline phosphatase) to be collected every 3 Cycles and at EOT (unless done in previous 28 days).
  For HCC subjects only:
    AFP (if elevated at baseline)
  Hepatitis B viral DNA quantitative in subjects with positive hepatitis B viral load at baseline and/or positive HBsAg, HBcAb total, and/or HBcAb IgM (odd cycles only starting with Cycle 3 or more frequently at investigator's discretion) and at EOT.
  For NEPC subjects only:
    PSA
  Neuroendocrine and tumor markers only need to be monitored if they are elevated at baseline with the exception of PSA in NEPC.
    SCLC—Pro-GRP and CgA
    NEC—Pro-GRP and CgA
    NEPC—PSA, Pro-GRP and CgA
    NEHCC—Alpha fetoprotein, Pro-GRP and CgA
    MTC—CEA, calcitonin, Pro-GRP and CgA
    NE Pancreatic Cancer—Pro-GRP, CgA and pancreastatin
    Other NEC—Pro-GRP and CgA An EOT evaluation (refer to Table 34 for procedures) should be performed for subjects who are withdrawn from treatment for any reason as soon as possible (≤28 days) after the decision to permanently discontinue treatment has been made.

All subjects will be followed for 28 days after the last dose of Compound A for AE reporting and concomitant medication information. The 28-day (±3 days) safety follow-up contact may be by telephone. In addition, any SAEs made known to the Investigator at any time thereafter that are suspected of being related to Compound A will be reported.

After the Safety Follow-up visit, all subjects will be followed every subsequent 3 months (±2 weeks) for survival follow-up for up to 2 years or until death, lost to follow-up, or the End of Trial, whichever occurs first. New disease therapies should be collected at the same time schedule.

Survival follow-up may be conducted by record review (including public records) and/or telephone contact with the subject, family, or the subject's treating physician.

Tumor assessments will be performed at Screening and will include CTs of the chest, abdomen and pelvis, and a brain scan (CT or MRI) for subjects with known or suspected cerebral involvement and all subjects with NEPC. After Screening, radiologic tumor assessments will be performed at the end (Day 28±7 days) of Cycles 2, 4, and 6, and then every 3 cycles thereafter, using the same CT/MRI scanning modalities used at Screening. An EOT scan does not need to be obtained if the prior scan was within 28 days.
  Additionally for NHL subjects, a Screening FDG PET or FDG PET/CT scan will be performed unless the tumors are known to be FDG-avid negative. A subsequent scan will be obtained to confirm a CR.
  For NHL subjects with known or suspected bone marrow involvement, a bone marrow evaluation with flow immunophenotyping will be performed at Screening, and to confirm a complete response (CR).
  For MTC subjects a screening isotope bone scan will be performed at baseline. If this is suggestive of bone metastases an X ray, CT or MRI of the bone lesion should be performed at BL and the same technique repeated at each scheduled efficacy assessment.
  For MTC subjects a liver MRI should be performed or if not available, a contrast enhanced triple phase CT scan.
  Also an MRI or CT scan of neck should be performed. These should be performed at baseline and as stipulated above.
  For NEPC subjects, a 99mTc-methylene diphosphonate radionuclide bone scan should be performed at screening and all subsequent efficacy assessments.
  For NEHCC subjects, a contrast enhanced triple phase CT/MRI scan of the abdomen should be performed at screening and all subsequent efficacy assessments.

All subjects who discontinue treatment for reasons other than disease progression, start of a new anticancer therapy, or withdrawal of consent from the entire study will be followed according to the specified tumor assessment schedule until progression and/or initiation of new systemic anticancer therapies.

Tumor response at each post-screening assessment will be determined by the Investigator, based on Response Evaluation Criteria in Solid Tumors (RECIST) v 1.1 as described in Appendix B for solid tumors, the Revised Response Criteria for Malignant Lymphoma as described in Appendix C for NHL, PCWG3 2016 for NEPC (Appendix J) and mRECIST for NEHCC (Appendix I).

Tumor markers ie, PSA for NEPC and Alpha fetoprotein (AFP) for NEHCC at screening, Day 1 of every cycle and EOT unless disease progression documented previously.

Neuroendocrine markers will be performed at the visits listed in Table 13, and results recorded in the source documents and on the eCRF. Any neuroendocrine marker known to be elevated at baseline should be followed on Day 1 of each cycle and end of therapy unless subject is documented to have progressed previously. However the following should be followed at a minimum:
  SCLC—Pro-GRP and CgA
  NEC—Pro-GRP and CgA
  MTC—CEA, calcitonin, Pro-GRP and CgA
  NEPC—Pro-GRP and CgA,
  NE pancreatic or small bowel NEC—Pro-GRP, CgA and pancreastatin The PK assessments for Part A are described below. PK assessments for Part B will be provided after sufficient PK data is collected in Part A of this study.

For evaluation of PK of Compound A in plasma, blood samples will be collected from all subjects at the time points listed in Table 35. The actual time of each sample collection will be recorded in the source documents and on the electronic case report forms (eCRFs). An exploratory analysis of Compound A metabolites in plasma may be performed utilizing the plasma samples collected for PK evaluation.

TABLE 35

Blood Pharmaceutic Sampling Schedule for Part A, Cycle 1

| Time in Hours Relative to Compound A Dose | Collection Window | Day 1 | Day 8 | Day 15 | Day 22 |
| --- | --- | --- | --- | --- | --- |
| 0 (predose) | Within 30 min prior | X | X | X | X |
| 1 | ±5 min | X | | | X |
| 2 | ±10 min | X | | | X |
| 4 | ±10 min | X | | | X |
| 6 | ±10 min | X | | | X |
| 8 | ±10 min | X | | | X |
| 11 | ±1 hour | X | | | X |
| 24 | ±1 hour | X | | | X |
| 48 | ±1 hour | X | | | X |
| 72 | ±2 hour | X | | | X |
| 96 | ±2 hour | X | | | X |

The Sponsor may conduct additional analyses on the PK samples in order to follow up the safety of the study treatment or to better understand the progression of the disease or the disease's response to the study treatment.

See the Laboratory Manual and Appendix G for sample collection, handling, and processing instructions.

The schedules for pharmacodynamic biomarkers are provided below:

Whole blood for PD biomarker studies
    Cycle 1 Day 1: pre-dose (≤3 hours)
    Cycle 1 Day 3
    Cycle 1 Day 5
    Cycle 1 Day 8: pre-dose (≤3 hours)
    Cycle 1 Day 24: pre-dose (≤3 hours)
Serum for PD biomarker studies (NEC and SCLC subjects only)
    Cycle 1 Day 1: pre-dose (≤3 hours)
    Cycle 1 Day 3
    Cycle 1 Day 8: pre-dose (≤3 hours)
Tumor tissue for PD biomarker studies
    Screening: Day −28 to Day 1 predose (after all inclusion and exclusion criteria are fulfilled)
    Cycle 1 Day 16 or 17 (+7 days)
    Optional, any other time until EOT visit.

The Sponsor may conduct additional analyses on the PD samples in order to follow up the safety of the study treatment or to better understand the progression of the disease or the disease's response to the study treatment.

Tumor biopsies will be collected whenever safe and feasible in Part A. Tumor biopsies are mandatory in Part B. The biopsy is collected by either surgical biopsy (preferred) or core needle (at least 3 passages, if possible) at Screening and in Cycle 1 on Day 16 or 17 (+7 days). If study drug treatment is interrupted or reduced before this time, the biopsy should be delayed until 1 to 2 days (+7 days) after the subject has received two consecutive planned doses of Compound A. An archival tumor sample must be provided if a fresh biopsy is not collected during Screening. Fine needle aspiration is not sufficient as a source of tumor biopsy material. Samples should be processed as formalin-fixed paraffin-embedded (FFPE). Optimally, the tumor tissue samples (Screening and on-treatment) will be obtained from the same tumor site.

Additionally, an optional tumor biopsy may be obtained in both Part A and Part B, during later treatment cycles or following treatment discontinuation (any time during the 28-day follow-up period), to elucidate effects of long-term treatment or resistance mechanisms, respectively.

Description of Study Treatments

Compound A is a besylate salt with a molecular weight of 609.65. It is a white to pale yellow solid. Compound A will be supplied to the clinic as opaque Swedish orange capsules containing only the active pharmaceutical ingredient at dosage strengths of 0.50 mg, 0.75 mg, and 2.00 mg. The capsules will be supplied in HDPE bottles with child-resistant caps, labeled appropriately for investigational use as per the regulations of the relevant country health authorities.

Compound A will be administered once weekly in the morning on an empty stomach (ie, ≥1 hour before breakfast) with at least 240 mL of water after an overnight fast lasting ≥6 hours in both Parts A and B. Subjects should abstain from food or other medication intake for ≥1 hour after each dose. Subjects will administer Compound A orally once weekly in each 4 week (28 day) Cycle. Alternative dosing schedules may be implemented based on the review of clinical safety and laboratory data by the SRC. Compound A will be administered in the clinic after any predose assessments are completed. Study treatment may be discontinued if there is evidence of clinically significant disease progression, unacceptable toxicity or subject/physician decision to withdraw.

For the purposes of dose escalation decisions, at least 3 subjects will be enrolled in successive cohorts. The first cohort will be treated with the starting dose of 1.25 mg once weekly. Subjects must complete a minimum of 1 cycle of treatment with the minimum safety evaluation and drug exposure or have had a DLT within the first cycle of treatment to be considered evaluable for dose escalation decisions. Dose escalation decisions will occur when the cohort of subjects has met these criteria. Dose escalation decisions will be made by the SRC. Decisions will be based on a synthesis of all relevant data available from all dose levels evaluated in the ongoing study including safety information, DLTs, all treatment related CTCAE grade ≥2 toxicity data during Cycle 1, and PK data from evaluable subjects. PK data from subjects will be made available on an on-going basis throughout the study and dosing will be adapted accordingly. The recommended dose for the next cohort of subjects will be guided by the BLRM with EWOC principle.

The adaptive Bayesian methodology provides an estimate of the dose levels of Compound A that do not exceed the MTD and incorporates all DLT information at all dose levels for this estimation. In general, the next recommended dose will have the highest chance that the DLT rate will fall in the target interval (the true DLT rate lying in 16-33%) and will always satisfy the EWOC principle. Per EWOC it should be unlikely (<25% posterior probability) that the DLT rate at the next dose will exceed 0.33. In all cases, the recommended dose for the next cohort will not exceed a 100% increase from the previous dose. Smaller increases in dose may be recommended by the SRC upon consideration of all of the available clinical data.

The procedure for subject accrual in each dose cohort and provisions for dose escalation/de-escalation decisions for the study is as follows:

1. This study will begin by evaluating Compound A in cohorts of at least 3 evaluable subjects at each dose level. Initially, the dosing increments between cohorts will be 100%. When a single subject experiences a DLT, or 2 subjects experience grade ≥2 treatment-related toxicity, the cohort size may be increased to 6 evaluable subjects for the current and subsequent cohorts. The increase in Compound A dose will be ≤50% for each subsequent dose escalation cohort. Once 2 subjects experience grade ≥2 treatment-related toxicity, the enrollment will be restricted to subjects with SCLC and other NECs such as MTC who secrete Pro-GRP or, CgA or calcitonin (for MTC subjects) or pancreastatin (for pancreatic or small bowel NEC).

2. Following completion of Cycle 1 for all evaluable subjects in a cohort, the two-parameter BLRM with EWOC principle will be used to make recommendations to the SRC for the next dose level with the following exceptions:

If the first 2 subjects in a cohort experience DLTs, no additional subjects will be enrolled into that cohort until the Bayesian model has been updated with this new information. Likewise, the model will be re-evaluated if 2 subjects in a cohort experience DLTs before the enrollment of any additional subject.

3. After each cohort, the SRC will meet and review data from the BLRM assessment and available safety (ie, DLT and non-DLT data), PK, PD, and preliminary efficacy information. The final dose escalation decisions will be made by the SRC.

After repeating the above steps, a Compound A dose can be declared the MTD after meeting the following conditions:
- at least 6 evaluable subjects have been treated at the dose,
- the posterior probability that the DLT rate lying in the target interval (16-33%) at the dose exceeds 60% or a sufficient number of subjects have been entered into the study to ensure the precision of the MTD estimate, as the posterior probability approaches but fails to exceed 60%, and
- the dose is recommended according to the BLRM and the SRC approves it.

Dose escalation may be terminated by SRC at any time based on emerging safety concerns without establishing the MTD. At the discretion of the SRC to better understand the safety, tolerability and PK of Compound A, additional cohorts of subjects may be enrolled at prior dose levels or to intermediate dose levels before or while proceeding with further dose escalation.

Dose decisions during escalation are however not limited to these doses. Based on the recommendation of the BLRM regarding the highest dose that may not be exceeded at any decision point during escalation and the maximum increase in dose allowed by the protocol, intermediate doses may be administered to subsequent new cohorts of subjects.

The decision to evaluate additional subjects within a dose cohort, a higher dose cohort, intermediate dose cohorts, smaller dose increments, alternative dosing schedules, or declare an MTD will also be determined by the SRC, based on their review of clinical and laboratory safety data.

All subjects who receive at least one dose of Compound A will be evaluable for safety.

After the first dose is administered in any cohort during dose escalation, subjects in each cohort are observed for 28 days (Cycle 1, DLT window) before the next dose cohort can begin. No more than one subject per day will be enrolled in a given dose escalation cohort. A subject evaluable for DLT is defined as one that:
- Has received ≥75% of the total planned dose amount of Compound A during Cycle 1 without experiencing a DLT,
or
- Experienced a DLT after receiving at least one dose of Compound A.

Subjects not evaluable for DLT will be replaced. Additional subjects within any dose cohort may be enrolled at the discretion of the SRC. Intra-subject dose escalation will not be allowed during the DLT assessment period.

The MTD is the highest dose at which less than 33% of the population (not sample of the population) treated with Compound A suffer a DLT in the first cycle and at least 6 evaluable subjects have been treated at this dose.

A variable dose cohort (eg, less frequent dosing) may be evaluated to accurately determine the MTD at the discretion of the SRC.

During dose escalation, the DLT assessment period is Cycle 1 (28 days).

National Cancer Institute (NCI) Common Terminology Criteria for Adverse Events (CTCAE), Version 4.03 are used as a guide for the grading of severity of adverse events. A DLT is defined as any of the following toxicities occurring within the DLT assessment unless the event can clearly be determined to be unrelated to Compound A. Dose-limiting toxicities are described below:

Any Grade 4 non-hematologic toxicity of any duration
Any non-hematologic toxicity Grade ≥3 EXCEPT for:
- Grade 3 diarrhea, nausea, or vomiting of ≤3 days duration (with optimal medical management).
- Grade 3 rash of the acneiform, pustular or maculopapular type which resolves to Grade ≤2 within 7 days of study drug interruption and does not recur at the same level with resumption of study drug at the same dose (with optimal medical management).
- Grade 3 fatigue which resolves to Grade ≤2 within 7 days of study drug interruption and does not recur at the same level with resumption of study drug at the same dose (with optimal medical management).

Hematological toxicities as follows:
- Febrile neutropenia
- Grade 4 neutropenia lasting >7 days
- Grade 4 thrombocytopenia lasting >7 days, Grade ≥3 thrombocytopenia with clinically significant bleeding Any AE, unless clearly determined to be unrelated to study drug, necessitating dose-level reduction during Cycle 1.

Any other toxicity at any time during the trial that the safety committee deem dose limiting.

Isolated laboratory changes without associated clinical signs or symptoms (eg, hypomagnesemia, hypermagnesemia, hypoalbuminemia, hypophosphatemia, lymphocyte count increased or decreased) may not be included in this definition. These findings will be discussed and reviewed by the SRC.

Dose reductions are permitted in any cycle, including Cycle 1. Dose reductions that occur in Cycle 1 during dose escalation will constitute DLT, but subjects will be allowed to continue on Compound A at a reduced dose.

When a dose adjustment is indicated, the dose frequency will be adjusted first. Dose omission and reduction are allowed after consultation with the Sponsor's study physician. Once the dose has been reduced, it can be escalated when toxicity reaches Grade ≤1. If toxicity recurs at the higher dose, the dose will be reduced a second time, but no re-escalation is then permitted. If any subject continues to experience unacceptable toxicity after two dose reductions (one for the dose level), Compound A will be discontinued permanently.

Intra-subject dose escalation will not be allowed during the DLT assessment period.

Any AE meeting the definition of DLT will require dose frequency adjustment and subsequent dose interruption if no recovery. Doses should be delayed if any treatment related Grade ≥2 toxicities are not resolved to Grade ≤1 by the time of the next dose. Such cases should be discussed with the Sponsor's study physician to determine the optimal duration of the dosing delay.

Treatment related Grade ≥3 toxicity or chronic Grade 2 toxicity may warrant dose reduction of Compound A. Such cases should be discussed with the Sponsor's study physician before dosing changes are made.

Intra-subject dose escalation will not be allowed during the DLT assessment period, however, in Cycles ≥3, subjects without evidence of disease progression who are tolerating their assigned dose of Compound A may (at the Investigator's discretion and in consultation and agreement with the Sponsor's study physician) escalate to the highest dose level shown to be adequately tolerated by at least one cohort of subjects in this study (ie, ≤33% of evaluable subjects having experienced a DLT at that dose level).

In Part B (expansion phase), no dose escalation beyond the MTD is allowed.

Treatment may be interrupted up to 4 weeks until toxicity (excluding alopecia) reaches either Grade ≤1 or baseline levels. Treatment may restart either at the same, or a reduced dose, at the Investigator's discretion. Any such treatment interruptions must be discussed with the Sponsor's study physician.

In the DLT assessment period of the dose escalation phase, a treatment interruption with >1 missed dose of Compound A for reasons other than DLT will make a subject non-evaluable for DLT and necessitate replacement of that subject in the dosing cohort. Any such treatment interruptions must be discussed with the Sponsor's study physician.

Hematopoietic growth factors or other hematologic support, such as erythropoietin, darbepoetin, granulocyte-colony stimulating factor (G-CSF), granulocyte macrophage colony stimulating factor (GM CSF), and RBC- or platelet-transfusions are allowed in the study with therapeutic intent. Therapeutic use of G-CSF is allowed at any time for subjects experiencing Grade 3/4 neutropenia or any grade febrile neutropenia. Prophylactic use of granulocyte (or granulocyte-macrophage) growth factors is not allowed during Cycle 1.

Subjects with Grade 3 or 4 neutropenia and/or Grade 3 or 4 thrombocytopenia should be monitored frequently with laboratory tests until resolution to Grade ≤1. Antimicrobial, antifungal, and antiviral prophylaxis should be considered, as appropriate.

Tumor pain or treatment-induced pain can be controlled with opioid and opioid-related analgesics, such as codeine, meperidine, propoxyphene or morphine, administered at the clinician's discretion, and as dictated by medical need. The risk of bleeding, especially in the setting of thrombocytopenia, should be considered prior to use of non-steroidal anti inflammatory drugs (NSAIDs) and aspirin. NSAIDS and aspirins should be avoided if possible and paracetamol should be administered instead.

Mucosa coating agents for protection of esophageal/gastric mucosa are recommended at the discretion of the Investigator as well as monitoring subjects for GI bleeding. However proton pump inhibitors may affect the neuroendocrine markers in NEC subjects, so histamine (H2) receptor antagonists should be administered preferentially if appropriate. Subjects will be encouraged to report all episodes of GI discomfort or pain, appetite loss, change of stool, or blood in stool.

It is recommended that subjects experiencing diarrhea be managed according to the guideline provided in Appendix F. Anti-diarrheal medication, such as loperamide, should be initiated at the earliest onset of Grade 1-2 diarrhea. Anti-diarrheal medication may be administered as prophylaxis and for treatment of diarrhea. Dehydration and electrolyte disturbances should be rapidly corrected. General measures to improve diarrhea, such as a low-fiber diet and increased liquid consumption, should be considered and weight should be closely monitored.

Overdose, as defined for this protocol, refers to Compound A dosing only. On a per dose basis, an overdose is defined as the following amount over the protocol-specified dose of Compound A assigned to a given subject, regardless of any associated adverse events or sequelae:

PO any amount over the protocol-specified dose

On a schedule or frequency basis, an overdose is defined as anything more frequent than the protocol required schedule or frequency.

Complete data about drug administration, including any overdose, regardless of whether the overdose was accidental or intentional, should be reported in the case report form.

Eligible subjects will be enrolled sequentially in Part A (dose escalation). Enrollment in Part B (dose expansion) will be stratified by disease cohort and dosing schedule, as applicable.

An Interactive Response Technology (IRT) system will be used to track subject assignments to the dose levels in Part A and tumor cohorts in Part B.

The label(s) for Compound A will include, but not limited to, sponsor name, address and telephone number, the protocol number, Compound A, dosage form and strength (where applicable), amount of Compound A per container, lot number, expiry date (where applicable), medication identification/kit number, dosing instructions, storage conditions, and required caution statements and/or regulatory statements as applicable. Additional information may be included on the label as applicable per local regulations.

Celgene (or designee) will review with the Investigator and relevant site personnel the procedures for documenting receipt of Compound A, as well as the procedures for counting, reconciling Compound A, and documenting this process. Celgene (or designee) will also review with the Investigator and relevant site personnel the process for Compound A return, disposal, and/or destruction including responsibilities for the site vs. Celgene (or designee).

Only the pharmacist or the Investigator's designee will dispense Compound A. A record of the number of capsules of Compound A dispensed to and taken by each subject must be maintained. The pharmacist or the Investigator's designee will document the doses dispensed/administered in the appropriate study records.

Concomitant Medications and Procedures

All medications (excluding prior cancer therapy for the tumor under evaluation) taken beginning when the subject signs the ICD and all concomitant therapy during the study until 28 days after treatment discontinuation, together with dose, dose frequency and reasons for therapy use will be documented in the source documents and on the concomitant medication eCRF.

All prior chemotherapy (biologic, immunologic, or radiation therapy) and anticancer surgery prior to the administration of study drug, will be recorded in the appropriate section of the eCRF.

The Investigator will instruct subjects to notify the study staff about any new medications taken after signing the ICD. All medications and significant non-drug therapies (herbal medicines, physical therapy, etc.) and any changes in dosing with existing medications will be documented on the eCRFs.

The use of any concomitant medication/therapies deemed necessary for the care of the subject should be used. Repeat PK evaluations may be conducted if changes are made to concomitant medications suspected of affecting drug absorption or metabolism. The following are permitted concomitant medications and procedures:

Subjects with ≥Grade 1 diarrhea should promptly initiate treatment with diphenyoxylate/atropine (Lomotil), or loperamide (Imodium) or an alternative over-the-counter remedy for diarrhea. Premedication with antidiarrheal medication for subsequent doses of Compound A may be appropriate and should be discussed with Sponsor's study physician.

Anti-emetics will be withheld until subjects have experienced CTCAE ≥Grade 1 nausea or vomiting. Subjects may then receive prophylactic anti-emetics at the discretion of the Investigator, including dexamethasone.

Prophylactic mucosa protective agents may be appropriate at the discretion of the Investigator. However proton pump inhibitors may affect the neuroendocrine markers in NEC subjects, so histamine (H2) receptor antagonists should be administered preferentially if appropriate.

Antiviral therapy with an appropriate antiviral agent for HBV is required in HCC subjects with positive hepatitis B surface antigen, HBcAb IgM, and/or viral load—appropriate first line agents include entecavir, tenofovir, and lamivudine (note that lamivudine has higher resistance rates). Regimens appropriate for the treatment of HCV should not be interrupted when administering Compound A.

Therapeutic use of granulocyte growth factors is allowed at any time for subjects experiencing febrile neutropenia or Grade 3/4 neutropenia. Routine prophylaxis with granulocyte colony stimulating factor or granulocyte-macrophage colony stimulating Subjects receiving stable doses of recombinant erythropoietin or darbepoetin alfa for at least 4 weeks prior to starting the Compound A may continue their pretreatment doses throughout the study. Subjects may initiate de novo treatment with erythropoietin stimulating agents (ESAs) beginning in Cycle 2 for hypoproliferative anemias secondary to prior chemotherapy exposure provided there is no clinical Parenteral flu vaccination is permitted.

Routine infectious disease prophylaxis is not required. However, antibiotic, antiviral, anti-*pneumocystis*, anti-fungal, or other prophylaxis may be implemented during the study at the discretion of the Investigator.

Treatment with bisphosphonates (eg, pamidronate, zolendronate) or other agents (eg, denosumab) is permitted to prevent or delay progression of bone metastases. Maintenance of a stable dosing regimen throughout the study is recommended.

Focal palliative radiotherapy for treatment of cancer-related symptoms (eg, localized bone pain) is allowed during study treatment at the discretion of the investigator, provided this is not indicative of disease progression, in which case the subject should Subjects may receive physiologic replacement doses of glucocorticoids (up to the equivalent of 10 mg daily prednisone) as maintenance therapy.

Maintenance hormonal therapies are allowed in subjects with a history of breast or prostate cancer.

Somatostatin analogs (SSA) may be used for symptom control as appropriate.

Other investigational therapies must not be used while the subject is on the study.

Anticancer therapy (chemotherapy, biologic or investigational therapy, and surgery) other than the study treatments must not be given to subjects while the subject is on the study. If such treatment is required the subject must be discontinued from the study. Treatment with immunosuppressive agents is not allowed while the subject is on the study. If such treatment is required the subject must be discontinued from the study.

Treatment with chronic, therapeutic dosing of anti-coagulants (eg, warfarin, low molecular weight heparin, Factor Xa inhibitors, thrombin antagonists) is not allowed. Short-term, prophylactic dosing of anticoagulants may be considered in subjects if medically indicated (eg, hospitalized subjects, post-operatively) under careful consideration by the Investigator.

Compound A may be a substrate of CYP3A4. Drugs that are known strong inducers or inhibitors of these CYP enzymes should be avoided. If use of one of these drugs is necessary, the risks and benefits should be discussed with the Sponsor's study physician prior to its concomitant use with Compound A.

Examples of these drugs are (not inclusive):
CYP3A4/5 inhibitors: atazanavir, clarithromycin, indinavir, itraconazole, ketoconazole, nefazodone, nelfinavir, ritonavir, saquinavir, and telithromycin
CYP3A4/5 inducers: rifampin and carbamazepine Proton pump inhibitors should be avoided, if possible, in the NEC subjects due to a possible effect on the biomarkers. If clinically appropriate, subjects should be changed to a H2 antagonist at least 7 days prior to the first dose.

In view of the potential for thrombocytopenia, NSAIDS and aspirins should be avoided if possible and paracetamol should be administered instead.

Statsotocal Considerations

The primary objectives of this study are to determine the safety, tolerability, and MTD of Compound A when administered orally once a week for 4 weeks (28-day Cycle) to adult subjects with advanced solid tumors (including NEC) and relapsed/refractory NHL. The secondary objectives are to make a preliminary assessment of the antitumor activity of Compound A, and to determine its PK characteristics.

Data summaries/statistical analyses will be performed by study part (Part A or B), dose schedule, dose level (Part A), and tumor cohort (Part B) as applicable.

The study population definitions are as follows:
Enrolled Population—All subjects who meet inclusion/exclusion criteria.
Treated Population—All subjects who enroll and receive at least one dose of Compound A
Efficacy Evaluable (EE) Population—All subjects who enroll in the study, meet eligibility criteria, complete at least one cycle of Compound A (taking at least 75% of assigned doses), and have baseline and at least one valid
Pharmacokinetic (PK) Evaluable Population—all subjects who enroll and receive at least one dose of Compound A and have at least one measurable concentration of Compound A
Biomarker Evaluable (BE) Population—all subjects who enroll, receive at least one dose of study drug, and have at least one biomarker assessment, excluding disqualified assessments.

During Part A of the study an adaptive Bayesian logistic regression (BLR) model (with 2 parameters) guided by the escalation with overdose control (EWOC) principle will be for dose escalation. No formal statistical power calculations to determine sample size were performed for this study. The actual number of subjects will depend on the number of dose levels/cohorts that are tested. However, the anticipated number of subjects will be approximately 50.

After the MTD is determined from Part A, Part B will enroll approximately 20 additional subjects per prespecified tumor types.

For Part B, sample sizes are not determined based on power calculation but rather on clinical, empirical and practical considerations traditionally used for exploratory studies of this kind. During the Part B dose expansion, at least 14 efficacy evaluable subjects for each tumor cohort will initially be accrued. The tumor cohort will be expanded to approximately 20 subjects if a responder or SD of 4 months or longer is observed.

In Part A, the baseline characteristics of subjects will be summarized by dose cohort for the enrolled population. In Part B, the baseline characteristics of subjects will be summarized by tumor type. The age, weight, height and other continuous demographic and baseline variables will be summarized using descriptive statistics. Performance status, gender, race and other categorical variables will be summarized with frequency tabulations. Medical history data will be summarized using frequency tabulations by system organ class and preferred term.

Subject disposition (analysis population allocation, ongoing, discontinued, along with primary reason) from treatment and study will be summarized using frequency and percent. A summary of subjects enrolled by site will be provided. Protocol violations will be summarized using frequency tabulations. Supportive corresponding subject listings will also be provided.

Efficacy analyses will be based on the treated population and include summaries of clinical benefit rate (CBR), objective response rate (ORR), duration of response or stable disease, progression-free survival (PFS), time to progression (TTP) and OS by dose cohort and dosing schedule (Part A) or tumor type and dosing schedule (Part B). Tumor response (CR, PR, SD, PD, or inevaluable) will be assessed by investigators according to Response Evaluation Criteria in Solid Tumors (RECIST), version 1.1, mRECIST for NEHC, PCWG23 for NEPC and IWG criteria. The CBR is defined as tumor responses (as assessed by the Investigators) of CR, PR and durable SD (SD of ≥4 months duration). The ORR is defined as the percent of subjects whose best response is CR or PR. When SD is the best response, it must be documented radiographically at least once after study entry after a minimal interval of 8 weeks from first dose (ie, coincident with the first post baseline response assessment time point minus assessment window). If the minimal time for a best response of SD is not met, the subject's best response will depend on the outcome of subsequent assessments. For example, a subject who exhibits SD at first assessment (where the first assessment does not meet minimal duration criteria for SD) and PD at the second assessment, would be classified as having a best response of PD. A subject lost to follow-up after the first SD assessment would be considered non-evaluable, if the minimal duration criteria for SD were not met.

Two-sided 95% Clopper-Pearson exact confidence intervals will be provided for ORR and CBR estimates. Similar analyses will be performed to include those subjects with confirmed responses as well as for the Efficacy Evaluable population.

For subjects with best response of CR or PR, duration of response is measured from the time when criteria for CR/PR are first met (whichever is first recorded) until the first date at which progressive disease is objectively documented. For subjects with best response of SD, duration of SD is measured from the first dose date until the criteria for progression are met. If progression is not documented prior to Compound A discontinuation, duration of overall response, and duration of SD will be censored at the date of the last adequate tumor assessment.

Duration of response/SD based on investigators' assessments will be summarized by descriptive statistics (mean, standard deviation, median, minimum and maximum) for the treated population. Except for medians, which will be calculated based on both observed and censored values using the Kaplan-Meier method, all other statistics (mean, standard deviation, minimum and maximum) will be calculated based on observed values only. TTP is defined as the time from the first dose until tumor progression.

Progression-Free Survival (PFS) is defined as the time from the first dose of Compound A to the first occurrence of disease progression or death from any cause. Subjects who neither progress nor die at a data cut-off date will be censored at the date of their last adequate tumor assessment. The PFS will be summarized using descriptive statistics (mean, standard deviation, median, minimum and maximum) for the treated population. Except for the median, which will be calculated based on both observed and censored values using the Kaplan-Meier method, all other statistics (mean, standard deviation, minimum and maximum) will be calculated based on observed values only.

Overall Survival (OS) is measured as the time from the first dose of Compound A to death due to any cause and will be analyzed in a manner similar to that described for PFS.

The assessments of serum neuroendocrine markers over time in neuroendocrine subjects will be summarized.

Adverse events, including treatment-emergent adverse events (TEAEs), laboratory assessments, vital signs, ECG results, ECOG performance status, LVEF assessments, physical examinations, vital signs, exposure to study treatment, assessment of concomitant medications, and pregnancy testing for females of childbearing potential will be summarized for the treated population (by dose cohort in Part A and tumor type in Part B).

Adverse events observed will be classified using the Medical Dictionary for Regulatory Activities (MedDRA), Version 18.1 or higher, system organ class (SOC) and preferred term (PT). In the by-subject analysis, a subject having the same AE more than once will be counted only once. All adverse events will also be summarized by SOC, PT, and NCI CTCAE grade (Version 4.0 or higher). Adverse events leading to discontinuation of study treatment, those classified as Grade 3 or 4, study drug-related AEs, and SAEs (including deaths) will be tabulated separately. By-subject listings of all AEs, TEAEs, SAEs (including deaths), and their attribution will be provided.

Clinical laboratory results will be summarized descriptively by dose cohort (Part A) or tumor type (Part B) and visit, which will also include a display of change from baseline. Shift tables demonstrating the changes (low/normal/high) from baseline to worst post-baseline laboratory value will be displayed in cross-tabulations by dose cohort (Part A) or tumor type (Part B). Similar shift tables demonstrating the change of NCI CTCAE grades from baseline to the worst post-baseline severity grade during the treatment period will also be presented by dose cohort (Part A) or tumor type (Part B) for applicable analytes. Listings of abnormal clinical laboratory data according to NCI CTCAE severity grades (if applicable), abnormal flags (low or high) and clinical significance of the latter will be provided.

Graphical displays (eg, "spaghetti" plots or box plots) will be provided for key laboratory analytes.

Descriptive statistics for vital signs, both observed values and changes from baseline, will be summarized by dose cohort (Part A) or tumor type (Part B) and visit. Shift tables demonstrating the changes from baseline to the worst post-baseline value will be displayed in cross-tabulations by dose cohort (Part A) or tumor type (Part B). Vital sign measurements will be listed by subject and by visit.

ECG parameters and changes from baseline will be summarized by dose cohort (Part A) or tumor type (Part B) and visit using descriptive statistics. Post-baseline abnormal QTc (both QTcF and QTcB) values will be summarized using frequency tabulations for the following 5 categories:

QTc>450 msec
QTc>480 msec
QTc>500 msec
QTc increase from baseline >30 msec
QTc increase from baseline >60 msec Shift from baseline to worst post-baseline qualitative assessment of abnormality (ie, 'Normal', 'Abnormal, not clinically significant', and 'Abnormal, clinically significant' or 'Normal' and 'Abnormal') will be displayed in cross-tabulations by dose cohort (Part A) or tumor type (Part B). A listing of ECG parameters by subject, by visit will be provided.

No formal interim analysis is planned. Data will be reviewed on an ongoing basis.

An adaptive BLRM guided by the escalation with EWOC principle will be used to make dose recommendations and estimate the MTD during the escalation phase of the study (refer to Appendix E for additional details).

The DLT relationship in the escalation part of the study will be described by the following Bayesian logistic regression model:

$$\log\left(\frac{p_j}{1-p_j}\right) = \log\alpha + \beta \cdot \log\left(\frac{d_j}{d^*}\right), \alpha > 0, \beta > 0$$

where $p_j$'s are DLT rates at dose, $d_j$'s are dose levels, $d^*=30$ mg reference dose, $\alpha$ is odds of DLT at $d^*$.

A vague bivariate normal prior for the model parameters $(\log(\alpha), \log(\beta))$ is elicited based on prior estimates (medians) from preclinical data and wide confidence intervals for the probabilities of a DLT at each dose. Prior MTD is assumed to be 30 mg based on preclinical data. The probability of DLT for the first dose is assumed to be low. The parameters of the prior distributions of model parameters are selected based on the method to construct weakly informative prior as described in Neuenschwander et al (2015) and are provided in Table 36.

TABLE 36

Prior Parameters for Bivariate Normal Distribution of Model Parameters

| Parameters | Means | Standard Deviation | Correlation |
|---|---|---|---|
| log(α), log(β) | (−0.693, 0.205) | (2, 0.75) | 0 |

The provisional dose levels are: 1.25 mg, 2.5 mg, 5 mg, 10 mg, 15 mg, 22.5 mg, 30 mg, and 37.5 mg. It is however possible that the actual dose levels selected for the trial may be different from the provisional dose levels, based on emerging safety information.

After each cohort of subjects the posterior distributions for the probabilities of a DLT rates at different dose levels are obtained. The results of this analysis are summarized in terms of the estimated probabilities that the true rate of DLT at each dose-level will have of lying in each of the following intervals:

[0, 0.16) under-dosing
[0.16, 0.33) targeted toxicity
[0.33, 1.00] excessive toxicity Following the principle of escalation with EWOC, after each cohort of subjects the recommended dose is the one with the highest posterior probability of the DLT rate falling in the target interval [16%, 33%) among the doses fulfilling EWOC, ie, it is unlikely (<25% posterior probability) that the DLT rate at the dose falls in the excessive toxicity interval.

Note that the dose that maximizes the posterior probability of targeted toxicity is the best estimate of the MTD, but it may not be an admissible dose according to the overdose criterion if the amount of data is insufficient. If vague prior information is used for the probabilities of DLT, in the early stages of the study this escalation procedure will reflect a conservative strategy.

The dose recommended by the adaptive Bayesian logistic model may be regarded as guidance and information to be integrated with a clinical assessment of the toxicity profiles observed at the time of the analysis in determining the next dose level to be investigated.

Plasma PK parameters such as AUC, $C_{max}$, $T_{max}$, $t_{1/2}$, CL/F, and Vz/F of Compound A will be calculated by the noncompartmental analysis method from the plasma concentration-time profiles of Compound A. Other PK parameters may be calculated as appropriate.

Summary statistics including number of subjects (N), mean, standard deviation (SD), coefficient of variation (CV %), geometric mean, geometric CV %, median, minimum, and maximum will be provided for Compound A concentration by nominal time point, study day, and dose cohort. Mean and individual plots of plasma concentrations will be presented in both original and semi-logarithmic scales. Summary statistics will also be provided for Compound A PK parameters by study day and dose cohort and be presented in tabular form.

A population PK analysis for Compound A may be conducted to explore the inter-individual variability of plasma drug exposure and the contributing factors (covariates). The relationship between Compound A dose, plasma exposures, and selected clinical endpoints (eg. measures of toxicities, effectiveness, and/or biomarkers) will be explored. The population PK model, in combination with the knowledge on exposure-response, may be used to assist identification of the dosing regimen for Part B or Phase 2 studies.

Descriptive statistics (N, mean, SD, median, min, and max) will be provided for baseline, post-baseline values, and changes from baseline or percent change from baseline for biomarkers including neuroendocrine markers by dose cohort (Part A) or tumor type (Part B) and visit.

Subjects' biomarker results over time will be plotted. Comparison of biomarker levels before and during treatment will be performed by Wilcoxon signed rank test. If sufficient and valid results from biomarker assays can be obtained, the relationship between percent changes in biomarker levels and clinical endpoints including ORR and CBR will be explored. The population PK model, in combination with the knowledge on exposure-response, may be used to assist in identification of the dosing regimen for Part B or Phase 2 studies.

Advserse Events

An AE is any noxious, unintended, or untoward medical occurrence that may appear or worsen in a subject during the course of a study. It may be a new intercurrent illness, a worsening concomitant illness, an injury, or any concomitant impairment of the subject's health, including laboratory test values, regardless of etiology. Any worsening (ie, any clinically significant adverse change in the frequency or intensity of a pre-existing condition) should be considered an AE. A diagnosis or syndrome should be recorded on the AE page of the CRF rather than the individual signs or symptoms of the diagnosis or syndrome.

Abuse, withdrawal, sensitivity or toxicity to an investigational product should be reported as an AE. Overdose, accidental or intentional, whether or not it is associated with an AE should be reported on the overdose CRF. Any sequela of an accidental or intentional overdose of an investigational product should be reported as an AE on the AE CRF. If the sequela of an overdose is an SAE, then the sequela must be reported on an SAE report form and on the AE CRF. The overdose resulting in the SAE should be identified as the cause of the event on the SAE report form and CRF but should not be reported as an SAE itself.

In the event of overdose, the subject should be monitored as appropriate and should receive supportive measures as necessary. There is no known specific antidote for Compound A overdose. Actual treatment should depend on the severity of the clinical situation and the judgment and experience of the treating physician.

All subjects will be monitored for AEs during the study. Assessments may include monitoring of any or all of the following parameters: the subject's clinical symptoms, laboratory, pathological, radiological or surgical findings, physical examination findings, or findings from other tests and/or procedures.

All AEs will be recorded by the Investigator from the time the subject signs informed consent until 28 days after the last dose of Compound A as well as those SAEs made known to the Investigator at any time thereafter that are suspected of being related to Compound A. AEs and SAEs will be recorded on the AE page of the CRF and in the subject's source documents. All SAEs must be reported to Celgene Drug Safety within 24 hours of the Investigator's knowledge of the event by facsimile, or other appropriate method, using the SAE Report Form, or approved equivalent form.

A qualified Investigator will evaluate all adverse events as to:

Seriousness

An SAE is any AE occurring at any dose that:

Results in death;

Is life-threatening (ie, in the opinion of the Investigator, the subject is at immediate risk of death from the AE);

Requires inpatient hospitalization or prolongation of existing hospitalization (hospitalization is defined as an inpatient admission, regardless of length of stay);

Results in persistent or significant disability/incapacity (a substantial disruption of the subject's ability to conduct normal life functions);

Is a congenital anomaly/birth defect;

Constitutes an important medical event.

Important medical events are defined as those occurrences that may not be immediately life-threatening or result in death, hospitalization, or disability, but may jeopardize the subject or require medical or surgical intervention to prevent one of the other outcomes listed above. Medical and scientific judgment should be exercised in deciding whether such an AE should be considered serious.

Events not considered to be SAEs are hospitalizations for:

a standard procedure for protocol therapy administration. However, hospitalization or prolonged hospitalization for a complication of therapy administration will be reported as an SAE.

routine treatment or monitoring of the studied indication not associated with any deterioration in condition.

the administration of blood or platelet transfusion as routine treatment of studied indication. However, hospitalization or prolonged hospitalization for a complication of such transfusion remains a reportable SAE.

a procedure for protocol/disease-related investigations (eg, surgery, scans, endoscopy, sampling for laboratory tests, bone marrow sampling). However, hospitalization or prolonged hospitalization for a complication of such procedures remains a reportable SAE.

hospitalization or prolongation of hospitalization for technical, practical, or social reasons, in absence of an AE.

a procedure that is planned (ie, planned prior to start of treatment on study); must be documented in the source document and the CRF. Hospitalization or prolonged hospitalization for a complication remains a reportable SAE.

an elective treatment of or an elective procedure for a pre-existing condition, unrelated to the studied indication, that has not worsened from baseline.

emergency outpatient treatment or observation that does not result in admission, unless fulfilling other seriousness criteria above.

If an AE is considered serious, both the AE page/screen of the CRF and the SAE Report Form must be completed. For each SAE, the Investigator will provide information on severity, start and stop dates, relationship to the IP, action taken regarding the IP, and outcome.

Severity/Intensity

For both AEs and SAEs, the Investigator must assess the severity/intensity of the event. The severity/intensity of AEs will be graded based upon the subject's symptoms according to the current active minor version of the Common Terminology Criteria for Adverse Events (CTCAE, Version 4.0); http://ctep.cancer.gov/protocolDevelopment/electronic_applications/ctc.htm#ctc_40

AEs that are not defined in the CTCAE should be evaluated for severity/intensity according to the following scale:

Grade 1=Mild—transient or mild discomfort; no limitation in activity; no medical intervention/therapy required Grade 2=Moderate—mild to moderate limitation in activity, some assistance may be needed; no or minimal medical intervention/therapy required Grade 3=Severe—marked limitation in activity, some assistance usually required; medical intervention/therapy required, hospitalization is possible Grade 4=Life-threatening—extreme limitation in activity, significant assistance required; significant medical intervention/therapy required, hospitalization or hospice care probable Grade 5=Death—the event results in death]

The term "severe" is often used to describe the intensity of a specific event (as in mild, moderate or severe myocardial infarction); the event itself, however, may be of relatively minor medical significance (such as severe headache). This criterion is not the same as "serious" which is based on subject/event outcome or action criteria associated with events that pose a threat to a subject's life or functioning. Seriousness, not severity, serves as a guide for defining regulatory obligations.

Causality

The Investigator must determine the relationship between the administration of the IP and the occurrence of an AE/SAE as Not Suspected or Suspected as defined below:

Not suspected: a causal relationship of the adverse event to IP administration is unlikely or remote, or other medications, therapeutic interventions, or underlying conditions provide a sufficient explanation for the observed event.

Suspected: there is a reasonable possibility that the administration of IP caused the adverse event. 'Reasonable possibility' means there is evidence to suggest a causal relationship between the IP and the adverse event.

Causality should be assessed and provided for every AE/SAE based on currently available information. Causality is to be reassessed and provided as additional information becomes available.

If an event is assessed as suspected of being related to a comparator, ancillary or additional Compound A that has not been manufactured or provided by Celgene, please provide the name of the manufacturer when reporting the event.

Duration

For both AEs and SAEs, the Investigator will provide a record of the start and stop dates of the event.

Action Taken

The Investigator will report the action taken with IP as a result of an AE or SAE, as applicable (eg, discontinuation, interruption, or dose reduction of IP, as appropriate) and report if concomitant and/or additional treatments were given for the event.

Outcome

The Investigator will report the outcome of the event for both AEs and SAEs.

All SAEs that have not resolved upon discontinuation of the subject's participation in the study must be followed until recovered (returned to baseline), recovered with sequelae, or death (due to the SAE).

An abnormal laboratory value is considered to be an AE if the abnormality:
  results in discontinuation from the study;
  requires treatment, modification/interruption of Compound A dose, or any other therapeutic intervention; or
  is judged to be of significant clinical importance, eg, one that indicates a new disease process and/or organ toxicity, or is an exacerbation or worsening of an existing condition.

Regardless of severity grade, only laboratory abnormalities that fulfill a seriousness criterion need to be documented as a serious adverse event.

If a laboratory abnormality is one component of a diagnosis or syndrome, then only the diagnosis or syndrome should be recorded on the AE page/screen of the CRF. If the abnormality was not a part of a diagnosis or syndrome, then the laboratory abnormality should be recorded as the AE. If possible, the laboratory abnormality should be recorded as a medical term and not simply as an abnormal laboratory result (eg, record thrombocytopenia rather than decreased platelets).

All pregnancies or suspected pregnancies occurring in either a female subject of childbearing potential or partner of childbearing potential of a male subject are immediately reportable events. The exposure of any pregnant female (eg, caregiver, pharmacist, study coordinator or monitor) to Compound A is also an immediately reportable event.

Pregnancies and suspected pregnancies (including elevated β-hCG or positive pregnancy test in a female subject of childbearing potential regardless of disease state) occurring while the subject is on Compound A, or within 90 days of the subject's last dose of Compound A, are considered immediately reportable events. Investigational product is to be discontinued immediately. The pregnancy, suspected pregnancy, or positive pregnancy test must be reported to Celgene Drug Safety immediately by email, phone or facsimile, or other appropriate method, using the Pregnancy Initial Report Form, or approved equivalent form.

The female subject should be referred to an obstetrician-gynecologist, preferably one experienced in reproductive toxicity for further evaluation and counseling. The Investigator will follow the female subject until completion of the pregnancy, and must notify Celgene Drug Safety immediately about the outcome of the pregnancy (either normal or abnormal outcome) using the Pregnancy Follow-up Report Form, or approved equivalent form.

If the outcome of the pregnancy was abnormal (eg, spontaneous abortion), the Investigator should report the abnormal outcome as an AE. If the abnormal outcome meets any of the serious criteria, it must be reported as an SAE to Celgene Drug Safety by facsimile, or other appropriate method, within 24 hours of the Investigator's knowledge of the event using the SAE Report Form, or approved equivalent form.

All neonatal deaths that occur within 28 days of birth should be reported, without regard to causality, as SAEs. In addition, any infant death after 28 days that the Investigator suspects is related to the in utero exposure to the Compound A should also be reported to Celgene Drug Safety by facsimile, or other appropriate method, within 24 hours of the Investigator's knowledge of the event using the SAE Report Form, or approved equivalent form.

If a female partner of a male subject taking Compound A becomes pregnant, the male subject taking Compound A should notify the Investigator, and the pregnant female partner should be advised to call their healthcare provider immediately. Where applicable, the Compound A may need to be discontinued in the male subject, but may be resumed later at the discretion of the Investigator and medical monitor.

Any AE that meets any criterion for an SAE requires the completion of an SAE Report Form in addition to being recorded on the AE page/screen of the CRF. All SAEs must be reported to Celgene Drug Safety within 24 hours of the Investigator's knowledge of the event by facsimile, or other appropriate method (eg, via email), using the SAE Report Form, or approved equivalent form. This instruction pertains to initial SAE reports as well as any follow-up reports.

The Investigator is required to ensure that the data on these forms is accurate and consistent. This requirement applies to all SAEs (regardless of relationship to Compound A) that occur during the study (from the time the subject signs informed consent until 28 days after the last dose of Compound A) or any SAE made known to the Investigator at anytime thereafter that are suspected of being related to Compound A. Serious adverse events occurring prior to treatment (after signing the ICD) will be captured.

The SAE report should provide a detailed description of the SAE and include a concise summary of hospital records and other relevant documents. If a subject died and an autopsy has been performed, copies of the autopsy report and death certificate are to be sent to Celgene Drug Safety as soon as these become available. Any follow-up data should be detailed in a subsequent SAE Report Form, or approved equivalent form, and sent to Celgene Drug Safety.

Where required by local legislation, the Investigator is responsible for informing the Institutional Review Board/Ethics Committee (IRB/EC) of the SAE and providing them with all relevant initial and follow-up information about the event. The Investigator must keep copies of all SAE information on file including correspondence with Celgene and the IRB/EC.

Queries pertaining to SAEs will be communicated from Celgene Drug Safety to the site via facsimile or electronic mail. The response time is expected to be no more than five (5) business days. Urgent queries (eg, missing causality assessment) may be handled by phone.

For the purpose of regulatory reporting, Celgene Drug Safety will determine the expectedness of events suspected of being related to Compound A based on the Investigator Brochure.

In the United States, all suspected unexpected serious adverse reactions (SUSARs) will be reported in an expedited manner in accordance with 21 CFR 312.32.]

For countries within the European Economic Area (EEA), Celgene or its authorized representative will report in an expedited manner to Regulatory Authorities and Ethics Committees concerned, suspected unexpected serious adverse reactions (SUSARs) in accordance with Directive 2001/20/EC and the Detailed Guidance on collection, verification and presentation of adverse reaction reports arising from clinical trials on investigational products for human use (ENTR/CT3) and also in accordance with country-specific requirements.

Adverse events such as disease progression, death related to disease progression (in the absence of serious Compound A-related events) and serious events due to the relapse of the studied indication will not be subject to expedited reporting by the Sponsor to regulatory authorities.

Celgene or its authorized representative shall notify the Investigator of the following information:

Any AE suspected of being related to the use of Compound A in this study or in other studies that is both serious and unexpected (eg, SUSAR);

Any finding from tests in laboratory animals that suggests a significant risk for human subjects including reports of mutagenicity, teratogenicity, or carcinogenicity.

Where required by local legislation, the Investigator shall notify his/her IRB/EC promptly of these new serious and unexpected AE(s) or significant risks to subjects.

The Investigator must keep copies of all pertinent safety information on file including correspondence with Celgene and the IRB/EC.

Discontinuations

The following events are considered sufficient reasons for discontinuing a subject from the investigational product(s):
Adverse Event
Withdrawal by subject
Lack of efficacy
Physician decision
Protocol violation
Progressive disease
Death
Lost to follow-up
Other (to be specified on the CRF)

The reason for discontinuation of treatment should be recorded in the CRF and in the source documents. In case of treatment discontinuation following an adverse event, every effort will be made to follow subjects for 28 days after the last dose of Compound A.

The decision to discontinue a subject from treatment remains the responsibility of the treating physician, which will not be delayed or refused by the Sponsor. However, prior to discontinuing a subject, the Investigator may contact the Medical Monitor and forward appropriate supporting documents for review and discussion.

Note: Any laboratory result, such as neutropenia, thrombocytopenia, other abnormalities, etc., which are felt to be clinically significant should be followed until return to baseline or Grade 1.

The following events are considered sufficient reasons for discontinuing a subject from the study:
Screen failure
Withdrawal by subject
Lack of efficacy
Physician decision
Protocol violation
Progressive disease
Death
Lost to follow-up
Other (to be specified on the CRF)

The reason for study discontinuation should be recorded in the CRF and in the source documents.

Emergency Procedures

In emergency situations, the Investigator should contact the responsible Sponsor's study physician/Medical Monitor or designee by telephone at the number(s) listed on the Emergency Contact Information page of the protocol (after title page).

In the unlikely event that the Sponsor's study physician/Medical Monitor or designee cannot be reached, please contact the global Emergency Call Center by telephone at the number listed on the Emergency Contact Information page of the protocol (after title page). This global Emergency Call Center is available 24 hours a day and 7 days a week. The representatives are responsible for obtaining your call-back information and contacting the on-call Celgene/contract research organization Medical Monitor, who will then contact you promptly.

Note: The back-up 24-hour global emergency contact call center should only be used if you are not able to reach the Sponsor's study physician(s) or Medical Monitor or designee for emergency calls.

This is an open-label study; therefore, Compound A will be identified on the package labeling. Subjects enrolled in this study will be issued an identification card showing the name of this study and an emergency contact number. This can be used by health care professionals seeking emergency information about a subject's participation in the study.

Regulatory Considerations

The procedures set out in this study protocol pertaining to the conduct, evaluation, and documentation of this study are designed to ensure that Celgene, its authorized representative, and Investigator abide by Good Clinical Practice (GCP), as described in International Conference on Harmonisation (ICH) Guideline E6 and in accordance with the general ethical principles outlined in the Declaration of Helsinki. The study will receive approval from an IRB/EC prior to commencement. The Investigator will conduct all aspects of this study in accordance with applicable national, state, and local laws of the pertinent regulatory authorities Investigator responsibilities are set out in the ICH Guideline for Good Clinical Practice and in the local regulations. Celgene staff or an authorized representative will evaluate and approve all Investigators who in turn will select their staff.

The Investigator should ensure that all persons assisting with the study are adequately informed about the protocol, amendments, study treatments, as well as study-related duties and functions, including obligations of confidentiality of Celgene information. The Investigator should maintain a list of Sub-investigators and other appropriately qualified persons to whom he or she has delegated significant study-related duties.

The Investigator is responsible for keeping a record of all subjects who sign an informed consent form (ICD) and are screened for entry into the study. Subjects who fail screening must have the reason(s) recorded in the subject's source documents.

The Investigator, or a designated member of the Investigator's staff, must be available during monitoring visits to review data, resolve queries and allow direct access to subject records (eg, medical records, office charts, hospital charts, and study-related charts) for source data verification. The Investigator must ensure timely and accurate completion of CRFs and queries.

The information contained in the protocol and amendments (with the exception of the information provided by Celgene on public registry websites) is considered Celgene confidential information. Only information that is previously disclosed by Celgene on a public registry website may be freely disclosed by the Investigator or its institution, or as outlined in the Clinical Trial Agreement. Celgene protocol, amendment and IB information is not to be made publicly available (for example on the Investigator's or their institution's website) without express written approval from Celgene. Information proposed for posting on the Investigator's or their institution's website must be submitted to Celgene for review and approval, providing at least 5 business days for review.

At the time results of this study are made available to the public, Celgene will provide Investigators with a summary of the results that is written for the lay person. The Investigator is responsible for sharing these results with the subject and/or their caregiver as agreed by the subject.

The Investigator must obtain informed consent of a subject and/or a subject's legal representative prior to any study related procedures.

Documentation that informed consent occurred prior to the study subject's entry into the study and of the informed consent process should be recorded in the study subject's source documents including the date. The original ICD signed and dated by the study subject and by the person consenting the study subject prior to the study subject's entry into the study, must be maintained in the Investigator's study files and a copy given to the study subject. In addition, if a protocol is amended and it impacts on the content of the informed consent, the ICD must be revised. Study subjects participating in the study when the amended protocol is implemented must be re-consented with the revised version of the ICD. The revised ICD signed and dated by the study subject and by the person consenting the study subject must be maintained in the Investigator's study files and a copy given to the study subject.

Celgene affirms the subject's right to protection against invasion of privacy and to be in compliance with ICH and other local regulations (whichever is most stringent). Celgene requires the Investigator to permit Celgene's representatives and, when necessary, representatives from regulatory authorities, to review and/or copy any medical records relevant to the study in accordance with local laws.

Should direct access to medical records require a waiver or authorization separate from the subject's signed ICD, it is the responsibility of the Investigator to obtain such permission in writing from the appropriate individual.

Any amendment to this protocol must be approved by the Sponsor's study physician/Medical Monitor. Amendments will be submitted to the IRB/EC for written approval. Written approval must be obtained before implementation of the amended version occurs. The written signed approval from the IRB/EC should specifically reference the Investigator name, protocol number, study title and amendment number(s) that is applicable. Amendments that are administrative in nature do not require IRB/IEC approval but will be submitted to the IRB/IEC for information purposes.

In the event of a substantial amendment in the study, the corresponding amendment will be submitted to the Competent Regulatory Authority in each country and will not be implemented until it has been approved.

Before the start of the study, the study protocol, ICD, and any other appropriate documents will be submitted to the IRB/EC with a cover letter or a form listing the documents submitted, their dates of issue, and the site (or region or area of jurisdiction, as applicable) for which approval is local legal requirements.

IP can only be supplied to an Investigator by Celgene or its authorized representative after documentation on all ethical and legal requirements for starting the study has been received by Celgene or its authorized representative. This documentation must also include a list of the members of the IRB/EC and their occupation and qualifications. If the IRB/EC will not disclose the names, occupations and qualifications of the committee members, it should be asked to issue a statement confirming that the composition of the committee is in accordance with GCP. For example, the IRB General Assurance Number may be accepted as a substitute for this list. Formal approval by the IRB/EC should mention the protocol title, number, amendment number (if applicable), study site (or region or area of jurisdiction, as applicable), and any other documents reviewed. It must mention the date on which the decision was made and must be officially signed by a committee member. Before the first subject is enrolled in the study, all ethical and legal requirements must be met.

The IRB/EC and, if applicable, the authorities, must be informed of all subsequent protocol amendments in accordance with local legal requirements. Amendments must be evaluated to determine whether formal approval must be sought and whether the ICD should also be revised.

The Investigator must keep a record of all communication with the IRB/EC and, if applicable, between a Coordinating Investigator and the IRB/EC. This statement also applies to any communication between the Investigator (or Coordinating Investigator, if applicable) and regulatory authorities.

Any advertisements used to recruit subjects for the study must be reviewed by Celgene and the IRB/EC prior to use.

If required by legislation or the IRB/EC, the Investigator must submit to the IRB/EC:

Information on serious or unexpected adverse events as soon as possible;
Periodic reports on the progress of the study;
Deviations from the protocol or anything that may involve added risk to subjects.

Celgene reserves the right to terminate this study prematurely at any time for reasonable medical or administrative reasons. Any premature discontinuation will be appropriately documented according to local requirements (eg, IRB/EC, regulatory authorities, etc).

In addition, the Investigator or Celgene has the right to discontinue a single site at any time during the study for medical or administrative reasons such as:

Unsatisfactory enrollment;
GCP noncompliance;
Inaccurate or incomplete data collection;
Falsification of records;
Failure to adhere to the study protocol.

Data Handling and Recordkeeping

The Investigator must ensure that the records and documents pertaining to the conduct of the study and the distribution of the investigational product are complete, accurate, filed and retained. Examples of source documents include: hospital records; clinic and office charts; laboratory notes; memoranda; subject's diaries or evaluation checklists; dispensing records; recorded data from automated instruments;

copies or transcriptions certified after verification as being accurate copies; microfiche; x-ray film and reports; and records kept at the pharmacy, and the laboratories, as well as copies of CRFs or CD-ROM.

Data will be collected via CRF and entered into the clinical database per Celgene SOPs. This data will be electronically verified through use of programmed edit checks specified by the clinical team. Discrepancies in the data will be brought to the attention of the clinical team, and investigational site personnel, if necessary. Resolutions to these issues will be reflected in the database. An audit trail within the system will track all changes made to the data.

Essential documents must be retained by the Investigator according to the period of time outlined in the clinical trial agreement. The Investigator must retain these documents for the time period described above or according to local laws or requirements, whichever is longer. Essential documents include, but are not limited to, the following:

Signed ICDs for all subjects;
Subject identification code list, screening log (if applicable), and enrollment log;
Record of all communications between the Investigator and the IRB/EC;
Composition of the IRB/EC;
Record of all communications between the Investigator, Celgene, and their authorized representative(s);
List of Sub-investigators and other appropriately qualified persons to whom the Investigator has delegated significant study-related duties, together with their roles in the study, curriculum vitae, and their signatures;
Copies of CRFs (if paper) and of documentation of corrections for all subjects;
IP accountability records;
Record of any body fluids or tissue samples retained;
All other source documents (subject records, hospital records, laboratory records, etc.);
All other documents as listed in Section 8 of the ICH consolidated guideline on GCP (Essential Documents for the Conduct of a Clinical Trial).

The Investigator must notify Celgene if he/she wishes to assign the essential documents to someone else, remove them to another location or is unable to retain them for a specified period. The Investigator must obtain approval in writing from Celgene prior to destruction of any records. If the Investigator is unable to meet this obligation, the Investigator must ask Celgene for permission to make alternative arrangements. Details of these arrangements should be documented.

All study documents should be made available if required by relevant health authorities. Investigator or institution should take measures to prevent accidental or premature destruction of these documents.

Quality Control and Quality Assurance

All aspects of the study will be carefully monitored by Celgene or its authorized representative for compliance with applicable government regulations with respect to current GCP and SOPs.

Celgene ensures that appropriate monitoring procedures are performed before, during and after the study. All aspects of the study are reviewed with the Investigator and the staff at a study initiation visit and/or at an Investigators' Meeting. Prior to enrolling subjects into the study, a Celgene representative will review the protocol, CRFs, procedures for obtaining informed consent, record keeping, and reporting of AEs/SAEs with the Investigator. Monitoring will include on-site visits with the Investigator and his/her staff as well as any appropriate communications by mail, email, fax, or telephone. During monitoring visits, the facilities, investigational product storage area, CRFs, subject's source documents, and all other study documentation will be inspected/reviewed by the Celgene representative in accordance with the Study Monitoring Plan.

Accuracy will be checked by performing source data verification that is a direct comparison of the entries made onto the CRFs against the appropriate source documentation. Any resulting discrepancies will be reviewed with the Investigator and/or his/her staff. Any necessary corrections will be made directly to the CRFs or via queries by the Investigator and/or his/her staff Monitoring procedures require that informed consents, adherence to inclusion/exclusion criteria and documentation of SAEs and their proper recording be verified. Additional monitoring activities may be outlined in a study-specific monitoring plan.

In addition to the routine monitoring procedures, a Good Clinical Practice Quality Assurance unit exists within Celgene. Representatives of this unit will conduct audits of clinical research activities in accordance with Celgene SOPs to evaluate compliance with Good Clinical Practice guidelines and regulations.

The Investigator is required to permit direct access to the facilities where the study took place, source documents, CRFs and applicable supporting records of study subject participation for audits and inspections by IRB/ECs, regulatory authorities (eg, FDA, EMA, Health Canada) and company authorized representatives. The Investigator should make every effort to be available for the audits and/or inspections. If the Investigator is contacted by any regulatory authority regarding an inspection, he/she should contact Celgene immediately.

PUBLICATIONS

All protocol- and amendment-related information, with the exception of the information provided by Celgene on public registry websites, is considered Celgene confidential information and is not to be used in any publications. Celgene protocol-related information proposed for use in a publication must be submitted to Celgene for review and approval, and should not be utilized in a publication without express written approval from Celgene, or as described in the Clinical Trial Agreement.

Celgene will ensure Celgene-sponsored studies are considered for publication in the scientific literature in a peer-reviewed journal, irrespective of the results. At a minimum, this applies to results from all Phase 3 clinical studies, and any other study results of significant medical importance. This also includes results relating to investigational medicines whose development programs have been discontinued.

Study results may also be presented at one or more medical congresses, and may be used for scientific exchange and teaching purposes. Additionally, this study and its results may be submitted for inclusion in all appropriate health authority study registries, as well as publication on health authority study registry websites, as required by local health authority regulations.

Eligibility for external authorship, as well as selection of first authorship, will be based on several considerations, including, but not limited to, contribution to protocol development, study recruitment, data quality, participation in data analysis, participation in study steering committee (when applicable) and contribution to abstract, presentation and/or publication development.

Appendix A:

Table of Abbreviations

| Abbreviation or Specialist Term | Explanation |
|---|---|
| ADA | Anti-drug antibodies |
| ADCC | Antibody-dependent cellular cytotoxicity |
| ADL | Activity of daily life |
| AE | Adverse event |
| ALL | Acute lymphoid leukemia |
| ALT | Alanine aminotransferase (SGPT) |
| AML | Acute myeloid leukemia |
| ANC | Absolute neutrophil count |
| Ara-C | Cytarabine |
| AST | Aspartate aminotransferase (SGOT) |
| AUC | Area under the curve |
| β-hCG | β-subunit of human chorionic gonadotropin |
| BID | Twice a day |
| BM | Bone marrow |
| BMI | Body mass index |
| BSA | Body surface area |
| BUN | Blood urea nitrogen |
| C | Cycle |
| CBC | Complete blood count |
| CD | Cluster of differentiation |
| CEBPα | CCAAT/enhancer binding protein alpha |
| CI | Confidence interval |
| c-Kit | Mast/stem cell growth factor receptor |
| CL | Clearance |
| $C_{max}$ | Maximum plasma concentration of drug |
| CNS | Central nervous system |
| CR | Complete remission |
| CRc | Cytogenetic complete remission |
| CRi | Complete remission with incomplete neutrophil recovery |
| CRp | Complete remission with incomplete platelet recovery |
| CRP | C-reactive protein |
| CRR | Complete remission rate |
| CRO | Contract research organization |
| CRF | Case report form |
| CRP | Clinical Research Physician |
| CRS | Clinical Research Scientist |
| CRT | Calreticulin |
| CT | Computed tomography |
| CTCAE | Common Terminology Criteria for Adverse Events |
| CV % | Coefficient of variation |
| DAT | Direct antiglobulin test |
| DCR | Disease control rate |
| DIC | Disseminated intravascular coagulation |
| DLT | Dose-limiting toxicity |
| DMC | Data Monitoring Committee |
| DOR | Duration of response |
| EC | Ethics Committee |
| ECG | Electrocardiogram |
| ECHO | Echocardiogram |
| ECOG PS | Eastern Cooperative Oncology Group Performance Status |
| eCRF | Electronic case report form |
| EEA | European Economic Area |
| ELISA | Enzyme-linked immunoassay |
| EOI | End of infusion |
| EOT | End of treatment |
| ESR | Erythrocyte sedimentation rate |
| FACS | Fluorescence-activated cell sorting |
| FCBP | Females of child bearing potential |
| FDA | Food and Drug Administration |
| FISH | Fluorescence in situ hybridization |
| FLT3 | Fms-related tyrosine kinase 3 |
| FLT3-ITD | Fms-related tyrosine kinase 3-internal tandem duplication |
| FOXP3 | Forkhead box P3 |
| GCP | Good Clinical Practice |
| GVHD | Graft-versus-host disease |
| HBV | Hepatitis B virus |
| HCV | Hepatitis C virus |
| HGB | Hemoglobin |
| HIV | Human immunodeficiency virus |
| HLA | Human leukocyte antigen |
| HNSTD | Highest non-severely toxic dose |
| HSCT | Hematopoietic stem cell transplant |
| huCD | Human cluster of differentiation |
| ICD | Informed consent document |
| ICF | Informed consent form |

Appendix A:-continued

Table of Abbreviations

| Abbreviation or Specialist Term | Explanation |
|---|---|
| ICH | International Conference on Harmonisation |
| ICSH | International Council for Standardization in Hematology |
| IFN | Interferon |
| IgE | Immunoglobulin E subclass |
| IgG | Immunoglobulin G subclass |
| IL | Interleukin |
| IL-1β | Interleukin-1 beta |
| IND | Investigational New Drug |
| INR | International normalized ratio |
| IP | Investigational Product |
| IPSS-R | Revised International Prognostic Index Scoring System |
| IRB | Institutional Review Board |
| IRR | Infusion related reaction |
| IRT | Integrated Response Technology |
| IV | Intravenous |
| IVIG | Intravenous immunoglobulin |
| IWG | International working group |
| KC-GRO | Keratinocyte-derived cytokine-growth-regulated oncogene |
| LDH | Lactate dehydrogenase |
| LSC | Leukemia stem cell |
| LVEF | Left ventricular ejection fraction |
| mCR | Molecular complete remission |
| MCP-1 | Monocyte chemoattractant protein-1 |
| MDR | Multi-drug resistance |
| MDS | Myelodysplastic syndrome |
| MedDRA | Medical Dictionary for Regulatory Activities |
| MIP-1α | Macrophage inflammatory protein-1 alpha |
| MM | Multiple myeloma |
| MRI | Magnetic resonance imaging |
| MTD | Maximum tolerated dose |
| MUGA | Multi-gated acquisition |
| N | Number |
| NCI | National Cancer Institute |
| NHL | Non-Hodgkin's lymphoma |
| NOD-SCID | Non-obese diabetic, severe-combine immunodeficiency |
| NOAEL | No observed adverse effect level |
| NOEL | No observed effect level |
| NPM1 | Nucleophosmin 1 |
| NSG | Non-obese diabetic, severe-combine immunodeficiency gamma |
| NTD | Non-tolerated dose |
| $O_2$ | Oxygen |
| ORR | Objective response rate |
| OS | Overall survival |
| PBMC | Peripheral blood mononuclear cells |
| PCR | Polymerase ch |
| PD | Pharmacodynamic |
| PFS | Progression-free survival |
| PK | Pharmacokinetics |
| PLT | Platelet |
| PR | Partial remission |
| PT | Prothrombin time |
| PTT | Partial thromboplastin time |
| Q2W | Every two weeks |
| QD | Once a day |
| QW | Once weekly |
| QW × 2 | Once a week for two weeks |
| QW × 4 | Once a week for four weeks |
| RAEB | Refractory anemia with excess blasts |
| RBC | Red blood cell count |
| RFS | Relapse free survival |
| RP2D | Recommended Phase 2 dose |
| SAE | Serious adverse event |
| SAP | Statistical analysis plan |
| SC | Steering committee |
| SD | Standard deviation |
| SE | Standard error |
| SGOT | Serum glutamic oxaloacetic transaminase |
| SGPT | Serum glutamic pyruvic transaminase |
| SIRPα | Signal-regulatory protein alpha |
| SOP | Standard operating procedure |
| SRC | Safety review committee |
| SUSAR | Suspected unexpected serious adverse reaction |
| $t_{1/2}$ | Half-life |
| $t_{max}$ | Time to peak plasma concentration |

Appendix A:-continued

Table of Abbreviations

| Abbreviation or Specialist Term | Explanation |
|---|---|
| TLS | Tumor lysis syndrome |
| TNBC | Triple-negative breast cancer |
| TNFα | Tumor necrosis factor alpha |
| ULN | Upper limit of normal |
| US | United States |
| USP | United States Pharmacopeia |
| $V_{ss}$ | Volume of distribution |
| WBC | White blood cell count |
| WHO | World Health Organization |
| Wks | Weeks |

APPENDIX B: RECIST VERSION 1.1

The following information is extracted/summarized from Eisenhauer, 2009, New Response Evaluation Criteria in Solid Tumors: Revised RECIST Guideline (Version 1.1). Please refer to the primary reference for further information.

Definitions

At screening, tumor lesions/lymph nodes will be categorized as measurable or non-measurable.

Measurable Disease

Tumor Lesions. Must be accurately measured in at least one dimension (longest diameter in the plane of measurement is to be recorded) with a minimum size of:

10 mm by CT scan (CT scan slice thickness no greater than 5 mm)

10 mm caliper measurement by clinical exam (lesions which cannot be accurately measured with calipers should be recorded as non-measurable)

20 mm by chest X-ray

Malignant Lymph Nodes: To be considered pathologically enlarged and measurable, a lymph node must be ≥15 mm in short axis when assessed by CT scan (CT scan slice thickness recommended to be no greater than 5 mm). At baseline and in follow-up, only the short axis will be measured and followed.

Non-Measurable Disease

All other lesions, including small lesions (longest diameter <10 mm or pathological lymph nodes with ≥10 to <15 mm short axis) as well as truly non-measurable lesions. Lesions considered truly non-measurable include: leptomeningeal disease, ascites, pleural or pericardial effusion, inflammatory breast disease, lymphangitic involvement of skin or lung, abdominal masses/abdominal organomegaly identified by physical exam that is not measurable by reproducible imaging techniques.

Tumor Response Evaluation

Target lesions: When more than one measurable tumor lesion is present at baseline all lesions up to a maximum of five lesions total (and a maximum of 2 lesions per organ) representative of all involved organs should be identified as target lesions and will be recorded and measured at baseline. Target lesions should be selected on the basis of their size (lesions with the longest diameter), be representative of all involved organs, but in addition should be those that lend themselves to reproducible repeated measurements. Note that pathological nodes must meet the measurable criterion of a short axis of ≥15 mm by CT scan and only the short axis of these nodes will contribute to the baseline sum. All other pathological nodes (those with short axis ≥10 mm but <15 mm) should be considered non-target lesions. Nodes that have a short axis <10 mm are considered non-pathological and should not be recorded or followed. At baseline, the sum of the target lesions (longest diameter of tumor lesions plus short axis of lymph nodes: overall maximum of 5) is to be recorded.

After baseline, a value should be provided on the eCRF for all identified target lesions for each assessment, even if very small. If extremely small and faint lesions cannot be accurately measured but are deemed to be present, a default value of 5 mm may be used. If lesions are too small to measure and indeed are believed to be absent, a default value of 0 mm may be used.

Non-target lesions: All non-measurable lesions (or sites of disease) plus any measurable lesions over and above those listed as target lesions are considered non-target lesions. Measurements are not required but these lesions should be noted at baseline and should be followed as "present," "absent," or "unequivocal progression."

Response Criteria: Target and non-target lesions are evaluated for response separately, and then the tumor burden as a whole is evaluated as the overall response.

Target Lesion Response: Target lesions are assessed as follows:

Complete Response (CR). Disappearance of all target lesions. Any pathological lymph nodes (whether target or non-target) must have reduction in short axis to <10 mm.

Partial Response (PR). At least a 30% decrease in the sum of diameters of target lesions, taking as reference the baseline sum diameters.

Progressive Disease (PD). At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression).

Stable Disease (SD). Neither sufficient shrinkage to qualify for PR nor sufficient increase to qualify for PD, taking as reference the smallest sum of diameters while on study.

Non-target Lesion Response: Non-target lesions will be assessed as follows:

Complete Response (CR). Disappearance of all non-target lesions and normalization of tumor marker level. All lymph nodes must be non-pathological in size (<10 mm short axis).

Non-CR/Non-PD. Persistence of one or more non-target lesion(s) and/or maintenance of tumor marker level above the normal limits.

Progressive Disease (PD). Unequivocal progression (see comments below) of existing non-target lesions. (Note: the appearance of one or more new lesions is also considered progression).

When the Subject Also Has Measurable Disease: In this setting, to achieve "unequivocal progression" on the basis of the non-target disease, there must be an overall level of substantial worsening in non-target disease such that, even in presence of SD or PR in target disease, the overall tumor burden has increased sufficiently to merit discontinuation of therapy. A modest "increase" in the size of one or more non-target lesions is usually not sufficient to quality for unequivocal progression status. The designation of overall progression solely on the basis of change in non-target disease in the face of SD or PR of target disease will therefore be extremely rare.

When the Subject Has Only Non-measurable Disease: This circumstance arises in some Phase 3 trials when it is not a criterion of study entry to have measurable disease. The same general concepts apply here as noted above; however, in this instance there is no measurable disease assessment to factor into the interpretation of an increase in non-measurable disease burden. Because worsening in non-target disease cannot be easily quantified (by definition: if all lesions are truly non-measurable) a useful test that can be applied when assessing subjects for unequivocal progression is to consider if the increase in overall disease burden based on the change in non-measurable disease is comparable in magnitude to the increase that would be required to declare PD for measurable disease: i.e., an increase in tumor burden representing an additional 73% increase in "volume" (which is equivalent to a 20% increase diameter in a measurable lesion). Examples include an increase in a pleural effusion from "trace" to "large," an increase in lymphangitic disease from localized to widespread, or may be described in protocols as "sufficient to require a change in therapy." If "unequivocal progression" is seen, the subject should be considered to have had overall PD at that point. While it would be ideal to have objective criteria to apply to non-measurable disease, the very nature of that disease makes it impossible to do so: therefore, the increase must be substantial.

Overall Response: Overall response should be assessed according to Table A for subjects with target lesions, and Table B for subjects with only non-target lesions.

TABLE A

Time Point Response: Subjects With Target (±Non-target) Disease

| Target Lesions Response | Non-target Lesion Response | New Lesions | Overall Response |
|---|---|---|---|
| CR | CR | No | CR |
| CR | Non-CR/non-PD | No | PR |
| CR | Not evaluated | No | PR |
| PR | Non-PD or not all evaluated | No | PR |
| SD | Non-PD or not all evaluated | No | SD |
| Not all evaluated | Non-PD | No | NE |
| PD | Any | Yes or No | PD |
| Any | PD | Yes or No | PD |
| Any | Any | Yes | PD |

CR = complete response, PR = partial response, SD = stable disease, PD = progressive disease, NE = inevaluable.

TABLE B

Time Point Response: Subjects With Non-target Disease Only

| Nontarget Lesions Response | New Lesions | Overall Response |
|---|---|---|
| CR | No | CR |
| Non-CR/non-PD | No | Non-CR/non-PD[a] |
| Not all evaluated | No | NE |
| Unequivocal PD | Yes or No | PD |
| Any | Yes | PD |

CR = complete response, PR = partial response, SD = stable disease, PD = progressive disease, NE = inevaluable.
[a]"Non-CR/non-PD" is preferred over "stable disease" for non-target disease since SD is increasingly used as endpoint for assessment of efficacy in some trials so to assign this category when no lesions can be measured is not advised.

Symptomatic Deterioration

Subjects with a global deterioration of health status requiring discontinuation of treatment without objective evidence of disease progression at that time should be reported as 'symptomatic deterioration'. Every effort should be made to document objective progression even after discontinuation of treatment. Symptomatic deterioration is not a descriptor of an objective response: it is a reason for stopping study therapy. The objective response status of such subjects is to be determined by evaluation of target and non-target disease.

APPENDIX C: REVISED RESPONSE CRITERIA FOR MALIGNANT LYMPHOMA INTERNATIONAL WORKING GROUP REVISED RESPONSE CRITERIA FOR MALIGNANT LYMPHOMA (CHESON, 2007) CAN BE ACCESSED ONLINE AT: HTTP://JCO.ASCOPUBS.ORG/CGI/REPRINT/25/5/579

APPENDIX D: PERFORMANCE STATUS CRITERIA

TABLE 37

Eastern Cooperative Oncology Group (ECOG) Performance Status

| Score | Description |
|---|---|
| 0 | Fully active, able to carry on all pre-disease performance without restriction |
| 1 | Restricted in physically strenuous activity but ambulatory and able to carry out work of a light or sedentary nature, eg, light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

APPENDIX E: CHARACTERISTICS OF THE BAYESIAN LOGISTIC REGRESSION MODEL

An adaptive Bayesian logistic regression model (Neuenschwander, 1998) for dose escalation with overdose control (Babb, 1988) will be used to guide dose escalation in this study.

The purpose of this appendix is to present performance metrics (operating characteristics) that illustrate the precision of the design in estimating the MTD under various dose-toxicity relationships through computer simulation. In addition, recommendations of the next dose level by BLRM with overdose control principle are provided under various hypothetical outcome scenarios in early cohorts (assuming exactly 3 evaluable patients in each cohort for simplicity) to show how it facilitates on-study dose-escalation decisions.

Specifications and Results of Simulation Study

This section presents the operating characteristics that illustrate the precision of the design in estimating the MTD under various assumed true dose-toxicity relationships.

Simulations are performed for the BLRM under a total of 5 scenarios of true dose-DLT Relationship (refer to Table 38):
1. Dose-DLT relationship is a steep curve and MTD is reached at early dose level (SE).
2. Dose-DLT relationship is a steep curve and MTD is reached at middle dose level (SM).
3. Dose-DLT relationship is a steep curve and MTD is reached at late dose level (SL).
4. Dose-DLT relationship is a flat curve and MTD is reached at middle dose level (FM).
5. Dose-DLT relationship is a flat curve and MTD is reached at late dose level (FL).

TABLE 38

P(DLT) for Five Simulated Scenarios with Numbers in Grey Indicating
Doses with True P(DLT) within the Target Toxicity Interval [16%, 33%]

| Scenario | P(DLT) at Different Dose Levels (mg) | | | | | | | |
|---|---|---|---|---|---|---|---|---|
| | 1.25 | 2.5 | 5 | 10 | 15 | 22.5 | 30 | 37.5 |
| SE | 0.091 | 0.1699 | 0.2951 | 0.4613 | 0.5655 | 0.6642 | 0.7269 | 0.7702 |
| SM | 0.0113 | 0.031 | 0.0827 | 0.2022 | 0.317 | 0.4594 | 0.5663 | 0.6455 |
| SL | 0 | 0.0002 | 0.0018 | 0.0155 | 0.0522 | 0.1618 | 0.3196 | 0.4836 |
| FM | 0.0513 | 0.0867 | 0.1428 | 0.2263 | 0.289 | 0.361 | 0.4165 | 0.4611 |
| FL | 0.0009 | 0.0033 | 0.0121 | 0.0438 | 0.09 | 0.176 | 0.2694 | 0.3603 |

Operating characteristics are reviewed to investigate overall performance of the BLRM under each true scenario. Table 39 summarizes the results from the simulations performed.

TABLE 39

Summary Metrics of Simulation for BLRM and Comparison with 3 + 3

| Scenario/ Method | Mean Number of Subjects | Proportion of subjects with DLT | Probability of recommeding a dose with true P(DLT) | | |
|---|---|---|---|---|---|
| | | | 0.16-0.33 | ≥0.33 | <0.16 |
| SE, N-CRM | 19.75 | 0.24 | 0.80 | 0.06 | 0.14 |
| SE, 3 + 3 | 14.72 | 0.24 | 0.63 | 0.06 | 0.31 |
| SM, N-CRM | 22.50 | 0.16 | 0.72 | 0.06 | 0.22 |
| SM, 3 + 3 | 20.48 | 0.16 | 0.55 | 0.05 | 0.40 |
| SL, N-CRM | 25.55 | 0.11 | 0.75 | 0.08 | 0.18 |
| SL, 3 + 3 | 26.85 | 0.11 | 0.68 | 0.08 | 0.24 |
| FM, N-CRM | 22.24 | 0.17 | 0.48 | 0.08 | 0.44 |
| FM, 3 + 3 | 20.38 | 0.18 | 0.37 | 0.10 | 0.52 |
| FL, N-CRM | 25.66 | 0.10 | 0.57 | 0.16 | 0.27 |
| FL, 3 + 3 | 26.80 | 0.11 | 0.51 | 0.16 | 0.33 |

Overall the BLRM model with specified prior is performing reasonably. With similar or a little more sample size, BLRM model can select MTD in the target range with higher probability, especially for scenarios 1, 2, and 4.

Aside from the overall operating characteristics studied above, the design should make reasonable decisions during a study based on the observed toxicities. After completion of a given cohort, the decision to dose escalate and actual dose chosen for the subsequent cohort will depend on the recommendation of the BLRM per EWOC principle and medical review of available clinical and laboratory data.

Some scenarios to illustrate the dose escalation up to the third dose cohort are listed in Table 40 using the 2-parameter BLRM. It is assumed that each cohort has exactly 3 evaluable patients.

TABLE 40

Possible Scenarios Up to the Third Dosing Cohort with Three Subjects per Cohort

| Scenario | Dose History (mg) | Number of DLTs/Number of Subjects | Next dose by N-CRM(mg) |
|---|---|---|---|
| 1 | 1.25 | 0/3 | 2.5 |
| 2 | 1.25 | 0/3 | 2.5 |
| | 2.5 | 0/3 | 5 |
| 3 | 1.25 | 0/3 | 2.5 |
| | 2.5 | 1/3 | 2.5 |
| 4 | 1.25 | 0/3 | 2.5 |
| | 2.5 | 2/3 | 1.25 |

TABLE 40-continued

Possible Scenarios Up to the Third Dosing Cohort with Three Subjects per Cohort

| Scenario | Dose History (mg) | Number of DLTs/Number of Subjects | Next dose by N-CRM(mg) |
|---|---|---|---|
| 5 | 1.25 | 0/3 | 2.5 |
| | 2.5 | 0/3 | 5 |
| | 5 | 0/3 | 10 |
| 6 | 1.25 | 0/3 | 2.5 |
| | 2.5 | 0/3 | 5 |
| | 5 | 1/3 | 5 |
| 7 | 1.25 | 0/3 | 2.5 |
| | 2.5 | 0/3 | 5 |
| | 5 | 2/3 | 2.5 |
| 8 | 1.25 | 0/3 | 2.5 |
| | 2.5 | 1/3 | 2.5 |
| | 2.5 | 1/3 | 2.5 |
| 9 | 1.25 | 0/3 | 2.5 |
| | 2.5 | 1/3 | 2.5 |
| | 2.5 | 2/3 | 1.25 |
| 10 | 1.25 | 0/3 | 2.5 |
| | 2.5 | 2/3 | 1.25 |
| | 1.25 | 1/3 | 1.25 |
| 11 | 1.25 | 0/3 | 2.5 |
| | 2.5 | 2/3 | 1.25 |
| | 1.25 | 0/3 | 2.5 |

Again the BLRM model is performing reasonably for the hypothetical dose escalation scenarios. The Bayesian Logistic Regression Model enables us to incorporate the preclinical information, as well as to update the recommended dose based on all safety data in the study. By reviewing the metrics presented in the table, it can be seen that the model is not sensitive to different scenarios of truth. In general, this model is conservative due to the overdose control criteria. In all scenarios, the probability of recommending a dose that is excessively toxic with true P(DLT) ≥33% is much smaller than that of recommending a dose with true P(DLT) between 16% and 33% as MTD. On-study recommendations based on the model are consistent with the clinical decision making process, and should be considered in conjunction with other available clinical information by the Celgene Clinical Trial Team and study investigators in deciding the dose levels to be tested in order to determine the MTD.

APPENDIX F: RECOMMENDATIONS FOR MANAGEMENT OF TREATMENT-INDUCED DIARRHEA

Figure 38:
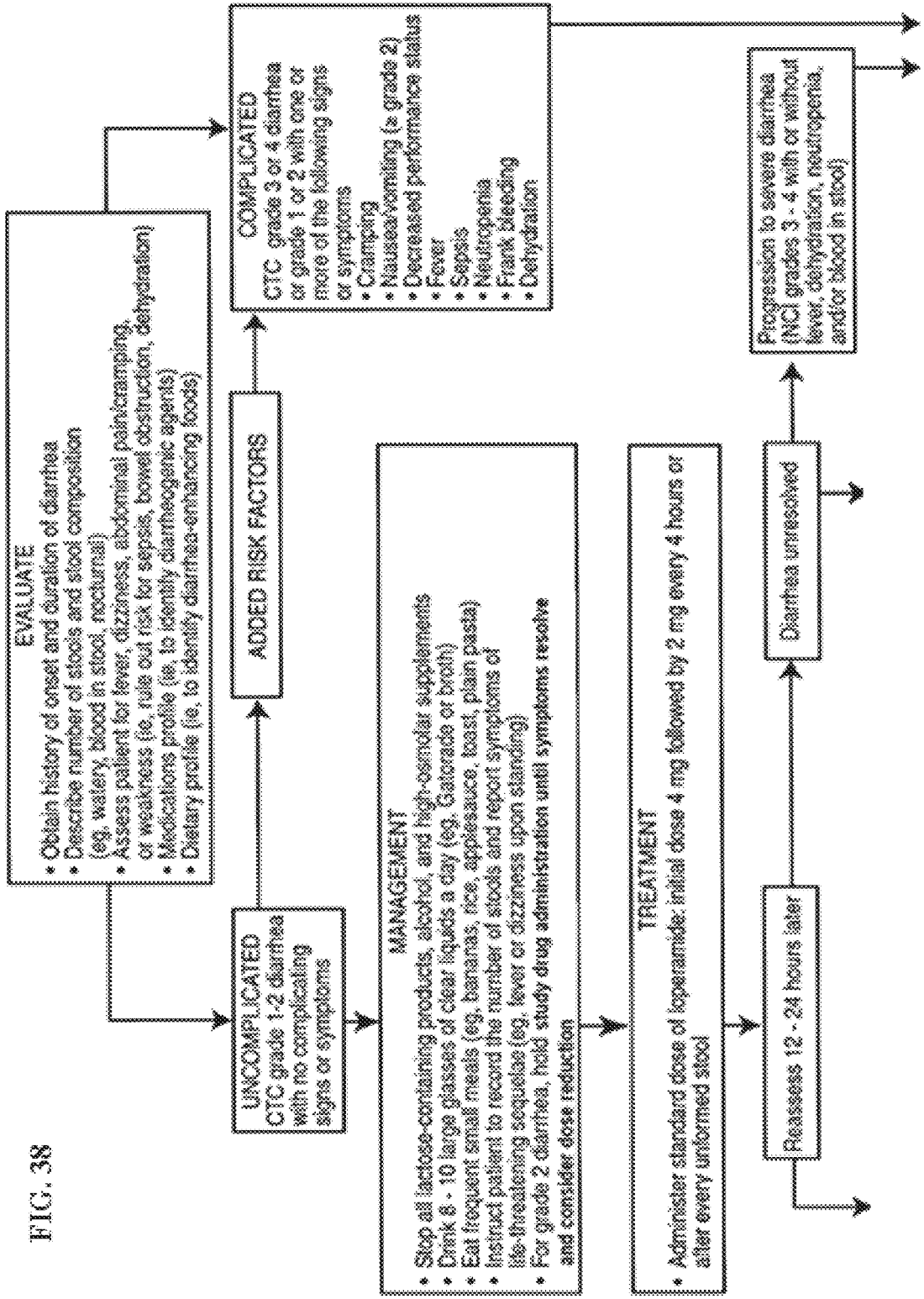
FIG. 38 is a scheme showing published recommendations for management of treatment-induced diarrhea (Benson et al., 22 J. Clin. Oncol. 2918 (2004)), modified for consistency with a study protocol

The published guidelines (Benson, 2004) provided in FIG. 38 were modified in order to be consistent with the study protocol.

APPENDIX G: MANAGEMENT OF BIOLOGIC SPECIMENS

This is an addendum to the Laboratory Manual.

Sample Handling and Storage

All blood and tissue samples collected for biomarker and genetic research as part of this study that are not depleted following analysis will be stored for use in research for up to 5 years after the study is completed. With subject consent, the storage period will be extended to 20 years after the study is completed for use in future research to learn more about cancer and other diseases. Samples will be stored in a secure laboratory facility designed for long term sample storage, with appropriate access control, monitoring and back-up systems.

Sample Coding

All biomarker and genetic research samples will be identified only by a code (subject identification number). These samples will not have any other personal information on them. The study doctor will keep the code key. The samples and the code key will be kept confidential and separate. Researchers who perform tests on samples will only see the code and will not see any information that specifically identifies the subject.

Research on Blood & Tissue Samples

Biomarker and genetic research samples will be tested by the sponsor or by companies contracted by the sponsor for use in future research to learn more about cancer and other diseases. This includes determining if biomarkers in blood cells or tumor cells demonstrate that Compound A is biologically active.

Reporting and Availability of Biomarker and Genetic Results

Biomarker and genetic research sample test results will not be shared with the subject, insurance companies nor any other third parties not involved in the sample analysis described above. The results will not be filed in the subject's medical records. Test results are for research purposes only and will not be used to make decisions about a subject's routine medical care.

Names of subjects and identifiers will not be mentioned in publications or reports, thereby minimizing the possibility of psychological or social risks that could arise from knowledge of this biomarker and genetic information, such as risk for employability or insurability or the risk of discrimination.

Mechanism to Request Sample Destruction Upon Withdrawal of Consent

If subjects withdraw consent to participate in the study, they may additionally request to have their biomarker and genetic research samples destroyed. In such cases, a subject will inform the study doctor that consent has been withdrawn and request to have any stored, unused samples destroyed. Any unused samples will then be destroyed by the sponsor. However, if samples were analyzed before consent was withdrawn, then the sponsor may still use data already available.

If subjects agree to allow biomarker and genetic research samples to be kept 20 years for future research, they are also free to reverse just that decision at any time. The subject will inform the study doctor that permission has been withdrawn for samples to be used for future research. Any unused samples will then be destroyed by the sponsor. However, if samples were analyzed before consent was withdrawn, then the sponsor may still use data already available.

APPENDIX H: CHILD-PUGH CLASSIFICATION

Subjects with a Child-Pugh A classification without hepatic encephalopathy meet this individual inclusion criterion for the study.

TABLE 41

Child-Pugh Classification

| | 1 point | 2 points | 3 points |
|---|---|---|---|
| Bilirubin (mg/dL) | <2 | 2-3 | >3 |
| Albumin (g/L) | >3.5 | 2.8-3.5 | <2.8 |
| Prothrombin time prolonged in seconds (INR) | 1-4 (<1.7) | 4-6 (1.7-2.3) | >6(>2.3) |
| Ascites | None | Slight | Moderate |
| Hepatic encephalopathy | None | Grade 1-2 | Grade 3-4 |
| Child A: 5-6 points; Child B: 7-9 points; Child C: ≥10 points | | | |

Source: Pugh, 1973.
INR = international normalized ratio.

APPENDIX J: PROSTATE CANCER CLINICAL TRIALS WORKING GROUP (PCWG23)

Recommendations of the PCWG23 on the design and end points of clinical trials for patients with progressive prostate cancer and castrate levels of testosterone (Scher, 20082016) can be accessed online at: http://jco.ascopubs.org/content/34/12/1402.

We claim:

1. A method for the treatment of small cell lung cancer comprising the administration to a patient in need thereof an effective amount of a compound having the structure of:

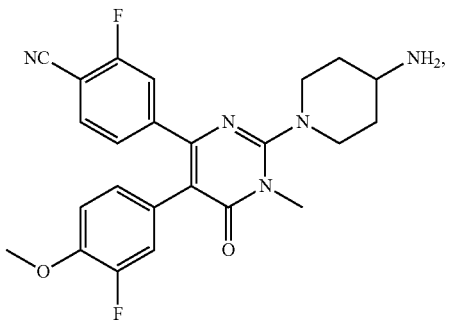 [SMILES: COc1ccc(-c2c(-c3ccc(C#N)c(F)c3)nc(N3CCC(N)CC3)n(C)c2=O)cc1F]

or a pharmaceutically acceptable salt thereof.

2. The method of claim 1, wherein the administration is affected by oral administration.

3. The method of claim 1, wherein the effective amount of the compound comprises about 1.5 mg/kg to about 10 mg/kg.

4. The method of claim 1, wherein the compound is in the form of a tablet, pill, sachet, or capsule of hard or soft gelatin.

5. The method of claim 1, wherein the compound is in the form of a capsule containing the compound at dosage strengths comprising about 0.50 mg, 0.75 mg, or 2.00 mg.

* * * * *